US008986963B2

(12) United States Patent
Lee

(10) Patent No.: US 8,986,963 B2
(45) Date of Patent: Mar. 24, 2015

(54) DESIGNER CALVIN-CYCLE-CHANNELED PRODUCTION OF BUTANOL AND RELATED HIGHER ALCOHOLS

(76) Inventor: James Weifu Lee, Cockeysville, MD (US)

( * ) Notice: Subject to any disclaimer, the term of this patent is extended or adjusted under 35 U.S.C. 154(b) by 714 days.

(21) Appl. No.: 13/075,153

(22) Filed: Mar. 29, 2011

(65) Prior Publication Data

US 2011/0177571 A1 Jul. 21, 2011

Related U.S. Application Data

(63) Continuation-in-part of application No. 12/918,784, filed as application No. PCT/US2009/034801 on Feb. 21, 2009, now Pat. No. 8,735,651.

(60) Provisional application No. 61/066,845, filed on Feb. 23, 2008, provisional application No. 61/066,835, filed on Feb. 23, 2008, provisional application No. 61/426,147, filed on Dec. 22, 2010.

(51) Int. Cl.
*C12P 7/16* (2006.01)
*C12P 7/04* (2006.01)
*C12N 15/113* (2010.01)
*C12Q 1/00* (2006.01)

(52) U.S. Cl.
CPC ... *C12P 7/16* (2013.01); *C12P 7/04* (2013.01); *C12Y 204/01021* (2013.01); *C12N 15/1137* (2013.01); *C12Q 1/00* (2013.01); *Y02E 50/10* (2013.01); *C12N 2310/11* (2013.01); *C12N 2310/14* (2013.01)
USPC .......... 435/160

(58) Field of Classification Search
None
See application file for complete search history.

(56) References Cited

U.S. PATENT DOCUMENTS

| | | | | |
|---|---|---|---|---|
| 6,699,696 | B2 * | 3/2004 | Woods et al. | 435/161 |
| 7,682,821 | B2 * | 3/2010 | Woods et al. | 435/292.1 |
| 2007/0037196 | A1 | 2/2007 | Gibson et al. | |
| 2007/0037197 | A1 | 2/2007 | Young et al. | |
| 2007/0122826 | A1 | 5/2007 | Glass et al. | |
| 2007/0128649 | A1 | 6/2007 | Young | |
| 2007/0264688 | A1 | 11/2007 | Venter et al. | |
| 2007/0269862 | A1 | 11/2007 | Glass et al. | |
| 2009/0081746 | A1 | 3/2009 | Liao et al. | |
| 2009/0111154 | A1 | 4/2009 | Liao et al. | |
| 2009/0176280 | A1 | 7/2009 | Hutchinson, III et al. | |
| 2009/0203070 | A1 | 8/2009 | Devroe et al. | |
| 2010/0105103 | A1 | 4/2010 | Juan et al. | |
| 2010/0151545 | A1 | 6/2010 | Roessler et al. | |
| 2010/0209986 | A1 | 8/2010 | Liao et al. | |
| 2010/0221800 | A1 | 9/2010 | Liao et al. | |
| 2010/0330637 | A1 * | 12/2010 | Lee | 435/160 |

FOREIGN PATENT DOCUMENTS

| | | | |
|---|---|---|---|
| WO | 2005100582 | A2 | 10/2005 |
| WO | 2006119066 | | 11/2006 |
| WO | 2007032837 | A2 | 3/2007 |
| WO | 2007047148 | | 4/2007 |
| WO | 2007065035 | | 6/2007 |
| WO | 2007134340 | A2 | 11/2007 |
| WO | 2008006038 | A2 | 1/2008 |
| WO | 2010068821 | A1 | 6/2010 |

OTHER PUBLICATIONS

Chen et al, Photo. Res., 2005, 86:165-173.*
Raines et al, 2003, Photosynthesis Res., 75:1-10.*
Pickett-Heaps et al, 1999, Am. J. of Botany, 86:153-172.*
Shen et al, 2008, Metabolic Engineering, 10:312-320.*
Sanderson, 2006, Nature, 444:673-676.*
Keneko Takakazu et al., Complete Genomic Sequence of the Filamentous Nitrogen-fixing Cyanobacterium Anabaena sp. Strain PCC 7120, DNA Research 8,205-213 (2001).
Ramesh V. Nair et al., Regulation of the sol Locus Genes for Butanol and Acetone Formation in *Clostridium acetobutylicum* ATCC 824 by a Putative Transcriptional Repressor, Journal of Bacteriology, Jan. 1999, vol. 181, No. 1, pp. 319-330.
(Gfeller and Gibbs (1984) "Fermentative metabolism of *Chlamydomonas reinhardtii*," Plant Physiol. 75:212-218).
(Lee, Blankinship and Greenbaum (1995), "Temperature effect on production of hydrogen and oxygen by Chlamydomonas cold strain CCMP1619 and wild type 137c," Applied Biochemistry and Biotechnology 51/52:379-386).
Lee et al., "Discovery of an Alternative Oxygen Sensitivity in Algal Photosynthetic H2 Production", Proceedings of the 2000 U.S. DOE Hydrogen Program Review, NREL/CP-570-28890.
(Lee, Mets, and Greenbaum (2002). "Improvement of photosynthetic efficiency at high light intensity through reduction of chlorophyll antenna size," Applied Biochemistry and Biotechnology, 98-100: 37-48).
(Nakajima, Tsuzuki, and Ueda (1999) "Reduced photoinhibition of a phycocyanin-deficient mutant of Synechocystis PCC 6714", Journal of Applied Phycology 10: 447-452).

(Continued)

*Primary Examiner* — Ashwin Mehta
*Assistant Examiner* — Jason Deveau Rosen
(74) *Attorney, Agent, or Firm* — August Law, LLC; George Willinghan

(57) ABSTRACT

Designer Calvin-cycle-channeled and photosynthetic NADPH-enhanced pathways, the associated designer genes and designer transgenic photosynthetic organisms for photobiological production of butanol and related higher alcohols from carbon dioxide and water are provided. The butanol and related higher alcohols include 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, and 6-methyl-1-heptanol. The designer photosynthetic organisms such as designer transgenic oxyphotobacteria and algae comprise designer Calvin-cycle-channeled and photosynthetic NADPH-enhanced pathway gene(s) and biosafety-guarding technology for enhanced photobiological production of butanol and related higher alcohols from carbon dioxide and water.

7 Claims, 12 Drawing Sheets

(56) References Cited

OTHER PUBLICATIONS (Quinn, Barraco, Ericksson and Merchant (2000). "Coordinate copper- and oxygen-responsive Cyc6 and Cpx1 expression in Chlamydomonas is mediated by the same element." J Biol Chem 275: 6080-6089).
(Loppes and Radoux (2002) "Two short regions of the promoter are essential for activation and repression of the nitrate reductase gene in *Chlamydomonas reinhardtii*," Mol Genet Genomics 268: 42-48).
(Sjoholm, Oliveira, and Lindblad (2007) "Transcription and regulation of the bidirectional hydrogenase in the Cyanobacterium Nostoc sp. strain PCC 7120," Applied and Environmental Microbiology, 73(17): 5435-5446).
(Qi, Hao, Ng, Slater, Baszis, Weiss, and Valentin (2005) "Application of the Synechococcus nirA promoter to establish an inducible expression system for engineering the Synechocystis tocopherol pathway," Applied and Environmental Microbiology, 71(10): 5678-5684.
Maeda, Kawaguchi, Ohe, and Omata (1998) "cis-Acting sequences required for NtcB-dependent, nitrite-responsive positive regulation of the nitrate assimilation operon in the *Cyanobacterium Synechococcus* sp. strain PCC 7942," Journal of Bacteriology, 180(16):4080-4088).
Kojima and Nakamoto (2007) "A novel light- and heat-responsive regulation of the groE transcription in the absence of HrcA or CIRCE in cyanobacteria," FEBS Letters 581:1871-1880).
7942 (Erbe, Adams, Taylor and Hall (1996) "Cyanobacteria carrying an smt-lux transcriptional fusion as biosensors for the detection of heavy metal cations," Journal of Industrial Microbiology, 17:80-83).
(Michel, Pistorius, and Golden (2001) "Unusual regulatory elements for iron deficiency induction of the idiA gene of Synechococcus elongatus PCC 7942" Journal of Bacteriology, 183(17):5015-5024).
(Patterson-Fortin, Colvin and Owttrim (2006) "A LexA-related protein regulates redox-sensitive expression of the cyanobacterial RNA helicase, crhR", Nucleic Acids Research, 34(12):3446-3454).
(Fang and Barnum (2004) "Expression of the heat shock gene hsp16.6 and promoter analysis in the Cyanobacterium, Synechocystis sp. PCC 6803," Current Microbiology 49:192-198).
(Nakamoto, Suzuki, and Roy (2000) "Constitutive expression of a small heat-shock protein confers cellular thermotolerance and thermal protection to the photosynthetic apparatus in cyanobacteria," FEBS Letters 483:169-174).
(Casey and Grossman (1994) "In vivo and in vitro characterization of the light-regulated cpcB2A2 promoter of Fremyella diplosiphont" Journal of Bacteriology, 176(20):6362-6374).
(Domain, Houot, Chauvat, and Cassier-Chauvat (2004) "Function and regulation of the cyanobacterial genes lexA, recA and ruvB: LexA is critical to the survival of cells facing inorganic carbon starvation," Molecular Microbiology, 53 (1):65-80).
(Keppetipola, Coffman, and et al (2003). Rapid detection of in vitro expressed proteins using LumioTM technology, Gene Expression, 25.3: 7-11).
(Griffin, Adams, and Tsien (1998), "Specific covalent labeling of recombinant protein molecules inside live cells", Science, 281:269-272).
(Pattanayak and Chatterjee (1998) "Nicotinamide adenine dinucleotide phosphate phosphatase facilitates dark reduction of nitrate: regulation by nitrate and ammonia," Biologia Plantarium 41(1):75-84).
(Muto, Miyachi, Usuda, Edwards and Bassham (1981) "Light-induced conversion of nicotinamide adenine dinucleotide to nicotinamide adenine dinucleotide phosphate in higher plant leaves," Plant Physiology 68(2):324-328.
Matsumura-Kadota, Muto, Miyachi (1982) "Light-induced conversion of NAD+ to NADP+ in Chlorella cells," Biochimica Biophysica Acta 679(2), pp. 300-307.
(Liszewski (Jun. 1, 2003) Progress in RNA interference, Genetic Engineering News, vol. 23, No. 11, pp. 8-17.
(Fire, Xu, Montgomery, Kostas, Driver, Mello (1998) "Potent and specific genetic interference by double-stranded RNA in Caenorhabditis elegans". Nature 391(6669):806-11.
(Fuhrmann, Stahlberg, Govorunova, Rank and Hegemann (2001) Journal of Cell Science 114:3857-3863).
(Durre, P. 1998 Appl Microbiol Biotechnol 49: 639-648).
Qureshi, Hughes, Maddox, and Cotta 2005 Bioprocess Biosyst Eng 27: 215-222).
(Deng and Coleman (1999) "Ethanol synthesis by genetic engineering in cyanobacteria. " Applied and Environmental Microbiology, 65(2):523-528).
(Hirano, Ueda, Hirayama, and Ogushi (1997) "CO2 fixation and ethanol production with microalgal photosynthesis and intracellular anaerobic fermentation" Energy 22(2/3): 137-142).
The Eurasian Patent Office, Search Report, Apr. 15, 2011.

* cited by examiner

DESIGNER CALVIN-CYCLE-CHANNELED PRODUCTION OF BUTANOL AND RELATED HIGHER ALCOHOLS

CROSS-REFERENCE TO RELATED APPLICATIONS

This application is a continuation-in-part of co-pending U.S. patent application Ser. No. 12/918,784 filed on Aug. 20, 2010, which is the National Stage of International Application No. PCT/US2009/034801 filed on Feb. 21, 2009, which claims the benefit of U.S. Provisional Application No. 61/066,845 filed on Feb. 23, 2008, and U.S. Provisional Application No. 61/066,835 filed on Feb. 23, 2008. This application also claims the benefit of U.S. Provisional Application No. 61/426,147 filed on Dec. 22, 2010. The entire disclosures of all of these applications are incorporated herein by reference.

FIELD OF THE INVENTION

The present invention generally relates to biosafety-guarded biofuel energy production technology. More specifically, the present invention provides a photobiological advanced-biofuels production methodology based on designer transgenic plants, such as transgenic algae, blue-green algae (cyanobacteria and oxychlorobacteria), or plant cells that are created to use the reducing power (NADPH) and energy (ATP) acquired from the photosynthetic process for photoautotrophic synthesis of butanol and/or related higher alcohols from carbon dioxide ($CO_2$) and water ($H_2O$).

REFERENCE TO SEQUENCE LISTING

The present invention contains references to amino acid sequences and/or nucleic acid sequences which have been submitted concurrently herewith as the sequence listing text file "JWL_004_US1_SeqListingFull_ST25.txt", file size 429 KB, created on Mar. 29, 2011, in electronic format using the Electronic Filing System of the U.S. Patent and Trademark Office. The aforementioned sequence listing was prepared with PatentIn 3.5, which complies with all format requirements specified in World Intellectual Property Organization Standard (WIPO) ST.25 and the related United States (US) final rule, and is incorporated herein by reference in its entirety including pursuant to 37 C.F.R. §1.52(e)(5) where applicable.

BACKGROUND OF THE INVENTION

Butanol and/or related higher alcohols can be used as a liquid fuel to run engines such as cars. Butanol can replace gasoline and the energy contents of the two fuels are nearly the same (110,000 Btu per gallon for butanol; 115,000 Btu per gallon for gasoline). Butanol has many superior properties as an alternative fuel when compared to ethanol as well. These include: 1) Butanol has higher energy content (110,000 Btu per gallon butanol) than ethanol (84,000 Btu per gallon ethanol); 2) Butanol is six times less "evaporative" than ethanol and 13.5 times less evaporative than gasoline, making it safer to use as an oxygenate and thereby eliminating the need for very special blends during the summer and winter seasons; 3) Butanol can be transported through the existing fuel infrastructure including the gasoline pipelines whereas ethanol must be shipped via rail, barge or truck; and 4) Butanol can be used as replacement for gasoline gallon for gallon e.g. 100% or any other percentage, whereas ethanol can only be used as an additive to gasoline up to about 85% (E-85) and then only after significant modification to the engine (while butanol can work as a 100% replacement fuel without having to modify the current car engine).

A significant potential market for butanol and/or related higher alcohols as a liquid fuel already exists in the current transportation and energy systems. Butanol is also used as an industrial solvent. In the United States, currently, butanol is manufactured primarily from petroleum. Historically (1900s-1950s), biobutanol was manufactured from corn and molasses in a fermentation process that also produced acetone and ethanol and was known as an ABE (acetone, butanol, ethanol) fermentation typically with certain butanol-producing bacteria such as *Clostridium acetobutylicum* and *Clostridium beijerinckii*. When the USA lost its low-cost sugar supply from Cuba around 1954, however, butanol production by fermentation declined mainly because the price of petroleum dropped below that of sugar. Recently, there is renewed R&D interest in producing butanol and/or ethanol from biomass such as corn starch using Clostridia- and/or yeast-fermentation process. However, similarly to the situation of "cornstarch ethanol production," the "cornstarch butanol production" process also requires a number of energy-consuming steps including agricultural corn-crop cultivation, corn-grain harvesting, corn-grain starch processing, and starch-to-sugar-to-butanol fermentation. The "cornstarch butanol production" process could also probably cost nearly as much energy as the energy value of its product butanol. This is not surprising, understandably because the cornstarch that the current technology can use represents only a small fraction of the corn crop biomass that includes the corn stalks, leaves and roots. The cornstovers are commonly discarded in the agricultural fields where they slowly decompose back to $CO_2$, because they represent largely lignocellulosic biomass materials that the current biorefinery industry cannot efficiently use for ethanol or butanol production. There are research efforts in trying to make ethanol or butanol from lignocellulosic plant biomass materials—a concept called "cellulosic ethanol" or "cellulosic butanol". However, plant biomass has evolved effective mechanisms for resisting assault on its cell-wall structural sugars from the microbial and animal kingdoms. This property underlies a natural recalcitrance, creating roadblocks to the cost-effective transformation of lignocellulosic biomass to fermentable sugars. Therefore, one of its problems known as the "lignocellulosic recalcitrance" represents a formidable technical barrier to the cost-effective conversion of plant biomass to fermentable sugars. That is, because of the recalcitrance problem, lignocellulosic biomasses (such as cornstover, switchgrass, and woody plant materials) could not be readily converted to fermentable sugars to make ethanol or butanol without certain pretreatment, which is often associated with high processing cost. Despite more than 50 years of R&D efforts in lignocellulosic biomass pretreatment and fermentative butanol-production processing, the problem of recalcitrant lignocellulosics still remains as a formidable technical barrier that has not yet been eliminated so far. Furthermore, the steps of lignocellulosic biomass cultivation, harvesting, pretreatment processing, and cellulose-to-sugar-to-butanol fermentation all cost energy. Therefore, any new technology that could bypass these bottleneck problems of the biomass technology would be useful.

Oxyphotobacteria (also known as blue-green algae including cyanobacteria and oxychlorobacteria) and algae (such as *Chlamydomonas reinhardtii, Platymonas subcordiformis, Chlorella fusca, Dunaliella salina, Ankistrodesmus braunii*, and *Scenedesmus obliquus*), which can perform photosynthetic assimilation of $CO_2$ with $O_2$ evolution from water in a liquid culture medium with a maximal theoretical solar-to-biomass energy conversion of about 10%, have tremendous potential to be a clean and renewable energy resource. However, the wild-type oxygenic photosynthetic green plants, such as blue-green algae and eukaryotic algae, do not possess the ability to produce butanol directly from $CO_2$ and $H_2O$. The wild-type photosynthesis uses the reducing power (NADPH) and energy (ATP) from the photosynthetic water splitting and proton gradient-coupled electron transport process through the algal thylakoid membrane system to reduce $CO_2$ into carbohydrates $(CH_2O)_n$ such as starch with a series of enzymes collectively called the "Calvin cycle" at the stroma region in an algal or green-plant chloroplast. The net result of the wild-type photosynthetic process is the conversion of $CO_2$ and $H_2O$ into carbohydrates $(CH_2O)_n$ and $O_2$ using sunlight energy according to the following process reaction:

$$nCO_2+nH_2O \rightarrow (CH_2O)n+nO_2 \quad [1]$$

The carbohydrates $(CH_2O)_n$ are then further converted to all kinds of complicated cellular (biomass) materials including proteins, lipids, and cellulose and other cell-wall materials during cell metabolism and growth.

In certain alga such as *Chlamydomonas reinhardtii*, some of the organic reserves such as starch could be slowly metabolized to ethanol (but not to butanol) through a secondary fermentative metabolic pathway. The algal fermentative metabolic pathway is similar to the yeast-fermentation process, by which starch is breakdown to smaller sugars such as glucose that is, in turn, transformed into pyruvate by a glycolysis process. Pyruvate may then be converted to formate, acetate, and ethanol by a number of additional metabolic steps (Gfeller and Gibbs (1984) "Fermentative metabolism of *Chlamydomonas reinhardtii*," *Plant Physiol.* 75:212-218). The efficiency of this secondary metabolic process is quite limited, probably because it could use only a small fraction of the limited organic reserve such as starch in an algal cell. Furthermore, the native algal secondary metabolic process could not produce any butanol. As mentioned above, butanol (and/or related higher alcohols) has many superior physical properties to serve as a replacement for gasoline as a fuel. Therefore, a new photobiological butanol (and/or related higher alcohols)-producing mechanism with a high solar-to-biofuel energy efficiency is needed.

International Application No. PCT/US2009/034801 discloses a set of methods on designer photosynthetic organisms (such as designer transgenic plant, plant cells, algae and oxyphotobacteria) for photobiological production of butanol from carbon dioxide ($CO_2$) and water ($H_2O$).

SUMMARY OF THE INVENTION

The present invention discloses designer Calvin-cycle-channeled and photosynthetic NADPH-enhanced pathways, the associated designer genes and designer transgenic photosynthetic organisms for photobiological production of butanol and/or related higher alcohols that are selected from the group that consists of: 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, 6-methyl-1-heptanol, and combinations thereof.

The designer photosynthetic organisms such as designer transgenic oxyphotobacteria and algae comprise designer Calvin-cycle-channeled and photosynthetic NADPH-enhanced pathway gene(s) and biosafety-guarding technology for enhanced photobiological production of butanol and related higher alcohols from carbon dioxide and water.

According to another embodiment, the transgenic photosynthetic organism comprises a transgenic designer plant or plant cells selected from the group consisting of aquatic plants, plant cells, green algae, red algae, brown algae, blue-green algae (oxyphotobacteria including cyanobacteria and oxychlorobacteria), diatoms, marine algae, freshwater algae, salt-tolerant algal strains, cold-tolerant algal strains, heat-tolerant algal strains, antenna-pigment-deficient mutants, butanol-tolerant algal strains, higher-alcohols-tolerant algal strains, butanol-tolerant oxyphotobacteria, higher-alcohols-tolerant oxyphotobacteria, and combinations thereof.

According to one of the various embodiments, a designer Calvin-cycle-channeled photosynthetic NADPH-enhanced pathway that takes the Calvin-cycle intermediate product, 3-phosphoglycerate, and converts it into 1-butanol comprises a set of enzymes selected from the group consisting of: NADPH-dependent glyceraldehyde-3-phosphate dehydrogenase, NAD-dependent glyceraldehyde-3-phosphate dehydrogenase, phosphoglycerate mutase, enolase, pyruvate kinase, citramalate synthase, 2-methylmalate dehydratase, 3-isopropylmalate dehydratase, 3-isopropylmalate dehydrogenase, 2-isopropylmalate synthase, isopropylmalate isomerase, 2-keto acid decarboxylase, alcohol dehydrogenase, NADPH-dependent alcohol dehydrogenase, and butanol dehydrogenase.

According to one of the various embodiments, another designer Calvin-cycle-channeled photosynthetic NADPH-enhanced 1-butanol-production pathway comprises a set of enzymes selected from the group consisting of: NADPH-dependent glyceraldehyde-3-phosphate dehydrogenase, NAD-dependent glyceraldehyde-3-phosphate dehydrogenase, phosphoglycerate mutase, enolase, phosphoenolpyruvate carboxylase, aspartate aminotransferase, aspartokinase, aspartate-semialdehyde dehydrogenase, homoserine dehydrogenase, homoserine kinase, threonine synthase, threonine ammonia-lyase, 2-isopropylmalate synthase, isopropylmalate isomerase, 3-isopropylmalate dehydrogenase, 2-keto acid decarboxylase, and NAD-dependent alcohol dehydrogenase, NADPH-dependent alcohol dehydrogenase, and butanol dehydrogenase.

According to another embodiment, a designer Calvin-cycle-channeled photosynthetic NADPH-enhanced pathway that takes the Calvin-cycle intermediate product, 3-phosphoglycerate, and converts it into 2-methyl-1-butanol, comprises a set of enzymes selected from the group consisting of: NADPH-dependent glyceraldehyde-3-phosphate dehydrogenase, NAD-dependent glyceraldehyde-3-phosphate dehydrogenase, phosphoglycerate mutase, enolase, pyruvate kinase, citramalate synthase, 2-methylmalate dehydratase, 3-isopropylmalate dehydratase, 3-isopropylmalate dehydrogenase, acetolactate synthase, ketol-acid reductoisomerase, dihydroxy-acid dehydratase, 2-keto acid decarboxylase, NAD-dependent alcohol dehydrogenase, NADPH-dependent alcohol dehydrogenase, and 2-methylbutyraldehyde reductase.

According to another embodiment, a designer Calvin-cycle-channeled photosynthetic NADPH-enhanced pathway for photobiological production of 2-methyl-1-butanol production comprises a set of enzymes selected from the group consisting of: NADPH-dependent glyceraldehyde-3-phosphate dehydrogenase, NAD-dependent glyceraldehyde-3-phosphate dehydrogenase, phosphoglycerate mutase, enolase, phosphoenolpyruvate carboxylase, aspartate aminotransferase, aspartokinase, aspartate-semialdehyde dehydrogenase, homoserine dehydrogenase, homoserine kinase, threonine synthase, threonine ammonia-lyase, acetolactate synthase, ketol-acid reductoisomerase, dihydroxy-acid dehydratase, 2-keto acid decarboxylase, and NAD dependent alcohol dehydrogenase, NADPH dependent alcohol dehydrogenase, and 2-methylbutyraldehyde reductase.

According to another embodiment, a designer Calvin-cycle-channeled photosynthetic NADPH-enhanced pathway for photobiological production of isobutanol comprises a set of enzymes selected from the group consisting of: NADPH-dependent glyceraldehyde-3-phosphate dehydrogenase, NAD-dependent glyceraldehyde-3-phosphate dehydrogenase, phosphoglycerate mutase, enolase, pyruvate kinase, acetolactate synthase, ketol-acid reductoisomerase, dihydroxy-acid dehydratase, 2-keto acid decarboxylase, and NAD-dependent alcohol dehydrogenase, and NADPH-dependent alcohol dehydrogenase.

Likewise, a number of other designer Calvin-cycle-channeled photosynthetic NADPH-enhanced pathways are also disclosed according to one of the various embodiments for photobiological production of butanol and/or related higher alcohols such as 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, and/or 6-methyl-1-heptanol.

According to one of various embodiments, a method for photobiological production and harvesting of butanol and related higher alcohols comprises: a) introducing a transgenic photosynthetic organism into a photobiological reactor system, the transgenic photosynthetic organism comprising transgenes coding for a set of enzymes configured to act on an intermediate product of a Calvin cycle and to convert the intermediate product into butanol and/or related higher alcohols; b) using reducing power NADPH and energy ATP associated with the transgenic photosynthetic organism acquired from photosynthetic water splitting and proton gradient coupled electron transport process in the photobioreactor to synthesize butanol and/or related higher alcohols from carbon dioxide and water; and c) using a product separation process to harvest the synthesized butanol and/or related higher alcohols from the photobioreactor.

DETAILED DESCRIPTION OF THE INVENTION

The present invention is directed to a photobiological butanol and related high alcohols production technology based on designer photosynthetic organisms such as designer transgenic plants (e.g., algae and oxyphotobacteria) or plant cells. In this context throughout this specification, a "higher alcohol" or "related higher alcohol" refers to an alcohol that comprises at least four carbon atoms, which includes both straight and branched alcohols such as 1-butanol and 2-methyl-1-butanol. The Calvin-cycle-channeled and photosynthetic-NADPH-enhanced pathways are constructed with designer enzymes expressed through use of designer genes in host photosynthetic organisms such as algae and oxyphotobacteria (including cyanobacteria and oxychlorobacteria) organisms for photobiological production of butanol and related higher alcohols. The said butanol and related higher alcohols are selected from the group consisting of: 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, and 6-methyl-1-heptanol. The designer plants and plant cells are created using genetic engineering techniques such that the endogenous photosynthesis regulation mechanism is tamed, and the reducing power (NADPH) and energy (ATP) acquired from the photosynthetic water splitting and proton gradient-coupled electron transport process can be used for immediate synthesis of higher alcohols, such as 1-butanol ($CH_3CH_2CH_2CH_2OH$) and 2-methyl-1-butanol ($CH_3CH_2CH(CH_3)CH_2OH$), from carbon dioxide ($CO_2$) and water ($H_2O$) according to the following generalized process reaction (where m, n, x and y are its molar coefficients) in accordance of the present invention:

$$m(CO_2)+n(H_2O)\rightarrow x(\text{higher alcohols})+y(O_2) \qquad [2]$$

Figure 1:
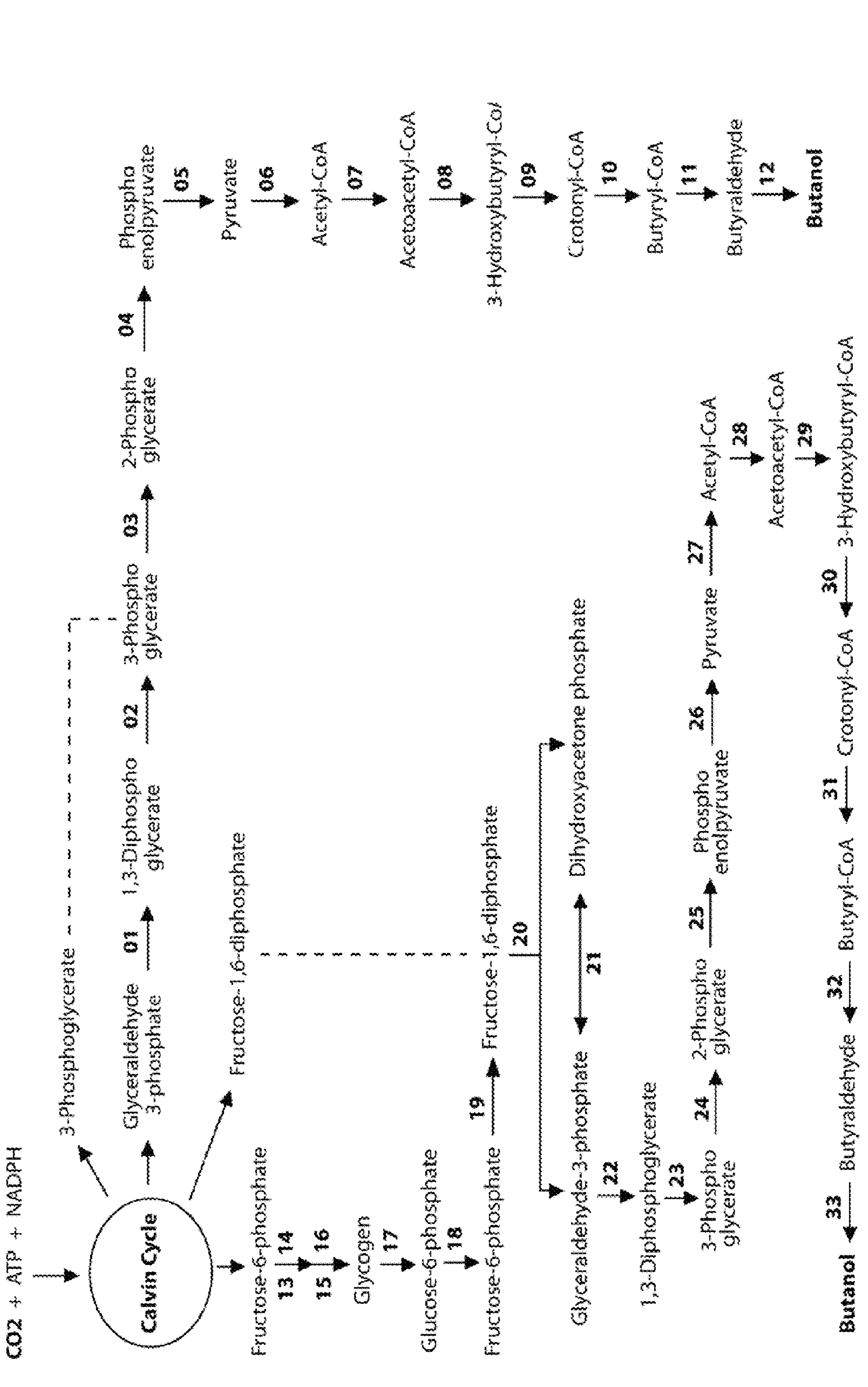
FIG. 1 presents designer butanol-production pathways branched from the Calvin cycle using the reducing power (NADPH) and energy (ATP) from the photosynthetic water splitting and proton gradient-coupled electron transport process to reduce carbon dioxide ($CO_2$) into butanol $CH_3CH_2CH_2CH_2OH$ with a series of enzymatic reactions.

The photobiological higher-alcohols-production methods of the present invention completely eliminate the problem of recalcitrant lignocellulosics by bypassing the bottleneck problem of the biomass technology. As shown in FIG. 1, for example, the photosynthetic process in a designer organism effectively uses the reducing power (NADPH) and energy (ATP) from the photosynthetic water splitting and proton gradient-coupled electron transport process for immediate synthesis of butanol ($CH_3CH_2CH_2CH_2OH$) directly from carbon dioxide ($CO_2$) and water ($H_2O$) without being drained into the other pathway for synthesis of the undesirable lignocellulosic materials that are very hard and often inefficient for the biorefinery industry to use. This approach is also different from the existing "cornstarch butanol production" process. In accordance with this invention, butanol can be produced directly from carbon dioxide ($CO_2$) and water ($H_2O$) without having to go through many of the energy consuming steps that the cornstarch butanol-production process has to go through, including corn crop cultivation, corn-grain harvesting, corn-grain cornstarch processing, and starch-to-sugar-to-butanol fermentation. As a result, the photosynthetic butanol-production technology of the present invention is expected to have a much (more than 10-times) higher solar-to-butanol energy-conversion efficiency than the current technology. Assuming a 10% solar energy conversion efficiency for the proposed photosynthetic butanol production process, the maximal theoretical productivity (yield) could be about 72,700 kg of butanol per acre per year, which could support about 70 cars (per year per acre). Therefore, this invention could bring a significant capability to the society in helping to ensure energy security. The present invention could also help protect the Earth's environment from the dangerous accumulation of $CO_2$ in the atmosphere, because the present methods convert $CO_2$ directly into clean butanol energy.

A fundamental feature of the present methodology is utilizing a plant (e.g., an alga or oxyphotobacterium) or plant cells, introducing into the plant or plant cells nucleic acid molecules encoding for a set of enzymes that can act on an intermediate product of the Calvin cycle and convert the intermediate product into butanol as illustrated in FIG. 1, instead of making starch and other complicated cellular (biomass) materials as the end products by the wild-type photosynthetic pathway. Accordingly, the present invention provides, inter alia, methods for producing butanol and/or related higher alcohols based on a designer plant (such as a designer alga and a designer oxyphotobacterium), designer plant tissue, or designer plant cells, DNA constructs encoding genes of a designer butanol- and/or related higher alcohols-production pathway(s), as well as the designer algae, designer oxyphotobacteria (including designer cyanobacteria), designer plants, designer plant tissues, and designer plant cells created. The various aspects of the present invention are described in further detail hereinbelow.

Host Photosynthetic Organisms

According to the present invention, a designer organism or cell for the photosynthetic butanol and/or related higher alcohols production of the invention can be created utilizing as host, any plant (including alga and oxyphotobacterium), plant tissue, or plant cells that have a photosynthetic capability, i.e., an active photosynthetic apparatus and enzymatic pathway that captures light energy through photosynthesis, using this energy to convert inorganic substances into organic matter. Preferably, the host organism should have an adequate photosynthetic $CO_2$ fixation rate, for example, to support photosynthetic butanol (and/or related higher alcohols) production from $CO_2$ and $H_2O$ at least about 1,450 kg butanol per acre per year, more preferably, 7,270 kg butanol per acre per year, or even more preferably, 72,700 kg butanol per acre per year.

In a preferred embodiment, an aquatic plant is utilized to create a designer plant. Aquatic plants, also called hydrophytic plants, are plants that live in or on aquatic environments, such as in water (including on or under the water surface) or permanently saturated soil. As used herein, aquatic plants include, for example, algae, blue-green algae (cyanobacteria and oxychlorobacteria), submersed aquatic herbs (*Hydrilla verticillate, Elodea densa, Hippuris vulgaris, Aponogeton Boivinianus Aponogeton Rigidifolius, Aponogeton Longiplumulosus, Didiplis Diandra, Vesicularia Dubyana, Hygrophilia Augustifolia, Micranthemum Umbrosum, Eichhornia Azurea, Saururus Cernuus, Cryptocoryne Lingua, Hydrotriche Hottoniiflora Eustralis Stellata, Vallisneria Rubra, Hygrophila Salicifolia, Cyperus Helferi, Cryptocoryne Petchii, Vallisneria americana, Vallisneria Torta, Hydrotriche Hottoniiflora, Crassula Helmsii, Limnophila Sessiliflora, Potamogeton Perfoliatus, Rotala Wallichii, Cryptocoryne Becketii, Blyxa Aubertii, Hygrophila Difformmis*), duckweeds (*Spirodela polyrrhiza, Wolffia globosa, Lemna trisulca, Lemna gibba, Lemna minor, Landoltia punctata*), water cabbage (*Pistia stratiotes*), buttercups (*Ranunculus*), water caltrop (*Trapa natans* and *Trapa bicornis*), water lily (*Nymphaea lotus*, Nymphaeaceae and Nelumbonaceae), water hyacinth (*Eichhornia crassipes*), *Bolbitis heudelotii, Cabomba* sp., seagrasses (*Heteranthera Zosterifolia*, Posidoniaceae, Zosteraceae, Hydrocharitaceae, and Cymodoceaceae). Butanol (and/or related higher alcohols) produced from an aquatic plant can diffuse into water, permitting normal growth of the plants and more robust production of butanol from the plants. Liquid cultures of aquatic plant tissues (including, but not limited to, multicellular algae) or cells (including, but not limited to, unicellular algae) are also highly preferred for use, since the butanol (and/or related higher alcohols) molecules produced from a designer butanol (and/or related higher alcohols) production pathway(s) can readily diffuse out of the cells or tissues into the liquid water medium, which can serve as a large pool to store the product butanol (and/or related higher alcohols) that can be subsequently harvested by filtration and/or distillation/evaporation techniques.

Although aquatic plants or cells are preferred host organisms for use in the methods of the present invention, tissue and cells of non-aquatic plants, which are photosynthetic and can be cultured in a liquid culture medium, can also be used to create designer tissue or cells for photosynthetic butanol (and/or related higher alcohols) production. For example, the following tissue or cells of non-aquatic plants can also be selected for use as a host organism in this invention: the photoautotrophic shoot tissue culture of wood apple tree *Feronia limonia*, the chlorophyllous callus-cultures of corn plant *Zea mays*, the green root cultures of Asteraceae and Solanaceae species, the tissue culture of sugarcane stalk parenchyma, the tissue culture of bryophyte *Physcomitrella patens*, the photosynthetic cell suspension cultures of soybean plant (*Glycine max*), the photoautotrophic and photomixotrophic culture of green Tobacco (*Nicofiana tabacum* L.) cells, the cell suspension culture of *Gisekia pharmaceoides* (a $C_4$ plant), the photosynthetic suspension cultured lines of *Amaranthus powellii* Wats., *Datura innoxia* Mill., *Gossypium hirsutum* L., and *Nicotiana tabacum* x *Nicotiana glutinosa* L. fusion hybrid.

By "liquid medium" is meant liquid water plus relatively small amounts of inorganic nutrients (e.g., N, P, K etc, commonly in their salt forms) for photoautotrophic cultures; and sometimes also including certain organic substrates (e.g., sucrose, glucose, or acetate) for photomixotrophic and/or photoheterotrophic cultures.

In an especially preferred embodiment, the plant utilized in the butanol (and/or related higher alcohols) production method of the present invention is an alga or a blue-green alga. The use of algae and/or blue-green algae has several advantages. They can be grown in an open pond at large amounts and low costs. Harvest and purification of butanol (and/or related higher alcohols) from the water phase is also easily accomplished by distillation/evaporation or membrane separation.

Algae suitable for use in the present invention include both unicellular algae and multi-unicellular algae. Multicellular algae that can be selected for use in this invention include, but are not limited to, seaweeds such as *Ulva latissima* (sea lettuce), *Ascophyllum nodosum, Codium fragile, Fucus vesiculosus, Eucheuma denticulatum, Gracilaria gracilis, Hydrodictyon reticulatum, Laminaria japonica, Undaria pinntifida, Saccharina japonica, Porphyra yezoensis*, and *Porphyra tenera*. Suitable algae can also be chosen from the following divisions of algae: green algae (Chlorophyta), red algae (Rhodophyta), brown algae (Phaeophyta), diatoms (Bacillariophyta), and blue-green algae (Oxyphotobacteria including Cyanophyta and Prochlorophytes). Suitable orders of green algae include Ulvales, Ulotrichales, Volvocales, Chlorellales, Schizogoniales, Oedogoniales, Zygnematales, Cladophorales, Siphonales, and Dasycladales. Suitable genera of Rhodophyta are *Porphyra, Chondrus, Cyanidioschyzon, Porphyridium, Gracilaria, Kappaphycus, Gelidium* and *Agardhiella*. Suitable genera of Phaeophyta are *Laminaria, Undaria, Macrocystis, Sargassum* and *Dictyosiphon*. Suitable genera of Cyanophyta (also known as Cyanobacteria) include (but not limited to) *Phoridium, Synechocystis, Syncechococcus, Oscillatoria*, and *Anabaena*. Suitable genera of Prochlorophytes (also known as oxychlorobacteria) include (but not limited to) *Prochloron, Prochlorothrix*, and *Prochlorococcus*. Suitable genera of Bacillariophyta are *Cyclotella, Cylindrotheca, Navicula, Thalassiosira*, and *Phaeodactylum*. Preferred species of algae for use in the present invention include *Chlamydomonas reinhardtii, Platymonas subcordiformis, Chlorella fusca, Chlorella sorokiniana, Chlorella vulgaris, 'Chlorella' ellipsoidea, Chlorella* spp., *Dunaliella salina, Dunaliella viridis, Dunaliella bardowil, Haematococcus pluvialis; Parachlorella kessleri, Betaphycus gelatinum, Chondrus crispus, Cyanidioschyzon merolae, Cyanidium caldarium, Galdieria sulphuraria, Gelidiella acerosa, Gracilaria changii, Kappaphycus alvarezii, Porphyra miniata, Ostreococcus tauri, Porphyra yezoensis, Porphyridium* sp., *Palmaria palmata, Gracilaria* spp., *Isochrysis galbana, Kappaphycus* spp., *Laminaria japonica, Laminaria* spp., *Monostroma* spp., *Nannochloropsis oculata, Porphyra* spp., *Porphyridium* spp., *Undaria pinnatifida, Ulva lactuca, Ulva* spp., *Undaria* spp., *Phaeodactylum Tricornutum, Navicula saprophila, Crypthecodinium cohnii, Cylindrotheca fusiformis, Cyclotella cryptica, Euglena gracilis, Amphidinium* sp., *Symbiodinium microadriaticum, Macrocystis pyrifera, Ankistrodesmus braunii*, and *Scenedesmus obliquus*.

Preferred species of blue-green algae (oxyphotobacteria including cyanobacteria and oxychlorobacteria) for use in the present invention include *Thermosynechococcus elongatus* BP-1, *Nostoc* sp. PCC 7120, *Synechococcus elongatus* PCC 6301, *Syncechococcus* sp. strain PCC 7942, *Syncechococcus* sp. strain PCC 7002, *Syncechocystis* sp. strain PCC 6803, *Prochlorococcus marinus* MED4, *Prochlorococcus marinus* MIT 9313, *Prochlorococcus marinus* NATL1A, *Prochlorococcus* SS120, *Spirulina platensis* (*Arthrospira platensis*), *Spirulina pacifica, Lyngbya majuscule, Anabaena* sp., *Synechocystis* sp., *Synechococcus elongates, Synechococcus* (MC-A), *Trichodesmium* sp., *Richelia intracellularis, Synechococcus* WH7803, *Synechococcus* WH8102, *Nostoc punctiforme, Syncechococcus* sp. strain PCC 7943, *Synechocyitis* PCC 6714 phycocyanin-deficient mutant PD-1, *Cyanothece* strain 51142, *Cyanothece* sp. CCY0110, *Oscillatoria limosa, Lyngbya majuscula, Symploca muscorum, Gloeobacter violaceus, Prochloron didemni, Prochlorothrix hollandica, Synechococcus* (MC-A), *Trichodesmium* sp., *Richelia intracellularis, Prochlorococcus marinus, Prochlorococcus* SS120, *Synechococcus* WH8102, *Lyngbya majuscula, Symploca muscorum, Synechococcus bigranulatus*, cryophilic *Oscillatoria* sp., *Phormidium* sp., *Nostoc* sp.-1, *Calothrix parietina*, thermophilic *Synechococcus bigranulatus, Synechococcus lividus*, thermophilic *Mastigocladus laminosus, Chlorogloeopsis fritschii* PCC 6912, *Synechococcus vulcanus, Synechococcus* sp. strain MA4, *Synechococcus* sp. strain MA19, and *Thermosynechococcus elongatus*.

Proper selection of host photosynthetic organisms for their genetic backgrounds and certain special features is also beneficial. For example, a photosynthetic-butanol-producing designer alga created from cryophilic algae (psychrophiles) that can grow in snow and ice, and/or from cold-tolerant host strains such as *Chlamydomonas* cold strain CCMG1619, which has been characterized as capable of performing photosynthetic water splitting as cold as 4° C. (Lee, Blankinship and Greenbaum (1995), "Temperature effect on production of hydrogen and oxygen by *Chlamydomonas* cold strain CCMP1619 and wild type 137c," *Applied Biochemistry and Biotechnology* 51/52:379-386), permits photobiological butanol production even in cold seasons or regions such as Canada. Meanwhile, a designer alga created from a thermophilic/thermotolerant photosynthetic organism such as thermophilic algae *Cyanidium caldarium* and *Galdieria sulphuraria* and/or thermophilic cyanobacteria (blue-green algae) such as *Thermosynechococcus elongatus* BP-1 and

*Synechococcus bigranulatus* may permit the practice of this invention to be well extended into the hot seasons or areas such as Mexico and the Southwestern region of the United States including Nevada, California, Arizona, New Mexico and Texas, where the weather can often be hot. Furthermore, a photosynthetic-butanol-producing designer alga created from a marine alga, such as *Platymonas subcordiformis*, permits the practice of this invention using seawater, while the designer alga created from a freshwater alga such as *Chlamydomonas reinhardtii* can use freshwater. Additional optional features of a photosynthetic butanol (and/or related higher alcohols) producing designer alga include the benefits of reduced chlorophyll-antenna size, which has been demonstrated to provide higher photosynthetic productivity (Lee, Mets, and Greenbaum (2002). "Improvement of photosynthetic efficiency at high light intensity through reduction of chlorophyll antenna size," *Applied Biochemistry and Biotechnology,* 98-100: 37-48) and butanol-tolerance (and/or related higher alcohols-tolerance) that allows for more robust and efficient photosynthetic production of butanol (and/or related higher alcohols) from $CO_2$ and $H_2O$. By use of a phycocyanin-deficient mutant of *Synechocystis* PCC 6714, it has been experimentally demonstrated that photoinhibition can be reduced also by reducing the content of light-harvesting pigments (Nakajima, Tsuzuki, and Ueda (1999) "Reduced photoinhibition of a phycocyanin-deficient mutant of *Synechocystis* PCC 6714", *Journal of Applied Phycology* 10: 447-452). These optional features can be incorporated into a designer alga, for example, by use of a butanol-tolerant and/or chlorophyll antenna-deficient mutant (e.g., *Chlamydomonas reinhardtii* strain DS521) as a host organism, for gene transformation with the designer butanol-production-pathway genes. Therefore, in one of the various embodiments, a host alga is selected from the group consisting of green algae, red algae, brown algae, blue-green algae (oxyphotobacteria including cyanobacteria and prochlorophytes), diatoms, marine algae, freshwater algae, unicellular algae, multicellular algae, seaweeds, cold-tolerant algal strains, heat-tolerant algal strains, light-harvesting-antenna-pigment-deficient mutants, butanol-tolerant algal strains, higher alcohols-tolerant algal strains, and combinations thereof.

Creating a Designer Butanol-Production Pathway in a Host

Selecting Appropriate Designer Enzymes

One of the key features in the present invention is the creation of a designer butanol-production pathway to tame and work with the natural photosynthetic mechanisms to achieve the desirable synthesis of butanol directly from $CO_2$ and $H_2O$. The natural photosynthetic mechanisms include (1) the process of photosynthetic water splitting and proton gradient-coupled electron transport through the thylakoid membrane, which produces the reducing power (NADPH) and energy (ATP), and (2) the Calvin cycle, which reduces $CO_2$ by consumption of the reducing power (NADPH) and energy (ATP).

In accordance with the present invention, a series of enzymes are used to create a designer butanol-production pathway that takes an intermediate product of the Calvin cycle and converts the intermediate product into butanol as illustrated in FIG. 1. A "designer butanol-production-pathway enzyme" is hereby defined as an enzyme that serves as a catalyst for at least one of the steps in a designer butanol-production pathway. According to the present invention, a number of intermediate products of the Calvin cycle can be utilized to create designer butanol-production pathway(s); and the enzymes required for a designer butanol-production pathway are selected depending upon from which intermediate product of the Calvin cycle the designer butanol-production pathway branches off from the Calvin cycle.

In one example, a designer pathway is created that takes glyceraldehydes-3-phosphate and converts it into butanol by using, for example, a set of enzymes consisting of, as shown with the numerical labels 01-12 in FIG. 1, glyceraldehyde-3-phosphate dehydrogenase 01, phosphoglycerate kinase 02, phosphoglycerate mutase 03, enolase 04, pyruvate kinase 05, pyruvate-ferredoxin oxidoreductase 06, thiolase 07, 3-hydroxybutyryl-CoA dehydrogenase 08, crotonase 09, butyryl-CoA dehydrogenase 10, butyraldehyde dehydrogenase 11, and butanol dehydrogenase 12. In this glyceraldehydes-3-phosphate-branched designer pathway, for conversion of two molecules of glyceraldehyde-3-phosphate to butanol, two NADH molecules are generated from $NAD^+$ at the step from glyceraldehyde-3-phosphate to 1,3-diphosphoglycerate catalyzed by glyceraldehyde-3-phosphate dehydrogenase 01; meanwhile two molecules of NADH are converted to $NAD^+$: one at the step catalyzed by 3-hydroxybutyryl-CoA dehydrogenase 08 in reducing acetoacetyl-CoA to 3-hydroxybutyryl-CoA and another at the step catalyzed by butyryl-CoA dehydrogenase 10 in reducing crotonyl-CoA to butyryl-CoA. Consequently, in this glyceraldehydes-3-phosphate-branched designer pathway (01-12), the number of NADH molecules consumed is balanced with the number of NADH molecules generated. Furthermore, both the pathway step catalyzed by butyraldehyde dehydrogenase 11 (in reducing butyryl-CoA to butyraldehyde) and the terminal step catalyzed by butanol dehydrogenase 12 (in reducing butyraldehyde to butanol) can use NADPH, which can be regenerated by the photosynthetic water splitting and proton gradient-coupled electron transport process. Therefore, this glyceraldehydes-3-phosphate-branched designer butanol-production pathway can operate continuously.

In another example, a designer pathway is created that takes the intermediate product, 3-phosphoglycerate, and converts it into butanol by using, for example, a set of enzymes consisting of (as shown with the numerical labels 03-12 in FIG. 1) phosphoglycerate mutase 03, enolase 04, pyruvate kinase 05, pyruvate-ferredoxin oxidoreductase 06, thiolase 07, 3-hydroxybutyryl-CoA dehydrogenase 08, crotonase 09, butyryl-CoA dehydrogenase 10, butyraldehyde dehydrogenase 11, and butanol dehydrogenase 12. It is worthwhile to note that the last ten enzymes (03-12) of the glyceraldehydes-3-phosphate-branched designer butanol-producing pathway (01-12) are identical with those utilized in the 3-phosphoglycerate-branched designer pathway (03-12). In other words, the designer enzymes (01-12) of the glyceraldehydes-3-phosphate-branched pathway permit butanol production from both the point of 3-phosphoglycerate and the point glyceraldehydes 3-phosphate in the Calvin cycle. These two pathways, however, have different characteristics. Unlike the glyceraldehyde-3-phosphate-branched butanol-production pathway, the 3-phosphoglycerate-branched pathway which consists of the activities of only ten enzymes (03-12) could not itself generate any NADH that is required for use at two places: one at the step catalyzed by 3-hydroxybutyryl-CoA dehydrogenase 08 in reducing acetoacetyl-CoA to 3-hydroxybutyryl-CoA, and another at the step catalyzed by butyryl-CoA dehydrogenase 10 in reducing crotonyl-CoA to butyryl-CoA. That is, if (or when) a 3-hydroxybutyryl-CoA dehydrogenase and/or a butyryl-CoA dehydrogenase that can use strictly only NADH but not NADPH is employed, it would require a supply of NADH for the 3-phosphoglycerate-branched pathway (03-12) to operate. Consequently, in order for the 3-phosphoglycerate-branched butanol-production pathway to operate, it is important to use a 3-hydroxybutyryl- CoA dehydrogenase 08 and a butyryl-CoA dehydrogenase 10 that can use NADPH which can be supplied by the photo-driven electron transport process. Therefore, it is a preferred practice to use a 3-hydroxybutyryl-CoA dehydrogenase and a butyryl-CoA dehydrogenase that can use NADPH or both NADPH and NADH (i.e., NAD(P)H) for this 3-phosphoglycerate-branched designer butanol-production pathway (03-12 in FIG. 1). Alternatively, when a 3-hydroxybutyryl-CoA dehydrogenase and a butyryl-CoA dehydrogenase that can use only NADH are employed, it is preferably here to use an additional embodiment that can confer an NADPH/NADH conversion mechanism (to supply NADH by converting NADPH to NADH, see more detail later in the text) in the designer organism to facilitate photosynthetic production of butanol through the 3-phosphoglycerate-branched designer pathway.

In still another example, a designer pathway is created that takes fructose-1,6-diphosphate and converts it into butanol by using, as shown with the numerical labels 20-33 in FIG. 1, a set of enzymes consisting of aldolase 20, triose phosphate isomerase 21, glyceraldehyde-3-phosphate dehydrogenase 22, phosphoglycerate kinase 23, phosphoglycerate mutase 24, enolase 25, pyruvate kinase 26, pyruvate-$NADP^+$ oxidoreductase (or pyruvate-ferredoxin oxidoreductase) 27, thiolase 28, 3-hydroxybutyryl-CoA dehydrogenase 29, crotonase 30, butyryl-CoA dehydrogenase 31, butyraldehyde dehydrogenase 32, and butanol dehydrogenase 33, with aldolase 20 and triose phosphate isomerase 21 being the only two additional enzymes relative to the glyceraldehydes-3-phosphate-branched designer pathway. The use of a pyruvate-$NADP^+$ oxidoreductase 27 (instead of pyruvate-ferredoxin oxidoreductase) in catalyzing the conversion of a pyruvate molecule to acetyl-CoA enables production of an NADPH, which can be used in some other steps of the butanol-production pathway. The addition of yet one more enzyme in the designer organism, phosphofructose kinase 19, permits the creation of another designer pathway which branches off from the point of fructose-6-phosphate of the Calvin cycle for the production of butanol. Like the glyceraldehyde-3-phosphate-branched butanol-production pathway, both the fructose-1,6-diphosphate-branched pathway (20-33) and the fructose-6-phosphate-branched pathway (19-33) can themselves generate NADH for use in the pathway at the step catalyzed by 3-hydroxybutyryl-CoA dehydrogenase 29 to reduce acetoacetyl-CoA to 3-hydroxybutyryl-CoA and at the step catalyzed by butyryl-CoA dehydrogenase 31 to reduce crotonyl-CoA to butyryl-CoA. In each of these designer butanol-production pathways, the numbers of NADH molecules consumed are balanced with the numbers of NADH molecules generated; and both the butyraldehyde dehydrogenase 32 (catalyzing the step in reducing butyryl-CoA to butyraldehyde) and the butanol dehydrogenase 33 (catalyzing the terminal step in reducing butyraldehyde to butanol) can all use NADPH, which can be regenerated by the photosynthetic water splitting and proton gradient-coupled electron transport process. Therefore, these designer butanol-production pathways can operate continuously.

Table 1 lists examples of the enzymes including those identified above for construction of the designer butanol-production pathways. Throughout this specification, when reference is made to an enzyme, such as, for example, any of the enzymes listed in Table 1, it includes their isozymes, functional analogs, and designer modified enzymes and combinations thereof. These enzymes can be selected for use in construction of the designer butanol-production pathways (such as those illustrated in FIG. 1). The "isozymes or functional analogs" refer to certain enzymes that have the same catalytic function but may or may not have exactly the same protein structures. The most essential feature of an enzyme is its active site that catalyzes the enzymatic reaction. Therefore, certain enzyme-protein fragment(s) or subunit(s) that contains such an active catalytic site may also be selected for use in this invention. For various reasons, some of the natural enzymes contain not only the essential catalytic structure but also other structure components that may or may not be desirable for a given application. With techniques of bioinformatics-assisted molecular designing, it is possible to select the essential catalytic structure(s) for use in construction of a designer DNA construct encoding a desirable designer enzyme. Therefore, in one of the various embodiments, a designer enzyme gene is created by artificial synthesis of a DNA construct according to bioinformatics-assisted molecular sequence design. With the computer-assisted synthetic biology approach, any DNA sequence (thus its protein structure) of a designer enzyme may be selectively modified to achieve more desirable results by design. Therefore, the terms "designer modified sequences" and "designer modified enzymes" are hereby defined as the DNA sequences and the enzyme proteins that are modified with bioinformatics-assisted molecular design. For example, when a DNA construct for a designer chloroplast-targeted enzyme is designed from the sequence of a mitochondrial enzyme, it is a preferred practice to modify some of the protein structures, for example, by selectively cutting out certain structure component(s) such as its mitochondrial transit-peptide sequence that is not suitable for the given application, and/or by adding certain peptide structures such as an exogenous chloroplast transit-peptide sequence (e.g., a 135-bp Rubisco small-subunit transit peptide (RbcS2)) that is needed to confer the ability in the chloroplast-targeted insertion of the designer protein. Therefore, one of the various embodiments flexibly employs the enzymes, their isozymes, functional analogs, designer modified enzymes, and/or the combinations thereof in construction of the designer butanol-production pathway(s).

Figures 2A, 2B, 2C, 2D, 2E, 2F, 2G, 2H:
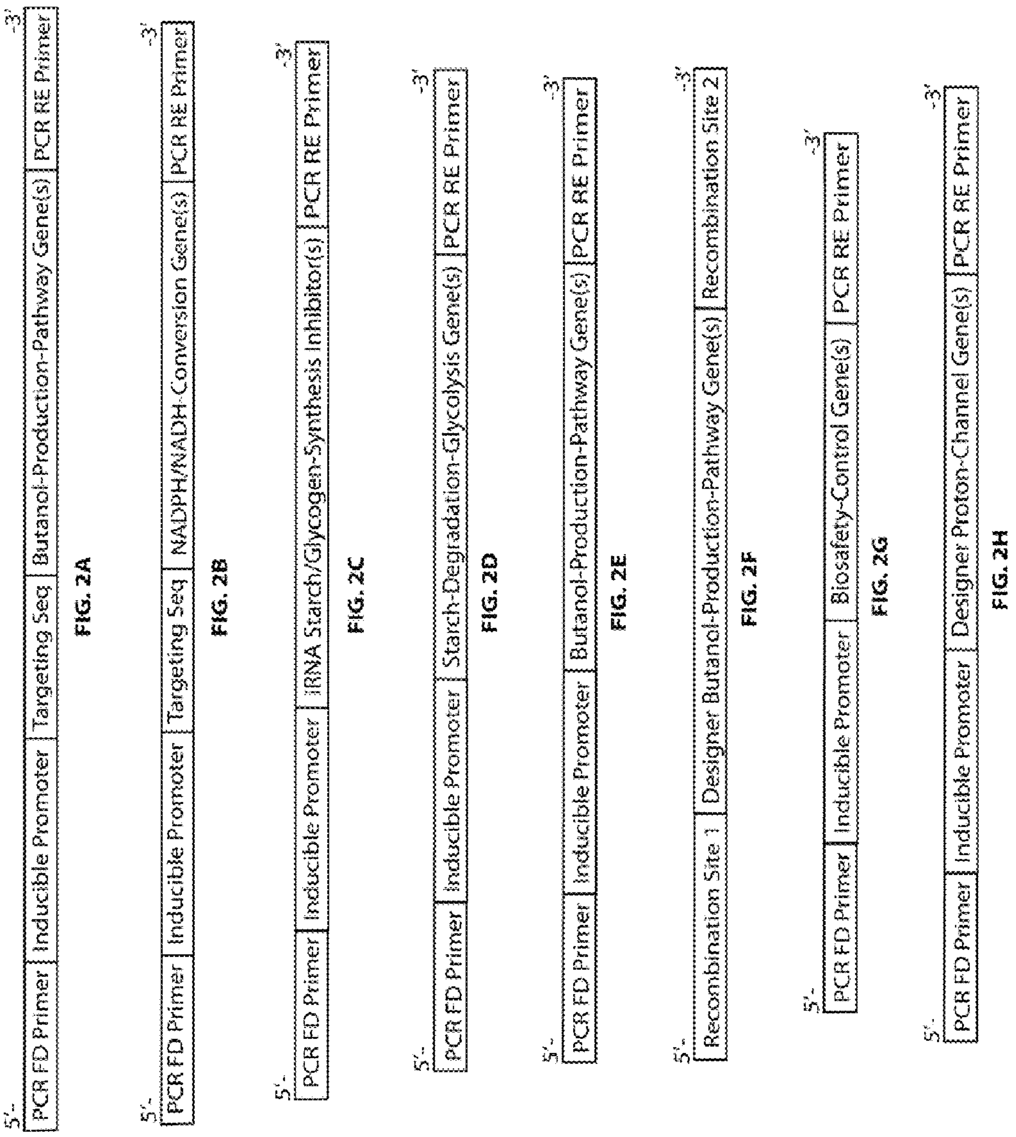
FIG. 2A presents a DNA construct for designer butanol-production-pathway gene(s).
FIG. 2B presents a DNA construct for NADPH/NADH-conversion designer gene for NADPH/NADH inter-conversion.
FIG. 2C presents a DNA construct for a designer iRNA starch/glycogen-synthesis inhibitor(s) gene.
FIG. 2D presents a DNA construct for a designer starch-degradation-glycolysis gene(s).
FIG. 2E presents a DNA construct of a designer butanol-production-pathway gene(s) for cytosolic expression.
FIG. 2F presents a DNA construct of a designer butanol-production-pathway gene(s) with two recombination sites for integrative genetic transformation in oxyphotobacteria.
FIG. 2G presents a DNA construct of a designer biosafety-control gene(s).
FIG. 2H presents a DNA construct of a designer proton-channel gene(s).

As shown in Table 1, many genes of the enzymes identified above have been cloned and/or sequenced from various organisms. Both genomic DNA and/or mRNA sequence data can be used in designing and synthesizing the designer DNA constructs for transformation of a host alga, oxyphotobacterium, plant, plant tissue or cells to create a designer organism for photobiological butanol production (FIG. 1). However, because of possible variations often associated with various source organisms and cellular compartments with respect to a specific host organism and its chloroplast/thylakoid environment where the butanol-production pathway(s) is designed to work with the Calvin cycle, certain molecular engineering art work in DNA construct design including codon-usage optimization and sequence modification is often necessary for a designer DNA construct (FIG. 2) to work well. For example, in creating a butanol-producing designer eukaryotic alga, if the source sequences are from cytosolic enzymes (sequences), a functional chloroplast-targeting sequence may be added to provide the capability for a designer unclear gene-encoded enzyme to insert into a host chloroplast to confer its function for a designer butanol-production pathway. Furthermore, to provide the switchability for a designer butanol-production pathway, it is also important to include a functional inducible promoter sequence such as the promoter of a hydrogenase (Hyd1) or nitrate reductase (Nia1) gene, or nitrite reductase (nirA) gene in certain designer DNA construct(s) as illustrated in FIG. 2A to control the expression of designer gene(s). In addition, as mentioned before, certain functional derivatives or fragments of these enzymes (sequences), chloroplast-targeting transit peptide sequences, and inducible promoter sequences can also be selected for use in full, in part or in combinations thereof, to create the designer organisms according to various embodiments of this invention. The arts in creating and using the designer organisms are further described hereinbelow.

Table 1 lists examples of enzymes for construction of designer butanol-production pathways.

| Enzyme | Source (Organism) | GenBank Accession Number, JGI Protein ID or Citation |
|---|---|---|
| Butanol dehydrogenase | *Clostridium saccharoperbutylacetonicum*; *Propionibacterium freudenreichii*; *Trichomonas vaginalis*; *Aeromonas hydrophila*; *Clostridium beijerinckii*; *Clostridium acetobutylicum* | GenBank: AB257439; AJ508920; AF112135; AF388671; AF157307; M96946, M96945 |
| Butyraldehyde dehydrogenase | *Clostridium saccharoperbutylacetonicum* | GenBank: AY251646 |
| Butyryl-CoA dehydrogenase | *Clostridium beijerinckii*; *Butyrivibrio fibrisolvens*; Butyrate-producing bacterium L2-50; *Thermoanaerobacterium thermosaccharolyticum*; | GenBank: AF494018; AB190764; DQ987697; Z92974 |
| Crotonase | *Clostridium beijerinckii*; *Butyrivibrio fibrisolvens*; Butyrate-producing bacterium L2-50; *Thermoanaerobacterium thermosaccharolyticum*; | GenBank: AF494018; AB190764; DQ987697; Z92974 |
| 3-Hydroxybutyryl-CoA dehydrogenase | *Clostridium beijerinckii*; *Butyrivibrio fibrisolvens; Ajellomyces capsulatus*; *Aspergillus fumigatus*; *Aspergillus clavatus*; *Neosartorya fischeri*; Butyrate-producing bacterium L2-50; *Arabidopsis thaliana*; *Thermoanaerobacterium thermosaccharolyticum*; | GenBank: AF494018; AB190764; XM_001537366; XM_741533; XM_001274776; XM_001262361; DQ987697; BT001208; Z92974 |
| Thiolase | *Butyrivibrio fibrisolvens*; butyrate-producing bacterium L2-50; *Thermoanaerobacterium thermosaccharolyticum*; | GenBank: AB190764; DQ987697; Z92974 |
| Glyceraldehyde-3-phosphate dehydrogenase | *Mesostigma viride* cytosol; *Triticum aestivum* cytosol; *Chlamydomonas reinhardtii* chloroplast; *Botryotinia fuckeliana*; *Saccharomyces cerevisiae*; *Zymomonas mobilis*; *Karenia brevis*; *Ajellomyces capsulatus*; *Pichia stipitis*; *Pichia guilliermondii*; *Kluyveromyces marxianus*, *Triticum aestivum*; *Arabidopsis thaliana*; *Zea mays* cytosolic | GenBank: DQ873404; EF592180; L27668; XM_001549497; J01324; M18802; EU078558; XM_001539393; XM_001386423, XM_001386568; XM_001485596; DQ681075; EF592180; NM_101214; U45857, ZMU45856, U45855 |
| Phosphoglycerate kinase | *Chlamydomonas reinhardtii* chloroplast; *Plasmodium vivax*; *Babesia bovis*; *Botryotinia fuckeliana*; *Monocercomonoides* sp.; *Lodderomyces elongisporus*; *Pichia guilliermondii*; *Arabidopsis thaliana*; *Helianthus annuus*; *Oryza sativa*; *Dictyostelium discoideum*; *Euglena gracilis*; *Chondrus crispus*; *Phaeodactylum tricornutum*; *Solanum tuberosum* | GenBank: U14912, AF244144; XM_001614707; XM_001610679; XM_001548271; DQ665858; XM_001523843; XM_001484377; NM_179576; DQ835564; EF122488; AF316577; AY647236; AY029776; AF108452; AF073473 |
| Phosphoglycerate mutase (phosphoglyceromutase) | *Chlamydomonas reinhardtii* cytoplasm; *Aspergillus fumigatus*; *Coccidioides immitis*; *Leishmania braziliensis*; *Ajellomyces capsulatus*; *Monocercomonoides* sp.; *Aspergillus clavatus*; *Arabidopsis thaliana*; *Zea mays* | JGI Chlre2 protein ID 161689, GenBank: AF268078; XM_747847; XM_749597; XM_001248115; XM_001569263; XM_001539892; DQ665859; XM_001270940; NM_117020; M80912 |
| Enolase | *Chlamydomonas reinhardtii* cytoplasm; *Arabidopsis thaliana*; *Leishmania Mexicana*; *Lodderomyces elongisporus*; *Babesia bovis*; *Sclerotinia sclerotiorum*; *Pichia guilliermondii*; *Spirotrichonympha leidyi*; *Oryza sativa*; *Trimastix pyriformis*; *Leuconostoc mesenteroides*; *Davidiella tassiana*; *Aspergillus oryzae*; *Schizosaccharomyces pombe*; *Brassica napus*; *Zea mays* | GenBank: X66412, P31683; AK222035; DQ221745; XM_001528071; XM_001611873; XM_001594215; XM_001483612; AB221057; EF122486, U09450; DQ845796; AB088633; U82438; D64113; U13799; AY307449; U17973 |

-continued

| Enzyme | Source (Organism) | GenBank Accession Number, JGI Protein ID or Citation |
|---|---|---|
| Pyruvate kinase | *Chlamydomonas reinhardtii* cytoplasm; *Arabidopsis thaliana*; *Saccharomyces cerevisiae*; *Babesia bovis*; *Sclerotinia sclerotiorum*; *Trichomonas vaginalis*; *Pichia guilliermondii*; *Pichia stipitis*; *Lodderomyces elongisporus*; *Coccidioides immitis*; *Trimastix pyriformis*; *Glycine max* (soybean) | JGI Chlre3 protein ID 138105; GenBank: AK229638; AY949876, AY949890, AY949888; XM_001612087; XM_001594710; XM_001329865; XM_001487289; XM_001384591; XM_001528210; XM_001240868; DQ845797; L08632 |
| Phosphofructose kinase | *Chlamydomonas reinhardtii*; *Arabidopsis thaliana*; *Ajellomyces capsulatus*; *Yarrowia lipolytica*; *Pichia stipitis*; *Dictyostelium discoideum*; *Tetrahymena thermophila*; *Trypanosoma brucei*; *Plasmodium falciparum*; *Spinacia oleracea*; | JGI Chlre2 protein ID 159495; GenBank: NM_001037043, NM_179694, NM_119066, NM_125551; XM_001537193; AY142710; XM_001382359, XM_001383014; XM_639070; XM_001017610; XM_838827; XM_001347929; DQ437575; |
| Fructose-diphosphate aldolase | *Chlamydomonas reinhardtii* chloroplast; *Fragaria* x *ananassa* cytoplasm; *Homo sapiens*; *Babesia bovis*; *Trichomonas vaginalis*; *Pichia stipitis*; *Arabidopsis thaliana* | GenBank: X69969; AF308587; NM_005165; XM_001609195; XM_001312327, XM_001312338; XM_001387466; NM_120057, NM_001036644 |
| Triose phosphate isomerase | *Arabidopsis thaliana*; *Chlamydomonas reinhardtii*; *Sclerotinia sclerotiorum*; *Chlorella pyrenoidosa*; *Pichia guilliermondii*; *Euglena intermedia*; *Euglena longa*; *Spinacia oleracea*; *Solanum chacoense*; *Hordeum vulgare*; *Oryza sativa* | GenBank: NM_127687, AF247559; AY742323; XM_001587391; AB240149; XM_001485684; DQ459379; AY742325; L36387; AY438596; U83414; EF575877; |
| Glucose-1-phosphate adenylyltransferase | *Arabidopsis thaliana*; *Zea mays*; *Chlamydia trachomatis*; *Solanum tuberosum* (potato); *Shigella flexneri*; *Lycopersicon esculentum* | GenBank: NM_127730, NM_124205, NM_121927, AY059862; EF694839, EF694838; AF087165; P55242; NP_709206; T07674 |
| Starch synthase | *Chlamydomonas reinhardtii*; *Phaseolus vulgaris*; *Oryza sativa*; *Arabidopsis thaliana*; *Colocasia esculenta*; *Amaranthus cruentus*; *Parachlorella kessleri*; *Triticum aestivum*; *Sorghum bicolor*; *Astragalus membranaceus*; *Perilla frutescens*; *Zea mays*; *Ipomoea batatas* | GenBank: AF026422, AF026421, DQ019314, AF433156; AB293998; D16202, AB115917, AY299404; AF121673, AK226881; NM_101044; AY225862, AY142712; DQ178026; AB232549; Y16340; AF168786; AF097922; AF210699; AF019297; AF068834 |
| Alpha-amylase | *Hordeum vulgare* aleurone cells; *Trichomonas vaginalis*; *Phanerochaete chrysosporium*; *Chlamydomonas reinhardtii*; *Arabidopsis thaliana*; *Dictyoglomus thermophilum* heat-stable amylase gene; | GenBank: J04202; XM_001319100; EF143986; AY324649; NM_129551; X07896 |
| Beta-amylase | *Arabidopsis thaliana*; *Hordeum vulgare*; *Musa acuminata* | GenBank: NM_113297; D21349; DQ166026 |
| Starch phosphorylase | Citrus hybrid cultivar root; *Solanum tuberosum* chloroplast; *Arabidopsis thaliana*; *Triticum aestivum*; *Ipomoea batatas* | Genbank: AY098895; P53535; NM_113857, NM_114564; AF275551; M64362 |
| Phosphoglucomutase | *Oryza sativa* plastid; *Ajellomyces capsulatus*; *Pichia stipitis*; *Lodderomyces elongisporus*; *Aspergillus fumigatus*; *Arabidopsis thaliana*; *Populus tomentosa*; *Oryza sativa*; *Zea mays* | GenBank: AC105932, AF455812; XM_001536436; XM_001383281; XM_001527445; XM_749345; NM_124561, NM_180508, AY128901; AY479974; AF455812; U89342, U89341 |
| Glucosephosphate (glucose-6-phosphate) isomerase | *Chlamydomonas reinhardtii*; *Saccharomyces cerevisiae*; *Pichia stipitis*; *Ajellomyces capsulatus*; *Spinacia oleracea* cytosol; *Oryza sativa* cytoplasm; *Arabidopsis thaliana*; *Zea mays* | JGI Chlre3 protein ID 135202; GenBank: M21696; XM_001385873; XM_001537043; T09154; P42862; NM_123638, NM_118595; U17225 |

-continued

| Enzyme | Source (Organism) | GenBank Accession Number, JGI Protein ID or Citation |
|---|---|---|
| Hexokinase (glucokinase) | *Ajellomyces capsulatus*; *Pichia stipitis*; *Pichia angusta*; *Thermosynechococcus elongates*; *Babesia bovis*; *Solanum chacoense*; *Oryza sativa*; *Arabidopsis thaliana* | GenBank: XM_001541513; XM_001386652, AY278027; XM_001386035; NC_004113; XM_001608698; DQ177440; DQ116383; NM_112895 |
| NADP(H) phosphatase | *Methanococcus jannaschii* | The Journal Of Biological Chemistry 280 (47): 39200-39207 (2005) |
| NAD kinase | *Babesia bovis*; *Trichomonas vaginalis* | GenBank: XM_001609395; XM_001324239 |
| Pyruvate-NADP$^+$ oxidoreductase | *Peranema trichophorum*; *Euglena gracilis* | GenBank: EF114757; AB021127, AJ278425 |
| Pyruvate-ferredoxin oxidoreductase | *Mastigamoeba balamuthi*; *Desulfovibrio africanus*; *Entamoeba histolytica*; *Trichomonas vaginalis*; *Cryptosporidium parvum*; *Cryptosporidium baileyi*; *Giardia lamblia*; *Entamoeba histolytica*; *Hydrogenobacter thermophilus*; *Clostridium pasteurianum*; | GenBank: AY101767; Y09702; U30149; XM_001582310, XM_001313670, XM_001321286, XM_001307087, XM_001311860, XM_001314776, XM_001307250; EF030517; EF030516; XM_764947; XM_651927; AB042412; Y17727 |

Targeting the Designer Enzymes to the Stroma Region of Chloroplasts

Some of the designer enzymes discussed above, such as, pyruvate-ferredoxin oxidoreductase, thiolase, 3-hydroxybutyryl-CoA dehydrogenase, crotonase, butyryl-CoA dehydrogenase, butyraldehyde dehydrogenase, and butanol dehydrogenase are known to function in certain special bacteria such as *Clostridium*; but wild-type plant chloroplasts generally do not possess these enzymes to function with the Calvin cycle. Therefore, in one of the various embodiments in creating a butanol-producing eukaryotic designer organism, designer nucleic acids encoding for these enzymes are expressed in the chloroplast(s) of a host cell. This can be accomplished by delivery of designer butanol-production-pathway gene(s) into the chloroplast genome of the eukaryotic host cell typically using a genegun. In certain extent, the molecular genetics of chloroplasts are similar to that of cyanobacteria. After being delivered into the chloroplast, a designer DNA construct that contains a pair of proper recombination sites as illustrated in FIG. 2F can be incorporated into the chloroplast genome through a natural process of homologous DNA double recombination.

In another embodiment, nucleic acids encoding for these enzymes are genetically engineered such that the enzymes expressed are inserted into the chloroplasts to operate with the Calvin cycle there. Depending on the genetic background of a particular host organism, some of the designer enzymes discussed above such as phosphoglycerate mutase and enolase may exist at some background levels in its native form in a wild-type chloroplast. For various reasons including often the lack of their controllability, however, some of the chloroplast background enzymes may or may not be sufficient to serve as a significant part of the designer butanol-production pathway(s). Furthermore, a number of useful inducible promoters happen to function in the nuclear genome. For example, both the hydrogenase (Hyd1) promoter and the nitrate reductase (Nia1) promoter that can be used to control the expression of the designer butanol-production pathways are located in the nuclear genome of *Chlamydomonas reinhardtii*, of which the genome has recently been sequenced. Therefore, in one of the various embodiments, it is preferred to use nuclear-genome-encodable designer genes to confer a switchable butanol-production pathway. Consequently, nucleic acids encoding for these enzymes also need to be genetically engineered with proper sequence modification such that the enzymes are controllably expressed and are inserted into the chloroplasts to create a designer butanol-production pathway.

According to one of the various embodiments, it is best to express the designer butanol-producing-pathway enzymes only into chloroplasts (at the stroma region), exactly where the action of the enzymes is needed to enable photosynthetic production of butanol. If expressed without a chloroplast-targeted insertion mechanism, the enzymes would just stay in the cytosol and not be able to directly interact with the Calvin cycle for butanol production. Therefore, in addition to the obvious distinctive features in pathway designs and associated approaches, another significant distinction is that one of the various embodiments innovatively employs a chloroplast-targeted mechanism for genetic insertion of many designer butanol-production-pathway enzymes into chloroplast to directly interact with the Calvin cycle for photobiological butanol production.

With a chloroplast stroma-targeted mechanism, the cells will not only be able to produce butanol but also to grow and regenerate themselves when they are returned to certain conditions under which the designer pathway is turned off, such as under aerobic conditions when designer hydrogenase promoter-controlled butanol-production-pathway genes are used. Designer algae, plants, or plant cells that contain normal mitochondria should be able to use the reducing power (NADH) from organic reserves (and/or some exogenous organic substrate such as acetate or sugar) to power the cells immediately after returning to aerobic conditions. Consequently, when the designer algae, plants, or plant cells are returned to aerobic conditions after use under anaerobic conditions for photosynthetic butanol production, the cells will stop making the butanol-producing-pathway enzymes and start to restore the normal photoautotrophic capability by synthesizing new and functional chloroplasts. Therefore, it is possible to use such genetically engineered designer alga/plant organisms for repeated cycles of photoautotrophic growth under normal aerobic conditions and efficient production of butanol directly from $CO_2$ and $H_2O$ under certain specific designer butanol-producing conditions such as under anaerobic conditions and/or in the presence of nitrate when a Nia1 promoter-controlled butanol-production pathway is used.

The targeted insertion of designer butanol-production-pathway enzymes can be accomplished through use of a DNA sequence that encodes for a stroma "signal" peptide. A stroma-protein signal (transit) peptide directs the transport and insertion of a newly synthesized protein into stroma. In accordance with one of the various embodiments, a specific targeting DNA sequence is preferably placed in between the promoter and a designer butanol-production-pathway enzyme sequence, as shown in a designer DNA construct (FIG. 2A). This targeting sequence encodes for a signal (transit) peptide that is synthesized as part of the apoprotein of an enzyme in the cytosol. The transit peptide guides the insertion of an apoprotein of a designer butanol-production-pathway enzyme from cytosol into the chloroplast. After the apoprotein is inserted into the chloroplast, the transit peptide is cleaved off from the apoprotein, which then becomes an active enzyme.

A number of transit peptide sequences are suitable for use for the targeted insertion of the designer butanol-production-pathway enzymes into chloroplast, including but not limited to the transit peptide sequences of: the hydrogenase apoproteins (such as HydA1 (Hyd1) and HydA2, GenBank accession number AJ308413, AF289201, AY090770), ferredoxin apoprotein (Frx1, accession numbers L10349, P07839), thioredoxin m apoprotein (Trx2, X62335), glutamine synthase apoprotein (Gs2, Q42689), LhcII apoproteins (AB051210, AB051208, AB051205), PSII-T apoprotein (PsbT), PSII-S apoprotein (PsbS), PSII-W apoprotein (PsbW), $CF_0CF_1$ subunit-γ apoprotein (AtpC), $CF_0CF_1$ subunit-δ apoprotein (AtpD, U41442), $CFoCF_1$ subunit-II apoprotein (AtpG), photosystem I (PSI) apoproteins (such as, of genes PsaD, PsaE, PsaF, PsaG, PsaH, and PsaK), Rubisco SSU apoproteins (such as RbcS2, X04472). Throughout this specification, when reference is made to a transit peptide sequence, such as, for example, any of the transit peptide sequence described above, it includes their functional analogs, modified designer sequences, and combinations thereof. A "functional analog" or "modified designer sequence" in this context refers to a peptide sequence derived or modified (by, e.g., conservative substitution, moderate deletion or addition of amino acids, or modification of side chains of amino acids) based on a native transit peptide sequence, such as those identified above, that has the same function as the native transit peptide sequence, i.e., effecting targeted insertion of a desired enzyme.

In certain specific embodiments, the following transit peptide sequences are used to guide the insertion of the designer butanol-production-pathway enzymes into the stroma region of the chloroplast: the Hyd1 transit peptide (having the amino acid sequence: msalylkpca aysirgsscr arqvaprapl aastvrvala tleaparrlg nvacaa (SEQ ID NO: 54)), the RbcS2 transit peptides (having the amino acid sequence: maaviakssv saavarpars svrpmaalkp avkaapvaap aqanq (SEQ ID NO: 55)), ferredoxin transit peptide (having the amino acid sequence: mamamrs (SEQ ID NO: 56)), the $CF_0CF_1$ subunit-δ transit peptide (having the amino acid sequence: mlaaksiagp rafkasavra apkagrrtvv vma (SEQ ID NO: 57)), their analogs, functional derivatives, designer sequences, and combinations thereof.

Use of a Genetic Switch to Control the Expression of a Designer Butanol-Producing Pathway.

Another key feature of the invention is the application of a genetic switch to control the expression of the designer butanol-producing pathway(s), as illustrated in FIG. 1. This switchability is accomplished through the use of an externally inducible promoter so that the designer transgenes are inducibly expressed under certain specific inducing conditions. Preferably, the promoter employed to control the expression of designer genes in a host is originated from the host itself or a closely related organism. The activities and inducibility of a promoter in a host cell can be tested by placing the promoter in front of a reporting gene, introducing this reporter construct into the host tissue or cells by any of the known DNA delivery techniques, and assessing the expression of the reporter gene.

In a preferred embodiment, the inducible promoter used to control the expression of designer genes is a promoter that is inducible by anaerobiosis, i.e., active under anaerobic conditions but inactive under aerobic conditions. A designer alga/plant organism can perform autotrophic photosynthesis using $CO_2$ as the carbon source under aerobic conditions, and when the designer organism culture is grown and ready for photosynthetic butanol production, anaerobic conditions will be applied to turn on the promoter and the designer genes that encode a designer butanol-production pathway(s).

A number of promoters that become active under anaerobic conditions are suitable for use in the present invention. For example, the promoters of the hydrogenase genes (HydA1 (Hyd1) and HydA2, GenBank accession number: AJ308413, AF289201, AY090770) of *Chlamydomonas reinhardtii*, which is active under anaerobic conditions but inactive under aerobic conditions, can be used as an effective genetic switch to control the expression of the designer genes in a host alga, such as *Chlamydomonas reinhardtii*. In fact, *Chlamydomonas* cells contain several nuclear genes that are coordinately induced under anaerobic conditions. These include the hydrogenase structural gene itself (Hyd1), the Cyc6 gene encoding the apoprotein of Cytochrome $C_6$, and the Cpxl gene encoding coprogen oxidase. The regulatory regions for the latter two have been well characterized, and a region of about 100 by proves sufficient to confer regulation by anaerobiosis in synthetic gene constructs (Quinn, Barraco, Ericksson and Merchant (2000). "Coordinate copper- and oxygen-responsive Cyc6 and Cpxl expression in *Chlamydomonas* is mediated by the same element." *J Biol Chem* 275: 6080-6089). Although the above inducible algal promoters may be suitable for use in other plant hosts, especially in plants closely related to algae, the promoters of the homologous genes from these other plants, including higher plants, can be obtained and employed to control the expression of designer genes in those plants.

In another embodiment, the inducible promoter used in the present invention is an algal nitrate reductase (Nia1) promoter, which is inducible by growth in a medium containing nitrate and repressed in a nitrate-deficient but ammonium-containing medium (Loppes and Radoux (2002) "Two short regions of the promoter are essential for activation and repression of the nitrate reductase gene in *Chlamydomonas reinhardtii," Mol Genet Genomics* 268: 42-48). Therefore, the Nia1 (gene accession number AF203033) promoter can be selected for use to control the expression of the designer genes in an alga according to the concentration levels of nitrate and ammonium in a culture medium. Additional inducible promoters that can also be selected for use in the present invention include, for example, the heat-shock protein promoter HSP70A (accession number: DQ059999, AY456093, M98823; Schroda, Blocker, Beek (2000) The HSP70A promoter as a tool for the improved expression of transgenes in *Chlamydomonas. Plant Journal* 21:121-131), the promoter of CabII-1 gene (accession number M24072), the promoter of Ca1 gene (accession number P20507), and the promoter of Ca2 gene (accession number P24258).

In the case of blue-green algae (oxyphotobacteria including cyanobacteria and oxychlorobacteria), there are also a number of inducible promoters that can be selected for use in the present invention. For example, the promoters of the anaerobic-responsive bidirectional hydrogenase hox genes of *Nostoc* sp. PCC 7120 (GenBank: BA000019), *Prochlorothrix hollandica* (GenBank: U88400; hoxUYH operon promoter), *Synechocystis* sp. strain PCC 6803 (CyanoBase: s111220 and s111223), *Synechococcus elongatus* PCC 6301 (CyanoBase: syc 1235c), *Arthrospira platensis* (GenBank: ABC26906), *Cyanothece* sp. CCY0110 (GenBank: ZP_01727419) and *Synechococcus* sp. PCC 7002 (GenBank: AAN03566), which are active under anaerobic conditions but inactive under aerobic conditions (Sjoholm, Oliveira, and Lindblad (2007) "Transcription and regulation of the bidirectional hydrogenase in the Cyanobacterium *Nostoc* sp. strain PCC 7120," *Applied and Environmental Microbiology,* 73(17): 5435-5446), can be used as an effective genetic switch to control the expression of the designer genes in a host oxyphotobacterium, such as *Nostoc* sp. PCC 7120, *Synechocystis* sp. strain PCC 6803, *Synechococcus elongatus* PCC 6301, *Cyanothece* sp. CCY0110, *Arthrospira platensis*, or *Synechococcus* sp. PCC 7002.

In another embodiment in creating switchable butanol-production designer organisms such as switchable designer oxyphotobacteria, the inducible promoter selected for use is a nitrite reductase (nirA) promoter, which is inducible by growth in a medium containing nitrate and repressed in a nitrate-deficient but ammonium-containing medium (Qi, Hao, Ng, Slater, Baszis, Weiss, and Valentin (2005) "Application of the Synechococcus nirA promoter to establish an inducible expression system for engineering the *Synechocystis* tocopherol pathway," *Applied and Environmental Microbiology,* 71(10): 5678-5684; Maeda, Kawaguchi, Ohe, and Omata (1998) "cis-Acting sequences required for NtcB-dependent, nitrite-responsive positive regulation of the nitrate assimilation operon in the Cyanobacterium *Synechococcus* sp. strain PCC 7942," *Journal of Bacteriology,* 180(16):4080-4088). Therefore, the nirA promoter sequences can be selected for use to control the expression of the designer genes in a number of oxyphotobacteria according to the concentration levels of nitrate and ammonium in a culture medium. The nirA promoter sequences that can be selected and modified for use include (but not limited to) the nirA promoters of the following oxyphotobacteria: *Synechococcus elongatus* PCC 6301 (GenBank: AP008231, region 355890-255950), *Synechococcus* sp. (GenBank: X67680.1, D16303.1, D12723.1, and D00677), *Synechocystis* sp. PCC 6803 (GenBank: NP 442378, BA000022, AB001339, D63999-D64006, D90899-D90917), *Anabaena* sp. (GenBank: X99708.1), *Nostoc* sp. PCC 7120 (GenBank: BA000019.2 and AJ319648), *Plectonema boryanum* (GenBank: D31732.1), *Synechococcus elongatus* PCC 7942 (GenBank: P39661, CP000100.1), *Thermosynechococcus elongatus* BP-1 (GenBank: BAC08901, NP_682139), *Phormidium laminosum* (GenBank: CAA79655, Q51879), *Mastigocladus laminosus* (GenBank: ABD49353, ABD49351, ABD49349, ABD49347), *Anabaena variabilis* ATCC 29413 (GenBank: YP_325032), *Prochlorococcus marinus* str. MIT 9303 (GenBank: YP_001018981), *Synechococcus* sp. WH 8103 (GenBank: AAC17122), *Synechococcus* sp. WH 7805 (GenBank: ZP_01124915), and *Cyanothece* sp. CCY0110 (GenBank: ZP_01727861).

In yet another embodiment, an inducible promoter selected for use is the light- and heat-responsive chaperone gene groE promoter, which can be induced by heat and/or light [Kojima and Nakamoto (2007) "A novel light- and heat-responsive regulation of the groE transcription in the absence of HrcA or CIRCE in cyanobacteria," FEBS Letters 581:1871-1880). A number of groE promoters such as the groES and groEL (chaperones) promoters are available for use as an inducible promoter in controlling the expression of the designer butanol-production-pathway enzymes. The groE promoter sequences that can be selected and modified for use in one of the various embodiments include (but not limited to) the groES and/or groEL promoters of the following oxyphotobacteria: *Synechocystis* sp. (GenBank: D12677.1), *Synechocystis* sp. PCC 6803 (GenBank: BA000022.2), *Synechococcus elongatus* PCC 6301 (GenBank: AP008231.1), *Synechococcus* sp (GenBank: M58751.1), *Synechococcus elongatus* PCC 7942 (GenBank: CP000100.1), *Nostoc* sp. PCC 7120 (GenBank: BA000019.2), *Anabaena variabilis* ATCC 29413 (GenBank: CP000117.1), *Anabaena* sp. L-31 (GenBank: AF324500); *Thermosynechococcus elongatus* BP-1 (CyanoBase: tll0185, tll0186), *Synechococcus vulcanus* (GenBank: D78139), *Oscillatoria* sp. NKBG091600 (GenBank: AF054630), *Prochlorococcus marinus* MIT9313 (GenBank: BX572099), *Prochlorococcus marinus* str. MIT 9303 (GenBank: CP000554), *Prochlorococcus marinus* str. MIT 9211 (GenBank: ZP_01006613), *Synechococcus* sp. WH8102 (GenBank: BX569690), *Synechococcus* sp. CC9605 (GenBank: CP000110), *Prochlorococcus marinus* subsp. *marinus* str. CCMP1375 (GenBank: AE017126), and *Prochlorococcus marinus* MED4 (GenBank: BX548174).

Additional inducible promoters that can also be selected for use in the present invention include: for example, the metal (zinc)-inducible smt promoter of *Synechococcus* PCC 7942 (Erbe, Adams, Taylor and Hall (1996) "Cyanobacteria carrying an smt-lux transcriptional fusion as biosensors for the detection of heavy metal cations," *Journal of Industrial Microbiology,* 17:80-83); the iron-responsive idiA promoter of *Synechococcus elongatus* PCC 7942 (Michel, Pistorius, and Golden (2001) "Unusual regulatory elements for iron deficiency induction of the idiA gene of *Synechococcus elongatus* PCC 7942" *Journal of Bacteriology,* 183(17):5015-5024); the redox-responsive cyanobacterial crhR promoter (Patterson-Fortin, Colvin and Owttrim (2006) "A LexA-related protein regulates redox-sensitive expression of the cyanobacterial RNA helicase, crhR", *Nucleic Acids Research,* 34(12):3446-3454); the heat-shock gene hsp16.6 promoter of *Synechocystis* sp. PCC 6803 (Fang and Barnum (2004) "Expression of the heat shock gene hsp16.6 and promoter analysis in the Cyanobacterium, *Synechocystis* sp. PCC 6803," *Current Microbiology* 49:192-198); the small heat-shock protein (Hsp) promoter such as *Synechococcus vulcanus* gene hspA promoter (Nakamoto, Suzuki, and Roy (2000) "Constitutive expression of a small heat-shock protein confers cellular thermotolerance and thermal protection to the photosynthetic apparatus in cyanobacteria," FEBS Letters 483:169-174); the $CO_2$-responsive promoters of oxyphotobacterial carbonic-anhydrase genes (GenBank: EAZ90903, EAZ90685, ZP_01624337, EAW33650, ABB17341, AAT41924, CA089711, ZP_00111671, YP_400464, AAC44830; and CyanoBase: all2929, PMT1568 slr0051, slr1347, and syc0167c); the nitrate-reductase-gene (narB) promoters (such as GenBank accession numbers: BAC08907, NP_682145, AA025121; ABI46326, YP_732075, BAB72570, NP_484656); the green/red light-responsive promoters such as the light-regulated cpcB2A2 promoter of *Fremyella diplosiphon* (Casey and Grossman (1994) "In vivo and in vitro characterization of the light-regulated cpcB2A2 promoter of *Fremyella diplosiphont*" *Journal of Bacteriology,* 176(20):6362-6374); and the UV-light responsive promoters of cyanobacterial genes lexA, recA and ruvB (Domain, Houot, Chauvat, and Cassier-Chauvat (2004) "Function and regulation of the cyanobacterial genes lexA, recA and ruvB: LexA is critical to the survival of cells facing inorganic carbon starvation," *Molecular Microbiology,* 53(1):65-80).

Furthermore, in one of the various embodiments, certain "semi-inducible" or constitutive promoters can also be selected for use in combination of an inducible promoter(s) for construction of a designer butanol-production pathway(s) as well. For example, the promoters of oxyphotobacterial Rubisco operon such as the rbcL genes (GenBank: X65960, ZP_01728542, Q3M674, BAF48766, NP_895035, 0907262A; CyanoBase: PMT1205, PMM0550, Pro0551, tll1506, SYNW1718, glr2156, alr1524, slr0009), which have certain light-dependence but could be regarded almost as constitutive promoters, can also be selected for use in combination of an inducible promoter(s) such as the nirA, hox, and/or groE promoters for construction of the designer butanol-production pathway(s) as well.

Throughout this specification, when reference is made to inducible promoter, such as, for example, any of the inducible promoters described above, it includes their analogs, functional derivatives, designer sequences, and combinations thereof. A "functional analog" or "modified designer sequence" in this context refers to a promoter sequence derived or modified (by, e.g., substitution, moderate deletion or addition or modification of nucleotides) based on a native promoter sequence, such as those identified hereinabove, that retains the function of the native promoter sequence.

DNA Constructs and Transformation into Host Organisms

DNA constructs are generated in order to introduce designer butanol-production-pathway genes to a host alga, plant, plant tissue or plant cells. That is, a nucleotide sequence encoding a designer butanol-production-pathway enzyme is placed in a vector, in an operable linkage to a promoter, preferably an inducible promoter, and in an operable linkage to a nucleotide sequence coding for an appropriate chloroplast-targeting transit-peptide sequence. In a preferred embodiment, nucleic acid constructs are made to have the elements placed in the following 5' (upstream) to 3' (downstream) orientation: an externally inducible promoter, a transit targeting sequence, and a nucleic acid encoding a designer butanol-production-pathway enzyme, and preferably an appropriate transcription termination sequence. One or more designer genes (DNA constructs) can be placed into one genetic vector. An example of such a construct is depicted in FIG. 2A. As shown in the embodiment illustrated in FIG. 2A, a designer butanol-production-pathway transgene is a nucleic acid construct comprising: a) a PCR forward primer; b) an externally inducible promoter; c) a transit targeting sequence; d) a designer butanol-production-pathway-enzyme-encoding sequence with an appropriate transcription termination sequence; and e) a PCR reverse primer.

In accordance with various embodiments, any of the components a) through e) of this DNA construct are adjusted to suit for certain specific conditions. In practice, any of the components a) through e) of this DNA construct are applied in full or in part, and/or in any adjusted combination to achieve more desirable results. For example, when an algal hydrogenase promoter is used as an inducible promoter in the designer butanol-production-pathway DNA construct, a transgenic designer alga that contains this DNA construct will be able to perform autotrophic photosynthesis using ambient-air $CO_2$ as the carbon source and grows normally under aerobic conditions, such as in an open pond. When the algal culture is grown and ready for butanol production, the designer transgene(s) can then be expressed by induction under anaerobic conditions because of the use of the hydrogenase promoter. The expression of designer gene(s) produces a set of designer butanol-production-pathway enzymes to work with the Calvin cycle for photobiological butanol production (FIG. 1).

The two PCR primers are a PCR forward primer (PCR FD primer) located at the beginning (the 5' end) of the DNA construct and a PCR reverse primer (PCR RE primer) located at the other end (the 3' end) as shown in FIG. 2A. This pair of PCR primers is designed to provide certain convenience when needed for relatively easy PCR amplification of the designer DNA construct, which is helpful not only during and after the designer DNA construct is synthesized in preparation for gene transformation, but also after the designer DNA construct is delivered into the genome of a host alga for verification of the designer gene in the transformants. For example, after the transformation of the designer gene is accomplished in a *Chlamydomonas reinhardtii*-arg7 host cell using the techniques of electroporation and argininosuccinate lyase (arg7) complementation screening, the resulted transformants can be then analyzed by a PCR DNA assay of their nuclear DNA using this pair of PCR primers to verify whether the entire designer butanol-production-pathway gene (the DNA construct) is successfully incorporated into the genome of a given transformant. When the nuclear DNA PCR assay of a transformant can generate a PCR product that matches with the predicted DNA size and sequence according to the designer DNA construct, the successful incorporation of the designer gene(s) into the genome of the transformant is verified.

Therefore, the various embodiments also teach the associated method to effectively create the designer transgenic algae, plants, or plant cells for photobiological butanol production. This method, in one of embodiments, includes the following steps: a) Selecting an appropriate host alga, plant, plant tissue, or plant cells with respect to their genetic backgrounds and special features in relation to butanol production; b) Introducing the nucleic acid constructs of the designer genes into the genome of said host alga, plant, plant tissue, or plant cells; c) Verifying the incorporation of the designer genes in the transformed alga, plant, plant tissue, or plant cells with DNA PCR assays using the said PCR primers of the designer DNA construct; d) Measuring and verifying the designer organism features such as the inducible expression of the designer butanol-pathway genes for photosynthetic butanol production from carbon dioxide and water by assays of mRNA, protein, and butanol-production characteristics according to the specific designer features of the DNA construct(s) (FIG. 2A).

The above embodiment of the method for creating the designer transgenic organism for photobiological butanol production can also be repeatedly applied for a plurality of operational cycles to achieve more desirable results. In various embodiments, any of the steps a) through d) of this method described above are adjusted to suit for certain specific conditions. In various embodiments, any of the steps a) through d) of the method are applied in full or in part, and/or in any adjusted combination.

Examples of designer butanol-production-pathway genes (DNA constructs) are shown in the sequence listings. SEQ ID NO: 1 presents a detailed DNA construct of a designer Butanol Dehydrogenase gene (1809 bp) that includes a PCR FD primer (sequence 1-20), a 262-bp nitrate reductase Nia1 promoter (21-282), a 135-bp RbcS2 transit peptide (283-417), an enzyme-encoding sequence (418-1566) selected and modified from a *Clostridium saccharoperbutylacetonicum* Butanol Dehydrogenase sequence (AB257439), a 223-bp RbcS2 terminator (1567-1789), and a PCR RE primer (1790-1809). The 262-bp Nia1 promoter (DNA sequence 21-282) is used as an example of an inducible promoter to control the expression of a designer butanol-production-pathway Butanol Dehydrogenase gene (DNA sequence 418-1566). The 135-bp RbcS2 transit peptide (DNA sequence 283-417) is used as an example to guide the insertion of the designer enzyme (DNA sequence 418-1566) into the chloroplast of the host organism. The RbcS2 terminator (DNA sequence 1567-1789) is employed so that the transcription and translation of the designer gene is properly terminated to produce the designer apoprotein (RbcS2 transit peptide-Butanol Dehydrogenase) as desired. Because the Nia1 promoter is a nuclear DNA that can control the expression only for nuclear genes, the synthetic butanol-production-pathway gene in this example is designed according to the codon usage of *Chlamydomonas* nuclear genome. Therefore, in this case, the designer enzyme gene is transcribed in nucleus. Its mRNA is naturally translocated into cytosol, where the mRNA is translated to an apoprotein that consists of the RbcS2 transit peptide (corresponding to DNA sequence 283-417) with its C-terminal end linked together with the N-terminal end of the Butanol Dehydrogenase protein (corresponding to DNA sequence 418-1566). The transit peptide of the apoprotein guides its transportation across the chloroplast membranes and into the stroma area, where the transit peptide is cut off from the apoprotein. The resulting Butanol Dehydrogenase then resumes its function as an enzyme for the designer butanol-production pathway in chloroplast. The two PCR primers (sequences 1-20 and 1790-1809) are selected and modified from the sequence of a Human actin gene and can be paired with each other. Blasting the sequences against *Chlamydomonas* GenBank found no homologous sequences of them. Therefore, they can be used as appropriate PCR primers in DNA PCR assays for verification of the designer gene in the transformed alga.

SEQ ID NO: 2 presents example 2 for a designer Butyraldehyde Dehydrogenase DNA construct (2067 bp) that includes a PCR FD primer (sequence 1-20), a 262-bp nitrate reductase Nia1 promoter (21-282), a 135-bp RbcS2 transit peptide (283-417), a Butyraldehyde Dehydrogenase-encoding sequence (418-1824) selected and modified from a *Clostridium saccharoperbutylacetonicum* Butyraldehyde Dehydrogenase sequence (AY251646), a 223-bp RbcS2 terminator (1825-2047), and a PCR RE primer (2048-2067). This DNA construct is similar to example 1, SEQ ID NO: 1, except that a Butyraldehyde Dehydrogenase-encoding sequence (418-1824) selected and modified from a *Clostridium saccharoperbutylacetonicum* Butyraldehyde Dehydrogenase sequence (AY251646) is used.

SEQ ID NO: 3 presents example 3 for a designer Butyryl-CoA Dehydrogenase construct (1815 bp) that includes a PCR FD primer (sequence 1-20), a 262-bp nitrate reductase promoter (21-282), a 9-bp Xho I NdeI site (283-291), a 135-bp RbcS2 transit peptide (292-426), a Butyryl-CoA Dehydrogenase encoding sequence (427-1563) selected/modified from the sequences of a *Clostridium beijerinckii* Butyryl-CoA Dehydrogenase (AF494018), a 9-bp XbaI site (1564-1572), a 223-bp RbcS2 terminator (1573-1795), and a PCR RE primer (1796-1815) at the 3' end. This DNA construct is similar to example 1, SEQ ID NO: 1, except that a Butyryl-CoA Dehydrogenase encoding sequence (427-1563) selected/modified from the sequences of a *Clostridium beijerinckii* Butyryl-CoA Dehydrogenase (AF494018) is used and restriction sites of Xho I NdeI and XbaI are added to make the key components such as the targeting sequence (292-426) and the designer enzyme sequence (427-1563) as a modular unit that can be flexible replaced when necessary to save cost of gene synthesis and enhance work productivity. Please note, the enzyme does not have to be *Clostridium beijerinckii* Butyryl-CoA Dehydrogenase; a number of butyryl-CoA dehydrogenase enzymes (such as those listed in Table 1) including their isozymes, designer modified enzymes, and functional analogs from other sources such as *Butyrivibrio fibrisolvens*, Butyrate producing bacterium L2-50*, Thermoanaerobacterium thermosaccharolyticum*, can also be selected for use.

SEQ ID NO: 4 presents example 4 for a designer Crotonase DNA construct (1482 bp) that includes a PCR FD primer (sequence 1-20), a 262-bp nitrate reductase promoter (21-282), a 9-bp Xho I NdeI site (283-291) a 135-bp RbcS2 transit peptide (292-426), a Crotonase-encoding sequence (427-1209) selected/modified from the sequences of a *Clostridium beijerinckii* Crotonase (Genbank: AF494018), a 21-bp Lumio-tag-encoding sequence (1210-1230), a 9-bp XbaI site (1231-1239) containing a stop codon, a 223-bp RbcS2 terminator (1240-1462), and a PCR RE primer (1463-1482) at the 3' end. This DNA construct is similar to example 3, SEQ ID NO: 3, except that a Crotonase-encoding sequence (427-1209) selected/modified from the sequences of a *Clostridium beijerinckii* Crotonase (Genbank: AF494018) is used and a 21-bp Lumio-tag-encoding sequence (1210-1230) is added at the C -terminal end of the enolase sequence. The 21-bp Lumio-tag sequence (1210-1230) is employed here to encode a Lumio peptide sequence Gly-Cys-Cys-Pro-Gly-Cys-Cys, which can become fluorescent when treated with a Lumio reagent that is now commercially available from Invitrogen. Lumio molecular tagging technology is based on an EDT (1,2-ethanedithiol) coupled biarsenical derivative (the Lumio reagent) of fluorescein that binds to an engineered tetracysteine sequence (Keppetipola, Coffman, and et al (2003). Rapid detection of in vitro expressed proteins using LumioTM technology, Gene Expression, 25.3: 7-11). The tetracysteine sequence consists of Cys-Cys-Xaa-Xaa-Cys-Cys, where Xaa is any non-cysteine amino acid such as Pro or Gly in this example. The EDT-linked Lumio reagent allows free rotation of the arsenic atoms that quenches the fluorescence of fluorescein. Covalent bond formation between the thiols of the Lumio's arsenic groups and the tetracysteines prevents free rotation of arsenic atoms that releases the fluorescence of fluorescein (Griffin, Adams, and Tsien (1998), "Specific covalent labeling of recombinant protein molecules inside live cells", *Science,* 281:269-272). This also permits the visualization of the tetracysteine-tagged proteins by fluorescent molecular imaging. Therefore, use of the Lumio tag in this manner enables monitoring and/or tracking of the designer Crotonase when expressed to verify whether the designer butanol-production pathway enzyme is indeed delivered into the chloroplast of a host organism as designed. The Lumio tag (a short 7 amino acid peptide) that is linked to the C-terminal end of the Crotonase protein in this example should have minimal effect on the function of the designer enzyme, but enable the designer enzyme molecule to be visualized when treated with the Lumio reagent. Use of the Lumio tag is entirely optional. If the Lumio tag somehow affects the designer enzyme function, this tag can be deleted in the DNA sequence design.

SEQ ID NO: 5 presents example 5 for a designer 3-Hydroxybutyryl-CoA Dehydrogenase DNA construct (1367 bp) that includes a PCR FD primer (sequence 1-20), a 84-bp nitrate reductase promoter (21-104), a 9-bp Xho I NdeI site (105-113) a 135-bp RbcS2 transit peptide (114-248), a 3-Hydroxybutyryl-CoA Dehydrogenase-encoding sequence (249-1094) selected/modified from a *Clostridium beijerinckii* 3-Hydroxybutyryl-CoA Dehydrogenase sequence (Genbank: AF494018), a 21-bp Lumio-tag sequence (1095-1115), a 9-bp XbaI site (1116-1124), a 223-bp RbcS2 terminator (1125-1347), and a PCR RE primer (1348-1367). This DNA construct is similar to example 4, SEQ ID NO: 4, except that an 84-bp nitrate reductase promoter (21-104) and a 3-Hydroxybutyryl-CoA Dehydrogenase-encoding sequence (249-1094) selected/modified from a *Clostridium beijerinckii* 3-Hydroxybutyryl-CoA Dehydrogenase sequence (Genbank: AF494018) are used. The 84-bp nitrate-reductase promoter is artificially created by joining two partially homologous sequence regions (−231 to −201 and −77 to −25 with respect to the start site of transcription) of the native *Chlamydomonas reinhardtii* Nia1 promoter. Experimental studies have demonstrated that the 84-bp sequence is more active than the native Nia1 promoter (Loppes and Radoux (2002) "Two short regions of the promoter are essential for activation and repression of the nitrate reductase gene in *Chlamydomonas reinhardtii," Mol Genet Genomics* 268: 42-48). Therefore, this is also an example where functional synthetic sequences, analogs, functional derivatives and/or designer modified sequences such as the synthetic 84-bp sequence can be selected for use according to various embodiments in this invention.

SEQ ID NO: 6 presents example 6 for a designer Thiolase DNA construct (1721 bp) that includes a PCR FD primer (sequence 1-20), a 84-bp nitrate reductase promoter (21-104), a 9-bp Xho I NdeI site (105-113) a 135-bp RbcS2 transit peptide (114-248), a Thiolase-encoding sequence (248-1448) selected/modified from a *Butyrivibrio fibrisolvens* Thiolase sequence (AB190764), a 21-bp Lumio-tag sequence (1449-1469), a 9-bp XbaI site (1470-1478), a 223-bp RbcS2 terminator (1479-1701), and a PCR RE primer (1702-1721). This DNA construct is also similar to example 4, SEQ ID NO: 4, except that a Thiolase-encoding-encoding sequence (249-1448) and an 84-bp synthetic Nia1 promoter (21-104) are used. This is another example that functional synthetic sequences can also be selected for use in designer DNA constructs.

SEQ ID NO: 7 presents example 7 for a designer Pyruvate-Ferredoxin Oxidoreductase DNA construct (4211 bp) that includes a PCR FD primer (sequence 1-20), a 2×84-bp nitrate reductase promoter (21-188), a 9-bp Xho I NdeI site (189-197) a 135-bp RbcS2 transit peptide (198-332), a Pyruvate-Ferredoxin Oxidoreductase-encoding sequence (333-3938) selected/modified from the sequences of a *Mastigamoeba balamuthi* Pyruvate-ferredoxin oxidoreductase (GenBank: AY101767), a 21-bp Lumio-tag sequence (3939-3959), a 9-bp XbaI site (3960-3968), a 223-bp RbcS2 terminator (3969-4191), and a PCR RE primer (4192-4211). This DNA construct is also similar to example 4, SEQ ID NO: 4, except a designer 2×84-bp Nia1 promoter and a Pyruvate-Ferredoxin Oxidoreductase-encoding sequence (333-3938) selected/modified from the sequences of a *Mastigamoeba balamuthi* Pyruvate-ferredoxin oxidoreductase (GenBank: AY101767) are used. The 2×84-bp Nia1 promoter is constructed as a tandem duplication of the 84-bp synthetic Nia1 promoter sequence presented in SEQ ID NO: 6 above. Experimental tests have shown that the 2×84-bp synthetic Nia1 promoter is even more powerful than the 84-bp sequence which is more active than the native Nia1 promoter (Loppes and Radoux (2002) "Two short regions of the promoter are essential for activation and repression of the nitrate reductase gene in *Chlamydomonas reinhardtii," Mol Genet Genomics* 268: 42-48). Use of this type of inducible promoter sequences with various promoter strengths can also help in adjusting the expression levels of the designer enzymes for the butanol-production pathway(s).

SEQ ID NO: 8 presents example 8 for a designer Pyruvate Kinase DNA construct (2021 bp) that includes a PCR FD primer (sequence 1-20), a 84-bp nitrate reductase promoter (21-104), a 9-bp Xho I NdeI site (105-113) a 135-bp RbcS2 transit peptide (114-248), a pyruvate kinase-encoding sequence (249-1748) selected/modified from a *Saccharomyces cerevisiae* Pyruvate Kinase sequence (GenBank: AY949876), a 21-bp Lumio-tag sequence (1749-1769), a 9-bp XbaI site (1770-1778), a 223-bp RbcS2 terminator (1779-2001), and a PCR RE primer (2002-2021). This DNA construct is similar to example 6, SEQ ID NO: 6, except that a pyruvate kinase-encoding sequence (249-1748) is used.

SEQ ID NO: 9 presents example 9 for a designer Enolase gene (1815 bp) consisting of a PCR FD primer (sequence 1-20), a 262-bp nitrate reductase promoter (21-282), a 9-bp Xho I NdeI site (283-291) a 135-bp RbcS2 transit peptide (292-426), a enolase-encoding sequence (427-1542) selected/modified from the sequences of a *Chlamydomonas reinhardtii* cytosolic enolase (Genbank: X66412, P31683), a 21-bp Lumio-tag-encoding sequence (1507-1527), a 9-bp XbaI site (1543-1551) containing a stop codon, a 223-bp RbcS2 terminator (1552-1795), and a PCR RE primer (1796-1815) at the 3' end. This DNA construct is similar to example 3, SEQ ID NO: 3, except that an enolase-encoding sequence (427-1542) selected/modified from the sequences of a *Chlamydomonas reinhardtii* cytosolic enolase is used.

SEQ ID NO: 10 presents example 10 for a designer Phosphoglycerate-Mutase DNA construct (2349 bp) that includes a PCR FD primer (sequence 1-20), a 262-bp nitrate reductase promoter (21-282), a 9-bp Xho I NdeI site (283-291), a 135-bp RbcS2 transit peptide (292-426), a phosphoglycerate-mutase encoding sequence (427-2097) selected/modified from the sequences of a *Chlamydomonas reinhardtii* cytosolic phosphoglycerate mutase (JGI Chlre2 protein ID 161689, Genbank: AF268078), a 9-bp XbaI site (2098-2106), a 223-bp RbcS2 terminator (2107-2329), and a PCR RE primer (2330-2349) at the 3' end. This DNA construct is similar to example 3, SEQ ID NO: 3, except that a phosphoglycerate-mutase encoding sequence (427-2097) selected/modified from the sequences of a *Chlamydomonas reinhardtii* cytosolic phosphoglycerate mutase is used.

SEQ ID NO: 11 presents example 11 for a designer Phosphoglycerate Kinase DNA construct (1908 bp) that includes a PCR FD primer (sequence 1-20), a 262-bp nitrate reductase Nia1 promoter (21-282), a phosphoglycerate-kinase-encoding sequence (283-1665) selected from a *Chlamydomonas reinhardtii* chloroplast phosphoglycerate-kinase sequence including its chloroplast signal peptide and mature enzyme sequence (GenBank: U14912), a 223-bp RbcS2 terminator (1666-1888), and a PCR RE primer (1889-1908). This DNA construct is similar to example 1, SEQ ID NO: 1, except a phosphoglycerate-kinase-encoding sequence (283-1665) selected from a *Chlamydomonas reinhardtii* chloroplast phosphoglycerate-kinase sequence including its chloroplast signal peptide and mature enzyme sequence is used. Therefore, this is also an example where the sequence of a nuclear-encoded chloroplast enzyme such as the *Chlamydomonas reinhardtii* chloroplast phosphoglycerate kinase can also be used in design and construction of a designer butanol-production pathway gene when appropriate with a proper inducible promoter such as the Nia1 promoter (DNA sequence 21-282).

SEQ ID NO: 12 presents example 12 for a designer Glyceraldehyde-3-Phosphate Dehydrogenase gene (1677 bp) that includes a PCR FD primer (sequence 1-20), a 262-bp nitrate reductase Nia1 promoter (21-282), a 135-bp RbcS2 transit peptide (283-417), an enzyme-encoding sequence (418-1434) selected and modified from a *Mesostigma viride* cytosolic glyceraldehyde-3-phosphate dehydrogenase (mRNA) sequence (GenBank accession number DQ873404), a 223-bp RbcS2 terminator (1435-1657), and a PCR RE primer (1658-1677). This DNA construct is similar to example 1, SEQ ID NO: 1, except that an enzyme-encoding sequence (418-1434) selected and modified from a *Mesostigma viride* cytosolic glyceraldehyde-3-phosphate dehydrogenase (mRNA) sequence (GenBank accession number DQ873404) is used.

SEQ ID NO: 13 presents example 13 for a designer HydA1-promoter-linked Phosphoglycerate Mutase DNA construct (2351 bp) that includes a PCR FD primer (sequence 1-20), a 282-bp HydA1 promoter (21-302), a 135-bp RbcS2 transit peptide (303-437), a phosphoglycerate-mutase encoding sequence (438-2108) selected/modified from the sequences of a *Chlamydomonas reinhardtii* cytosolic phosphoglycerate mutase (JGI Chlre2 protein ID 161689, Genbank: AF268078), a 223-bp RbcS2 terminator (2109-2331), and a PCR RE primer (2332-2351). This designer DNA construct is quite similar to example 1, SEQ ID NO:1, except that a 282-bp HydA1 promoter (21-302) and a phosphoglycerate-mutase encoding sequence (438-2108) selected/modified from the sequences of a *Chlamydomonas reinhardtii* cytosolic phosphoglycerate mutase are used. The 282-bp HydA1 promoter (21-302) has been proven active by experimental assays at the inventor's laboratory. Use of the HydA1 promoter (21-302) enables activation of designer enzyme expression by using anaerobic culture-medium conditions.

With the same principle of using an inducible anaerobic promoter and a chloroplast-targeting sequence as that shown in SEQ ID NO: 13 (example 13), SEQ ID NOS: 14-23 show designer-gene examples 14-23. Briefly, SEQ ID NO: 14 presents example 14 for a designer HydA1-promoter-linked Enolase DNA construct (1796 bp) that includes a PCR FD primer (sequence 1-20), a 282-bp HydA1 promoter (21-302), a 135-bp RbcS2 transit peptide (303-437), a Enolase-encoding sequence (438-1553) selected/modified from the sequences of a *Chlamydomonas reinhardtii* cytosolic enolase (Genbank: X66412, P31683), a 223-bp RbcS2 terminator (1554-1776), and a PCR RE primer (1777-1796).

SEQ ID NO: 15 presents example 15 for a designer HydA1-promoter-controlled Pyruvate-Kinase DNA construct that includes a PCR FD primer (sequence 1-20), a 282-bp HydA1 promoter (21-302), a 135-bp RbcS2 transit peptide (303-437), a Pyruvate Kinase-encoding sequence (438-1589) selected/modified from a *Chlamydomonas reinhardtii* cytosolic pyruvate kinase sequence (JGI Chlre3 protein ID 138105), a 223-bp RbcS2 terminator (1590-1812), and a PCR RE primer (1813-1832).

SEQ ID NO:16 presents example 16 for a designer HydA1-promoter-linked Pyruvate-ferredoxin oxidoreductase DNA construct (4376 bp) that includes a PCR FD primer (sequence 1-20), a 282-bp HydA1 promoter (21-302), a 135-bp RbcS2 transit peptide (303-437), a Pyruvate-ferredoxin oxidoreductase-encoding sequence (438-4133) selected/modified from a *Desulfovibrio africanus* Pyruvate-ferredoxin oxidoreductase sequence (GenBank Accession Number Y09702), a 223-bp RbcS2 terminator (4134-4356), and a PCR RE primer (4357-4376).

SEQ ID NO:17 presents example 17 for a designer HydA1-promoter-linked Pyruvate-$NADP^+$ oxidoreductase DNA construct (6092 bp) that includes a PCR FD primer (sequence 1-20), a 282-bp HydA1 promoter (21-302), a 135-bp RbcS2 transit peptide (303-437), a Pyruvate-$NADP^+$ oxidoreductase-encoding sequence (438-5849) selected/modified from a *Euglena gracilis* Pyruvate-$NADP^+$ oxidoreductase sequence (GenBank Accession Number AB021127), a 223-bp RbcS2 terminator (5850-6072), and a PCR RE primer (6073-6092).

SEQ ID NO:18 presents example 18 for a designer HydA1-promoter-linked Thiolase DNA construct (1856 bp) that includes a PCR FD primer (sequence 1-20), a 282-bp HydA1 promoter (21-302), a 135-bp RbcS2 transit peptide (303-437), a Thiolase-encoding sequence (438-1613) selected/modified from the sequences of a *Thermoanaerobacterium thermosaccharolyticum* Thiolase (GenBank Z92974), a 223-bp RbcS2 terminator (1614-1836), and a PCR RE primer (1837-1856).

SEQ ID NO:19 presents example 19 for a designer HydA1-promoter-linked 3-Hydroxybutyryl-CoA dehydrogenase DNA construct (1550 bp) that includes a PCR FD primer (sequence 1-20), a 282-bp HydA1 promoter (21-302), a 135-bp RbcS2 transit peptide (303-437), a 3-Hydroxybutyryl-CoA dehydrogenase-encoding sequence (438-1307) selected/modified from the sequences of a *Thermoanaerobacterium thermosaccharolyticum* 3-Hydroxybutyryl-CoA dehydrogenase (GenBank Z92974), a 223-bp RbcS2 terminator (1308-1530), and a PCR RE primer (1531-1550).

SEQ ID NO:20 presents example 20 for a designer HydA1-promoter-linked Crotonase DNA construct (1457 bp) that includes a PCR FD primer (sequence 1-20), a 282-bp HydA1 promoter (21-302), a 135-bp RbcS2 transit peptide (303-437), a Crotonase-encoding sequence (438-1214) selected/modified from the sequences of a *Thermoanaerobacterium thermosaccharolyticum* Crotonase (GenBank Z92974), a 223-bpRbcS2 terminator (1215-1437), and a PCR RE primer (1438-1457).

SEQ ID NO:21 presents example 21 for a designer HydA1-promoter-linked Butyryl-CoA dehydrogenase DNA construct (1817 bp) that includes a PCR FD primer (sequence 1-20), a 282-bp HydA1 promoter (21-302), a 135-bp RbcS2 transit peptide (303-437), a Butyryl-CoA dehydrogenase-encoding sequence (438-1574) selected/modified from the sequences of a *Thermoanaerobacterium thermosaccharolyticum* Butyryl-CoA dehydrogenase (GenBank Z92974), a 223-bp RbcS2 terminator (1575-1797), and a PCR RE primer (1798-1817).

SEQ ID NO: 22 presents example 22 for a designer HydA1-promoter-linked Butyraldehyde dehydrogenase DNA construct (2084 bp) that includes a PCR FD primer (sequence 1-20), a 282-bp HydA1 promoter (21-302), a 135-bp RbcS2 transit peptide (303-437), a Butyraldehyde dehydrogenase-encoding sequence (438-1841) selected/modified from the sequences of a *Clostridium saccharoperbutylacetonicum* Butyraldehyde dehydrogenase (GenBank AY251646), a 223-bp RbcS2 terminator (1842-2064), and a PCR RE primer (2065-2084).

SEQ ID NO: 23 presents example 23 for a designer HydA1-promoter-linked Butanol dehydrogenase DNA construct (1733 bp) that includes a PCR FD primer (sequence 1-20), a 282-bp HydA1 promoter (21-302), a 135-bp RbcS2 transit peptide (303-437), a Butanol dehydrogenase-encoding sequence (438-1490) selected/modified from the sequences of a *Clostridium beijerinckii* Butanol dehydrogenase (GenBank AF157307), a 223-bp RbcS2 terminator (1491-1713), and a PCR RE primer (1714-1733).

With the same principle of using a 2×84 synthetic Nia1 promoter and a chloroplast-targeting mechanism as mentioned previously, SEQ ID NOS:24-26 show more examples of designer-enzyme DNA-constructs. Briefly, SEQ ID NO: 24 presents example 24 for a designer Fructose-Diphosphate-Aldolase DNA construct that includes a PCR FD primer (sequence 1-20), a 2×84-bp NR promoter (21-188), a Fructose-Diphosphate Aldolase-encoding sequence (189-1313) selected/modified from a *C. reinhardtii* chloroplast fructose-1,6-bisphosphate aldolase sequence (GenBank: X69969), a 223-bpRbcS2 terminator (1314-1536), and a PCR RE primer (1537-1556).

SEQ ID NO: 25 presents example 24 for a designer Triose-Phosphate-Isomerase DNA construct that includes a PCR FD primer (sequence 1-20), a 2×84-bp NR promoter (21-188), a Triose-Phosphate Isomerase-encoding sequence (189-1136) selected and modified from a *Arabidopsis thaliana* chloroplast triosephosphate-isomerase sequence (GenBank: AF247559), a 223-bp RbcS2 terminator (1137-1359), and a PCR RE primer (1360-1379).

SEQ ID NO: 26 presents example 26 for a designer Phosphofructose-Kinase DNA construct that includes a PCR FD primer (sequence 1-20), a 2×84-bp NR promoter (21-188), a 135-bp RbcS2 transit peptide (189-323), a Phosphofructose Kinase-encoding sequence (324-1913) selected/modified from *Arabidopsis thaliana* 6-phosphofructokinase sequence (GenBank: NM_001037043), a 223-bp RbcS2 terminator (1914-2136), and a PCR RE primer (2137-2156).

The nucleic acid constructs, such as those presented in the examples above, may include additional appropriate sequences, for example, a selection marker gene, and an optional biomolecular tag sequence (such as the Lumio tag described in example 4, SEQ ID NO: 4). Selectable markers that can be selected for use in the constructs include markers conferring resistances to kanamycin, hygromycin, spectinomycin, streptomycin, sulfonyl urea, gentamycin, chloramphenicol, among others, all of which have been cloned and are available to those skilled in the art. Alternatively, the selective marker is a nutrition marker gene that can complement a deficiency in the host organism. For example, the gene encoding argininosuccinate lyase (arg7) can be used as a selection marker gene in the designer construct, which permits identification of transformants when *Chlamydomonas reinhardtii* arg7-(minus) cells are used as host cells.

Nucleic acid constructs carrying designer genes can be delivered into a host alga, blue-green alga, plant, or plant tissue or cells using the available gene-transformation techniques, such as electroporation, PEG induced uptake, and ballistic delivery of DNA, and *Agrobacterium*-mediated transformation. For the purpose of delivering a designer construct into algal cells, the techniques of electroporation, glass bead, and biolistic genegun can be selected for use as preferred methods; and an alga with single cells or simple thallus structure is preferred for use in transformation. Transformants can be identified and tested based on routine techniques.

The various designer genes can be introduced into host cells sequentially in a step-wise manner, or simultaneously using one construct or in one transformation. For example, the ten DNA constructs shown in SEQ ID NO: 13-16 (or 17) and 18-23 for the ten-enzyme 3-phosphoglycerate-branched butanol-production pathway can be placed into a genetic vector such as p389-Arg7 with a single selection marker (Arg7). Therefore, by use of a plasmid in this manner, it is possible to deliver all the ten DNA constructs (designer genes) into an arginine-requiring *Chlamydomonas reinhardtii*-arg7 host (CC-48) in one transformation for expression of the 3-phosphoglycerate-branched butanol-production pathway (03-12 in FIG. 1). When necessary, a transformant containing the ten DNA constructs can be further transformed to get more designer genes into its genomic DNA with an additional selection marker such as streptomycin. By using combinations of various designer-enzymes DNA constructs such as those presented in SEQ ID NO: 1-26 in genetic transformation with an appropriate host organism, various butanol-production pathways such as those illustrated in FIG. 1 can be constructed. For example, the designer DNA constructs of SEQ ID NO: 1-12 can be selected for construction of the glyceraldehydes-3-phosphate-branched butanol-production pathway (01-12 in FIG. 1); The designer DNA constructs of SEQ ID NO: 1-12, 24, and 25 can be selected for construction of the fructose-1,6-diphosphate-branched butanol-production pathway (20-33); and the designer DNA constructs of SEQ ID NO: 1-12 and 24-26 can be selected for construction of the fructose-6-phosphate-branched butanol-production pathway (19-33).

Additional Host Modifications to Enhance Photosynthetic Butanol Production

An NADPH/NADH Conversion Mechanism

According to the photosynthetic butanol production pathway(s), to produce one molecule of butanol from $4CO_2$ and $5H_2O$ is likely to require 14 ATP and 12 NADPH, both of which are generated by photosynthetic water splitting and photophosphorylation across the thylakoid membrane. In order for the 3-phosphoglycerate-branched butanol-production pathway (03-12 in FIG. 1) to operate, it is a preferred practice to use a butanol-production-pathway enzyme(s) that can use NADPH that is generated by the photo-driven electron transport process. *Clostridium saccharoperbutylacetonicum* butanol dehydrogenase (GenBank accession number: AB257439) and butyaldehyde dehydrogenase (GenBank: AY251646) are examples of a butanol-production-pathway enzyme that is capable of accepting either NADP(H) or NAD (H). Such a butanol-production-pathway enzyme that can use both NADPH and NADH (i.e., NAD(P)H) can also be selected for use in this 3-phosphoglycerate-branched and any of the other designer butanol-production pathway(s) (FIG. 1) as well. *Clostridium beijerinckii* Butyryl-CoA dehydrogenase (GenBank: AF494018) and 3-Hydroxybutyryl-CoA dehydrogenase (GenBank: AF494018) are examples of a butanol-production-pathway enzyme that can accept only NAD(H). When a butanol-production-pathway enzyme that can only use NADH is employed, it may require an NADPH/NADH conversion mechanism in order for this 3-phosphoglycerate-branched butanol-production pathway to operate well. However, depending on the genetic backgrounds of a host organism, a conversion mechanism between NADPH and NADH may exist in the host so that NADPH and NADH may be interchangeably used in the organism. In addition, it is known that NADPH could be converted into NADH by a NADPH-phosphatase activity (Pattanayak and Chatterjee (1998) "Nicotinamide adenine dinucleotide phosphate phosphatase facilitates dark reduction of nitrate: regulation by nitrate and ammonia," *Biologia Plantarium* 41(1):75-84) and that NAD can be converted to NADP by a NAD kinase activity (Muto, Miyachi, Usuda, Edwards and Bassham (1981) "Light-induced conversion of nicotinamide adenine dinucleotide to nicotinamide adenine dinucleotide phosphate in higher plant leaves," *Plant Physiology* 68(2):324-328; Matsumura-Kadota, Muto, Miyachi (1982) "Light-induced conversion of NAD' to $NADP^+$ in *Chlorella* cells," *Biochimica Biophysica Acta* 679(2):300-300). Therefore, when enhanced NADPH/NADH conversion is desirable, the host may be genetically modified to enhance the NADPH phosphatase and NAD kinase activities. Thus, in one of the various embodiments, the photosynthetic butanol-producing designer plant, designer alga or plant cell further contains additional designer transgenes (FIG. 2B) to inducibly express one or more enzymes to facilitate the NADPH/NADH interconversion, such as the NADPH phosphatase and NAD kinase (GenBank: XM_001609395, XM_001324239), in the stroma region of the algal chloroplast.

Another embodiment that can provide an NADPH/NADH conversion mechanism is by properly selecting an appropriate branching point at the Calvin cycle for a designer butanol-production pathway to branch from. To confer this NADPH/NADH conversion mechanism by pathway design according to this embodiment, it is a preferred practice to branch a designer butanol-production pathway at or after the point of glyceraldehydes-3-phosphate of the Calvin cycle as shown in FIG. 1. In these pathway designs, the NADPH/NADH conversion is achieved essentially by a two-step mechanism: 1) Use of the step with the Calvin-cycle's glyceraldehyde-3-phosphate dehydrogenase, which uses NADPH in reducing-1,3-diphosphoglycerate to glyceraldehydes-3-phosphate; and 2) use of the step with the designer pathway's $NAD^+$-dependent glyceraldehyde-3-phosphate dehydrogenase 01, which produces NADH in oxidizing glyceraldehyde-3-phosphate to 1,3-diphosphoglycerate. The net result of the two steps described above is the conversion of NADPH to NADH, which can supply the needed reducing power in the form of NADH for the designer butanol-production pathway(s). For step 1), use of the Calvin-cycle's NADPH-dependent glyceraldehyde-3-phosphate dehydrogenase naturally in the host organism is usually sufficient. Consequently, introduction of a designer $NAD^+$-dependent glyceraldehyde-3-phosphate dehydrogenase 01 to work with the Calvin-cycle's NADPH-dependent glyceraldehyde-3-phosphate dehydrogenase may confer the function of an NADPH/NADH conversion mechanism, which is needed for the 3-phosphoglycerate-branched butanol-production pathway (03-12 in FIG. 1) to operate well. For this reason, the designer $NAD^+$-dependent glyceraldehyde-3-phosphate-dehydrogenase DNA construct (example 12, SEQ ID NO:12) is used also as an NADPH/NADH-conversion designer gene (FIG. 2B) to support the 3-phosphoglycerate-branched butanol-production pathway (03-12 in FIG. 1) in one of the various embodiments. This also explains why it is important to use a $NAD^+$-dependent glyceraldehyde-3-phosphate dehydrogenase 01 to confer this two-step NADPH/NADH conversion mechanism for the designer butanol-production pathway(s). Therefore, in one of the various embodiments, it is also a preferred practice to use a $NAD^+$-dependent glyceraldehyde-3-phosphate dehydrogenase, its isozymes, functional derivatives, analogs, designer modified enzymes and/or combinations thereof in the designer butanol-production pathway(s) as illustrated in FIG. 1.

iRNA Techniques to Further Tame Photosynthesis Regulation Mechanism

In another embodiment of the present invention, the host plant or cell is further modified to tame the Calvin cycle so that the host can directly produce liquid fuel butanol instead of synthesizing starch (glycogen in the case of oxyphotobacteria), celluloses and lignocelluloses that are often inefficient and hard for the biorefinery industry to use. According to the one of the various embodiments, inactivation of starch-synthesis activity is achieved by suppressing the expression of any of the key enzymes, such as, starch synthase (glycogen synthase in the case of oxyphotobacteria) 13, glucose-1-phosphate (G-1-P) adenylyltransferase 14, phosphoglucomutase 15, and hexose-phosphate-isomerase 16 of the starch-synthesis pathway which connects with the Calvin cycle (FIG. 1).

Introduction of a genetically transmittable factor that can inhibit the starch-synthesis activity that is in competition with designer butanol-production pathway(s) for the Calvin-cycle products can further enhance photosynthetic butanol production. In a specific embodiment, a genetically encoded-able inhibitor (FIG. 2C) to the competitive starch-synthesis pathway is an interfering RNA (iRNA) molecule that specifically inhibits the synthesis of a starch-synthesis-pathway enzyme, for example, starch synthase 16, glucose-1-phosphate (G-1-P) adenylyltransferase 15, phosphoglucomutase 14, and/or hexose-phosphate-isomerase 13 as shown with numerical labels 13-16 in FIG. 1. The DNA sequences encoding starch synthase iRNA, glucose-1-phosphate (G-1-P) adenylyltransferase iRNA, a phosphoglucomutase iRNA and/or a G-P-isomerase iRNA, respectively, can be designed and synthesized based on RNA interference techniques known to those skilled in the art (Liszewski (Jun. 1, 2003) Progress in RNA interference, *Genetic Engineering News*, Vol. 23, number 11, pp. 1-59). Generally speaking, an interfering RNA (iRNA) molecule is anti-sense but complementary to a normal mRNA of a particular protein (gene) so that such iRNA molecule can specifically bind with the normal mRNA of the particular gene, thus inhibiting (blocking) the translation of the gene-specific mRNA to protein (Fire, Xu, Montgomery, Kostas, Driver, Mello (1998) "Potent and specific genetic interference by double-stranded RNA in *Caenorhabditis elegans*". *Nature* 391(6669):806-11; Dykxhoorn, Novina, Sharp (2003) "Killing the messenger: short RNAs that silence gene expression", *Nat Rev Mol Cell Biol.* 4(6):457-67).

Examples of a designer starch-synthesis iRNA DNA construct (FIG. 2C) are shown in SEQ ID NO: 27 and 28 listed. Briefly, SEQ ID NO: 27 presents example 27 for a designer Nia1-promoter-controlled Starch-Synthase-iRNA DNA construct (860 bp) that includes a PCR FD primer (sequence 1-20), a 262-bp Nia1 promoter (21-282), a Starch-Synthase iRNA sequence (283-617) consisting of start codon atg and a reverse complement sequence of two unique sequence fragments of a *Chlamydomonas reinhardtii* starch-synthase-mRNA sequence (GenBank: AF026422), a 223-bp RbcS2 terminator (618-850), and a PCR RE primer (851-860). Because of the use of a Nia1 promoter (21-282), this designer starch-synthesis iRNA gene is designed to be expressed only when needed to enhance photobiological butanol production in the presence of its specific inducer, nitrate ($NO_3^-$), which can be added into the culture medium as a fertilizer for induction of the designer organisms. The Starch-Synthase iRNA sequence (283-617) is designed to bind with the normal mRNA of the starch synthase gene, thus blocking its translation into a functional starch synthase. The inhibition of the starch/glycogen synthase activity at 16 in this manner is to channel more photosynthetic products of the Calvin cycle into the Calvin-cycle-branched butanol-production pathway(s) such as the glyceraldehydes-3-phosphate-branched butanol-production pathway 01-12 as illustrated in FIG. 1.

SEQ ID NO: 28 presents example 28 for a designer HydA1-promoter-controlled Starch-Synthase-iRNA DNA construct (1328 bp) that includes a PCR FD primer (sequence 1-20), a 282-bp HydA1 promoter (21-302), a designer Starch-Synthase iRNA sequence (303-1085), a 223-bp RbcS2 terminator (1086-1308), and a PCR RE primer (1309-1328). The designer Starch-Synthase-iRNA sequence (303-1085) comprises of: a 300-bp sense fragment (303-602) selected from the first 300-bp unique coding sequence of a *Chlamydomonas reinhardtii* starch synthase mRNA sequence (GenBank:

AF026422), a 183-bp designer intron-like loop (603-785), and a 300-bp antisense sequence (786-1085) complement to the first 300-bp coding sequence of a *Chlamydomonas reinhardtii* starch-synthase-mRNA sequence (GenBank: AF026422). This designer Starch-Synthase-iRNA sequence (303-1085) is designed to inhibit the synthesis of starch synthase by the following two mechanisms. First, the 300-bp antisense complement iRNA sequence (corresponding to DNA sequence 786-1085) binds with the normal mRNA of the starch synthase gene, thus blocking its translation into a functional starch synthase. Second, the 300-bp antisense complement iRNA sequence (corresponding to DNA sequence 786-1085) can also bind with the 300-bp sense counterpart (corresponding to DNA sequence 303-602) in the same designer iRNA molecule, forming a hairpin-like double-stranded RNA structure with the 183-bp designer intron-like sequence (603-785) as a loop. Experimental studies have shown that this type of hairpin-like double-stranded RNA can also trigger post-transcriptional gene silencing (Fuhrmann, Stahlberg, Govorunova, Rank and Hegemann (2001) *Journal of Cell Science* 114:3857-3863). Because of the use of a HydA1 promoter (21-302), this designer starch-synthesis-iRNA gene is designed to be expressed only under anaerobic conditions when needed to enhance photobiological butanol production by channeling more photosynthetic products of the Calvin cycle into the butanol-production pathway(s) such as 01-12, 03-12, and/or 20-33 as illustrated in FIG. 1.

Designer Starch-Degradation and Glycolysis Genes

In yet another embodiment of the present invention, the photobiological butanol production is enhanced by incorporating an additional set of designer genes (FIG. 2D) that can facilitate starch/glycogen degradation and glycolysis in combination with the designer butanol-production gene(s) (FIG. 2A). Such additional designer genes for starch degradation include, for example, genes coding for 17: amylase, starch phosphorylase, hexokinase, phosphoglucomutase, and for 18: glucose-phosphate-isomerase (G-P-isomerase) as illustrated in FIG. 1. The designer glycolysis genes encode chloroplast-targeted glycolysis enzymes: glucosephosphate isomerase 18, phosphofructose kinase 19, aldolase 20, triose phosphate isomerase 21, glyceraldehyde-3-phosphate dehydrogenase 22, phosphoglycerate kinase 23, phosphoglycerate mutase 24, enolase 25, and pyruvate kinase 26. The designer starch-degradation and glycolysis genes in combination with any of the butanol-production pathways shown in FIG. 1 can form additional pathway(s) from starch/glycogen to butanol (17-33). Consequently, co-expression of the designer starch-degradation and glycolysis genes with the butanol-production-pathway genes can enhance photobiological production of butanol as well. Therefore, this embodiment represents another approach to tame the Calvin cycle for enhanced photobiological production of butanol. In this case, some of the Calvin-cycle products flow through the starch synthesis pathway (13-16) followed by the starch/glycogen-to-butanol pathway (17-33) as shown in FIG. 1. In this case, starch/glycogen acts as a transient storage pool of the Calvin-cycle products before they can be converted to butanol. This mechanism can be quite useful in maximizing the butanol-production yield in certain cases. For example, at high sunlight intensity such as around noon, the rate of Calvin-cycle photosynthetic $CO_2$ fixation can be so high that may exceed the maximal rate capacity of a butanol-production pathway(s); use of the starch-synthesis mechanism allows temporary storage of the excess photosynthetic products to be used later for butanol production as well.

FIG. 1 also illustrates the use of a designer starch/glycogen-to-butanol pathway with designer enzymes (as labeled from 17 to 33) in combination with a Calvin-cycle-branched designer butanol-production pathway(s) such as the glyceraldehydes-3-phosphate-branched butanol-production pathway 01-12 for enhanced photobiological butanol production. Similar to the benefits of using the Calvin-cycle-branched designer butanol-production pathways, the use of the designer starch/glycogen-to-butanol pathway (17-33) can also help to convert the photosynthetic products to butanol before the sugars could be converted into other complicated biomolecules such as lignocellulosic biomasses which cannot be readily used by the biorefinery industries. Therefore, appropriate use of the Calvin-cycle-branched designer butanol-production pathway(s) (such as 01-12, 03-12, and/or 20-33) and/or the designer starch/glycogen-to-butanol pathway (17-33) may represent revolutionary inter alia technologies that can effectively bypass the bottleneck problems of the current biomass technology including the "lignocellulosic recalcitrance" problem.

Another feature is that a Calvin-cycle-branched designer butanol-production pathway activity (such as 01-12, 03-12, and/or 20-33) can occur predominantly during the days when there is light because it uses an intermediate product of the Calvin cycle which requires supplies of reducing power (NADPH) and energy (ATP) generated by the photosynthetic water splitting and the light-driven proton-translocation-coupled electron transport process through the thylakoid membrane system. The designer starch/glycogen-to-butanol pathway (17-33) which can use the surplus sugar that has been stored as starch/glycogen during photosynthesis can operate not only during the days, but also at nights. Consequently, the use of a Calvin-cycle-branched designer butanol-production pathway (such as 01-12, 03-12, and/or 20-33) together with a designer starch/glycogen-to-butanol pathway(s) (17-33) as illustrated in FIG. 1 enables production of butanol both during the days and at nights.

Because the expression for both the designer starch/glycogen-to-butanol pathway(s) and the Calvin-cycle-branched designer butanol-production pathway(s) is controlled by the use of an inducible promoter such as an anaerobic hydrogenase promoter, this type of designer organisms is also able to grow photoautotrophically under aerobic (normal) conditions. When the designer photosynthetic organisms are grown and ready for photobiological butanol production, the cells are then placed under the specific inducing conditions such as under anaerobic conditions [or an ammonium-to-nitrate fertilizer use shift, if designer Nia1/nirA promoter-controlled butanol-production pathway(s) is used] for enhanced butanol production, as shown in FIGS. 1 and 3.

Examples of designer starch (glycogen)-degradation genes are shown in SEQ ID NO: 29-33 listed. Briefly, SEQ ID NO:29 presents example 29 for a designer Amylase DNA construct (1889 bp) that includes a PCR FD primer (sequence 1-20), a 2×84-bp NR promoter (21-188), a 9-bp Xho I NdeI site (189-197), a 135-bp RbcS2 transit peptide (198-332), an Amylase-encoding sequence (333-1616) selected and modified from a Barley alpha-amylase (GenBank: J04202A my46 expression tested in aleurone cells), a 21-bp Lumio-tag sequence (1617-1637), a 9-bp XbaI site (1638-1646), a 223-bp RbcS2 terminator (1647-1869), and a PCR RE primer (1870-1889).

SEQ ID NO: 30 presents example 30 for a designer Starch-Phosphorylase DNA construct (3089 bp) that includes a PCR FD primer (sequence 1-20), a 2×84-bp NR promoter (21-188), a 135-bp RbcS2 transit peptide (189-323), a Starch Phosphorylase-encoding sequence (324-2846) selected and modified from a Citrus root starch-phosphorylase sequence (GenBank: AY098895, expression tested in citrus root), a 223-bp RbcS2 terminator (2847-3069), and a PCR RE primer (3070-3089).

SEQ ID NO: 31 presents example 31 for a designer Hexose-Kinase DNA construct (1949 bp) that includes a PCR FD primer (sequence 1-20), a 2×84-bp NR promoter (21-188), a 135-bp RbcS2 transit peptide (189-323), a Hexose Kinase-encoding sequence (324-1706) selected and modified from Ajellomyces capsulatus hexokinase mRNA sequence (Genbank: XM_001541513), a 223-bp RbcS2 terminator (1707-1929), and a PCR RE primer (1930-1949).

SEQ ID NO: 32 presents example 32 for a designer Phosphoglucomutase DNA construct (2249 bp) that includes a PCR FD primer (sequence 1-20), a 2×84-bp NR promoter (21-188), a 135-bp RbcS2 transit peptide (189-323), a Phosphoglucomutase-encoding sequence (324-2006) selected and modified from *Pichia stipitis* phosphoglucomutase sequence (GenBank: XM_001383281), a 223-bp RbcS2 terminator (2007-2229), and a PCR RE primer (2230-2249).

SEQ ID NO: 33 presents example 33 for a designer Glucosephosphate-Isomerase DNA construct (2231 bp) that includes a PCR FD primer (sequence 1-20), a 2×84-bp NR promoter (21-188), a 135-bp RbcS2 transit peptide (189-323), a Glucosephosphate Isomerase-encoding sequence (324-1988) selected and modified from a *S. cerevisiae* phosphoglucoisomerase sequence (GenBank: M21696), a 223-bp RbcS2 terminator (1989-2211), and a PCR RE primer (2212-2231).

The designer starch-degradation genes such as those shown in SEQ ID NO: 29-33 can be selected for use in combination with various designer butanol-production-pathway genes for construction of various designer starch-degradation butanol-production pathways such as the pathways shown in FIG. 1. For example, the designer genes shown in SEQ ID NOS: 1-12, 24-26, and 29-33 can be selected for construction of a Nia1 promoter-controlled starch-to-butanol production pathway that comprises of the following designer enzymes: amylase, starch phosphorylase, hexokinase, phosphoglucomutase, glucosephosphate isomerase, phosphofructose kinase, fructose diphosphate aldolase, triose phosphate isomerase, glyceraldehyde-3-phosphate dehydrogenase, phosphoglycerate kinase, phosphoglycerate mutase, enolase, pyruvate kinase, pyruvate-$NADP^+$ oxidoreductase (or pyruvate-ferredoxin oxidoreductase), thiolase, 3-hydroxybutyryl-CoA dehydrogenase, crotonase, butyryl-CoA dehydrogenase, butyraldehyde dehydrogenase, and butanol dehydrogenase. This starch/glycogen-to-butanol pathway 17-33 may be used alone and/or in combinations with other butanol-production pathway(s) such as the 3-phosphoglycerate-branched butanol-production pathway 03-12 as illustrated in FIG. 1.

Distribution of Designer Butanol-Production Pathways Between Chloroplast and Cytoplasm In yet another embodiment of the present invention, photobiological butanol productivity is enhanced by a selected distribution of the designer butanol-production pathway(s) between chloroplast and cytoplasm in a eukaryotic plant cell. That is, not all the designer butanol-production pathway(s) (FIG. 1) have to operate in the chloroplast; when needed, part of the designer butanol-production pathway(s) can operate in cytoplasm as well. For example, in one of the various embodiments, a significant part of the designer starch-to-butanol pathway activity from dihydroxyacetone phosphate to butanol (21-33) is designed to occur at the cytoplasm while the steps from starch to dihydroxyacetone phosphate (17-20) are in the chloroplast. In this example, the linkage between the chloroplast and cytoplasm parts of the designer pathway is accomplished by use of the triose phosphate-phosphate translocator, which facilitates translocation of dihydroxyacetone across the chloroplast membrane. By use of the triose phosphate-phosphate translocator, it also enables the glyceraldehyde-3-phospahte-branched designer butanol-production pathway to operate not only in chloroplast, but also in cytoplasm as well. The cytoplasm part of the designer butanol-production pathway can be constructed by use of designer butanol-production pathway genes (DNA constructs of FIG. 2A) with their chloroplast-targeting sequence omitted as shown in FIG. 2E.

Designer Oxyphotobacteria with Designer Butanol-Production Pathways in Cytoplasm In prokaryotic photosynthetic organisms such as blue-green algae (oxyphotobacteria including cyanobacteria and oxychlorobacteria), which typically contain photosynthetic thylakoid membrane but no chloroplast structure, the Calvin cycle is located in the cytoplasm. In this special case, the entire designer butanol-production pathway(s) (FIG. 1) including (but not limited to) the glyceraldehyde-3-phosphate branched butanol-production pathway (01-12), the 3-phosphpglycerate-branched butanol-production pathway (03-12), the fructose-1,6-diphosphate-branched pathway (20-33), the fructose-6-phosphate-branched pathway (19-33), and the starch (or glycogen)-to-butanol pathways (17-33) are adjusted in design to operate with the Calvin cycle in the cytoplasm of a blue-green alga. The construction of the cytoplasm designer butanol-production pathways can be accomplished by use of designer butanol-production pathway genes (DNA construct of FIG. 2A) with their chloroplast-targeting sequence all omitted. When the chloroplast-targeting sequence is omitted in the designer DNA construct(s) as illustrated in FIG. 2E, the designer gene(s) is transcribed and translated into designer enzymes in the cytoplasm whereby conferring the designer butanol-production pathway(s). The designer gene(s) can be incorporated into the chromosomal and/or plasmid DNA in host blue-green algae (oxyphotobacteria including cyanobacteria and oxychlorobacteria) by using the techniques of gene transformation known to those skilled in the art. It is a preferred practice to integrate the designer genes through an integrative transformation into the chromosomal DNA that can usually provide better genetic stability for the designer genes. In oxyphotobacteria such as cyanobacteria, integrative transformation can be achieved through a process of homologous DNA double recombination into the host's chromosomal DNA using a designer DNA construct as illustrated in FIG. 2F, which typically, from the 5' upstream to the 3' downstream, consists of: recombination site 1, a designer butanol-production-pathway gene(s), and recombination site 2. This type of DNA constructs (FIG. 2F) can be delivered into oxyphotobacteria (blue-green algae) with a number of available genetic transformation techniques including electroporation, natural transformation, and/or conjugation. The transgenic designer organisms created from blue-green algae are also called designer blue-green algae (designer oxyphotobacteria including designer cyanobacteria and designer oxychlorobacteria).

Examples of designer oxyphotobacterial butanol-production-pathway genes are shown in SEQ ID NO: 34-45 listed. Briefly, SEQ ID NO:34 presents example 34 for a designer oxyphotobacterial Butanol Dehydrogenase DNA construct (1709 bp) that includes a PCR FD primer (sequence 1-20), a 400-bp nitrite reductase (nirA) promoter from *Thermosynechococcus elongatus* BP-1 (21-420), an enzyme-encoding sequence (421-1569) selected and modified from a *Clostridium saccharoperbutylacetonicum* Butanol Dehydrogenase sequence (AB257439), a 120-bp rbcS terminator from *Thermosynechococcus elongatus* BP-1 (1570-1689), and a PCR RE primer (1690-1709) at the 3' end.

SEQ ID NO:35 presents example 35 for a designer oxyphotobacterial Butyraldehyde Dehydrogenase DNA construct (1967 bp) that includes a PCR FD primer (sequence 1-20), a 400-bp *Thermosynechococcus elongatus* BP-1 nitrite reductase nirA promoter (21-420), an enzyme-encoding sequence (421-1827) selected and modified from a *Clostridium saccharoperbutylacetonicum* Butyraldehyde Dehydrogenase sequence (AY251646), a 120-bp rbcS terminator from *Thermosynechococcus elongatus* BP-1 (1828-1947), and a PCR RE primer (1948-1967) at the 3' end.

SEQ ID NO:36 presents example 36 for a designer oxyphotobacterial Butyryl-CoA Dehydrogenase DNA construct (1602 bp) that includes a PCR FD primer (sequence 1-20), a 305-bp *Thermosynechococcus elongatus* BP-1 nitrate reductase promoter (21-325), a Butyryl-CoA Dehydrogenase encoding sequence (326-1422) selected/modified from the sequences of a *Clostridium beijerinckii* Butyryl-CoA Dehydrogenase (AF494018), a 120-bp *Thermosynechococcus elongatus* BP-1 rbcS terminator (1423-1582), and a PCR RE primer (1583-1602) at the 3' end.

SEQ ID NO:37 presents example 37 for a designer oxyphotobacterial Crotonase DNA construct (1248 bp) that includes a PCR FD primer (sequence 1-20), a 305-bp *Thermosynechococcus elongatus* BP-1 nitrate reductase promoter (21-325), a Crotonase-encoding sequence (326-1108) selected/modified from the sequences of a *Clostridium beijerinckii* Crotonase (GenBank: AF494018), 120-bp *Thermosynechococcus elongatus* BP-1 rbcS terminator (1109-1228), and a PCR RE primer (1229-1248).

SEQ ID NO:38 presents example 38 for a designer oxyphotobacterial 3-Hydroxybutyryl-CoA Dehydrogenase DNA construct (1311 bp) that include of a PCR FD primer (sequence 1-20), a 305-bp nirA promoter from (21-325), a 3-Hydroxybutyryl-CoA Dehydrogenase-encoding sequence (326-1171) selected/modified from a *Clostridium beijerinckii* 3-Hydroxybutyryl-CoA Dehydrogenase sequence Crotonase (GenBank: AF494018), a 120-bp *Thermosynechococcus elongatus* BP-1 rbcS terminator (1172-1291), and a PCR RE primer (1292-1311).

SEQ ID NO:39 presents example 39 for a designer oxyphotobacterial Thiolase DNA construct (1665 bp) that includes a PCR FD primer (sequence 1-20), a 305-bp nirA promoter from *Thermosynechococcus elongatus* BP-1 (21-325), a Thiolase-encoding sequence (326-1525) selected/modified from a *Butyrivibrio fibrisolvens* Thiolase sequence (AB190764), a 120-bp rbcS terminator from *Thermosynechococcus elongatus* BP-1 (1526-1645), and a PCR RE primer (1646-1665).

SEQ ID NO:40 presents example 40 for a designer oxyphotobacterial Pyruvate-Ferredoxin Oxidoreductase DNA construct (4071 bp) that includes a PCR FD primer (sequence 1-20), a 305-bp nirA promoter from *Thermosynechococcus elongatus* BP-1 (21-325), a Pyruvate-Ferredoxin Oxidoreductase-encoding sequence (326-3931) selected/modified from the sequences of a *Mastigamoeba balamuthi* Pyruvate-ferredoxin oxidoreductase (GenBank: AY101767), a 120-bp rbcS terminator from *Thermosynechococcus elongatus* BP-1 (3932-4051), and a PCR RE primer (4052-4071).

SEQ ID NO:41 presents example 41 for a designer oxyphotobacterial Pyruvate Kinase DNA construct (1806 bp) that includes a PCR FD primer (sequence 1-20), a 305-bp nirA promoter from *Thermosynechococcus elongatus* BP-1 (21-325), a pyruvate kinase-encoding sequence (326-1666) selected/modified from a *Thermoproteus tenax* pyruvate kinase (GenBank: AF065890), a 120-bp *Thermosynechococcus elongatus* BP-1 rbcS terminator (1667-1786), and a PCR RE primer (1787-1806) at the 3' end.

SEQ ID NO:42 presents example 42 for a designer oxyphotobacterial Enolase DNA construct (1696 bp) that includes a PCR FD primer (sequence 1-20), a 231-bp nirA promoter from *Thermosynechococcus elongatus* BP-1 (21-251), a enolase-encoding sequence (252-1556) selected/modified from the sequences of a *Chlamydomonas reinhardtii* cytosolic enolase (GenBank: X66412, P31683), a 120-bp rbcS terminator from *Thermosynechococcus elongatus* BP-1 (1557-1676), and a PCR RE primer (1677-1696) at the 3' end.

SEQ ID NO:43 presents example 43 for a designer oxyphotobacterial Phosphoglycerate-Mutase DNA construct (2029 bp) that includes a PCR FD primer (sequence 1-20), a 231-bp nirA promoter from *Thermosynechococcus elongatus* BP-1 (21-251), a phosphoglycerate-mutase encoding sequence (252-1889) selected/modified from the sequences of a *Pelotomaculum thermopropionicum* SI phosphoglycerate mutase (GenBank: YP_001213270), a 120-bp *Thermosynechococcus elongatus* BP-1 rbcS terminator (1890-2009), and a PCR RE primer (2010-2029) at the 3' end.

SEQ ID NO:44 presents example 44 for a designer oxyphotobacterial Phosphoglycerate Kinase DNA construct (1687 bp) that includes a PCR FD primer (sequence 1-20), a 231-bp nirA promoter from *Thermosynechococcus elongatus* BP-1 (21-251), a phosphoglycerate-kinase-encoding sequence (252-1433) selected from *Pelotomaculum thermopropionicum* SI phosphoglycerate kinase (BAF60903), a 234-bp *Thermosynechococcus elongatus* BP-1 rbcS terminator (1434-1667), and a PCR RE primer (1668-1687).

SEQ ID NO:45 presents example 45 for a designer oxyphotobacterial Glyceraldehyde-3-Phosphate Dehydrogenase DNA construct (1514 bp) that includes a PCR FD primer (sequence 1-20), a 305-bp *Thermosynechococcus elongatus* BP-1 nirA promoter (21-325), an enzyme-encoding sequence (326-1260) selected and modified from *Blastochloris viridis* NAD-dependent Glyceraldehyde-3-phosphate dehydrogenase (CAC80993), a 234-bp rbcS terminator from *Thermosynechococcus elongatus* BP-1 (1261-1494), and a PCR RE primer (1495-1514).

The designer oxyphotobacterial genes such as those shown in SEQ ID NO: 34-45 can be selected for use in full or in part, and/or in combination with various other designer butanol-production-pathway genes for construction of various designer oxyphotobacterial butanol-production pathways such as the pathways shown in FIG. 1. For example, the designer genes shown in SEQ ID NOS: 34-45 can be selected for construction of an oxyphotobacterial nirA promoter-controlled and glyceraldehyde-3-phosphate-branched butanol-production pathway (01-12) that comprises of the following designer enzymes: NAD-dependent glyceraldehyde-3-phosphate dehydrogenase 01, phosphoglycerate kinase 02, phosphoglycerate mutase 03, enolase 04, pyruvate kinase 05, pyruvate-ferredoxin oxidoreductase (or pyruvate-$NADP^+$ oxidoreductase) 06, thiolase 07, 3-hydroxybutyryl-CoA dehydrogenase 08, crotonase 09, butyryl-CoA dehydrogenase 10, butyraldehyde dehydrogenase 11, and butanol dehydrogenase 12. Use of these designer oxyphotobacterial butanol-production-pathway genes (SEQ ID NOS: 34-45) in a thermophilic and/or thermotolerant cyanobacterium may represent a thermophilic and/or thermotolerant butanol-producing oxyphotobacterium. Fox example, use of these designer genes (SEQ ID NOS: 34-45) in a thermophilic/thermotolerant cyanobacterium such as *Thermosynechococcus elongatus* BP-1 may represent a designer thermophilic/ thermotolerant butanol-producing cyanobacterium such as a designer butanol-producing *Thermosynechococcus*.

Further Host Modifications to Help Ensure Biosafety

The present invention also provides biosafety-guarded photosynthetic biofuel (e.g., butanol and/or related higher alcohols) production methods based on cell-division-controllable designer transgenic plants (such as algae and oxyphotobacteria) or plant cells. For example, the cell-division-controllable designer photosynthetic organisms (FIG. 3) are created through use of a designer biosafety-control gene(s) (FIG. 2G) in conjunction with the designer butanol-production-pathway gene(s) (FIGS. 2A-2F) such that their cell division and mating function can be controllably stopped to provide better biosafety features.

In one of the various embodiments, a fundamental feature is that a designer cell-division-controllable photosynthetic organism (such as an alga, plant cell, or oxyphotobacterium) contains two key functions (FIG. 3A): a designer biosafety mechanism(s) and a designer biofuel-production pathway(s). As shown in FIG. 3B, the designer biosafety feature(s) is conferred by a number of mechanisms including: (1) the inducible insertion of designer proton-channels into cytoplasm membrane to permanently disable any cell division and mating capability, (2) the selective application of designer cell-division-cycle regulatory protein or interference RNA (iRNA) to permanently inhibit the cell division cycle and preferably keep the cell at the $G_1$ phase or $G_0$ state, and (3) the innovative use of a high-$CO_2$-requiring host photosynthetic organism for expression of the designer biofuel-production pathway(s). Examples of the designer biofuel-production pathway(s) include the designer butanol-production pathway(s), which work with the Calvin cycle to synthesize biofuel such as butanol directly from carbon dioxide ($CO_2$) and water ($H_2O$). The designer cell-division-control technology can help ensure biosafety in using the designer organisms for photosynthetic biofuel production. Accordingly, this embodiment provides, inter alia, biosafety-guarded methods for producing biofuel (e.g., butanol and/or related higher alcohols) based on a cell-division-controllable designer biofuel-producing alga, cyanobacterium, oxychlorobacterium, plant or plant cells.

In one of the various embodiments, a cell-division-controllable designer butanol-producing eukaryotic alga or plant cell is created by introducing a designer proton-channel gene (FIG. 2H) into a host alga or plant cell (FIG. 3B). SEQ ID NO: 46 presents example 46 for a detailed DNA construct of a designer Nia1-promoter-controlled proton-channel gene (609 bp) that includes a PCR FD primer (sequence 1-20), a 262-bp nitrate reductase Nia1 promoter (21-282), a Melittin proton-channel encoding sequence (283-366), a 223-bp RbcS2 terminator (367-589), and a PCR RE primer (590-609).

The expression of the designer proton-channel gene (FIG. 2H) is controlled by an inducible promoter such as the nitrate reductase (Nia1) promoter, which can also be used to control the expression of a designer biofuel-production-pathway gene(s). Therefore, before the expression of the designer gene(s) is induced, the designer organism can grow photoautotrophically using $CO_2$ as the carbon source and $H_2O$ as the source of electrons just like wild-type organism. When the designer organism culture is grown and ready for photobiological production of biofuels, the cell culture is then placed under a specific inducing condition (such as by adding nitrate into the culture medium if the nitrate reductase (Nia1) promoter is used as an inducible promoter) to induce the expression of both the designer proton-channel gene and the designer biofuel-production-pathway gene(s). The expression of the proton-channel gene is designed to occur through its transcription in the nucleus and its translation in the cytosol. Because of the specific molecular design, the expressed proton channels are automatically inserted into the cytoplasm membrane, but leave the photosynthetic thylakoid membrane intact. The insertion of the designer proton channels into cytoplasm membrane collapses the proton gradient across the cytoplasm membrane so that the cell division and mating function are permanently disabled. However, the photosynthetic thylakoid membrane inside the chloroplast is kept intact (functional) so that the designer biofuel-production-pathway enzymes expressed into the stroma region can work with the Calvin cycle for photobiological production of biofuels from $CO_2$ and $H_2O$. That is, when both the designer proton-channel gene and the designer biofuel-production-pathway gene(s) are turned on, the designer organism becomes a non-reproducible cell for dedicated photosynthetic production of biofuels. Because the cell division and mating function are permanently disabled (killed) at this stage, the designer-organism culture is no longer a living matter except its catalytic function for photochemical conversion of $CO_2$ and $H_2O$ into a biofuel. It will no longer be able to mate or exchange any genetic materials with any other cells, even if it somehow comes in contact with a wild-type cell as it would be the case of an accidental release into the environments.

According to one of the various embodiments, the nitrate reductase (Nia1) promoter or nitrite reductase (nirA) promoter is a preferred inducible promoter for use to control the expression of the designer genes. In the presence of ammonium (but not nitrate) in culture medium, for example, a designer organism with Nia1-promoter-controlled designer proton-channel gene and biofuel-production-pathway gene(s) can grow photoauotrophically using $CO_2$ as the carbon source and $H_2O$ as the source of electrons just like a wild-type organism. When the designer organism culture is grown and ready for photobiological production of biofuels, the expression of both the designer proton-channel gene and the designer biofuel-production-pathway gene(s) can then be induced by adding some nitrate fertilizer into the culture medium. Nitrate is widely present in soils and nearly all surface water on Earth. Therefore, even if a Nia1-promoter-controlled designer organism is accidentally released into the natural environment, it will soon die since the nitrate in the environment will trig the expression of a Nia1-promoter-controlled designer proton-channel gene which inserts proton-channels into the cytoplasm membrane thereby killing the cell. That is, a designer photosynthetic organism with Nia1-promoter-controlled proton-channel gene is programmed to die as soon as it sees nitrate in the environment. This characteristic of cell-division-controllable designer organisms with Nia1-promoter-controlled proton-channel gene provides an added biosafety feature.

The art in constructing proton-channel gene (FIG. 2H) with a thylakoid-membrane targeting sequence has recently been disclosed [James W. Lee (2007). Designer proton-channel transgenic algae for photobiological hydrogen production, PCT International Publication Number: WO 2007/134340 A2]. In the present invention of creating a cell-division-controllable designer organism, the thylakoid-membrane-targeting sequence must be omitted in the proton-channel gene design. For example, the essential components of a Nia1-promoter-controlled designer proton-channel gene can simply be a Nia1 promoter linked with a proton-channel-encoding sequence (without any thylakoid-membrane-targeting sequence) so that the proton channel will insert into the cytoplasm membrane but not into the photosynthetic thylakoid membrane.

According to one of the various embodiments, it is a preferred practice to use the same inducible promoter such as the Nia1 promoter to control the expression of both the designer proton-channel gene and the designer biofuel-production pathway genes. In this way, the designer biofuel-production pathway(s) can be inducibly expressed simultaneously with the expression of the designer proton-channel gene that terminates certain cellular functions including cell division and mating.

In one of the various embodiments, an inducible promoter that can be used in this designer biosafety embodiment is selected from the group consisting of the hydrogenase promoters [HydA1 (Hyd1) and HydA2, accession number: AJ308413, AF289201, AY090770], the Cyc6 gene promoter, the Cpxl gene promoter, the heat-shock protein promoter HSP70A, the CabII-1 gene (accession number M24072) promoter, the Ca1 gene (accession number P20507) promoter, the Ca2 gene (accession number P24258) promoter, the nitrate reductase (Nia1) promoter, the nitrite-reductase-gene (nirA) promoters, the bidirectional-hydrogenase-gene hox promoters, the light- and heat-responsive groE promoters, the Rubisco-operon rbcL promoters, the metal (zinc)-inducible smt promoter, the iron-responsive idiA promoter, the redox-responsive crhR promoter, the heat-shock-gene hsp16.6 promoter, the small heat-shock protein (Hsp) promoter, the $CO_2$-responsive carbonic-anhydrase-gene promoters, the green/red light responsive cpcB2A2 promoter, the UV-light responsive lexA, recA and ruvB promoters, the nitrate-reductase-gene (narB) promoters, and combinations thereof.

In another embodiment, a cell-division-controllable designer photosynthetic organism is created by use of a carbonic anhydrase deficient mutant or a high-$CO_2$-requiring mutant as a host organism to create the designer biofuel-production organism. High-$CO_2$-requiring mutants that can be selected for use in this invention include (but not limited to): *Chlamydomonas reinhardtii* carbonic-anhydrase-deficient mutantl2-1C (CC-1219 cal mt-), *Chlamydomonas reinhardtii* cia3 mutant (*Plant Physiology* 2003, 132:2267-2275), the high-$CO_2$-requiring mutant M3 of *Synechococcus* sp. Strain PCC 7942, or the carboxysome-deficient cells of *Synechocystis* sp. PCC 6803 (*Plant biol* (Stuttg) 2005, 7:342-347) that lacks the $CO_2$-concentrating mechanism can grow photoautotrophically only under elevated $CO_2$ concentration level such as 0.2-3% $CO_2$.

Under atmospheric $CO_2$ concentration level (380 ppm), the carbonic anhydrase deficient or high-$CO_2$-requiring mutants commonly cannot survive. Therefore, the key concept here is that a high-$CO_2$-requiring designer biofuel-production organism that lacks the $CO_2$ concentrating mechanism will be grown and used for photobiological production of biofuels always under an elevated $CO_2$ concentration level (0.2-5% $CO_2$) in a sealed bioreactor with $CO_2$ feeding. Such a designer transgenic organism cannot survive when it is exposed to an atmospheric $CO_2$ concentration level (380 ppm=0.038% $CO_2$) because its $CO_2$-concetrating mechanism (CCM) for effective photosynthetic $CO_2$ fixation has been impaired by the mutation. Even if such a designer organism is accidentally released into the natural environment, its cell will soon not be able to divide or mate, but die quickly of carbon starvation since it cannot effectively perform photosynthetic $CO_2$ fixation at the atmospheric $CO_2$ concentration (380 ppm). Therefore, use of such a high-$CO_2$-requiring mutant as a host organism for the genetic transformation of the designer biofuel-production-pathway gene(s) represents another way in creating the envisioned cell-division-controllable designer organisms for biosafety-guarded photobiological production of biofuels from $CO_2$ and $H_2O$. No designer proton-channel gene is required here.

In another embodiment, a cell-division-controllable designer organism (FIG. 3B) is created by use of a designer cell-division-cycle regulatory gene as a biosafety-control gene (FIG. 2G) that can control the expression of the cell-division-cycle (cdc) genes in the host organism so that it can inducibly turn off its reproductive functions such as permanently shutting off the cell division and mating capability upon specific induction of the designer gene.

Biologically, it is the expression of the natural cdc genes that controls the cell growth and cell division cycle in cyanobacteria, algae, and higher plant cells. The most basic function of the cell cycle is to duplicate accurately the vast amount of DNA in the chromosomes during the S phase (S for synthesis) and then segregate the copies precisely into two genetically identical daughter cells during the M phase (M for mitosis). Mitosis begins typically with chromosome condensation: the duplicated DNA strands, packaged into elongated chromosomes, condense into the much-more compact chromosomes required for their segregation. The nuclear envelope then breaks down, and the replicated chromosomes, each consisting of a pair of sister chromatids, become attached to the microtubules of the mitotic spindle. As mitosis proceeds, the cell pauses briefly in a state called metaphase, when the chromosomes are aligned at the equator of the mitotic spindle, poised for segregation. The sudden segregation of sister chromatids marks the beginning of anaphase during which the chromosomes move to opposite poles of the spindle, where they decondense and reform intact nuclei. The cell is then pinched into two by cytoplasmic division (cytokinesis) and the cell division is then complete. Note, most cells require much more time to grow and double their mass of proteins and organelles than they require to replicate their DNA (the S phase) and divide (the M phase). Therefore, there are two gap phases: a $G_1$ phase between M phase and S phase, and a G2 phase between S phase and mitosis. As a result, the eukaryotic cell cycle is traditionally divided into four sequential phases: $G_1$, S, $G_2$, and M. Physiologically, the two gap phases also provide time for the cell to monitor the internal and external environment to ensure that conditions are suitable and preparation are complete before the cell commits itself to the major upheavals of S phase and mitosis. The $G_1$ phase is especially important in this aspect. Its length can vary greatly depending on external conditions and extracellular signals from other cells. If extracellular conditions are unfavorable, for example, cells delay progress through $G_1$ and may even enter a specialized resting state known as $G_0$ (G zero), in which they remain for days, weeks, or even for years before resuming proliferation. Indeed, many cells remain permanently in $G_0$ state until they die.

In one of the various embodiments, a designer gene(s) that encodes a designer cdc-regulatory protein or a specific cdc-iRNA is used to inducibly inhibit the expression of certain cdc gene(s) to stop cell division and disable the mating capability when the designer gene(s) is trigged by a specific inducing condition. When the cell-division-controllable designer culture is grown and ready for photosynthetic production of biofuels, for example, it is a preferred practice to induce the expression of a specific designer cdc-iRNA gene(s) along with induction of the designer biofuel-production-pathway gene(s) so that the cells will permanently halt at the $G_1$ phase or $G_0$ state. In this way, the grown designer-organism cells become perfect catalysts for photosynthetic production of biofuels from $CO_2$ and $H_2O$ while their functions of cell division and mating are permanently shut off at the $G_1$ phase or $G_0$ state to help ensure biosafety.

Figure 3A:
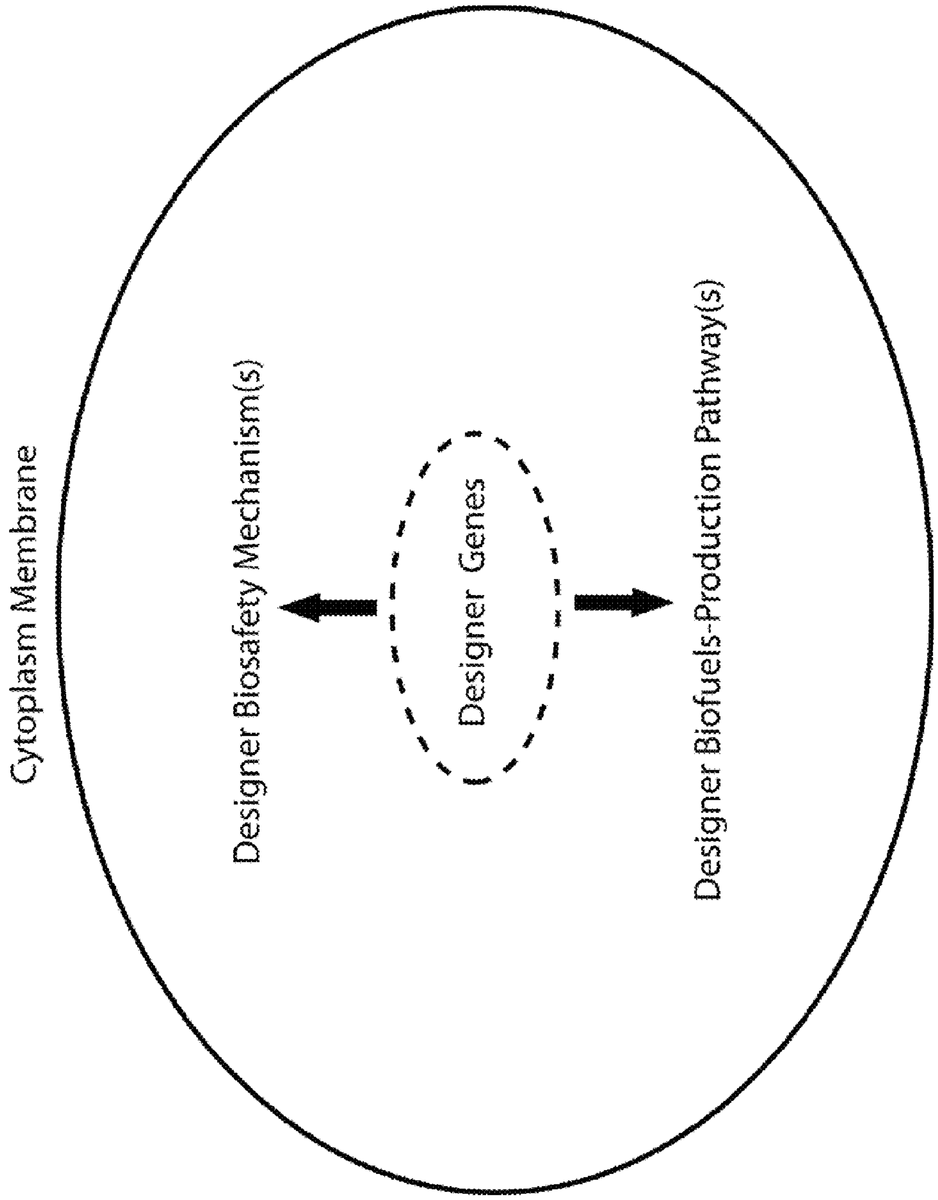
FIG. 3A illustrates a cell-division-controllable designer organism that contains two key functions: designer biosafety mechanism(s) and designer biofuel-production pathway(s).
Figure 3B:
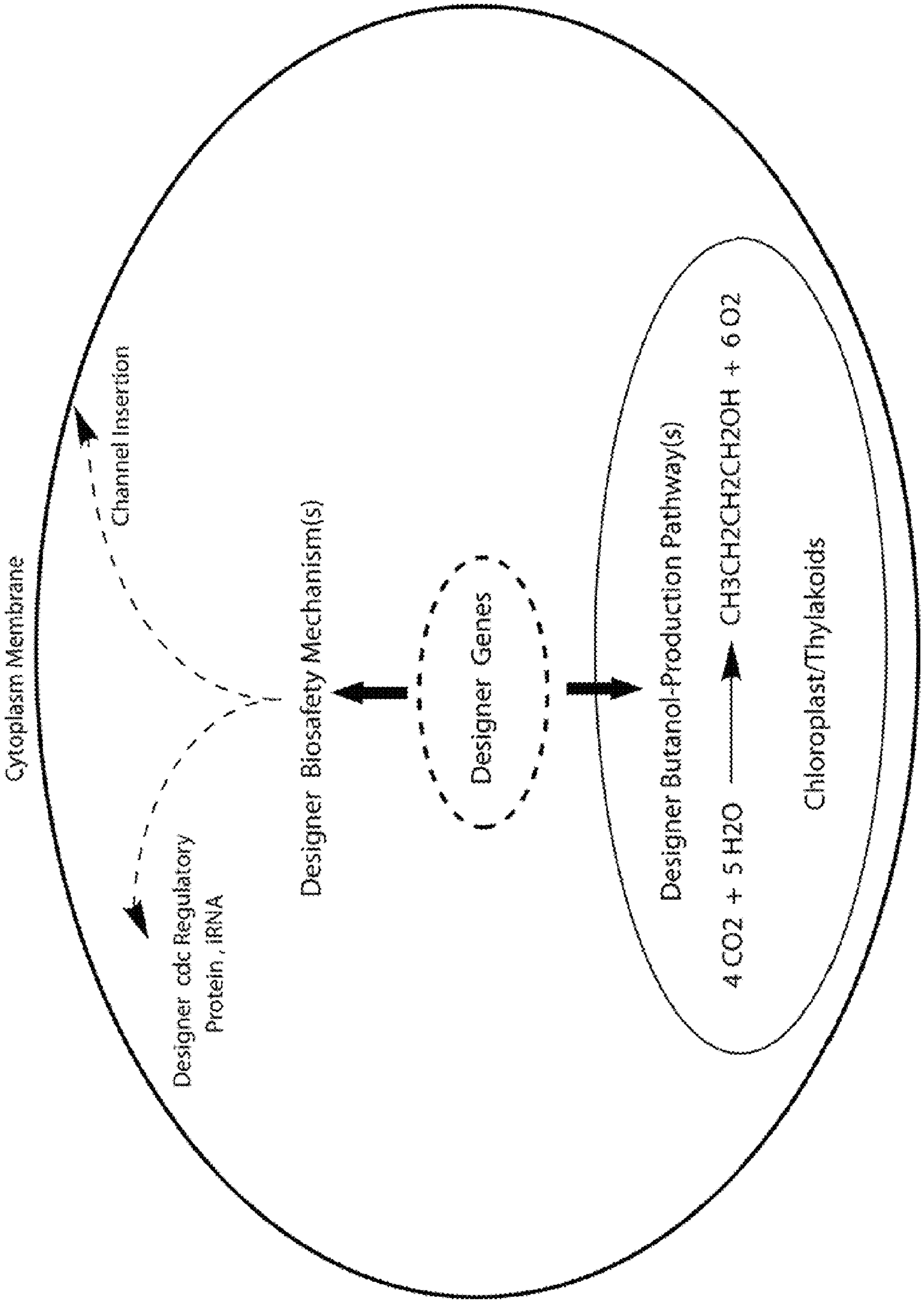
FIG. 3B illustrates a cell-division-controllable designer organism for photobiological production of butanol ($CH_3CH_2CH_2CH_2OH$) from carbon dioxide ($CO_2$) and water ($H_2O$) with designer biosafety mechanism(s).
Figure 3C:
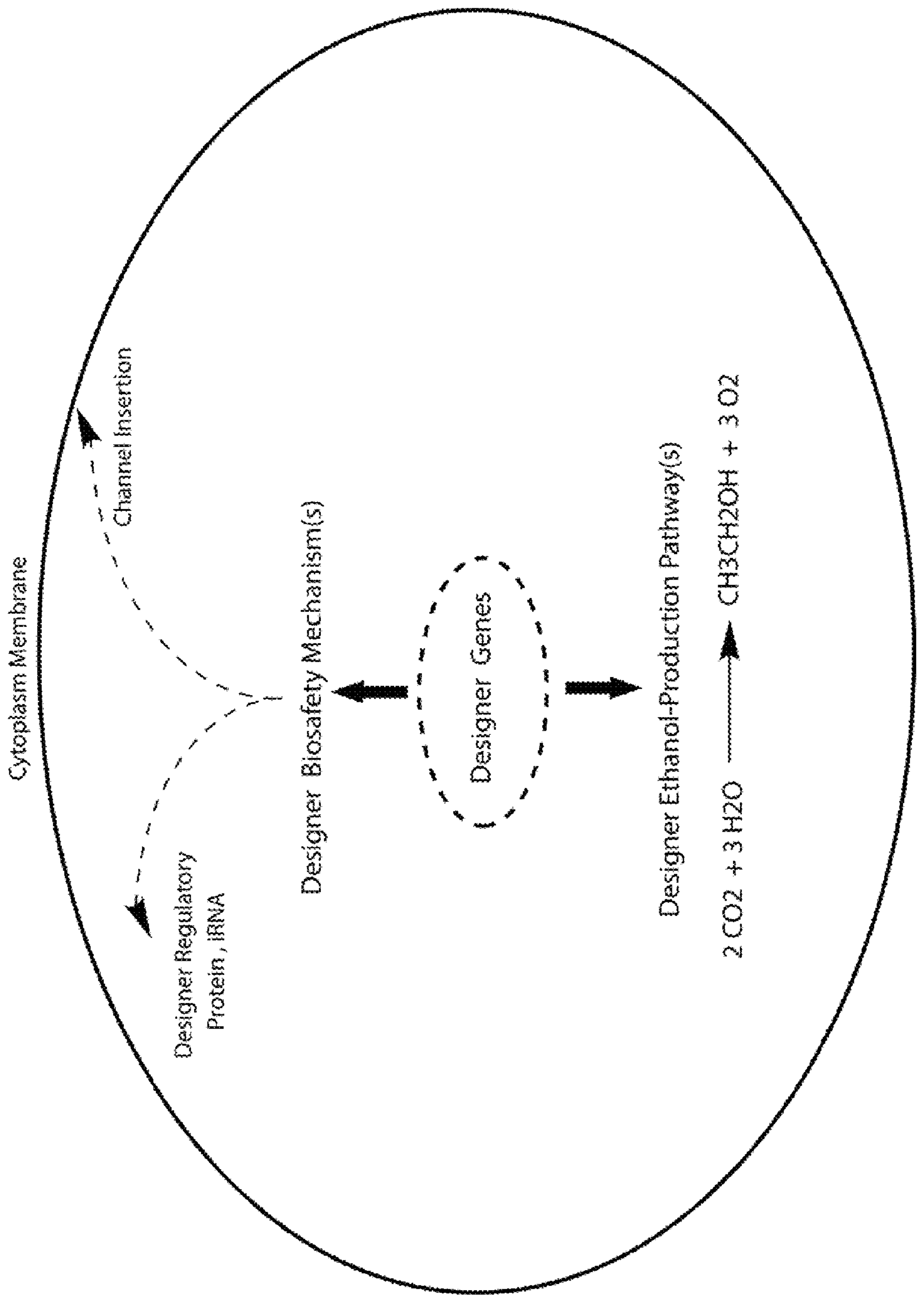
FIG. 3C illustrates a cell-division-controllable designer organism for biosafety-guarded photobiological production of other biofuels such as ethanol ($CH_3CH_2OH$) from carbon dioxide ($CO_2$) and water ($H_2O$).

Use of the biosafety embodiments with various designer biofuel-production-pathways genes listed in SEQ ID NOS: 1-45 (and 58-165) can create various biosafety-guarded photobiological biofuel producers (FIGS. 3A, 3B, and 3C). Note, SEQ ID NOS: 46 and 1-12 (examples 1-12) represent an example for a cell-division-controllable designer eukaryotic organism such as a cell-division-controllable designer alga (e.g., *Chlamydomonas*) that contains a designer Nia1-promoter-controlled proton-channel gene (SEQ ID NO: 46) and a set of designer Nia1-promoter-controlled butanol-production-pathway genes (SEQ ID NOS: 1-12). Because the designer proton-channel gene and the designer biofuel-production-pathway gene(s) are all controlled by the same Nia1-promoter sequences, they can be simultaneously expressed upon induction by adding nitrate fertilizer into the culture medium to provide the biosafety-guarded photosynthetic biofuel-producing capability as illustrated in FIG. 3B. Use of the designer Nia1-promoter-controlled butanol-production-pathway genes (SEQ ID NOS: 1-12) in a high $CO_2$-requiring host photosynthetic organism, such as *Chlamydomonas reinhardtii* carbonic-anhydrase-deficient mutant12-1C (CC-1219 cal mt-) or *Chlamydomonas reinhardtii* cia3 mutant, represents another example in creating a designer cell-division-controllable photosynthetic organism to help ensure biosafety.

This designer biosafety feature may be useful to the production of other biofuels such as biooils, biohydrogen, ethanol, and intermediate products as well. For example, this biosafety embodiment in combination with a set of designer ethanol-production-pathway genes such as those shown SEQ ID NOS: 47-53 can represent a cell-division-controllable ethanol producer (FIG. 3C). Briefly, SEQ ID NO: 47 presents example 47 for a detailed DNA construct (1360 base pairs (bp)) of a nirA-promoter-controlled designer NAD-dependent Glyceraldehyde-3-Phosphate-Dehydrogenase gene including: a PCR FD primer (sequence 1-20), a 88-bp nirA promoter (21-108) selected from the *Synechococcus* sp. strain PCC 7942 (freshwater cyanobacterium) nitrite-reductase-gene promoter sequence, an enzyme-encoding sequence (109-1032) selected and modified from a *Cyanidium caldarium* cytosolic NAD-dependent glyceraldehyde-3-phosphate-dehydrogenase sequence (GenBank accession number: CAC85917), a 308-bp *Synechococcus* sp. strain PCC 7942 rbcS terminator (1033-1340), and a PCR RE primer (1341-1360) at the 3' end.

SEQ ID NO: 48 presents example 48 for a designer nirA-promoter-controlled Phosphoglycerate Kinase DNA construct (1621 bp) that includes a PCR FD primer (sequence 1-20), a 88-bp *Synechococcus* sp. strain PCC 7942 nitrite-reductase nirA promoter (21-108), a phosphoglycerate-kinase-encoding sequence (109-1293) selected from a *Geobacillus kaustophilus* HTA426 phosphoglycerate-kinase sequence (GenBank: BAD77342), a 308-bp *Synechococcus* sp. strain PCC 7942 rbcS terminator (1294-1601), and a PCR RE primer (1602-1621).

SEQ ID NO: 49 presents example 49 for a designer nirA-promoter-controlled Phosphoglycerate-Mutase DNA construct (1990 bp) that includes a PCR FD primer (sequence 1-20), a 88-bp *Synechococcus* sp. strain PCC 7942 nitrite-reductase nirA promoter (21-108), a 9-bp Xho I NdeI site (109-117), a phosphoglycerate-mutase encoding sequence (118-1653) selected from the sequences of a *Caldicellulosiruptor saccharolyticus* DSM 8903 phosphoglycerate mutase (GenBank: ABP67536), a 9-bp XbaI site (1654-1662), a 308-bp *Synechococcus* sp. strain PCC 7942 rbcS terminator (1663-1970), and a PCR RE primer (1971-1990).

SEQ ID NO: 50 presents example 50 for a designer nirA-promoter-controlled Enolase DNA construct (1765 bp) that includes a PCR FD primer (sequence 1-20), a 88-bp *Synechococcus* sp. strain PCC 7942 nitrite reductase nirA promoter (21-108), a 9-bp Xho I NdeI site (109-117), an enolase-encoding sequence (118-1407) selected from the sequence of a *Cyanothece* sp. CCY0110 enolase (GenBank: ZP_01727912), a 21-bp Lumio-tag-encoding sequence (1408-1428), a 9-bp XbaI site (1429-1437) containing a stop codon, a 308-bp *Synechococcus* sp. strain PCC 7942 rbcS terminator (1438-1745), and a PCR RE primer (1746-1765) at the 3' end.

SEQ ID NO: 51 presents example 51 for a designer nirA-promoter-controlled Pyruvate Kinase DNA construct (1888 bp) that includes a PCR FD primer (sequence 1-20), a 88-bp *Synechococcus* sp. strain PCC 7942 nitrite reductase nirA promoter (21-108), a 9-bp Xho I NdeI site (109-117), a Pyruvate-Kinase-encoding sequence (118-1530) selected from a *Selenomonas ruminantium* Pyruvate Kinase sequence (GenBank: AB037182), a 21-bp Lumio-tag sequence (1531-1551), a 9-bp XbaI site (1552-1560), a 308-bp *Synechococcus* sp. strain PCC 7942 rbcS terminator (1561-1868), and a PCR RE primer (1869-1888).

SEQ ID NO: 52 presents example 52 for a designer nirA-promoter-controlled Pyruvate Decarboxylase DNA construct (2188 bp) that includes a PCR FD primer (sequence 1-20), a 88-bp *Synechococcus* sp. strain PCC 7942 nitrite reductase nirA promoter (21-108), a 9-bp Xho I NdeI site (109-117), a Pyruvate-Decarboxylase-encoding sequence (118-1830) selected from the sequences of a *Pichia stipitis* pyruvate-decarboxylase sequence (GenBank: XM_001387668), a 21-bp Lumio-tag sequence (1831-1851), a 9-bp XbaI site (1852-1860), a 308-bp *Synechococcus* sp. strain PCC 7942 rbcS terminator (1861-2168), and a PCR RE primer (2169-2188) at the 3' end.

SEQ ID NO: 53 presents example 53 for a nirA-promoter-controlled designer NAD(P)H-dependent Alcohol Dehydrogenase DNA construct (1510 bp) that includes a PCR FD primer (sequence 1-20), a 88-bp *Synechococcus* sp. strain PCC 7942 nitrite-reductase nirA promoter (21-108), a NAD(P)H dependent Alcohol-Dehydrogenase-encoding sequence (109-1161) selected/modified (its mitochondrial signal peptide sequence removed) from the sequence of a *Kluyveromyces lactis* alcohol dehydrogenase (ADH3) gene (GenBank: X62766), a 21-bp Lumio-tag sequence (1162-1182), a 308-bp *Synechococcus* sp. strain PCC 7942 rbcS terminator (1183-1490), and a PCR RE primer (1491-1510) at the 3' end.

Note, SEQ ID NOS: 47-53 (DNA-construct examples 47-53) represent a set of designer nirA-promoter-controlled ethanol-production-pathway genes that can be used in oxyphotobacteria such as *Synechococcus* sp. strain PCC 7942. Use of this set of designer ethanol-production-pathway genes in a high-$CO_2$-requiring cyanobacterium such as the *Synechococcus* sp. Strain PCC 7942 mutant M3 represents another example of cell-division-controllable designer cyanobacterium for biosafety-guarded photosynthetic production of biofuels from $CO_2$ and $H_2O$.

More on Designer Calvin-Cycle-Channeled Production of Butanol and Related Higher Alcohols The present invention further discloses designer Calvin-cycle-channeled and photosynthetic-NADPH (reduced nicotinamide adenine dinucleotide phosphate)-enhanced pathways, associated designer DNA constructs (designer genes) and designer transgenic photosynthetic organisms for photobiological production of butanol and related higher alcohols from carbon dioxide and water. In this context throughout this specification as mentioned before, a "higher alcohol" or "related higher alcohol" refers to an alcohol that comprises at least four carbon atoms, including both straight and branched higher alcohols such as 1-butanol and 2-methyl-1-butanol. The Calvin-cycle-channeled and photosynthetic-NADPH-enhanced pathways are constructed with designer enzymes expressed through use of designer genes in host photosynthetic organisms such as algae and oxyphotobacteria (including cyanobacteria and oxychlorobacteria) organisms for photobiological production of butanol and related higher alcohols. The said butanol and related higher alcohols are selected from the group consisting of: 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, and 6-methyl-1-heptanol. The designer photosynthetic organisms such as designer transgenic algae and oxyphotobacteria (including cyanobacteria and oxychlorobacteria) comprise designer Calvin-cycle-channeled and photosynthetic NADPH-enhanced pathway gene(s) and biosafety-guarding technology for enhanced photobiological production of butanol and related higher alcohols from carbon dioxide and water.

Photosynthetic water splitting and its associated proton gradient-coupled electron transport process generates chemical energy intermediate in the form of adenosine triphosphate (ATP) and reducing power in the form of reduced nicotinamide adenine dinucleotide phosphate (NADPH). However, certain butanol-related metabolic pathway enzymes such as the NADH-dependent butanol dehydrogenase (GenBank accession numbers: YP_148778, NP_561774, AAG23613, ZP_05082669, AD012118, ADC48983) can use only reduced nicotinamide adenine dinucleotide (NADH) but not NADPH. Therefore, to achieve a true coupling of a designer pathway with the Calvin cycle for photosynthetic production of butanol and related higher alcohols, it is a preferred practice to use an effective NADPH/NADH conversion mechanism and/or NADPH-using enzyme(s) (such as NADPH-dependent enzymes) in construction of a compatible designer pathway(s) to couple with the photosynthesis/Calvin-cycle process in accordance with the present invention.

According to one of the various embodiments, a number of various designer Calvin-cycle-channeled pathways can be created by use of an NADPH/NADH conversion mechanism in combination with certain amino-acids-metabolic pathways for production of butanol and higher alcohols from carbon dioxide and water. The Calvin-cycle-channeled and photosynthetic-NADPH-enhanced pathways are constructed typically with designer enzymes that are selectively expressed through use of designer genes in a host photosynthetic organism such as a host alga or oxyphotobacterium for production of butanol and higher alcohols. A list of exemplary enzymes that can be selected for use in construction of the Calvin-cycle-channeled and photosynthetic-NADPH-enhanced pathways are presented in Table 2. As shown in FIGS. 4-10, the net results of the designer Calvin-cycle-channeled and photosynthetic NADPH-enhanced pathways in working with the Calvin cycle are production of butanol and related higher alcohols from carbon dioxide ($CO_2$) and water ($H_2O$) using photosynthetically generated ATP (Adenosine triphosphate) and NADPH (reduced nicotinamide adenine dinucleotide phosphate). A significant feature is the innovative utilization of an NADPH-dependent glyceraldehyde-3-phosphate dehydrogenase 34 and a nicotinamide adenine dinucleotide (NAD)-dependent glyceraldehyde-3-phosphate dehydrogenase 35 to serve as a NADPH/NADH conversion mechanism that can convert certain amount of photosynthetically generated NADPH to NADH which can then be used by NADH-requiring pathway enzymes such as an NADH-dependent alcohol dehydrogenase 43 (examples of its encoding gene with GenBank accession numbers are: BAB59540, CAA89136, NP_148480) for production of butanol and higher alcohols.

More specifically, an NADPH-dependent glyceraldehyde-3-phosphate dehydrogenase 34 (e.g., GenBank accession numbers: ADC37857, ADC87332, YP_003471459, ZP_04395517, YP_003287699, ZP_07004478, ZP_04399616) catalyzes the following reaction that uses NADPH in reducing 1,3-Diphosphoglycerate (1,3-DiPGA) to 3-Phosphoglyaldehyde (3-PGAld) and inorganic phosphate (Pi):

$$1,3\text{-DiPGA}+\text{NADPH}+\text{H}^+\rightarrow 3\text{-PGAld}+\text{NADP}^+ +\text{Pi} \quad [3]$$

Meanwhile, an NAD-dependent glyceraldehyde-3-phosphate dehydrogenase 35 (e.g., GenBank: ADM41489, YP_003095198, ADC36961, ZP_07003925, ACQ61431, YP_002285269, ADN80469, ACI60574) catalyzes the oxidation of 3-PGAld by oxidized nicotinamide adenine dinucleotide ($NAD^+$) back to 1,3-DiPGA:

$$3\text{-PGAld}+\text{NAD}^+ +\text{Pi}\rightarrow 1,3\text{-DiPGA}+\text{NADH}+\text{H}^+ \quad [4]$$

The net result of the enzymatic reactions [3] and [4] is the conversion of photosynthetically generated NADPH to NADH, which various NADH-requiring designer pathway enzymes such as NADH-dependent alcohol dehydrogenase 43 can use in producing butanol and related higher alcohols. When there is too much NADH, this NADPH/NADH conversion system can run also reversely to balance the supply of NADH and NADPH. Therefore, it is a preferred practice to innovatively utilize this NADPH/NADH conversion system under control of a designer switchable promoter such as nirA (or Nia1 for eukaryotic system) promoter when/if needed to achieve robust production of butanol and related higher alcohols. Various designer Calvin-cycle-channeled pathways in combination of a NADPH/NADH conversion mechanism with certain amino-acids-metabolism-related pathways for photobiological production of butanol and related higher alcohols are further described hereinbelow.

Table 2 lists examples of enzymes for construction of designer Calvin-cycle-linked pathways for production of butanol and related higher alcohols.

| Enzyme/callout number | Source (Organism) | GenBank Accession Number, JGI Protein ID or Citation |
|---|---|---|
| 03: Phosphoglycerate mutase (phosphoglyceromutase) | *Oceanithermus profundus* DSM 14977;<br>'*Nostoc azollae*' 0708;<br>*Thermotoga lettingae* TMO;<br>*Syntrophothermus lipocalidus* DSM 12680; | ADR35708;<br>ADI65627, YP_003722750;<br>YP_001470593, ABV33529;<br>ADI02216, YP_003702781;<br>YP_001212148;<br>YP_001409891; |

-continued

| Enzyme/callout number | Source (Organism) | GenBank Accession Number, JGI Protein ID or Citation |
|---|---|---|
| | *Pelotomaculum thermopropionicum* SI; *Fervidobacterium nodosum* Rt17-B1; *Caldicellulosiruptor bescii* DSM 6725; *Fervidobacterium nodosum* Rt17-B1; *Thermotoga petrophila* RKU-1; *Deferribacter desulfuricans* SSM1; *Cyanobium* sp. PCC 7001; *Cyanothece* sp. PCC 8802; *Chlamydomonas reinhardtii* cytoplasm; *Aspergillus fumigatus*; *Coccidioides immitis*; *Leishmania braziliensis*; *Ajellomyces capsulatus*; *Monocercomonoides* sp.; *Aspergillus clavatus*; *Arabidopsis thaliana*; *Zea mays* | YP_002573254, YP_002573195; ABS60234; ABQ47079, YP_001244998; YP_003496402, BAI80646; ZP_05046421; YP_003138980, YP_003138979; JGI Chlre2 protein ID 161689, GenBank: AF268078; XM_747847; XM_749597; XM_001248115; XM_001569263; XM_001539892; DQ665859; XM_001270940; NM_117020; M80912 |
| 04: Enolase | *Syntrophothermus lipocalidus* DSM 12680; '*Nostoc azollae*' 0708; *Thermotoga petrophila* RKU-1; *Spirochaeta thermophila* DSM 6192; *Cyanothece* sp. PCC 7822; *Hydrogenobacter thermophilus* TK-6; *Thermosynechococcus elongatus* BP-1, *Prochlorococcus marinus* str. MIT 9301; *Synechococcus* sp. WH 5701; *Trichodesmium erythraeum* IMS101; *Anabaena variabilis* ATCC 29413; *Nostoc* sp. PCC 7120; *Chlamydomonas reinhardtii* cytoplasm; *Arabidopsis thaliana*; *Leishmania Mexicana*; *Lodderomyces elongisporus*; *Babesia bovis*; *Sclerotinia sclerotiorum*; *Pichia guilliermondii*; *Spirotrichonympha leidyi*; *Oryza sativa*; *Trimastix pyriformis*; *Leuconostoc mesenteroides*; *Davidiella tassiana*; *Aspergillus oryzae*; *Schizosaccharomyces pombe*; *Brassica napus*; *Zea mays* | ADI02602, YP_003703167; ADI63801; ABQ46079; YP_003875216, ADN02943; YP_003886899, ADN13624; YP_003432637, BAI69436; BAC08209; ABO16851; ZP_01083626; ABG51970; ABA23124; BAB75237; GenBank: X66412, P31683; AK222035; DQ221745; XM_001528071; XM_001611873; XM_001594215; XM_001483612; AB221057; EF122486, U09450; DQ845796; AB088633; U82438; D64113; U13799; AY307449; U17973 |
| 05: Pyruvate kinase | *Syntrophothermus lipocalidus* DSM 12680; *Cyanothece* sp. PCC 8802; *Thermotoga lettingae* TMO; *Caldicellulosiruptor bescii* DSM 6725; *Geobacillus kaustophilus* HTA426; *Thermosynechococcus elongatus* BP-1; *Thermosipho melanesiensis* BI429; *Thermotoga petrophila* RKU-1; *Caldicellulosiruptor saccharolyticus* DSM 8903; *Cyanothece* sp. PCC 7425; *Acaryochloris marina* MBIC11017; *Cyanothece* sp. PCC 8801; *Microcystis aeruginosa* NIES-843; *Cyanothece* sp. PCC 7822; *cyanobacterium* UCYN-A; *Arthrospira maxima* CS-328; *Synechococcus* sp. PCC 7335; *Chlamydomonas reinhardtii* cytoplasm; *Arabidopsis thaliana*; *Saccharomyces cerevisiae*; *Babesia bovis*; *Sclerotinia sclerotiorum*; *Trichomonas vaginalis*; *Pichia guilliermondii*; *Pichia stipitis*; *Lodderomyces elongisporus*; *Coccidioides immitis*; *Trimastix pyriformis*; *Glycine max* (soybean) | ADI02459, YP_003703024; YP_002372431; YP_001471580, ABV34516; YP_002573139; YP_148872; NP_681306, BAC08068; YP_001306168, ABR30783; YP_001244312, ABQ46736; ABP67416, YP_001180607; ACL43749, YP_002482578; YP_001514814; YP_003138017; YP_001655408; YP_003890281; YP_003422225; ZP_03273505; ZP_05035056; JGI Chlre3 protein ID 138105; GenBank: AK229638; AY949876, AY949890, AY949888; XM_001612087; XM_001594710; XM_001329865; XM_001487289; XM_001384591; XM_001528210; XM_001240868; DQ845797; L08632 |
| 06a: Pyruvate-NADP$^+$ oxidoreductase | *Peranema trichophorum*; *Euglena gracilis* | GenBank: EF114757; AB021127, AJ278425 |

-continued

| Enzyme/callout number | Source (Organism) | GenBank Accession Number, JGI Protein ID or Citation |
|---|---|---|
| 06b: Pyruvate-ferredoxin oxidoreductase | *Mastigamoeba balamuthi*; *Desulfovibrio africanus*; *Entamoeba histolytica*; *Trichomonas vaginalis*; *Cryptosporidium parvum*; *Cryptosporidium baileyi*; *Giardia lamblia*; *Entamoeba histolytica*; *Hydrogenobacter thermophilus*; *Clostridium pasteurianum*; | GenBank: AY101767; Y09702; U30149; XM_001582310, XM_001313670, XM_001321286, XM_001307087, XM_001311860, XM_001314776, XM_001307250; EF030517; EF030516; XM_764947; XM_651927; AB042412; Y17727 |
| 07: Thiolase | *Butyrivibrio fibrisolvens*; butyrate-producing bacterium L2-50; *Thermoanaerobacterium thermosaccharolyticum*; | GenBank: AB190764; DQ987697; Z92974; |
| 08: 3-Hydroxybutyryl-CoA dehydrogenase | *Clostridium beijerinckii*; *Butyrivibrio fibrisolvens*; *Ajellomyces capsulatus*; *Aspergillus fumigatus*; *Aspergillus clavatus*; *Neosartorya fischeri*; Butyrate-producing bacterium L2-50; *Arabidopsis thaliana*; *Thermoanaerobacterium thermosaccharolyticum*; | GenBank: AF494018; AB190764; XM_001537366; XM_741533; XM_001274776; XM_001262361; DQ987697; BT001208; Z92974; |
| 09: Crotonase | *Clostridium beijerinckii*;*Butyrivibrio fibrisolvens*; Butyrate-producing bacterium L2-50; *Thermoanaerobacterium thermosaccharolyticum*; | GenBank: AF494018; AB190764; DQ987697; Z92974 |
| 10: Butyryl-CoA dehydrogenase | *Clostridium beijerinckii*; *Butyrivibrio fibrisolvens*; Butyrate-producing bacterium L2-50; *Thermoanaerobacterium thermosaccharolyticum*; | GenBank: AF494018; AB190764; DQ987697; Z92974 |
| 11: Butyraldehyde dehydrogenase | *Clostridium saccharoperbutylacetonicum* | GenBank: AY251646 |
| 12a: NADH-dependent Butanol dehydrogenase | *Geobacillus kaustophilus* HTA426; *Clostridium perfringens* str. 13; *Carboxydothermus hydrogenoformans*; *Pseudovibrio* sp. JE062; *Clostridium carboxidivorans* P7; *Bacillus pseudofirmus* OF4; *Oceanobacillus iheyensis* HTE831; *Slackia exigua* ATCC 700122; *Fusobacterium ulcerans* ATCC 49185; *Listeria monocytogenes* FSL J1-175; *Chlorobium chlorochromatii* CaD3; *Clostridium perfringens* D str. JGS1721; *Clostridium perfringens* NCTC 8239; *Clostridium perfringens* CPE str. F4969; *Clostridium perfringens* B str. ATCC 3626; *Clostridium botulinum* NCTC 2916; *Nostoc* sp. PCC 7120; | YP_148778, BAD77210; NP_561774, BAB80564; AAG23613; ZP_05082669, EEA96294; ADO12118; ADC48983, YP_003425875; NP_693981, BAC15015; ZP_06159969, EEZ61452; ZP_05633940; ZP_05388801; ABB28961; ZP_02952811; ZP_02641897; ZP_02638128; ZP_02634798; EDT24774; ZP_02614964, ZP_02614746; NP_488606, BAB76265; |
| 12b: NADPH-dependent Butanol dehydrogenase | *Clostridium perfringens* str. 13; *Clostridium saccharobutylicum*; *Subdoligranulum* variabile DSM 15176; *Butyrivibrio crossotus* DSM 2876; *Oribacterium* sp. oral taxon 078 str. F0262; *Clostridium* sp. M62/1; *Clostridium hathewayi* DSM 13479; *Subdoligranulum* variabile DSM 15176; *Faecalibacterium prausnitzii* A2-165; *Blautia hansenii* DSM 20583; *Roseburia intestinalis* L1-82, *Bacillus cereus* Rock3-28; *Eubacterium rectale* ATCC 33656; *Clostridium* sp. HGF2; *Atopobium rimae* ATCC 49626; *Clostridium perfringens* D str. JGS1721; *Clostridium perfringens* NCTC 8239; *Clostridium butyricum* 5521; *Clostridium carboxidivorans* P7; | NP_562172, BAB80962; AAA83520; EFB77036; EFF67629, ZP_05792927; ZP_06597730, EFE92592; EFE12215, ZP_06346636; EFC98086, ZP_06115415; ZP_05979561; ZP_05615704, EEU95840; ZP_05853889, EEX22072; ZP_04745071, EEU99657; ZP_04236939, EEL31374; YP_002938098, ACR75964; EFR36834; ZP_03568088; ZP_02952006; ZP_02642725; ZP_02950013, ZP_02950012; ZP_06856327; YP_001922606, |

-continued

| Enzyme/callout number | Source (Organism) | GenBank Accession Number, JGI Protein ID or Citation |
| --- | --- | --- |
| | *Clostridium botulinum* E3 str. Alaska E43; *Clostridium novyi* NT; *Clostridium botulinum* B str. Eklund 17B; *Thermococcus* sp. AM4; *Fusobacterium* sp. D11; *Anaerococcus vaginalis* ATCC 51170; *Clostridium perfringens* CPE str. F4969; *Clostridium perfringens* B str. ATCC 3626; | YP_001922335, ACD52989; YP_878939; YP_001887401; EEB74113; EFD81183; ZP_05473100, EEU12061; EDT27639; EDT24389; |
| 13: Starch synthase | *Chlamydomonas reinhardtii*; *Phaseolus vulgaris*; *Oryza sativa*; *Arabidopsis thaliana*; *Colocasia esculenta*; *Amaranthus cruentus*; *Parachlorella kessleri*; *Triticum aestivum*; *Sorghum bicolor*; *Astragalus membranaceus*; *Perilla frutescens*; *Zea mays*; *Ipomoea batatas* | GenBank: AF026422, AF026421, DQ019314, AF433156; AB293998; D16202, AB115917, AY299404; AF121673, AK226881; NM_101044; AY225862, AY142712; DQ178026; AB232549; Y16340; AF168786; AF097922; AF210699; AF019297; AF068834 |
| 14: Glucose-1-phosphate adenylyltransferase | *Arabidopsis thaliana*; *Zea mays*; *Chlamydia trachomatis*; *Solanum tuberosum* (potato); *Shigella flexneri*; *Lycopersicon esculentum* | GenBank: NM_127730, NM_124205, NM_121927, AY059862; EF694839, EF694838; AF087165; P55242; NP_709206; T07674 |
| 15: Phosphoglucomutase | *Oryza sativa* plastid; *Ajellomyces capsulatus*; *Pichia stipitis*; *Lodderomyces elongisporus*; *Aspergillus fumigatus*; *Arabidopsis thaliana*; *Populus tomentosa*; *Oryza sativa*; *Zea mays* | GenBank: AC105932, AF455812; XM_001536436; XM_001383281; XM_001527445; XM_749345; NM_124561, NM_180508, AY128901; AY479974; AF455812; U89342, U89341 |
| 16: Hexose-phosphate-isomerase | *Staphylococcus carnosus* subsp. *carnosus* TM300; | YP_002633806, CAL27621; |
| 17: Alpha-amylase; | *Hordeum vulgare* aleuron cells; *Trichomonas vaginalis*; *Phanerochaete chrysosporium*; *Chlamydomonas reinhardtii*; *Arabidopsis thaliana*; *Dictyoglomus thermophilum* heat-stable amylase gene; | GenBank: J04202; XM_001319100; EF143986; AY324649; NM_129551; X07896; |
| Beta-amylase; | *Arabidopsis thaliana*; *Hordeum vulgare*; *Musa acuminate*; | GenBank: NM_113297; D21349; DQ166026; |
| Starch phosphorylase; | Citrus hybrid cultivar root; *Solanum tuberosum* chloroplast; *Arabidopsis thaliana*; *Triticum aestivum*; *Ipomoea batatas*; | GenBank: AY098895; P53535; NM_113857, NM_114564; AF275551; M64362 |
| 18: Glucose-phosphate (glucose-6-phosphate) isomerase | *Chlamydomonas reinhardtii*; *Saccharomyces cerevisiae*; *Pichia stipitis*; *Ajellomyces capsulatus*; *Spinacia oleracea* cytosol; *Oryza sativa* cytoplasm; *Arabidopsis thaliana*; *Zea mays* | JGI Chlre3 protein ID 135202; GenBank: M21696; XM_001385873; XM_001537043; T09154; P42862; NM_123638, NM_118595; U17225 |
| 19: Phosphofructose kinase | *Chlamydomonas reinhardtii*; *Arabidopsis thaliana*; *Ajellomyces capsulatus*; *Yarrowia lipolytica*; *Pichia stipitis*; *Dictyostelium discoideum*; *Tetrahymena thermophila*; *Trypanosoma brucei*; *Plasmodium falciparum*; *Spinacia oleracea*; | JGI Chlre2 protein ID 159495; GenBank: NM_001037043, NM_179694, NM_119066, NM_125551; XM_001537193; AY142710; XM_001382359, XM_001383014; XM_639070; XM_001017610; XM_838827; XM_001347929; DQ437575; |
| 20: Fructose-diphosphate aldolase | *Chlamydomonas reinhardtii* chloroplast; *Fragaria* x *ananassa* cytoplasm; *Homo sapiens*; *Babesia bovis*; *Trichomonas vaginalis*; *Pichia stipitis*; *Arabidopsis thaliana* | GenBank: X69969; AF308587; NM_005165; XM_001609195; XM_001312327, XM_001312338; XM_001387466; NM_120057, NM_001036644 |
| 21: Triose phosphate isomerase | *Arabidopsis thaliana*; *Chlamydomonas reinhardtii*; *Sclerotinia sclerotiorum*; *Chlorella pyrenoidosa*; *Pichia guilliermondii*; *Euglena intermedia*; *Euglena longa*; *Spinacia oleracea*; *Solanum chacoense*; *Hordeum vulgare*; *Oryza sativa* | GenBank: NM_127687, AF247559; AY742323; XM_001587391; AB240149; XM_001485684; DQ459379; AY742325; L36387; AY438596; U83414; EF575877; |

-continued

| Enzyme/callout number | Source (Organism) | GenBank Accession Number, JGI Protein ID or Citation |
|---|---|---|
| 34: NADPH-dependent Glyceraldehyde-3-phosphate dehydrogenase | *Staphylococcus aureus* 04-02981; | ADC37857; |
| | *Staphylococcus lugdunensis*; | ADC87332; |
| | *Staphylococcus lugdunensis* HKU09; | YP_003471459; |
| | *Vibrio cholerae* BX 330286; | ZP_04395517; |
| | *Vibrio* sp. Ex25; | YP_003287699; |
| | *Pseudomonas savastanoi* pv.; | ZP_07004478, EFI00105; |
| | *Vibrio cholerae* B33; | ZP_04399616 |
| | *Grimontia hollisae* CIP 101886; | ZP_06052988, EEY71738; |
| | *Vibrio mimicus* MB-451, | ZP_06041160; |
| | *Vibrio coralliilyticus* ATCC BAA-450; | ZP_05886203; |
| | *Vibrio cholerae* MJ-1236; | YP_002876243; |
| | *Zea mays* cytosolic NADP dependent; | NP_001105589; |
| | *Apium graveolens*; | AAF08296; |
| | *Vibrio cholerae* B33; | EEO17521; |
| | *Vibrio cholerae* TMA 21; | EEO13209; |
| | *Vibrio cholerae* bv. *albensis* VL426; | EEO01829; |
| | *Vibrio orientalis* CIP 102891; | ZP_05943395; |
| | *Vibrio cholerae* MJ-1236; | ACQ62447; |
| | *Vibrio cholerae* CT 5369-93; | ZP_06049761; |
| | *Vibrio* sp. RC586; | ZP_06079970; |
| | *Vibrio furnissii* CIP 102972; | ZP_05878983; |
| | *Vibrio metschnikovii* CIP 69.14; | ZP_05883187; |
| 35: NAD-dependent Glyceraldehyde-3-phosphate dehydrogenase | *Edwardsiella tarda* FL6-60; | ADM41489; |
| | *Flavobacteriaceae bacterium* 3519-10; | YP_003095198; |
| | *Staphylococcus aureus* 04-02981; | ADC36961; |
| | *Pseudomonas savastanoi* pv. | ZP_07003925; |
| | *savastanoi* NCPPB 3335; | ACQ61431, YP_002878104; |
| | *Vibrio cholerae* MJ-1236; | YP_002285269; |
| | *Streptococcus pyogenes* NZ131; | ADN80469; |
| | *Helicobacter pylori* 908; | ACI60574; |
| | *Streptococcus pyogenes* NZ131; | ADC88142; |
| | *Staphylococcus lugdunensis* HKU09; | ACY51070; |
| | *Vibrio* sp. Ex25; | ADK67090; |
| | *Stenotrophomonas chelatiphaga*; | ADK67075; |
| | *Pseudoxanthomonas dokdonensis*; | ADK67085, ACH90636; |
| | *Stenotrophomonas maltophilia*; | ZP_04401333; |
| | *Vibrio cholerae* B33; *Photobacterium* | ZP_06155532; |
| | *damselae* subsp. *damselae* CIP | ZP_06080908; |
| | 102761; *Vibrio* sp. RC586; | ZP_06052393; |
| | *Grimontia hollisae* CIP 101886; | EEX42220; |
| | *Vibrio furnissii CIP 102972;* | ZP_05292346; |
| | *Acidithiobacillus caldus* ATCC 51756; | CAC41000; |
| | *Nostoc* sp. PCC 7120; | EEO22474; |
| | *Vibrio cholerae* BX 330286; | EEO13042; |
| | *Vibrio cholerae* TMA 21; | CAC41000; |
| | *Nostoc* sp. PCC 7120; | CAA04942; |
| | *Pinus sylvestris*; | ACO58643, ACO58642; |
| | *Cheilanthes yavapensis*; | ACO58624, ACO58623; |
| | *Cheilanthes wootonii*; | CBH41484, CBH41483; |
| | *Astrolepis laevis*; | |
| 36: (R)-Citramalate Synthase (EC 2.3.1.182) | *Hydrogenobacter thermophilus* TK-6; | YP_003433013, ADO45737, |
| | *Geobacter bemidjiensis* Bem; | BAI69812; |
| | *Geobacter sulfurreducens* KN400; | ACH38284; |
| | *Methanobrevibacter ruminantium* M1; | ADI84633; |
| | *Leptospira biflexa serovar Patoc* | CP001719; |
| | strain 'Patoc 1 (Paris)'; *Leptospira* | ABK13757; |
| | *biflexa serovar Monteralerio*; | ABK13756; |
| | *Leptospira interrogans serovar* | ABK13755; |
| | *Australis*; *Leptospira interrogans* | ABK13753; |
| | *serovar Pomona*; *Leptospira* | ABK13754; |
| | *interrogans serovar Autumnalis*; | ABK13752; |
| | *Leptospira interrogans serovar* | ABK13751; |
| | *Pyrogenes*; *Leptospira interrogans* | ABK13750; |
| | *serovar Canicola*; *Leptospira* | ABK13749; |
| | *interrogans serovar Lai*; | ADL11763, |
| | *Acetohalobium arabaticum* DSM | YP_003998693; |
| | 5501; *Leadbetterella byssophila* DSM | CBK66631; |
| | 17132; *Bacteroides xylanisolvens* | EFQ72644; |
| | XB1A; *Mucilaginibacter paludis* DSM | ADE82919; |
| | 18603; *Prevotella ruminicola* 23; | ABQ04337; |
| | *Flavobacterium johnsoniae* UW101; | ZP_06244204, |
| | *Victivallis vadensis* ATCC BAA-548; | EFA99692; |
| | *Prevotella copri* DSM 18205; | EFB36404, ZP_06251228; |

-continued

| Enzyme/callout number | Source (Organism) | GenBank Accession Number, JGI Protein ID or Citation |
|---|---|---|
| | *Alistipes shahii* WAL 8301; | CBK64953; |
| | *Methylobacter tundripaludum* SV96; | ZP_07654184; |
| | *Methanosarcina mazei* Go1; | NP_632695; |
| 37: | *Eubacterium eligens* ATCC 27750 | YP_002930810, |
| (R)-2-Methylmalate | *Methanocaldococcus jannaschii*; | YP_002930809; |
| dehydratase (large and | *Sebaldella termitidis* ATCC 33386; | P81291; |
| small subunits) | *Eubacterium eligens* ATCC 27750; | ACZ06998; |
| (EC 4.2.1.35) | | ACR72362, ACR72361, |
| | | ACR72363, YP_002930808; |
| 38: | *Thermotoga petrophila* RKU-1; | ABQ46641, ABQ46640; |
| 3-Isopropylmalate | *Cyanothece* sp. PCC 7822; | YP_003886427, |
| dehydratase (large + | *Syntrophothermus lipocalidus* DSM | YP_003889452; |
| small subunits) | 12680; | ADI02900, ADI02899, |
| (EC 4.2.1.33) | *Caldicellulosiruptor saccharolyticus* | YP_003703465, ADI01294; |
| | DSM 8903; | ABP66933, ABP66934; |
| | *Pelotomaculum thermopropionicum* | YP_001211082, |
| | SI, | YP_001211083; |
| | *Caldicellulosiruptor bescii* DSM 6725; | YP_002573950, |
| | *Caldicellulosiruptor saccharolyticus* | YP_002573949; |
| | DSM 8903; | YP_001180124, |
| | *E. coli*; | YP_001180125; |
| | *Spirochaeta thermophila* DSM 6192; | leuC, ECK0074, JW0071; |
| | *Pelotomaculum thermopropionicum* | leuD, ECK0073, JW0070; |
| | SI; | YP_003875294, |
| | *Hydrogenobacter thermophilus* TK-6; | YP_003873373; |
| | *Deferribacter desulfuricans* SSM1; | YP_001213069, |
| | *Anoxybacillus flavithermus* WK1; | YP_001213068; |
| | *Thermosynechococcus elongatus* BP- | YP_003433547, |
| | 1; | YP_003432351; |
| | *Geobacillus kaustophilus* HTA426; | YP_003495505, |
| | *Synechocystis* sp. PCC 6803; | YP_003495504; |
| | *Chlamydomonas reinhardtii;* | ACJ32977, ACJ32978; |
| | | BAC08461, BAC08786; |
| | | BAD76941, BAD76940; |
| | | BAA18738, BAA18298; |
| | | XP_001702135, |
| | | XP_001696402; |
| 39: | *Thermotoga petrophila* RKU-1; | ABQ46392, YP_001243968; |
| 3-Isopropylmalate | *Cyanothece* sp. PCC 7822; | YP_003888480, ADN15205; |
| dehydrogenase | *Thermosynechococcus elongatus* BP- | BAC09152, NP_682390; |
| (EC 1.1.1.85) | 1; | ADI02898, YP_003703463; |
| | *Syntrophothermus lipocalidus* DSM | ADQ78220; |
| | 12680; | YP_002573948; |
| | *Caldicellulosiruptor bescii* DSM 6725; | YP_003998692; |
| | *Paludibacter propionicigenes* WB4; | ABP66935; |
| | *Leadbetterella byssophila* DSM | AAA16706, YP_001180126; |
| | 17132; | YP_001211084; |
| | *Caldicellulosiruptor saccharolyticus* | YP_148510, BAD76942; |
| | DSM 8903; *Thermus thermophilus*; | YP_003433176; |
| | *Pelotomaculum thermopropionicum* | YP_003873639; |
| | SI; | YP_003495917; |
| | *Geobacillus kaustophilus* HTA426; | YP_002314961; |
| | *Hydrogenobacter thermophilus* TK-6; | XP_002955062, EFJ43816; |
| | *Spirochaeta thermophila* DSM 6192; | XP_001701074, |
| | *Deferribacter desulfuricans* SSM1; | XP_001701073; |
| | *Anoxybacillus flavithermus* WK1; | XP_003083133; |
| | *Volvox carteri f. nagariensis*; | |
| | *Chlamydomonas reinhardtii*; | |
| | *Ostreococcus tauri*; | |
| 40: | *Thermotoga petrophila* RKU-1; | ABQ46395, YP_001243971; |
| 2-Isopropylmalate | *Cyanothece* sp. PCC 7822; | YP_003890122, ADN16847; |
| Synthase | *Cyanothece* sp. PCC 8802; | ACU99797; |
| (EC 2.3.3.13) | *Nostoc punctiforme* PCC 73102; | ACC82459; |
| | *Pelotomaculum thermopropionicum* | YP_001211081; |
| | SI; | YP_003432474, BAI69273; |
| | *Hydrogenobacter thermophilus* TK-6; | NP_414616, AAC73185; |
| | *E. coli*; *Caldicellulosiruptor* | ABP66753, YP_001179944; |
| | *saccharolyticus* DSM 8903; | YP_003703466, ADI02901; |
| | *Syntrophothermus lipocalidus* DSM | YP_148511, BAD76943; |
| | 12680; *Geobacillus kaustophilus* | YP_002572404; |
| | HTA426; *Caldicellulosiruptor bescii* | YP_002314960, ACJ32975; |
| | DSM 6725; *Anoxybacillus* | YP_003496874, BAI81118; |
| | *flavithermus* WK1; *Deferribacter* | NP_682187, BAC08949; |
| | *desulfuricans* SSM1; | ADN03009, YP_003875282; |
| | *Thermosynechococcus elongatus* BP- | YP_001469896, ABV32832; |

-continued

| Enzyme/callout number | Source (Organism) | GenBank Accession Number, JGI Protein ID or Citation |
|---|---|---|
| | 1; *Spirochaeta thermophila* DSM 6192; *Thermotoga lettingae* TMO; *Volvox carteri f. nagariensis*; *Micromonas* sp. RCC299; *Micromonas pusilla* CCMP1545; *Chlamydomonas reinhardtii*; | XP_002945733, EFJ52728; ACO69978, XP_002508720; XP_003063010, EEH52949; XP_001696603, EDP08580; |
| 41: isopropylmalate isomerase large/small subunits (EC 4.2.1.33) | *Geobacillus kaustophilus* HTA426; *Anabaena variabilis* ATCC 29413; *Synechocystis* sp. PCC 6803; *Anoxybacillus flavithermus* WK1; *Thermosynechococcus elongatus* BP-1; *Spirochaeta thermophila* DSM 6192; *Salmonella enterica* subsp. *enterica serovar Typhimurium* str. D23580; *Staphylococcus aureus* A5937; *Francisella philomiragia* subsp. *philomiragia* ATCC 25015; *Neisseria lactamica*; *Francisella novicida* U112; *Staphylococcus aureus* A5937; *Staphylococcus aureus* subsp. *aureus* 68-397; *Fusobacterium* sp. 2_1_31; *Francisella novicida* GA99-3549; marine bacterium HP15; *Bacillus licheniformis* ATCC 14580; *Rhodobacter sphaeroides* 2.4.1; *Bordetella petrii* DSM 12804; *Agrobacterium vitis* S4; | YP_148509, YP_148508; YP_324467, YP_324466; NP_442926, NP_441618; YP_002314962, YP_002314963; NP_682024, NP_681699; YP_003873372; CBG23133, CBG23132; ZP_05702396; EET20545; AAA53236; ABK88972; EEV86047; ZP_05607839; EEO38992; EDN35429; ADP98363, ADP98362; YP_092517, YP_092516; YP_353947, YP_353945; YP_001631647, YP_001631646; YP_002551071, YP_002551071; |
| 42: 2-keto acid decarboxylase (EC 4.1.1.72, etc) | *Lactococcus lactis*; *Lactococcus lactis* subsp. *lactis* KF147; *Lactococcus lactis* subsp. *Lactis*; *Kluyveromyces marxianus*; *Kluyveromyces lactis*; *Mycobacterium avium* 104; *Mycobacterium ulcerans* Agy99; *Mycobacterium bovis*; *Mycobacterium leprae*; *Proteus mirabilis* HI4320; *Staphylococcus aureus* 04-02981; *Acetobacter pasteurianus*; *Saccharomyces cerevisiae*; *Zymomonas mobilis* subsp. *mobilis* CP4; *Mycobacterium tuberculosis*; *Mycobacterium smegmatis* str. MC2 155; *Mycobacterium bovis* BCG str. *Pasteur* 1173P2; | AAS49166; ADA65057, YP_003353820; CAG34226; AAA35267; CAA59953; A0QBE6; A0PL16; Q7U140; Q9CBD6; YP_002150004; ADC36400; AAM21208; CAA39398; AAA27696; O53865; A0R480; A1KGY5; |
| 43: Alcohol dehydrogenase (NAD dependent) (EC 1.1.1.1); | *Thermoplasma volcanium* GSS1; *Gluconacetobacter hansenii* ATCC 23769; *Saccharomyces cerevisiae*; *Aeropyrum pernix* K1; *Rhodobacterales bacterium* HTCC2083; *Bradyrhizobium japonicum* USDA 110; *Syntrophothermus lipocalidus* DSM 12680; *Fervidobacterium nodosum* Rt17-B1; *Desulfotalea psychrophila* LSv54; *Acetobacter pasteurianus* IFO 3283-03; *Gluconobacter oxydans* 621H; *Aeromonas hydrophila* subsp. *hydrophila* ATCC 7966; *Acetobacter pasteurianus* IFO 3283-01; *Streptomyces hygroscopicus* ATCC 53653; | BAB59540 ZP_06834544; CAA89136; NP_148480; ZP_05073895; NP_769420; ADI01021; YP_001411173; YP_065604; BAI03878; YP_192500; ABK38651; BAI00830; EFL29096; |
| 44: Alcohol dehydrogenase (NADPH dependent) (EC 1.1.1.2); | *Pelotomaculum thermopropionicum* SI; *Fusobacterium* sp. 7_1; *Pichia pastoris* GS115; *Pichia pastoris* GS115; *Escherichia coli* str. K-12 substr. MG1655; *Clostridium hathewayi* DSM 13479; *Clostridium butyricum* 5521; *Fusobacterium ulcerans* ATCC 49185; | YP_001211038, BAF58669; ZP_04573952, EEO43462; XP_002494014, XP_002490014; CAY71835, XP_002492217, CAY67733; yqhD, NP_417484, AAC76047; EFC99049; ZP_02948287 ZP_05632371; |

-continued

| Enzyme/callout number | Source (Organism) | GenBank Accession Number, JGI Protein ID or Citation |
|---|---|---|
| | *Fusobacterium* sp. D11; Desulfovibrio | ZP_05440863; |
| | *desulfuricans* subsp. *desulfuricans* str. | YP_389756; |
| | G20; *Clostridium novyi* NT; | YP_878957; |
| | *Clostridium tetani* E88; | NP_782735; |
| | *Aureobasidium pullulans*; | ADG56699; |
| | *Scheffersomyces stipitis* CBS 6054, | ABN66271, XP_001384300; |
| | *Thermotoga lettingae* TMO; | YP_001471424; |
| | *Thermotoga petrophila* RKU-1; | YP_001244106; |
| | *Coprinopsis cinerea* okayama7#130; | XP_001834460; |
| | *Saccharomyces cerevisiae* EC1118; | CAY82157; |
| | *Saccharomyces cerevisiae* JAY291; | EEU07174; |
| 45: | *Thermaerobacter subterraneus* DSM | EFR61439; |
| Phosphoenolpyruvate | 13965; *Cyanothece* sp. PCC 7822; | YP_003887888; |
| carboxylase | *Thermus* sp.; *Rhodothermus marinus*; | BAA07723; CAA67760; |
| (EC 4.1.1.31) | *Thermosynechococcus elongatus* BP- | NP_682702, BAC09464; |
| | 1; | YP_003998059, ADQ17706; |
| | *Leadbetterella byssophila* DSM | ADQ81501, YP_004045007; |
| | 17132; | EFQ77722; |
| | *Riemerella anatipestifer* DSM 15868; | YP_003706036; |
| | *Mucilaginibacter paludis* DSM 18603; | YP_003911597, ADN74523; |
| | *Truepera radiovictrix* DSM 17093; | YP_003685046; |
| | *Ferrimonas balearica* DSM 9799; | YP_003681843; |
| | *Meiothermus silvanus* DSM 9946; | ZP_07594313, ZP_07565817; |
| | *Nocardiopsis dassonvillei* subsp. | ADD27759; |
| | *dassonvillei* DSM 43111; *E. coli*, | YP_003801346, ADK68466; |
| | *Meiothermus ruber* DSM 1279; | ZP_06967036, EFH90147; |
| | *Olsenella uli* DSM 7084; | NP_866412, CAD78193; |
| | *Ktedonobacter racemifer* DSM 44963; | ADR36285; |
| | *Rhodopirellula baltica* SH 1; | ADP96559; |
| | *Oceanithermus profundus* DSM | ADR23252; |
| | 14977; | ZP_07746438; |
| | marine bacterium HP15; | NP_627344; |
| | *Marivirga tractuosa* DSM 4126; | ABX34873; |
| | *Mucilaginibacter paludis* DSM 18603; | ZP_07544559; |
| | *Streptomyces coelicolor* A3(2); | ABO18389; |
| | *Delftia acidovorans* SPH-1; | ABM76577; |
| | *Actinobacillus pleuropneumoniae* | ABM72969; |
| | *serovar* 13 str. N273; | YP_003842669, ADL50905; |
| | *Prochlorococcus marinus* str. MIT | CAM07667; |
| | 9301; *Prochlorococcus marinus* str. | ABF44963; |
| | NATL1A | ZP_06399624; |
| | *Prochlorococcus marinus* str. MIT | ABL64615; |
| | 9515; *Clostridium cellulovorans* | YP_830113; |
| | 743B; | YP_004010507; |
| | *Neisseria meningitidis* Z2491; | YP_003273502; |
| | *Deinococcus geothermalis* DSM | ZP_03496338; |
| | 11300; *Micromonospora* sp. L5; | ZP_02894226; |
| | *Chlorobium phaeobacteroides* DSM | |
| | 266; Arthrobacter sp. FB24; | |
| | *Rhodomicrobium vannielii* ATCC | |
| | 17100; *Gordonia bronchialis* DSM | |
| | 43247; *Thermus aquaticus* Y51MC23; | |
| | *Burkholderia ambifaria* IOP40-10; | |
| 46: | *Thermotoga lettingae* TMO; | YP_001470126; |
| Aspartate | *Synechococcus elongatus* PCC 6301; | YP_172275; |
| aminotransferase | *Synechococcus elongatus* PCC 7942; | YP_401562; |
| (EC 2.6.1.1) | *Thermosipho melanesiensis* BI429; | YP_001306480; |
| | *Thermotoga petrophila* RKU-1; | YP_001244588; |
| | *Thermus thermophilus*; | BAA07487; |
| | *Anoxybacillus flavithermus* WK1; | YP_002315494; |
| | *Bacillus* sp.; *E. coli*, | AAA22250; aspC: BAB34434; |
| | *Pelotomaculum thermopropionicum* | YP_001211971; |
| | SI; | BAB86290; |
| | *Phormidium lapideum*; | YP_001410686, |
| | *Fervidobacterium nodosum* Rt17-B1; | YP_001409589; |
| | *Geobacillus kaustophilus* HTA426; | YP_148025, YP_147632, |
| | *Thermosynechococcus elongatus* BP- | YP_146225; NP_683147; |
| | 1; | ACJ34747; |
| | *Anoxybacillus flavithermus* WK1; | BAD77213, BAD76064; |
| | *Geobacillus kaustophilus* HTA426; | YP_003874653; |
| | *Spirochaeta thermophila* DSM 6192; | YP_002572445; |
| | *Caldicellulosiruptor bescii* DSM 6725; | YP_001179582; |
| | *Caldicellulosiruptor saccharolyticus* | AAA79371; |
| | DSM 8903; | AAA33942; |
| | *Arabidopsis thaliana*; | CAA42430; |

-continued

| Enzyme/callout number | Source (Organism) | GenBank Accession Number, JGI Protein ID or Citation |
|---|---|---|
| | *Glycine max*; | XP_001696609; |
| | *Lupinus angustifolius*; | XP_003060871; |
| | *Chlamydomonas reinhardtii*; | |
| | *Micromonas pusilla* CCMP1545; | |
| 47: | *Thermotoga lettingae* TMO; | YP_001470361, ABV33297; |
| Aspartokinase | *Cyanothece* sp. PCC 8802; | YP_003136939; |
| (EC = 2.7.2.4) | *Thermotoga petrophila* RKU-1 | YP_001244864, |
| | *Hydrogenobacter thermophilus* TK-6; | YP_001243977; |
| | *Anoxybacillus flavithermus* WK1; | YP_003432105, BAI68904; |
| | *Bacillus* sp.; | ACJ35001; |
| | *Spirochaeta thermophila* DSM 6192; | AAA22251; |
| | *Anoxybacillus flavithermus* WK1; | YP_003873788, ADN01515; |
| | *Geobacillus kaustophilus* HTA426; | ACJ34043, YP_002316986; |
| | *Syntrophothermus lipocalidus* DSM | BAD77480, YP_149048; |
| | 12680; *E. coli*; | ADI02230, YP_003702795; |
| | *Thermosynechococcus elongatus* BP- | ZP_07594328, ZP_07565832; |
| | 1; | NP_682623, BAC09385; |
| | *Fervidobacterium nodosum* Rt17-B1; | ABS59942, YP_001410786; |
| | *Spirochaeta thermophila* DSM 6192; | YP_003873302, ADN01029; |
| | *Pelotomaculum thermopropionicum* | YP_001212149, |
| | SI; | YP_001211837; |
| | *Caldicellulosiruptor saccharolyticus* | ABP66605; |
| | DSM 8903; *Caldicellulosiruptor bescii* | YP_002573821; |
| | DSM 6725; *Thermosipho melanesiensis* | YP_001307097, ABR31712; |
| | BI429; *Thermotoga lettingae* TMO; | YP_001470985, ABV33921; |
| | *Arabidopsis thaliana*; | CAA67376; |
| | *Chlamydomonas reinhardtii*; | XP_001698576, EDP08069, |
| | | XP_001695256; |
| 48: | *Thermotoga lettingae* TMO; | YP_001470981, ABV33917; |
| Aspartate-semialdehyde | *Trichodesmium erythraeum* IMS101; | ABG50031; |
| dehydrogenase | *Prochlorococcus marinus* str. MIT | ABM76828; |
| | 9303; | ABQ47283, YP_001244859; |
| | *Thermotoga petrophila* RKU-1; | ABP67176, YP_001180367; |
| | *Caldicellulosiruptor saccharolyticus* | ADI01804, YP_003702369; |
| | DSM 8903; *Syntrophothermus* | YP_001460230, |
| | *lipocalidus* DSM 12680; *E. coli*; | YP_001464895; |
| | *Fervidobacterium nodosum* Rt17-B1 | YP_001409594, ABS59937; |
| | *Caldicellulosiruptor bescii* DSM 6725; | YP_002573009; |
| | *Thermosipho melanesiensis* BI429; | YP_001307092, ABR31707; |
| | *Spirochaeta thermophila* DSM 6192; | YP_003875128, ADN02855; |
| | *Pelotomaculum thermopropionicum* | YP_001211836, BAF59467; |
| | SI; | YP_003432252, BAI69051; |
| | *Hydrogenobacter thermophilus* TK-6; | YP_002316029, ACJ34044; |
| | *Anoxybacillus flavithermus* WK1; | YP_147128, BAD75560; |
| | *Geobacillus kaustophilus* HTA426; | YP_003496635, BAI80879; |
| | *Deferribacter desulfuricans* SSM1; | NP_680860, BAC07622; |
| | *Thermosynechococcus elongatus* BP- | AAG23574, AAG23573; |
| | 1; | XP_001695059, EDP02211; |
| | *Carboxydothermus* | ABH11018; |
| | *hydrogenoformans*; | ACU30050; |
| | *Chlamydomonas reinhardtii*; | ACG41594; |
| | *Polytomella parva*; | ABR26065; |
| | *Glycine max*; | |
| | *Zea mays*; | |
| | *Oryza sativa Indica* Group; | |
| 49: | *Syntrophothermus lipocalidus* DSM | ADI02231, YP_003702796; |
| Homoserine | 12680; *Cyanothece* sp. PCC 7822; | YP_003887242; |
| dehydrogenase | *Caldicellulosiruptor bescii* DSM 6725; | YP_002573819; |
| | *Caldicellulosiruptor saccharolyticus* | ABP66607, YP_001179798; |
| | DSM 8903; *E. coli*; | EFJ98002; |
| | *Spirochaeta thermophila* DSM 6192; | YP_003873441, ADN01168; |
| | *Pelotomaculum thermopropionicum* | YP_001212151, BAF59782; |
| | SI; | YP_003431981, BAI68780; |
| | *Hydrogenobacter thermophilus TK-6;* | YP_002316756, ACJ34771; |
| | *Anoxybacillus flavithermus WK1;* | YP_148817, BAD77249; |
| | *Geobacillus kaustophilus* HTA426; | YP_003496401, BAI80645; |
| | *Deferribacter desulfuricans* SSM1; | NP_681068, BAC07830; |
| | *Thermosynechococcus elongatus* BP- | ABG78600, AAZ98830; |
| | 1; | XP_001699712, EDP07408; |
| | *Glycine max*; | ACO69662, XP_002508404; |
| | *Chlamydomonas reinhardtii*; | |
| | *Micromonas* sp. RCC299; | |

-continued

| Enzyme/callout number | Source (Organism) | GenBank Accession Number, JGI Protein ID or Citation |
|---|---|---|
| 50: Homoserine kinase (EC 2.7.1.39) | *Thermotoga petrophila* RKU-1; *Cyanothece* sp. PCC 7822; *Caldicellulosiruptor bescii* DSM 6725; *Caldicellulosiruptor saccharolyticus* DSM 8903; *E. coli*; *Anoxybacillus flavithermus* WK1; *Geobacillus kaustophilus* HTA426; *Thermosynechococcus elongatus* BP-1; *Pelotomaculum thermopropionicum* SI; *Hydrogenobacter thermophilus* TK-6; *Chlamydomonas reinhardtii*; *Prototheca wickerhamii*; *Arabidopsis thaliana*; *Glycine max*; *Zea mays*; | YP_001243979, ABQ46403; YP_003886645; YP_002573820; ABP66606, YP_001179797; AP_000667, BAB96580; YP_002316754, ACJ34769; YP_148815, BAD77247; NP_682555, BAC09317; YP_001212150, BAF59781; YP_003433124, BAI69923; XP_001701899, EDP06874; ABC24954; NP_179318, AAD33097; ACU26535; ACG46592; |
| 51: Threonine synthase (EC 4.2.99.2) | *Thermotoga petrophila* RKU-1; *Cyanothece* sp. PCC 7425; *Thermosipho melanesiensis* BI429; *Syntrophothermus lipocalidus* DSM 12680; *E. coli*; *Pelotomaculum thermopropionicum* SI; *Anoxybacillus flavithermus* WK1; *Caldicellulosiruptor bescii* DSM 6725; *Caldicellulosiruptor saccharolyticus* DSM 8903; *Hydrogenobacter thermophilus* TK-6; *Geobacillus kaustophilus* HTA426; *Thermosynechococcus elongatus* BP-1; *Spirochaeta thermophila DSM 6192; Deferribacter desulfuricans* SSM1; *Geobacillus kaustophilus HTA426;* | YP_001243978, ABQ46402; YP_002485009; YP_001306558, ABR31173; ADI02519, YP_003703084; AP_000668, NP_414545; YP_001213220; YP_002316755, ACJ34770; YP_002572552; YP_001180015, ABP66824; YP_003433070, YP_003433019, BAI69869, BAI69818; YP_148816, YP_147614; NP_682017, NP_681772, BAC08534, BAC08779; YP_003873303, ADN01030; YP_003495358, BAI79602; |
| 52: Threonine ammonia-lyase (EC 4.3.1.19) | *Geobacillus kaustophilus* HTA426; *Prochlorococcus marinus* str. MIT 9202; *Synechococcus* sp. PCC 7335; *Thermotoga petrophila* RKU-1; *Pelotomaculum thermopropionicum* SI; *Anoxybacillus flavithermus* WK1; *Deferribacter desulfuricans* SSM1; *E. coli*; *Neisseria lactamica* ATCC 23970; *Citrobacter youngae* ATCC 29220; *Neisseria polysaccharea* ATCC 43768; *Providencia rettgeri* DSM 1131; *Neisseria subflava* NJ9703; *Mannheimia haemolytica* PHL213; *Achromobacter piechaudii* ATCC 43553; *Neisseria meningitidis* ATCC 13091; *Synechococcus* sp. CC9902; *Synechococcus* sp. PCC 7002; *Synechococcus* sp. WH 8109; *Cyanobium* sp. PCC 7001; *Anabaena variabilis* ATCC 29413; *Microcoleus chthonoplastes* PCC 7420; *Chlamydomonas reinhardtii;* | BAD76058, BAD75876, YP_147626, YP_147444; ZP_05137562; ZP_05035047; ABQ46585, YP_001244161; YP_001210652, BAF58283; YP_002315804, YP_002315746; YP_003497384, BAI81628; YP_001746093, ZP_07690697; EEZ76650, ZP_05986317; EFE07783, ZP_06571237; EFH23894, ZP_06863451; EFE52186, ZP_06127162; EFC51529, ZP_05985502; ZP_04978734; ZP_06687730, ZP_06684811; ZP_07369980, EFM04207; ABB26032; ACA99606; ZP_05790446, EEX07646; EDY39077, ZP_05045768; ABA20300; ZP_05029756; XP_001701816, EDP06791; |
| 53: Acetolactate synthase (EC 2.2.1.6) | *Caldicellulosiruptor saccharolyticus* DSM 8903; *Thermotoga petrophila* RKU-1; *Thermosynechococcus elongatus* BP-1; *Syntrophothermus lipocalidus* DSM 12680; *Pelotomaculum thermopropionicum* SI; *Geobacillus kaustophilus* HTA426; *Caldicellulosiruptor bescii* DSM 6725; *Hydrogenobacter thermophilus* TK-6; | ABP66750, ABP66751, YP_001179942, ABP66455, YP_001179941, YP_001179646; YP_001243976, YP_003345845, ADA66432, ADA66431, ABQ46399, YP_001243975, ABQ46400, YP_003345846; NP_682614, BAC09376, NP_681670, BAC08432, NP_682086; ADI02904, YP_003703469, ADI02903, YP_003703468; BAF58709, BAF58917, YP_001211286, |

-continued

| Enzyme/callout number | Source (Organism) | GenBank Accession Number, JGI Protein ID or Citation |
|---|---|---|
| | *Spirochaeta thermophila* DSM 6192; *Anoxybacillus flavithermus* WK1; *Deferribacter desulfuricans* SSM1; *Escherichia coli* str. K-12 substr. W3110; *Saccharomyces cerevisiae*, *Thermus aquaticus*; *Synechococcus* sp. PCC 7002; *Cyanothece* sp. PCC 7424; *Anabaena variabilis* ATCC 29413; *Nostoc* sp. PCC 7120; *Microcystis aeruginosa* NIES-843; *Synechocystis* sp. PCC 6803; *Synechococcus* sp. JA-2-3B'a(2-13); *Synechococcus* sp. JA-3-3Ab; *Chlamydomonas reinhardtii*; *Volvox carteri*; *Bacillus subtilis* subsp. *subtilis* str. 168; *Bacillus licheniformis* ATCC 14580; | YP_001211078; BAD76946, YP_148514, BAD76945, YP_148513; ACM59790, ACM59628, ACM59629, YP_002572563, YP_002572401, YP_002572402; YP_003432299, YP_03432300, BAI69099, BAI69098; YP_003874926, YP_003874927, ADN02654, ADN02653, ACJ33615, YP_002314957, ACJ32972, ACJ32973, YP_002314958; YP_003496879, BAI81123, YP_003496878, BAI81122; AP_004121, BAE77622, AP_004122, BAE77623, BAE77528, AP_004027, BAB96646, AP_000741; BAA12700; EDN64495, CAA89744, EDV09697; YP_001735999, ACB00744; YP_002376012; YP_324035; NP_487595, BAB75254; YP_001655615; NP_441297, BAA17984, CAA66718, NP_441304, NP_442206, BAA10276; YP_478353; YP_475372, ABD00213, ABD00270, YP_475476, YP_475533; AAC03784, AAB88292, XP_001700185, EDO98300, XP_001695168, EDP01876; AAC04854, AAB88296; CAB07802 (AlsS); AAU42663 (AlsS); |
| 54: Ketol-acid reductoisomerase (EC 1.1.1.86) | *Syntrophothermus lipocalidus* DSM 12680; *Caldicellulosiruptor saccharolyticus* DSM 8903; E. coli; *Thermotoga petrophila* RKU-1; *Calditerrivibrio nitroreducens* DSM 19672; *Spirochaeta thermophila* DSM 6192; *Pelotomaculum thermopropionicum* SI; *Cyanothece* sp. PCC 7822; *Hydrogenobacter thermophilus* TK-6; *Anoxybacillus flavithermus* WK1; *Caldicellulosiruptor bescii* DSM 6725; *Geobacillus kaustophilus* HTA426; *Deferribacter desulfuricans* SSM1; *Thermosynechococcus elongatus* BP-1; *Cyanothece* sp. PCC 7425; *Nostoc punctiforme* PCC 73102; *Trichodesmium erythraeum* IMS101; *Synechococcus* sp. PCC 7335; *Microcoleus chthonoplastes* PCC 7420; *Prochlorococcus marinus* str. MIT 9301; *Cyanobium* sp. PCC 7001; *Arthrospira* sp. PCC 8005; *Arabidopsis thaliana*; *Pisum sativum* (pea); *Zea mays*; *Chlamydomonas reinhardtii*; *Polytomella parva*; | ADI02902, YP_003703467; ABP66752, YP_001179943; AAA67577, YP_001460567; ABQ46398, YP_001243974; YP_004050904; YP_003874858, ADN02585; YP_001211079, BAF58710; YP_003885458; YP_003433279, BAI70078; YP_002314959, ACJ32974; YP_002572403; YP_148512, BAD76944; YP_003496877, BAI81121; NP_683044, BAC09806; YP_002482078; ACC82013; ABG53327; ZP_05036558; ZP_05026584; ABO18124; EDY39000; ZP_07166132; CAA48253, NP_001078309; CAA76854; ACG35752; XP_001702649, EDP06428; ABH11013; |
| 55: Dihydroxy-acid dehydratase (EC 4.2.1.9) | *Thermotoga petrophila* RKU-1; *Cyanothece* sp. PCC 7822; *Marivirga tractuosa* DSM 4126; *Geobacillus kaustophilus* HTA426; | YP_001243973, ABQ46397; YP_003887466; YP_004053736; YP_147899, BAD76331, |

-continued

| Enzyme/callout number | Source (Organism) | GenBank Accession Number, JGI Protein ID or Citation |
|---|---|---|
| | *Syntrophothermus lipocalidus* DSM | YP_147822, BAD76254; |
| | 12680; | ADI02905, YP_003703470; |
| | *Spirochaeta thermophila* DSM 6192; | YP_003874669, ADN02396; |
| | *Anoxybacillus flavithermus* WK1; | YP_002315593; |
| | *Caldicellulosiruptor bescii* DSM 6725; | YP_002572562; |
| | *Caldicellulosiruptor saccharolyticus* | YP_001179645, ABP66454; |
| | DSM 8903; *E. coli*; | ADR29155, YP_001460564; |
| | *Deferribacter desulfuricans* SSM1; | YP_003496880, BAI81124; |
| | *Thermosynechococcus elongatus* BP- | NP_681848, BAC08610; |
| | 1; | YP_003431766, BAI68565; |
| | *Hydrogenobacter thermophilus* TK-6; | ACC82168, ADN14191; |
| | *Nostoc punctiforme* PCC 73102; | ADI62939; |
| | '*Nostoc azollae*' 0708; | EDZ97146; |
| | *Arthrospira maxima* CS-328; | ABO17457; |
| | *Prochlorococcus marinus* str. MIT | ZP_05044537, EDY37846; |
| | 9301; *Cyanobium* sp. PCC 7001; | ZP_05037932; |
| | *Synechococcus* sp. PCC 7335; | ZP_06383646; |
| | *Arthrospira platensis* str. *Paraca*; | BAG02689; |
| | *Microcystis aeruginosa* NIES-843; | XP_001693179, EDP03205; |
| | *Chlamydomonas reinhardtii*; | BAB03011; |
| | *Arabidopsis thaliana*; | ABR25557; |
| | *Oryza sativa Indica* Group; | ACU26534; |
| | *Glycine max*; | |
| 56: | *Schizosaccharomyces japonicus* | XP_002173231, EEB06938; |
| 2-Methylbutyraldehyde | yFS275; | XP_002490018, CAY67737, |
| reductase | *Pichia pastoris* GS115; | XM_002489973; |
| (EC 1.1.1.265) | *Saccharomyces cerevisiae* S288c; | DAA12209, NP_010656, |
| | *Aspergillus fumigatus* Af293; | NM_001180676; |
| | *Debaryomyces hansenii* CBS767; | XP_752003; |
| | *Debaryomyces hansenii* | XP_002770138; |
| | *Kluyveromyces lactis*; | CAR65507; |
| | *Lachancea thermotolerans* CBS 6340; | CAH02579; |
| | *Lachancea thermotolerans*; | XP_002554884; |
| | *Saccharomyces cerevisiae* EC1118; | CAR24447, CAR23718; |
| | *Saccharomyces cerevisiae* JAY291; | CAY78868; |
| | | EEU08013; |
| 57: | *Saccharomyces cerevisiae* S288c; | DAA10635, NM_001183405, |
| 3-Methylbutanal | *Saccharomyces cerevisiae* EC1118; | NP_014490; |
| reductase | *Saccharomyces cerevisiae* JAY291; | CAY86141; |
| (EC 1.1.1.265) | | EEU07090; |
| 07': | *Geobacillus kaustophilus* HTA426; | YP_147173, BAD75605; |
| 3-Ketothiolase | *Azohydromonas lata*; | YP_523526; |
| (reversible) | *Rhodoferax ferrireducens* T118; | CAA01849, CAA01846; |
| | *Allochromatium vinosum*; | YP_286222; |
| | *Dechloromonas aromatica* RCB; | YP_001041914; |
| | *Rhodobacter sphaeroides* ATCC | YP_001166229; |
| | 17029; *Rhodobacter sphaeroides* | ABX11181; |
| | ATCC 17025; *Bacillus* sp. 256; | ZP_05785678; |
| | *Silicibacter lacuscaerulensis* ITI-1157; | XP_752635; |
| | *Aspergillus fumigatus* Af293; | AAK21958; |
| | *Rhizobium etli*; | ZP_05784120, ZP_05781517; |
| | *Citreicella* sp. SE45; | ZP_05742998; |
| | *Silicibacter* sp. TrichCH4B; | AAC83659, AAD10275; |
| | *Azohydromonas lata*; | AAC69616; |
| | *Chromobacterium violaceum*; | ABV95064; |
| | *Dinoroseobacter shibae* DFL 12; | AAP41838; |
| | *Alcaligenes* sp. SH-69; | CAX43351, XP_002418052; |
| | *Candida dubliniensis* CD36; | CAK18903; |
| | *Pseudomonas* sp. 14-3; | XP_002375989; |
| | *Aspergillus flavus* NRRL3357; | EAT37298, EAT37297, |
| | *Aedes aegypti*; | XP_001654752, |
| | *Scheffersomyces stipitis* CBS 6054; | XP_001654751; |
| | *Cyanothece* sp. PCC 7424; | ABN68380, XP_001386409; |
| | *Cyanothece* sp. PCC 7822; | YP_002375827, ACK68959; |
| | *Microcystis aeruginosa* NIES-843; | YP_003886602, ADN13327; |
| | | BAG04828; |
| 08': | *Syntrophothermus lipocalidus* DSM | YP_003702743, ADI02178, |
| 3-Hydroxyacyl-CoA | 12680; | ADI01287, ADI01071; |
| dehydrogenase | *Oceanithermus profundus* DSM | ADR36325; |
| | 14977; | YP_002317076, |
| | *Anoxybacillus flavithermus* WK1; | YP_002315864; |
| | *Pelotomaculum thermopropionicum* | YP_001210823, BAF58454; |
| | SI; | YP_149248, YP_147889; |

-continued

| Enzyme/callout number | Source (Organism) | GenBank Accession Number, JGI Protein ID or Citation |
|---|---|---|
| | *Geobacillus kaustophilus* HTA426; | YP_003497047, BAI81291; |
| | *Deferribacter desulfuricans* SSM1; | EFQ32520, EFQ35765; |
| | *Glomerella graminicola* M1.001; | YP_001250712, ABQ55366; |
| | *Legionella pneumophila* str. Corby; | XP_748706, XP_748351; |
| | *Aspergillus fumigatus* Af293; | EAU80763; |
| | *Coprinopsis cinerea* okayama7#130; | XP_001559519; |
| | *Botryotinia fuckeliana* B05.10; | ABH10642; YP_001462756; |
| | *Coccidioides posadasii*; *E. coli*; | YP_675197; |
| | *Chelativorans* sp. BNC1; | ACC81853, YP_001866796; |
| | *Nostoc punctiforme* PCC 73102; | ZP_07114022, CBN59220; |
| | *Oscillatoria* sp. PCC 6506; | |
| 09': | *Bordetella petrii*; | CAP41574; |
| Enoyl-CoA dehydratase | *Bordetella petrii* DSM 12804; | YP_001629844; |
| | *Anoxybacillus flavithermus* WK1; | YP_002315700, |
| | *Geobacillus kaustophilus* HTA426; | YP_002314932; |
| | *Geobacillus kaustophilus*; | YP_148541, YP_147845, |
| | *Syntrophothermus lipocalidus* DSM | BAD76199; BAD18341; |
| | 12680; | ADI02939, ADI02740, |
| | *Acinetobacter* sp. SE19; | ADI02007, ADI01364; |
| | *Scheffersomyces stipitis* CBS 6054; | AAG10018; |
| | *Laccaria bicolor* S238N-H82; | ABN64617, XP_001382646; |
| | *Alternaria alternate*; | EDR09131, XP_001888157; |
| | *Ajellomyces dermatitidis* ER-3; | BAH83503, |
| | *Aspergillus fumigatus* Af293; | EEQ91989; |
| | *Cryptococcus neoformans* var. | EAL93360, XP_755398; |
| | *neoformans* JEC21; *E. Coli*; | XP_572730; |
| | *Aspergillus flavus* NRRL3357; | ADN73405, YP_001458194; |
| | *Laccaria bicolor* S238N-H82; | XP_002377859; |
| | *Neosartorya fischeri* NRRL 181; | EDR01115; |
| | *Nostoc* sp. '*Peltigera membranacea* | EAW18645; |
| | *cyanobiont*'; | ADA69246; |
| 10': | *Xanthomonas campestris* pv. | CAP53709; |
| 2-Enoyl-CoA reductase | *Campestris*; *Xanthomonas campestris* | YP_001905744; |
| | pv. *campestris* str. B100; | ZP_06489037; |
| | *Xanthomonas campestris* pv. | ZP_06487845; |
| | *musacearum* NCPPB4381; | ZP_07718056, EFQ82338; |
| | *Xanthomonas campestris* pv. | ZP_05074461, EDZ42121; |
| | *vasculorum* NCPPB702; | ZP_07049092, EFI69525; |
| | *Aeromicrobium marinum* DSM 15272; | YP_886510, ABK76225; |
| | *Rhodobacterales bacterium* | YP_001699417, ACA41287; |
| | HTCC2083; | XP_002910885, EFI27391; |
| | *Lysinibacillus fusiformis* ZC1; | EFR05506; |
| | *Mycobacterium smegmatis* str. MC2 | XP_002796528, EEH39074; |
| | 155; | EEH43955; |
| | *Lysinibacillus sphaericus* C3-41; | EEH03439; |
| | *Coprinopsis cinerea* okayama7#130; | XP_003083795, CAL57762; |
| | *Arthroderma gypseum* CBS 118893; | ACS32302; |
| | *Paracoccidioides brasiliensis* Pb01; | |
| | *Paracoccidioides brasiliensis* Pb18; | |
| | *Ajellomyces capsulatus* G186AR; | |
| | *Ostreococcus tauri*; | |
| | *Jatropha curcas*; | |
| 11': | *Clostridium cellulovorans* 743B; | YP_003845606, ADL53842; |
| Acyl-CoA reductase | *Thermosphaera aggregans* DSM | YP_003649571, ADG90619; |
| (EC 1.2.1.50) | 11486; | YP_001565543, ABX37158; |
| | *Delftia acidovorans* SPH-1; | ZP_03543536; |
| | *Comamonas testosteroni* KF-1; | YP_002321654, ACJ51276; |
| | *Bifidobacterium longum* subsp. | ZP_05497968, EEU57047; |
| | *infantis* ATCC 15697; | ZP_06211782, EFA39209; |
| | *Clostridium papyrosolvens* DSM 2782; | EED67822; |
| | *Acidovorax avenae* subsp. *avenae* | ZP_07740542, EFQ24431; |
| | ATCC 19860; | ABX07240, YP_001547368; |
| | *Comamonas testosteroni* KF-1; | ABR34265, YP_001309221; |
| | *Aminomonas paucivorans* DSM | ZP_03148237, EDY05596; |
| | 12260; | ZP_06885967, EFG96716; |
| | *Herpetosiphon aurantiacus* ATCC | YP_003997212, ADQ16859; |
| | 23779; | YP_003101455, ACU37609; |
| | *Clostridium beijerinckii* NCIMB 8052; | ACY16972, YP_003268865; |
| | *Geobacillus* sp. G11MC16; | AAT00788; |
| | *Clostridium lentocellum* DSM 5427; | AAD38039; |
| | *Leadbetterella byssophila* DSM | AAR88762; |
| | 17132; | ABE65991; |
| | *Actinosynnema mirum* DSM 43827; | |
| | *Haliangium ochraceum* DSM 14365; | |
| | *Photobacterium phosphoreum*; | |

-continued

| Enzyme/callout number | Source (Organism) | GenBank Accession Number, JGI Protein ID or Citation |
|---|---|---|
| | *Simmondsia chinensis*; *Hevea brasiliensis*; *Arabidopsis thaliana*; | |
| 12': Hexanol dehydrogenase | *Mycobacterium chubuense* NBB4; | ACZ56328; |
| 12": Octanol dehydrogenase EC 1.1.1.73 | *Drosophila subobscura*; | ABO61862, ABO65263, CAD43362, CAD43361, CAD54410, CAD43360, CAD43359, CAD43358 CAD43357, CAD43356; |
| 43': Short chain alcohol dehydrogenase | *Pyrococcus furiosus* DSM 3638; *Burkholderia vietnamiensis* G4; *Geobacillus thermoleovorans*; *Geobacillus kaustophilus* HTA426; *Anoxybacillus flavithermus* WK1; *Helicobacter pylori* PeCan4; *Mycobacterium chubuense* NBB4; *Mycobacterium avium* subsp. *avium* ATCC 25291; *Aspergillus oryzae*; *cyanobacterium* UCYN-A; *Anabaena circinalis* AWQC131C; *Cylindrospermopsis raciborskii* T3; *Helicobacter pylori* Sat464; *Helicobacter pylori* Cuz20; *Mycobacterium intracellulare* ATCC 13950; *Mycobacterium avium* subsp. *avium* ATCC 25291; *Gluconacetobacter hansenii* ATCC 23769; *Helicobacter pylori* Shi470; *Mycobacterium avium* 104; *Citrus sinensis*; *Gossypium hirsutum*; *Arabidopsis halleri*; *Paracoccidioides brasiliensis* Pb01; *Pyrenophora tritici-repentis* Pt-1C-BFP; *Ajellomyces capsulatus* H143; *Scheffersomyces stipitis* CBS 6054; | AAC25556; ABO56626; BAA94092; YP_146837, BAD75269; YP_002314715, ACJ32730; YP_003927327, ADO07277; ACZ56328; ZP_05215778; BAE71320; YP_003421738, ADB95357; ABI75134; ABI75108; ADO05766; ADO04259; ZP_05228059, ZP_05228058; ZP_05215779; ZP_06834730, EFG83978; YP_001910563, ACD48533; YP_880627, ABK67217; ADH82118; ABD65462; ABZ02361, ABZ02360; XP_002792148, EEH34889; XP_001940779, EDU43498; EER38733; XP_001382930, ABN64901; |

Designer Calvin-Cycle-Channeled 1-Butanol Producing Pathways

According to one of the various embodiments, a designer Calvin-cycle-channeled pathway is created that takes the Calvin-cycle intermediate product, 3-phosphoglycerate, and converts it into 1-butanol by using, for example, a set of enzymes consisting of (as shown with the numerical labels 34, 35, 03-05, 36-43 in FIG. 4): NADPH-dependent glyceraldehyde-3-phosphate dehydrogenase 34, NAD-dependent glyceraldehyde-3-phosphate dehydrogenase 35, phosphoglycerate mutase 03, enolase 04, pyruvate kinase 05, citramalate synthase 36, 2-methylmalate dehydratase 37, 3-isopropylmalate dehydratase 38, 3-isopropylmalate dehydrogenase 39, 2-isopropylmalate synthase 40, isopropylmalate isomerase 41, 2-keto acid decarboxylase 42, and alcohol dehydrogenase (NAD dependent) 43. In this pathway design, as mentioned above, the NADPH-dependent glyceraldehyde-3-phosphate dehydrogenase 34 and NAD-dependent glyceraldehyde-3-phosphate dehydrogenase 35 serve as a NADPH/NADH conversion mechanism that can covert certain amount of photosynthetically generated NADPH to NADH which can be used by the NADH-requiring alcohol dehydrogenase 43 (examples of its encoding gene with the following GenBank accession numbers: BAB59540, CAA89136, NP_148480) for production of 1-butanol by reduction of butyraldehyde.

According to one of the various embodiments, it is a preferred practice to also use an NADPH-dependent alcohol dehydrogenase 44 that can use NADPH as the source of reductant so that it can help alleviate the requirement of NADH supply for enhanced photobiological production of butanol and other alcohols. As listed in Table 2, examples of NADPH-dependent alcohol dehydrogenase 44 include (but not limited to) the enzyme with any of the following GenBank accession numbers: YP_001211038, ZP_04573952, XP_002494014, CAY71835, NP_417484, EFC99049, and ZP_02948287.

Note, the 2-keto acid decarboxylase 42 (e.g., AAS49166, ADA65057, CAG34226, AAA35267, CAA59953, AOQBE6, AOPL16) and alcohol dehydrogenase 43 (and/or 44) have quite broad substrate specificity. Consequently, their use can result in production of not only 1-butanol but also other alcohols such as propanol depending on the genetic and metabolic background of the host photosynthetic organisms. This is because all 2-keto acids can be converted to alcohols by the 2-keto acid decarboxylase 42 and alcohol dehydrogenase 43 (and/or 44) owning to their broad substrate specificity. Therefore, according to another embodiment, it is a preferred practice to use a substrate-specific enzyme such as butanol dehydrogenase 12 when/if production of 1-butanol is desirable. As listed in Table 2, examples of butanol dehydrogenase 12 are NADH-dependent butanol dehydrogenase (e.g., GenBank: YP_148778, NP_561774, AAG23613, ZP_05082669, AD012118) and/or NAD(P)H-dependent butanol dehydrogenase (e.g., NP_562172, AAA83520, EFB77036, EFF67629, ZP_06597730, EFE12215, EFC98086, ZP_05979561).

Figure 4:
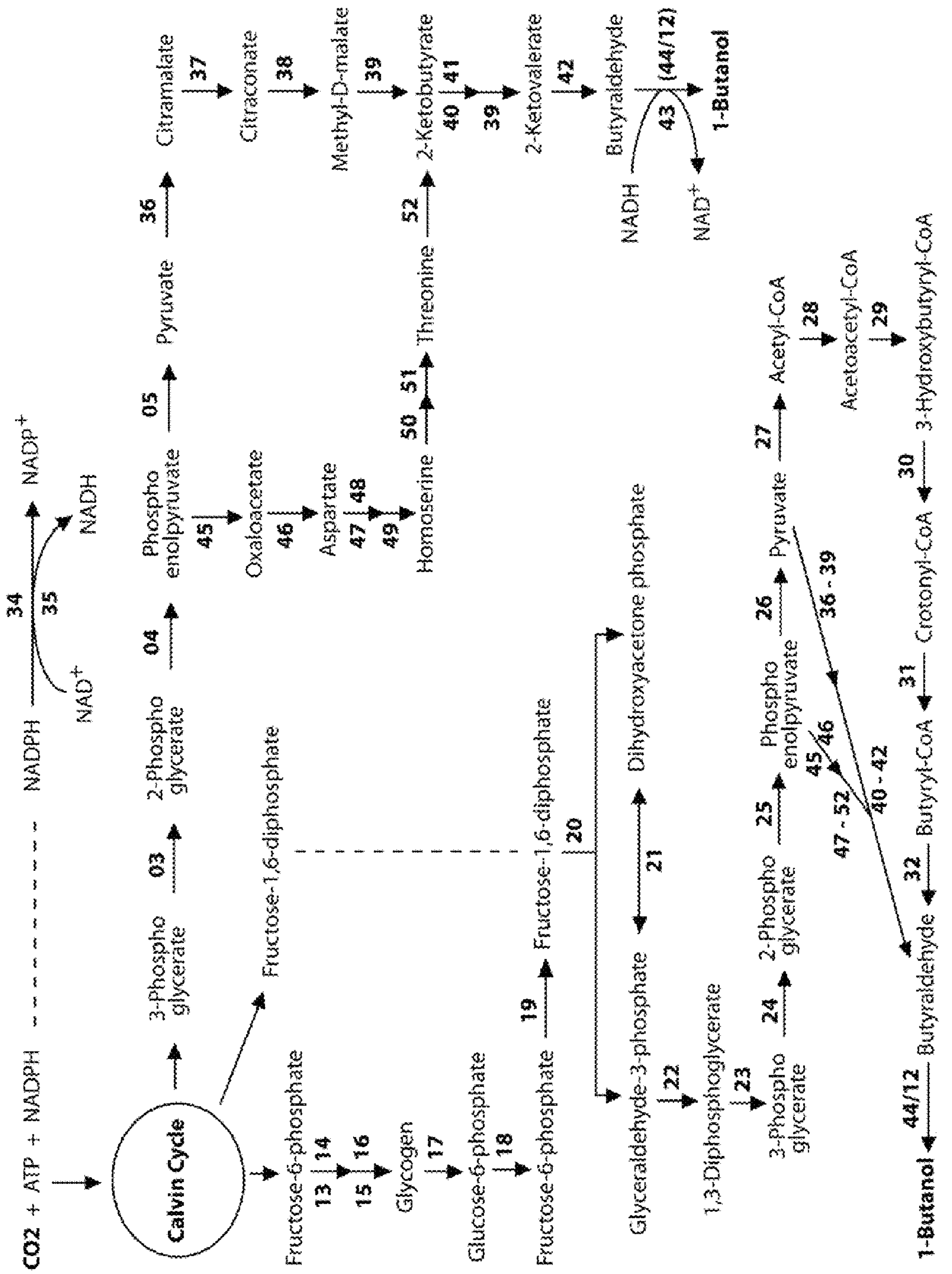
FIG. 4 presents designer Calvin-cycle-channeled and photosynthetic NADPH-enhanced pathways using the reducing power (NADPH) and energy (ATP) from the photosynthetic water splitting and proton gradient-coupled electron transport process to reduce carbon dioxide ($CO_2$) into 1-butanol ($CH_3CH_2CH_2CH_2OH$) with a series of enzymatic reactions.

In one of the various embodiments, another designer Calvin-cycle-channeled 1-butanol production pathway is created that takes the Calvin-cycle intermediate product, 3-phosphoglycerate, and converts it into 1-butanol by using, for example, a set of enzymes consisting of (as shown with the numerical labels 34, 35, 03, 04, 45-52 and 40-43 (44/12) in FIG. 4): NADPH-dependent glyceraldehyde-3-phosphate dehydrogenase 34, NAD-dependent glyceraldehyde-3-phosphate dehydrogenase 35, phosphoglycerate mutase 03, enolase 04, phosphoenolpyruvate carboxylase 45, aspartate aminotransferase 46, aspartokinase 47, aspartate-semialdehyde dehydrogenase 48, homoserine dehydrogenase 49, homoserine kinase 50, threonine synthase 51, threonine ammonia-lyase 52, 2-isopropylmalate synthase 40, isopropylmalate isomerase 41, 3-isopropylmalate dehydrogenase 39, 2-keto acid decarboxylase 42, and NAD-dependent alcohol dehydrogenase 43 (and/or NADPH-dependent alcohol dehydrogenase 44, or butanol dehydrogenase 12).

According to another embodiment, the amino-acids-metabolism-related 1-butanol production pathways [numerical labels 03-05, 36-43; and/or 03, 04, 45-52 and 39-43 (44/12)] can operate in combination and/or in parallel with other photobiological butanol production pathways. For example, as shown also in FIG. 4, the Frctose-6-photophate-branched 1-butanol production pathway (numerical labels 13-32 and 44/12) can operate with the parts of amino-acids-metabolism-related pathways [numerical labels 36-42, and/or 45-52 and 40-42) with pyruvate and/or phosphoenolpyruvate as their joining points.

Examples of designer Calvin-cycle-channeled 1-butanol production pathway genes (DNA constructs) are shown in the DNA sequence listings. SEQ ID NOS: 58-70 represent a set of designer genes for a designer nirA-promoter-controlled Calvin-cycle-channeled 1-butanol production pathway (as shown with numerical labels 34, 35, 03-05, and 36-43 in FIG. 4) in a host oxyphotobacterium such as *Thermosynechococcus elongatus* BP1. Briefly, SEQ ID NO: 58 presents example 58 of a designer nirA-promoter-controlled NADPH-dependent Glyceraldehyde-3-Phosphate Dehydrogenase (34) DNA construct (1417 bp) that comprises: a PCR FD primer (sequence 1-20), a 231-bp nirA promoter from *Thermosynechococcus elongatus* BP1 (21-251), an enzyme-encoding sequence (252-1277) selected/modified from the sequences of a *Staphylococcus aureus* 04-02981 NADPH-dependent glyceraldehyde-3-phosphate dehydrogenase (GenBank: ADC37857), a 120-bp rbcS terminator from BP1 (1278-1397), and a PCR RE primer (1398-1417) at the 3' end.

SEQ ID NO: 59 presents example 59 of a designer nirA-promoter-controlled NAD-dependent glyceraldehyde-3-phosphate dehydrogenase (35) DNA construct (1387 bp) that comprises: a PCR FD primer (sequence 1-20), a 231-bp nirA promoter from *Thermosynechococcus elongatus* BP1 (21-251), an enzyme-encoding sequence (252-1247) selected/modified from the sequences of an Edwardsiella tarda FL6-60 NAD-dependent glyceraldehyde-3-phosphate dehydrogenase (GenBank: ADM41489), a 120-bp rbcS terminator from BP1 (1248-1367), and a PCR RE primer (1368-1387) at the 3' end.

SEQ ID NO: 60 presents example 60 of a designer nirA-promoter-controlled Phosphoglycerate Mutase (03) DNA construct (1627 bp) that includes a PCR FD primer (sequence 1-20), a 231-bp nirA promoter from *Thermosynechococcus elongatus* BP1 (21-251), an enzyme-encoding sequence (252-1487) selected/modified from the sequences of a Oceanithermus profundus DSM 14977 phosphoglycerate mutase (GenBank: ADR35708), a 120-bp rbcS terminator from BP1 (1488-1607), and a PCR RE primer (1608-1627) at the 3' end.

SEQ ID NO: 61 presents example 61 of a designer nirA-promoter-controlled Enolase (04) DNA construct (1678 bp) that includes a PCR FD primer (sequence 1-20), a 231-bp nirA promoter from *Thermosynechococcus elongatus* BP1 (21-251), an enzyme-encoding sequence (252-1538) selected/modified from the sequences of a *Syntrophothermus lipocalidus* DSM 12680 Enolase (GenBank: ADIO2602), a 120-bp rbcS terminator from BP1 (1539-1658), and a PCR RE primer (1659-1678) at the 3' end.

SEQ ID NO: 62 presents example 62 of a designer nirA-promoter-controlled Pyruvate Kinase (05) DNA construct (2137 bp) that includes a PCR FD primer (sequence 1-20), a 231-bp nirA promoter from *Thermosynechococcus elongatus* BP1 (21-251), an enzyme-encoding sequence (252-1997) selected/modified from the sequences of a *Syntrophothermus lipocalidus* DSM 12680 pyruvate kinase (GenBank: ADIO2459), a 120-bp rbcS terminator from BP1 (1998-2117), and a PCR RE primer (2118-2137) at the 3' end.

SEQ ID NO: 63 presents example 63 of a designer nirA-promoter-controlled Citramalate Synthase (36) DNA construct (2163 bp) that includes a PCR FD primer (sequence 1-20), a 305-bp nirA promoter (21-325), an enzyme-encoding sequence (326-1909) selected and modified from *Hydrogenobacter thermophilus* TK-6 citramalate synthase (YP_003433013), a 234-bp rbcS terminator from BP1 (1910-2143), and a PCR RE primer (2144-2163).

SEQ ID NO: 64 presents example 64 of a designer nirA-promoter-controlled 3-Isopropylmalate/(R)-2-Methylmalate Dehydratase (37) DNA construct (2878 bp) consisting of a PCR FD primer (sequence 1-20), a 231-bp nirA promoter from *Thermosynechococcus elongatus* BP1 (21-251), a 3-isopropylmalate/(R)-2-methylmalate dehydratase large subunit-encoding sequence (252-2012) selected/modified from the sequences of an *Eubacterium eligens* ATCC 27750 3-isopropylmalate/(R)-2-methylmalate dehydratase large subunit (YP_002930810), a 231-bp nirA promoter from *Thermosynechococcus elongatus* BP1 (2013-2243), a 3-isopropylmalate/(R)-2-methylmalate dehydratase small subunit-encoding sequence (2244-2738) selected/modified from the sequences of an *Eubacterium eligens* ATCC 27750 3-isopropylmalate/(R)-2-methylmalate dehydratase small subunit (YP_002930809), a 120-bp rbcS terminator from BP1 (2739-2858), and a PCR RE primer (2859-2878) at the 3' end.

SEQ ID NO: 65 presents example 65 of a designer nirA-promoter-controlled 3-Isopropylmalate Dehydratase (38) DNA construct (2380 bp) comprises: a PCR FD primer (sequence 1-20), a 231-bp nirA promoter from *Thermosynechococcus elongatus* BP1 (21-251), a 3-isopropylmalate dehydratase large subunit-encoding sequence (252-1508) selected/modified from the sequences of a *Thermotoga petrophila* RKU-1 3-isopropylmalate dehydratase large subunit (ABQ46641), a 231-bp nirA promoter from *Thermosynechococcus elongatus* BP1 (1509-1739), a 3-isopropylmalate dehydratase small subunit-encoding sequence (1740-2240) selected/modified from the sequences of a *Thermotoga petrophila* RKU-1 3-isopropylmalate dehydratase small subunit (ABQ46640), a 120-bp rbcS terminator from BP1 (2241-2360), and a PCR RE primer (2361-2380) at the 3' end.

SEQ ID NO: 66 presents example 66 of a designer nirA-promoter-controlled 3-Isopropylmalate Dehydrogenase (39) DNA construct (1456 bp) consisting of: a PCR FD primer (sequence 1-20), a 231-bp nirA promoter from *Thermosynechococcus elongatus* BP1 (21-251), a 3-isopropylmalate dehydrogenase-encoding sequence (252-1316) selected/modified from the sequences of a *Thermotoga petrophila* RKU-1 3-isopropylmalate dehydrogenase (GenBank: CP000702 Region 349983.351047), a 120-bp rbcS terminator from BP1 (1317-1436), and a PCR RE primer (1437-1456) at the 3' end.

SEQ ID NO: 67 presents example 67 of a designer nirA-promoter-controlled 2-Isopropylmalate Synthase (40, EC 4.1.3.12) DNA construct (1933 bp) consisting of: a PCR FD primer (sequence 1-20), a 231-bp nirA promoter from *Thermosynechococcus elongatus* BP1 (21-251), an enzyme-encoding sequence (252-1793) selected/modified from the sequences of a *Thermotoga petrophila* RKU-1 3-isopropylmalate dehydrogenase (CP000702 Region: 352811.354352), a 120-bp rbcS terminator from BP1 (1794-1913), and a PCR RE primer (1914-1933) at the 3' end.

SEQ ID NO: 68 presents example 68 of a designer nirA-promoter-controlled Isopropylmalate Isomerase (41) DNA construct (2632 bp) comprises: a PCR FD primer (sequence 1-20), a 231-bp nirA promoter from *Thermosynechococcus elongatus* BP1 (21-251), a isopropylmalate isomerase large subunit-encoding sequence (252-1667) selected/modified from the sequences of a *Geobacillus kaustophilus* HTA426 3-isopropylmalate isomerase large subunit (YP__148509), a 231-bp nirA promoter from *Thermosynechococcus elongatus* BP1 (1668-1898), a isopropylmalate isomerase small subunit-encoding sequence (1899-2492) selected/modified from the sequences of a *Geobacillus kaustophilus* HTA426 isopropylmalate isomerase small subunit (YP__148508), a 120-bp rbcS terminator from BP1 (2493-2612), and a PCR RE primer (2613-2632) at the 3' end.

SEQ ID NO: 69 presents example 69 of a designer nirA-promoter-controlled 2-Keto Acid Decarboxylase (42) DNA construct (2035 bp) consisting of: a PCR FD primer (sequence 1-20), a 231-bp nirA promoter from *Thermosynechococcus elongatus* BP1 (21-251), a 2-keto acid decarboxylase-encoding sequence (252-1895) selected/modified from the sequences of a *Lactococcus lactis* branched-chain alpha-ketoacid decarboxylase (AAS49166), a 120-bp rbcS terminator from BP1 (1896-2015), and a PCR RE primer (2016-2035) at the 3' end.

SEQ ID NO: 70 presents example 70 of a designer nirA-promoter-controlled NAD-dependent Alcohol Dehydrogenase (43) DNA construct (1426 bp) consisting of: a PCR FD primer (sequence 1-20), a 231-bp nirA promoter from *Thermosynechococcus elongatus* BP1 (21-251), an enzyme-encoding sequence (252-1286) selected/modified from the sequences of an *Aeropyrum pernix* $K_1$ NAD-dependent alcohol dehydrogenase (NP__148480), a 120-bp rbcS terminator from BP1 (1287-1406), and a PCR RE primer (1407-1426) at the 3' end.

As mentioned before, use of an NADPH-dependent alcohol dehydrogenase 44 that can use NADPH as the source of reductant can help alleviate the requirement of NADH supply for enhanced photobiological production of butanol and other alcohols. SEQ ID NO: 71 presents example 71 of a designer nirA-promoter-controlled NADPH-dependent Alcohol Dehydrogenase (44) DNA construct (1468 bp) that comprises: a PCR FD primer (sequence 1-20), a 231-bp nirA promoter from *Thermosynechococcus elongatus* BP1 (21-251), an enzyme-encoding sequence (252-1328) selected/modified from the sequences of a *Pichia pastoris* GS115 NADPH-dependent medium chain alcohol dehydrogenase with broad substrate specificity (XP__002494014), a 120-bp rbcS terminator from BP1 (1329-1458), and a PCR RE primer (1459-1468) at the 3' end. In one of the examples, this type of NADPH-dependent alcohol dehydrogenase gene (SEQ ID NO: 71) is also used in construction of Calvin-cycle-channeled butanol production pathway.

However, because of the broad substrate specificity of the 2-keto acid decarboxylase (42, SEQ ID NO: 69) and the alcohol dehydrogenase (43, SEQ ID NO: 70; or 44, SEQ ID NO: 71), the pathway expressed with designer genes of SEQ ID NO: 69 and SEQ ID NO: 71 (and/or SEQ ID NO: 70) can result in the production of alcohol mixtures rather than single alcohols since all 2-keto acids can be converted to alcohols by the two broad substrate specificity enzymes. Therefore, to improve the specificity for 1-butanol production, it is a preferred practice to use a more substrate-specific butanol dehydrogenase 12. SEQ ID NO: 72 presents example 72 of a designer nirA-promoter-controlled NADH-dependent Butanol Dehydrogenase (12a) DNA construct (1555 bp) that includes a PCR FD primer (sequence 1-20), a 231-bp nirA promoter from *Thermosynechococcus elongatus* BP1 (21-251), an enzyme-encoding sequence (252-1415) selected/modified from the sequences of a *Geobacillus kaustophilus* HTA426 NADH-dependent butanol dehydrogenase (YP__148778), a 120-bp rbcS terminator from BP1 (1416-1535), and a PCR RE primer (1536-1555) at the 3' end.

SEQ ID NO: 73 presents example 73 of a designer nirA-promoter-controlled NADPH-dependent Butanol Dehydrogenase (12b) DNA construct (1558 bp) consisting of a PCR FD primer (sequence 1-20), a 231-bp nirA promoter from *Thermosynechococcus elongatus* BP1 (21-251), a NADPH-dependent butanol dehydrogenase-encoding sequence (252-1418) selected/modified from the sequences of a *Clostridium perfringens* str. 13 NADPH-dependent butanol dehydrogenase (NP__562172), a 120-bp rbcS terminator from BP1 (1419-1528), and a PCR RE primer (1529-1558) at the 3' end.

Use of SEQ ID NOS: 72 and/or 73 (12a and/or 12b) along with SEQ ID NOS: 58-69 represents a specific Calvin-cycle-channeled 1-butanol production pathway numerically labeled as 34, 35, 03-05, 36-42 and 12 in FIG. 4.

SEQ ID NOS: 74-81 represent an alternative (amino acids metabolism-related) pathway (45-52 in FIG. 4) that branches from the point of phosphoenolpyruvate and merges at the point of 2-ketobutyrate in the Calvin-cycle-channeled 1-butanol production pathway. Briefly, SEQ ID NO: 74 presents example 74 of a designer nirA-promoter-controlled Phosphoenolpyruvate Carboxylase (45) DNA construct (3646 bp) consisting of: a PCR FD primer (sequence 1-20), a 231-bp nirA promoter from *Thermosynechococcus elongatus* BP1 (21-251), an enzyme-encoding sequence (252-3506) selected/modified from the sequences of a *Thermaerobacter subterraneus* DSM 13965 Phosphoenolpyruvate carboxylase (EFR61439), a 120-bp rbcS terminator from BP1 (3507-3626), and a PCR RE primer (3627-3646) at the 3' end.

SEQ ID NO: 75 presents example 75 of a designer nirA-promoter-controlled Aspartate Aminotransferase (46) DNA construct (1591 bp) that includes a PCR FD primer (sequence 1-20), a 231-bp nirA promoter from *Thermosynechococcus elongatus* BP1 (21-251), an enzyme-encoding sequence (252-1451) selected/modified from the sequences of a *Thermotoga lettingae* TMO aspartate aminotransferase (YP__001470126), a 120-bp rbcS terminator from BP1 (1452-1471), and a PCR RE primer (1472-1591) at the 3' end.

SEQ ID NO: 76 presents example 76 of a designer nirA-promoter-controlled Aspartate Kinase (47) DNA construct (1588 bp) that includes a PCR FD primer (sequence 1-20), a 231-bp nirA promoter from *Thermosynechococcus elongatus* BP1 (21-251), an enzyme-encoding sequence (252-1448) selected/modified from the sequences of a *Thermotoga lettingae* TMO aspartate kinase (YP__001470361), a 120-bp rbcS terminator from BP1 (1449-1568), and a PCR RE primer (1569-1588) at the 3' end.

SEQ ID NO: 77 presents example 77 of a designer nirA-promoter-controlled Aspartate-Semialdehyde Dehydrogenase (48) DNA construct (1411 bp) that includes a PCR FD primer (sequence 1-20), a 231-bp nirA promoter from *Thermosynechococcus elongatus* BP1 (21-251), an enzyme-encoding sequence (252-1271) selected/modified from the sequences of a *Thermotoga lettingae* TMO aspartate-semialdehyde dehydrogenase (YP_001470981), a 120-bp rbcS terminator from BP1 (1272-1391), and a PCR RE primer (1392-1411) at the 3' end.

SEQ ID NO: 78 presents example 78 of a designer nirA-promoter-controlled Homoserine Dehydrogenase (49) DNA construct (1684 bp) that includes a PCR FD primer (sequence 1-20), a 231-bp nirA promoter from *Thermosynechococcus elongatus* BP1 (21-251), an enzyme-encoding sequence (252-1544) selected/modified from the sequences of a *Syntrophothermus lipocalidus* DSM 12680 homoserine dehydrogenase (ADIO2231), a 120-bp rbcS terminator from BP1 (1545-1664), and a PCR RE primer (1665-1684) at the 3' end.

SEQ ID NO: 79 presents example 79 of a designer nirA-promoter-controlled Homoserine Kinase (50) DNA construct (1237 bp) that includes a PCR FD primer (sequence 1-20), a 231-bp nirA promoter from *Thermosynechococcus elongatus* BP1 (21-251), an enzyme-encoding sequence (252-1097) selected/modified from the sequences of a *Thermotoga petrophila* RKU-1 Homoserine Kinase (YP_001243979), a 120-bp rbcS terminator from BP1 (1098-1217), and a PCR RE primer (1218-1237) at the 3' end.

SEQ ID NO: 80 presents example 80 of a designer nirA-promoter-controlled Threonine Synthase (51) DNA construct (1438 bp) that includes a PCR FD primer (sequence 1-20), a 231-bp nirA promoter from *Thermosynechococcus elongatus* BP1 (21-251), an enzyme-encoding sequence (252-1298) selected/modified from the sequences of a *Thermotoga petrophila* RKU-1 Threonine Synthase (YP_001243978), a 120-bp rbcS terminator from BP1 (1299-1418), and a PCR RE primer (1419-1438) at the 3' end.

SEQ ID NO: 81 presents example 81 of a designer nirA-promoter-controlled Threonine Ammonia-Lyase (52) DNA construct (1600 bp) consisting of a PCR FD primer (sequence 1-20), a 231-bp nirA promoter from *Thermosynechococcus elongatus* BP1 (21-251), an enzyme-encoding sequence (252-1460) selected/modified from the sequences of a *Geobacillus kaustophilus* HTA426 threonine ammonia-lyase (BAD75876), a 120-bp rbcS terminator from BP1 (1461-1580), and a PCR RE primer (1581-1600) at the 3' end.

Note, SEQ ID NOS: 58-61, 74-81, 66-69, and 72 (and/or 73) represent a set of sample designer genes that can express a Calvin-cycle 3-phophoglycerate-branched photosynthetic NADPH-enhanced 1-butanol production pathway of 34, 35, 03, 04, 45-52 40, 41, 39, 42, and 12 while SEQ ID NOS: 58-69 and 72 (and/or 73) represent another set of sample designer genes that can express another Calvin-cycle 3-phophoglycerate-branched photosynthetic NADPH-enhanced 1-butanol production pathway as numerically labeled as 34, 35, 03-05, 36-42, and 12 in FIG. 4. The net results of the designer photosynthetic NADPH-enhanced pathways in working with the Calvin cycle are photobiological production of 1-butanol ($CH_3CH_2CH_2CH_2OH$) from carbon dioxide ($CO_2$) and water ($H_2O$) using photosynthetically generated ATP (Adenosine triphosphate) and NADPH (reduced nicotinamide adenine dinucleotide phosphate) according to the following process reaction:

$$4CO_2+5H_2O \rightarrow CH_3CH_2CH_2CH_2OH+6O_2 \quad [5]$$

Designer Calvin-Cycle-Channeled 2-Methyl-1-Butanol Producing Pathways

Figure 5:
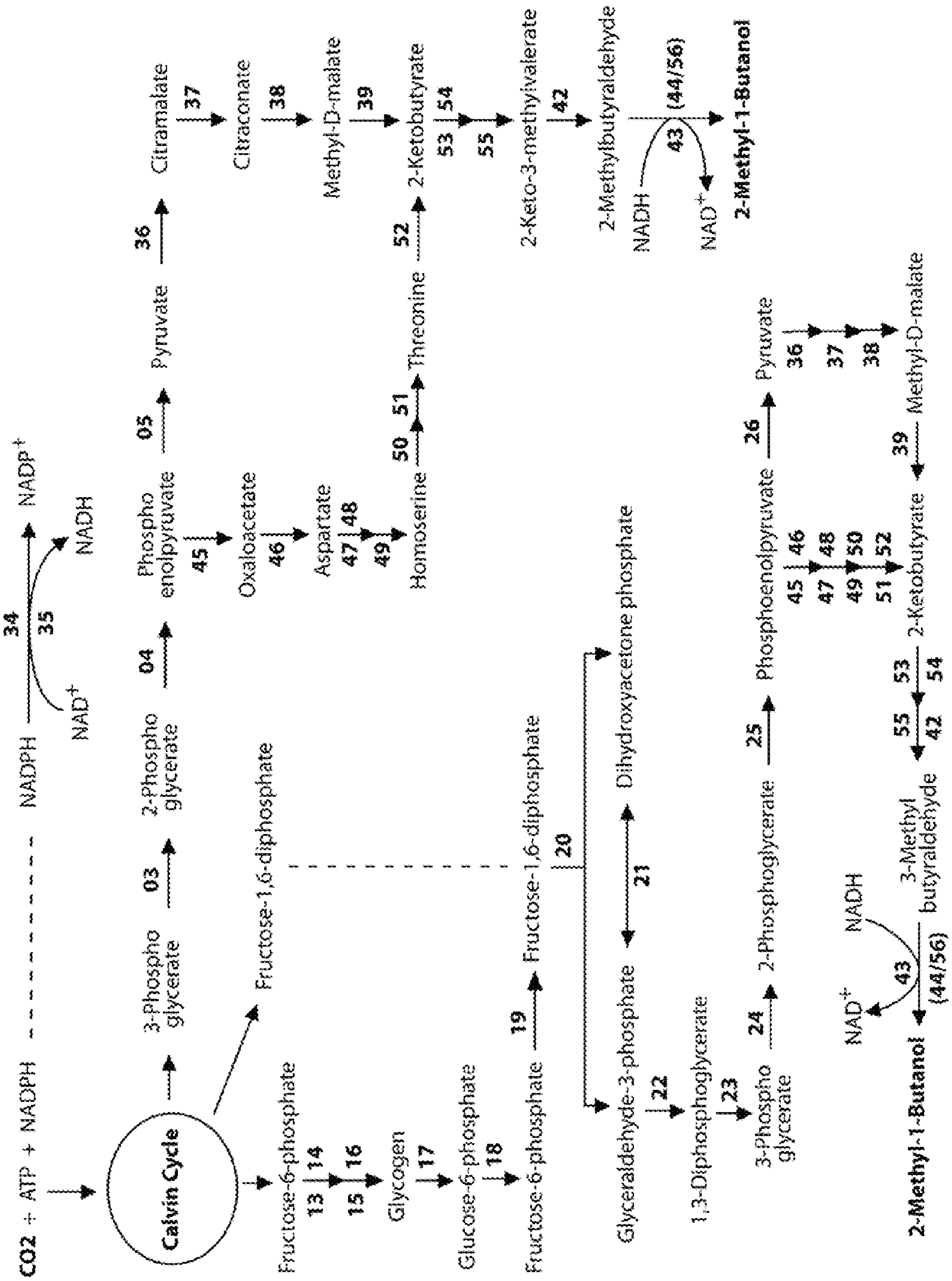
FIG. 5 presents designer Calvin-cycle-channeled and photosynthetic NADPH-enhanced pathways using NADPH and ATP from the photosynthetic water splitting and proton gradient-coupled electron transport process to reduce carbon dioxide ($CO_2$) into 2-methyl-1-butanol ($CH_3CH_2CH(CH_3)CH_2OH$) with a series of enzymatic reactions.

According to one of the various embodiments, a designer Calvin-cycle-channeled 2-Methyl-1-Butanol production pathway is created that takes the Calvin-cycle intermediate product, 3-phosphoglycerate, and converts it into 2-methyl-1-butanol by using, for example, a set of enzymes consisting of (as shown with the numerical labels 34, 35, 03-05, 36-39, 53-55, 42, 43 or 44/56 in FIG. 5): NADPH-dependent glyceraldehyde-3-phosphate dehydrogenase 34, NAD-dependent glyceraldehyde-3-phosphate dehydrogenase 35, phosphoglycerate mutase 03, enolase 04, pyruvate kinase 05, citramalate synthase 36, 2-methylmalate dehydratase 37, 3-isopropylmalate dehydratase 38, 3-isopropylmalate dehydrogenase 39, acetolactate synthase 53, ketol-acid reductoisomerase 54, dihydroxy-acid dehydratase 55, 2-keto acid decarboxylase 42, and NAD-dependent alcohol dehydrogenase 43 (or NADPH-dependent alcohol dehydrogenase 44; more preferably, 2-methylbutyraldehyde reductase 56).

In another embodiment, a designer Calvin-cycle-channeled 2-methyl-1-butanol production pathway is created that takes the intermediate product, 3-phosphoglycerate, and converts it into 2-methyl-1-butanol by using, for example, a set of enzymes consisting of (as shown with the numerical labels 34, 35, 03, 04, 45-55, 42, 43 or 44/56 in FIG. 5): NADPH-dependent glyceraldehyde-3-phosphate dehydrogenase 34, NAD-dependent glyceraldehyde-3-phosphate dehydrogenase 35, phosphoglycerate mutase 03, enolase 04, phosphoenolpyruvate carboxylase 45, aspartate aminotransferase 46, aspartokinase 47, aspartate-semialdehyde dehydrogenase 48, homoserine dehydrogenase 49, homoserine kinase 50, threonine synthase 51, threonine ammonia-lyase 52, acetolactate synthase 53, ketol-acid reductoisomerase 54, dihydroxy-acid dehydratase 55, 2-keto acid decarboxylase 42, and NAD dependent alcohol dehydrogenase 43 (or NADPH dependent alcohol dehydrogenase 44; more preferably, 2-methylbutyraldehyde reductase 56).

These pathways (FIG. 5) are quite similar to those of FIG. 4, except that acetolactate synthase 53, ketol-acid reductoisomerase 54, dihydroxy-acid dehydratase 55, and 2-methylbutyraldehyde reductase 56 are used to produce 2-Methyl-1-Butanol.

SEQ ID NO: 82 presents example 82 of a designer nirA-promoter-controlled Acetolactate Synthase (53) DNA construct (2107 bp) that includes a PCR FD primer (sequence 1-20), a 231-bp nirA promoter from *Thermosynechococcus elongatus* BP1 (21-251), an acetolactate synthase-encoding sequence (252-1967) selected/modified from the sequences of a *Bacillus subtilis* subsp. *subtilis* str. 168 acetolactate synthase (CAB07802), a 120-bp rbcS terminator from BP1 (1968-2087), and a PCR RE primer (2088-2107) at the 3' end.

SEQ ID NO: 83 presents example 83 of a designer nirA-promoter-controlled Ketol-Acid Reductoisomerase (54) DNA construct (1405 bp) that includes a PCR FD primer (sequence 1-20), a 231-bp nirA promoter from *Thermosynechococcus elongatus* BP1 (21-251), a ketol-acid reductoisomerase-encoding sequence (252-1265) selected/modified from the sequences of a *Syntrophothermus lipocalidus* DSM 12680 ketol-acid reductoisomerase (ADIO2902), a 120-bp rbcS terminator from BP1 (1266-1385), and a PCR RE primer (1386-1405) at the 3' end.

SEQ ID NO: 84 presents example 84 of a designer nirA-promoter-controlled Dihydroxy-Acid Dehydratase (55) DNA construct (2056 bp) that includes a PCR FD primer (sequence 1-20), a 231-bp nirA promoter from *Thermosynechococcus elongatus* BP1 (21-251), an enzyme-encoding sequence (252-1916) selected/modified from the sequences of a *Thermotoga petrophila* RKU-1 dihydroxy-acid dehydratase (YP_001243973), a 120-bp rbcS terminator from BP1 (1917-2036), and a PCR RE primer (2037-2056) at the 3' end.

SEQ ID NO: 85 presents example 85 of a designer nirA-promoter-controlled 2-Methylbutyraldehyde Reductase (56) DNA construct (1360 bp) that includes a PCR FD primer (sequence 1-20), a 231-bp nirA promoter from *Thermosynechococcus elongatus* BP1 (21-251), an enzyme-encoding sequence (252-1220) selected/modified from the sequences of a *Schizosaccharomyces japonicus* yFS275 2-methylbutyraldehyde reductase (XP_002173231), a 120-bp rbcS terminator from BP1 (1221-1340), and a PCR RE primer (1341-1360) at the 3' end.

Note, SEQ ID NOS: 58-66, 82-84, 69 and 85 represent another set of sample designer genes that can express a Calvin-cycle 3-phophoglycerate-branched photosynthetic NADPH-enhanced 2-methyl-1-butanol production pathway numerically labeled as 34, 35, 03-05, 36-39, 53-55, 42 and 56; while SEQ ID NOS: 58-61, 74-84, 69 and 85 represent a set of sample designer genes that can express another Calvin-cycle 3-phophoglycerate-branched photosynthetic NADPH-enhanced 2-methyl-1-butanol production pathway of 34, 35, 03, 04, 45-55, 42 and 56 in FIG. 5. These designer genes can be used in combination with other pathway gene(s) to express certain other pathways such as a Calvin-cycle Fructose-6-phosphate branched 2-methyl-1-butanol production pathway numerically labeled as 13-26, 36-39, 53-55, 42 and 56 (and/or, as 13-25, 45-55, 42 and 56) in FIG. 5 as well. The net results of the designer photosynthetic NADPH-enhanced pathways in working with the Calvin cycle are production of 2-methyl-1-butanol [$CH_3CH_2CH(CH_3)CH_2OH$] from carbon dioxide ($CO_2$) and water ($H_2O$) using photosynthetically generated ATP and NADPH according to the following process reaction:

$$10CO_2+12H_2O \rightarrow 2CH_3CH_2CH(CH_3)CH_2OH+15O_2 \quad [6]$$

Figure 6:
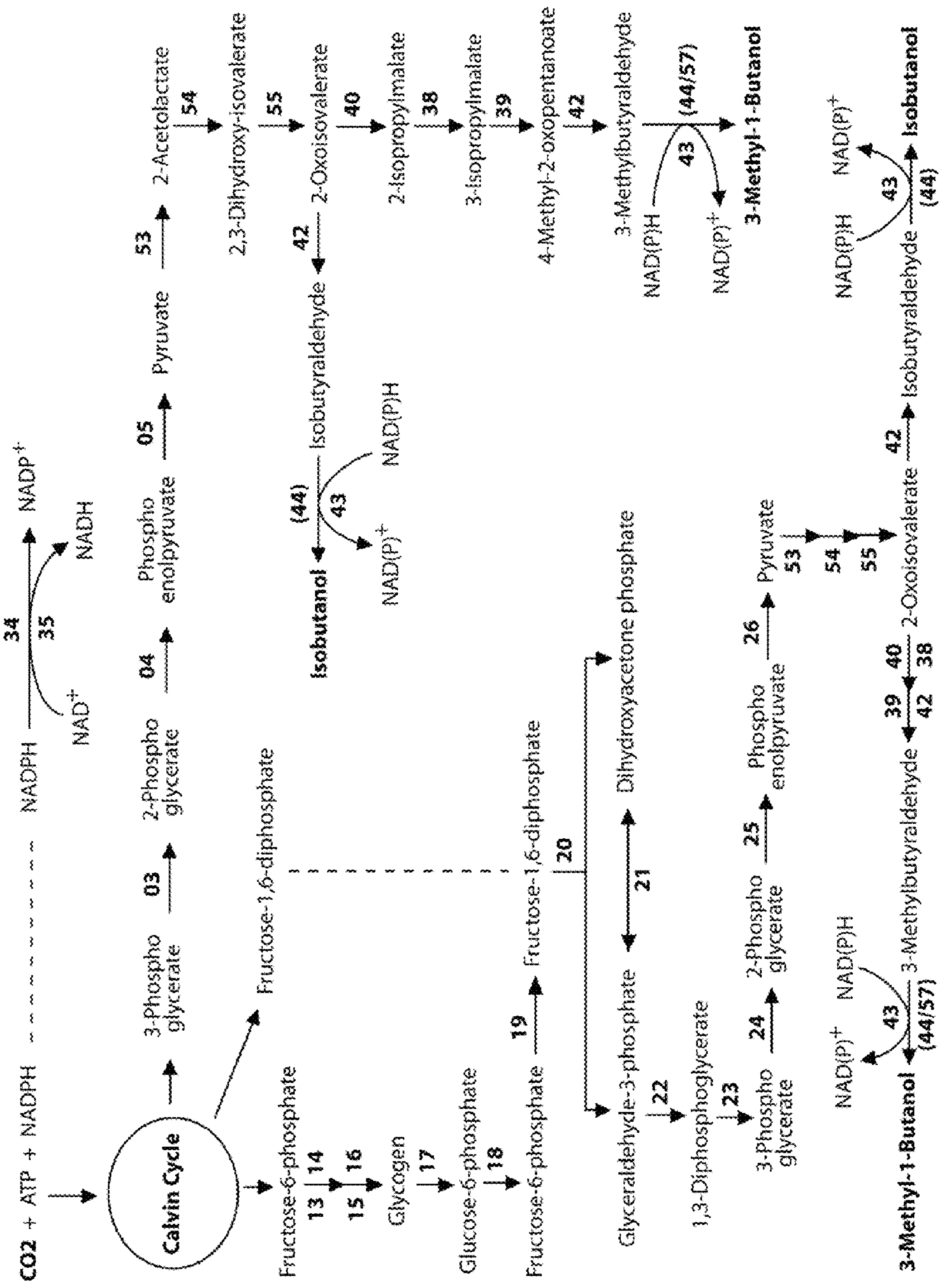
FIG. 6 presents designer Calvin-cycle-channeled and photosynthetic NADPH-enhanced pathways using NADPH and ATP from the photosynthetic water splitting and proton gradient-coupled electron transport process to reduce carbon dioxide ($CO_2$) into isobutanol ($(CH_3)_2CHCH_2OH$) and 3-methyl-1-butanol ($CH_3CH(CH_3)CH_2CH_2OH$) with a series of enzymatic reactions.

Designer Calvin-Cycle-Channeled Pathways for Production of Isobutanol and 3-Methyl-1-Butanol According to one of the various embodiments, a designer Calvin-cycle-channeled pathway is created that takes the Calvin-cycle intermediate product, 3-phosphoglycerate, and converts it into isobutanol by using, for example, a set of enzymes consisting of (as shown with numerical labels 34, 35, 03-05, 53-55, 42, 43 (or 44) in FIG. 6): NADPH-dependent glyceraldehyde-3-phosphate dehydrogenase 34, NAD-dependent glyceraldehyde-3-phosphate dehydrogenase 35, phosphoglycerate mutase 03, enolase 04, pyruvate kinase 05, acetolactate synthase 53, ketol-acid reductoisomerase 54, dihydroxy-acid dehydratase 55, 2-keto acid decarboxylase 42, and NAD-dependent alcohol dehydrogenase 43 (or NADPH-dependent alcohol dehydrogenase 44). The net result of this pathway in working with the Calvin cycle is photobiological production of isobutanol ($(CH_3)_2CHCH_2OH$) from carbon dioxide ($CO_2$) and water ($H_2O$) using photosynthetically generated ATP and NADPH according to the following process reaction:

$$4CO_2+5H_2O \rightarrow (CH_3)_2CHCH_2OH+6O_2 \quad [7]$$

According to another embodiment, a designer Calvin-cycle-channeled pathway is created that takes the intermediate product, 3-phosphoglycerate, and converts it into 3-methyl-1-butanol by using, for example, a set of enzymes consisting of (as shown with the numerical labels 34, 35, 03-05, 53-55, 40, 38, 39, 42, 43 (or 44/57) in FIG. 6): NADPH-dependent glyceraldehyde-3-phosphate dehydrogenase 34, NAD-dependent glyceraldehyde-3-phosphate dehydrogenase 35, phosphoglycerate mutase 03, enolase 04, pyruvate kinase 05, acetolactate synthase 53, ketol-acid reductoisomerase 54, dihydroxy-acid dehydratase 55, 2-isopropylmalate synthase 40, 3-isopropylmalate dehydratase 38, 3-isopropylmalate dehydrogenase 39, 2-keto acid decarboxylase 42, and NAD-dependent alcohol dehydrogenase 43 (or NADPH-dependent alcohol dehydrogenase 44; or more preferably, 3-methylbutanal reductase 57). The net result of this pathway in working with the Calvin cycle is photobiological production of 3-methyl-1-butanol ($CH_3CH(CH_3)CH_2CH_2OH$) from carbon dioxide ($CO_2$) and water ($H_2O$) using photosynthetically generated ATP and NADPH according to the following process reaction:

$$10CO_2+12H_2O \rightarrow 4CH_3CH(CH_3)CH_2CH_2OH+15O_2 \quad [8]$$

These designer pathways (FIG. 6) share a number of designer pathway enzymes with those of FIGS. 4 and 5, except that a 3-methylbutanal reductase 57 is preferably used for production of 3-methyl-1-butanol; they all have a common feature of using an NADPH-dependent glyceraldehyde-3-phosphate dehydrogenase 34 and an NAD-dependent glyceraldehyde-3-phosphate dehydrogenase 35 as an NADPH/NADH conversion mechanism to covert certain amount of photosynthetically generated NADPH to NADH which can be used by NADH-requiring pathway enzymes such as an NADH-requiring alcohol dehydrogenase 43.

SEQ ID NO: 86 presents example 86 of a designer nirA-promoter-controlled 3-Methylbutanal Reductase (57) DNA construct (1420 bp) that includes a PCR FD primer (sequence 1-20), a 231-bp nirA promoter from *Thermosynechococcus elongatus* BP1 (21-251), an enzyme-encoding sequence (252-1280) selected/modified from the sequences of a *Saccharomyces cerevisiae* S288c 3-Methylbutanal reductase (DAA10635), a 120-bp rbcS terminator from BP1 (1281-1400), and a PCR RE primer (1401-1420) at the 3' end.

SEQ ID NOS: 58-62, 82-84, 69, 70 (or 71) represent a set of sample designer genes that can express a Calvin-cycle 3-phosphoglycerate-branched photosynthetic NADPH-enhanced isobutanol production pathway (34, 35, 03-05, 53-55, 42, 43 or 44); while SEQ ID NOS: 58-62, 82-84, 65-67, 69 and 86 represent another set of sample designer genes that can express a Calvin-cycle 3-phosphoglycerate-branched photosynthetic NADPH-enhanced 3-methyl-1-butanol production pathway (numerical labels 34, 35, 03-05, 53-55, 40, 38, 39, 42, and 57 in FIG. 6).

These designer genes can be used with certain other designer genes to express certain other pathways such as a Calvin-cycle Fructose-6-phosphate-branched 3-methyl-1-butanol production pathway shown as 13-26, 53-54, 39-40, 42 and 57 (or 43/44) in FIG. 6 as well. The net results of the designer photosynthetic NADPH-enhanced pathways in working with the Calvin cycle are also production of isobutanol ($(CH_3)_2CHCH_2OH$) and/or 3-methyl-1-butanol ($CH_3CH(CH_3)CH_2CH_2OH$) from carbon dioxide ($CO_2$) and water ($H_2O$) using photosynthetically generated ATP and NADPH.

Figure 7:
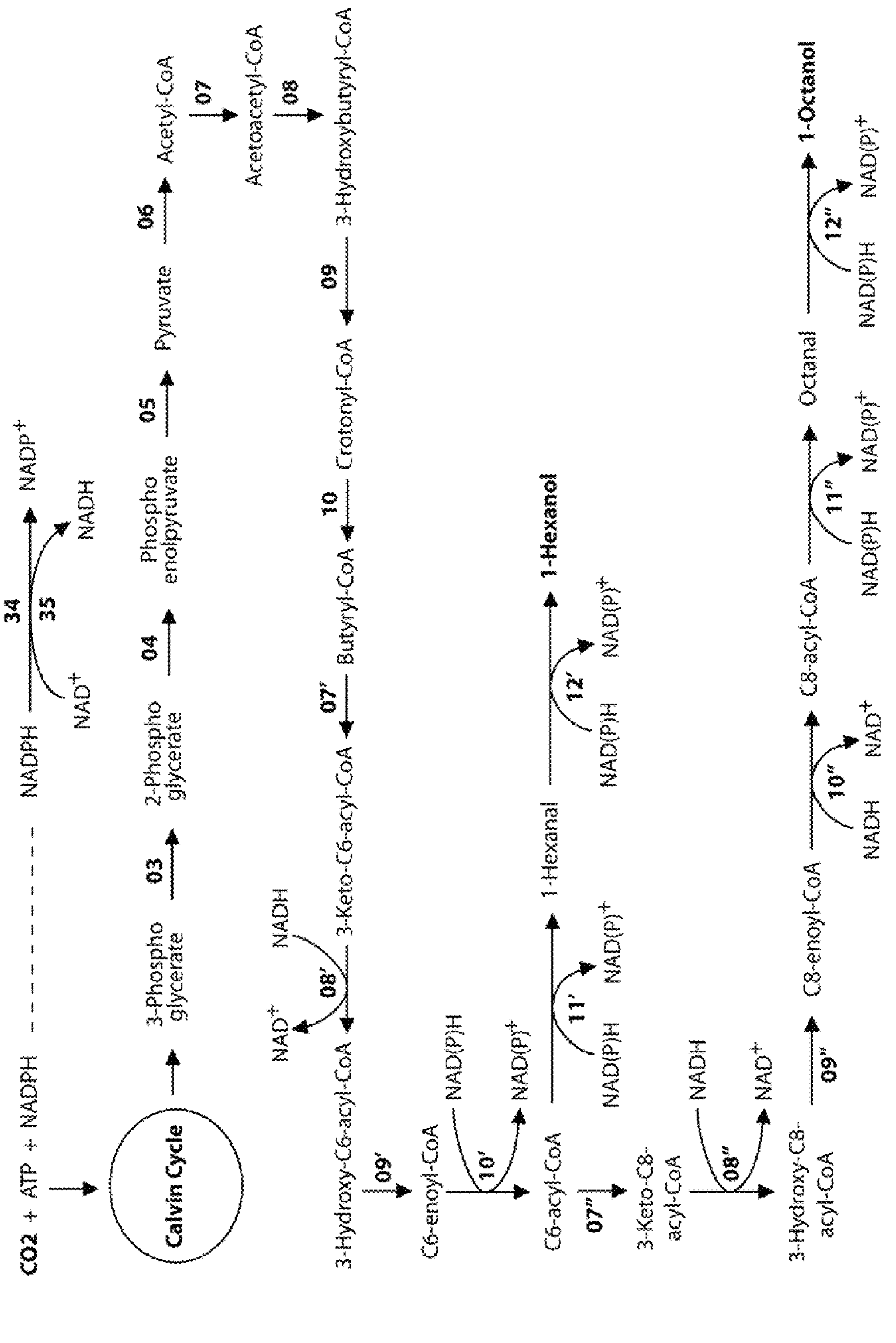
FIG. 7 presents designer Calvin-cycle-channeled and photosynthetic NADPH-enhanced pathways using NADPH and ATP from the photosynthetic water splitting and proton gradient-coupled electron transport process to reduce carbon dioxide ($CO_2$) into 1-hexanol ($CH_3CH_2CH_2CH_2CH_2CH_2OH$) and 1-octanol ($CH_3CH_2CH_2CH_2CH_2CH_2CH_2CH_2OH$) with a series of enzymatic reactions.

Designer Calvin-Cycle-Channeled Pathways for Production of 1-Hexanol and 1-Octanol According to one of the various embodiments, a designer Calvin-cycle-channeled pathway is created that takes the Calvin-cycle intermediate product, 3-phosphoglycerate, and converts it into 1-hexanol by using, for example, a set of enzymes consisting of (as shown with the numerical labels 34, 35, 03-10, 07'-12' in FIG. 7): NADPH-dependent glyceraldehyde-3-phosphate dehydrogenase 34, NAD-dependent glyceraldehyde-3-phosphate dehydrogenase 35, phosphoglycerate mutase 03, enolase 04, pyruvate kinase 05, pyruvate-ferredoxin oxidoreductase 06, thiolase 07, 3-hydroxybutyryl-CoA dehydrogenase 08, crotonase 09, butyryl-CoA dehydrogenase 10, designer 3-ketothiolase 07', designer 3-hydroxyacyl-CoA dehydrogenase 08', designer enoyl-CoA dehydratase 09', designer 2-enoyl-CoA reductase 10', designer acyl-CoA reductase 11', and hexanol dehydrogenase 12'. The net result of this designer pathway in working with the Calvin cycle is photobiological production of 1-hexanol ($CH_3CH_2CH_2CH_2CH_2CH_2OH$) from carbon dioxide ($CO_2$) and water ($H_2O$) using photosynthetically generated ATP and NADPH according to the following process reaction:

$$6CO_2+7H_2O \rightarrow CH_3CH_2CH_2CH_2CH_2CH_2OH+9O_2 \quad [9]$$

According to another embodiment, a designer Calvin-cycle-channeled pathway is created that takes the intermediate product, 3-phosphoglycerate, and converts it into 1-octanol by using, for example, a set of enzymes consisting of (as shown with the numerical labels 34, 35, 03-10, 07'-10', and 07"-12" in FIG. 7): NADPH-dependent glyceraldehyde-3-phosphate dehydrogenase 34, NAD-dependent glyceraldehyde-3-phosphate dehydrogenase 35, phosphoglycerate mutase 03, enolase 04, pyruvate kinase 05, pyruvate-ferredoxin oxidoreductase 06, thiolase 07, 3-hydroxybutyryl-CoA dehydrogenase 08, crotonase 09, butyryl-CoA dehydrogenase 10, designer 3-ketothiolase 07', designer 3-hydroxyacyl-CoA dehydrogenase 08', designer enoyl-CoA dehydratase 09', designer 2-enoyl-CoA reductase 10', designer 3-ketothiolase 07", designer 3-hydroxyacyl-CoA dehydrogenase 08", designer enoyl-CoA dehydratase 09", designer 2-enoyl-CoA reductase 10", designer acyl-CoA reductase 11", and octanol dehydrogenase 12".

These pathways represent a significant upgrade in the pathway designs with part of a previously disclosed 1-butanol production pathway (03-10). The key feature is the utilization of an NADPH-dependent glyceraldehyde-3-phosphate dehydrogenase 34 and an NAD-dependent glyceraldehyde-3-phosphate dehydrogenase 35 as a mechanism for NADPH/NADH conversion to drive an NADH-requiring designer hydrocarbon chain elongation pathway (07'-10') for 1-hexanol production (07'-12' as shown in FIG. 7).

SEQ ID NOS: 87-92 represent a set of designer genes that can express the designer hydrocarbon chain elongation pathway for 1-hexanol production (07'-12' as shown in FIG. 7). Briefly, SEQ ID NO: 87 presents example 87 of a designer nirA-promoter-controlled 3-Ketothiolase (07') DNA construct (1540 bp) that includes a PCR FD primer (sequence 1-20), a 231-bp nirA promoter from *Thermosynechococcus elongatus* BP1 (21-251), an enzyme-encoding sequence (252-1400) selected/modified from the sequences of a *Geobacillus kaustophilus* HTA426 3-Ketothiolase (YP__147173), a 120-bp rbcS terminator from BP1 (1401-1520), and a PCR RE primer (1521-1540) at the 3' end.

SEQ ID NO: 88 presents example 88 of a designer nirA-promoter-controlled 3-Hydroxyacyl-CoA Dehydrogenase (08') DNA construct (1231 bp) that includes a PCR FD primer (sequence 1-20), a 231-bp nirA promoter from *Thermosynechococcus elongatus* BP1 (21-251), an enzyme-encoding sequence (252-1091) selected/modified from the sequences of a *Syntrophothermus lipocalidus* DSM 12680 3-Hydroxyacyl-CoA dehydrogenase (YP__003702743), a 120-bp rbcS terminator from BP1 (1092-1211), and a PCR RE primer (1212-1231) at the 3' end.

SEQ ID NO: 89 presents example 89 of a designer nirA-promoter-controlled Enoyl-CoA Dehydratase (09') DNA construct (1162 bp) that includes a PCR FD primer (sequence 1-20), a 231-bp nirA promoter from *Thermosynechococcus elongatus* BP1 (21-251), an enzyme-encoding sequence (252-1022) selected/modified from the sequences of a *Bordetella petrii* Enoyl-CoA dehydratase (CAP41574), a 120-bp rbcS terminator from BP1 (1023-1442), and a PCR RE primer (1443-1162) at the 3' end.

SEQ ID NO: 90 presents example 90 of a designer nirA-promoter-controlled 2-Enoyl-CoA Reductase (10') DNA construct (1561 bp) that includes a PCR FD primer (sequence 1-20), a 231-bp nirA promoter from *Thermosynechococcus elongatus* BP1 (21-251), an enzyme-encoding sequence (252-1421) selected/modified from the sequences of a *Xanthomonas campestris* pv. *campestris* 2-Enoyl-CoA Reductase (CAP53709), a 120-bp rbcS terminator from BP1 (1422-1541), and a PCR RE primer (1542-1561) at the 3' end.

SEQ ID NO: 91 presents example 91 of a designer nirA-promoter-controlled Acyl-CoA Reductase (11') DNA construct (1747 bp) that includes a PCR FD primer (sequence 1-20), a 231-bp nirA promoter from *Thermosynechococcus elongatus* BP1 (21-251), an enzyme-encoding sequence (252-1607) selected/modified from the sequences of a *Clostridium* cellulovorans 743B Acyl-CoA reductase (YP__003845606), a 120-bp rbcS terminator from BP1 (1608-1727), and a PCR RE primer (1728-1747) at the 3' end.

SEQ ID NO: 92 presents example 92 of a designer nirA-promoter-controlled Hexanol Dehydrogenase (12') DNA construct (1450 bp) that includes a PCR FD primer (sequence 1-20), a 231-bp nirA promoter from *Thermosynechococcus elongatus* BP1 (21-251), an enzyme-encoding sequence (252-1310) selected/modified from the sequences of a *Mycobacterium chubuense* NBB4 hexanol dehydrogenase (ACZ56328), a 120-bp rbcS terminator from BP1 (1311-1430), and a PCR RE primer (1431-1450) at the 3' end.

SEQ ID NO: 93 presents example 93 of a designer nirA-promoter-controlled Octanol Dehydrogenase (12") DNA construct (1074 bp) that includes a PCR FD primer (sequence 1-20), a 231-bp nirA promoter from *Thermosynechococcus elongatus* BP1 (21-251), an enzyme-encoding sequence (252-934) selected/modified from the sequences of a *Drosophila subobscura* octanol dehydrogenase (AB065263), a 120-bp rbcS terminator from BP1 (935-1054), and a PCR RE primer (1055-1074) at the 3' end.

Note, the designer enzymes of SEQ ID NOS: 87-91 have certain broad substrate specificity. Consequently, they can also be used as designer 3-ketothiolase 07", designer 3-hydroxyacyl-CoA dehydrogenase 08", designer enoyl-CoA dehydratase 09", designer 2-enoyl-CoA reductase 10", and designer acyl-CoA reductase 11". Therefore, SEQ ID NOS: 87-91 and 93 represent a set of designer genes that can express another designer hydrocarbon chain elongation pathway for 1-octanol production (07'-10' and 07"-12" as shown in FIG. 7). SEQ ID NO: 93 (encoding for octanol dehydrogenase 12") is one of the key designer genes that enable production of 1-octanol production in this pathway. The net result of this pathway in working with the Calvin cycle are photobiological production of 1-octanol ($CH_3CH_2CH_2CH_2CH_2CH_2CH_2CH_2OH$) from carbon dioxide ($CO_2$) and water ($H_2O$) using photosynthetically generated ATP and NADPH according to the following process reaction:

$$8CO_2+9H_2O \rightarrow CH_3CH_2CH_2CH_2CH_2CH_2CH_2CH_2OH+12O_2 \quad [10]$$

Figure 8:
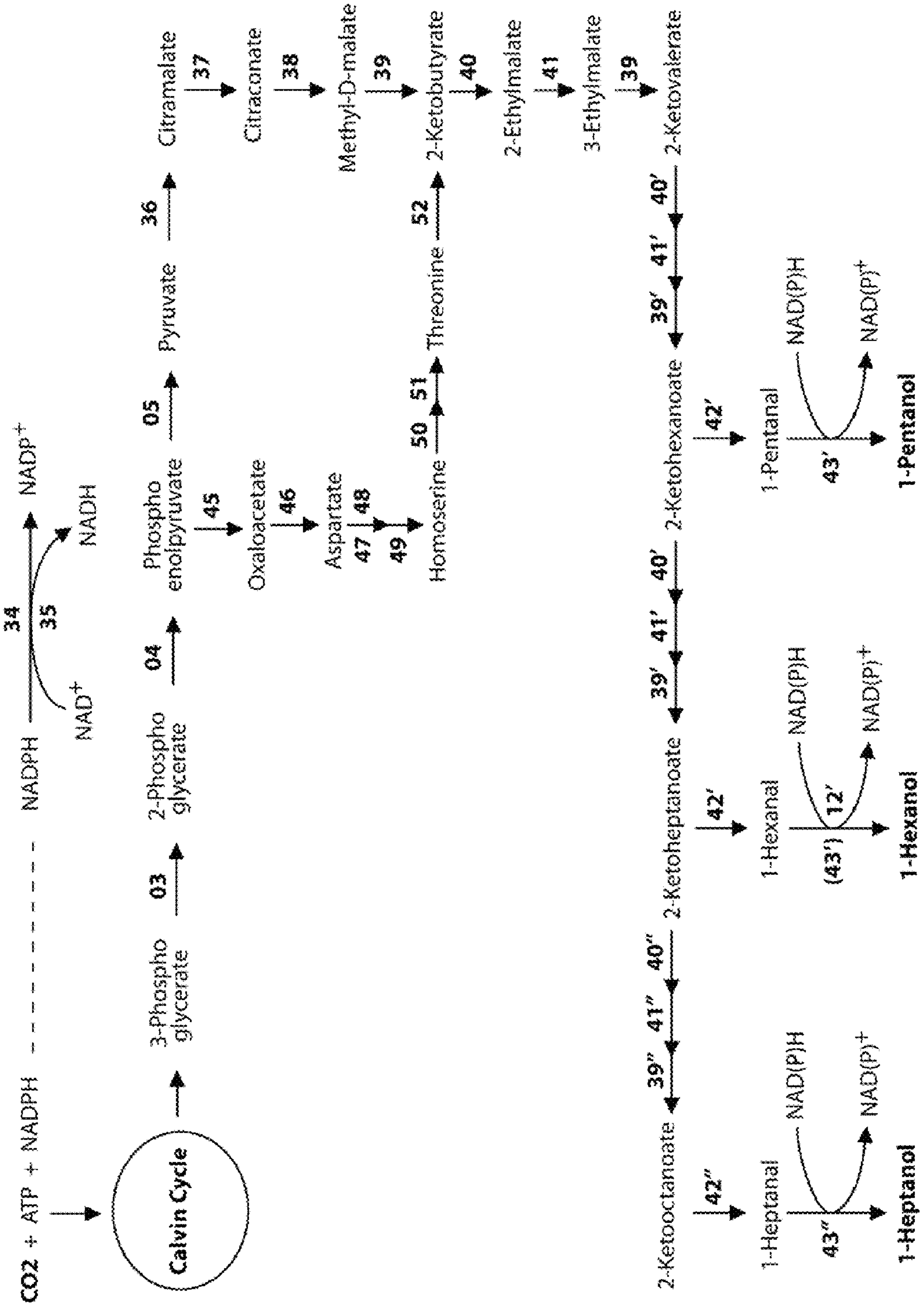
FIG. 8 presents designer Calvin-cycle-channeled and photosynthetic NADPH-enhanced pathways using NADPH and ATP from the photosynthetic water splitting and proton gradient-coupled electron transport process to reduce carbon dioxide ($CO_2$) into 1-pentanol ($CH_3CH_2CH_2CH_2CH_2OH$), 1-hexanol ($CH_3CH_2CH_2CH_2CH_2CH_2OH$), and 1-heptanol ($CH_3CH_2CH_2CH_2CH_2CH_2CH_2OH$) with a series of enzymatic reactions.

Designer Calvin-Cycle-Channeled Pathways for Production of 1-Pentanol, 1-Hexanol and 1-Heptanol According to one of the various embodiments, a designer Calvin-cycle-channeled pathway is created that takes the Calvin-cycle intermediate product, 3-phosphoglycerate, and converts it into 1-pentanol, 1-hexanol, and/or 1-heptanol by using, for example, a set of enzymes consisting of (as shown with the numerical labels 34, 35, 03-05, 36-41, 39, 39'-43', 39'-43', 12', and 39"-43" in FIG. 8): NADPH-dependent glyceraldehyde-3-phosphate dehydrogenase 34, NAD-dependent glyceraldehyde-3-phosphate dehydrogenase 35, phosphoglycerate mutase 03, enolase 04, pyruvate kinase 05, citramalate synthase 36, 2-methylmalate dehydratase 37, 3-isopropylmalate dehydratase 38, 3-isopropylmalate dehydrogenase 39, 2-isopropylmalate synthase 40, isopropylmalate isomerase 41, 3-isopropylmalate dehydrogenase 39, designer isopropylmalate synthase 40', designer isopropylmalate isomerase 41', designer 3-isopropylmalate dehydrogenase 39', designer 2-keto acid decarboxylase 42', short-chain alcohol dehydrogenase 43', hexanol dehydrogenase 12', designer isopropylmalate synthase 40", designer isopropylmalate isomerase 41", designer 3-isopropylmalate dehydrogenase 39", designer 2-keto acid decarboxylase 42", and designer short-chain alcohol dehydrogenase 43". This designer pathway works with the Calvin cycle using photosynthetically generated ATP and NADPH for photobiological production of 1-pentanol ($CH_3CH_2CH_2CH_2CH_2OH$), 1-hexanol ($CH_3CH_2CH_2CH_2CH_2CH_2OH$), and/or 1-heptanol ($CH_3CH_2CH_2CH_2CH_2CH_2CH_2OH$) from carbon dioxide ($CO_2$) and water ($H_2O$) according to the following process reactions:

$$10CO_2+12H_2O\rightarrow 2CH_3CH_2CH_2CH_2CH_2OH+15O_2 \quad [11]$$

$$6CO_2+7H_2O\rightarrow CH_3CH_2CH_2CH_2CH_2CH_2OH+9O_2 \quad [12]$$

$$14CO_2+16H_2O\rightarrow 2CH_3CH_2CH_2CH_2CH_2CH_2CH_2OH+21O_2 \quad [13]$$

According to another embodiment, a designer Calvin-cycle-channeled pathway is created that takes the intermediate product, 3-phosphoglycerate, and converts it into 1-pentanol, 1-hexanol, and/or 1-heptanol by using, for example, a set of enzymes consisting of (as shown with the numerical labels 34, 35, 03, 04, 45-52, 40, 41, 39, 39'-43', 39'-43', 12', and 39"-43" in FIG. 8): NADPH-dependent glyceraldehyde-3-phosphate dehydrogenase 34, NAD-dependent glyceraldehyde-3-phosphate dehydrogenase 35, phosphoglycerate mutase 03, enolase 04, phosphoenolpyruvate carboxylase 45, aspartate aminotransferase 46, aspartokinase 47, aspartate-semialdehyde dehydrogenase 48, homoserine dehydrogenase 49, homoserine kinase 50, threonine synthase 51, threonine ammonia-lyase 52, 2-isopropylmalate synthase 40, isopropylmalate isomerase 41, 3-isopropylmalate dehydrogenase 39, designer isopropylmalate synthase 40', designer isopropylmalate isomerase 41', designer 3-isopropylmalate dehydrogenase 39', designer 2-keto acid decarboxylase 42', short-chain alcohol dehydrogenase 43', hexanol dehydrogenase 12', designer isopropylmalate synthase 40", designer isopropylmalate isomerase 41", designer 3-isopropylmalate dehydrogenase 39", designer 2-keto acid decarboxylase 42", and designer short-chain alcohol dehydrogenase 43".

These pathways (FIG. 8) share a common feature of using an NADPH-dependent glyceraldehyde-3-phosphate dehydrogenase 34 and an NAD-dependent glyceraldehyde-3-phosphate dehydrogenase 35 as a mechanism for NADPH/NADH conversion to drive production of 1-pentanol, 1-hexanol, and/or 1-heptanol through a designer Calvin-cycle-channeled pathway in combination with a designer hydrocarbon chain elongation pathway (40', 41', 39'). This embodiment also takes the advantage of the broad substrate specificity (promiscuity) of 2-isopropylmalate synthase 40, isopropylmalate isomerase 41, 3-isopropylmalate dehydrogenase 39, 2-keto acid decarboxylase 42, and short-chain alcohol dehydrogenase 43 so that they can be used also as: designer isopropylmalate synthase 40', designer isopropylmalate isomerase 41', designer 3-isopropylmalate dehydrogenase 39', designer 2-keto acid decarboxylase 42', and short-chain alcohol dehydrogenase 43'; isopropylmalate synthase 40", designer isopropylmalate isomerase 41", designer 3-isopropylmalate dehydrogenase 39", designer 2-keto acid decarboxylase 42", and designer short-chain alcohol dehydrogenase 43".

In this case, proper selection of a short-chain alcohol dehydrogenase with certain promiscuity is also essential. SEQ ID NO: 94 presents example 94 of a designer nirA-promoter-controlled Short Chain Alcohol Dehydrogenase DNA construct (1096 bp) that includes a PCR FD primer (sequence 1-20), a 231-bp nirA promoter from *Thermosynechococcus elongatus* BP1 (21-251), an enzyme-encoding sequence (252-956) selected/modified from the sequences of a *Pyrococcus furiosus* DSM 3638 Short chain alcohol dehydrogenase (AAC25556), a 120-bp rbcS terminator from BP1 (957-1076), and a PCR RE primer (1077-1096) at the 3' end.

Therefore, SEQ ID NOS: 58-69 and 94 represent a set of designer genes that can express a designer Calvin-cycle 3-phosphoglycerate-braned photosynthetic NADPH-enhanced pathway for production of 1-pentanol, 1-hexanol, and/or 1-heptanol as shown with numerical labels 34, 35, 03-05, 36-41, 39, 39'-43', 39'-43', 39"-43" in FIG. 8. Similarly, SEQ ID NOS: 58-61, 74-81, 66-69, and 94 represent another set of sample designer genes that can express another Calvin-cycle 3-phophoglycerate-branched NADPH-enhanced pathway for production of 1-pentanol, 1-hexanol, and/or 1-heptanol as numerically labeled as 34, 35, 03, 04, 45-52, 40, 41, 39, 39'-43', 39'-43', 39"-43" in FIG. 8. Note, both of these two pathways produce alcohol mixtures with different chain lengths rather than single alcohols since all 2-keto acids (such as 2-ketohexanoate, 2-ketaheptanoate, and 2-ketooctanoate) can be converted to alcohol because of the use of the promiscuity of designer 2-keto acid decarboxylase 42' and designer short-chain alcohol dehydrogenase 43'.

To improve product specificity, it is a preferred practice to use substrate specific designer enzymes. For example, use of substrate specific designer 1-hexanol dehydrogenase 12' (SEQ ID NO: 92) instead of short-chain alcohol dehydrogenase with promiscuity (43') can improve product specificity more toward 1-hexanol. Consequently, SEQ ID NOS: 58-69 and 92 represent a set of designer genes that can express a designer Calvin-cycle 3-phosphoglycerate-braned photosynthetic NADPH-enhanced pathway for production of 1-hexanol as shown with numerical labels 34, 35, 03-05, 36-41, 39, 39'-40', 39'-42' and 12' in FIG. 8.

Figure 9:
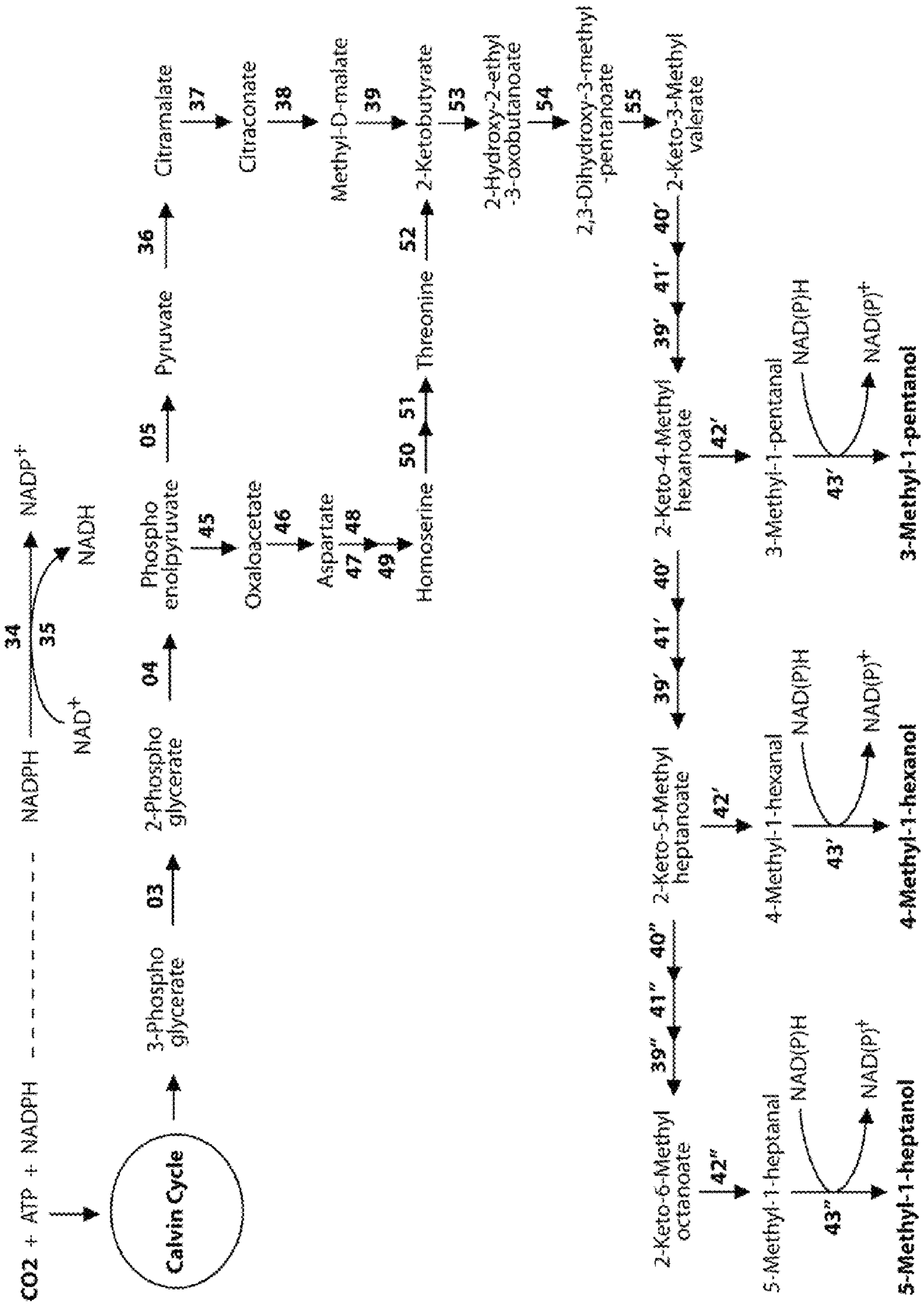
FIG. 9 presents designer Calvin-cycle-channeled and photosynthetic NADPH-enhanced pathways using NADPH and ATP from the photosynthetic water splitting and proton gradient-coupled electron transport process to reduce carbon dioxide ($CO_2$) into 3-methyl-1-pentanol ($CH_3CH_2CH(CH_3)CH_2CH_2OH$), 4-methyl-1-hexanol ($CH_3CH_2CH(CH_3)CH_2CH_2CH_2OH$), and 5-methyl-1-heptanol ($CH_3CH_2CH(CH_3)CH_2CH_2CH_2CH_2OH$) with a series of enzymatic reactions.

Designer Calvin-Cycle-Channeled Pathways for Production of 3-Methyl-1-Pentanol, 4-Methyl-1-Hexanol, and 5-Methyl-1-Heptanol According to one of the various embodiments, a designer Calvin-cycle-channeled pathway is created that takes the Calvin-cycle intermediate product, 3-phosphoglycerate, and converts it into 3-methyl-1-pentanol, 4-methyl-1-hexanol, and/or 5-methyl-1-heptanol by using, for example, a set of enzymes consisting of (as shown with the numerical labels 34, 35, 03-05, 36-39, 53-55, 39'-43', 39'-43', and 39"-43" in FIG. 9): NADPH-dependent glyceraldehyde-3-phosphate dehydrogenase 34, NAD-dependent glyceraldehyde-3-phosphate dehydrogenase 35, phosphoglycerate mutase 03, enolase 04, pyruvate kinase 05, citramalate synthase 36, 2-methylmalate dehydratase 37, 3-isopropylmalate dehydratase 38, 3-isopropylmalate dehydrogenase 39, acetolactate synthase 53, ketol-acid reductoisomerase 54, dihydroxy-acid dehydratase 55, designer isopropylmalate synthase 40', designer isopropylmalate isomerase 41', designer 3-isopropylmalate dehydrogenase 39', designer 2-keto acid decarboxylase 42', short-chain alcohol dehydrogenase 43', designer isopropylmalate synthase 40", designer isopropylmalate isomerase 41", designer 3-isopropylmalate dehydrogenase 39", designer 2-keto acid decarboxylase 42", and designer short-chain alcohol dehydrogenase 43".

According to another embodiment, a designer Calvin-cycle-channeled pathway is created that takes the intermediate product, 3-phosphoglycerate, and converts it into 3-methyl-1-pentanol, 4-methyl-1-hexanol, and/or 5-methyl-1-heptanol by using, for example, a set of enzymes consisting of (as shown with the numerical labels 34, 35, 03, 04, 45-55, 39'-43', 39'-43', and 39"-43" in FIG. 9): NADPH-dependent glyceraldehyde-3-phosphate dehydrogenase 34, NAD-dependent glyceraldehyde-3-phosphate dehydrogenase 35, phosphoglycerate mutase 03, enolase 04, phosphoenolpyruvate carboxylase 45, aspartate aminotransferase 46, aspartokinase 47, aspartate-semialdehyde dehydrogenase 48, homoserine dehydrogenase 49, homoserine kinase 50, threonine synthase 51, threonine ammonia-lyase 52, acetolactate synthase 53, ketol-acid reductoisomerase 54, dihydroxy-acid dehydratase 55, designer isopropylmalate synthase 40', designer isopropylmalate isomerase 41', designer 3-isopropylmalate dehydrogenase 39', designer 2-keto acid decarboxylase 42', short-chain alcohol dehydrogenase 43', designer isopropylmalate synthase 40", designer isopropylmalate isomerase 41", designer 3-isopropylmalate dehydrogenase 39", designer 2-keto acid decarboxylase 42", and designer short-chain alcohol dehydrogenase 43".

These pathways (FIG. 9) are similar to those of FIG. 8, except they use acetolactate synthase 53, ketol-acid reductoisomerase 54, dihydroxy-acid dehydratase 55 as part of the pathways for production of 3-methyl-1-pentanol, 4-methyl-1-hexanol, and/or 5-methyl-1-heptanol. They all share a common feature of using an NADPH-dependent glyceraldehyde-3-phosphate dehydrogenase 34 and an NAD-dependent glyceraldehyde-3-phosphate dehydrogenase 35 as a mechanism for NADPH/NADH conversion to drive production of 3-methyl-1-pentanol, 4-methyl-1-hexanol, and/or 5-methyl-1-heptanol through a designer Calvin-cycle-channeled pathway in combination with a hydrocarbon chain elongation pathway (40', 41', 39'). This embodiment also takes the advantage of the broad substrate specificity (promiscuity) of 2-isopropylmalate synthase 40, isopropylmalate isomerase 41, 3-isopropylmalate dehydrogenase 39, 2-keto acid decarboxylase 42, and short-chain alcohol dehydrogenase 43 so that they can also serve as: designer isopropylmalate synthase 40', designer isopropylmalate isomerase 41', designer 3-isopropylmalate dehydrogenase 39', designer 2-keto acid decarboxylase 42', and short-chain alcohol dehydrogenase 43'; designer isopropylmalate synthase 40", designer isopropylmalate isomerase 41", designer 3-isopropylmalate dehydrogenase 39", designer 2-keto acid decarboxylase 42", and designer short-chain alcohol dehydrogenase 43".

Therefore, SEQ ID NOS: 58-69, 82-84, and 94 represent a set of designer genes that can express a designer Calvin-cycle 3-phosphoglycerate-braned photosynthetic NADPH-enhanced pathway for production of 3-methyl-1-pentanol, 4-methyl-1-hexanol, and 5-methyl-1-heptanol as shown with numerical labels 34, 35, 03-05, 36-39, 53-55, 39'-43', 39'-43', and 39"-43" in FIG. 9. Similarly, SEQ ID NOS: 58-61, 74-81, 82-84, 66-69, and 94 represent another set of sample designer genes that can express another Calvin-cycle 3-phophoglycerate-branched NADPH-enhanced pathway for production of 3-methyl-1-pentanol, 4-methyl-1-hexanol, and/or 5-methyl-1-heptanol as numerically labeled as 34, 35, 03, 04, 45-55, 39'-43', 39'-43', 39"-43" in FIG. 9. The net results of the designer photosynthetic NADPH-enhanced pathways in working with the Calvin cycle are production of 3-methyl-1-pentanol ($CH_3CH_2CH(CH_3)CH_2CH_2OH$), 4-methyl-1-hexanol ($CH_3CH_2CH(CH_3)CH_2CH_2CH_2OH$), and 5-methyl-1-heptanol ($CH_3CH_2CH(CH_3)CH_2CH_2CH_2CH_2OH$) from carbon dioxide ($CO_2$) and water ($H_2O$) using photosynthetically generated ATP and NADPH according to the following process reactions:

$$6CO_2+7H_2O\rightarrow CH_3CH_2CH(CH_3)CH_2CH_2OH+9O_2 \quad [14]$$

$$14CO_2+16H_2O\rightarrow 2CH_3CH_2CH(CH_3)CH_2CH_2CH_2OH+21O_2 \quad [15]$$

$$8CO_2+9H_2O\rightarrow CH_3CH_2CH(CH_3)CH_2CH_2CH_2CH_2OH+12O_2 \quad [16]$$

Figure 10:
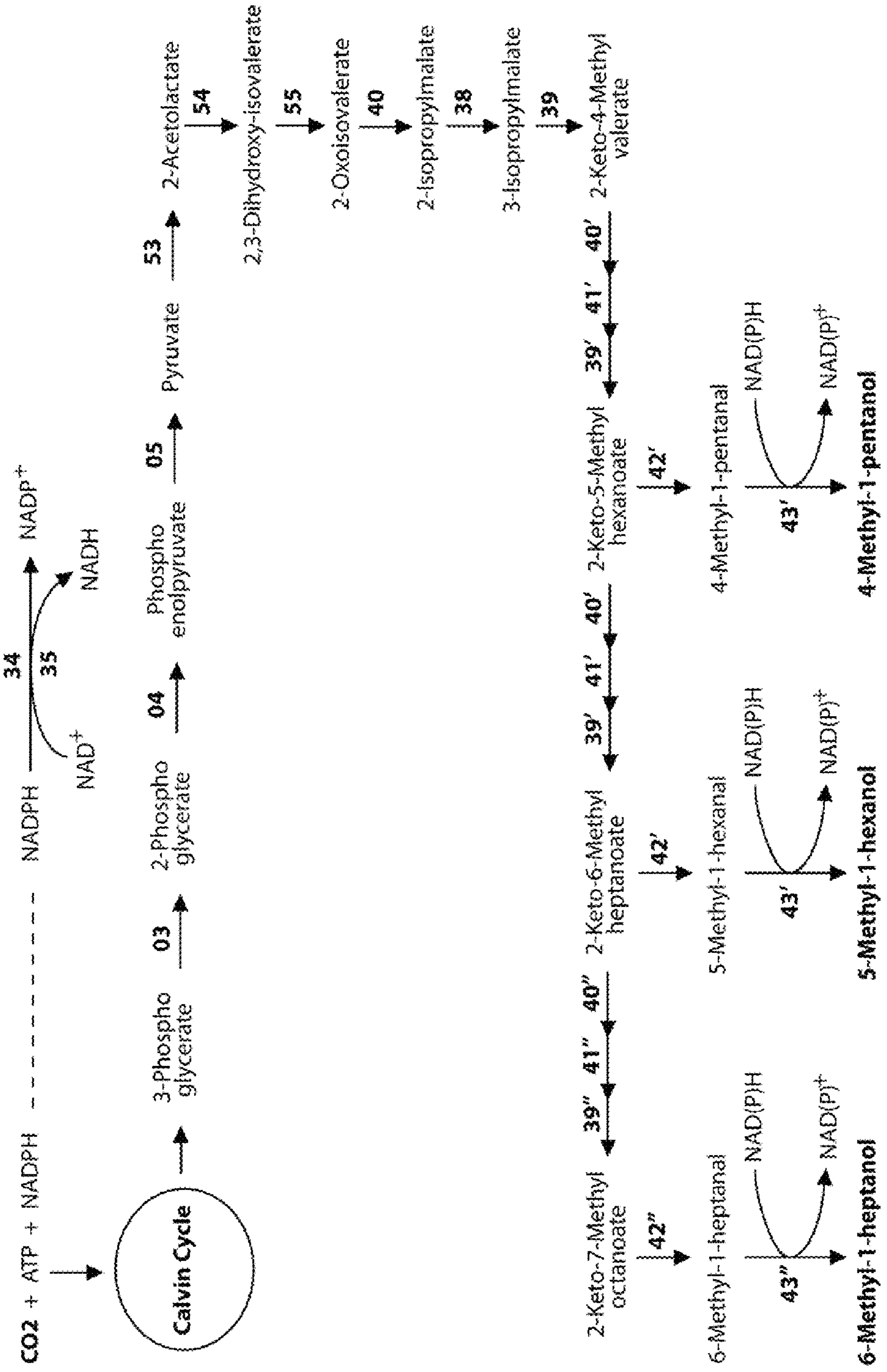
FIG. 10 presents designer Calvin-cycle-channeled and photosynthetic NADPH-enhanced pathways using NADPH and ATP from the photosynthetic water splitting and proton gradient-coupled electron transport process to reduce carbon dioxide ($CO_2$) into 4-methyl-1-pentanol ($CH_3CH(CH_3)CH_2CH_2CH_2OH$), 5-methyl-1-hexanol ($CH_3CH(CH_3)CH_2CH_2CH_2CH_2OH$), and 6-methyl-1-heptanol ($CH_3CH(CH_3)CH_2CH_2CH_2CH_2CH_2OH$) with a series of enzymatic reactions.

Designer Calvin-Cycle-Channeled Pathways for Production of 4-Methyl-1-Pentanol, 5-Methyl-1-Hexanol, and 6-Methyl-1-Heptanol According to one of the various embodiments, a designer Calvin-cycle-channeled pathway is created that takes the Calvin-cycle intermediate product, 3-phosphoglycerate, and converts it into 4-methyl-1-pentanol, 5-methyl-1-hexanol, and 6-methyl-1-heptanol by using, for example, a set of enzymes consisting of (as shown with the numerical labels 34, 35, 03-05, 53-55, 40, 38, 39, 39'-43', 39'-43', and 39"-43" in FIG. 10): NADPH-dependent glyceraldehyde-3-phosphate dehydrogenase 34, NAD-dependent glyceraldehyde-3-phosphate dehydrogenase 35, phosphoglycerate mutase 03, enolase 04, pyruvate kinase 05, acetolactate synthase 53, ketol-acid reductoisomerase 54, dihydroxy-acid dehydratase 55, isopropylmalate synthase 40, dehydratase 38, 3-isopropylmalate dehydrogenase 39, designer isopropylmalate synthase 40', designer isopropylmalate isomerase 41', designer 3-isopropylmalate dehydrogenase 39', designer 2-keto acid decarboxylase 42', short-chain alcohol dehydrogenase 43', designer isopropylmalate synthase 40", designer isopropylmalate isomerase 41", designer 3-isopropylmalate dehydrogenase 39", designer 2-keto acid decarboxylase 42", and designer short-chain alcohol dehydrogenase 43".

This pathway (FIG. 10) is similar to those of FIG. 8, except that it does not use citramalate synthase 36 and 2-methylmalate dehydratase 37, but uses acetolactate synthase 53, ketol-acid reductoisomerase 54, dihydroxy-acid dehydratase 55 as part of the pathways for production of 4-methyl-1-pentanol, 5-methyl-1-hexanol, and/or 6-methyl-1-heptanol. They all share a common feature of using an NADPH-dependent glyceraldehyde-3-phosphate dehydrogenase 34 and an NAD-dependent glyceraldehyde-3-phosphate dehydrogenase 35 as a mechanism for NADPH/NADH conversion to drive production of 3-methyl-1-butanol, 4-methyl-1-butanol, and 5-methyl-1-butanol through a Calvin-cycle-channeled pathway in combination with a designer hydrocarbon chain elongation pathway (40', 41', 39'). This embodiment also takes the advantage of the broad substrate specificity (promiscuity) of 2-isopropylmalate synthase 40, isopropylmalate isomerase 41, 3-isopropylmalate dehydrogenase 39, 2-keto acid decarboxylase 42, and short-chain alcohol dehydrogenase 43 so that they may also serve as: designer isopropylmalate synthase 40', designer isopropylmalate isomerase 41', designer 3-isopropylmalate dehydrogenase 39', designer 2-keto acid decarboxylase 42', and short-chain alcohol dehydrogenase 43', designer isopropylmalate synthase 40", designer isopropylmalate isomerase 41", designer 3-isopropylmalate dehydrogenase 39", designer 2-keto acid decarboxylase 42", and designer short-chain alcohol dehydrogenase 43".

Therefore, SEQ ID NOS: 58-62, 82-84, 65-69 and 94 represent a set of sample designer genes that can be used to express a designer Calvin-cycle 3-phosphoglycerate-braned photosynthetic NADPH-enhanced pathway for production of 4-methyl-1-pentanol, 5-methyl-1-hexanol, and/or 6-methyl- 1-heptanol as shown with numerical labels 34, 35, 03-05, 53-55, 40, 38, 39, 39'-43', 39'-43', and 39"-43" in FIG. 10. The net results of the designer photosynthetic NADPH-enhanced pathway in working with the Calvin cycle are production of 4-methyl-1-pentanol ($CH_3CH(CH_3)CH_2CH_2CH_2OH$), 5-methyl-1-hexanol ($CH_3CH(CH_3)CH_2CH_2CH_2CH_2OH$), and 6-methyl-1-heptanol ($CH_3CH(CH_3)CH_2CH_2CH_2CH_2CH_2OH$) from carbon dioxide ($CO_2$) and water ($H_2O$) using photosynthetically generated ATP and NADPH according to the following process reactions:

$$6CO_2+7H_2O\rightarrow CH_3CH(CH_3)CH_2CH_2CH_2OH+9O_2 \quad [17]$$

$$14CO_2+16H_2O\rightarrow 2CH_3CH(CH_3)CH_2CH_2CH_2CH_2OH+21O_2 \quad [18]$$

$$8CO_2+9H_2O\rightarrow CH_3CH(CH_3)CH_2CH_2CH_2CH_2CH_2OH+12O_2 \quad [19]$$

Designer Oxyphotobacteria with Calvin-Cycle-Channeled Pathways for Production of Butanol and Related Higher Alcohols According to one of the various embodiments, use of designer DNA constructs in genetic transform of certain oxyphotobacteria hosts can create various designer transgenic oxyphotobacteria with Calvin-cycle-channeled pathways for photobiological production of butanol and related higher alcohols from carbon dioxide and water. To ensure biosafety for use of the designer transgenic photosynthetic organism-based biofuels production technology, it is a preferred practice to incorporate biosafety-guarded features into the designer transgenic photosynthetic organisms as well. Therefore, in accordance with the present invention, various designer photosynthetic organisms including designer transgenic oxyphotobacteria are created with a biosafety-guarded photobiological biofuel-production technology based on cell-division-controllable designer transgenic photosynthetic organisms. The cell-division-controllable designer photosynthetic organisms contain two key functions: a designer biosafety mechanism(s) and a designer biofuel-production pathway(s). The designer biosafety feature(s) is conferred by a number of mechanisms including: a) the inducible insertion of designer proton-channels into cytoplasm membrane to permanently disable any cell division and/or mating capability, b) the selective application of designer cell-division-cycle regulatory protein or interference RNA (iRNA) to permanently inhibit the cell division cycle and preferably keep the cell at the $G_1$ phase or $G_0$ state, and c) the innovative use of a high-$CO_2$-requiring host photosynthetic organism for expression of the designer biofuel-production pathway(s). The designer cell-division-control technology can help ensure biosafety in using the designer organisms for photosynthetic biofuel production.

Oxyphotobacteria (including cyanobacteria and oxychlorobacteria) that can be selected for use as host organisms to create designer transgenic oxyphotobacteria for photobiological production of butanol and related higher alcohols include (but not limited to): *Thermosynechococcus elongatus* BP-1, *Nostoc* sp. PCC 7120, *Synechococcus elongatus* PCC 6301, *Syncechococcus* sp. strain PCC 7942, *Syncechococcus* sp. strain PCC 7002, *Syncechocystis* sp. strain PCC 6803, *Prochlorococcus marinus* MED4, *Prochlorococcus marinus* MIT 9313, *Prochlorococcus marinus* NATL1A, *Prochlorococcus* SS120, *Spirulina platensis* (*Arthrospira platensis*), *Spirulina pacifica, Lyngbya majuscule, Anabaena* sp., *Synechocystis* sp., *Synechococcus elongates, Synechococcus* (MC-A), *Trichodesmium* sp., *Richelia intracellularis, Synechococcus* WH7803, *Synechococcus* WH8102, *Nostoc punctiforme, Syncechococcus* sp. strain PCC 7943, *Synechocyitis* PCC 6714 phycocyanin-deficient mutant PD-1, *Cyanothece* strain 51142, *Cyanothece* sp. CCY0110, *Oscillatoria limosa, Lyngbya majuscula, Symploca muscorum, Gloeobacter violaceus, Prochloron didemni, Prochlorothrix hollandica, Prochlorococcus marinus, Prochlorococcus* SS120, *Synechococcus* WH8102, *Lyngbya majuscula, Symploca muscorum, Synechococcus bigranulatus*, cryophilic *Oscillatoria* sp., *Phormidium* sp., *Nostoc* sp.-1, *Calothrix parietina*, thermophilic *Synechococcus bigranulatus, Synechococcus lividus*, thermophilic *Mastigocladus laminosus, Chlorogloeopsis fritschii* PCC 6912, *Synechococcus vulcanus, Synechococcus* sp. strain MA4, *Synechococcus* sp. strain MA19, and *Thermosynechococcus elongatus*.

According to one of the examples, use of designer DNA constructs such as SEQ ID NOS: 58-94 in genetic transform of certain oxyphotobacteria hosts such as *Thermosynechococcus elongatus* BP1 can create a series of designer transgenic oxyphotobacteria with Calvin-cycle-channeled pathways for production of butanol and related higher alcohols. Consequently, SEQ ID NOS: 58-61, 74-81, 66-69, and 72 (and/or 73) represent a designer transgenic oxyphotobacterium such as a designer transgenic *Thermosynechococcus* that comprises the designer genes of a Calvin-cycle 3-phophoglycerate-branched photosynthetic NADPH-enhanced pathway (numerically labeled as 34, 35, 03, 04, 45-52, 39-42, and 12 in FIG. 4) for photobiological production of 1-butanol from carbon dioxide and water. SEQ ID NOS: 58-69 and 72 (and/or 73) represent another designer transgenic oxyphotobacterium such as designer transgenic *Thermosynechococcus* that comprises the designer genes of a Calvin-cycle 3-phophoglycerate-branched photosynthetic NADPH-enhanced pathway (numerically labeled as 34, 35, 03-05, 36-42, and 12 in FIG. 4) for photobiological production of 1-butanol from carbon dioxide and water as well.

Similarly, SEQ ID NOS: 58-66, 82-84, 69 and 85 represent another designer transgenic oxyphotobacterium such as designer transgenic *Thermosynechococcus* with a Calvin-cycle 3-phophoglycerate-branched photosynthetic NADPH-enhanced pathway (numerically labeled as 34, 35, 03-05, 36-39, 53-55, 42 and 56 in FIG. 5) for photobiological production of 2-methyl-1-butanol production from carbon dioxide and water; while SEQ ID NOS: 58-61, 74-84, 69 and 85 represent another designer transgenic *Thermosynechococcus* with a Calvin-cycle 3-phophoglycerate-branched photosynthetic NADPH-enhanced 2-methyl-1-butanol production pathway (34, 35, 03, 04, 45-55, 42 and 56 in FIG. 5) for photobiological production of 2-methyl-1-butanol production from carbon dioxide and water.

SEQ ID NOS: 58-63, 82-84, 69, 70 (or 71) represent another designer transgenic oxyphotobacterium such as designer transgenic *Thermosynechococcus* with a Calvin-cycle 3-phosphoglycerate-branched photosynthetic NADPH-enhanced isobutanol production pathway (34, 35, 03-05, 53-5, 42, 43 or 44); while SEQ ID NOS: 58-62, 81-83, 65-67, 69 and 86 represent another designer transgenic *Thermosynechococcus* with a Calvin-cycle 3-phosphoglycerate-branched photosynthetic NADPH-enhanced 3-methyl-1-butanol production pathway (numerical labels 34, 35, 03-05, 53-55, 40, 38, 39, 42, and 57 in FIG. 6).

SEQ ID NOS: 87-92 represent another designer transgenic *Thermosynechococcus* with a designer hydrocarbon chain elongation pathway (07'-12' as shown in FIG. 7) for photobiological production of 1-hexanol. SEQ ID NOS: 87-91 and 93 represent another designer transgenic *Thermosynechococcus* with a designer hydrocarbon chain elongation pathway (07'-10' and 07"-12" as shown in FIG. 7) for photobiological production of 1-octanol.

SEQ ID NOS: 58-69 and 92 represent another designer transgenic *Thermosynechococcus* with a designer Calvin-cycle 3-phosphoglycerate-braned photosynthetic NADPH-enhanced pathway (34, 35, 03-05, 36-41, 39, 39'-40', 39'-42' and 12' in FIG. 8) for photobiological production of 1-hexanol from carbon dioxide and water.

SEQ ID NOS: 58-69, 82-84, and 94 represent a designer transgenic *Thermosynechococcus* with a designer Calvin-cycle 3-phosphoglycerate-braned photosynthetic NADPH-enhanced pathway (34, 35, 03-05, 36-39, 53-55, 39'-43', 39'-43', 39"-43" in FIG. 9) for production of 3-methyl-1-pentanol, 4-methyl-1-hexanol, and 5-methyl-1-heptanol from carbon dioxide and water. Similarly, SEQ ID NOS: 58-61, 74-81, 82-84, 66-69, and 94 represent another designer transgenic *Thermosynechococcus* with a Calvin-cycle 3-phophoglycerate-branched NADPH-enhanced pathway (34, 35, 03, 04, 45-55, 39'-43', 39'-43', 39"-43" in FIG. 9) for photobiological production of 3-methyl-1-pentanol, 4-methyl-1-hexanol, and 5-methyl-1-heptanol from carbon dioxide and water as well.

SEQ ID NOS: 58-62, 82-84, 65-69 and 94 represent a designer transgenic *Thermosynechococcus* with a designer Calvin-cycle 3-phosphoglycerate-braned photosynthetic NADPH-enhanced pathway labels (34, 35, 03-05, 53-55, 40, 38, 39, 39'-43', 39'-43', and 39"-43" in FIG. 10) for photobiological production of 4-methyl-1-pentanol, 5-methyl-1-hexanol, and/or 6-methyl-1-heptanol from carbon dioxide and water.

Use of other host oxyphotobacteria such as *Synechococcus* sp. strain PCC 7942, *Synechocystis* sp. strain PCC 6803, *Prochlorococcus marinus, Cyanothece* sp. ATCC 51142, for genetic transformation with proper designer DNA constructs (genes) can create other designer oxyphotobacteria for photobiological production of butanol and higher alcohols as well. For example, use of *Synechococcus* sp. strain PCC 7942 as a host organism in genetic transformation with SEQ ID NOS: 95-98 (and/or 99) can create a designer transgenic *Synechococcus* for photobiological production of 1-butanol. Briefly, SEQ ID NO: 95 presents example 95 of a detailed DNA construct (1438 base pairs (bp)) of a designer NADPH-dependent Glyceraldehyde-3-Phosphate-Dehydrogenase (34) gene that includes a PCR FD primer (sequence by 1-20), a 88-bp nirA promoter (21-108) selected from the *Synechococcus* sp. strain PCC 7942 (freshwater cyanobacterium) nitrite-reductase-gene promoter sequence, an enzyme-encoding sequence (109-1110) selected and modified from a *Staphylococcus lugdunensis* HKU09-01 NADPH-dependent glyceraldehyde-3-phosphate-dehydrogenase sequence (GenBank accession number: YP_003471459), a 308-bp *Synechococcus* sp. strain PCC 7942 rbcS terminator (1111-1418), and a PCR RE primer (1419-1438) at the 3' end.

SEQ ID NO: 96 presents example 96 of a detailed DNA construct (1447 bp) of a designer NAD-dependent Glyceraldehyde-3-Phosphate-Dehydrogenase (35) gene that includes a PCR FD primer (sequence by 1-20), a 88-bp nirA promoter (21-108) selected from the *Synechococcus* sp. strain PCC 7942 nitrite-reductase-gene promoter sequence, an enzyme-encoding sequence (109-1119) selected and modified from a *Staphylococcus aureus* 04-02981 NAD-dependent glyceraldehyde-3-phosphate-dehydrogenase sequence (GenBank accession number: ADC36961), a 308-bp *Synechococcus* sp. strain PCC 7942 rbcS terminator (1120-1427), and a PCR RE primer (1428-1447) at the 3' end.

SEQ ID NO: 97 presents example 97 of a detailed DNA construct (2080 bp) of a designer 2-Keto Acid Decarboxylase (42) gene that includes a PCR FD primer (sequence by 1-20), a 88-bp nirA promoter (21-108) selected from the *Synechococcus* sp. strain PCC 7942 nitrite-reductase-gene promoter sequence, an enzyme-encoding sequence (109-1752) selected and modified from a *Lactococcus lactis* branched-chain alpha-ketoacid decarboxylase (GenBank accession number: AAS49166), a 308-bp *Synechococcus* sp. strain PCC 7942 rbcS terminator (1753-2060), and a PCR RE primer (2061-2080) at the 3' end.

SEQ ID NO: 98 presents a detailed DNA construct (1603 bp) of a designer NADH-dependent butanol dehydrogenase (12a) gene that include a PCR FD primer (sequence by 1-20), a 88-bp nirA promoter (21-108) selected from the *Synechococcus* sp. strain PCC 7942 nitrite-reductase-gene promoter sequence, an enzyme-encoding sequence (109-1275) selected and modified from a *Clostridium carboxidivorans* P7 NADH-dependent butanol dehydrogenase (GenBank accession number: AD012118), a 308-bp *Synechococcus* sp. strain PCC 7942 rbcS terminator (1276-1583), and a PCR RE primer (1584-1603) at the 3' end.

SEQ ID NO: 99 presents example 99 of a detailed DNA construct (1654 bp) of a designer NADPH-dependent Butanol Dehydrogenase (12b) gene including: a PCR FD primer (sequence by 1-20), a 88-bp nirA promoter (21-108) selected from the *Synechococcus* sp. strain PCC 7942 nitrite-reductase-gene promoter sequence, an enzyme-encoding sequence (109-1326) selected and modified from a *Butyrivibrio crossotus* DSM 2876 NADPH-dependent butanol dehydrogenase (GenBank accession number: EFF67629), a 308-bp *Synechococcus* sp. strain PCC 7942 rbcS terminator (1327-1634), and a PCR RE primer (1635-1654) at the 3' end.

Note, in the designer transgenic *Synechococcus* that is represented by SEQ ID NOS: 95-98 (and/or 99), *Synechococcus*'s native enzymes of 03-05, 36-41 and 45-52 are used in combination with the designer nirA-promoter-controlled enzymes of 34, 35, 42 and 12 [encoded by SEQ ID NOS: 95-98 (and/or 99)] to confer the Calvin-cycle 3-phophoglycerate-branched photosynthetic NADPH-enhanced pathways for photobiological production of 1-butanol from carbon dioxide and water (FIG. 4).

Similarly, use of *Synechocystis* sp. strain PCC 6803 as a host organism in genetic transformation with SEQ ID NOS: 100-102 (and/or 103) creates a designer transgenic *Synechocystis* for photobiological production of 1-butanol. Briefly, SEQ ID NO: 100 presents example 100 of a designer nirA-promoter-controlled NAD-dependent Glyceraldehyde-3-Phosphate Dehydrogenase (35) DNA construct (1440 bp) that includes a PCR FD primer (sequence 1-20), a 89-bp *Synechocystis* sp. strain PCC 6803 nitrite-reductase nirA promoter (21-109), an enzyme-encoding sequence (110-1011) selected from a *Streptococcus pyogenes* NZ131 NAD-dependent Glyceraldehyde-3-phosphate dehydrogenase (GenBank: YP_002285269), a 409-bp *Synechocystis* sp. PCC 6803 rbcS terminator (1012-1420), and a PCR RE primer (1421-1440).

SEQ ID NO: 101 presents example 101 of a designer nirA-promoter-controlled 2-Keto Acid Decarboxylase (42) DNA construct (2182 bp) that includes a PCR FD primer (sequence 1-20), a 89-bp *Synechocystis* sp. strain PCC 6803 nitrite-reductase nirA promoter (21-109), an enzyme-encoding sequence (110-1753) selected from a *Lactococcus lactis* branched-chain alpha-ketoacid decarboxylase (GenBank: AAS49166), a 409-bp *Synechocystis* sp. PCC 6803 rbcS terminator (1754-2162), and a PCR RE primer (2163-2182).

SEQ ID NO: 102 presents example 102 of a designer nirA-promoter-controlled NADH-dependent Butanol Dehydrogenase (12a) DNA construct (1705 bp) that includes a PCR FD primer (sequence 1-20), a 89-bp *Synechocystis* sp. strain PCC 6803 nitrite-reductase nirA promoter (21-109), an enzyme-encoding sequence (110-1276) selected from a *Clostridium carboxidivorans* P7 NADH-dependent butanol dehydrogenase (GenBank: AD012118), a 409-bp *Synechocystis* sp. PCC 6803 rbcS terminator (1277-1685), and a PCR RE primer (1686-1705).

SEQ ID NO: 103 presents example 103 of a designer nirA-promoter-controlled NADPH-dependent butanol dehydrogenase (12b) DNA construct (1756 bp) that includes a PCR FD primer (sequence 1-20), a 89-bp *Synechocystis* sp. strain PCC 6803 nitrite-reductase nirA promoter (21-109), an enzyme-encoding sequence (110-1327) selected from a *Butyrivibrio crossotus* DSM 2876 NADPH-dependent butanol dehydrogenase (GenBank: EFF67629), a 409-bp *Synechocystis* sp. PCC 6803 rbcS terminator (1328-1736), and a PCR RE primer (1737-1756).

Note, in the designer transgenic *Synechocystis* that contains the designer genes of SEQ ID NOS: 100-102 (and/or 103), *Synechocystis*'s native enzymes of 34, 03-05, 36-41 and 45-52 are used in conjunction with the designer nirA-promoter-controlled enzymes of 35, 42 and 12 [encoded by SEQ ID NOS: 100-102 (and/or 103)] to confer the Calvin-cycle 3-phophoglycerate-branched photosynthetic NADPH-enhanced pathways for photobiological production of 1-butanol from carbon dioxide and water (FIG. 4).

Use of *Nostoc* sp. strain PCC 7120 as a host organism in genetic transformation with SEQ ID NOS: 104-109 can create a designer transgenic Nostoc for photobiological production of 2-methyl-1-butanol (FIG. 5). Briefly, SEQ ID NO: 104 presents example 104 of a designer hox-promoter-controlled NAD-dependent Glyceraldehyde-3-Phosphate Dehydrogenase (35) DNA construct (1655 bp) that includes a PCR FD primer (sequence 1-20), a 172-bp *Nostoc* sp. strain PCC 7120 (*Anabaena* PCC 7120) hox promoter (21-192), an enzyme-encoding sequence (193-1203) selected/modified from the sequence of a *Streptococcus pyogenes* NZ131 NAD-dependent glyceraldehyde-3-phosphate dehydrogenase (GenBank: YP_002285269), a 432-bp *Nostoc* sp. strain PCC 7120 gor terminator (1204-1635), and a PCR RE primer (1636-1655) at the 3' end.

SEQ ID NO: 105 presents example 105 of a designer hox-promoter-controlled Acetolactate Synthase (53) DNA construct (2303 bp) that includes a PCR FD primer (sequence 1-20), a 172-bp *Nostoc* sp. strain PCC 7120 (*Anabaena* PCC 7120) hox promoter (21-192), an enzyme-encoding sequence (193-1851) selected/modified from the sequence of a *Thermosynechococcus elongatus* BP-1 acetolactate synthase (GenBank: NP_682614), a 432-bp *Nostoc* sp. strain PCC 7120 gor terminator (1852-2283), and a PCR RE primer (2284-2303) at the 3' end.

SEQ ID NO: 106 presents example 106 of a designer hox-promoter-controlled Ketol-Acid Reductoisomerase (54) DNA construct (1661 bp) that includes a PCR FD primer (sequence 1-20), a 172-bp *Nostoc* sp. strain PCC 7120 (*Anabaena* PCC 7120) hox promoter (21-192), an enzyme-encoding sequence (193-1209) selected/modified from the sequence of a *Calditerrivibrio nitroreducens* DSM 19672 ketol-acid reductoisomerase (GenBank: YP_004050904), a 432-bp *Nostoc* sp. strain PCC 7120 gor terminator (1210-1641), and a PCR RE primer (1642-1661) at the 3' end.

SEQ ID NO: 107 presents example 107 of a designer hox-promoter-controlled Dihydroxy-Acid Dehydratase (55) DNA construct (2324 bp) that includes a PCR FD primer (sequence 1-20), a 172-bp *Nostoc* sp. strain PCC 7120 (*Anabaena* PCC 7120) hox promoter (21-192), an enzyme-encoding sequence (193-1872) selected/modified from the sequence of a *Marivirga tractuosa* DSM 4126 dihydroxy-acid dehydratase (GenBank: YP_004053736), a 432-bp *Nostoc* sp. strain PCC 7120 gor terminator (1873-2304), and a PCR RE primer (2305-2324) at the 3' end.

SEQ ID NO: 108 presents example 108 of a designer hox-promoter-controlled branched-chain alpha-Ketoacid Decarboxylase (42) DNA construct (2288 bp) that includes a PCR FD primer (sequence 1-20), a 172-bp *Nostoc* sp. strain PCC 7120 (*Anabaena* PCC 7120) hox promoter (21-192), an enzyme-encoding sequence (193-1836) selected/modified from the sequence of a *Lactococcus lactis* branched-chain alpha-ketoacid decarboxylase (GenBank: AAS49166), a 432-bp *Nostoc* sp. strain PCC 7120 gor terminator (1837-2268), and a PCR RE primer (2269-2288) at the 3' end.

SEQ ID NO: 109 presents example 109 of a designer hox-promoter-controlled 2-Methylbutyraldehyde Reductase (56) DNA construct (1613 bp) that includes a PCR FD primer (sequence 1-20), a 172-bp *Nostoc* sp. strain PCC 7120 (*Anabaena* PCC 7120) hox promoter (21-192), an enzyme-encoding sequence (193-1461) selected/modified from the sequence of a *Schizosaccharomyces japonicus* yFS275 2-methylbutyraldehyde reductase (GenBank: XP_002173231), a 432-bp *Nostoc* sp. strain PCC 7120 gor terminator (1462-1893), and a PCR RE primer (1894-1613) at the 3' end.

Note, in the designer transgenic *Nostoc* that contains designer hox-promoter-controlled genes of SEQ ID NOS: 104-109, *Nostoc*'s native enzymes (genes) of 34, 03-05, 36-39 and 45-52 are used in combination with the designer hox-promoter-controlled enzymes of 35, 53-55, 42 and 56 (encoded by DNA constructs of SEQ ID NOS: 104-109) to confer the Calvin-cycle 3-phophoglycerate-branched photosynthetic NADPH-enhanced pathways for photobiological production of 2-methyl-1-butanol from carbon dioxide and water (FIG. 5).

Use of *Prochlorococcus marinus* MIT 9313 as a host organism in genetic transformation with SEQ ID NOS: 110-122 can create a designer transgenic *Prochlorococcus marinus* for photobiological production of isobutanol and/or 3-methyl-1-butanol (FIG. 6). Briefly, SEQ ID NO:110 presents example 110 for a designer groE-promoter-controlled NAD-dependent Glyceraldehyde-3-Phosphate Dehydrogenase (35) DNA construct (1300 bp) that includes a PCR FD primer (sequence 1-20), a 137-bp *Prochlorococcus marinus* MIT 9313 heat- and light-responsive groE promoter (21-157), an enzyme-encoding sequence (158-1159) selected from a *Vibrio cholerae* MJ-1236 NAD-dependent Glyceraldehyde-3-phosphate dehydrogenase (GenBank: ACQ61431), a 121-bp *Prochlorococcus marinus* MIT9313 rbcS terminator (1160-1280), and a PCR RE primer (1281-1300).

SEQ ID NO:111 presents example 111 for a designer groE-promoter-controlled Phosphoglycerate Mutase (03) DNA construct (1498 bp) that includes a PCR FD primer (sequence 1-20), a 137-bp *Prochlorococcus marinus* MIT9313 heat- and light-responsive groE promoter (21-157), an enzyme-encoding sequence (158-1357) selected from a *Pelotomaculum thermopropionicum* SI phosphoglycerate mutase (GenBank: YP_001212148), a 121-bp *Prochlorococcus marinus* MIT9313 rbcS terminator (1358-1478), and a PCR RE primer (1479-1498).

SEQ ID NO:112 presents example 112 for a designer groE-promoter-controlled Enolase (04) DNA construct (1588 bp) that includes a PCR FD primer (sequence 1-20), a 137-bp *Prochlorococcus marinus* MIT9313 heat- and light-responsive groE promoter (21-157), an enzyme-encoding sequence (158-1447) selected from a *Thermotoga petrophila* RKU-1 enolase (GenBank: ABQ46079), a 121-bp *Prochlorococcus marinus* MIT9313 rbcS terminator (1448-1568), and a PCR RE primer (1569-1588).

SEQ ID NO:113 presents example 113 for a designer groE-promoter-controlled Pyruvate Kinase (05) DNA construct (1717 bp) that includes a PCR FD primer (sequence 1-20), a 137-bp *Prochlorococcus marinus* MIT9313 heat- and light-responsive groE promoter (21-157), an enzyme-encoding sequence (158-1576) selected from a *Thermotoga lettingae* TMO pyruvate kinase (GenBank: YP_001471580), a 121-bp *Prochlorococcus marinus* MIT9313 rbcS terminator (1577-1697), and a PCR RE primer (1698-1717).

SEQ ID NO:114 presents example 114 for a designer groE-promoter-controlled Acetolactate Synthase (53) DNA construct (2017 bp) that includes a PCR FD primer (sequence 1-20), a 137-bp *Prochlorococcus marinus* MIT 9313 heat- and light-responsive groE promoter (21-157), an enzyme-encoding sequence (158-1876) selected from a *Bacillus licheniformis* ATCC 14580 acetolactate synthase (GenBank: AAU42663), a 121-bp *Prochlorococcus marinus* MIT 9313 rbcS terminator (1877-1997), and a PCR RE primer (1998-2017).

SEQ ID NO:115 presents example 115 for a designer groE-promoter-controlled Ketol-Acid Reductoisomerase (54) DNA construct (1588 bp) that includes a PCR FD primer (sequence 1-20), a 137-bp *Prochlorococcus marinus* MIT9313 heat- and light-responsive groE promoter (21-157), an enzyme-encoding sequence (158-1168) selected from a *Thermotoga petrophila* RKU-1 ketol-acid reductoisomerase (GenBank: ABQ46398), a 400-bp *Prochlorococcus marinus* MIT9313 rbcS terminator (1169-1568), and a PCR RE primer (1569-1588).

SEQ ID NO:116 presents example 116 for a designer groE-promoter-controlled Dihydroxy-Acid Dehydratase (55) DNA construct (1960 bp) that includes a PCR FD primer (sequence 1-20), a 137-bp *Prochlorococcus marinus* MIT9313 heat- and light-responsive groE promoter (21-157), an enzyme-encoding sequence (158-1819) selected from a *Syntrophothermus lipocalidus* DSM 12680 dihydroxy-acid dehydratase (GenBank: ADIO2905), a 121-bp *Prochlorococcus marinus* MIT9313 rbcS terminator (1820-1940), and a PCR RE primer (1941-1960).

SEQ ID NO:117 presents example 117 for a designer groE-promoter-controlled 2-Keto Acid Decarboxylase (42) DNA construct (1945 bp) that includes a PCR FD primer (sequence 1-20), a 137-bp *Prochlorococcus marinus* MIT9313 heat- and light-responsive groE promoter (21-157), an enzyme-encoding sequence (158-1804) selected from a *Lactococcus lactis* subsp. *lactis* KF147 Alpha-ketoisovalerate decarboxylase (GenBank: ADA65057), a 121-bp *Prochlorococcus marinus* MIT9313 rbcS terminator (1805-1925), and a PCR RE primer (1926-1945).

SEQ ID NO:118 presents example 118 for a designer nirA-promoter-controlled Alcohol Dehydrogenase (43/44) DNA construct (1138 bp) that includes a PCR FD primer (sequence 1-20), a 251-bp *Prochlorococcus marinus* MIT9313 nirA promoter (21-271), an enzyme-encoding sequence (272-997) selected from a *Geobacillus kaustophilus* HTA426 short chain alcohol dehydrogenase (GenBank: YP_146837), a 121-bp *Prochlorococcus marinus* MIT9313 rbcS terminator (998-1118), and a PCR RE primer (1119-1138).

Note, in the designer transgenic *Prochlorococcus* that contains the designer genes of SEQ ID NOS: 110-118, *Prochlorococcus*'s native gene (enzyme) of 34 is used in combination with the designer groE and nirA-promoters-controlled genes (enzymes) of 35, 03-05, 53-55, 42 and 43/44 (encoded by DNA constructs of SEQ ID NOS: 110-118) to confer the Calvin-cycle 3-phophoglycerate-branched photosynthetic NADPH-enhanced pathways for photobiological production of isobutanol from carbon dioxide and water (FIG. 6). Addition of the following four designer groE promoter-controlled genes (SEQ ID NO:119-122) results in another designer transgenic *Prochlorococcus* that can produce both isobutanol and 3-methyl-1-butanol from carbon dioxide and water (35, 03-05, 53-55, 42, 43/44, plus 38-40 and 57 as shown in FIG. 6).

Briefly, SEQ ID NO:119 presents example 119 for a designer groE-promoter-controlled 2-Isopropylmalate Synthase (40) DNA construct (1816 bp) that includes a PCR FD primer (sequence 1-20), a 137-bp *Prochlorococcus marinus* MIT9313 heat- and light-responsive groE promoter (21-157), an enzyme-encoding sequence (158-1675) selected from a *Pelotomaculum thermopropionicum* S12-isopropylmalate synthase (GenBank: YP_001211081), a 121-bp *Prochlorococcus marinus* MIT9313 rbcS terminator (1676-1796), and a PCR RE primer (1797-1816).

SEQ ID NO:120 presents example 120 for a designer groE-promoter-controlled 3-Isopropylmalate Dehydratase (38) DNA construct (2199 bp) that includes a PCR FD primer (sequence 1-20), a 137-bp *Prochlorococcus marinus* MIT9313 heat- and light-responsive groE promoter (21-157), a 3-isopropylmalate dehydratase large subunit-encoding sequence (158-1420) selected from a *Pelotomaculum thermopropionicum* S13-isopropylmalate dehydratase large subunit (GenBank: YP_001211082), a 137-bp *Prochlorococcus marinus* MIT9313 heat- and light-responsive groE promoter (1421-1557), a 3-isopropylmalate dehydratase small subunit-encoding sequence (1558-2058) selected from a *Pelotomaculum thermopropionicum* S13-isopropylmalate dehydratase small subunit (GenBank: YP_001211083), a 121-bp *Prochlorococcus marinus* MIT9313 rbcS terminator (2059-2179), and a PCR RE primer (2180-2199).

SEQ ID NO:121 presents example 121 for a designer groE-promoter-controlled 3-Isopropylmalate Dehydrogenase (39) DNA construct (1378 bp) that includes a PCR FD primer (sequence 1-20), a 137-bp *Prochlorococcus marinus* MIT9313 heat- and light-responsive groE promoter (21-157), an enzyme-encoding sequence (158-1237) selected from a *Syntrophothermus lipocalidus* DSM 12680 3-isopropylmalate dehydrogenase (GenBank: ADIO2898), a 121-bp *Prochlorococcus marinus* MIT9313 rbcS terminator (1238-1358), and a PCR RE primer (1359-1378).

SEQ ID NO:122 presents example 122 for a designer groE-promoter-controlled 3-Methylbutanal Reductase (57) DNA construct (1327 bp) that includes a PCR FD primer (sequence 1-20), a 137-bp *Prochlorococcus marinus* MIT9313 heat- and light-responsive groE promoter (21-157), an enzyme-encoding sequence (158-1186) selected from a *Saccharomyces cerevisiae* S288c 3-Methylbutanal reductase (GenBank: DAA10635), a 121-bp *Prochlorococcus marinus* MIT9313 rbcS terminator (1187-1307), and a PCR RE primer (1308-1327).

Note, the use of SEQ ID NOS: 110-117 and 119-122 in genetic transformation of *Prochlorococcus marinus* MIT 9313 creates another designer transgenic *Prochlorococcus marinus* with a groE promoter-controlled designer Calvin-cycle-channeled pathway (identified as 34 (native), 35, 03-05, 53-55, 38-40, 42 and 57 in FIG. 6) for photobiological production of 3-methyl-1-butanol from carbon dioxide and water.

Use of *Cyanothece* sp. ATCC 51142 as a host organism in genetic transformation with SEQ ID NOS: 123-128 can create a designer transgenic *Cyanothece* for photobiological production of 1-pentanol, 1-hexanol, and/or 1-heptanol (FIG. 8). Briefly, SEQ ID NO:123 presents example 123 for a designer nirA-promoter-controlled 2-Isopropylmalate Synthase (40) DNA construct (2004 bp) that includes a PCR FD primer (sequence 1-20), a 203-bp *Cyanothece* sp. ATCC 51142 nirA promoter (21-223), an enzyme-encoding sequence (224-1783) selected from a *Hydrogenobacter thermophilus* TK-6 2-isopropylmalate synthase sequence (GenBank: BAI69273), a 201-bp *Cyanothece* sp. ATCC 51142 rbcS terminator (1784-1984), and a PCR RE primer (1985-2004).

SEQ ID NO:124 presents example 124 for a designer nirA-promoter-controlled Isopropylmalate Isomerase (41) large/small subunits DNA construct (2648 bp) that includes a PCR FD primer (sequence 1-20), a 203-bp *Cyanothece* sp. ATCC 51142 nirA promoter (21-223), an enzyme-large-subunit-encoding sequence (224-1639) selected from a *Anoxybacillus flavithermus* WK1 isopropylmalate isomerase large subunit sequence (GenBank: YP_002314962), a 203-bp *Cyanothece* sp. ATCC 51142 nirA promoter (1640-1842), an enzyme-small-subunit-encoding sequence (1843-2427) selected from a *Anoxybacillus flavithermus* WK1 isopropylmalate isomerase small subunit sequence (GenBank: YP_002314963), a 201-bp *Cyanothece* sp. ATCC 51142 rbcS terminator (2428-1628), and a PCR RE primer (2629-2648).

SEQ ID NO:125 presents example 125 for a designer g nirA-promoter-controlled 3-Isopropylmalate Dehydrogenase (39) DNA construct (1530 bp) that includes a PCR FD primer (sequence 1-20), a 203-bp *Cyanothece* sp. ATCC 51142 nirA promoter (21-223), an enzyme-encoding sequence (224-1309) selected from a *Thermosynechococcus elongatus* BP-1 3-isopropylmalate dehydrogenase sequence (GenBank: BAC09152), a 201-bp *Cyanothece* sp. ATCC 51142 rbcS terminator (1310-1310), and a PCR RE primer (1311-1530).

SEQ ID NO:126 presents example 126 for a designer nirA-promoter-controlled 2-Keto Acid Decarboxylase (42') DNA construct (2088 bp) that includes a PCR FD primer (sequence 1-20), a 203-bp *Cyanothece* sp. ATCC 51142 nirA promoter (21-223), an enzyme-encoding sequence (224-1867) selected from a *Lactococcus lactis* 2-keto acid decarboxylase (GenBank: AAS49166), a 201-bp *Cyanothece* sp. ATCC 51142 rbcS terminator (1868-2068), and a PCR RE primer (2069-2088).

SEQ ID NO:127 presents example 127 for a designer nirA-promoter-controlled Hexanol Dehydrogenase (12') DNA construct (1503 bp) that includes a PCR FD primer (sequence 1-20), a 203-bp *Cyanothece* sp. ATCC 51142 nirA promoter (21-223), an enzyme-encoding sequence (224-1282) selected from a *Mycobacterium chubuense* NBB4 hexanol dehydrogenase (GenBank: ACZ56328), a 201-bp *Cyanothece* sp. ATCC 51142 rbcS terminator (1283-1483), and a PCR RE primer (1484-1503).

SEQ ID NO:128 presents example 128 for a designer nirA-promoter-controlled short-chain Alcohol Dehydrogenase (43', 43") DNA construct (1149 bp) that includes a PCR FD primer (sequence 1-20), a 203-bp *Cyanothece* sp. ATCC 51142 nirA promoter (21-223), an enzyme-encoding sequence (224-928) selected from a *Pyrococcus furiosus* DSM 3638 Short chain alcohol dehydrogenase (GenBank: AAC25556), a 201-bp *Cyanothece* sp. ATCC 51142 rbcS terminator (929-1129), and a PCR RE primer (1130-1149).

Note, in the designer transgenic *Cyanothece* that contains designer nirA promoter-controlled genes of SEQ ID NOS: 123-127, *Cyanothece*'s native enzymes of 34, 03-05, 36-38, and 45-52 are used in combination with the designer nirA-promoters-controlled enzymes of 35, 39-41 (39'-41', 39'-41'), 42' and 12' (encoded by DNA constructs of SEQ ID NOS: 123-127) to confer the Calvin-cycle 3-phophoglycerate-branched photosynthetic NADPH-enhanced pathways for photobiological production of 1-hexanol from carbon dioxide and water (FIG. 8). Addition of a designer nirA-promoters-controlled gene (SEQ ID NO: 128) of a short chain alcohol dehydrogenase 43' (43") with promiscuity results in another designer transgenic *Cyanothece* containing a Calvin-cycle-channeled pathway (35, 39-41, 39'-43', 39'-43', and 39"-43" as shown in FIG. 8) that can produce 1-pentanol, 1-hexanol, and 1-hexanol from carbon dioxide and water.

Designer Advanced Photosynthetic Organisms with Calvin-Cycle-Channeled Pathways for Production of Butanol and Related Higher Alcohols According to one of the various embodiments, use of certain designer DNA constructs in genetic transformation of eukaryotic photosynthetic organisms such as plant cells, eukaryotic aquatic plants (including, for example, eukaryotic algae, submersed aquatic herbs, duckweeds, water cabbage, water lily, water hyacinth, *Bolbitis heudelotii, Cabomba* sp., and seagrasses) can create designer transgenic eukaryotic photosynthetic organisms for production of butanol and related higher alcohols from carbon dioxide and water. Eukaryotic algae that can be selected for use as host organisms to create designer algae for photobiological production of butanol and related higher alcohols include (but not limited to): *Dunaliella salina, Dunaliella viridis, Dunaliella bardowil, Crypthecodinium cohnii, Schizochytrium* sp., *Chlamydomonas reinhardtii, Platymonas subcordiformis, Chlorella fusca, Chlorella sorokiniana, Chlorella vulgaris, 'Chlorella' ellipsoidea, Chlorella* spp., *Haematococcus pluvialis; Parachlorella kessleri, Betaphycus gelatinum, Chondrus crispus, Cyanidioschyzon merolae, Cyanidium caldarium, Galdieria sulphuraria, Gelidiella acerosa, Gracilaria changii, Kappaphycus alvarezii, Porphyra miniata, Ostreococcus tauri, Porphyra yezoensis, Porphyridium* sp., *Palmaria palmata, Gracilaria* spp., *Isochrysis galbana, Kappaphycus* spp., *Laminaria japonica, Laminaria* spp., *Monostroma* spp., *Nannochloropsis oculata, Porphyra* spp., *Porphyridium* spp., *Undaria pinnatifida, Ulva lactuca, Ulva* spp., *Undaria* spp., *Phaeodactylum Tricornutum, Navicula saprophila, Cylindrotheca fusiformis, Cyclotella cryptica, Euglena gracilis, Amphidinium* sp., *Symbiodinium microadriaticum, Macrocystis pyrifera, Ankistrodesmus braunii, Scenedesmus obliquus, Stichococcus* sp., *Platymonas* sp., *Dunalielki sauna*, and *Stephanoptera gracilis.*

According to another embodiment, the transgenic photosynthetic organism comprises a designer transgenic plant or plant cells selected from the group consisting of aquatic plants, plant cells, green algae, red algae, brown algae, blue-green algae (oxyphotobacteria including cyanobacteria and oxychlorobacteria), diatoms, marine algae, freshwater algae, salt-tolerant algal strains, cold-tolerant algal strains, heat-tolerant algal strains, antenna-pigment-deficient mutants, butanol-tolerant algal strains, higher-alcohols-tolerant algal strains, butanol-tolerant oxyphotobacteria, higher-alcohols-tolerant oxyphotobacteria, and combinations thereof.

According to another embodiment, said transgenic photosynthetic organism comprises a biosafety-guarded feature selected from the group consisting of: a designer proton-channel gene inducible under pre-determined inducing conditions, a designer cell-division-cycle iRNA gene inducible under pre-determined inducing conditions, a high-$CO_2$-requiring mutant as a host organism for transformation with designer biofuel-production-pathway genes in creating designer cell-division-controllable photosynthetic organisms, and combinations thereof.

The greater complexity and compartmentalization of eukaryotic plant cells allow for creation of a wider range of photobiologically active designer organisms and novel metabolic pathways compartmentally segregated for production of butanol and/or higher alcohols from water and carbon dioxide. In a eukaryotic algal cell, for example, the translation of designer nuclear genes occurs in cytosol whereas the photosynthesis/Calvin cycle is located inside an algal chloroplast. This clear separation of algal chloroplast photosynthesis from other subcellular functions such as the functions of cytoplasm membrane, cytosol and mitochondria can be used as an advantage in creation of a biosafety-guarded designer algae through an inducible insertion of designer proton-channels into cytoplasm membrane to permanently disable any cell division and/or mating capability while keeping the algal chloroplast functional work with the designer biofuel production, pathways to produce butanol and related higher alcohols. However, it is essential to genetically deliver designer enzyme(s) into the chloroplast to tame the Calvin cycle and funnel metabolism toward butanol directly from $CO_2$ and $H_2O$. This requires more complicated gene design to achieve desirable results.

According to one of various embodiments, designer Calvin-cycle-channeled pathway enzymes encoded with designer unclear genes are targetedly expressed into algal chloroplast through use of a transit signal peptide sequence. The said signal peptide is selected from the group consisting of the hydrogenase transit-peptide sequences (HydA1 and HydA2), ferredoxin transit-peptide sequence (Frx1), thioredoxin-m transit-peptide sequence (Trx2), glutamine synthase transit-peptide sequence (Gs2), LhcII transit-peptide sequences, PSII-T transit-peptide sequence (PsbT), PSII-S transit-peptide sequence (PsbS), PSII-W transit-peptide sequence (PsbW), $CF_0CF_1$ subunit-γ transit-peptide sequence (AtpC), $CF_0CF_1$ subunit-δ transit-peptide sequence (AtpD), $CFoCF_1$ subunit-II transit-peptide sequence (AtpG), photosystem I (PSI) transit-peptide sequences, Rubisco SSU transit-peptide sequences, and combinations thereof. Preferred transit peptide sequences include the Hyd1 transit peptide, the Frx1 transit peptide, and the Rubisco SSU transit peptides (such as RbcS2).

SEQ ID NOS. 129-165 present examples for designer DNA constructs of designer chloroplast-targeted enzymes for creation of designer eukaryotic photosynthetic organisms such as designer algae with Calvin-cycle-channeled photosynthetic NADPH-enhanced pathways for photobiological production of butanol and related higher alcohols. Briefly, SEQ ID NO. 129 presents example 129 for a designer Nia1-promoter-controlled chloroplast-targeted Phosphoglycerate Mutase (03) DNA construct (1910 bp) that includes a PCR FD primer (sequence 1-20), a 2×84-bp *Chlamydomonas reinhardtii* Nia1 (nitrate reductase) promoter (21-188), a 135-bp *Chlamydomonas reinhardtii* RbcS2 transit peptide (189-323), a Phosphoglycerate Mutase-encoding sequence (324-1667) selected/modified from '*Nostoc azollae*' 0708 Phosphoglycerate Mutase (ADI65627), a 223-bp *Chlamydomonas reinhardtii* RbcS2 terminator (1668-1890), and a PCR RE primer (1891-1910).

SEQ ID NO. 130 presents example 130 for a designer Nia1-promoter-controlled chloroplast-targeted Enolase (04) DNA construct (1856 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an Enolase-encoding sequence (324-1613) selected/modified from '*Nostoc azollae*' 0708 Enolase (ADI63801), a 223-bp *Chlamydomonas reinhardtii* RbcS2 terminator (1614-1836), and a PCR RE primer (18837-1856).

SEQ ID NO. 131 presents example 131 for a designer Nia1-promoter-controlled chloroplast-targeted Pyruvate-Kinase (05) DNA construct (1985 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an enzyme-encoding sequence (324-1742) selected/modified from *Cyanothece* sp. PCC 8802 pyruvate-kinase (YP_003138017), a 223-bp *Chlamydomonas reinhardtii* RbcS2 terminator (1743-1965), and a PCR RE primer (1966-1985).

SEQ ID NO. 132 presents example 132 for a designer Nia1-promoter-controlled chloroplast-targeted NADPH-dependent Glyceraldehyde-3-Phosphate Dehydrogenase (34) DNA construct (1568 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a NADPH-dependent Glyceraldehyde-3-phosphate dehydrogenase-encoding sequence (324-1325) selected/modified from *Staphylococcus lugdunensis* HKU09-01 NADPH-dependent glyceraldehyde-3-phosphate dehydrogenase (ADC87332), a 223-bp *Chlamydomonas reinhardtii* RbcS2 terminator (1326-1548), and a PCR RE primer (1549-1568).

SEQ ID NO. 133 presents example 133 for a designer Nia1-promoter-controlled chloroplast-targeted NAD-dependent Glyceraldehyde-3-phosphate dehydrogenase (35) DNA construct (1571 bp) that includes a PCR FD primer (sequence 1-20), a 2×84-bp *Chlamydomonas reinhardtii* Nia1 (nitrate reductase) promoter (21-188), a 135-bp *Chlamydomonas reinhardtii* RbcS2 transit peptide (189-323), a NAD-dependent Glyceraldehyde-3-phosphate dehydrogenase-encoding sequence (324-1328) selected/modified from *Flavobacteriaceae bacterium* 3519-10 NAD-dependent Glyceraldehyde-3-phosphate dehydrogenase (YP_003095198), a 223-bp *Chlamydomonas reinhardtii* RbcS2 terminator (1329-1551), and a PCR RE primer (1552-1571).

SEQ ID NO. 134 presents example 134 for a designer Nia1-promoter-controlled chloroplast-targeted Citramalate Synthase (36) DNA construct (2150 bp) that includes a PCR FD primer (sequence 1-20), a 2×84-bp *Chlamydomonas reinhardtii* Nia1 (nitrate reductase) promoter (21-188), a 135-bp *Chlamydomonas reinhardtii* RbcS2 transit peptide (189-323), a Citramalate Synthase-encoding sequence (324-1907) selected/modified from *Hydrogenobacter thermophilus* TK-6 Citramalate Synthase (AD045737), a 223-bp *Chlamydomonas reinhardtii* RbcS2 terminator (1908-2130), and a PCR RE primer (2131-2150).

SEQ ID NO. 135 presents example 135 for a designer Nia1-promoter-controlled chloroplast-targeted 3-Isopropylmalate/(R)-2-Methylmalate Dehydratase (37) large/small subunits DNA construct (3125 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a 3-isopropylmalate/(R)-2-methylmalate dehydratase large subunit-encoding sequence (324-2084) selected/modified from *Eubacterium eligens* ATCC 27750 3-isopropylmalate/(R)-2-methylmalate dehydratase large subunit (YP_002930810), a 2×84-bp *Chlamydomonas reinhardtii* Nia1 promoter (2085-2252), a 135-bp *Chlamydomonas reinhardtii* RbcS2 transit peptide (2253-2387), a 3-isopropylmalate/(R)-2-methylmalate dehydratase small subunit-encoding sequence (2388-2882) selected/modified from *Eubacterium eligens* ATCC 27750 3-isopropylmalate/(R)-2-methylmalate dehydratase small subunit (YP_002930809), a 223-bp *Chlamydomonas reinhardtii* RbcS2 terminator (2883-3105), and a PCR RE primer (3106-3125).

SEQ ID NO. 136 presents example 136 for a designer Nia1-promoter-controlled chloroplast-targeted 3-Isopropylmalate Dehydratase (38) large/small subunits DNA construct (2879 bp) that includes a PCR FD primer (sequence 1-20), a 2×84-bp *Chlamydomonas* reinhardtii Nia1 promoter (21-188), a 135-bp *Chlamydomonas reinhardtii* RbcS2 transit peptide (189-323), a 3-isopropylmalate dehydratase large subunit-encoding sequence (324-1727) selected/modified from *Cyanothece* sp. PCC 7822 3-isopropylmalate dehydratase large subunit (YP_003886427), a 2×84-bp *Chlamydomonas reinhardtii* Nia1 promoter (1727-1894), a 135-bp *Chlamydomonas reinhardtii* RbcS2 transit peptide (1895-2029), a 3-isopropylmalate dehydratase small subunit-encoding sequence (2030-2636) selected/modified from *Cyanothece* sp. PCC 7822 3-isopropylmalate dehydratase small subunit (YP_003889452), a 223-bp *Chlamydomonas reinhardtii* RbcS2 terminator (2637-2859), and a PCR RE primer (2860-2879).

SEQ ID NO. 137 presents example 137 for a designer Nia1-promoter-controlled chloroplast-targeted 3-Isopropylmalate Dehydrogenase (39) DNA construct (1661 bp) that includes a PCR FD primer (sequence 1-20), a 2×84-bp *Chlamydomonas reinhardtii* Nia1 (nitrate reductase) promoter (21-188), a 135-bp *Chlamydomonas reinhardtii* RbcS2 transit peptide (189-323), a 3-isopropylmalate dehydrogenase-encoding sequence (324-1418) selected/modified from *Cyanothece* sp. PCC 7822 3-isopropylmalate dehydrogenase (YP_003888480), a 223-bp *Chlamydomonas reinhardtii* RbcS2 terminator (1419-1641), and a PCR RE primer (1642-1661).

SEQ ID NO. 138 presents example 138 for a designer Nia1-promoter-controlled chloroplast-targeted 2-Isopropylmalate Synthase (40) DNA construct (2174 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a 2-isopropylmalate synthase-encoding sequence (324-1931) selected/modified from *Cyanothece* sp. PCC 7822 2-isopropylmalate synthase (YP_003890122), a 223-bp *Chlamydomonas reinhardtii* RbcS2 terminator (1932-2154), and a PCR RE primer (2155-2174).

SEQ ID NO. 139 presents example 139 for a designer Nia1-promoter-controlled chloroplast-targeted Isopropylmalate Isomerase (41) large/small subunit DNA construct (2882 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an isopropylmalate isomerase large subunit-encoding sequence (324-1727) selected/modified from *Anabaena variabilis* ATCC 29413 isopropylmalate isomerase large subunit (YP_324467), a 2×84-bp *Chlamydomonas reinhardtii* Nia1 promoter (1728-1895), a 135-bp *Chlamydomonas reinhardtii* RbcS2 transit peptide (1896-2030), an isopropylmalate isomerase small subunit-encoding sequence (2031-2639) selected/modified from *Anabaena variabilis* ATCC 29413 isopropylmalate isomerase small subunit (YP_324466), a 223-bp *Chlamydomonas reinhardtii* RbcS2 terminator (2640-2862), and a PCR RE primer (2863-2882).

SEQ ID NO. 140 presents example 140 for a designer Nia1-promoter-controlled chloroplast-targeted 2-Keto Acid Decarboxylase (42) DNA construct (2210 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a 2-keto acid decarboxylase-encoding sequence (324-1967) selected/modified from *Lactococcus lactis* 2-keto acid decarboxylase (AAS49166), a 223-bp *Chlamydomonas reinhardtii* RbcS2 terminator (1968-2190), and a PCR RE primer (2191-2210).

SEQ ID NO. 141 presents example 141 for a designer Nia1-promoter-controlled chloroplast-targeted NADH-dependent Alcohol Dehydrogenase (43) DNA construct (1724 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a NADH-dependent alcohol dehydrogenase-encoding sequence (324-1481) selected/modified from *Gluconacetobacter hansenii* ATCC 23769 NADH-dependent alcohol dehydrogenase (ZP_06834544), a 223-bp *Chlamydomonas reinhardtii* RbcS2 terminator (1482-1704), and a PCR RE primer (1705-1724).

SEQ ID NO. 142 presents example 142 for a designer Nia1-promoter-controlled chloroplast-targeted NADPH-dependent Alcohol Dehydrogenase (44) DNA construct (1676 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a NADPH-dependent alcohol dehydrogenase-encoding sequence (324-1433) selected/modified from *Fusobacterium* sp. 7_1 NADPH-dependent alcohol dehydrogenase (ZP_04573952), a 223-bp *Chlamydomonas reinhardtii* RbcS2 terminator (1434-1656), and a PCR RE primer (1657-1676).

Note, use of SEQ ID NOS. 129-141 (and/or 142) in genetic transformation of an eukaryotic photosynthetic organism such as *Chlamydomonas* can create a designer eukaryotic photosynthetic organism such as designer *Chlamydomonas* with a Calvin-cycle 3-phosphogylcerate-branched NADPH-enhanced pathway (03-05, 34-43/44 in FIG. 4) for photobiological production of 1-butanol from carbon dioxide and water.

SEQ ID NO. 143 presents example 143 for a designer Nia1-promoter-controlled chloroplast-targeted Phosphoenolpyruvate Carboxylase (45) DNA construct (3629 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a Phosphoenolpyruvate Carboxylase-encoding sequence (324-3386) selected/modified from *Cyanothece* sp. PCC 7822 Phosphoenolpyruvate Carboxylase (YP_003887888), a 223-bp *Chlamydomonas reinhardtii* RbcS2 terminator (3387-3609), and a PCR RE primer (3610-3629).

SEQ ID NO. 144 presents example 144 for a designer Nia1-promoter-controlled chloroplast-targeted Aspartate Aminotransferase (46) DNA construct (1745 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a Aspartate Aminotransferase-encoding sequence (324-1502) selected/modified from *Synechococcus elongatus* PCC 6301 Aspartate Aminotransferase (YP_172275), a 223-bp *Chlamydomonas reinhardtii* RbcS2 terminator (1503-1525), and a PCR RE primer (1526-1745).

SEQ ID NO. 145 presents example 145 for a designer Nia1-promoter-controlled chloroplast-targeted Aspartokinase (47) DNA construct (2366 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an Aspartokinase-encoding sequence (324-2123) selected/modified from *Cyanothece* sp. PCC 8802 Aspartokinase (YP_003136939), a 223-bp *Chlamydomonas reinhardtii* RbcS2 terminator (2124-2346), and a PCR RE primer (2347-2366).

SEQ ID NO. 146 presents example 146 for a designer Nia1-promoter-controlled chloroplast-targeted Aspartate-Semialdehyde Dehydrogenase (48) DNA construct (1604 bp)

that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an Aspartate-semialdehyde dehydrogenase-encoding sequence (324-1361) selected/modified from *Trichodesmium erythraeum* IMS101 Aspartate-semialdehyde dehydrogenase (ABG50031), a 223-bp *Chlamydomonas reinhardtii* RbcS2 terminator (1362-1584), and a PCR RE primer (1585-1604).

SEQ ID NO. 147 presents example 147 for a designer Nia1-promoter-controlled chloroplast-targeted Homoserine Dehydrogenase (49) DNA construct (1868 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a homoserine dehydrogenase-encoding sequence (324-1625) selected/modified from *Cyanothece* sp. PCC 7822 homoserine dehydrogenase (YP_003887242), a 223-bp *Chlamydomonas reinhardtii* RbcS2 terminator (1626-1848), and a PCR RE primer (1849-1868).

SEQ ID NO. 148 presents example 148 for a designer Nia1-promoter-controlled chloroplast-targeted Homoserine Kinase (50) DNA construct (1472 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a Homoserine kinase-encoding sequence (324-1229) selected/modified from *Cyanothece* sp. PCC 7822 Homoserine kinase (YP_003886645), a 223-bp *Chlamydomonas reinhardtii* RbcS2 terminator (1230-1452), and a PCR RE primer (1453-1472).

SEQ ID NO. 149 presents example 149 for a designer Nia1-promoter-controlled chloroplast-targeted Threonine Synthase (51) DNA construct (1655 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a Threonine synthase-encoding sequence (324-1412) selected/modified from *Cyanothece* sp. PCC 7425 Threonine synthase (YP_002485009), a 223-bp *Chlamydomonas reinhardtii* RbcS2 terminator (1413-1635), and a PCR RE primer (1636-1655).

SEQ ID NO. 150 presents example 150 for a designer Nia1-promoter-controlled chloroplast-targeted Threonine Ammonia-Lyase (52) DNA construct (2078 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a threonine ammonia-lyase-encoding sequence (324-1835) selected/modified from *Synechococcus* sp. PCC 7335 threonine ammonia-lyase (ZP_05035047), a 223-bp *Chlamydomonas reinhardtii* RbcS2 terminator (1836-2058), and a PCR RE primer (2059-2078).

Note, use of SEQ ID NOS. 129,130,132,133, 143-150, 137-141 (and/or 141) through genetic transformation of an eukaryotic photosynthetic organism such as *Chlamydomonas* can create a designer eukaryotic photosynthetic organism such as designer *Chlamydomonas* with a Calvin-cycle 3-phosphogylcerate-branched NADPH-enhanced pathway (03, 04, 34, 35, 45-52, 39-43/44 in FIG. 4) for photobiological production of 1-butanol from carbon dioxide and water.

SEQ ID NO. 151 presents example 151 for a designer Nia1-promoter-controlled chloroplast-targeted Acetolactate Synthase (53) DNA construct (2282 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an acetolactate synthase-encoding sequence (324-2039) selected/modified from *Bacillus subtilis* subsp. *subtilis* str. 168 acetolactate synthase (CAB07802), a 223-bp *Chlamydomonas reinhardtii* RbcS2 terminator (2040-2262), and a PCR RE primer (2263-2282).

SEQ ID NO. 152 presents example 152 for a designer Nia1-promoter-controlled chloroplast-targeted Ketol-Acid Reductoisomerase (54) DNA construct (1562 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an enzyme-encoding sequence (324-1319) selected/modified from *Cyanothece* sp. PCC 7822 ketol-acid reductoisomerase (YP_003885458), a 223-bp *Chlamydomonas reinhardtii* RbcS2 terminator (1320-1542), and a PCR RE primer (1543-1562).

SEQ ID NO. 153 presents example 153 for a designer Nia1-promoter-controlled chloroplast-targeted Dihydroxy-Acid Dehydratase (55) DNA construct (2252 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a dihydroxy-acid dehydratase-encoding sequence (324-2009) selected/modified from *Cyanothece* sp. PCC 7822 dihydroxy-acid dehydratase (YP_003887466), a 223-bp *Chlamydomonas reinhardtii* RbcS2 terminator (2010-2232), and a PCR RE primer (2233-2252).

SEQ ID NO. 154 presents example 154 for a designer Nia1-promoter-controlled chloroplast-targeted 2-Methylbutyraldehyde Reductase (56) DNA construct (1496 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an enzyme-encoding sequence (324-1253) selected/modified from *Pichia pastoris* GS115 2-methylbutyraldehyde reductase (XP_002490018), a 223-bp *Chlamydomonas reinhardtii* RbcS2 terminator (1254-1476), and a PCR RE primer (1477-1496).

Note, use of SEQ ID NOS. 129-137,140, and 151-154 in genetic transformation of an eukaryotic photosynthetic organism such as *Chlamydomonas* can create a designer eukaryotic photosynthetic organism such as designer *Chlamydomonas* with a Calvin-cycle 3-phosphogylcerate-branched NADPH-enhanced pathway (03-05, 34-39, 53-55, 42, and 56 in FIG. 5) for photobiological production of 2-methyl-1-butanol from carbon dioxide and water.

SEQ ID NO. 155 presents example 155 for a designer Nia1-promoter-controlled chloroplast-targeted 3-Methylbutanal Reductase (57) DNA construct (1595 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), a 3-methylbutanal reductase-encoding sequence (324-1352) selected/modified from *Saccharomyces cerevisiae* S288c 3-methylbutanal reductase (DAA10635), a 223-bp *Chlamydomonas reinhardtii* RbcS2 terminator (1353-1575), and a PCR RE primer (1576-1595).

Note, use of SEQ ID NOS. 129-133, 151-153,140 and 141 (or 142) in genetic transformation of an eukaryotic photosynthetic organism such as *Chlamydomonas* can create a designer eukaryotic photosynthetic organism such as designer *Chlamydomonas* with a Calvin-cycle 3-phosphogylcerate-branched NADPH-enhanced pathway (03-05, 34, 35, 53-55, 42, and 43 (44) in FIG. 6) for photobiological production of isobutanol from carbon dioxide and water. Whereas, SEQ ID NOS. 129-133, 151-153, 136-138,140 and 155 represent a designer eukaryotic photosynthetic organism such as designer *Chlamydomonas* with a Calvin-cycle 3-phosphogylcerate-branched NADPH-enhanced pathway (03-05, 34, 35, 53-55, 40, 38, 39, 42, and 57 in FIG. 6) that can photobiologically produce 3-methyl-1-butanol from carbon dioxide and water.

SEQ ID NO. 156 presents example 156 for a designer Nia1-promoter-controlled chloroplast-targeted NADH-dependent Butanol Dehydrogenase (12a) DNA construct (1739 bp) that includes a PCR FD primer (sequence 1-20), a 2×84-bp *Chlamydomonas reinhardtii* Nia1 (nitrate reductase) promoter (21-188), a 135-bp *Chlamydomonas reinhardtii* RbcS2 transit peptide (189-323), an enzyme-encoding sequence (324-1496) selected/modified from *Clostridium perfringens* str. 13 NADH-dependent butanol dehydrogenase (NP__561774), a 223-bp *Chlamydomonas reinhardtii* RbcS2 terminator (1497-1719), and a PCR RE primer (1720-1739).

SEQ ID NO. 157 presents example 157 for a designer Nia1-promoter-controlled chloroplast-targeted NADPH-dependent Butanol Dehydrogenase (12b) DNA construct (1733 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an enzyme-encoding sequence (324-1490) selected/modified from *Clostridium saccharobutylicum* NADPH-dependent butanol dehydrogenase (AAA83520), a 223-bp *Chlamydomonas reinhardtii* RbcS2 terminator (1491-1713), and a PCR RE primer (1714-1733).

Note, use of SEQ ID NOS. 129-140 and 156 (and/or 157) in genetic transformation of an eukaryotic photosynthetic organism such as *Chlamydomonas* can create a designer eukaryotic photosynthetic organism such as designer *Chlamydomonas* with a Calvin-cycle 3-phosphogylcerate-branched NADPH-enhanced butanol production pathway (03-05, 34-42 and 12 in FIG. 4) for more specific photobiological production of 1-butanol from carbon dioxide and water. Similarly, SEQ ID NOS. 129,130,132,133, 143-150, 137-140, and 156 (and/or 157) represent another designer eukaryotic photosynthetic organism such as designer *Chlamydomonas* with a Calvin-cycle 3-phosphogylcerate-branched NADPH-enhanced butanol-production pathway (03, 04, 34, 35, 45-52, 39-42 and 12 in FIG. 4) for photobiological production of 1-butanol from carbon dioxide and water.

SEQ ID NO. 158 presents example 158 for a designer Nia1-promoter-controlled chloroplast-targeted 3-Ketothiolase (07') DNA construct (1745 bp) that includes a PCR FD primer (sequence 1-20), a 2×84-bp *Chlamydomonas reinhardtii* Nia1 (nitrate reductase) promoter (21-188), a 135-bp *Chlamydomonas reinhardtii* RbcS2 transit peptide (189-323), a 3-Ketothiolase-encoding sequence (324-1502) selected/modified from *Azohydromonas lata* 3-Ketothiolase (AAD10275), a 223-bp *Chlamydomonas reinhardtii* RbcS2 terminator (1503-1725), and a PCR RE primer (1726-1745).

SEQ ID NO. 159 presents a designer Nia1-promoter-controlled chloroplast-targeted 3-Hydroxyacyl-CoA dehydrogenase (08') DNA construct (1439 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an enzyme-encoding sequence (324-1196) selected/modified from Oceanithermus profundus DSM 14977 3-Hydroxyacyl-CoA dehydrogenase (ADR36325), a 223-bp *Chlamydomonas reinhardtii* RbcS2 terminator (1197-1419), and a PCR RE primer (1420-1439).

SEQ ID NO. 160 presents example 160 for a designer Nia1-promoter-controlled chloroplast-targeted Enoyl-CoA dehydratase (09') DNA construct (1337 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an enzyme-encoding sequence (324-1094) selected/modified from *Bordetella petrii* DSM 12804 Enoyl-CoA dehydratase (YP__001629844), a 223-bp *Chlamydomonas reinhardtii* RbcS2 terminator (1095-1317), and a PCR RE primer (1318-1337).

SEQ ID NO. 161 presents example 161 for a designer Nia1-promoter-controlled 2-Enoyl-CoA reductase (10') DNA construct (1736 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an enzyme-encoding sequence (324-1493) selected/modified from *Xanthomonas campestris* pv. *campestris* str. B100 2-Enoyl-CoA reductase (YP__001905744), a 223-bp *Chlamydomonas reinhardtii* RbcS2 terminator (1494-1716), and a PCR RE primer (1717-1736).

SEQ ID NO. 162 presents example 162 for a designer Nia1-promoter-controlled chloroplast-targeted Acyl-CoA reductase (11') DNA construct (2036 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an enzyme-encoding sequence (324-1793) selected/modified from *Thermosphaera aggregans* DSM 11486 Acyl-CoA reductase (YP__003649571), a 223-bp *Chlamydomonas reinhardtii* RbcS2 terminator (1794-2016), and a PCR RE primer (2017-2036).

SEQ ID NO. 163 presents example 163 for a designer Nia1-promoter-controlled chloroplast-targeted Hexanol Dehydrogenase (12') DNA construct (1625 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an enzyme-encoding sequence (324-1382) selected/modified from *Mycobacterium* chubuense NBB4 hexanol dehydrogenase (ACZ56328), a 223-bp *Chlamydomonas reinhardtii* RbcS2 terminator (1383-1605), and a PCR RE primer (1606-1625).

Note, use of SEQ ID NOS. 158-163 with other proper DNA constructs such as SEQ ID NOS. 132 and 133 in genetic transformation of an eukaryotic photosynthetic organism such as *Chlamydomonas* can create a designer eukaryotic photosynthetic organism such as designer *Chlamydomonas* with a Calvin-cycle 3-phosphogylcerate-branched NADPH-enhanced hexanol production pathway (34, 35, 03-10, and 07'-12' in FIG. 7) for photobiological production of 1-hexanol from carbon dioxide and water.

SEQ ID NO. 164 presents example 164 for a designer Nia1-promoter-controlled chloroplast-targeted Octanol Dehydrogenase (12") DNA construct (1249 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an enzyme-encoding sequence (324-1006) selected/modified from *Drosophila subobscura* Octanol dehydrogenase (AB065263), a 223-bp *Chlamydomonas reinhardtii* RbcS2 terminator (1007-1229), and a PCR RE primer (1230-1249).

Note, SEQ ID NOS. 132,133, and 158-163 represent a designer eukaryotic photosynthetic organism such as a designer *Chlamydomonas* with a designer hydrocarbon chain elongation pathway (34, 35, 07'-12' as shown in FIG. 7) for photobiological production of 1-hexanol. SEQ ID NOS: 132, 133, 158-162 and 164 represent another designer eukaryotic photosynthetic organism such as a designer *Chlamydomonas* with a designer hydrocarbon chain elongation pathway (34, 35, 07'-10' and 07"-12" as shown in FIG. 7) for photobiological production of 1-octanol.

SEQ ID NO. 165: a designer Nia1-promoter-controlled chloroplast-targeted Short Chain Alcohol Dehydrogenase (43') DNA construct (1769 bp) that includes a PCR FD primer (sequence 1-20), a 2×84-bp *Chlamydomonas reinhardtii* Nia1 promoter (21-188), a 135-bp *Chlamydomonas reinhardtii* RbcS2 transit peptide (189-323), an enzyme-encoding sequence (324-1526) selected/modified from *Burkholderia vietnamiensis* G4 Short chain alcohol dehydrogenase (AB056626), a 223-bp *Chlamydomonas reinhardtii* RbcS2 terminator (1527-1749), and a PCR RE primer (1750-1769).

Note, use of SEQ ID NOS. 129-140 and 165 in genetic transformation of an eukaryotic photosynthetic organism such as *Chlamydomonas* can create a designer eukaryotic photosynthetic organism such as designer *Chlamydomonas* with a Calvin-cycle 3-phosphogylcerate-branched NADPH-enhanced pathway (03-05, 34-41, 39'-43', 39'-43' and 39"-43" in FIG. 8) for photobiological production of 1-pentanol, 1-hexanol, and 1-heptanol from carbon dioxide and water. Similarly, SEQ ID NOS. 129-140 and 163 represent another designer eukaryotic photosynthetic organism such as designer *Chlamydomonas* with a Calvin-cycle 3-phosphogylcerate-branched NADPH-enhanced pathway (03-05, 34-41, 39'-41', 39'-42' and 12' in FIG. 8) for photobiological production of 1-hexanol from carbon dioxide and water.

Likewise, use of SEQ ID NOS. 129-137, 151-153, 138-140 and 165 through genetic transformation of an eukaryotic photosynthetic organism such as *Chlamydomonas* can create a designer eukaryotic photosynthetic organism such as designer *Chlamydomonas* with a Calvin-cycle 3-phosphogylcerate-branched NADPH-enhanced pathway (03-05, 34-39, 53-55, 39'-43', 39'-43', and 39"-43" in FIG. 9) for photobiological production of 3-methyl-1-pentanol, 4-methyl-1-hexanol, and 5-methyl-1-heptanol from carbon dioxide and water; The expression of SEQ ID NOS. 129, 130, 132, 133, 143-150, 151-153, 137-140 and 165 in an eukaryotic photosynthetic organism such as a host *Chlamydomonas* represent another designer eukaryotic photosynthetic organism with a Calvin-cycle 3-phosphogylcerate-branched NADPH-enhanced pathway (03, 05, 34, 35, 42-55, 39'-43', 39'-43', and 39"-43" in FIG. 9) for photobiological production of 3-methyl-1-pentanol, 4-methyl-1-hexanol, and 5-methyl-1-heptanol from carbon dioxide and water; The expression of SEQ ID NOS. 129-133, 151-153, 136-140 and 165 in a host eukaryotic photosynthetic organism such as *Chlamydomonas* represent yet another designer eukaryotic photosynthetic organism with a Calvin-cycle 3-phosphogylcerate-branched NADPH-enhanced pathway (03-05, 34, 35, 53-55, 40, 38, 39, 39'-43', 39'-43', and 39"-43" in FIG. 10) for photobiological production of 4-methyl-1-pentanol, 5-methyl-1-hexanol, and 6-methyl-1-heptanol from carbon dioxide and water.

Use of Designer Photosynthetic Organisms with Photobioreactor for Production and Harvesting of Butanol and Related Higher Alcohols The designer photosynthetic organisms with designer Calvin-cycle channeled photosynthetic NADPH-enhanced pathways (FIGS. 1, and 4-10) can be used with photobioreactors for production and harvesting of butanol and/or related higher alcohols. The said butanol and/or related higher alcohols are selected from the group consisting of: 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, 6-methyl-1-heptanol, and combinations thereof.

The said designer photosynthetic organisms such as designer transgenic oxyphotobacteria and algae comprise designer Calvin-cycle-channeled and photosynthetic NADPH-enhanced pathway gene(s) and biosafety-guarding technology for enhanced photobiological production of butanol and related higher alcohols from carbon dioxide and water. According to one of the various embodiments, it is a preferred practice to grow designer photosynthetic organisms photoautotrophically using carbon dioxide ($CO_2$) and water ($H_2O$) as the sources of carbon and electrons with a culture medium containing inorganic nutrients. The nutrient elements that are commonly required for oxygenic photosynthetic organism growth are: N, P, and K at the concentrations of about 1-10 mM, and Mg, Ca, S, and Cl at the concentrations of about 0.5 to 1.0 mM, plus some trace elements Mn, Fe, Cu, Zn, B, Co, Mo among others at μM concentration levels. All of the mineral nutrients can be supplied in an aqueous minimal medium that can be made with well-established recipes of oxygenic photosynthetic organism (such as algal) culture media using water (freshwater for the designer freshwater algae; seawater for the salt-tolerant designer marine algae) and relatively small of inexpensive fertilizers and mineral salts such as ammonium bicarbonate ($NH_4HCO_3$) (or ammonium nitrate, urea, ammonium chloride), potassium phosphates ($K_2HPO_4$ and $KH_2PO_4$), magnesium sulfate heptahydrate ($MgSO_4.7H_2O$), calcium chloride ($CaCl_2$), zinc sulfate heptahydrate ($ZnSO_4.7H_2O$), iron (II) sulfate heptahydrate ($FeSO_4.7H_2O$), and boric acid ($H_3BO_3$), among others. That is, large amounts of designer algae (or oxyphotobacteria) cells can be inexpensively grown in a short period of time because, under aerobic conditions such as in an open pond, the designer algae can photoautotrophically grow by themselves using air $CO_2$ as rapidly as their wild-type parental strains. This is a significant feature (benefit) of the invention that could provide a cost-effective solution in generation of photoactive biocatalysts (the designer photosynthetic biofuel-producing organisms such as designer algae or oxyphotobacteria) for renewable solar energy production.

According to one of the various embodiments, when designer photosynthetic organism culture is grown and ready for photobiological production of butanol and/or related higher alcohols, the designer photosynthetic organism cells are then induced to express the designer Calvin-cycle channeled photosynthetic NADPH-enhanced pathway(s) to photobiologically produce butanol and/or related higher alcohols from carbon dioxide and water. The method of induction is designer pathway gene(s) specific. For example, if/when a nirA promoter is used to control the designer Calvin-cycle channeled pathway gene(s) such as those of SEQ ID NOS: 58-69 and 72 (and/or 73) which represent a designer transgenic *Thermosynechococcus* that comprises the designer genes of a Calvin-cycle 3-phophoglycerate-branched photosynthetic NADPH-enhanced pathway (numerically labeled as 34, 35, 03-05, 36-42, and 12 in FIG. 4) for photobiological production of 1-butanol from carbon dioxide and water, the designer transgenic *Thermosynechococcus* is grown in a minimal liquid culture medium containing ammonium (but no nitrate) and other inorganic nutrients. When the designer transgenic *Thermosynechococcus* culture is grown and ready for photobiological production of biofuel 1-butanol, nitrate fertilizer will then be added into the culture medium to induce the expression of the designer nirA-controlled Calvin-cycle-channeled pathway to photobiologically produce 1-butanol from carbon dioxide and water in this example.

For the designer photosynthetic organism(s) with anaerobic promoter-controlled pathway(s) such as the designer transgenic *Nostoc* that contains designer hox-promoter-controlled Calvin-cycle 3-phophoglycerate-branched pathway genes of SEQ ID NOS. 104-109, anaerobic conditions can be used to induce the expression of the designer pathway gene(s)

for photobiological production of 2-methyl-1-butanol from carbon dioxide and water (FIG. 5). That is, when the designer transgenic *Nostoc* culture is grown and ready for photobiological biofuel production, its cells will then be placed (or sealed) into certain anaerobic conditions to induce the expression of the designer hox-controlled pathway gene(s) to photobiologically produce 2-methyl-1-butanol from carbon dioxide and water.

For those designer photosynthetic organism(s) that contains a heat- and light-responsive promoter-controlled and nirA-promoter-controlled pathway(s) such as the designer transgenic *Prochlorococcus* that contains a set of designer groE-promoter-controlled and nirA-promoter-controlled Calvin-cycle 3-phophoglycerate-branched pathway genes of SEQ ID NOS. 110-118, light and heat are used in conjunction of nitrate addition to induce the expression of the designer pathway genes for photobiological production of isobutanol from carbon dioxide and water (FIG. 6).

According to another embodiment, use of designer marine algae or marine oxyphotobacteria enables the use of seawater and/or groundwater for photobiological production of biofuels without requiring freshwater or agricultural soil. For example, designer *Prochlorococcus marinus* that contains the designer genes of SEQ ID NOS: 110-117 and 119-122 can use seawater and/or certain groundwater for photoautotrophic growth and synthesis of 3-methyl-1-butanol from carbon dioxide and water with its groE promoter-controlled designer Calvin-cycle-channeled pathway (identified as 34 (native), 35, 03-05, 53-55, 38-40, 42 and 57 in FIG. 6). The designer photosynthetic organisms can be used also in a sealed photobioreactor that is operated on a desert for production of isobutanol with highly efficient use of water since there will be little or no water loss by evaporation and/or transpiration that a common crop system would suffer. That is, this embodiment may represent a new generation of renewable energy (butanol and related higher alcohols) production technology without requiring arable land or freshwater resources.

According to another embodiment, use of nitrogen-fixing designer oxyphotobacteria enables photobiological production of biofuels without requiring nitrogen fertilizer. For example, the designer transgenic Nostoc that contains designer hox-promoter-controlled genes of SEQ ID NOS. 104-109 is capable of both fixing nitrogen ($N_2$) and photobiologically producing 2-methyl-1-butanol from carbon dioxide and water (FIG. 6). Therefore, use of the designer transgenic *Nostoc* enables photoautotrophic growth and 2-methyl-1-butanol synthesis from carbon dioxide and water.

Certain designer oxyphotobacteria are designed to perform multiple functions. For example, the designer transgenic *Cyanothece* that contains designer nirA promoter-controlled genes of SEQ ID NOS. 123-127 is capable of (1) using seawater, (2) $N_2$ fixing nitrogen, and photobiological producing 1-hexanol from carbon dioxide and water (FIG. 8). Use of this type of designer oxyphotobacteria enables photobiological production of advanced biofuels such as 1-hexanol using seawater without requiring nitrogen fertilizer According to one of various embodiments, a method for photobiological production and harvesting of butanol and related higher alcohols comprises: a) introducing a transgenic photosynthetic organism into a photobiological reactor system, the transgenic photosynthetic organism comprising transgenes coding for a set of enzymes configured to act on an intermediate product of a Calvin cycle and to convert the intermediate product into butanol and related higher alcohols; b) using reducing power and energy associated with the transgenic photosynthetic organism acquired from photosynthetic water splitting and proton gradient coupled electron transport process in the photobioreactor to synthesize butanol and related higher alcohols from carbon dioxide and water; and c) using a product separation process to harvest the synthesized butanol and/or related higher alcohols from the photobioreactor.

In summary, there are a number of embodiments on how the designer organisms may be used for photobiological butanol (and/or related higher alcohols) production. One of the preferred embodiments is to use the designer organisms for direct photosynthetic butanol production from $CO_2$ and $H_2O$ with a photobiological reactor and butanol-harvesting (filtration and distillation/evaporation) system, which includes a specific operational process described as a series of the following steps: a) Growing a designer transgenic organism photoautotrophically in minimal culture medium using air $CO_2$ as the carbon source under aerobic (normal) conditions before inducing the expression of the designer butanol-production-pathway genes; b) When the designer organism culture is grown and ready for butanol production, sealing or placing the culture into a specific condition to induce the expression of designer Calvin-cycle-channeled pathway genes; c) When the designer pathway enzymes are expressed, supplying visible light energy such as sunlight for the designer-genes-expressed cells to work as the catalysts for photosynthetic production of butanol and/or related higher alcohols from $CO_2$ and $H_2O$; d) Harvesting the product butanol and/or related higher alcohols by any method known to those skilled in the art. For example, harvesting the butanol and/or related higher alcohols from the photobiological reactor can be achieved by a combination of membrane filtration and distillation/evaporation butanol-harvesting techniques.

The above process to use the designer organisms for photosynthetic production and harvesting of butanol and related higher alcohols can be repeated for a plurality of operational cycles to achieve more desirable results. Any of the steps a) through d) of this process described above can also be adjusted in accordance of the invention to suit for certain specific conditions. In practice, any of the steps a) through d) of the process can be applied in full or in part, and/or in any adjusted combination as well for enhanced photobiological production of butanol and higher alcohol in accordance of this invention.

In addition to butanol and/or related higher alcohols production, it is also possible to use a designer organism or part of its designer butanol-production pathway(s) to produce certain intermediate products of the designer Calvin-cycle-channeled pathways (FIGS. 1 and 4-10) including (but not limited to): butyraldehyde, butyryl-CoA, crotonyl-CoA, 3-hydroxybutyryl-CoA, acetoacetyl-CoA, acetyl-CoA, pyruvate, phosphoenolpyruvate, 2-phosphoglycerate, 1,3-diphosphoglycerate, glyceraldehye-3-phosphate, dihydroxyacetone phosphate, fructose-1,6-diphosphate, fructose-6-phosphate, glucose-6-phosphate, glucose, glucose-1-phosphate, citramalate, citraconate, methyl-D-malate, 2-ketobutyrate, 2-ketovalerate, oxaloacetate, aspartate, homoserine, threonine, 2-keto-3-methylvalerate, 2-methylbutyraldehyde, 3-methylbutyraldehyde, 4-methyl-2-oxopentanoate, 3-isopropylmalate, 2-isopropylmalate, 2-oxoisovalerate, 2,3-dihydroxyisovalerate, 2-acetolactate, isobutyraldehyde, 3-keto-C6-acyl-CoA, 3-hydroxy-C6-acyl-CoA, C6-enoyl-CoA, C6-acyl-CoA, 3-keto-C8-acyl-CoA, 3-hydroxy-C8-acyl-CoA, C8-enoyl-CoA, C8-acyl-CoA, octanal, 1-pentanol, 1-hexanal, 1-heptanal, 2-ketohexanoate, 2-ketoheptanoate, 2-ketooctanoate, 2-ethylmalate, 3-ethylmalate, 3-methyl-1-pentanal, 4-methyl-1-hexanal, 5-methyl-1-heptanal, 2-hydroxy-2-ethyl-3-oxobutanoate, 2,3-dihydroxy-3-methylpentanoate, 2-keto-4-methyl-hexanoate, 2-keto-5-methyl-heptnoate, 2-keto-6-methyl-octanoate, 4-methyl-1-pentanal, 5-methyl-1-hexanal, 6-methyl-1-heptanal, 2-keto-7-methyl-octanoate, 2-keto-6-methyl-heptanoate, and 2-keto-5-methyl-hexanoate. According to one of various embodiments, therefore, a further embodiment comprises an additional step of harvesting the intermediate products that can be produced also from an induced transgenic designer organism. The production of an intermediate product can be selectively enhanced by switching off a designer-enzyme activity that catalyzes its consumption in the designer pathways. The production of a said intermediate product can be enhanced also by using a designer organism with one or some of designer enzymes omitted from the designer butanol-production pathways. For example, a designer organism with the butanol dehydrogenase or butyraldehyde dehydrogenase omitted from the designer pathway(s) of FIG. 1 may be used to produce butyraldehyde or butyryl-CoA, respectively.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A method for photobiological production of butanol and related higher alcohols comprising:

introducing a transgenic photosynthetic organism into a photobiological reactor system, the transgenic photosynthetic organism comprising transgenes coding for a set of enzymes configured to act on certain intermediate products of the Calvin cycle selected from the group consisting of glyceraldehyde 3-phosphate, 3-phosphoglycerate, fructose-1,6-diphosphate and fructose-6-phosphate and to convert the intermediate product into a higher alcohol comprising at least four carbon atoms;

using photosynthetically generated NADPH and energy ATP associated with the transgenic photosynthetic organism acquired from photosynthetic water splitting and proton gradient coupled electron transport process in the photobiological reactor to synthesize the higher alcohol from carbon dioxide and water; and using a product separation process to harvest the synthesized alcohol from the photobioreactor, wherein the transgenes coding for a set of enzymes comprises at least one of the designer Calvin-cycle-channeled pathway genes exemplified with exemplary designer DNA constructs of SEQ ID NOS. 58-70 shown in the sequence listings.

2. The method of claim 1, wherein:

the transgenic photosynthetic organism comprises at least one of a transgenic photosynthetic plant and a transgenic photosynthetic cell comprising the designer Calvin-cycle-channeled pathway for photobiological production of the higher alcohol; and the higher alcohol is selected from the group consisting of 1-butanol, 2-methyl-1 -butanol, isobutanol, 3 -methyl-1-butanol, 1-hexanol, 1-octanol, 1-pentanol, 1-heptanol, 3-methyl-1-pentanol, 4-methyl-1-hexanol, 5-methyl-1 -heptanol, 4-methyl- 1 -pentanol, 5 -methyl- 1 -hexanol, 6-methyl-1-heptanol and combinations thereof.

3. The method of claim 1, wherein the transgenic photosynthetic organism comprises at least one of a transgenic designer plant or transgenic designer plant cell selected from the group consisting of aquatic plants, plant cells, green algae, red algae, brown algae, blue-green algae, oxyphotobacteria, cyanobacteria, oxychlorobacteria, diatoms, marine algae, freshwater algae, salt-tolerant algal strains, cold-tolerant algal strains, heat-tolerant algal strains, antenna-pigment-deficient mutants, butanol-tolerant algal strains, higher-alcohols-tolerant algal strains, butanol-tolerant oxyphotobacteria, higher-alcohols-tolerant oxyphotobacteria and combinations thereof.

4. The method of claim 1, wherein the transgenic photosynthetic organism comprises *Thermosynechococcus elongatus.*

5. The method of claim 1, wherein the transgenic photosynthetic organism comprises oxyphotobacteria selected from the group consisting of *Thermosynechococcus elongatus* BP-1, Nostoc sp. PCC 7120, *Synechococcus elongatus* PCC 6301, *Syncechococcus* sp. strain PCC 7942, *Syncechococcus* sp. strain PCC 7002, *Syncechocystis* sp. strain PCC 6803, *Prochlorococcus marinus* MED4, *Prochlorococcus marinus* MIT 9313, *Prochlorococcus marinus* NATL1A, *Prochlorococcus* SS120, *Spirulina platensis* (Arthrospira platensis), *Spirulina pacifica, Lyngbya majuscule, Anabaena* sp., *Synechocystis* sp., *Synechococcus elongates, Synechococcus* (MC-A), *Trichodesmium* sp., *Richelia intracellularis, Synechococcus* WH7803, *Synechococcus* WH8102, *Nostoc punctiforme, Syncechococcus* sp. strain PCC 7943, *Synechocyitis* PCC 6714 phycocyanin-deficient mutant PD-1, *Cyanothece* strain 51142, *Cyanothece* sp. CCY0110, *Oscillatoria limosa, Lyngbya majuscula, Symploca muscorum, Gloeobacter violaceus, Prochloron didemni, Prochlorothrix hollandica, Synechococcus* (MC-A), *Trichodesmium* sp., *Richelia intracellularis, Prochlorococcus marinus, Prochlorococcus* SS120, WH102, *Lyngbya majuscula, Symploca muscorum, Synechococcus bigranulatus, cryophilic Oscillatoria* sp., *Phormidium* sp., *Nostoc* sp.-1, *Calothrix parietina, thermophilic Synechococcus bigranulatus, Synechococcus lividus, thermophilic Mastigocladus laminosus, Chlorogloeopsis fritschii* PCC 6912, *Synechococcus vulcanus, Synechococcus* sp. strain MA4, *Synechococcus* sp. strain MA19, and *Thermosynechococcus elongatus.*

6. The method of claim 1, wherein said transgenic photosynthetic organism comprises at least one of the designer Calvin-cycle-channeled pathways for producing at least one of the higher alcohols selected from the group consisting of: 1-butanol, 2-methyl-1-butanol, isobutanol, 3-methyl-1-butanol, 1-hexanol, 1-octanol, 1-pentanol, 1-heptanol, 3-methyl-1 -pentanol, 4-methyl- 1 -hexanol, 5-methyl- 1 -heptanol, 4-methyl- 1 -pentanol, 5-methyl- 1 -hexanol, 6-methyl-1-heptanol and combinations thereof.

7. The method of claim 1, wherein the transgenic photosynthetic organism comprises a nirA-promoter-controlled NADPH/NADH conversion system to achieve robust photobiological production of butanol and related higher alcohols that is selected from the group consisting of 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, and 6-methyl1-1-heptanol; wherein the said NADPH/NADH conversion is achieved by a special two-step mechanism:

1) The step with an NADPH-dependent glyceraldehyde-3-phosphate dehydrogenase, which uses NADPH in reducing 1,3-diphosphoglycerate to glyceraldehydes-3-phosphate; and 2) The step with an NAD+-dependent glyceraldehyde-3-phosphate dehydrogenase, which produces NADH in oxidizing glyceraldehyde-3-phosphate to 1,3-diphosphoglycerate.

* * * * *

SEQUENCE LISTING

<160> NUMBER OF SEQ ID NOS: 165

<210> SEQ ID NO 1
<211> LENGTH: 1809
<212> TYPE: DNA
<213> ORGANISM: Artificial Sequence
<220> FEATURE:
<223> OTHER INFORMATION: Synthetic Construct- Sequence No. 1, Example
      1: designer Butanol-Dehydrogenase DNA construct (1809 bp)

<400> SEQUENCE: 1
agaaaatctg gcaccacacc tatatggtag ggtgcgagtg accccgcgcg acttggagct     60
cgatggcccc gggttgtttg gggcgtccgc ctctcgcgct attctgagct ggagaccgag    120
gcgcatgaaa atgcattcgc ttccatagga cgctgcattg tggcttgaag gttcaaggga    180
agggttcaaa cgaccccgcc gtacgaactt ttgtcggggg gcgctcccgg ccccgggctc    240
ttgtgcgcgc attagggctt cgggtcgcaa gcaagacgat acatggccgc cgtcattgcc    300
aagtcctccg tctccgcggc cgtggctcgc ccggcccgct ccagcgtgcg ccccatggcc    360
gcgctgaagc ccgccgtcaa ggctgccccc gtggctgccc cggctcaggc caaccagatg    420
gagaatttta gatttaatgc atatacagag atgctttttg gaaagggaca aatagagaag    480
cttccagagg ttttaaaaag atatggtaaa aatatattac ttgcatatgg tggtggaagt    540
ataaaaaaga atggactcta tgatactatc caaaagctat tgaaagattt taatattgtt    600
gaattaagtg gtattgaacc aaatccaaga attgaaactg taagacgtgg agttgaactt    660
tgcagaaaaa ataaagtaga tgttatttta gctgttggtg gagggagtac aatagactgc    720
tcaaaggtta taggggcagg ttattattat gctggagatg catgggacct tgtaaaaaat    780
ccagctaaaa taggtgaggt tttaccaata gtgacagttt taacaatggc agctactggt    840
tctgaaatga atagaaatgc tgttatttca aagatggata caaatgaaaa gcttggaaca    900
ggatcaccta agatgatccc tcaaacttct attttagatc cagaatattt gtatacattg    960
ccagcaattc aaacagctgc aggttgtgct gatattatgt cacacatatt tgaacaatat   1020
tttaataaaa ctacagatgc ttttgtacaa gataaatttg cggaaggttt gttgcaaact   1080
tgtataaaat attgccctgt tgctttaaag gaaccaaaga attatgaagc tagagcaaat   1140
ataatgtggg ctagttcaat ggctcttaac ggactttttag gaagtgggaa agctggagct   1200
tggacttgtc atccaataga acatgaatta agtgcatttt atgatataac tcatggagta   1260
ggtcttgcaa ttttaactcc aagttggatg agatatatct taagtgatgt aacagttgat   1320
aagtttgtta acgtatggca tttagaacaa aaagaagata aatttgctct tgcaaatgaa   1380

```
gcaatagatg caacagaaaa attctttaaa gcttgtggta ttccaatgac tttaactgaa   1440

cttggaatag ataaagcaaa ctttgaaaag atggcaaaag ctgcagtaga acatggtgct   1500

ttagaatatg catatgtttc attaaatgcc gaggatgtat ataaaatttt agaaatgtcc   1560

ctttaataaa tggaggcgct cgttgatctg agccttgccc cctgacgaac ggcggtggat   1620

ggaagatact gctctcaagt gctgaagcgg tagcttagct ccccgtttcg tgctgatcag   1680

tctttttcaa cacgtaaaaa gcggaggagt tttgcaattt tgttggttgt aacgatcctc   1740

cgttgatttt ggcctctttc tccatgggcg ggctgggcgt atttgaagcg gttctctctt   1800

ctgccgtta                                                           1809
```

<210> SEQ ID NO 2
<211> LENGTH: 2067
<212> TYPE: DNA
<213> ORGANISM: Artificial Sequence
<220> FEATURE:
<223> OTHER INFORMATION: Synthetic Construct- Sequence No. 2, Example 2: designer Butyraldehyde-Dehydrogenase DNA construct (2067 bp)

<400> SEQUENCE: 2

```
agaaaatctg gcaccacacc tatatggtag ggtgcgagtg accccgcgcg acttggagct     60

cgatggcccc gggttgtttg gggcgtccgc ctctcgcgct attctgagct ggagaccgag    120

gcgcatgaaa atgcattcgc ttccatagga cgctgcattg tggcttgaag gttcaaggga    180

agggttcaaa cgaccccgcc gtacgaactt ttgtcggggg gcgctcccgg ccccgggctc    240

ttgtgcgcgc attagggctt cgggtcgcaa gcaagacgat acatggccgc cgtcattgcc    300

aagtcctccg tctccgcggc cgtggctcgc ccggcccgct ccagcgtgcg ccccatggcc    360

gcgctgaagc ccgccgtcaa ggctgccccc gtggctgccc cggctcaggc caaccagatg    420

attaaagaca cgctagtttc tataacaaaa gatttaaaat taaaaacaaa tgttgaaaat    480

gccaatctaa agaactacaa ggatgattct tcatgtttcg gagttttcga aaatgttgaa    540

aatgctataa gcaatgccgt acacgcacaa aagatattat cccttcatta tacaaaagaa    600

caaagagaaa aaatcataac tgagataaga aaggccgcat tagaaaataa agagattcta    660

gctacaatga ttcttgaaga aacacatatg ggaagatatg aagataaaat attaaagcat    720

gaattagtag ctaaatacac tcctgggaca gaagatttaa ctactactgc ttggtcagga    780

gataacgggc ttacagttgt agaaatgtct ccatatggcg ttataggtgc aataactcct    840

tctacgaatc caactgaaac tgtaatatgt aatagtatag gcatgatagc tgctggaaat    900

actgtggtat ttaacggaca tccaggcgct aaaaaatgtg ttgcttttgc tgtcgaaatg    960

ataaataaag ctattatttc atgtggtggt cctgagaatt tagtaacaac tataaaaaat   1020

ccaactatgg actctctaga tgcaattatt aagcaccctt caataaaact actttgcgga   1080

actggagggc caggaatggt aaaaaccctc ttaaattctg gtaagaaagc tataggtgct   1140

ggtgctggaa atccaccagt tattgtagat gatactgctg atatagaaaa ggctggtaag   1200

agtatcattg aaggctgttc ttttgataat aatttacctt gtattgcaga aaaagaagta   1260

tttgtttttg agaacgttgc agatgattta atatctaaca tgctaaaaaa taatgctgta   1320

attataaatg aagatcaagt atcaaagtta atagatttag tattacaaaa aaataatgaa   1380

actcaagaat actctataaa taagaaatgg gtcggaaaag atgcaaaatt attcttagat   1440

gaaatagatg ttgagtctcc ttcaagtgtt aaatgcataa tctgcgaagt aagtgcaagg   1500

catccatttg ttatgacaga actcatgatg ccaatattac caattgtaag agttaaagat   1560
```

```
atagatgaag ctattgaata tgcaaaaata gcagaacaaa atagaaaaca tagtgcctat   1620

atttattcaa aaaatataga caacctaaat aggtttgaaa gagaaatcga tactactatc   1680

tttgtaaaga atgctaaatc ttttgccggt gttggttatg aagcagaagg ctttacaact   1740

ttcactattg ctggatccac tggtgaagga ataacttctg caagaaattt tacaagacaa   1800

agaagatgtg tactcgccgg ttaataaatg gaggcgctcg ttgatctgag ccttgccccc   1860

tgacgaacgg cggtggatgg aagatactgc tctcaagtgc tgaagcggta gcttagctcc   1920

ccgtttcgtg ctgatcagtc tttttcaaca cgtaaaaagc ggaggagttt tgcaattttg   1980

ttggttgtaa cgatcctccg ttgattttgg cctctttctc catgggcggg ctgggcgtat   2040

ttgaagcggt tctctcttct gccgtta                                        2067
```

<210> SEQ ID NO 3
<211> LENGTH: 1815
<212> TYPE: DNA
<213> ORGANISM: Artificial Sequence
<220> FEATURE:
<223> OTHER INFORMATION: Synthetic Construct- Sequence No. 3, Example 3: designer Butyryl-CoA-Dehydrogenase DNA construct (1815 bp)

<400> SEQUENCE: 3

```
agaaaatctg gcaccacacc tatatggtag ggtgcgagtg accccgcgcg acttggagct     60

cgatggcccc gggttgtttg gggcgtccgc ctctcgcgct attctgagct ggagaccgag    120

gcgcatgaaa atgcattcgc ttccatagga cgctgcattg tggcttgaag gttcaaggga    180

agggttcaaa cgaccccgcc gtacgaactt ttgtcggggg gcgctcccgg ccccgggctc    240

ttgtgcgcgc attagggctt cgggtcgcaa gcaagacgat acctcgagca tatggccgcc    300

gtcattgcca agtcctccgt ctccgcggcc gtggctcgcc cggcccgctc cagcgtgcgc    360

cccatggccg cgctgaagcc cgccgtcaag gctgcccccg tggctgcccc ggctcaggcc    420

aaccagatga atttccaatt aactagagaa caacaattag tacaacaaat ggttagagaa    480

ttcgcagtaa atgaagttaa gccaatagct gctgaaatcg acgaaacaga aagattccct    540

atggaaaacg ttgaaaaaat ggctaagctt aaaatgatgg gtatcccatt ttctaaagaa    600

tttggtggag caggcggaga tgttctttca tatataatag ctgtggaaga attatcaaaa    660

gtttgtggta ctacaggagt tattctttca gcgcatacat cattatgtgc atcagtaatt    720

aatgaaaatg gaactaacga acaaagagca aaatatttac ctgatctttg cagcggtaaa    780

aagatcggtg ctttcggatt aactgaacca ggtgctggta cagatgctgc aggacaacaa    840

acaactgctg tattagaagg ggatcattat gtattaaatg gttcaaaaat cttcataaca    900

aatggtggag ttgctgaaac tttcataata tttgctatga cagataagag tcaaggaaca    960

aaaggaattt ctgcattcat agtagaaaag tcattcccag gattctcaat aggaaaatta   1020

gaaaataaga tggggatcag agcatcttca actactgagt tagttatgga aaactgcata   1080

gtaccaaaag aaaacctact tagcaaagaa ggtaagggat ttggtatagc aatgaaaact   1140

cttgatggag gaagaattgg tatagctgct caagctttag gtattgcaga aggagctttt   1200

gaagaagctg ttaactatat gaaagaaaga aaacaatttg gtaaaccatt atcagcattc   1260

caaggattac aatggtatat agctgaaatg gatgttaaaa tccaagctgc taaatactta   1320

gtatacctag ctgcaacaaa gaagcaagct ggtgagcctt actcagtaga tgctgcaaga   1380

gctaaattat ttgctgcaga tgttgcaatg gaagttacaa ctaaagcagt tcaaatcttt   1440
```

-continued

```
ggtggatatg gttacactaa agaataccca gtagaaagaa tgatgagaga tgctaaaata   1500

tgcgaaatct acgaaggaac ttcagaagtt caaaagatgg ttatcgcagg aagcatttta   1560

agataatcta gataaatgga ggcgctcgtt gatctgagcc ttgcccccctg acgaacggcg   1620

gtggatggaa gatactgctc tcaagtgctg aagcggtagc ttagctcccc gtttcgtgct   1680

gatcagtctt tttcaacacg taaaaagcgg aggagttttg caattttgtt ggttgtaacg   1740

atcctccgtt gattttggcc tctttctcca tgggcgggct gggcgtattt gaagcggttc   1800

tctcttctgc cgtta                                                    1815
```

<210> SEQ ID NO 4
<211> LENGTH: 1482
<212> TYPE: DNA
<213> ORGANISM: Artificial Sequence
<220> FEATURE:
<223> OTHER INFORMATION: Synthetic Construct- Sequence No. 4,
Example 4: designer Crotonase DNA construct (1482 bp)

<400> SEQUENCE: 4

```
agaaaatctg gcaccacacc tatatggtag ggtgcgagtg accccgcgcg acttggagct     60

cgatggcccc gggttgtttg gggcgtccgc ctctcgcgct attctgagct ggagaccgag    120

gcgcatgaaa atgcattcgc ttccatagga cgctgcattg tggcttgaag gttcaaggga    180

agggttcaaa cgaccccgcc gtacgaactt ttgtcggggg gcgctcccgg ccccgggctc    240

ttgtgcgcgc attagggctt cgggtcgcaa gcaagacgat acctcgagca tatggccgcc    300

gtcattgcca agtcctccgt ctccgcggcc gtggctcgcc cggcccgctc cagcgtgcgc    360

cccatggccg cgctgaagcc cgccgtcaag gctgcccccg tggctgcccc ggctcaggcc    420

aaccagatgg aattaaaaaa tgttattctt gaaaaagaag ggcatttagc tattgttaca    480

atcaatagac caaaggcatt aaatgcattg aattcagaaa cactaaaaga tttaaatgtt    540

gttttagatg atttagaagc agacaacaat gtgtatgcag ttatagttac tggtgctggt    600

gagaaatctt ttgttgctgg agcagatatt tcagaaatga aagatcttaa tgaagaacaa    660

ggtaaagaat ttggtatttt aggaaataat gtcttcagaa gattagaaaa attggataag    720

ccagttatcg cagctatatc aggatttgct cttggtggtg gatgtgaact tgctatgtca    780

tgtgacataa gaatagcttc agttaaagct aaatttggtc aaccagaagc aggacttgga    840

ataactccag gatttggtgg aactcaaaga ttagcaagaa tagttggacc aggaaaagct    900

aaagaattaa tttatacttg tgaccttata aatgcagaag aagcttatag aataggctta    960

gttaataaag tagttgaatt agaaaaattg atggaagaag caaaagcaat ggctaacaag   1020

attgcagcta atgctccaaa agcagttgca tattgtaaag atgctataga cagaggaatg   1080

caagttgata tagatgcagc tatattaata gaagcagaag actttgggaa gtgctttgca   1140

acagaagatc aaacagaagg aatgactgcg ttcttagaaa gaagagcaga aaagaatttt   1200

caaaataaag gctgctgccc cggctgctgc taatctagat aaatggaggc gctcgttgat   1260

ctgagccttg ccccctgacg aacggcggtg gatggaagat actgctctca agtgctgaag   1320

cggtagctta gctccccgtt tcgtgctgat cagtcttttt caacacgtaa aaagcggagg   1380

agttttgcaa ttttgttggt tgtaacgatc ctccgttgat tttggcctct ttctccatgg   1440

gcgggctggg cgtatttgaa gcggttctct cttctgccgt ta                      1482
```

<210> SEQ ID NO 5
<211> LENGTH: 1367
<212> TYPE: DNA

<213> ORGANISM: Artificial Sequence
<220> FEATURE:
<223> OTHER INFORMATION: Synthetic Construct- Sequence No. 5,
Example 5: designer 3-Hydroxybutyryl-CoA-Dehydrogenase DNA
construct (1367 bp)

<400> SEQUENCE: 5

```
agaaaatctg gcaccacacc atggtagggt gcgagtgacc ccgcgcgact tggaagggtt     60

caaacgaccc cgccgtacga acttttgtcg gggggcgctc ccggctcgag catatggccg    120

ccgtcattgc caagtcctcc gtctccgcgg ccgtggctcg cccggcccgc tccagcgtgc    180

gccccatggc cgcgctgaag cccgccgtca aggctgcccc cgtggctgcc ccggctcagg    240

ccaaccagat gaaaaagatt tttgtacttg gagcaggaac tatgggtgct ggtatcgttc    300

aagcattcgc tcaaaaaggt tgtgaggtaa ttgtaagaga cataaaggaa gaatttgttg    360

acagaggaat agctggaatc actaaaggat tagaaaagca agttgctaaa ggaaaaatgt    420

ctgaagaaga taaagaagct atactttcaa gaatttcagg aacaactgat atgaagttag    480

ctgctgactg tgatttagta gttgaagctg caatcgaaaa catgaaaatt aagaaggaaa    540

tctttgctga gttagatgga atttgtaagc cagaagcgat tttagcttca aacacttcat    600

ctttatcaat tactgaagtt gcttcagcta caaagagacc tgataaagtt atcggaatgc    660

atttctttaa tccagctcca gtaatgaagc ttgttgaaat tattaaagga atagctactt    720

ctcaagaaac ttttgatgct gttaaggaat tatcagttgc tattggaaaa gaaccagtag    780

aagttgcaga agctccagga ttcgttgtaa acggaatctt aatcccaatg attaacgaag    840

cttcattcat ccttcaagaa ggaatagctt cagttgaaga tattgataca gctatgaaat    900

atggtgctaa ccatccaatg ggacctttag ctttaggaga tcttattgga ttagatgttt    960

gcttagctat catggatgtt ttattcactg aaacaggtga taacaagtac agagctagca   1020

gcatattaag aaaatatgtt agagctggat ggcttggaag aaaatcagga aaaggattct   1080

atgattattc taaaggctgc tgccccggct gctgctaatc tagataaatg gaggcgctcg   1140

ttgatctgag ccttgccccc tgacgaacgg cggtggatgg aagatactgc tctcaagtgc   1200

tgaagcggta gcttagctcc ccgtttcgtg ctgatcagtc tttttcaaca cgtaaaaagc   1260

ggaggagttt tgcaattttg ttggttgtaa cgatcctccg ttgattttgg cctctttctc   1320

catgggcggg ctgggcgtat ttgaagcggt tctctcttct gccgtta                 1367
```

<210> SEQ ID NO 6
<211> LENGTH: 1721
<212> TYPE: DNA
<213> ORGANISM: Artificial Sequence
<220> FEATURE:
<223> OTHER INFORMATION: Synthetic Construct- Sequence No. 6,
Example 6: designer Thiolase DNA construct (1721 bp)

<400> SEQUENCE: 6

```
agaaaatctg gcaccacacc atggtagggt gcgagtgacc ccgcgcgact tggaagggtt     60

caaacgaccc cgccgtacga acttttgtcg gggggcgctc ccggctcgag catatggccg    120

ccgtcattgc caagtcctcc gtctccgcgg ccgtggctcg cccggcccgc tccagcgtgc    180

gccccatggc cgcgctgaag cccgccgtca aggctgcccc cgtggctgcc ccggctcagg    240

ccaaccagat gggcaaagaa agtagtttta gctgtgcatg tcgtacagcc atcggaacaa    300

tgggtggatc tcttagcaca attcctgcag tagatttagg tgctatcgtt atcaaagagg    360

ctcttaaccg cgcaggtgtt aaacctgaag atgttgatca cgtatacatg ggatgcgtta    420
```

```
ttcaggcagg acagggacag aacgttgctc gtcaggcttc tatcaaggct ggtcttcctg    480

tagaagtacc tgcagttaca actaacgttg tatgtggttc aggtcttaac tgtgttaacc    540

aggcagctca gatgatcatg gctggagatg ctgatatcgt tgttgccggt ggtatggaaa    600

acatgtcact tgcaccattt gcacttccta atggccgtta cggatatcgt atgatgtggc    660

caagccagag ccagggtggt cttgtagaca ctatggttaa ggatgctctt tgggatgctt    720

tcaatgatta tcatatgatc cagacagcag acaacatctg cacagagtgg ggtcttacac    780

gtgaagagct cgatgagttt gcagctaaga gccagaacaa ggcttgtgca gcaatcgaag    840

ctggcgcatt caaggatgag atcgttcctg tagagatcaa gaagaagaaa gagacagtta    900

tcttcgatac agatgaaggc ccaagacagg gtgttacacc tgaatctctt tcaaagcttc    960

gtcctatcaa caaggatgga ttcgttacag ctggtaacgc ttcaggtatc aacgacggtg   1020

ctgcagcact cgtagttatg tctgaagaga aggctaagga gctcggcgtt aagcctatgg   1080

ctacattcgt agctggagca cttgctggtg ttcgtcctga agttatgggt atcggtcctg   1140

tagcagctac tcagaaggct atgaagaagg ctggtatcga gaacgtatct gagttcgata   1200

tcatcgaggc taacgaagca ttcgcagctc agtctgtagc agttggtaag gatcttggaa   1260

tcgacgtcca caagcagctc aatcctaacg gtggtgctat cgctcttgga cacccagttg   1320

gagcttcagg tgctcgtatc cttgttacac ttcttcacga gatgcagaag aaagacgcta   1380

agaagggtct tgctacactt tgcatcggtg gcggtatggg atgcgctact atcgttgaga   1440

agtacgaagg ctgctgcccc ggctgctgct aatctagata aatggaggcg ctcgttgatc   1500

tgagccttgc cccctgacga acggcggtgg atggaagata ctgctctcaa gtgctgaagc   1560

ggtagcttag ctccccgttt cgtgctgatc agtctttttc aacacgtaaa aagcggagga   1620

gttttgcaat tttgttggtt gtaacgatcc tccgttgatt ttggcctctt tctccatggg   1680

cgggctgggc gtatttgaag cggttctctc ttctgccgtt a                       1721
```

```
<210> SEQ ID NO 7
<211> LENGTH: 4211
<212> TYPE: DNA
<213> ORGANISM: Artificial Sequence
<220> FEATURE:
<223> OTHER INFORMATION: Synthetic Construct- Sequence No. 7,
      Example 7: designer Pyruvate-Ferredoxin-Oxidoreductase DNA
      construct (4211 bp)

<400> SEQUENCE: 7

agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcggggggc    180

gctcccggct cgagcatatg gccgccgtca ttgccaagtc ctccgtctcc gcggccgtgg    240

ctcgcccggc ccgctccagc gtgcgcccca tggccgcgct gaagcccgcc gtcaaggctg    300

cccccgtggc tgccccggct caggccaacc agatggcgca gaggtgcaag gagcccgtcg    360

acggaacgac agccacgacg cacgtggcct acttcatgag cgacagcgcg ttcatcttcc    420

ccatcacgcc cagctcggtc atgtccgagg tcgcccacga gtggtccatg aacggccgca    480

agaacgcctt cggccagccc acgatggtcc gccagatgca gagcgaggct gggtctgccg    540

gcgccctgca cggcgcgctc agcgagggag cgctggcgac gacgttcacg agcagccagg    600

gcctgctgct catgatcccc aacatgtaca agatcgccgg cgagctcctg ccctgcgtca    660

tgcacatcgc cgcccgcacc gtcgccaccg aggccctctc tatcttcggc gaccacacgg    720
```

-continued

```
atgtctacgc ggtgaggtcg acggggttcg cgttcctgtg ctccgcgacc gtccaggagt    780
gcatccacat gtccgccgcc gcgcacgccg ccaccctgtc cagcgaggtc ccgttcgccc    840
acttcttcga cggcttccgc acgtcccacg agatccagaa gatcgacttc ccctcggacg    900
ccgacctgct ggcctgcatg aactttgacg acgtccgcag gttccgtggc cgctcgctgt    960
gctgcgagcg cccgctgctg cgcgggacgg cgcagaaccc cgacgtcttc atgcaggcgt   1020
ccgagtcgaa cctggcgacg ctggccaggg tccccgcggc catcgacgag gcgctggctc   1080
gtgtgaacaa ggtgttcggg accaactaca ggacctacga gtactatggc caccccgagg   1140
ccacggacgt gatcgtggcc atgggaagcg gcaccgaagt ggccatctcg actgccaact   1200
tcctcaactc gcgcgacgcg aactcgaggg tcggcgtcgt gagggtgcgg ctgttccggc   1260
cgtttgtgtc ggcggcgttt gtggctgcgc tgcccaagac cgtcaagagg atctgcgttc   1320
tggaccgcgg gagggacggg caggcggccg cggacccccct gcaccaggac gtcctgtcgg  1380
cgctgggtct ggcagcgccc gggagggttc aggtgtgcgt gggaggcgtg tacggtctgt   1440
cgtccaagga cttcaacccc gaccacgtga tcgccgtgta caggaacctc gcgtcggcga   1500
gccccaagaa caggttcagc gtcggcatcg tcgacgacgt gacgcacaac agcctggaca   1560
tgggagagca cgtggacgcg ctgccgcagg ggacgaagca gtgcctgctg tggggcatcg   1620
gcggagacgg gaccatcggg gcgaacaaga cggccatcaa gctgatcgcg gaccacacgg   1680
agctgcacgc gcaggggtac tttgcgtacg acgccaacaa ggccggcggc ctgacagtct   1740
cgcacctgcg gttcggcccg acgcggttcg aggcgccgta cctggtgaac gacagcaact   1800
acgtggcgtg ccacaacttc tcgtacgtgc acaggttcaa cctgctgtcg tcgctgcgca   1860
ccgggggcac gttcgtgctc aactgcccgt gccggaccgt ggaggagctg gacacggcac   1920
tcccggtgcg cctgaggcgc gagatcgcca ggcggcaggc caagttctat gtgatcgacg   1980
cgaccaagat cgccaaggac aacgggatgg gcccgttcat caacatggtc ctccaggccg   2040
tgttcttcta tctgtcccac gtgctcgatg tgaacgaggc agtggcactc ctgaagaaga   2100
gcatccagaa gatgtacgcg cgcaagggcg aggaggttgt caggaagaac gtggcatcgg   2160
tcgacgcgtc gctggatccc aaggcgttgc tgcacatcga gtaccccgca gacaggtggc   2220
ttgcgctggc cgacgagcac gtgccccgca tgggtctgct cactgtcccc gagcgcctgc   2280
agaagttcaa cgccgagctg tacgagccga ccctcgcgta cgatggggag agcatcccgg   2340
tcagcaggtt ccctcgcggc ggcgagacgc cgacgggcac gactcagctg ggcaagcgtg   2400
gcatcgccga gagcgtgccg cactggaacc acgagaagtg cgtgcagtgc aaccagtgct   2460
cgttcgtgtg cccgcacgcc gtcatccggt cgtaccagat cagcgaggag gagatgaaga   2520
acgcccctgc cggcttcgac actcttaagt cgcgcaagcc cgggtatcgt ttccgcatca   2580
acgtcagcgc cctggactgc actggctgca gcgtgtgcgt ggagcagtgc ccagtcaagt   2640
gcctggagat gaagcctctc gagtccgagt tcgagatgca gaaggacgcc atcaggttcg   2700
tccgcgagat ggtcgcgccc aagcccgagc tgggagaccg caagactccc gtcggcatcg   2760
cgtctcacac gccgctgttc gagttcccgg gagcctgcgc cgggtgcggt gagaccccgc   2820
tggtgcgcct cgtgacgcag atgttcggtg agcgcatggt catcgccgcg gccactgggt   2880
gcaactcgat ctggggagcg tcgttcccga acgtgccgta cacaaccaac gcccgcgggg   2940
agggccccgc gtggcacaac tcgctgttcg aggacgcggc ggagctcggg tatggcatta   3000
cgtgtgcgta tcgccagcgc cgcgagcgcc tcatcggcat cgtgcggagc gtcgtcgacg   3060
```

```
atgcgggatc cgtgcagggt ctgtctgctg agctgaaggc tctgctggtc gagtggctcg   3120

cgcacgtcag ggacttcgag aagacccgcg agctccgcga caggatgaac cccctgatcg   3180

acgcaatccc agcgaacgcg gactgcaggg ttctggagct cagggagaag cacaaccgcg   3240

agctgatcgc gcgcacgagt ttctggatcc tcggtggcga cgggtgggcg tacgacatcg   3300

gcttcggtgg actggaccac gtgatcgcca acaacgagga cgtcaacatc cttgttctcg   3360

acacggaggt ctactccaac actggtggcc agcgctccaa gtcgacgccg ctcggcgccc   3420

gcgccaagta cgctgtgctg ggcaaggaca ctgggaagaa ggacctgggg cgcatcgcga   3480

tgacctacga gaccgcgtac gtggccagca tcgcgcaggg agccaaccag cagcagtgca   3540

tggacgcgct gagggaggcc gaggcctacc agggcccctc gatcgtcatt gcgtacactc   3600

cgtgcatgga gcaccagatg gtccgcggga tgaaggagag ccagaagaac cagaagctgg   3660

ctgtggagac gggctactgg ctgctgtacc gcttcaaccc cgacctcatc cacgagggca   3720

agaacccctt caccctcgac tcgaagcctc cctcgaagcc tcccaaggag ttcctggaca   3780

cgcagggccg tttcattact ctgcagcgcg agcaccccga gcaggcccac ctccttcacg   3840

aggcactcac ccgctctctg gccacccgct tcgtgcgcta ccagcgcctc gtgcagctgt   3900

acgagcccgc tgcccctgcc gcagctcctg ccacgcatgg ctgctgcccc ggctgctgct   3960

aatctagata aatggaggcg ctcgttgatc tgagccttgc cccctgacga acggcggtgg   4020

atggaagata ctgctctcaa gtgctgaagc ggtagcttag ctccccgttt cgtgctgatc   4080

agtctttttc aacacgtaaa aagcggagga gttttgcaat tttgttggtt gtaacgatcc   4140

tccgttgatt ttggcctctt tctccatggg cgggctgggc gtatttgaag cggttctctc   4200

ttctgccgtt a                                                         4211
```

<210> SEQ ID NO 8
<211> LENGTH: 2021
<212> TYPE: DNA
<213> ORGANISM: Artificial Sequence
<220> FEATURE:
<223> OTHER INFORMATION: Synthetic Construct- Sequence No. 8, Example 8: designer Pyruvate-Kinase DNA construct (2021 bp)

<400> SEQUENCE: 8

```
agaaaatctg gcaccacacc atggtagggt gcgagtgacc ccgcgcgact tggaagggtt     60

caaacgaccc cgccgtacga acttttgtcg gggggcgctc ccggctcgag catatggccg    120

ccgtcattgc caagtcctcc gtctccgcgg ccgtggctcg cccggcccgc tccagcgtgc    180

gccccatggc cgcgctgaag cccgccgtca aggctgcccc cgtggctgcc ccggctcagg    240

ccaaccagat gtctagatta gaaagattga cctcattaaa cgttgttgct ggttctgact    300

tgagaagaac ctccatcatt ggtaccatcg gtccaaagac caacaaccca gaaaccttgg    360

ttgctttgag aaaggctggt ttgaacattg tccgtatgaa cttctctcac ggttcttacg    420

aataccacaa gtctgtcatt gacaacgcca gaaagtccga agaattgtac ccaggtagac    480

cattggccat tgctttggac accaagggtc cagaaatcag aactggtacc accaccaacg    540

atgttgacta cccaatccca ccaaaccacg aaatgatctt caccaccgat gacaagtacg    600

ctaaggcttg tgacgacaag atcatgtacg ttgactacaa gaacatcacc aaggtcatct    660

ccgctggtag aatcatctac gttgatgatg gtgttttgtc tttccaagtt ttggaagtcg    720

ttgacgacaa gactttgaag gtcaaggctt tgaacgccgg taagatctgt tcccacaagg    780

gtgtcaactt accaggtacc gatgtcgatt tgccagcttt gtctgaaaag gacaaggaag    840
```

atttgagatt cggtgtcaag aacggtgtcc acatggtctt cgcttctttc atcagaaccg 900
ccaacgatgt tttgaccatc agagaagtct tgggtgaaca aggtaaggac gtcaagatca 960
ttgtcaagat tgaaaaccaa caaggtgtta acaacttcga cgaaatcttg aaggtcactg 1020
acggtgttat ggttgccaga ggtgacttgg gtattgaaat cccagcccca gaagtcttgg 1080
ctgtccaaaa gaaattgatt gctaagtcta acttggctgg taagccagtt atctgtgcta 1140
cccaaatgtt ggaatccatg acttacaacc caagaccaac cagagctgaa gtttccgatg 1200
tcggtaacgc tatcttggat ggtgctgact gtgttatgtt gtctggtgaa accgccaagg 1260
gtaactaccc aatcaacgcc gttaccacta tggctgaaac cgctgtcatt gctgaacaag 1320
ctatcgctta cttgccaaac tacgatgaca tgagaaactg tactccaaag ccaacctcca 1380
ccaccgaaac cgtcgctgcc tccgctgtcg ctgctgtttt cgaacaaaag gccaaggcta 1440
tcattgtctt gtccacttcc ggtaccaccc caagattggt ttccaagtac agaccaaact 1500
gtccaatcat cttggttacc agatgcccaa gagctgctag attctctcac ttgtacagag 1560
gtgtcttccc attcgttttc gaaaaggaac ctgtctctga ctggactgat gatgttgaag 1620
cccgtatcaa cttcggtatt gaaaaggcta aggaattcgg tatcttgaag aagggtgaca 1680
cttacgtttc catccaaggt ttcaaggccg gtgctggtca ctccaacact ttgcaagtct 1740
ctaccgttgg ctgctgcccc ggctgctgct aatctagata aatggaggcg ctcgttgatc 1800
tgagccttgc cccctgacga acggcggtgg atggaagata ctgctctcaa gtgctgaagc 1860
ggtagcttag ctccccgttt cgtgctgatc agtctttttc aacacgtaaa aagcggagga 1920
gttttgcaat tttgttggtt gtaacgatcc tccgttgatt ttggcctctt tctccatggg 1980
cgggctgggc gtatttgaag cggttctctc ttctgccgtt a 2021

<210> SEQ ID NO 9
<211> LENGTH: 1815
<212> TYPE: DNA
<213> ORGANISM: Artificial Sequence
<220> FEATURE:
<223> OTHER INFORMATION: Synthetic Construct- Sequence No. 9, Example 9: designer Enolase DNA construct (1815 bp)

<400> SEQUENCE: 9
agaaaatctg gcaccacacc tatatggtag ggtgcgagtg accccgcgcg acttggagct 60
cgatggcccc gggttgtttg gggcgtccgc ctctcgcgct attctgagct ggagaccgag 120
gcgcatgaaa atgcattcgc ttccatagga cgctgcattg tggcttgaag gttcaaggga 180
agggttcaaa cgaccccgcc gtacgaactt ttgtcggggg gcgctcccgg ccccgggctc 240
ttgtgcgcgc attagggctt cgggtcgcaa gcaagacgat acctcgagca tatggccgcc 300
gtcattgcca agtcctccgt ctccgcggcc gtggctcgcc cggcccgctc cagcgtgcgc 360
cccatggccg cgctgaagcc cgccgtcaag gctgcccccg tggctgcccc ggctcaggcc 420
aaccaggtga ccaaggctgt tgagaacatc aacgctatta ttgcccccgc cctgaagggc 480
atggaccccg tcaagcaggc ggagattgac cagaagatga aggacctgga cggcactgac 540
aacaagggca agctgggtgc caacgccatc ctggccgtct ccatggccgt gtgcaaggcc 600
ggtgccgctg agaagggcgt gcccctgtac aagcacattg cggacctggc cggcaacagc 660
aagctgatcc tgcccgtgcc ctcgttcaac atcatcaacg gcggcagcca cgccggcaac 720
gccctggcta tgcaggagtt catgatcctg cccgttggcg cctcgagctt ctctgaggcc 780
atgcgcatgg gctgcgaggt gtaccacgcc ctgaagggcc tgatcaaggc caagtacggc 840
caggacgcct gcaacgtggg tgatgagggt ggcttcgccc ccaacatcgg ctccaacgat 900
gagggcctga acttggtgaa cgaggccatc gagaaggccg gctacaccgg caaggtgaag 960
atcggcatgg acgtggcctc gtcggagttc tacaccgagg acggcatgta cgacctggac 1020
ttcaagaacc agcccaacga tggctcgcag aagaagacca aggagcagat gctggagctg 1080
tacaacgagt tctgcaagaa gtacccggtc atctccatcg aggacccctt cgagcaggac 1140
gactgggagc cctgcgccaa gctgaccacc gagaacatct gccaggtggt cggcgacgac 1200
atcctggtga ccaaccccgt gcgcgtgaag aaggccatcg acgccaaggc cgtcaacgct 1260
ctgctgctca aggtcaacca gatcggtacc attaccgagt ccattgaggc cgtgcgcatg 1320
gccaaggagg ccggctgggg tgtcatgacc agccaccgct cgggtgagac tgaggactct 1380
ttcatcgccg acctggcggt gggcctggcc tccggccaga tcaagaccgg cgccccctgc 1440
cgctcggagc gcaatgccaa gtacaaccag ctgctgcgca tcgaggagga gctgggcgag 1500
aacgctgtgt acgctggcga gagctggcgc cacatcggct ggggctgctg ccccggctgc 1560
tgctaatcta gataaatgga ggcgctcgtt gatctgagcc ttgccccctg acgaacggcg 1620
gtggatggaa gatactgctc tcaagtgctg aagcggtagc ttagctcccc gtttcgtgct 1680
gatcagtctt tttcaacacg taaaaagcgg aggagttttg caattttgtt ggttgtaacg 1740
atcctccgtt gattttggcc tctttctcca tgggcgggct gggcgtattt gaagcggttc 1800
tctcttctgc cgtta 1815

<210> SEQ ID NO 10
<211> LENGTH: 2349
<212> TYPE: DNA
<213> ORGANISM: Artificial Sequence
<220> FEATURE:
<223> OTHER INFORMATION: Synthetic Construct- Sequence No. 10,
Example 10: designer Phosphoglycerate-Mutase DNA construct
(2349 bp)

<400> SEQUENCE: 10
agaaaatctg gcaccacacc tatatggtag ggtgcgagtg accccgcgcg acttggagct 60
cgatggcccc gggttgtttg gggcgtccgc ctctcgcgct attctgagct ggagaccgag 120
gcgcatgaaa atgcattcgc ttccatagga cgctgcattg tggcttgaag gttcaaggga 180
agggttcaaa cgaccccgcc gtacgaactt ttgtcggggg gcgctcccgg ccccgggctc 240
ttgtgcgcgc attagggctt cgggtcgcaa gcaagacgat acctcgagca tatggccgcc 300
gtcattgcca agtcctccgt ctccgcggcc gtggctcgcc cggcccgctc cagcgtgcgc 360
cccatggccg cgctgaagcc cgccgtcaag gctgccccccg tggctgcccc ggctcaggcc 420
aaccagatgg cgcacgacta caagctgaag gcccacccgg cgattcctgc gcccgagggc 480
ccgctgctgg tctgcattct ggacggcttc ggcgagaacg agtacaagga tgagttcaac 540
gccgtgcacg tggctaagac gcccactgtg gacgcgctgc gcgctgtgcc ccatcgcttc 600
cgttccatca aggcgcacgg aaaggctgtg ggcctgccca gcgatgccga catgggcaac 660
agcgaggtgg ggcacaacgc cctgggctcg ggccaggtgg tggaccaagg cgcgcgcctg 720
gtggacctgg cgctggagac cggccgtatg ttctcggacc ccggctggaa gctcatcagc 780
gaggccttcc cctcccacac cgtccacttc atcggcctgc tgtccgacgg cggcgtgcac 840
tcgcgcgccg atcagctgca cggctgcctg cgcggcgccg tggagcgcgg cgccaagcgc 900
gtgcgcgtgc acatcctgac tgacggccgc gacgtgccgg acggcagcag catccggttc 960
gtggaggagc tggaggcggt gctggcggag ctgcgcggca agggctgcga catcgccatc 1020

```
gcctcgggcg gcggccgcat gcaggtcacc atggaccgct acgaggcgga ctggagcatg   1080

gtgaagcgcg gctgggacgc gcacgtgctg ggcaaggcgc cccactactt caaggacgcc   1140

aagaccgcgg tcaccaccct gcgcggctcc gaggacgcgc cggtgtctga ccagtacgtg   1200

gccccctttg tgattgtgga cgaggcggac aagccggtgg gcaccattga ggacggcgac   1260

gcggtggtgc tgttcaactt ccgcgcggac cgcatggtgg agatcagcaa ggccttcgag   1320

tacgaggacg gcttcaccgc ctttgagcgc gagcgcttcc ccaagggcct gcgcttcgtg   1380

ggcatgatgc agtacgacgg cgacctgaag ctgcccgcca acttcctggt gccgccgccc   1440

ctgattgagc acgtgtcggg cgagtacctg tgcaagaacg ggctgagcac cttcgcctgc   1500

tccgagactc agaagttcgg gcacgtgacg ttcttctgga acggcaaccg ctccggctac   1560

ctggacgcca agcaggagca gtacctggag atcccgtcgg acaagatcga gttcaacaag   1620

gctccggaca tgaaggcgcg cgagatcacc gccgccggca ttgaggcgct caagagcggc   1680

aagtacaagg tggtgcgcat caactacgcc aacccggaca tggtcggcca caccggcgac   1740

atggctgcca ccgtccgcgc ctgcgagacc gtggacgggt gcgtgaagga gctgctggag   1800

gtggtggaca gcctgaacgg ccgctggatc gtcacgtccg accacggcaa cgccgacgac   1860

atggtgcagc gcgacaagaa gggcaagccc ctgctgggcg aggacggcaa gccgctgccc   1920

ctgaccagcc acacgctggc gcccgtgccg ttcttcatcg gcggcaaggg cctgccggac   1980

ggcgtggtgc tgcgcgacga cctgccggac gccgggctgg ccaacgtggc cgccaccacc   2040

ttcaacctgc tgggcttcga ggcgcccggc atctacaagc ccagcatggt caaggcgtaa   2100

tctagataaa tggaggcgct cgttgatctg agccttgccc cctgacgaac ggcggtggat   2160

ggaagatact gctctcaagt gctgaagcgg tagcttagct ccccgtttcg tgctgatcag   2220

tctttttcaa cacgtaaaaa gcggaggagt tttgcaattt tgttggttgt aacgatcctc   2280

cgttgatttt ggcctctttc tccatgggcg ggctgggcgt atttgaagcg gttctctctt   2340

ctgccgtta                                                           2349
```

<210> SEQ ID NO 11
<211> LENGTH: 1908
<212> TYPE: DNA
<213> ORGANISM: Artificial Sequence
<220> FEATURE:
<223> OTHER INFORMATION: Synthetic Construct- Sequence No. 11, Example 11: designer Phosphoglycerate-Kinase DNA construct (1908 bp)

<400> SEQUENCE: 11

```
agaaaatctg gcaccacacc tatatggtag ggtgcgagtg accccgcgcg acttggagct     60

cgatggcccc gggttgtttg gggcgtccgc ctctcgcgct attctgagct ggagaccgag    120

gcgcatgaaa atgcattcgc ttccatagga cgctgcattg tggcttgaag gttcaaggga    180

agggttcaaa cgaccccgcc gtacgaactt ttgtcggggg gcgctcccgg ccccgggctc    240

ttgtgcgcgc attagggctt cgggtcgcaa gcaagacgat acatggccct ctctatgaag    300

atgcgcgcca acgcgcgcgt gtccggtcgc cgcgtcgccg ctgtggcccc ccgcgtggtg    360

cccttctcgt cggcctccag ctccgtgctg cgctctggct tcgcgctgag gtgtctgtgg    420

acatccgccg cgtgggccgc tctcgcatcc gtcgtcgagg cggtgaagaa gtcggttggc    480

gacctgcaca aggctgacct ggagggcaag cgcgtgttcg tccgcgcgga cctgaacgtg    540

cctcttgaca aggccaccct ggccatcacc gacgacaccc gcattcgcgc ggccgtcccc    600
```

accctgaagt acctgctgga caacggtgct aaggtcctgc tgacctcgca cctgggtcgc 660
ccgaagggcg gtcccgagga caagtaccgc ctgacccccg tggtggcccg cctgtcggag 720
ctgctgggca agcccgtgac caaggtcgat gactgcatcg gccccgaggt ggagaaggcg 780
gtgggcgcca tgaagaacgg cgagctgctg ctgctggaga actgccgctt ctacaaggag 840
gaggagaaga acgagcccga gttcgccaag aagctggccg ccaacgccga cctgtacgtg 900
aacgacgcgt tcggcactgc ccaccgcgcc cacgcctcca ccgagggtgt gaccaagttc 960
ctgaagccct ccgtggccgg cttcctgctg cagaaggagc tggactacct tgatggcgcc 1020
gtgtccaacc ccaagcgccc cttcgtggcc attgtgggcg gctccaaggt gtcctccaag 1080
atcaccgtca ttgaggcgct gatggagaag tgcgacaaga tcatcatcgg cggtggcatg 1140
atcttcacct tctacaaggc ccgcgcgctg aaggtgggct cctcgctggt tgaggacgac 1200
aagatcgagc tggccaagaa gctggaggag atggccaagg ccaagggtgt gcagctgctg 1260
ctgcccaccg acgtggtggt ggccgacaag ttcgacgcca acgccaacac ccagaccgtg 1320
cccatcaccg ccatccccga tggctggatg ggtctggaca ttggcccgga ctccgtcaag 1380
accttcaacg acgccctggc cgacgccaag accgttgtgt ggaacggccc catgggtgtg 1440
ttcgagtttc cccaagttcg ccaacgcacc gtgtcgatcg ccaacaccct ggccggcctg 1500
acgcccaagg gctgcatcac catcattggt ggcggtgact ccgtggctgc cgtcgagcag 1560
gccggcgttg ccgagaagat gagccacatc tccaccggcg gcggtgcctc cctggagctg 1620
ctggagggca aggtcctgcc cggcgtggcc gccctggacg agaagtaaat ggaggcgctc 1680
gttgatctga gccttgcccc ctgacgaacg gcggtggatg gaagatactg ctctcaagtg 1740
ctgaagcggt agcttagctc cccgtttcgt gctgatcagt ctttttcaac acgtaaaaag 1800
cggaggagtt ttgcaatttt gttggttgta acgatcctcc gttgattttg gcctctttct 1860
ccatgggcgg gctgggcgta tttgaagcgg ttctctcttc tgccgtta 1908

<210> SEQ ID NO 12
<211> LENGTH: 1677
<212> TYPE: DNA
<213> ORGANISM: Artificial Sequence
<220> FEATURE:
<223> OTHER INFORMATION: Synthetic Construct- Sequence No. 12, Example 12: designer NAD-dependent Glyceraldehyde-3-Phosphate-Dehydrogenase DNA construct (1677 bp)

<400> SEQUENCE: 12
agaaaatctg gcaccacacc tatatggtag ggtgcgagtg accccgcgcg acttggagct 60
cgatggcccc gggttgtttg gggcgtccgc ctctcgcgct attctgagct ggagaccgag 120
gcgcatgaaa atgcattcgc ttccatagga cgctgcattg tggcttgaag gttcaaggga 180
agggttcaaa cgaccccgcc gtacgaactt ttgtcggggg gcgctcccgg ccccgggctc 240
ttgtgcgcgc attagggctt cgggtcgcaa gcaagacgat acatggccgc cgtcattgcc 300
aagtcctccg tctccgcggc cgtggctcgc ccggcccgct ccagcgtgcg ccccatggcc 360
gcgctgaagc ccgccgtcaa ggctgccccc gtggctgccc cggctcaggc caaccagatg 420
gctcccatca agatcggcat caatggtttt ggtcgtattg gccgcctcgt gtggcgtgcc 480
actcttaacc gtgacgatgt cgaggtcgtc gccatcaatg atccattcat tgatgtgcca 540
tacatggtct acatggccaa gtatgactcg gtccacggca acctgaccca cgacgttcag 600
caaggcgacg gcaagctgat ggtcaatggc aagtcaatca ccatcttcgg caagatggat 660
gccaaggaga tcccatggaa ggaggccggc gcgaccttcg tcgttgagtc gactggtgtg 720

```
ttcaccaccc tggagggcgc cagctctcac ctggtcggcg gtgctgagac cgtcgtcatc    780

tccgccccat caaacgatgc ccccatgttc gtcatgggtg tcaacgagga gggctacaag    840

ccagacatga aagtggtgtc caacgcgtct tgcaccacca actgcctggg ccccctggcc    900

aaggtcatcc accttaagtt cggcatcctg gagggcctga tgaccaccgt ccacgcgacc    960

accgccaccc agaagaccgt cgacgggccg tccaagaagg actggcgcgg cgggcgcggc   1020

atcctggaca acatcatccc ctcggcgact ggtgccgcca aggccgtcgg caaggtgctg   1080

cctgccctga acggcaagct caccggcatg gccttccgcg tgcccacccc cgatgtctcg   1140

gtcgtcgatc tgaccgtgcg cctggagaag ggtgcgtcgt acgacgccat caaggccgag   1200

atcaagcgcg cgagcgagaa cgagctcaag ggcatcctgg cctacaccga ggatgccgtg   1260

gtctccaccg acttcatcgg caacaagcac agctccatct tcgacgccga ggccggcatc   1320

gccctcaacg acaactttgt caagctggtc tcctggtacg acaacgagtg gggctactcc   1380

aaccgtgtcg tcgacctgat cgcgcacatg gccaaggtca aggccgccag ccactaaatg   1440

gaggcgctcg ttgatctgag ccttgccccc tgacgaacgg cggtggatgg aagatactgc   1500

tctcaagtgc tgaagcggta gcttagctcc ccgtttcgtg ctgatcagtc tttttcaaca   1560

cgtaaaaagc ggaggagttt tgcaattttg ttggttgtaa cgatcctccg ttgattttgg   1620

cctctttctc catgggcggg ctgggcgtat ttgaagcggt tctctcttct gccgtta      1677
```

<210> SEQ ID NO 13
<211> LENGTH: 2351
<212> TYPE: DNA
<213> ORGANISM: Artificial Sequence
<220> FEATURE:
<223> OTHER INFORMATION: Synthetic Construct- Sequence No. 13, Example 13: designer HydA1-promoter-linked Phosphoglycerate-Mutase DNA construct (2351 bp)

<400> SEQUENCE: 13

```
agaaaatctg gcaccacacc gagctgtcat gcgttgttcc gttatgtgtc gtcaaacgcc     60

ttcgagcgct gcccggaaca atgcgtacta gtataggagc catgaggcaa gtgaacagaa    120

gcgggctgac tggtcaaggc gcacgatagg gctgacgagc gtgctgacgg ggtgtaccgc    180

cgagtgtccg ctgcattccc gccggattgg gaaatcgcga tggtcgcgca taggcaagct    240

cgcaaatgct gtcagcttat cttacatgaa cacacaaaca ctctcgcagg cactagcctc    300

aaatggccgc cgtcattgcc aagtcctccg tctccgcggc cgtggctcgc ccggcccgct    360

ccagcgtgcg ccccatggcc gcgctgaagc ccgccgtcaa ggctgccccc gtggctgccc    420

cggctcaggc caaccagatg gcgcacgact acaagctgaa ggcccacccg gcgattcctg    480

cgcccgaggg cccgctgctg gtctgcattc tggacggctt cggcgagaac gagtacaagg    540

atgagttcaa cgccgtgcac gtggctaaga cgcccactgt ggacgcgctg cgcgctgtgc    600

cccatcgctt ccgttccatc aaggcgcacg gaaaggctgt gggcctgccc agcgatgccg    660

acatgggcaa cagcgaggtg gggcacaacg ccctgggctc gggccaggtg gtggaccaag    720

gcgcgcgcct ggtggacctg gcgctggaga ccggccgtat gttctcggac cccggctgga    780

agctcatcag cgaggccttc ccctcccaca ccgtccactt catcggcctg ctgtccgacg    840

gcggcgtgca ctcgcgcgcc gatcagctgc acggctgcct gcgcggcgcc gtggagcgcg    900

gcgccaagcg cgtgcgcgtg cacatcctga ctgacggccg cgacgtgccg gacggcagca    960

gcatccggtt cgtggaggag ctggaggcgg tgctggcgga gctgcgcggc aagggctgcg   1020
```

```
acatcgccat cgcctcgggc ggcggccgca tgcaggtcac catggaccgc tacgaggcgg   1080

actggagcat ggtgaagcgc ggctgggacg cgcacgtgct gggcaaggcg ccccactact   1140

tcaaggacgc caagaccgcg gtcaccaccc tgcgcggctc cgaggacgcg ccggtgtctg   1200

accagtacgt ggcccccttt gtgattgtgg acgaggcgga caagccggtg ggcaccattg   1260

aggacggcga cgcggtggtg ctgttcaact tccgcgcgga ccgcatggtg gagatcagca   1320

aggccttcga gtacgaggac ggcttcaccg cctttgagcg cgagcgcttc cccaagggcc   1380

tgcgcttcgt gggcatgatg cagtacgacg gcgacctgaa gctgcccgcc aacttcctgg   1440

tgccgccgcc cctgattgag cacgtgtcgg gcgagtacct gtgcaagaac gggctgagca   1500

ccttcgcctg ctccgagact cagaagttcg ggcacgtgac gttcttctgg aacggcaacc   1560

gctccggcta cctggacgcc aagcaggagc agtacctgga gatcccgtcg gacaagatcg   1620

agttcaacaa ggctccggac atgaaggcgc gcgagatcac cgccgccggc attgaggcgc   1680

tcaagagcgg caagtacaag gtggtgcgca tcaactacgc caacccggac atggtcggcc   1740

acaccggcga catggctgcc accgtccgcg cctgcgagac cgtggacggg tgcgtgaagg   1800

agctgctgga ggtggtggac agcctgaacg gccgctggat cgtcacgtcc gaccacggca   1860

acgccgacga catggtgcag cgcgacaaga agggcaagcc cctgctgggc gaggacggca   1920

agccgctgcc cctgaccagc cacacgctgg cgcccgtgcc gttcttcatc ggcggcaagg   1980

gcctgccgga cggcgtggtg ctgcgcgacg acctgccgga cgccgggctg gccaacgtgg   2040

ccgccaccac cttcaacctg ctgggcttcg aggcgcccgg catctacaag cccagcatgg   2100

tcaaggcgta aatggaggcg ctcgttgatc tgagccttgc cccctgacga acggcggtgg   2160

atggaagata ctgctctcaa gtgctgaagc ggtagcttag ctccccgttt cgtgctgatc   2220

agtctttttc aacacgtaaa aagcggagga gttttgcaat tttgttggtt gtaacgatcc   2280

tccgttgatt ttggcctctt tctccatggg cgggctgggc gtatttgaag cggttctctc   2340

ttctgccgtt a                                                        2351
```

```
<210> SEQ ID NO 14
<211> LENGTH: 1796
<212> TYPE: DNA
<213> ORGANISM: Artificial Sequence
<220> FEATURE:
<223> OTHER INFORMATION: Synthetic Construct- Sequence No. 14,
      Example 14: designer HydA1-promoter-linked Enolase DNA construct
      (1796 bp)

<400> SEQUENCE: 14
```

```
agaaaatctg gcaccacacc gagctgtcat gcgttgttcc gttatgtgtc gtcaaacgcc     60

ttcgagcgct gcccggaaca atgcgtacta gtataggagc catgaggcaa gtgaacagaa    120

gcgggctgac tggtcaaggc gcacgatagg gctgacgagc gtgctgacgg ggtgtaccgc    180

cgagtgtccg ctgcattccc gccggattgg gaaatcgcga tggtcgcgca taggcaagct    240

cgcaaatgct gtcagcttat cttacatgaa cacacaaaca ctctcgcagg cactagcctc    300

aaatggccgc cgtcattgcc aagtcctccg tctccgcggc cgtggctcgc ccggcccgct    360

ccagcgtgcg ccccatggcc gcgctgaagc ccgccgtcaa ggctgccccc gtggctgccc    420

cggctcaggc caaccaggtg accaaggctg ttgagaacat caacgctatt attgcccccg    480

ccctgaaggg catggacccc gtcaagcagg cggagattga ccagaagatg aaggacctgg    540

acggcactga caacaagggc aagctgggtg ccaacgccat cctggccgtc tccatggccg    600

tgtgcaaggc cggtgccgct gagaagggcg tgcccctgta caagcacatt gcggacctgg    660
```

```
ccggcaacag caagctgatc ctgcccgtgc cctcgttcaa catcatcaac ggcggcagcc    720

acgccggcaa cgccctggct atgcaggagt tcatgatcct gcccgttggc gcctcgagct    780

tctctgaggc catgcgcatg ggctgcgagg tgtaccacgc cctgaagggc ctgatcaagg    840

ccaagtacgg ccaggacgcc tgcaacgtgg gtgatgaggg tggcttcgcc cccaacatcg    900

gctccaacga tgagggcctg aacttggtga acgaggccat cgagaaggcc ggctacaccg    960

gcaaggtgaa gatcggcatg gacgtggcct cgtcggagtt ctacaccgag gacggcatgt   1020

acgacctgga cttcaagaac cagcccaacg atggctcgca gaagaagacc aaggagcaga   1080

tgctggagct gtacaacgag ttctgcaaga agtacccggt catctccatc gaggacccct   1140

tcgagcagga cgactgggag ccctgcgcca agctgaccac cgagaacatc tgccaggtgg   1200

tcggcgacga catcctggtg accaaccccg tgcgcgtgaa gaaggccatc gacgccaagg   1260

ccgtcaacgc tctgctgctc aaggtcaacc agatcggtac cattaccgag tccattgagg   1320

ccgtgcgcat ggccaaggag gccggctggg gtgtcatgac cagccaccgc tcgggtgaga   1380

ctgaggactc tttcatcgcc gacctggcgg tgggcctggc ctccggccag atcaagaccg   1440

gcgcccctg ccgctcggag cgcaatgcca agtacaacca gctgctgcgc atcgaggagg   1500

agctgggcga gaacgctgtg tacgctggcg agagctggcg ccacatcggc tggtaaatgg   1560

aggcgctcgt tgatctgagc cttgccccct gacgaacggc ggtggatgga agatactgct   1620

ctcaagtgct gaagcggtag cttagctccc cgtttcgtgc tgatcagtct ttttcaacac   1680

gtaaaaagcg gaggagtttt gcaattttgt tggttgtaac gatcctccgt tgattttggc   1740

ctctttctcc atgggcgggc tgggcgtatt tgaagcggtt ctctcttctg ccgtta       1796
```

<210> SEQ ID NO 15
<211> LENGTH: 1832
<212> TYPE: DNA
<213> ORGANISM: Artificial Sequence
<220> FEATURE:
<223> OTHER INFORMATION: Synthetic Construct- Sequence No. 15, Example 15: designer HydA1-promoter-linked Pyruvate-Kinase DNA construct (1832 bp)

<400> SEQUENCE: 15

```
agaaaatctg gcaccacacc gagctgtcat gcgttgttcc gttatgtgtc gtcaaacgcc     60

ttcgagcgct gcccggaaca atgcgtacta gtataggagc catgaggcaa gtgaacagaa    120

gcgggctgac tggtcaaggc gcacgatagg gctgacgagc gtgctgacgg ggtgtaccgc    180

cgagtgtccg ctgcattccc gccggattgg gaaatcgcga tggtcgcgca taggcaagct    240

cgcaaatgct gtcagcttat cttacatgaa cacacaaaca ctctcgcagg cactagcctc    300

aaatggccgc cgtcattgcc aagtcctccg tctccgcggc cgtggctcgc ccggcccgct    360

ccagcgtgcg ccccatggcc gcgctgaagc ccgccgtcaa ggctgccccc gtggctgccc    420

cggctcaggc caaccagatg tgcgagatgc tggacgcggg cgtggtgggc tgccgcgtgg    480

acctgacgtg gggcccgctg gagttccacc gcaagtcgct tgccaatctg cagcaggcca    540

tgcgcaagag ccgccgcctg tgttgcacca tggtggacac gctgggccgc gagctcatga    600

tccgccgcca gagaggggca ggctggaccc agcgccagag gggtggggtg atcatcacca    660

cgcgcacgga cgtggacgcc agcagcaacg tgctgcccat cacttacagc aagttcacgg    720

agatggcggt caagggcgac accatctaca tcggccgcta cctggtgtgc ggcgcagaca    780

gcgcctcgct gtacctggag gtcatggacg tgcagggcga cgacgtgtac tgcatcgcca    840
```

-continued

```
agaacgacgc ggtgctggac ggcctgctga cggtgttcca cgcggagcgc tccgtggagg    900

ggctggccaa cgtgcagaac gacctgccgc tgctgtccga ctacgacaag gagtgcctgc    960

acatcctggc gcaggacttc gagcgcgcgc cctacatctc caagctggag tccatcgcct   1020

cctccgccgt gcgcgccgcc gaccgcgtgg gcgccagcct gattgtggtg tacacgcaca   1080

ccggcaagac ggcgcagctg gtggccaagt accggccgcc catgcccatc ctgacgctgg   1140

tggtgccgca cctggtgtct gaccagctca agtggaagct ggagggcagg tccagcgcgc   1200

gccagtgcct catcagtcgc gcgctgctgc cggtgctggc cgcgccctcg cccagcggcg   1260

accagctgct gcaggaggcg gtggccatgg cgggccgcgt caagctggtc aagccgcacg   1320

accacgtggt gtgcgtgcag cgcatccacg acgacttctg cgtcaagatc atctccgtgg   1380

acgacatggg cgcgggcatc aagcgcgacg acacggtcat gtcgcacagc gtgtttggca   1440

gcagccccat ggccgtgcag ggctcgtccg gctacgactc gccgcgcgtg cacaacaacc   1500

ccatcggcaa caagttcggc cccatgccgc ccgccatcat caccaccggc aatagcttca   1560

ccctgggcgg catgggcgtg ggcgtgctgt aaatggaggc gctcgttgat ctgagccttg   1620

ccccctgacg aacggcggtg gatggaagat actgctctca agtgctgaag cggtagctta   1680

gctccccgtt tcgtgctgat cagtcttttt caacacgtaa aaagcggagg agttttgcaa   1740

ttttgttggt tgtaacgatc ctccgttgat tttggcctct ttctccatgg gcgggctggg   1800

cgtatttgaa gcggttctct cttctgccgt ta                                 1832
```

<210> SEQ ID NO 16
<211> LENGTH: 4376
<212> TYPE: DNA
<213> ORGANISM: Artificial Sequence
<220> FEATURE:
<223> OTHER INFORMATION: Synthetic Construct- Sequence No. 16, Example 16: designer HydA1-promoter-linked Pyruvate-Ferredoxin-Oxidoreductase DNA construct (4376 bp)

<400> SEQUENCE: 16

```
agaaaatctg gcaccacacc gagctgtcat gcgttgttcc gttatgtgtc gtcaaacgcc     60

ttcgagcgct gcccggaaca atgcgtacta gtataggagc catgaggcaa gtgaacagaa    120

gcgggctgac tggtcaaggc gcacgatagg gctgacgagc gtgctgacgg ggtgtaccgc    180

cgagtgtccg ctgcattccc gccggattgg gaaatcgcga tggtcgcgca taggcaagct    240

cgcaaatgct gtcagcttat cttacatgaa cacacaaaca ctctcgcagg cactagcctc    300

aaatggccgc cgtcattgcc aagtcctccg tctccgcggc cgtggctcgc ccggcccgct    360

ccagcgtgcg ccccatggcc gcgctgaagc ccgccgtcaa ggctgccccc gtggctgccc    420

cggctcaggc caaccagatg ggaaagaaaa tgatgacgac tgatggcaat acagcgacag    480

cgcacgtggc gtatgccatg agcgaagtcg ccgccatcta ccccatcacc ccttcctcga    540

ccatgggcga ggaggctgac gactgggcgg cgcaaggacg caagaacatc tttggccaga    600

ccctgaccat acgcgaaatg cagtccgagg ccggcgccgc cggcgcggtg cacggggccc    660

tggcggccgg cgccctgacc acgaccttca cggcgtcgca gggtctgctg ctgatgatcc    720

ccaacatgta caagatctcc ggcgaacttc tgcccggcgt gttccacgtc accgcccgcg    780

ccatcgccgc gcacgccctg tccatcttcg gtgaccacca ggatatctac gccgcgcgcc    840

agacaggctt cgccatgctc gcctccagct cggtgcagga ggcccacgac atggccctgg    900

tggcccactt ggcggccatc gagtccaacg tgccgttcat gcacttcttc gacggattcc    960

gcacctcgca cgaaatccag aagatcgagg tcctggacta cgcggacatg gcctcgctgg   1020
```

-continued

```
tgaaccagaa ggccctggcg gaattccgcg ccaagtccat gaaccccgag cacccccacg   1080
tgcgcggcac ggcccagaac cccgacatct acttccaggg tcgcgaggca gccaacccct   1140
actacctcaa ggtgcccggc atcgttgccg agtacatgca gaaggtcgcc tccctcacgg   1200
gccgcagcta caagctcttt gactacgtgg gtgctcccga cgccgagcgc gtcatcgtgt   1260
ccatgggctc ctcgtgcgag accatcgagg aggtcatcaa ccacctcgcg gccaagggcg   1320
aaaagatcgg cctgatcaag gtccgcctgt acaggccctt cgtaagcgag gccttcttcg   1380
ctgctctgcc cgcttcggcc aaggtcatca cggtcctcga ccgcaccaag gaacccggcg   1440
cgcccggcga tccgctctac ctcgacgtgt gctcggcctt cgtggagcgc ggcgaagcca   1500
tgcccaagat cctggccggc cgctacggcc tgggttccaa ggaattcagc ccggccatgg   1560
tcaagtccgt gtacgacaac atgtccggcg ctaagaagaa ccacttcacc gtgggcatcg   1620
aagacgacgt gaccggcact tcgctgccgg tggacaacgc cttcgccgac accacgccca   1680
agggcaccat ccagtgccag ttctggggcc tcggcgccga cggcactgtg ggcgccaaca   1740
agcaggccat caagatcatc ggcgacaaca cggacctgtt tgcccagggt tacttctcct   1800
acgactccaa gaaatcgggc ggcatcacca tctcgcacct gcgcttcggc gagaagccca   1860
tccagtccac ctacctggtc aacagggccg actatgtcgc ctgtcacaac ccggcctacg   1920
tgggcatata cgacatcctc gaaggcatca aggatggcgg aaccttcgtg ctcaactcgc   1980
cttggagcag cctcgaggac atggacaagc acctgccctc cggcatcaag cgcaccatcg   2040
cgaacaagaa gctcaagttc tacaacatcg acgcggtgaa aatcgccacc gatgtgggac   2100
tgggcggccg catcaacatg atcatgcaga cggccttctt caagctggcc ggagtgctgc   2160
ccttcgaaaa ggccgtggat ctgctcaaga agtccatcca caaggcctac ggcaaaaagg   2220
gcgagaagat cgtcaagatg aacaccgacg ccgtggacca ggccgtcacc tccctgcagg   2280
aattcaagta tccggattcc tggaaggacg ctcccgctga gaccaaggcc gagcccatga   2340
cgaacgagtt cttcaagaac gtcgtcaagc ccatcctgac ccagcagggc gacaagctgc   2400
cggtgagcgc cttcgaggcc gacggccgtt tccccctcgg caccagccag ttcgagaagc   2460
gcggcgtggc catcaacgtg ccgcagtggg tccccgagaa ctgcatccag tgcaaccagt   2520
gcgccttcgt ctgtccgcac agcgccatcc tgcccgtgct ggccaaggaa gaggagttgg   2580
tcggcgcgcc ggcgaacttc acggccctgg aagccaaggg caaggagctc aagggctaca   2640
agttccgcat ccagatcaac accctggact gcatgggctg cggcaactgc gccgacatct   2700
gtccgcccaa ggaaaaggct ctggtcatgc agcccctgga tacccagcgc gacgcgcagg   2760
tgcccaacct ggagtacgca gcgcgcatcc cggtcaaatc cgaggtgctg ccgcgcgact   2820
cgctcaaggg cagccagttc caggagcctc tcatggaatt ctcgggcgcc tgctcgggct   2880
gcggcgagac gccctacgtg cgcgtcatca cccagctctt cggcgagcgc atgttcattg   2940
ccaacgccac gggttgctcg tccatctggg gcgcgtcggc tccttccatg ccttacaaga   3000
ccaaccgcct cggacaaggc ccggcctggg gtaactccct gttcgaagac gcggccgaat   3060
acggcttcgg catgaacatg tccatgttcg cccgccgcac gcatttggcc gatcttgccg   3120
ccaaggccct ggagagcgat gcctccggcg atgtcaagga agccctgcag ggctggcttg   3180
ccggcaagaa cgatcccatc aagtccaagg aatacggcga caagctcaag aagctgctgg   3240
ctggtcagaa ggatggtctg ctcggacaga tcgccgccat gtccgacctg tacaccaaga   3300
agagcgtgtg gatcttcggt ggcgacggct gggcctacga catcggttac ggcggcctgg   3360
```

-continued

```
accatgtgct cgcctcgggc gaggacgtga acgtcttcgt catggatacc gaggtctact   3420
ccaacaccgg cggccagtcc tccaaggcaa cgcccacggg cgccgtggcc aagttcgcgg   3480
cggccggcaa gcgtaccggc aagaaggacc tggcgcgcat ggtcatgacc tacggctacg   3540
tctacgtggc tacggtctcc atgggttaca gcaagcagca gttcctcaag gtgctcaagg   3600
aagccgaaag cttccccggc ccctcgctgg tcatcgccta tgctacctgc atcaaccagg   3660
gtctgcgcaa gggcatgggc aagagccagg acgtcatgaa caccgcggtc aagtccggtt   3720
actggccgct gttccgctac gatccgcgct tggccgccca gggcaagaac cccttccagc   3780
tcgactccaa ggctcctgac ggttccgtcg aggagttcct gatggcccag aaccgcttcg   3840
ccgtcctcga tcggtccttc cccgaggacg ccaagagact gcgcgcccag gtcgctcacg   3900
aattggacgt gcgtttcaag gagttggagc acatggccgc cacgaacatc ttcgagtcct   3960
tcgcgccagc gggcggcaag gccgatggtt cggtggattt cggcgaaggt gcggagttct   4020
gcacgcgcga cgatactccc atgatggccc gacctgattc cggtgaggcc tgcgaccaga   4080
accgcgctgg cacgagcgaa cagcagggag acctcagcaa gcggacgaag aagtaaatgg   4140
aggcgctcgt tgatctgagc cttgccccct gacgaacggc ggtggatgga agatactgct   4200
ctcaagtgct gaagcggtag cttagctccc cgtttcgtgc tgatcagtct ttttcaacac   4260
gtaaaaagcg gaggagtttt gcaattttgt tggttgtaac gatcctccgt tgattttggc   4320
ctctttctcc atgggcgggc tgggcgtatt tgaagcggtt ctctcttctg ccgtta       4376
```

<210> SEQ ID NO 17
<211> LENGTH: 6092
<212> TYPE: DNA
<213> ORGANISM: Artificial Sequence
<220> FEATURE:
<223> OTHER INFORMATION: Synthetic Construct- Sequence No. 17, Example 17: designer HydA1-promoter-linked Pyruvate-NADP+-Oxidoreductase DNA construct (6092 bp)

<400> SEQUENCE: 17

```
agaaaatctg gcaccacacc gagctgtcat gcgttgttcc gttatgtgtc gtcaaacgcc     60
ttcgagcgct gcccggaaca atgcgtacta gtataggagc catgaggcaa gtgaacagaa    120
gcgggctgac tggtcaaggc gcacgatagg gctgacgagc gtgctgacgg ggtgtaccgc    180
cgagtgtccg ctgcattccc gccggattgg gaaatcgcga tggtcgcgca taggcaagct    240
cgcaaatgct gtcagcttat cttacatgaa cacacaaaca ctctcgcagg cactagcctc    300
aaatggccgc cgtcattgcc aagtcctccg tctccgcggc cgtggctcgc ccggcccgct    360
ccagcgtgcg ccccatggcc gcgctgaagc ccgccgtcaa ggctgccccc gtggctgccc    420
cggctcaggc caaccagatg aagcagtctg tccgcccaat tatttccaat gtactgcgca    480
aggaggttgc tctgtactca acaatcattg gacaagacaa ggggaaggaa ccaactggtc    540
gaacatacac cagtggccca aaaccggcat ctcacattga agttccccat catgtgactg    600
tgcctgccac tgaccgcacc ccgaatcccg atgctcaatt ctttcagtct gtagatgggt    660
cacaagccac cagtcacgtt gcgtacgctc tgtctgacac agcgttcatt tacccaatta    720
cacccagttc tgtgatgggc gagctggctg atgtttggat ggctcaaggg aggaagaacg    780
cctttggtca ggttgtggat gtccgtgaga tgcaatctga ggctggagcc gcaggcgccc    840
tgcatggggc actggctgct ggagctattg ctacaacctt cactgcctct caagggttgt    900
tgttgatgat tcccaacatg tataagattg caggtgagct gatgccctct gtcatccacg    960
ttgcagcccg agagcttgca ggccacgctc tgtccatttt tggaggacac gctgatgtca   1020
```

-continued

```
tggctgtccg ccaaacagga tggggctatgc tgtgctccca cacagtgcag cagtctcacg   1080
acatggctct catctcccac gtggccaccc tcaagtccag catccccttc gttcacttct   1140
ttgatggttt ccgcacaagc cacgaagtga acaaaatcaa aatgctgcct tatgcagaac   1200
tgaagaaact ggtgcctcct ggcaccatgg aacagcactg ggctcgttcg ctgaacccca   1260
tgcaccccac catccgagga acaaaccagt ctgcagacat ctacttccag aatatggaaa   1320
gtgcaaacca gtactacact gatctggccg aggtcgttca ggagacaatg gacgaagttg   1380
caccatacat cggtcgccac tacaagatct ttgagtatgt tggtgcacca gatgcagaag   1440
aagtgacagt gctcatgggt tctggtgcaa ccacagtcaa cgaggcagtg gaccttcttg   1500
tgaagcgtgg aaagaaggtt ggtgcagtct tggtgcacct ctaccgacca tggtcaacaa   1560
aggcatttga aaaggtcctg cccaagacag tgaagcgcat tgctgctctg gatcgctgca   1620
aggaggtgac tgcactgggt gagcctctgt atctggatgt gtcggcaact ctgaatttgt   1680
tcccggaacg ccagaatgtg aaagtcattg gaggacgtta cggattgggc tcaaaggatt   1740
tcatcccgga gcatgccctg gcaatttacg ccaacttggc cagcgagaac cccattcaaa   1800
gattcactgt gggtatcaca gatgatgtca ctggcacatc cgttcctttc gtcaacgagc   1860
gtgttgacac gttgcccgag ggcacccgcc agtgtgtctt ctggggaatt ggttcagatg   1920
gaacagtggg agccaatcgc tctgccgtga gaatcattgg agacaacagc gatttgatgg   1980
ttcaggccta cttccaattt gatgctttca agtcaggtgg tgtcacttcc tcgcatctcc   2040
gttttggacc aaagcccatc acagcgcaat accttgttac caatgctgac tacatcgcgt   2100
gccacttcca ggagtatgtc aagcgctttg acatgcttga tgccatccgt gagggggggca   2160
cctttgttct caattctcgg tggaccacgg aggacatgga gaaggagatt ccggctgact   2220
tccggcgcaa gctggcacag aagaaggtcc gcttctacaa tgtggatgct cgaaagatct   2280
gtgacagttt tggtcttggg aagcgcatca atatgctgat gcaggcttgt ttcttcaagc   2340
tgtctggggt gctcccactg gccgaagctc agcggctgct gaacgagtcc attgtgcatg   2400
agtatggaaa gaagggtggc aaggtggtgg agatgaacca agcagtggtg aatgctgtct   2460
ttgctggtga cctgccccag gaagttcaag tccctgccgc ctgggcaaac gcagttgata   2520
catccacccg taccccccacc gggattgagt ttgttgacaa gatcatgcgc ccgctgatgg   2580
atttcaaggg tgaccagctc ccagtcagtg tgatgactcc tggtggaacc ttccctgtcg   2640
ggacaacaca gtatgccaag cgtgcaattg ctgctttcat tccccagtgg attcctgcca   2700
actgcacaca gtgcaactat tgttcgtatg tttgccccca cgccaccatc cgacctttcg   2760
tgctgacaga ccaggaggtg cagctggccc cggagagctt tgtgacacgc aaggcgaagg   2820
gtgattacca ggggatgaat ttccgcatcc aagttgctcc tgaggattgc actggctgcc   2880
aggtgtgcgt ggagacgtgc cccgatgatg ccctggagat gaccgacgct ttcaccgcca   2940
cccctgtgca acgcaccaac tgggagttcg ccatcaaggt gcccaaccgc ggcaccatga   3000
cggaccgcta ctccctgaag ggcagccagt tccagcagcc cctcctggag ttctccgggg   3060
cctgcgaggg ctgcggcgag accccatatg tcaagctgct cacccagctc ttcggcgagc   3120
ggacggtcat cgccaacgcc accggctgca gttccatctg ggtggcact gccggcctgg   3180
cgccgtacac caccaacgcc aagggccagg gcccggcctg ggcaacagc ctgttcgagg   3240
acaacgccga gttcggcttt ggcattgcag tggccaacgc ccagaagagg tcccgcgtga   3300
gggactgcat cctgcaggca gtggagaaga aggtcgccga tgagggtttg accacattgt   3360
```

-continued

```
tggcgcaatg gctgcaggat tggaacacag gagacaagac cttgaagtac caagaccaga   3420
tcattgcagg gctggcacag cagcgcagca aggatcccct tctggagcag atctatggca   3480
tgaaggacat gctgcctaac atcagccagt ggatcattgg tggtgatggc tgggccaacg   3540
acattggttt cggtgggctg gaccacgtgc tggcctctgg gcagaacctc aacgtcctgg   3600
tgctggacac cgagatgtac agcaacaccg gtgggcaggc ctccaagtcc acccacatgg   3660
cctctgtggc caagtttgcc ctgggaggga agcgcaccaa caagaagaac ttgacggaga   3720
tggcaatgag ctatggcaac gtctatgtgg ccaccgtctc ccatggcaac atggcccagt   3780
gcgtcaaggc gtttgtggag gctgagtctt atgatggacc ttcgctcatt gttggctatg   3840
cgccatgcat cgagcatggt ctgcgtgctg gtatggcaag gatggttcaa gagtctgagg   3900
ctgccatcgc cacgggatac tggcccctgt accgctttga cccccgcctg gcgaccgagg   3960
gcaagaaccc cttccagctg gactccaagc gcatcaaggg caacctgcag gagtacctgg   4020
accgccagaa ccggtatgtc aacctgaaga agaacaaccc gaagggtgcg gatctgctga   4080
agtctcagat ggccgacaac atcaccgccc ggttcaaccg ctaccgacgc atgttggagg   4140
gccccaatac aaaagccgcc gcccccagcg gcaaccatgt gaccatcctg tacggctccg   4200
aaactggcaa cagtgagggt ctggcaaagg agctggccac cgacttcgag cgccgggagt   4260
actccgtcgc agtgcaggct ttggatgaca tcgacgttgc tgacttggag aacatgggct   4320
tcgtggtcat tgcggtgtcc acctgtgggc agggacagtt cccccgcaac agccagctgt   4380
tctggcggga gctgcagcgg gacaagcctg agggctggct gaagaacttg aagtacactg   4440
tcttcgggct gggcgacagc acatactact tctactgcca caccgccaag cagatcgacg   4500
ctcgcctggc cgccttgggc gctcagcggg tggtgcccat tggcttcggc gacgatgggg   4560
atgaggacat gttccacacc ggcttcaaca actggatccc cagtgtgtgg aatgagctca   4620
agaccaagac tccggaggaa gcgctgttca ccccgagcat cgccgtgcag ctcacccccca   4680
acgccacccc gcaggatttc catttcgcca agtccacccc agtgctgtcc atcaccggtg   4740
ccgaacgcat cacgccggca gaccacaccc gcaacttcgt cactatccga tggaagaccg   4800
atttgtcgta ccaggtgggt gactctcttg gtgtcttccc tgagaacacc cggtcagtgg   4860
tggaggagtt cctgcagtat tacggcttga accccaagga cgtcatcacc atcgaaaaca   4920
agggcagccg ggagttgccc cactgcatgg ctgttgggga tctcttcacg aaggtgttgg   4980
acatcttggg caaacccaac aaccggttct acaagaccct ttcttacttt gcagtggaca   5040
aggccgagaa ggagcgcttg ttgaagatcg ccgagatggg gccggagtac agcaacatcc   5100
tgtctgagac gtaccactac gcggacatct tccacatgtt cccgtccgcc cggcccacgc   5160
tgcagtacct catcgagatg atccccaaca tcaagccccg gtactactcc atctcctccg   5220
cccccatcca cacccctggc gaggtccaca gcctggtgct catcgacacc tggatcacgc   5280
tgtccggcaa gcaccgcacg gggctgacct gcaccatgct ggagcacctg caggcgggcc   5340
aggtggtgga tggctgcatc caccccacgg cgatggagtt ccccgaccac gagaagccgg   5400
tggtgatgtg cgccatgggc agtggcctgg caccgttcgt tgctttcctg cgcgacggct   5460
ccacgctgcg gaagcagggc aagaagaccg ggaacatggc attgtacttc ggcaacaggt   5520
atgagaagac ggagttcctg atgaaggagg agctgaaggg tcacatcaac gatggtttgc   5580
tgacacttcg atgcgctttc agccgagatg accccaagaa gaaggtgtat gtgcaggacc   5640
ttatcaagat ggacgaaaag atgatgtacg attacctcgt ggtgcagaag ggttctatgt   5700
attgctgtgg atcccgcagt ttcatcaagc ctgtccagga gtcattgaaa cattgcttca   5760
```

tgaaagctgg tgggctgact gcagagcaag ctgagaacga ggtcatcgat atgttcacga 5820
ccgggcggta caatatcgag gcatggtaat aaatggaggc gctcgttgat ctgagccttg 5880
ccccctgacg aacggcggtg gatggaagat actgctctca agtgctgaag cggtagctta 5940
gctccccgtt tcgtgctgat cagtcttttt caacacgtaa aaagcggagg agttttgcaa 6000
ttttgttggt tgtaacgatc ctccgttgat tttggcctct ttctccatgg gcgggctggg 6060
cgtatttgaa gcggttctct cttctgccgt ta 6092

<210> SEQ ID NO 18
<211> LENGTH: 1856
<212> TYPE: DNA
<213> ORGANISM: Artificial Sequence
<220> FEATURE:
<223> OTHER INFORMATION: Synthetic Construct- Sequence No. 18,
Example 18: designer HydA1-promoter-linked Thiolase DNA construct
(1856 bp)

<400> SEQUENCE: 18
agaaaatctg gcaccacacc gagctgtcat gcgttgttcc gttatgtgtc gtcaaacgcc 60
ttcgagcgct gcccggaaca atgcgtacta gtataggagc catgaggcaa gtgaacagaa 120
gcgggctgac tggtcaaggc gcacgatagg gctgacgagc gtgctgacgg ggtgtaccgc 180
cgagtgtccg ctgcattccc gccggattgg gaaatcgcga tggtcgcgca taggcaagct 240
cgcaaatgct gtcagcttat cttacatgaa cacacaaaca ctctcgcagg cactagcctc 300
aaatggccgc cgtcattgcc aagtcctccg tctccgcggc cgtggctcgc ccggcccgct 360
ccagcgtgcg ccccatggcc gcgctgaagc ccgccgtcaa ggctgccccc gtggctgccc 420
cggctcaggc caaccagatg aaagaagtag ttattgcaag tggtgtaagg actgctgtcg 480
ggaaatttgg tggcacgctt ctaaatgtac ctgcagtaga tttaggtgct gtgaataata 540
aaagaagcat aaaaagagcc aatgtgaaac ctgaagatgt tagtgaagtg ataatgggaa 600
atgtattgca ggcaggtctt gggcagaacc ccgcaagaca agctgaaata aaagcgggca 660
taccagtaga agttccggct atgactgtaa acatggtatg tggatcaggt cttagagctg 720
tgacacttgc tgctcaggca gttatgcttg gtgatgctga cattgttgta gccggtggaa 780
tggaaaatat gtcaagagca ccatatatat taaatgatgc tcgctttggg tacaggatga 840
acaatggcca gcttgtagat gaaatggtat atgatggttt aacagatgtt tttaaccaat 900
atcacatggg aatcactgcc gaaaatcttg ctgaaaaata cggcatatca agagaagagc 960
aggatgaatt tgcatataga agccaaaaat tagcgtcaga agcgatatca tcaggaagat 1020
ttgaggatga gatagttcct gtgattgtgc cgcagaaaaa aggtgaaccg atagaattta 1080
aagttgatga acatgtgaga cctaatacga caattgaagc acttgcaaaa ttaaaaccag 1140
cattccaaaa agatggaact gtaactgctg gaaatgcatc aggaattaac gatgcagctg 1200
cagcagtagt tgtgatgtca aaagaaaagg catgtgaact tggaataaag accattgcaa 1260
cgattaaatc atttggttat gcaggtgttg accccagcat cacgggaatt ggtccagtat 1320
atgctacgag aaaggcatta gaaaaagcta atctaactgt agatgattta gatttaattg 1380
aagcaaatga agcatttgca gcacaatcac tggctgttgc aaaagaatta aaatttaata 1440
tggacagagt gaatgtaaat ggtggcgcaa ttgcgatagg tcatccaatc ggcgccagcg 1500
gatgtagaat tctagtgacg cttttatatg agatgcagaa gaggaattcg catactggac 1560
ttgcaacatt gtgcatcggc ggaggaatgg gaatagcaat ggttgtcgaa agataaatgg 1620
aggcgctcgt tgatctgagc cttgcccct gacgaacggc ggtggatgga agatactgct 1680
ctcaagtgct gaagcggtag cttagctccc cgtttcgtgc tgatcagtct ttttcaacac 1740
gtaaaaagcg gaggagtttt gcaattttgt tggttgtaac gatcctccgt tgattttggc 1800
ctctttctcc atgggcgggc tgggcgtatt tgaagcggtt ctctcttctg ccgtta 1856

<210> SEQ ID NO 19
<211> LENGTH: 1550
<212> TYPE: DNA
<213> ORGANISM: Artificial Sequence
<220> FEATURE:
<223> OTHER INFORMATION: Synthetic Construct- Sequence No. 19, Example 19: designer HydA1-promoter-linked 3-Hydroxybutyryl-CoA-Dehydrogenase DNA construct (1550 bp)

<400> SEQUENCE: 19
agaaaatctg gcaccacacc gagctgtcat gcgttgttcc gttatgtgtc gtcaaacgcc 60
ttcgagcgct gcccggaaca atgcgtacta gtataggagc catgaggcaa gtgaacagaa 120
gcgggctgac tggtcaaggc gcacgatagg gctgacgagc gtgctgacgg ggtgtaccgc 180
cgagtgtccg ctgcattccc gccggattgg gaaatcgcga tggtcgcgca taggcaagct 240
cgcaaatgct gtcagcttat cttacatgaa cacacaaaca ctctcgcagg cactagcctc 300
aaatggccgc cgtcattgcc aagtcctccg tctccgcggc cgtggctcgc ccggcccgct 360
ccagcgtgcg ccccatggcc gcgctgaagc ccgccgtcaa ggctgccccc gtggctgccc 420
cggctcaggc caaccagatg caaaagattt gtgtaatagg tgctggaaca atgggctcag 480
gcatcgctca agtatttgca caaaatggct ttgaagtaat tttacgcgat attgatatga 540
agttcgtaga aaaaggattt ggcacaattg aaaaaattta caaagaaatg ttgacaaagg 600
gaaaattaca gcagatgaga aaacgaattt taagcagaat cagaggtaca acaaatttgg 660
aagacgcaaa agaagcagat tttgtagttg aagcggctat agaaaatatg gatctcaaga 720
aacaaatatt caaagagcta gatgaaatat gcaaaatgga aacaatcctt gcgtcaaata 780
catcatcact atccataaca gaaatagcaa gtgcgacaaa aagacctgag aaagtcatag 840
gaatgcattt cttcaaccca gttccagtaa tgaaacttgt tgaagtcata aaaggattaa 900
agacatcaga gcaaacattt aatgtcgtca gagaattggc tttaaaagta gacaaaacac 960
ctatagaggt caaagaagca cctggatttg ttgtaaatag gattttaatc ccaatgatta 1020
atgaagcaat tggaatactt gcagtggtgt tggcaactga caagagcata gatgaagcta 1080
tgaaacttgg tgcaaatcat ccaataggac ctttggcatt gtctagtttg ataggcaatg 1140
acgtcgttct tgctataatg aatgtgcttt atgaagagta cggcgattcg aaatacagac 1200
cacatccact tctaaaaaaa gtggtaagag gcggattgct gggtagaaaa actggcaaag 1260
gtttctttga atacaaaatt aatcttttaa ggaggagaat atcatgataa atggaggcgc 1320
tcgttgatct gagccttgcc ccctgacgaa cggcggtgga tggaagatac tgctctcaag 1380
tgctgaagcg gtagcttagc tccccgtttc gtgctgatca gtctttttca acacgtaaaa 1440
agcggaggag ttttgcaatt ttgttggttg taacgatcct ccgttgattt tggcctcttt 1500
ctccatgggc gggctgggcg tatttgaagc ggttctctct tctgccgtta 1550

<210> SEQ ID NO 20
<211> LENGTH: 1457
<212> TYPE: DNA
<213> ORGANISM: Artificial Sequence
<220> FEATURE:
<223> OTHER INFORMATION: Synthetic Construct- Sequence No. 20, Example 20: designer HydA1-promoter-linked Crotonase DNA construct (1457 bp)

<400> SEQUENCE: 20

```
agaaaatctg gcaccacacc gagctgtcat gcgttgttcc gttatgtgtc gtcaaacgcc      60
ttcgagcgct gcccggaaca atgcgtacta gtataggagc catgaggcaa gtgaacagaa     120
gcgggctgac tggtcaaggc gcacgatagg gctgacgagc gtgctgacgg ggtgtaccgc     180
cgagtgtccg ctgcattccc gccggattgg gaaatcgcga tggtcgcgca taggcaagct     240
cgcaaatgct gtcagcttat cttacatgaa cacacaaaca ctctcgcagg cactagcctc     300
aaatggccgc cgtcattgcc aagtcctccg tctccgcggc cgtggctcgc ccggcccgct     360
ccagcgtgcg ccccatggcc gcgctgaagc ccgccgtcaa ggctgccccc gtggctgccc     420
cggctcaggc caaccagatg gattttaata atgttttatt aaataaggat gatgggatag     480
ctctcatcat tataaatcgt ccaaaggctt taaatgcatt aaactatgag acactaaaag     540
agttagatag tgtgcttgat atagttgaaa atgataaaga gataaaagtt ttaattataa     600
ctggcagcgg tgaaaaaacc ttcgttgcag gtgctgatat agctgagatg agtaatatga     660
caccacttga agcgaagaag ttctctcttt atggacagaa agtatttagg aagatagaaa     720
tgctaagtaa gcctgttata gcagcggtaa atggttttgc acttggtggt ggatgcgagc     780
tttctatggc atgtgacata cgtattgcaa gtaaaaatgc aaaatttggt caacctgaag     840
taggacttgg aataatacct ggcttttcag gaactcaaag attaccacgt cttataggca     900
cttctaaagc taaagagctt attttcacag gtgacatgat aaattctgat gaagcatata     960
aaataggcct tatatctaaa gttgttgaac tatctgatct cattgaagaa gcaaaaaaac    1020
tcgcgaaaaa aatgatgtca aaaagtcaaa tagcaatttc tctagcaaag gaagcaataa    1080
ataagggaat ggaaacagac ttagatacag gcaatactat agaagctgag aaattttcct    1140
tatgttttac aacagatgat caaaaagaag gtatgattgc gtttctgaa aagagggcgc     1200
ctaaatttgg caaataaatg gaggcgctcg ttgatctgag ccttgccccc tgacgaacgg    1260
cggtggatgg aagatactgc tctcaagtgc tgaagcggta gcttagctcc ccgtttcgtg    1320
ctgatcagtc tttttcaaca cgtaaaaagc ggaggagttt tgcaattttg ttggttgtaa    1380
cgatcctccg ttgattttgg cctctttctc catgggcggg ctgggcgtat ttgaagcggt    1440
tctctcttct gccgtta                                                   1457
```

<210> SEQ ID NO 21
<211> LENGTH: 1817
<212> TYPE: DNA
<213> ORGANISM: Artificial Sequence
<220> FEATURE:
<223> OTHER INFORMATION: Synthetic Construct- Sequence No. 21, Example 21: designer HydA1-promoter-linked Butyryl-CoA-Dehydrogenase DNA construct (1817 bp)

<400> SEQUENCE: 21

```
agaaaatctg gcaccacacc gagctgtcat gcgttgttcc gttatgtgtc gtcaaacgcc      60
ttcgagcgct gcccggaaca atgcgtacta gtataggagc catgaggcaa gtgaacagaa     120
gcgggctgac tggtcaaggc gcacgatagg gctgacgagc gtgctgacgg ggtgtaccgc     180
cgagtgtccg ctgcattccc gccggattgg gaaatcgcga tggtcgcgca taggcaagct     240
cgcaaatgct gtcagcttat cttacatgaa cacacaaaca ctctcgcagg cactagcctc     300
aaatggccgc cgtcattgcc aagtcctccg tctccgcggc cgtggctcgc ccggcccgct     360
```

```
ccagcgtgcg ccccatggcc gcgctgaagc ccgccgtcaa ggctgccccc gtggctgccc    420

cggctcaggc caaccagatg gacttttcat taacaaagga gcaagaaatg gtaaggcgtg    480

ttgtgagaga attcgctgaa aaagaagttg ctcctaaagc aaaagaaata gatatcacag    540

aagagtttcc atgggataca gtaagaaaaa tggctcaaaa cgatatgatg ggtattcctt    600

atccagaaga gtatggtgga gcaggtggag attacttgag ttatatcata gctgttgaag    660

agatatcaag agcttgtgct acgactggag taattttatc tgctcatact tcattgggaa    720

gttttccaat atatcaatgg ggaacagaag aacaaaaaag aaaatatcta gtgccacttg    780

caaaaggtga aaaattgggc gcttttggcc ttacagaacc taacgcaggt acagatgcag    840

ctggacagca gacaactgca gtattagatg gtgatcacta cgtattaaac ggctcaatat    900

ttattacaaa cggaggaaaa gctgacatat atataatctt tgcaatgaca gacaaatcaa    960

aaggcacaag aggcattagt gcatttatag ttgagaaaga ttttccgggt tttagcattg   1020

gcaaaattga agaaaaaatg ggtataagag cttcatcaac tgccgaactt gtgtttgaag   1080

attgtattgt accaaaagaa aatttacttg gtaaagaagg agaaggtttt aaaattgcga   1140

tggctacact agatggtgga agaataggaa tagcagcgca acgccttgga atagctcagg   1200

ctgctttaga tgaagagata aaatatgcaa aggaaagaca acagtttgga agaccaattg   1260

gaaaatttca aggcattcaa tggtatatag ctgatatggc aacgagaata aatgcttcaa   1320

gatggcttgt atacaatgcc gcttggagaa agcaggtagg tcttccgtac acaatggaag   1380

cagctatggc aaaattatat gcttccgaaa cagcaatgtt tgtaacgaca aaaacagttc   1440

agatatttgg cggctatggc tttacaaaag attatccagt ggaaagattt atgagagatg   1500

caaaaataac agaaatttat gaaggcacat cggaagtcca gaaaatggtt atttccggta   1560

acctattgaa aatgtaaatg gaggcgctcg ttgatctgag ccttgccccc tgacgaacgg   1620

cggtggatgg aagatactgc tctcaagtgc tgaagcggta gcttagctcc ccgtttcgtg   1680

ctgatcagtc tttttcaaca cgtaaaaagc ggaggagttt tgcaattttg ttggttgtaa   1740

cgatcctccg ttgattttgg cctctttctc catgggcggg ctgggcgtat ttgaagcggt   1800

tctctcttct gccgtta                                                  1817
```

<210> SEQ ID NO 22
<211> LENGTH: 2084
<212> TYPE: DNA
<213> ORGANISM: Artificial Sequence
<220> FEATURE:
<223> OTHER INFORMATION: Synthetic Construct- Sequence No. 22, Example 22: designer HydA1-promoter-linked Butyraldehyde-Dehydrogenase DNA construct (2084 bp)

<400> SEQUENCE: 22

```
agaaaatctg gcaccacacc gagctgtcat gcgttgttcc gttatgtgtc gtcaaacgcc     60

ttcgagcgct gcccggaaca atgcgtacta gtataggagc catgaggcaa gtgaacagaa    120

gcgggctgac tggtcaaggc gcacgatagg gctgacgagc gtgctgacgg ggtgtaccgc    180

cgagtgtccg ctgcattccc gccggattgg gaaatcgcga tggtcgcgca taggcaagct    240

cgcaaatgct gtcagcttat cttacatgaa cacacaaaca ctctcgcagg cactagcctc    300

aaatggccgc cgtcattgcc aagtcctccg tctccgcggc cgtggctcgc ccggcccgct    360

ccagcgtgcg ccccatggcc gcgctgaagc ccgccgtcaa ggctgccccc gtggctgccc    420

cggctcaggc caaccagatg attaaagaca cgctagtttc tataacaaaa gatttaaaat    480

taaaaacaaa tgttgaaaat gccaatctaa agaactacaa ggatgattct tcatgtttcg    540
```

```
gagttttcga aaatgttgaa aatgctataa gcaatgccgt acacgcacaa aagatattat    600

cccttcatta tacaaaagaa caaagagaaa aaatcataac tgagataaga aaggccgcat    660

tagaaaataa agagattcta gctacaatga ttcttgaaga aacacatatg ggaagatatg    720

aagataaaat attaaagcat gaattagtag ctaaatacac tcctgggaca gaagatttaa    780

ctactactgc ttggtcagga gataacgggc ttacagttgt agaaatgtct ccatatggcg    840

ttataggtgc aataactcct tctacgaatc caactgaaac tgtaatatgt aatagtatag    900

gcatgatagc tgctggaaat actgtggtat ttaacggaca tccaggcgct aaaaaatgtg    960

ttgcttttgc tgtcgaaatg ataaataaag ctattatttc atgtggtggt cctgagaatt   1020

tagtaacaac tataaaaaat ccaactatgg actctctaga tgcaattatt aagcaccctt   1080

caataaaact actttgcgga actggagggc caggaatggt aaaaaccctc ttaaattctg   1140

gtaagaaagc tataggtgct ggtgctggaa atccaccagt tattgtagat gatactgctg   1200

atatagaaaa ggctggtaag agtatcattg aaggctgttc ttttgataat aatttacctt   1260

gtattgcaga aaaagaagta tttgtttttg agaacgttgc agatgattta atatctaaca   1320

tgctaaaaaa taatgctgta attataaatg aagatcaagt atcaaagtta atagatttag   1380

tattacaaaa aaataatgaa actcaagaat actctataaa taagaaatgg gtcggaaaag   1440

atgcaaaatt attcttagat gaaatagatg ttgagtctcc ttcaagtgtt aaatgcataa   1500

tctgcgaagt aagtgcaagg catccatttg ttatgacaga actcatgatg ccaatattac   1560

caattgtaag agttaaagat atagatgaag ctattgaata tgcaaaaata gcagaacaaa   1620

atagaaaaca tagtgcctat atttattcaa aaaatataga caacctaaat aggtttgaaa   1680

gagaaatcga tactactatc tttgtaaaga atgctaaatc ttttgccggt gttggttatg   1740

aagcagaagg ctttacaact ttcactattg ctggatccac tggtgaagga ataacttctg   1800

caagaaattt tacaagacaa agaagatgtg tactcgccgg ttaaatggag gcgctcgttg   1860

atctgagcct tgccccctga cgaacggcgg tggatggaag atactgctct caagtgctga   1920

agcggtagct tagctccccg tttcgtgctg atcagtcttt ttcaacacgt aaaaagcgga   1980

ggagttttgc aattttgttg gttgtaacga tcctccgttg attttggcct ctttctccat   2040

gggcgggctg ggcgtatttg aagcggttct ctcttctgcc gtta                   2084
```

```
<210> SEQ ID NO 23
<211> LENGTH: 1733
<212> TYPE: DNA
<213> ORGANISM: Artificial Sequence
<220> FEATURE:
<223> OTHER INFORMATION: Synthetic Construct- Sequence No. 23,
      Example 23: designer HydA1-promoter-linked Butanol-Dehydrogenase
      DNA construct (1733 bp)

<400> SEQUENCE: 23

agaaaatctg gcaccacacc gagctgtcat gcgttgttcc gttatgtgtc gtcaaacgcc     60

ttcgagcgct gcccggaaca atgcgtacta gtataggagc catgaggcaa gtgaacagaa    120

gcgggctgac tggtcaaggc gcacgatagg gctgacgagc gtgctgacgg ggtgtaccgc    180

cgagtgtccg ctgcattccc gccggattgg gaaatcgcga tggtcgcgca taggcaagct    240

cgcaaatgct gtcagcttat cttacatgaa cacacaaaca ctctcgcagg cactagcctc    300

aaatggccgc cgtcattgcc aagtcctccg tctccgcggc cgtggctcgc ccggcccgct    360

ccagcgtgcg ccccatggcc gcgctgaagc ccgccgtcaa ggctgccccc gtggctgccc    420
```

```
cggctcaggc caaccagatg aaaggttttg caatgctagg tattaataag ttaggatgga    480

tcgaaaaaga aaggccagtt gcgggttcat atgatgctat tgtacgccca ttagcagtat    540

ctccgtgtac atcagatata catactgttt ttgagggagc tcttggagat aggaagaata    600

tgattttagg gcatgaagct gtaggtgaag ttgttgaagt aggaagtgaa gtgaaggatt    660

ttaaacctgg tgacagagtt atagttcctt gtacaactcc agattggaga tctttggaag    720

ttcaagctgg ttttcaacag cactcaaacg gtatgctcgc aggatggaaa ttttcaaatt    780

tcaaggatgg agtttttggt gaatattttc atgtaaatga tgcggatatg aatcttgcga    840

ttctacctaa agacatgcca ttagaaaatg ctgttatgat aacagatatg atgactactg    900

gatttcatgg agcagaactt gcagatattc aaatgggttc aagtgttgtg gtaattggca    960

ttggagctgt tggcttaatg ggaatagcag gtgctaaatt acgtggagca ggtagaataa   1020

ttggagtggg gagcaggccg atttgtgttg aggctgcaaa attttatgga gcaacagata   1080

ttctaaatta taaaaatggt catatagttg atcaagttat gaaattaacg aatggaaaag   1140

gcgttgaccg cgtaattatg gcaggcggtg gttctgaaac attatcccaa gcagtatcta   1200

tggttaaacc aggaggaata atttctaata taaattatca tggaagtgga gatgctttac   1260

taataccacg tgtagaatgg ggatgtggaa tggctcacaa gactataaaa ggaggtcttt   1320

gtcctggggg acgtttgaga gcagaaatgt taagagatat ggtagtatat aatcgtgttg   1380

atctaagtaa attagttaca catgtatatc atggatttga tcacatagaa gaagcactgt   1440

tattaatgaa agacaagcca aaagacttaa ttaaagcagt agttatatta taaatggagg   1500

cgctcgttga tctgagcctt gccccctgac gaacggcggt ggatggaaga tactgctctc   1560

aagtgctgaa gcggtagctt agctccccgt ttcgtgctga tcagtctttt tcaacacgta   1620

aaaagcggag gagttttgca attttgttgg ttgtaacgat cctccgttga ttttggcctc   1680

tttctccatg ggcgggctgg gcgtatttga agcggttctc tcttctgccg tta          1733
```

```
<210> SEQ ID NO 24
<211> LENGTH: 1556
<212> TYPE: DNA
<213> ORGANISM: Artificial Sequence
<220> FEATURE:
<223> OTHER INFORMATION: Synthetic Construct- Sequence No. 24,
      Example 24: designer Fructose-Diphosphate-Aldolase DNA construct
      (1556 bp)

<400> SEQUENCE: 24

agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcggggggc    180

gctcccggat ggccctgatg atgaagtcgt cggccagcct gaaggctgtg tcgctggccg    240

ctctcgccgc gccgtcgttg tgcgcgccgg gcaagtacga tgaggagctg attaagaccg    300

ctggcaccgt tgcctccaag ggccgcggta tcctggccat ggacgagtca aacgccacct    360

gcggcaaacg cctggactcc atcggcgtgg agaacaccga ggagaaccgc cgcgcctacc    420

gcgagctgct ggtgaccgcc cccggcctgg gccagtacat ctccggcgct atcctgttcg    480

aggagaccct gtatcagtcc accgcctccg gcaagaagtt cgtcgatgtg atgaaggagc    540

agaacatcgt gcccggcatc aaggtcgaca agggcctggt gccctgtcca acaccaacga    600

tgagctggtg catgggcctg gacggctgga caagcgctgc tgagtactac aaggccggcg    660

ctcgcttcgc caagtggcgc tcggtcgtct cgatccccca cggcccctcg atcatgctgc    720
```

```
cgcgactggc ctacggcctg gcccgctacg ccgccatcgc ccagaacgcc ggtctggtgc    780
ccattgtgga gcccgaggtc ctgctggacg gtgagcacga catcgaccgc tgcctggagg    840
tgcaggaggc catctgggcc gagaccttca agtacatggc cgacaacaag gtcatgttgc    900
agggtatcct gctgaagccc gccatggtca cccccggcgc tgactgcaag aacaaggccg    960
gccccgccaa ggttgccgag tacaccctga agatgctggc cgcgcgtgcc cccccggtcc   1020
ccggcatcat gttcctgtcg ggcggccagt ccgagctgga gtcgaccctg aacctgaacg   1080
ccatgaacca gagccccaac ccgtggcacg tgtcgttctc gtacgcccgc gctctgacga   1140
acaccgttct gaagacctgg caggcaagcc cgagaacggt ccaggcgccc aggctcgctg   1200
ctcaagcgcg caaggccaac tcggacgctc agcagggcaa gtacgacgcc accaccgagg   1260
gcaaggaggc tgcccagggc atgtacgaga agggaaaagg ctacgtctac taataaatgg   1320
aggcgctcgt tgatctgagc cttgccccct gacgaacggc ggtggatgga agatactgct   1380
ctcaagtgct gaagcggtag cttagctccc cgtttcgtgc tgatcagtct ttttcaacac   1440
gtaaaaagcg gaggagtttt gcaattttgt tggttgtaac gatcctccgt tgattttggc   1500
ctctttctcc atgggcgggc tgggcgtatt tgaagcggtt ctctcttctg ccgtta       1556
```

```
<210> SEQ ID NO 25
<211> LENGTH: 1379
<212> TYPE: DNA
<213> ORGANISM: Artificial Sequence
<220> FEATURE:
<223> OTHER INFORMATION: Synthetic Construct- Sequence No. 25,
      Example 25: designer Triose-Phosphate-Isomerase DNA construct
      (1379 bp)

<400> SEQUENCE: 25
```

```
agaaaatctg gcaccacacc atggtagggt gcgagtgacc ccgcgcgact tggaagggtt     60
caaacgaccc cgccgtacga acttttgtcg gggggcgctc ccggatggta gggtgcgagt    120
gaccccgcgc gacttggaag ggttcaaacg accccgccgt acgaactttt gtcggggggc    180
gctcccggat ggcagctacc tctctcactg cccctccttc tttctccggt ctccgccgca    240
tttctcccaa gctcgacgct gccgccgtct cctcccacca atccttcttc caccgcgtca    300
attcctctac ccgtctcgtt tcttcctctt cttcttctca tcgctccccc agaggtgttg    360
ttgccatggc tggatccgga aagtttttcg ttggaggaaa ctggaagtgt aacgggacta    420
aggactccat cgccaagctt atctccgatc tcaacagtgc aaccttggaa gcagatgtag    480
atgttgttgt gtcacctcca tttgtctaca tcgaccaggt caaatcctcg ttgacagacc    540
gtattgacat atcaggtcag aactcttggg ttgggaaagg tggagccttc actggtgaaa    600
tcagcgtgga acagctcaaa gaccttggct gcaagtgggt cattcttggg cattccgaac    660
ggagacatgt catcggagaa aaagatgagt ttatcgggaa gaaagctgca tatgcattga    720
gtgagggtct tggagtgata gcttgtattg gggaaaagct agaagagagg gaagcaggca    780
agacgtttga tgtttgcttc gcgcaactga aggcgtttgc tgatgctgtg cctagctggg    840
acaatatagt tgttgcatac gagcctgtat gggcaattgg aactggtaaa gttgcatctc    900
ctcagcaagc acaagaagtc catgtagctg tccgcggttg gctaaagaag aatgtctctg    960
aggaagttgc ttccaaaacg agaatcatat atggaggttc tgtcaatgga ggcaacagtg   1020
cagagcttgc caaagaagaa gacattgatg gatttcttgt tggtggtgcc tccttgaagg   1080
gtcctgagtt tgcaaccatt gtgaactcag tcacgtcgaa gaaagttgct gcttgataaa   1140
```

```
tggaggcgct cgttgatctg agccttgccc cctgacgaac ggcggtggat ggaagatact   1200

gctctcaagt gctgaagcgg tagcttagct ccccgtttcg tgctgatcag tctttttcaa   1260

cacgtaaaaa gcggaggagt tttgcaattt tgttggttgt aacgatcctc cgttgatttt   1320

ggcctctttc tccatgggcg ggctgggcgt atttgaagcg gttctctctt ctgccgtta    1379
```

<210> SEQ ID NO 26
<211> LENGTH: 2156
<212> TYPE: DNA
<213> ORGANISM: Artificial Sequence
<220> FEATURE:
<223> OTHER INFORMATION: Synthetic Construct- Sequence No. 26, Example 26: designer Phosphofructose-Kinase DNA construct (2156 bp)

<400> SEQUENCE: 26

```
agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcggggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatggaag cttcgatttc gtttctgggg tcaacaaaac    360

ccaatatttc cttgtttaac ccttcttcaa acgtccttcc tcgtagagat ttccctcttc    420

ctgctttgaa attgaagaaa gtttcagtgc tgcctcgaat cttgcaccag aaacgactca    480

tcagagctca gtgctctgat ggattcaaac cagaggaaga cgatgggttt gtcctagaag    540

acgttcctca cttgaccaaa tttctccctg atttaccgtc atatccaaat ccattgaaag    600

aaagccaagc atatgccatt gttaagcgaa cttttgtcag ttccgaagat gtggttgcgc    660

aaaatattgt agtccagaag ggaagtaagc gaggagtaca ctttaggcga gcagggcctc    720

gagaaagagt gtacttcaga tcagatgaag taaaagcttg catagtgact tgtgggggct    780

tgtgccctgg aatcaatact gttatacggg aaattgtatg tggattgaac aatatgtatg    840

gtgttaataa cattctcggc attcagggag gatatagagg cttttactcc aaaaacacta    900

tgaacctgac acctaaagta gttaacgata ttcataaacg cggtggcact tttcttcaaa    960

cctcaagagg aggacatgat acagcgaaga ttgttgataa tattcaagat agaggaataa   1020

atcaggtata tattattgga ggtggtggga cgcaaaaggg tgcagagaag atatacgagg   1080

aagttgagag gcgtggtctt caagtggcgg tttctggcat tcctaagaca attgataatg   1140

atattgctgt gattgacaaa tcatttggct ttgatacggc ggttgaggaa gcacaacgag   1200

ctattaatgc tgcacatgta gaggtcgaga gcgtggaaaa tggagttggt atcgttaaac   1260

tcatgggcag atacagtggt tttattgcca tgattgcaac tttagcgaat cgtgatgtgg   1320

attgttgctt gattccagag tctccatttt ttcttgaagg aaagggtggg ctctttgagt   1380

ttattgaaga acgactcaaa gagaataggc acatggttat tgtgatagct gaaggagctg   1440

gacaggatta tgttgctcaa agcatgcgtg catctgaaac taaagacgcc tcaggaaata   1500

gactcttgct tgatgttggt ctatggttga ctcaacagat aaaggatcac tttacaaatg   1560

ttcggaaaat gatgataaat atgaagtaca tagacccaac gtatatgata agagcaatac   1620

cgagtaacgc atcagacaat gtctattgca ctcttcttgc ccaaagtgca gttcatggag   1680

caatggctgg gtactcaggt ttcactgtag gaccagttaa cagtagacat gcttacatcc   1740

caatttctgt gacggaagtg acaaatacgg tgaagttaac tgataggatg tgggctagac   1800
```

```
tccttgcatc gacaaatcaa ccgagtttct tgactggtga aggagcattg cagaatgtga   1860

tcgacatgga aactcaagaa aagatcgata acatgaagat ctcttctatc taataaatgg   1920

aggcgctcgt tgatctgagc cttgcccct gacgaacggc ggtggatgga agatactgct   1980

ctcaagtgct gaagcggtag cttagctccc cgtttcgtgc tgatcagtct ttttcaacac   2040

gtaaaaagcg gaggagtttt gcaattttgt tggttgtaac gatcctccgt tgattttggc   2100

ctctttctcc atgggcgggc tgggcgtatt tgaagcggtt ctctcttctg ccgtta       2156
```

<210> SEQ ID NO 27
<211> LENGTH: 860
<212> TYPE: DNA
<213> ORGANISM: Artificial Sequence
<220> FEATURE:
<223> OTHER INFORMATION: Synthetic Construct- Sequence No. 27, Example 27: designer Nia1-promoter-linked Starch-Synthase-iRNA DNA construct (860 bp)

<400> SEQUENCE: 27

```
agaaaatctg gcaccacacc tatatggtag ggtgcgagtg accccgcgcg acttggagct     60

cgatggcccc gggttgtttg gggcgtccgc ctctcgcgct attctgagct ggagaccgag    120

gcgcatgaaa atgcattcgc ttccatagga cgctgcattg tggcttgaag gttcaaggga    180

agggttcaaa cgaccccgcc gtacgaactt ttgtcggggg gcgctcccgg ccccgggctc    240

ttgtgcgcgc attagggctt cgggtcgcaa gcaagacgat acatgccagc cggctcacca    300

ccgccaccag cggcttgcgg gggtccacct ccaggcccag acccttctgc agaaactcct    360

tgcacagcgc cttcccggcg gggcggtcgg cgtcgaagtt ggctggcagc agcgcgtcag    420

tggccgggtt ccactcctca cagtcaatgc cgttcaggat gccgtggaac ttggagcgca    480

gctcggggcg cgcgaaggtg gatctcgccg tcccagcggt agcccttggg cacctcgatg    540

tcgcattcgt gcttgaggcc ctcaatctgg tccttgggca ggcactcgta gaacggcagc    600

atgaccgtca cgaagtgtaa atggaggcgc tcgttgatct gagccttgcc ccctgacgaa    660

cggcggtgga tggaagatac tgctctcaag tgctgaagcg gtagcttagc tccccgtttc    720

gtgctgatca gtctttttca acacgtaaaa agcggaggag ttttgcaatt ttgttggttg    780

taacgatcct ccgttgattt tggcctcttt ctccatgggc gggctgggcg tatttgaagc    840

ggttctctct tctgccgtta                                                860
```

<210> SEQ ID NO 28
<211> LENGTH: 1328
<212> TYPE: DNA
<213> ORGANISM: Artificial Sequence
<220> FEATURE:
<223> OTHER INFORMATION: Synthetic Construct- Sequence No. 28, Example 28: designer HydA1-promoter-linked Starch-Synthase-iRNA DNA construct (1328 bp)

<400> SEQUENCE: 28

```
agaaaatctg gcaccacacc gagctgtcat gcgttgttcc gttatgtgtc gtcaaacgcc     60

ttcgagcgct gcccggaaca atgcgtacta gtataggagc catgaggcaa gtgaacagaa    120

gcgggctgac tggtcaaggc gcacgatagg gctgacgagc gtgctgacgg ggtgtaccgc    180

cgagtgtccg ctgcattccc gccggattgg gaaatcgcga tggtcgcgca taggcaagct    240

cgcaaatgct gtcagcttat cttacatgaa cacacaaaca ctctcgcagg cactagcctc    300

aaatgaagag cttcatgcgg agggatgcgc tcggcgcggg gctccgcggt gcagccagca    360
```

```
caaagcccgt ctcaagggtc gccagcgtga ggcctgcgcc taccgcctac cgcactgcct    420

gccaagttgc gaaggtggat gaaatggtgt cggtggatga ggagcttact cgtctccgca    480

aggagaacga gctcctgcgc gcccaactgg cgctgtacca gcagaaccag cagccgtccg    540

tgggtgccgc tgccgttgcc ccgcctgctg ccgccacgaa ggtgctggag aagccggcgc    600

cgtaagtaac ctaacggtga gcagcatgca atattttagc gtcgatactc ggaaactata    660

ggagcgcatc agccgaccga tgttcgcgtt gctgtcgcag gcccaaccgt gccaccgccg    720

tggtgtgcaa ggcgcagaag gcggccaggc cgccgctgcc gctgctctgg ccataagtaa    780

cctaacggcg ccggcttctc cagcaccttc gtggcggcag caggcggggc aacggcagcg    840

gcacccacgg acggctgctg gttctgctgg tacagcgcca gttgggcgcg caggagctcg    900

ttctccttgc ggagacgagt aagctcctca tccaccgaca ccatttcatc caccttcgca    960

acttggcagg cagtgcggta ggcggtaggc gcaggcctca cgctggcgac ccttgagacg   1020

ggctttgtgc tggctgcacc gcggagcccc gcgccgagcg catccctccg catgaagctc   1080

ttcattaaat ggaggcgctc gttgatctga gccttgcccc ctgacgaacg gcggtggatg   1140

gaagatactg ctctcaagtg ctgaagcggt agcttagctc cccgtttcgt gctgatcagt   1200

ctttttcaac acgtaaaaag cggaggagtt ttgcaatttt gttggttgta acgatcctcc   1260

gttgattttg gcctctttct ccatgggcgg gctgggcgta tttgaagcgg ttctctcttc   1320

tgccgtta                                                            1328
```

<210> SEQ ID NO 29
<211> LENGTH: 1889
<212> TYPE: DNA
<213> ORGANISM: Artificial Sequence
<220> FEATURE:
<223> OTHER INFORMATION: Synthetic Construct- Sequence No. 29,
      Example 29: designer Amylase DNA construct (1889 bp)

<400> SEQUENCE: 29

```
agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcggggggc    180

gctcccggct cgagcatatg gccgccgtca ttgccaagtc ctccgtctcc gcggccgtgg    240

ctcgcccggc ccgctccagc gtgcgcccca tggccgcgct gaagcccgcc gtcaaggctg    300

cccccgtggc tgccccggct caggccaacc agatggcgaa caaacacatg tccctttctc    360

tcttcatcgt cctccttggc ctctcgtgca gcttggcctc cgggcaagtc ctgtttcagg    420

gttttaactg ggagtcgtgg aagcacaatg gcgggtggta caacttcctg atgggcaagg    480

tggacgacat cgccgccgct ggcgtcacgc acgtgtggct ccccccggcg tcgcagtccg    540

tcgccgagca agggtacatg ccgggccggc tctacgacct ggacgcctcc aagtacggca    600

acaaggcgca gctcaagtcc ctcatcggcg cgctccacgg caagggcgtc aaggccatcg    660

ccgacatcgt catcaaccac cgcacggcgg agcgcaagga cggccggggc atctactgca    720

tcttcgaggg cggcaccccg gacgcgcgcc tcgactgggg cccccacatg atctgccgcg    780

acgaccggcc ctacgccgac ggcaccggca acccggacac cggcgccgac ttcggggccg    840

cgccggacat cgaccacctc aacccgcgcg tccagaagga gctcgtcgag tggctcaact    900

ggctcaggac cgacgtcggc ttcgacggct ggcgcttcga cttcgccaag ggctactccg    960

cggacgtggc caagatctac gtcgaccgct ccgagcccag cttcgccgtc gccgagatat   1020
```

```
ggacgtcgct ggcgtacggc ggggacggca agccgaacct caaccaggac ccgcaccggc   1080

aggagctggt gaactgggtg aacaaggtgg gcggctccgg ccccgccacc acgttcgact   1140

tcaccaccaa gggcatcctc aacgtggccg tggagggcga gctgtggcgc ctgcgcggca   1200

ccgacggcaa ggcgccgggc atgatcgggt ggtggccggc caaggcggtg accttcgtcg   1260

acaaccacga caccggctcc acgcagcaca tgtggccctt cccttccgac agggtcatgc   1320

agggatatgc ctacatcctc acgcacccag ggaccccatg catcttctac gatcatttct   1380

tcgactgggg cttgaaggag gagatcgatc gtctggtgtc aatcaggacc cgacagggga   1440

tacacagtga gagcaagctg cagatcatgg aggccgacgc cgacctttac cttgccgaga   1500

tcgacggcaa ggtcatcgtc aagctcgggc caagatacga tgtcggacac ctcattcctg   1560

aaggcttcaa ggtggtcgcg catggcaatg actatgccgt atgggagaaa gtataaggct   1620

gctgccccgg ctgctgctaa tctagataaa tggaggcgct cgttgatctg agccttgccc   1680

cctgacgaac ggcggtggat ggaagatact gctctcaagt gctgaagcgg tagcttagct   1740

ccccgtttcg tgctgatcag tctttttcaa cacgtaaaaa gcggaggagt tttgcaattt   1800

tgttggttgt aacgatcctc cgttgatttt ggcctctttc tccatgggcg ggctgggcgt   1860

atttgaagcg gttctctctt ctgccgtta                                     1889
```

```
<210> SEQ ID NO 30
<211> LENGTH: 3089
<212> TYPE: DNA
<213> ORGANISM: Artificial Sequence
<220> FEATURE:
<223> OTHER INFORMATION: Synthetic Construct- Sequence No. 30,
      Example 30: designer Starch-Phosphorylase DNA construct (3089 bp)

<400> SEQUENCE: 30
```

```
agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcggggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatggcgg atgcgaaagc aaacggaaag aatgaggcgg    360

ccaaactggc gaaaattccg gcggctgcga atccattggc taatgaacca tcggcgattg    420

catcaaatat aagttaccac gtgcagtaca gtcctcattt ctcgccgact aagttcgagc    480

cggagcaagc tttctttgcc acggcggagg ttgtccgcga tcgtcttatt caacaatgga    540

atgagacata ccaccatttt aataaagttg atccgaagca aacatactac ctatcaatgg    600

aatttcttca aggaaggact ttgactaatg caattggcag tttggacatt cagaatgcat    660

atgctgatgc tttaaataat ttggggcatg tccttgagga gatagctgaa caggaaaaag    720

atgctgcact aggaaatggt gggctgggca ggctagcttc atgcttctta gactccatgg    780

caacattgaa tttgcctgca tggggttatg gtttgagata ccggtatggg ctgttcaagc    840

agaagatcac caagcagggt caagaagaag ttgctgaaga ttggcttgag aaatttagtc    900

cttgggaagt tgtcaggcat gatgtggtat ttccggtcag attttttggg agtgttatgg    960

ttaatccaaa tggaacgaga aaatgggttg ggggtgaagt tgtccaagcc gtagcttatg   1020

atataccaat tccagggtac aaaaccaaga acactatcag tcttcgtctc tgggacgcta   1080

aagctagcgc tgaggatttc aatttatttc agtttaatga tggacaatac gaatctgctg   1140
```

-continued cacagcttca ttctcgagct caacagattt gtgctgtgct ctaccccggg gattctactg 1200
aagaagggaa gcttttaagg ctgaaacaac aattctttct ctgcagtgct tcacttcagg 1260
atatgattct tagattcaag gagaggaaaa gtggaaggca gtggtctgaa tttcccagca 1320
aggtagctgt acaactgaat gatactcatc caacacttgc aattccagag ttgatgcgat 1380
tgctaatgga tgaggaagga cttggatggg atgaagcatg ggatataaca acaaggactg 1440
ttgcttatac caatcacaca gtacttcctg aagcacttga gaagtggtca caagcagtaa 1500
tgtggaagct tcttcctcgc catatggaaa taattgaaga gattgacaag agattcattg 1560
caatggtccg ctccacaagg agtgaccttg agagtaagat tcccagcatg tgcatcttgg 1620
ataataatcc caaaaagccg gttgttagga tggcaaactt atgtgtagta tctgcgcata 1680
cggtaaatgg tgttgctcag ttgcacagtg atatcttaaa ggccgacttg ttcgctgact 1740
atgtttctct atggccaaac aaactccaaa ataaaactaa tggcattact cctcgtcgat 1800
ggctccggtt ttgcaatcct gagctcagca aaattatcac aaaatggtta aaaaccgatc 1860
agtgggttac gaaccttgac ctgcttgtag gtcttcgtca gtttgctgac aacacagaac 1920
tccaagctga atgggaatct gctaagatgg ccagtaagaa acatttggca gactacatat 1980
ggcgagtaac cggtgtaacg attgatccta atagcttatt tgacatacaa gtcaagcgca 2040
ttcatgaata caagagacaa ctgctaaata ttttgggcgc aatctacaga tacaagaagt 2100
tgaaggagat gagccctcag gagcggaaga aaactactcc acgcaccatt atgtttggag 2160
ggaaagcatt tgcaacatat acaaacgcaa aaagaatagt aaagttggtt aatgatgttg 2220
gtgaagtcgt caacaccgat cctgaggtca atagttattt gaaggtggta tttgttccaa 2280
attacaatgt ctctgttgcg gagttgctta ttccaggaag tgagctatct cagcatatta 2340
gcacagcagg catggaggca agtggcacaa gcaacatgaa attttctcta aatggttgcc 2400
tcattatagg aacattggat ggagctaatg tggaaatcag gcaggagata ggagaggaga 2460
atttctttct ctttggtgca ggagcagacc aagtccctaa gctgcggaag gaaagagaag 2520
atggattgtt caaaccagat cctcggtttg aagaggccaa gcaatttata agaagtggag 2580
catttggaag ctatgactac aacccgcttc ttgattccct ggaggggaac actggttatg 2640
gtcgtggtga ttattttcta gttggttatg acttcccaag ttacttagag gctcaggaca 2700
gagttgacca agcttacaag gaccggaaga agtggctgaa gatgtctata ttaagtacag 2760
ctggcagtgg gaaattcagc agtgatcgca caattgcaca gtatgctaag gaaatctgga 2820
acataacaga atgccgtaca tcatgataaa tggaggcgct cgttgatctg agccttgccc 2880
cctgacgaac ggcggtggat ggaagatact gctctcaagt gctgaagcgg tagcttagct 2940
ccccgtttcg tgctgatcag tctttttcaa cacgtaaaaa gcggaggagt tttgcaattt 3000
tgttggttgt aacgatcctc cgttgatttt ggcctctttc tccatgggcg ggctgggcgt 3060
atttgaagcg gttctctctt ctgccgtta 3089

<210> SEQ ID NO 31
<211> LENGTH: 1949
<212> TYPE: DNA
<213> ORGANISM: Artificial Sequence
<220> FEATURE:
<223> OTHER INFORMATION: Synthetic Construct- Sequence No. 31,
Example 31: designer Hexose-Kinase DNA construct (1949 bp)

<400> SEQUENCE: 31
agaaaatctg gcaccacacc atggtagggt gcgagtgacc ccgcgcgact tggaagggtt 60

-continued

```
caaacgaccc cgccgtacga acttttgtcg gggggcgctc ccggatggta gggtgcgagt    120
gaccccgcgc gacttggaag ggttcaaacg accccgccgt acgaactttt gtcggggggc    180
gctcccggat ggccgccgtc attgccaagt cctccgtctc cgcggccgtg gctcgcccgg    240
cccgctccag cgtgcgcccc atggccgcgc tgaagcccgc cgtcaaggct gcccccgtgg    300
ctgccccggc tcaggccaac cagatggcta taacaccccg ccgaaaacct tcccggaagg    360
gatcaatggc tgatatgccg aaggatgtgc ttgaccagct caagacgctg gaagagctct    420
tcacagttga ccaggagaag ctgaagcaga tcgttgagca tttcatcaag gagttacaga    480
agggcctcag tgtcgaaggc ggaaacattc ccatgaacgt gacttgggtt ctgggatttc    540
ccactggcca tgagaaaggt acatttctgg ctctggacat ggggggcacc aacctgcgcg    600
tctgcgaaat tgagctctcc gaagagaagg gcgagtttga tgtcacacag tccaagtatc    660
gaatccccga agagctcaag agcggtgaat catcagaact atgggaatat attgccgact    720
gtgtacagca gttcatagaa tactaccatg acggttgcac ggctttgcca gacctgccgc    780
tgggctttac cttttcgtac cctgctactc aagaatatgt tgaccacggt gtcctacaga    840
gatggaccaa gggttttgat attgacggcg tcgagggcaa agacgtcgtc ccaatgttag    900
aagaagcttt ggctaagaag gttaaaaatt cagctctttc cccatttttc tttggctata    960
tggtgctaat tactttacag ggtctcccca ttaaagttgc cgctctagta aacgacacga   1020
ctggcacact tattgcttcc gcctacactg acccagagat gaaaatcggc tgtatcttcg   1080
gcacaggcgt caacgccgcc tacatggaaa atgcgggctc tatccctaaa atagcccact   1140
acaatttacc tcccgacacc ccagtcgcta tcaactgcga atacggcgcc ttcgacaacg   1200
aactcattgt cctcccccga acgcagtatg acgacgtatc ccaactacgt aaaccatact   1260
ccctggactc ctccttccta gccttcatcg aagaagatcc cttcgagaac ctgtcagaaa   1320
cgcgagatct cttcgaacgc accctgggga tctacgcatt gccctcggag ctagaattct   1380
gcagacgcct ggcggaattg atcggcacac gtgccgcacg cctctccgct tgcggtgttg   1440
cggccatctg caagaagaaa aatatcaccc attgccatgt cggagcggac gggtcggtgt   1500
tcgagaagta cccgcatttc aaggccaggg gcgccagagc cctgcgggag atccttgact   1560
ggccagatag tgaaccggat cgggttgtga tgagcggagc ggaggatggg tctggcgttg   1620
gtgcggcgct tattgcggct ttgacgcttg agagggttaa acaagcttct tgggaatgga   1680
agtacatcgg aagcggtctg tcttaataaa tggaggcgct cgttgatctg agccttgccc   1740
cctgacgaac ggcggtggat ggaagatact gctctcaagt gctgaagcgg tagcttagct   1800
ccccgtttcg tgctgatcag tctttttcaa cacgtaaaaa gcggaggagt tttgcaattt   1860
tgttggttgt aacgatcctc cgttgatttt ggcctctttc tccatgggcg ggctgggcgt   1920
atttgaagcg gttctctctt ctgccgtta                                     1949
```

<210> SEQ ID NO 32
<211> LENGTH: 2249
<212> TYPE: DNA
<213> ORGANISM: Artificial Sequence
<220> FEATURE:
<223> OTHER INFORMATION: Synthetic Construct- Sequence No. 32,
Example 32: designer Phosphoglucomutase DNA construct (2249 bp)

<400> SEQUENCE: 32

```
agaaaatctg gcaccacacc atggtagggt gcgagtgacc ccgcgcgact tggaagggtt     60
caaacgaccc cgccgtacga acttttgtcg gggggcgctc ccggatggta gggtgcgagt    120
```

-continued gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatgtccg atttctccgt ccagaccatt gccaccacgg 360
ccttcacaga ccaaaagcct ggaacctctg gtctcagaaa gaaagttact gtgtttcaac 420
agcctcacta cactgaaaac ttcattcagg ctattctcga tgccattccg gaaggtgccc 480
aaggtgccac tcttgttgta ggaggtgatg gccgtttcta caacgacaag gtcatcaact 540
tgatcgccaa aatcgcctcg gccaacggag tttccaagtt gattttgggt caagacggga 600
ttctttccac tccagcaact tcgcatgtaa tcaggatcag gggtgcaact ggaggaatta 660
ttctcactgc ttcacacaac cccggaggcc ccaaaaacga tttgggtatt aagtacaact 720
tgggaaacgg tgcaccagct ccagaatcgg ttaccaacaa gatctatgat gtctccaagg 780
aattgacttc gtacaagctc attgatttac ccgacattga tttgtccaaa acccagaccg 840
tgcaattggg ccctcttgaa gtggaaatca ttgactccac ctctgattac gtagccatgt 900
tgaaggatat ctttgacttc cccttgatca agtcgttcct cgagactgcc actaaggagc 960
agggattcaa ggttttattt gattcgctca atggtgtcac tggcccctac ggctacaaga 1020
tcttcgttga agaattagga ttgcctctta actcaatcca aaattaccac ccattgcctg 1080
actttggtgg tttacaccca gatccaaact tgacctatgc tcatactttg gtcgagaggg 1140
tcgataagga gaatattgcc tttggtgctg catctgatgg tgacggtgac agaaacatga 1200
tctacggtgc tggtaccttt gtttcgcctg gtgactctgt agccatcatc tcggaatacg 1260
ccgattccat cccttacttc aagaagcaag gtgtctacgg tttggccaga tccatgccta 1320
cctctggagc catcgatttg gtagcaaagg ctaaaggatt gaatgtttac gaagtgccaa 1380
ccggttggaa gttcttctgc aaccttttcg acgctgacaa gttgagtatc tgtggtgaag 1440
agtcgtttgg aacaggctcc aaccacatca gagaaaagga cggcctttgg gctgtagttg 1500
cctggttgaa cgtgctagca gattacaacg tcaagaatcc agaatccaag acatctattt 1560
ctgtagtgca gaactcgttt tggaagaaat acggaagaac tttcttcact agatatgact 1620
acgaaaacgt atcgtctgaa ggtgctgccg agctcatcaa cttgttgtct tctattgttg 1680
actctaagaa accaggaagt agcttagctg atggctacgt cgtcaaggaa gctgctaact 1740
tctcgtacac cgatttggac ggctctgttt cgtccaacca aggtttgttc atcaagtttg 1800
aaagcggctt gagattcata gtaagattgt ctggtactgg atcatccggt gctacagtca 1860
gattatatct cgaaaagcac tctgccgacg aatccaccta tggcttaggc gtagaccagt 1920
acttagttga tgacatcaag tttgtcttgg acttgttgaa gttcaagcag ttcttgggaa 1980
aggatgaacc agatgttcgt acctagtaaa tggaggcgct cgttgatctg agccttgccc 2040
cctgacgaac ggcggtggat ggaagatact gctctcaagt gctgaagcgg tagcttagct 2100
ccccgtttcg tgctgatcag tctttttcaa cacgtaaaaa gcggaggagt tttgcaattt 2160
tgttggttgt aacgatcctc cgttgatttt ggcctctttc tccatgggcg ggctgggcgt 2220
atttgaagcg gttctctctt ctgccgtta 2249

<210> SEQ ID NO 33
<211> LENGTH: 2231
<212> TYPE: DNA
<213> ORGANISM: Artificial Sequence
<220> FEATURE:
<223> OTHER INFORMATION: Synthetic Construct- Sequence No. 33, Example 33: designer Glucosephosphate-Isomerase DNA construct
(2231 bp)

<400> SEQUENCE: 33
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatgtcca ataactcatt cactaacttc aaactggcca 360
ctgaattgcc agcctggtct aagttgcaaa aaatttatga atctcaaggt aagactttgt 420
ctgtcaagca agaattccaa aaagatgcca agcgttttga aaaattgaac aagactttca 480
ccaactatga tggttccaaa atcttgttcg actactcaaa gaacttggtc aacgatgaaa 540
tcattgctgc attgattgaa ctggccaagg aggctaacgt caccggtttg agagatgcta 600
tgttcaaagg tgaacacatc aactccactg aagatcgtgc tgtctaccac gtcgcattga 660
gaaacagagc taacaagcca atgtacgttg atggtgtcaa cgttgctcca gaagtcgact 720
ctgtcttgaa gcacatgaag gagttctctg aacaagttcg ttctggtgaa tggaagggtt 780
ataccggtaa gaagatcacc gatgttgtta acatcggtat tggtggttcc gatttgggtc 840
cagtcatggt cactgaggct ttgaagcact acgctggtgt cttggatgtc cacttcgttt 900
ccaacattga cggtactcac attgctgaaa ccttgaaggt tgttgaccca gaaactactt 960
tgtttttgat tgcttccaag actttcacta ccgctgaaac tatcactaac gctaacactg 1020
ccaagaactg gttcttgtcg aagacaggta atgatccatc tcacattgct aagcatttcg 1080
ctgctttgtc cactaacgaa accgaagttg ccaagttcgg tattgacacc aaaaacatgt 1140
ttggtttcga aagttgggtc ggtggtcgtt actctgtctg gtcggctatt ggtttgtctg 1200
ttgccttgta cattggctat gacaactttg aggctttctt gaagggtgct gaagccgtcg 1260
acaaccactt cacccaaacc ccattggaag acaacattcc attgttgggt ggtttgttgt 1320
ctgtctggta caacaacttc tttggtgctc aaacccattt ggttgctcca ttcgaccaat 1380
acttgcacag attcccagcc tacttgcaac aattgtcaat ggaatctaac ggtaagtctg 1440
ttaccagagg taacgtgttt actgactact ctactggttc tatcttgttt ggtgaaccag 1500
ctaccaacgc tcaacactct ttcttccaat tggttcacca aggtaccaag ttgattccat 1560
ctgatttcat cttagctgct caatctcata acccaattga gaacaaatta catcaaaaga 1620
tgttggcttc aaacttcttt gctcaagctg aagctttaat ggttggtaag gatgaagaac 1680
aagttaaggc tgaaggtgcc actggtggtt tggtcccaca caaggtcttc tcaggtaaca 1740
gaccaactac ctctatcttg gctcaaaaga ttactccagc tactttgggt gctttgattg 1800
cctactacga acatgttact ttcactgaag gtgccatttg gaatatcaac tctttcgacc 1860
aatggggtgt tgaattgggt aaagtcttgg ctaaagtcat cggcaaggaa ttggacaact 1920
cctccaccat ttctacccac gatgcttcta ccaacggttt aatcaatcaa ttcaaggaat 1980
ggatgtgata aatggaggcg ctcgttgatc tgagccttgc cccctgacga acggcggtgg 2040
atggaagata ctgctctcaa gtgctgaagc ggtagcttag ctccccgttt cgtgctgatc 2100
agtctttttc aacacgtaaa aagcggagga gttttgcaat tttgttggtt gtaacgatcc 2160
tccgttgatt ttggcctctt tctccatggg cgggctgggc gtatttgaag cggttctctc 2220
ttctgccgtt a 2231

<210> SEQ ID NO 34
<211> LENGTH: 1709
<212> TYPE: DNA
<213> ORGANISM: Artificial Sequence
<220> FEATURE:
<223> OTHER INFORMATION: Synthetic Construct- Sequence No. 34,
Example 34: designer oxyphotobacterial Butanol Dehydrogenase DNA
construct (1709 bp)

<400> SEQUENCE: 34
agaaaatctg gcaccacacc atccaaactc gccacccgca aaccaatggc atggccgagc 60
gctgcaacgg tcgcattgcc aagattctgc gtgctgagcg ctttgtctcc gctgctgatc 120
tgcaagagac gctcacgcga tacctctggg cgtgcaatca ccgcattccc caacgcgctt 180
tgggccacat gacccccatc gagagactcc gaacgtggca aatggaggga ccagagttgt 240
tcagttcaca ggtagataat gtcgcgggtc ttgatagtta gcaataaata cagtttcaga 300
atatctgtaa tacaaaaact gtatcgagac aagaaaaaag tagcaaaatt tacaaatgtt 360
catgattcat ctggctaaat tggatgttca actgacccat tgaagacaag ggcaacaacc 420
atggagaatt ttagatttaa tgcatataca gagatgcttt ttggaaaggg acaaatagag 480
aagcttccag aggttttaaa aagatatggt aaaaatatat tacttgcata tggtggtgga 540
agtataaaaa agaatggact ctatgatact atccaaaagc tattgaaaga ttttaatatt 600
gttgaattaa gtggtattga accaaatcca agaattgaaa ctgtaagacg tggagttgaa 660
ctttgcagaa aaaataaagt agatgttatt ttagctgttg gtggagggag tacaatagac 720
tgctcaaagg ttataggggc aggttattat tatgctggag atgcatggga ccttgtaaaa 780
aatccagcta aaataggtga ggttttacca atagtgacag ttttaacaat ggcagctact 840
ggttctgaaa tgaatagaaa tgctgttatt tcaaagatgg atacaaatga aaagcttgga 900
acaggatcac ctaagatgat ccctcaaact tctattttag atccagaata tttgtataca 960
ttgccagcaa ttcaaacagc tgcaggttgt gctgatatta tgtcacacat atttgaacaa 1020
tattttaata aaactacaga tgcttttgta caagataaat ttgcggaagg tttgttgcaa 1080
acttgtataa aatattgccc tgttgcttta aaggaaccaa agaattatga agctagagca 1140
aatataatgt gggctagttc aatggctctt aacggacttt taggaagtgg gaaagctgga 1200
gcttggactt gtcatccaat agaacatgaa ttaagtgcat tttatgatat aactcatgga 1260
gtaggtcttg caattttaac tccaagttgg atgagatata tcttaagtga tgtaacagtt 1320
gataagtttg ttaacgtatg gcatttagaa caaaaagaag ataaatttgc tcttgcaaat 1380
gaagcaatag atgcaacaga aaaattcttt aaagcttgtg gtattccaat gactttaact 1440
gaacttggaa tagataaagc aaactttgaa aagatggcaa aagctgcagt agaacatggt 1500
gctttagaat atgcatatgt ttcattaaat gccgaggatg tatataaaat tttagaaatg 1560
tccctttaat aaggctgaga tcttcttcag tgcattgtag ttgaatgaag ggttaggggg 1620
gaaatgcccc cctatttttt gtctagccat cctgccacgt ttgacagggt agcaatttcg 1680
acacgatagg gttctctctt ctgccgtta 1709

<210> SEQ ID NO 35
<211> LENGTH: 1967
<212> TYPE: DNA
<213> ORGANISM: Artificial Sequence
<220> FEATURE:
<223> OTHER INFORMATION: Synthetic Construct- Sequence No. 35, Example 35: designer oxyphotobacterial Butyraldehyde Dehydrogenase DNA construct (1967 bp)

<400> SEQUENCE: 35

```
agaaaatctg gcaccacacc atccaaactc gccacccgca aaccaatggc atggccgagc     60
gctgcaacgg tcgcattgcc aagattctgc gtgctgagcg ctttgtctcc gctgctgatc    120
tgcaagagac gctcacgcga tacctctggg cgtgcaatca ccgcattccc caacgcgctt    180
tgggccacat gacccccatc gagagactcc gaacgtggca aatggaggga ccagagttgt    240
tcagttcaca ggtagataat gtcgcgggtc ttgatagtta gcaataaata cagtttcaga    300
atatctgtaa tacaaaaact gtatcgagac aagaaaaaag tagcaaaatt tacaaatgtt    360
catgattcat ctggctaaat tggatgttca actgacccat tgaagacaag ggcaacaacc    420
atgattaaag acacgctagt ttctataaca aaagatttaa aattaaaaac aaatgttgaa    480
aatgccaatc taaagaacta caaggatgat tcttcatgtt tcggagtttt cgaaaatgtt    540
gaaaatgcta taagcaatgc cgtacacgca caaaagatat tatcccttca ttatacaaaa    600
gaacaaagag aaaaaatcat aactgagata agaaaggccg cattagaaaa taaagagatt    660
ctagctacaa tgattcttga agaaacacat atgggaagat atgaagataa aatattaaag    720
catgaattag tagctaaata cactcctggg acagaagatt taactactac tgcttggtca    780
ggagataacg ggcttacagt tgtagaaatg tctccatatg gcgttatagg tgcaataact    840
ccttctacga atccaactga aactgtaata tgtaatagta taggcatgat agctgctgga    900
aatactgtgg tatttaacgg acatccaggc gctaaaaaat gtgttgcttt tgctgtcgaa    960
atgataaata aagctattat ttcatgtggt ggtcctgaga atttagtaac aactataaaa   1020
aatccaacta tggactctct agatgcaatt attaagcacc cttcaataaa actactttgc   1080
ggaactggag ggccaggaat ggtaaaaacc ctcttaaatt ctggtaagaa agctataggt   1140
gctggtgctg gaaatccacc agttattgta gatgatactg ctgatataga aaaggctggt   1200
aagagtatca ttgaaggctg ttcttttgat aataatttac cttgtattgc agaaaaagaa   1260
gtatttgttt ttgagaacgt tgcagatgat ttaatatcta acatgctaaa aaataatgct   1320
gtaattataa atgaagatca agtatcaaag ttaatagatt tagtattaca aaaaaataat   1380
gaaactcaag aatactctat aaataagaaa tgggtcggaa aagatgcaaa attattctta   1440
gatgaaatag atgttgagtc tccttcaagt gttaaatgca taatctgcga agtaagtgca   1500
aggcatccat ttgttatgac agaactcatg atgccaatat taccaattgt aagagttaaa   1560
gatatagatg aagctattga atatgcaaaa atagcagaac aaaatagaaa acatagtgcc   1620
tatatttatt caaaaaatat agacaaccta aataggtttg aaagagaaat cgatactact   1680
atctttgtaa agaatgctaa atcttttgcc ggtgttggtt atgaagcaga aggctttaca   1740
actttcacta ttgctggatc cactggtgaa ggaataactt ctgcaagaaa ttttacaaga   1800
caaagaagat gtgtactcgc cggttaataa ggctgagatc ttcttcagtg cattgtagtt   1860
gaatgaaggg ttaggggga aatgcccccc tattttttgt ctagccatcc tgccacgttt   1920
gacagggtag caatttcgac acgatagggt tctctcttct gccgtta                 1967
```

<210> SEQ ID NO 36
<211> LENGTH: 1602
<212> TYPE: DNA
<213> ORGANISM: Artificial Sequence
<220> FEATURE:
<223> OTHER INFORMATION: Synthetic Construct- Sequence No. 36, Example 36: designer oxyphotobacterial Butyryl-CoA Dehydrogenase DNA construct (1602 bp)

<400> SEQUENCE: 36

```
agaaaatctg gcaccacacc tgatctgcaa gagacgctca cgcgatacct ctgggcgtgc     60
aatcaccgca ttccccaacg cgctttgggc cacatgaccc ccatcgagag actccgaacg    120
tggcaaatgg agggaccaga gttgttcagt tcacaggtag ataatgtcgc gggtcttgat    180
agttagcaat aaatacagtt tcagaatatc tgtaatacaa aaactgtatc gagacaagaa    240
aaaagtagca aaatttacaa atgttcatga ttcatctggc taaattggat gttcaactga    300
cccattgaag acaagggcaa caaccatgaa tttccaatta actagagaac aacaattagt    360
acaacaaatg gttagagaat tcgcagtaaa tgaagttaag ccaatagctg ctgaaatcga    420
cgaaacagaa agattcccta tggaaaacgt tgaaaaaatg gctaagctta aaatgatggg    480
tatcccattt tctaaagaat ttggtggagc aggcggagat gttctttcat atataatagc    540
tgtggaagaa ttatcaaaag tttgtggtac tacaggagtt attctttcag cgcatacatc    600
attatgtgca tcagtaatta atgaaaatgg aactaacgaa caaagagcaa aatatttacc    660
tgatctttgc agcggtaaaa agatcggtgc tttcggatta actgaaccag gtgctggtac    720
agatgctgca ggacaacaaa caactgctgt attagaaggg gatcattatg tattaaatgg    780
ttcaaaaatc ttcataacaa atggtggagt tgctgaaact ttcataatat ttgctatgac    840
agataagagt caaggaacaa aaggaatttc tgcattcata gtagaaaagt cattcccagg    900
attctcaata ggaaaattag aaaataagat ggggatcaga gcatcttcaa ctactgagtt    960
agttatggaa aactgcatag taccaaaaga aaacctactt agcaaagaag gtaagggatt   1020
tggtatagca atgaaaactc ttgatggagg aagaattggt atagctgctc aagctttagg   1080
tattgcagaa ggagcttttg aagaagctgt taactatatg aaagaaagaa aacaatttgg   1140
taaaccatta tcagcattcc aaggattaca atggtatata gctgaaatgg atgttaaaat   1200
ccaagctgct aaatacttag tatacctagc tgcaacaaag aagcaagctg gtgagcctta   1260
ctcagtagat gctgcaagag ctaaattatt tgctgcagat gttgcaatgg aagttacaac   1320
taaagcagtt caaatctttg gtggatatgg ttacactaaa gaatacccag tagaaagaat   1380
gatgagagat gctaaaatat gcgaaatcta cgaaggaact tcagaagttc aaaagatggt   1440
tatcgcagga agcattttaa gataaggctg agatcttctt cagtgcattg tagttgaatg   1500
aagggttagg ggggaaatgc ccccctattt tttgtctagc catcctgcca cgtttgacag   1560
ggtagcaatt tcgacacgat agggttctct cttctgccgt ta                       1602
```

<210> SEQ ID NO 37
<211> LENGTH: 1248
<212> TYPE: DNA
<213> ORGANISM: Artificial Sequence
<220> FEATURE:
<223> OTHER INFORMATION: Synthetic Construct- Sequence No. 37,
Example 37: designer oxyphotobacterial Crotonase DNA construct
(1248 bp)

<400> SEQUENCE: 37

```
agaaaatctg gcaccacacc tgatctgcaa gagacgctca cgcgatacct ctgggcgtgc     60
aatcaccgca ttccccaacg cgctttgggc cacatgaccc ccatcgagag actccgaacg    120
tggcaaatgg agggaccaga gttgttcagt tcacaggtag ataatgtcgc gggtcttgat    180
agttagcaat aaatacagtt tcagaatatc tgtaatacaa aaactgtatc gagacaagaa    240
aaaagtagca aaatttacaa atgttcatga ttcatctggc taaattggat gttcaactga    300
```

-continued

```
cccattgaag acaagggcaa caaccatgga attaaaaaat gttattcttg aaaaagaagg    360

gcatttagct attgttacaa tcaatagacc aaaggcatta aatgcattga attcagaaac    420

actaaaagat ttaaatgttg ttttagatga tttagaagca gacaacaatg tgtatgcagt    480

tatagttact ggtgctggtg agaaatcttt tgttgctgga gcagatattt cagaaatgaa    540

agatcttaat gaagaacaag gtaaagaatt tggtatttta ggaaataatg tcttcagaag    600

attagaaaaa ttggataagc cagttatcgc agctatatca ggatttgctc ttggtggtgg    660

atgtgaactt gctatgtcat gtgacataag aatagcttca gttaaagcta aatttggtca    720

accagaagca ggacttggaa taactccagg atttggtgga actcaaagat tagcaagaat    780

agttggacca ggaaaagcta aagaattaat ttatacttgt gaccttataa atgcagaaga    840

agcttataga ataggcttag ttaataaagt agttgaatta gaaaaattga tggaagaagc    900

aaaagcaatg gctaacaaga ttgcagctaa tgctccaaaa gcagttgcat attgtaaaga    960

tgctatagac agaggaatgc aagttgatat agatgcagct atattaatag aagcagaaga   1020

ctttgggaag tgctttgcaa cagaagatca aacagaagga atgactgcgt tcttagaaag   1080

aagagcagaa aagaattttc aaaataaata aggctgagat cttcttcagt gcattgtagt   1140

tgaatgaagg gttagggggg aaatgccccc ctatttttg tctagccatc ctgccacgtt    1200

tgacagggta gcaatttcga cacgataggg ttctctcttc tgccgtta                1248
```

<210> SEQ ID NO 38
<211> LENGTH: 1311
<212> TYPE: DNA
<213> ORGANISM: Artificial Sequence
<220> FEATURE:
<223> OTHER INFORMATION: Synthetic Construct- Sequence No. 38, Example 38: designer oxyphotobacterial 3-Hydroxybutyryl-CoA Dehydrogenase DNA construct (1311 bp)

<400> SEQUENCE: 38

```
agaaaatctg gcaccacacc tgatctgcaa gagacgctca cgcgatacct ctgggcgtgc     60

aatcaccgca ttccccaacg cgctttgggc cacatgaccc ccatcgagag actccgaacg    120

tggcaaatgg agggaccaga gttgttcagt tcacaggtag ataatgtcgc gggtcttgat    180

agttagcaat aaatacagtt tcagaatatc tgtaatacaa aaactgtatc gagacaagaa    240

aaaagtagca aaatttacaa atgttcatga ttcatctggc taaattggat gttcaactga    300

cccattgaag acaagggcaa caaccatgaa aaagattttt gtacttggag caggaactat    360

gggtgctggt atcgttcaag cattcgctca aaaaggttgt gaggtaattg taagagacat    420

aaaggaagaa tttgttgaca gaggaatagc tggaatcact aaaggattag aaaagcaagt    480

tgctaaagga aaaatgtctg aagaagataa agaagctata ctttcaagaa tttcaggaac    540

aactgatatg aagttagctg ctgactgtga tttagtagtt gaagctgcaa tcgaaaacat    600

gaaaattaag aaggaaatct ttgctgagtt agatggaatt tgtaagccag aagcgatttt    660

agcttcaaac acttcatctt tatcaattac tgaagttgct tcagctacaa agagacctga    720

taaagttatc ggaatgcatt tctttaatcc agctccagta atgaagcttg ttgaaattat    780

taaaggaata gctacttctc aagaaacttt tgatgctgtt aaggaattat cagttgctat    840

tggaaaagaa ccagtagaag ttgcagaagc tccaggattc gttgtaaacg gaatcttaat    900

cccaatgatt aacgaagctt cattcatcct tcaagaagga atagcttcag ttgaagatat    960

tgatacagct atgaaatatg gtgctaacca tccaatggga cctttagctt taggagatct   1020
```

-continued

```
tattggatta gatgtttgct tagctatcat ggatgtttta ttcactgaaa caggtgataa   1080

caagtacaga gctagcagca tattaagaaa atatgttaga gctggatggc ttggaagaaa   1140

atcaggaaaa ggattctatg attattctaa ataaggctga gatcttcttc agtgcattgt   1200

agttgaatga agggttaggg gggaaatgcc cccctatttt ttgtctagcc atcctgccac   1260

gtttgacagg gtagcaattt cgacacgata gggttctctc ttctgccgtt a            1311
```

<210> SEQ ID NO 39
<211> LENGTH: 1665
<212> TYPE: DNA
<213> ORGANISM: Artificial Sequence
<220> FEATURE:
<223> OTHER INFORMATION: Synthetic Construct- Sequence No. 39, Example 39: designer oxyphotobacterial Thiolase DNA construct (1665 bp)

<400> SEQUENCE: 39

```
agaaaatctg gcaccacacc tgatctgcaa gagacgctca cgcgatacct ctgggcgtgc     60

aatcaccgca ttccccaacg cgctttgggc cacatgaccc ccatcgagag actccgaacg    120

tggcaaatgg agggaccaga gttgttcagt tcacaggtag ataatgtcgc gggtcttgat    180

agttagcaat aaatacagtt tcagaatatc tgtaatacaa aaactgtatc gagacaagaa    240

aaaagtagca aaatttacaa atgttcatga ttcatctggc taaattggat gttcaactga    300

cccattgaag acaagggcaa caaccatggg caaagaaagt agttttagct gtgcatgtcg    360

tacagccatc ggaacaatgg gtggatctct tagcacaatt cctgcagtag atttaggtgc    420

tatcgttatc aaagaggctc ttaaccgcgc aggtgttaaa cctgaagatg ttgatcacgt    480

atacatggga tgcgttattc aggcaggaca gggacagaac gttgctcgtc aggcttctat    540

caaggctggt cttcctgtag aagtacctgc agttacaact aacgttgtat gtggttcagg    600

tcttaactgt gttaaccagg cagctcagat gatcatggct ggagatgctg atatcgttgt    660

tgccggtggt atggaaaaca tgtcacttgc accatttgca cttcctaatg gccgttacgg    720

atatcgtatg atgtggccaa gccagagcca gggtggtctt gtagacacta tggttaagga    780

tgctctttgg gatgctttca atgattatca tatgatccag acagcagaca acatctgcac    840

agagtggggt cttacacgtg aagagctcga tgagtttgca gctaagagcc agaacaaggc    900

ttgtgcagca atcgaagctg gcgcattcaa ggatgagatc gttcctgtag agatcaagaa    960

gaagaaagag acagttatct tcgatacaga tgaaggccca agacagggtg ttacacctga   1020

atctctttca aagcttcgtc ctatcaacaa ggatggattc gttacagctg gtaacgcttc   1080

aggtatcaac gacggtgctg cagcactcgt agttatgtct gaagagaagg ctaaggagct   1140

cggcgttaag cctatggcta cattcgtagc tggagcactt gctggtgttc gtcctgaagt   1200

tatgggtatc ggtcctgtag cagctactca gaaggctatg aagaaggctg gtatcgagaa   1260

cgtatctgag ttcgatatca tcgaggctaa cgaagcattc gcagctcagt ctgtagcagt   1320

tggtaaggat cttggaatcg acgtccacaa gcagctcaat cctaacggtg gtgctatcgc   1380

tcttggacac ccagttggag cttcaggtgc tcgtatcctt gttacacttc ttcacgagat   1440

gcagaagaaa gacgctaaga agggtcttgc tacactttgc atcggtggcg gtatgggatg   1500

cgctactatc gttgagaagt acgaataagg ctgagatctt cttcagtgca ttgtagttga   1560

atgaagggtt aggggggaaa tgcccccccta tttttgtct agccatcctg ccacgtttga   1620

cagggtagca atttcgacac gatagggttc tctcttctgc cgtta                  1665
```

<210> SEQ ID NO 40
<211> LENGTH: 4071
<212> TYPE: DNA
<213> ORGANISM: Artificial Sequence
<220> FEATURE:
<223> OTHER INFORMATION: Synthetic Construct- Sequence No. 40, Example 40: designer oxyphotobacterial Pyruvate-Ferredoxin Oxidoreductase DNA construct (4071 bp)

<400> SEQUENCE: 40

```
agaaaatctg gcaccacacc tgatctgcaa gagacgctca cgcgatacct ctgggcgtgc     60

aatcaccgca ttccccaacg cgctttgggc cacatgaccc ccatcgagag actccgaacg    120

tggcaaatgg agggaccaga gttgttcagt tcacaggtag ataatgtcgc gggtcttgat    180

agttagcaat aaatacagtt tcagaatatc tgtaatacaa aaactgtatc gagacaagaa    240

aaaagtagca aaatttacaa atgttcatga ttcatctggc taaattggat gttcaactga    300

cccattgaag acaagggcaa caaccatggc gcagaggtgc aaggagcccg tcgacggaac    360

gacagccacg acgcacgtgg cctacttcat gagcgacagc gcgttcatct tccccatcac    420

gcccagctcg gtcatgtccg aggtcgccca cgagtggtcc atgaacggcc gcaagaacgc    480

cttcggccag cccacgatgg tccgccagat gcagagcgag gctgggtctg ccggcgccct    540

gcacggcgcg ctcagcgagg gagcgctggc gacgacgttc acgagcagcc agggcctgct    600

gctcatgatc cccaacatgt acaagatcgc cggcgagctc ctgccctgcg tcatgcacat    660

cgccgcccgc accgtcgcca ccgaggccct ctctatcttc ggcgaccaca cggatgtcta    720

cgcggtgagg tcgacggggt tcgcgttcct gtgctccgcg accgtccagg agtgcatcca    780

catgtccgcc gccgcgcacg ccgccaccct gtccagcgag gtcccgttcg cccacttctt    840

cgacggcttc cgcacgtccc acgagatcca gaagatcgac ttcccctcgg acgccgacct    900

gctggcctgc atgaactttg acgacgtccg caggttccgt ggccgctcgc tgtgctgcga    960

gcgcccgctg ctgcgcggga cggcgcagaa ccccgacgtc ttcatgcagg cgtccgagtc   1020

gaacctggcg acgctggcca gggtccccgc ggccatcgac gaggcgctgg ctcgtgtgaa   1080

caaggtgttc gggaccaact acaggaccta cgagtactat ggccaccccg aggccacgga   1140

cgtgatcgtg gccatgggaa gcggcaccga agtggccatc tcgactgcca acttcctcaa   1200

ctcgcgcgac gcgaactcga gggtcggcgt cgtgagggtg cggctgttcc ggccgtttgt   1260

gtcggcggcg tttgtggctg cgctgcccaa gaccgtcaag aggatctgcg ttctggaccg   1320

cgggagggac gggcaggcgg ccgcggaccc cctgcaccag gacgtcctgt cggcgctggg   1380

tctggcagcg cccgggaggg ttcaggtgtg cgtgggaggc gtgtacggtc tgtcgtccaa   1440

ggacttcaac cccgaccacg tgatcgccgt gtacaggaac ctcgcgtcgg cgagccccaa   1500

gaacaggttc agcgtcggca tcgtcgacga cgtgacgcac aacagcctgg acatgggaga   1560

gcacgtggac gcgctgccgc aggggacgaa gcagtgcctg ctgtggggca tcggcggaga   1620

cgggaccatc ggggcgaaca agacggccat caagctgatc gcggaccaca cggagctgca   1680

cgcgcagggg tactttgcgt acgacgccaa caaggccggc ggcctgacag tctcgcacct   1740

gcggttcggc ccgacgcggt tcgaggcgcc gtacctggtg aacgacagca actacgtggc   1800

gtgccacaac ttctcgtacg tgcacaggtt caacctgctg tcgtcgctgc gcaccggggg   1860

cacgttcgtg ctcaactgcc cgtgccggac cgtggaggag ctggacacgg cactcccggt   1920

gcgcctgagg cgcgagatcg ccaggcggca ggccaagttc tatgtgatcg acgcgaccaa   1980

gatcgccaag gacaacggga tgggcccgtt catcaacatg gtcctccagg ccgtgttctt   2040
```

```
ctatctgtcc cacgtgctcg atgtgaacga ggcagtggca ctcctgaaga agagcatcca   2100
gaagatgtac gcgcgcaagg gcgaggaggt tgtcaggaag aacgtggcat cggtcgacgc   2160
gtcgctggat cccaaggcgt tgctgcacat cgagtacccc gcagacaggt ggcttgcgct   2220
ggccgacgag cacgtgcccc gcatgggtct gctcactgtc cccgagcgcc tgcagaagtt   2280
caacgccgag ctgtacgagc cgaccctcgc gtacgatggg gagagcatcc cggtcagcag   2340
gttccctcgc ggcggcgaga cgccgacggg cacgactcag ctgggcaagc gtggcatcgc   2400
cgagagcgtg ccgcactgga accacgagaa gtgcgtgcag tgcaaccagt gctcgttcgt   2460
gtgcccgcac gccgtcatcc ggtcgtacca gatcagcgag gaggagatga agaacgcccc   2520
tgccggcttc gacactctta agtcgcgcaa gcccgggtat cgtttccgca tcaacgtcag   2580
cgccctggac tgcactggct gcagcgtgtg cgtggagcag tgcccagtca agtgcctgga   2640
gatgaagcct ctcgagtccg agttcgagat gcagaaggac gccatcaggt tcgtccgcga   2700
gatggtcgcg cccaagcccg agctgggaga ccgcaagact cccgtcggca tcgcgtctca   2760
cacgccgctg ttcgagttcc cgggagcctg cgccgggtgc ggtgagaccc cgctggtgcg   2820
cctcgtgacg cagatgttcg gtgagcgcat ggtcatcgcc gcggccactg ggtgcaactc   2880
gatctgggga gcgtcgttcc cgaacgtgcc gtacacaacc aacgcccgcg gggagggccc   2940
cgcgtggcac aactcgctgt tcgaggacgc ggcggagctc gggtatggca ttacgtgtgc   3000
gtatcgccag cgccgcgagc gcctcatcgg catcgtgcgg agcgtcgtcg acgatgcggg   3060
atccgtgcag ggtctgtctg ctgagctgaa ggctctgctg gtcgagtggc tcgcgcacgt   3120
cagggacttc gagaagaccc gcgagctccg cgacaggatg aaccccctga tcgacgcaat   3180
cccagcgaac gcggactgca gggttctgga gctcagggag aagcacaacc gcgagctgat   3240
cgcgcgcacg agtttctgga tcctcggtgg cgacgggtgg gcgtacgaca tcggcttcgg   3300
tggactggac cacgtgatcg ccaacaacga ggacgtcaac atccttgttc tcgacacgga   3360
ggtctactcc aacactggtg gccagcgctc caagtcgacg ccgctcggcg cccgcgccaa   3420
gtacgctgtg ctgggcaagg acactgggaa gaaggacctg ggcgcatcg cgatgaccta   3480
cgagaccgcg tacgtggcca gcatcgcgca gggagccaac cagcagcagt gcatggacgc   3540
gctgagggag gccgaggcct accagggccc ctcgatcgtc attgcgtaca ctccgtgcat   3600
ggagcaccag atggtccgcg ggatgaagga gagccagaag aaccagaagc tggctgtgga   3660
gacgggctac tggctgctgt accgcttcaa ccccgacctc atccacgagg gcaagaaccc   3720
cttcaccctc gactcgaagc ctccctcgaa gcctcccaag gagttcctgg acacgcaggg   3780
ccgtttcatt actctgcagc gcgagcaccc cgagcaggcc cacctccttc acgaggcact   3840
cacccgctct ctggccaccc gcttcgtgcg ctaccagcgc ctcgtgcagc tgtacgagcc   3900
cgctgcccct gccgcagctc ctgccacgca ttaaggctga gatcttcttc agtgcattgt   3960
agttgaatga agggttaggg gggaaatgcc cccctatttt ttgtctagcc atcctgccac   4020
gtttgacagg gtagcaattt cgacacgata gggttctctc ttctgccgtt a            4071
```

<210> SEQ ID NO 41
<211> LENGTH: 1806
<212> TYPE: DNA
<213> ORGANISM: Artificial Sequence
<220> FEATURE:
<223> OTHER INFORMATION: Synthetic Construct- Sequence No. 41, Example 41: designer oxyphotobacterial Pyruvate Kinase DNA construct (1806 bp)

<400> SEQUENCE: 41

```
agaaaatctg gcaccacacc tgatctgcaa gagacgctca cgcgatacct ctgggcgtgc     60
aatcaccgca ttccccaacg cgctttgggc cacatgaccc ccatcgagag actccgaacg    120
tggcaaatgg agggaccaga gttgttcagt tcacaggtag ataatgtcgc gggtcttgat    180
agttagcaat aaatacagtt tcagaatatc tgtaatacaa aaactgtatc gagacaagaa    240
aaaagtagca aaatttacaa atgttcatga ttcatctggc taaattggat gttcaactga    300
cccattgaag acaagggcaa caaccgtgtt cactaaaatt gtagctacat tggggccttc    360
gactgataga ctgccggata taacggccct gttgagcaag gttcacggcg tgcggataaa    420
tatgtctcac gcatcgccat cggaggtaga ggcccgcgtg aacgccgtga ggaagtatga    480
ggagaccagc gggaggtata tagccattat agcggatcta aggggcccca gcgtcaggac    540
cggccttatg cgccctctac agataacggc gggcgcccgc gtctccttta aattagccga    600
gaagggggac ggcttcgtac ctgtgccgcg gcgtgagttc ttcgaagtaa tcgaggaggg    660
agacgaggtt cttatgttag acggaaaact cgtcttgagg ataatcagcg cagcgcagac    720
ctcggccgag gccgagtcgt tatcctccgg cgtcatatcc agcaataagg caatagtggt    780
caaaggcaag gaatatcata tagagcagcc tgtggaggaa gacataaggg cgcttcagac    840
gctctctcgg ttcagagacg acgtagacta cgtggccctc agccttgtga gagacggagc    900
agacgtgagg aaaatgagga gcgtcgtcga ggaggctggg ctcacctccg gcataatggc    960
caaaatagag acgaagagcg cagtagataa aatcgaggag ataatcaatg cggccgacta   1020
catagttata gcgagaggcg atctggcgct gcactacgga ctggagtaca ttcctaaagt   1080
acagaggctc ttggtggaga gatctctctc ggcaggaagg cccgtggcgg tggccacgca   1140
gcttttggac tctatgcaga ccaacacgac gcccactagg gcggaggtca acgacgtgta   1200
cacaacggcg agtctcggag tggactctct gtggctgacc aacgagactg cgagcggaga   1260
gcacccgtta gaggcagtgg attggctgag gaggatagtg tcgcaggtcg agttcgggag   1320
acttaaggct gcgtcgccgg ccgacgcacg cgataggttc gccaaagccg tggtagatat   1380
ggccgaggac atgggagggg aaatcgcagt atactcaatg acgggaactc tggcgaagag   1440
aatagctaaa tttaggccga tgacgacagt ctacgtcgga gtcaacgaga ggaggctcgc   1500
gaggatgttg gagctccgcg aggatgttgg agctcatatg gggcctagag cctgtggtcg   1560
tgccggcgca tacttacgag gagggcctcg agaggctcct ctccagattc tccgacaaag   1620
tcttgatagc cacgtatggg ctcagaggcg gcacacatac tattaataag gctgagatct   1680
tcttcagtgc attgtagttg aatgaagggt tagggggaa atgcccccct attttttgtc   1740
tagccatcct gccacgtttg acagggtagc aatttcgaca cgatagggtt ctctcttctg   1800
ccgtta                                                              1806
```

<210> SEQ ID NO 42
<211> LENGTH: 1696
<212> TYPE: DNA
<213> ORGANISM: Artificial Sequence
<220> FEATURE:
<223> OTHER INFORMATION: Synthetic Construct- Sequence No. 42, Example 42: designer oxyphotobacterial Enolase DNA construct (1696 bp)

<400> SEQUENCE: 42

```
agaaaatctg gcaccacacc tgacccccat cgagagactc cgaacgtggc aaatggaggg     60
accagagttg ttcagttcac aggtagataa tgtcgcgggt cttgatagtt agcaataaat    120
```

-continued

```
acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac cttatttttt cttcaagtta aagaatgcgt tcattccagg ataaacggca    300

atgctgccaa gctcttcttc aattctcaag agctgattgt attttgctac tctgtctgtt    360

cttgacggtg cacctgtctt tatctgacca gcatttactg caacaacaag gtcagcaatt    420

gttgtatctt cagtctcacc tgatctgtgg gatacaactg cagtgtagcc tgctctattt    480

gccatttcaa tagcttctaa agtttctgta agtgttccta tctgattaag cttaatcaat    540

attgagtttg caacgccaag ttctattccc tttgcaagcc tctttgtgtt tgtaacaaac    600

aaatcatcac ccacaagctg aatcttcttg ccaagtgctt cagttagcat cttccagcct    660

tcccagtcct cttctgcaac accgtcttca attgatacaa ttgggtactt ttcaacaagt    720

tttacccaga attctaccat ttcttctttt gttctaactt taccttctct ttcgaaatga    780

tactttccat cttcttcatt gtagagctca gatgttgcag ggtcaagcgc aattgcaata    840

tccttaccag gagtataacc agctttttca attgcttcga caattacttc caatggctct    900

tcgttagact tcaagtttgg tgcaaatcca ccttcatcac ccactgttgt gttgtatcct    960

cttgccttca atacatttct taattgatgg aatgtctcag cacacatcct gagtgcttcg   1020

ctaaaagatt ttgcaccaac tggcattatc ataaactctt gtaggtcaac agagttgtca   1080

gcatgctttc caccgttcaa aatattcatc attggcacag gtaaatactt tgcattgaca   1140

ccaccaatgt attggtacag tggaagacca agtgcgtttg ccgctgcctt cgcaactgcc   1200

aaagatacac ccaaaattgc atttgcacca agcttgctct tgttctctgt cccatcaagc   1260

tcaatcataa gcctgtcaat ctcaacttgg ttaagagcgt tcattccaat tatttctggc   1320

gcaataacct cgtttacatt ttcgactgct ttgagaaccc cttttcccat atatcttttt   1380

ttatcaccgt ctctgagttc aacagcctcg aacatacctg ttgacgcacc tgatggaaca   1440

gcagctctac ctacaaattc atcatttaca acaacttcta cttcaacagt tgggtttcct   1500

cttgaatcca gaatttctct tgcttttaca gctgtaattg aaagatcaac cttcattaag   1560

gctgagatct tcttcagtgc attgtagttg aatgaagggt taggggggaa atgcccccct   1620

atttttgtc tagccatcct gccacgtttg acagggtagc aatttcgaca cgatagggtt   1680

ctctcttctg ccgtta                                                   1696
```

<210> SEQ ID NO 43
<211> LENGTH: 2029
<212> TYPE: DNA
<213> ORGANISM: Artificial Sequence
<220> FEATURE:
<223> OTHER INFORMATION: Synthetic Construct- Sequence No. 43,
Example 43: designer oxyphotobacterial Phosphoglycerate-Mutase
DNA construct (2029 bp)

<400> SEQUENCE: 43

```
agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac cctacgccgg cgcctgcttc tcctcctgcc ggcagcactt ctccaaaggg    300

tgcacgttcg cttctcttgt aatcagggtc tggccggtca tctcggccgg tttcgggatg    360

cccagcaggt gcaggatggt gggggccaca tcccgcaggc tgccgtcccg cagcgcaatg    420
```

```
ccggcggtat cccgcccgat caggatgaac ggcaccgggc tggtggtgtg ggccgtatga    480
ggctgtccct cttcgtccac catctcatcc gcattgccgt ggtctgccgt tatcaggagc    540
gtgccgtcct tttccaggac ggcccgcgcc acctttccaa ggcagcggtc gattgtttct    600
atggccttta ccgttgcctt catgtcgccg gtatgcccga ccatgtcggg attggcgtaa    660
ttcattatga ttacgtcgta cttgcccgag gccagccgct ccagaaaggt gccggtgacc    720
tcgttggcgc tcatttcggg cttcaggtcg taggtggcca cccgcgggga gggcaccagg    780
atcctgtctt cgccggggta tggcttttct aagccgccgt tgaagaagaa ggtcacatgg    840
gcgtactttt ccgtttcggc caggcggagc tgggtcatgc cgtgcctgct taaaacctcg    900
cccagggtat tgcgcagctc ctgcggctga aacgccaccg gcgccttaat ggtcttgtcg    960
taaagggtca tgcaggtaaa atgcacggca gggtagccct gctttctggc aaacccggtg   1020
aaatcctcgt ccacaaaggc cctggtaatc tggcgggccc ggtccggccg gaagttaaag   1080
aaaataacgg cgtcgccctt cattattttg gcggccggcc cacccgaccc gtttaccacg   1140
acggtgggct ggataaactc gtcggtttca tcccttccgt accccaggtc aaccgcctcc   1200
agcgggcttg ttgcctgaat gccctcgcct aaaaccattg cgttgtacgc ccgctcggtg   1260
cggtcccagc ggcggtctct gtccatggcg taatagcgcc ccattaccgt tgccaccgcc   1320
ccaaagccca gttcgcccag cttcttcctt aactgctcga agtattcttt tgcgttggcc   1380
ggcggcacgt cgcgcccgtc caggaaggca tggacaaaga cgttgcgcat gttctcgcgg   1440
gcggccaggt ccaggagggc gaaaaggtgg ctgatatggc tgtgcactcc gccgtccgat   1500
aaaagcccca tcaggtgaag ggccttatta ttctccctgg cgtatctcac cgcctccagc   1560
aggacttcgt tcttgaaaaa ggtcccgtcc ttgatggcgc ggcttattct ggtaagctcc   1620
tggtacacca ccctgccggc gcctatgttc aagtgtccca cctcggaatt gcccatctgg   1680
ccctcgggaa gccccacgtc ctcgccggaa cagctcaggg cacagtgggg gtaaccggcc   1740
agaaagctct tgaaattcgg tgtgctggcc agggctatgg cattgccccg gacattggaa   1800
ctgaggcccc agccgtccag aaccaccagc accaggggcc tgccgccggc ataccggccg   1860
cagggcgttg cagctacgtc ttccttcaat aaggctgaga tcttcttcag tgcattgtag   1920
ttgaatgaag ggttaggggg gaaatgcccc cctatttttt gtctagccat cctgccacgt   1980
ttgacagggt agcaatttcg acacgatagg gttctctctt ctgccgtta              2029
```

<210> SEQ ID NO 44
<211> LENGTH: 1687
<212> TYPE: DNA
<213> ORGANISM: Artificial Sequence
<220> FEATURE:
<223> OTHER INFORMATION: Synthetic Construct- Sequence No. 44, Example 44: designer oxyphotobacterial Phosphoglycerate Kinase DNA construct (1687 bp)

<400> SEQUENCE: 44

```
agaaaatctg gcaccacacc tgacccccat cgagagactc cgaacgtggc aaatggaggg     60
accagagttg ttcagttcac aggtagataa tgtcgcgggt cttgatagtt agcaataaat    120
acagtttcag aatatctgta atacaaaaac tgtatcgaga caagaaaaaa gtagcaaaat    180
ttacaaatgt tcatgattca tctggctaaa ttggatgttc aactgaccca ttgaagacaa    240
gggcaacaac cttatttatc gagcagcgcc cttactcccg gcagttgctt cccttccaga    300
aactccaggg aagcgccgcc gccggttgag atatgggtca ttttgccggc tacgccggcc    360
```

```
ttcttggccg ccgccgccgt gtcaccgccg ccgattacgg tgacggcgtt taattcggcc    420

agcgtccggg ctattgcttc ggtgcccctg gcaaaaggat ccatttcaaa aacgcccatt    480

ggtccgttcc agaccacggt cctggccgcc ctgagggctt cggtgaaaag tctgatggac    540

tcgggcccta tatccagggc catccactcc gccgggattt gatcgaccgg caccgtcctt    600

tgctcctggc cgggcgccgg ccccggcgcc accaccacat ccaccggcag gaggagcttt    660

acttccctgc ttctggcttc tgcaatcagc ttcctggcca ggtcaatctt gtcggcctcc    720

agcagggact taccgacgct gtacccttgt gccttcagaa aggtattggc catcccgccg    780

ccaatgataa ccgtatcgac tttggtcagc aggttgaaaa ttactcccag cttgtcggaa    840

actttcgagc cgcccacgac ggctgcaaaa gggcgctccg ggctggtcag cagcctgccc    900

agtatttcca gctctttttc catcagcagg cctgccacgg ccggcaaaaa cccggcaacg    960

ccctcggtgg aggcgtgggc ccggtgtgcg gttccaaacg catcgtttac aaagacatct   1020

gccagctcag ccagttgccg ggcaaacttc tcgtcgtttt tctcctcctc cgggtggaaa   1080

cggacgtttt ccagcagcac cacgtccccg tcctgcatct gggcaacggc ggacctggcg   1140

gcttctccca cgcagtcgcc ggccttaacc accgttttcc ccagcagttc ggaaaggcgc   1200

ctggcaacgg gatccatttt gtacctctcg tccaccctgc ccttgggccg gcccaggtgc   1260

gaaaccagaa taaccctggc tttttgtccg ataaggtagt ttatggtggg cacggcctcc   1320

tttattttaa cgtcatcggc cacccggccg ttttccatcg gcacgttgaa gtccacccgc   1380

aacaggaccc gcttgccctt tacatctata tcccttaccg tttttttggc cactaaggct   1440

gagatcttct tcagtgcatt gtagttgaat gaagggttag gggggaaatg ccccccctatt   1500

ttttgtctag ccatcctgcc acgtttgaca gggtagcaat ttcgacacga tagcgtgctg   1560

tactgttttt tgctcgtcag ggttgggttt tgtcatcgac acccaaggat tggagtcggt   1620

gctcaataat cgccagttgc tgttgggcag ccgccaattg cgcctgaggt tctctcttct   1680

gccgtta                                                             1687
```

<210> SEQ ID NO 45
<211> LENGTH: 1514
<212> TYPE: DNA
<213> ORGANISM: Artificial Sequence
<220> FEATURE:
<223> OTHER INFORMATION: Synthetic Construct- Sequence No. 45, Example: designer oxyphotobacterial Glyceraldehyde-3-Phosphate Dehydrogenase DNA construct (1514 bp)

<400> SEQUENCE: 45

```
agaaaatctg gcaccacacc tgatctgcaa gagacgctca cgcgatacct ctgggcgtgc     60

aatcaccgca ttccccaacg cgctttgggc cacatgaccc ccatcgagag actccgaacg    120

tggcaaatgg agggaccaga gttgttcagt tcacaggtag ataatgtcgc gggtcttgat    180

agttagcaat aaatacagtt tcagaatatc tgtaatacaa aaactgtatc gagacaagaa    240

aaaagtagca aaatttacaa atgttcatga ttcatctggc taaattggat gttcaactga    300

cccattgaag acaagggcaa caaccaatgg atttgggcgg atcggacgtt tagcattcag    360

aagaattcaa gatgtagaag gtcttgaagt agttgcagtt aacgacttaa cagatgacga    420

tatgttagct catttattaa aatacgatac tatgcaaggt cgtttcactg gagaagttga    480

agttatcgaa ggtggattcc gtgttaacgt aaaagaaatt aaatcattcg atgaccagat    540

gctgggtaaa ttaccatggg gcgatttaga tatcgacgta gtattagaat gtactggttt    600

ctatactgat aaagaaaaag cacaagctca catcgatgca ggtgctaaaa aagtattaat    660
```

ctcagctcca gctaaaggtg atgtaaaaac aatcgtattc aacactaacc atgacgcatt 720
agacggttca gaaacagttg tttcaggtgc ttcttgtact actaactcat tagcaccagt 780
tgcaaaagtt ttaagtgatg aattcggttt agttgaaggt ttcatgacta caattcacgc 840
ttacactggt gaccaaaata cacaagacgc acctcacaga aaaggtgaca aacgtcgtgc 900
acgtgcagca gcagaaaata ttatccctaa ctcaacaggt gctgctaaag ctatcggtaa 960
agttattcca gaaatcgatg gtaaattaga cggtggagca caacgtgttc cagttgctac 1020
tgggtcttta actgaattaa ctgtagtatt agacaaacaa gatgtaactg ttgaccaagt 1080
taacagtgct atgaaacaag cttcagacga atcattcggt tacactgaag acgaaatcgt 1140
atcttctgat atcgttggta tgacttacgg ttcattattc gatgcgactc aaactcgtgt 1200
tatgactgtt ggagatcgtc aattagttaa agttgcagct tggtacgaca aagagtgggg 1260
taaggctgag atcttcttca gtgcattgta gttgaatgaa gggttagggg ggaaatgccc 1320
ccctattttt tgtctagcca tcctgccacg tttgacaggg tagcaatttc gacacgatag 1380
cgtgctgtac tgtttttttgc tcgtcagggt tgggttttgt catcgacacc caaggattgg 1440
agtcggtgct caataatcgc cagttgctgt tgggcagccg ccaattgcgc ctgaggttct 1500
ctcttctgcc gtta 1514

<210> SEQ ID NO 46
<211> LENGTH: 609
<212> TYPE: DNA
<213> ORGANISM: Artificial Sequence
<220> FEATURE:
<223> OTHER INFORMATION: Synthetic Construct- Sequence No. 46,
Example 46: designer Nial-promoter-controlled Proton-Channel DNA
construct (609 bp)

<400> SEQUENCE: 46
agaaaatctg gcaccacacc tatatggtag ggtgcgagtg accccgcgcg acttggagct 60
cgatggcccc gggttgtttg gggcgtccgc ctctcgcgct attctgagct ggagaccgag 120
gcgcatgaaa atgcattcgc ttccatagga cgctgcattg tggcttgaag gttcaaggga 180
agggttcaaa cgaccccgcc gtacgaactt ttgtcggggg gcgctcccgg ccccgggctc 240
ttgtgcgcgc attagggctt cgggtcgcaa gcaagacgat acatggccgg catcggcgcc 300
gtgctgaagg tcctgaccac cggcctgccc gccctgatca gctggatcaa gcgcaagcgc 360
cagcagtaaa tggaggcgct cgttgatctg agccttgccc cctgacgaac ggcggtggat 420
ggaagatact gctctcaagt gctgaagcgg tagcttagct ccccgtttcg tgctgatcag 480
tctttttcaa cacgtaaaaa gcggaggagt tttgcaattt tgttggttgt aacgatcctc 540
cgttgatttt ggcctctttc tccatgggcg ggctgggcgt atttgaagcg gttctctctt 600
ctgccgtta 609

<210> SEQ ID NO 47
<211> LENGTH: 1360
<212> TYPE: DNA
<213> ORGANISM: Artificial Sequence
<220> FEATURE:
<223> OTHER INFORMATION: Synthetic Construct- Sequence No. 47,
Example 47: designer nirA-promoter-controlled NAD-dependent
Glyceraldehyde-3-Phosphate-Dehydrogenase DNA construct (1360 bp)

<400> SEQUENCE: 47
agaaaatctg gcaccacacc cttcttgcag aacatgcatg atttacaaaa agttgtagtt 60

```
tctgttacca attgcgaatc gagaactgcc taatctgccg agtatatgaa cggatttggc    120

aggataggac gactggtgtt gcgggcggcg gtggagaagg gcacggtgga ggtggtggcg    180

gtgaacgatc cgttcatctt cccggacgcg gcgtacgctg cgtacatgct gcagtacgac    240

tcgacgcacg gggcgttccc gggtgaggtg ggcagcgacg gggagcactt ggtggtgaac    300

gggaagaagc tggcgtgctt tgcgatccgc gatccggcgg agatcccgtg gggctcggtc    360

ggcgccgact acgtcgtgga gtccaccggc gtgttcaccg tgaccgagaa ggcgtcgttg    420

cacgtcaagg gcggcgcgaa gaaggtggtt atatcggcgc cgtcgaagga tgcgcccatg    480

tttgtgatgg gcgtgaacca tgacgcctac accaaggact tgacggtggt gtcgaatgcg    540

tcttgcacca ccaacttgtt tggcgccgct ggccaagatc atcgacgagg cgttcggcat    600

cgggatgggc ctcatgagca ccatccacgc ggtgacggcc acgcaaaaga cggtggatgg    660

gccgagctcc aaagactggc gcggtgtcgc ggcgcgttcc agtcgattat tcccagcagc    720

accggcgctg cgaaagcggt cggcaaggtg tacccgaagc tgaacggcaa gctgaccggc    780

atggcgttcc gcgtgccggt gcccgacgtg tccgtggtag acttgacagt gaccctgaag    840

aaggagacca actacgagga gatcaaaaag gctgtcaagc aggcgtcgca gagcccgcac    900

tacaagggca tcgtggcgta caccgagcac cccatcgtgt cggccgacct ggtgcacaac    960

ccgtactcgt cggtgttcga tgccgaagcc ggtatcatgc tgtcgcccac gtttgtgaaa   1020

ctggtcagct ggtaatagtg atcccggccg ctactaaagc ctgatttgtc ttgatagctg   1080

ctcctgcctt tgggcagggg ctttttttctg tctgccattc ttgaggatgg cggactcttt   1140

ccctttttgct ctacgcccat gaatgcgatc gcagtctccc ctgtccagca cgttggagtg   1200

attggtggtg gccagttagc ttggatgctg gcaccagcag cgcaacagtt ggggatgtcg   1260

ctgcacgttc aaacacccaa tgatcacgac ccagcagtag cgatcgcgga tcaaaccgta   1320

ttagcagcag ttgctgacgc ggttctctct tctgccgtta                          1360
```

<210> SEQ ID NO 48
<211> LENGTH: 1621
<212> TYPE: DNA
<213> ORGANISM: Artificial Sequence
<220> FEATURE:
<223> OTHER INFORMATION: Syntheitc Construct- Sequence No. 48, Example 48: designer nirA-promoter-controlled Phosphoglycerate-Kinase DNA construct (1621 bp)

<400> SEQUENCE: 48

```
agaaaatctg gcaccacacc cttcttgcag aacatgcatg atttacaaaa agttgtagtt     60

tctgttacca attgcgaatc gagaactgcc taatctgccg agtatatgtc atttgtcttc    120

gagcgcgacg acacccggca gctgttttcc ttccataaac tcgagcgaag cgccgccgcc    180

ggtggagata tgatccattt tgtcggccaa gccgaatttc tcaaccgccg ccgccgaatc    240

cccgccgccg atgaccgaat aggtgtcggg cgcttccgcc agtgcttcgg cgatcgcttt    300

tgtcccatgg gcgaacgctt ccatttcaaa gacgcccatc gggccgttcc agacaacgag    360

cttcgattga cgaatgacat cgcggtacaa ttcgcgcgtt ttcgggccga tgtcaagcgc    420

ctcccaatcg ctcggaatgg cgtcgatggc gacgactttc gtgttggcgt cgttcgcaaa    480

ccggtcggcg acgaccacgt ccaccggcat ataaaaacgg acgccttttt ctttcgcctt    540

ttccataaac gatttggcga gttcgatttt gtcctcctca agcagcgact tgccgacgtc    600

atggccgagc gctttgacga acgtatacgc cagtccgccg ccgatgatca agttgtcgac    660

tttttcaagc aaattgtcga tgacgccgat tttgtctttc actttcgcgc cgccgatgat    720
```

```
cgccgtaaac gggcggtccg gattcgagag cgctttgccg agcacttcga gttctttttc    780

catcaaaaac ccggccaccg caggcaagta atgggcgatg ccttccgtcg acgcatgagc    840

gcggtgggcg gcgccgaacg catcgttgac atacagatcc gcgagctccg caaacgcttt    900

ggccagctct ggatcgtttt tctcttcgcc agggtaaaaa cggacgttct caagcaagag    960

cacgtcgcct tcgttcaaac ggtcgaccgc cgctttcacc tcatcgccga ccgcttcatt   1020

cgttttggcg accggccgtt caagcagctc gccgagccgc ttcgcaacgg catccaaacg   1080

caattcttcg accacttttc ctttcgggcg gccgaggtgg ctcgccaaaa tgactttcgc   1140

cccgtgctcg atcaaatagc ggatcgtcgg gagtgcggcg cgaatgcgcg tgtcatcggt   1200

gatggcgcct tgctccatcg gaacgttgaa atcgacgcgg caaaagacgc gctttcccct   1260

cacctcaacg tcgcggatcg tcttcttgtt cattaatagt gatcccggcc gctactaaag   1320

cctgatttgt cttgatagct gctcctgcct ttgggcaggg gctttttct gtctgccatt    1380

cttgaggatg gcggactctt tccctttgc tctacgccca tgaatgcgat cgcagtctcc    1440

cctgtccagc acgttggagt gattggtggt ggccagttag cttggatgct ggcaccagca   1500

gcgcaacagt tggggatgtc gctgcacgtt caaacaccca atgatcacga cccagcagta   1560

gcgatcgcgg atcaaaccgt attagcagca gttgctgacg cggttctctc ttctgccgtt   1620

a                                                                   1621
```

<210> SEQ ID NO 49
<211> LENGTH: 1990
<212> TYPE: DNA
<213> ORGANISM: Artificial Sequence
<220> FEATURE:
<223> OTHER INFORMATION: Synthetic Construct- Sequence No. 49, Example 49: designer nirA-promoter-controlled Phosphoglycerate-Mutase DNA construct (1990 bp)

<400> SEQUENCE: 49

```
agaaaatctg gcaccacacc cttcttgcag aacatgcatg atttacaaaa agttgtagtt     60

tctgttacca attgcgaatc gagaactgcc taatctgccg agtatatgct cgagcattta    120

tttaataata agcgagcttc ccttcatctc tgaaggtttt tctaacccta agatgtctaa    180

gattgttgga gcaatgtctg ctaagattcc atcatctctt aatttaacat tgccatatcc    240

cacaagatac aaaggcacct tatttgttgt atgagctgta tgaggctcac ctgtctcata    300

atcaatcatc tgttcacagt tgccatggtc agcagtaata ataaccactc cacccttttc    360

taaaaccttg ttaacaactt ttccaataca ctcatctaca gcctcaactg cctttattgc    420

agcctctaaa acgcctgtgt gccctaccat gtcaccattt gcatagttac atattatcac    480

atcatattca tctctttcaa ttctctcaag taaagcttct gttacctcgt atgcactcat    540

ctcaggttta agatcatatg ttgcaacctt tggtgatggt accaataccc tgtcttctcc    600

gacatttggt acttccacac cgccgttgaa gaaaaaggtg acatgagcat acttttctgt    660

ctcagcaatt cgaagttgtt ttaaccctaa cttgctaaaa tactctccca aagtgtttgt    720

caggttctct ggtttgaatg caacatggca attttttatt gtcacatcat actgagtcat    780

gcatacaaag aacacttcga aatatccttt tttcctttca aaaccgtcaa attcaacatc    840

acaaaacgct cttgtaagct gtcttgctct gtcaggtctg aagttaaaga aaataatact    900

gtcatgttca tttattgttg cgacaggttt tccattttca agcacaacag tcggaattac    960

aaactcatca gtgttacctt ttttatacga cttttcaacc gcctctaatc ctgagcttgc   1020
```

```
atactcgcct tcaccaaaga ccattgcatt atatgccttt tcaactcttt cccatctttt   1080

gtctctgtcc attgcatagt atctgcccat cactgttgca atcttaccac aaccaatttc   1140

ttttatcttc tgttcaagct cttcaatgta aatttttgcg ctcgaaggtg gaacatctcg   1200

cccatccaaa aagcaatgaa catatacttt ttcaagattg tgcctctttg caagttttaa   1260

aagtgcgtaa agatgtgtgt tgtggctgtg aacaccacca tctgataaaa gtcccatcag   1320

atgaagagaa gagttatatt ttttgcaatt ctctattgcc atcaaaaact cttctttttc   1380

aaaaaaatca ccgtctttaa ttgactttgt tattcttgta aattcttggt aaacaattct   1440

tcctgcaccc aggttcagat gtccaacttc agaattcccc atttgtcctt cgggaagacc   1500

aacatccata ccactgctac caatcagggt atatgggtaa ttcttttcgt aatagtcaag   1560

gttaggggtc ttacccaaag caacagcgtt tccctcttgc tttgggttat aaccccaacc   1620

gtccatgata atcaacacaa caggtttttt cattaatcta gataatagtg atcccggccg   1680

ctactaaagc ctgatttgtc ttgatagctg ctcctgcctt tgggcagggg ctttttctg   1740

tctgccattc ttgaggatgg cggactcttt ccccttttgct ctacgcccat gaatgcgatc   1800

gcagtctccc ctgtccagca cgttggagtg attggtggtg gccagttagc ttggatgctg   1860

gcaccagcag cgcaacagtt ggggatgtcg ctgcacgttc aaacacccaa tgatcacgac   1920

ccagcagtag cgatcgcgga tcaaaccgta ttagcagcag ttgctgacgc ggttctctct   1980

tctgccgtta                                                          1990
```

```
<210> SEQ ID NO 50
<211> LENGTH: 1765
<212> TYPE: DNA
<213> ORGANISM: Artificial Sequence
<220> FEATURE:
<223> OTHER INFORMATION: Synthetic Construct- Sequence No. 50,
      Example 50: designer nirA-promoter-controlled Enolase DNA
      construct (1765 bp)

<400> SEQUENCE: 50

agaaaatctg gcaccacacc cttcttgcag aacatgcatg atttacaaaa agttgtagtt     60

tctgttacca attgcgaatc gagaactgcc taatctgccg agtatatgct cgagcatatg    120

ctaaataaac ccgtcgtttc cattgaagaa attaccgcta gagaaatttt agactctcgt    180

ggccgtccta ccattgaagc agaagtctta ctggaaacag ggcctttcgg tattgcccag    240

gttcccagtg gcgcgtcaac tggtagcttc gaggcccacg aattacggga tgatgacccc    300

aaccgctacg gtggtaaagg cgttctcaaa gcggttagta acgttataga cgaaattgcc    360

cctaaaatta tcggaatgga tgggttagat caaactgcga tcgatcacac catgattgag    420

ttagacggtt ctactaataa aaaagaatta ggggccaatg ctatccttgc cgtttcctta    480

gccactgcaa aagctgccgc cgatgaatta gcccttcccc tgtaccgtta tttagggggt    540

cccttggcca atgtcttacc cgtccccatg atgaacgtga ttaacggggg ttctcacgcg    600

gataataacg tagacttcca ggagtttatg attatgccag tgggtgcgga ctcttttaaa    660

gaagctttga ggtgggggc cgaagtgttt gcttccctca gtaaagttct aaaagagcgt    720

aaattgctct ctggggtagg agacgagggg ggatacgccc cgaacctggg atcgaaccag    780

gaagccttag atttgctcat agaagccatt gaaaaggcgg ggtataagcc aggggaacag    840

gtggctttag cgatggatgt ggcttcaagt gagttttata aggatggcga atatatttat    900

gatggttctc cccattcccc tcaagaattt atcgattatt taggtaaatt agtggatcaa    960

tatcctatta tttccattga agatggctta caagaagatg actgggatag ctggaaaagt   1020
```

```
ttgaccgata cgttaggatc tcgcattcag ttagttgggg acgatctttt tgtcacgaac   1080

cccactcgtc tgcaaaaagg cattgatatg ggtgtgggta atagtattct cattaaactc   1140

aatcaaattg gtagtttaac ggaaacgtta gatacgattg ctttagcgac tcgtcatcaa   1200

tatagttccg ttatttccca tcgttccgga gaaaccgaag acactaccat tgcagactta   1260

gccgtagcta cacgcgctgg acaaatcaaa accggttctc tgtgtcgtag tgaacgggta   1320

gccaaatata accgactatt acgtattgaa gaagaattag gcgatcgcgc agtttatgct   1380

gcaaaagtgg gtttaggccc tcaataaggc tgctgccccg gctgctgcta atctagataa   1440

tagtgatccc ggccgctact aaagcctgat ttgtcttgat agctgctcct gcctttgggc   1500

aggggctttt ttctgtctgc cattcttgag gatggcggac tctttccctt ttgctctacg   1560

cccatgaatg cgatcgcagt ctcccctgtc cagcacgttg gagtgattgg tggtggccag   1620

ttagcttgga tgctggcacc agcagcgcaa cagttgggga tgtcgctgca cgttcaaaca   1680

cccaatgatc acgacccagc agtagcgatc gcggatcaaa ccgtattagc agcagttgct   1740

gacgcggttc tctcttctgc cgtta                                         1765
```

<210> SEQ ID NO 51
<211> LENGTH: 1888
<212> TYPE: DNA
<213> ORGANISM: Artificial Sequence
<220> FEATURE:
<223> OTHER INFORMATION: Synthetic Construct- Sequence No. 51,
Example 51: designer nirA-promoter-controlled Pyruvate-Kinase
DNA construct (1888 bp)

<400> SEQUENCE: 51

```
agaaaatctg gcaccacacc cttcttgcag aacatgcatg atttacaaaa agttgtagtt     60

tctgttacca attgcgaatc gagaactgcc taatctgccg agtatatgct cgagcatatg    120

ttaaaaaaga cgaaaatcgt ttgcacgcag ggtccgtcca cagagaaacc gggcgtaatt    180

gatgcactga ttgccaatgg catgaactgc gcacgcttca atttctccca tggtgaccac    240

gaagaacatc ttggccgtat caatatggtt cgtgaagctg ccaagaaggc tggcaaggtt    300

atctctttaa tcctcgatac caaaggtccg gaaatgcgtc tgggcgagtt caaagatggc    360

aaagttatgc tcgaaaaggg caacaagttc actttgacct atgacgatga accgggtgat    420

gaaactcatg tttccgtaaa ccacaaaggt ctttacacgg aagttaagcc gggcgacacc    480

ctgctcctct ccgatggcct cgtagctctc aaagttgatg aaatcaaggg caaggatatc    540

gttacgacga ttcagaacag cggtaagatg agcacgcgca agcgcgtagc tgctccgggc    600

gtaccccttg gtctgcctcc tatctccgaa caggatgcta aggacatcat ctttggctgc    660

gaacaggata tggatttcgt agctgcttcc ttcatccagc gtccggatga tgttatcgcc    720

atccgcaagc tcatcgaaga gcacaatggc cacatggaaa ttctgccgaa gatcgaaaac    780

ctcgaaggtg ttaagaactt cgatgcaatc ctggaagttt ccgacggcat catggttgcc    840

cgtggtgacc tgggcgtaga agttccggca gaagatgtgc cccttattca gaaggaaatc    900

atccgcaagt gcaacgctgc tggcaagccg gttatcgttg ctacgcagat gctcgactcc    960

atggaacgca acccgcgtcc gacccgtgca gaagtttctg acgttggtaa cgccatcctc   1020

gatggtacgg atgccatcat gctgtccggc gaaacggctt ccggtgacta tccggtagaa   1080

gcagttgcca cgatgaaccg cattgcacag cgcatggaaa gctcccttga atacaaggaa   1140

ctctatgtag aacgtggtct gcagcacatg gaatcccgta cgcgtgctat cgctcatgct   1200
```

```
acggttcaga tggcttatga gctcgatgct ccggctatta tcacgccgac cgaatccggt   1260
tacacgacga aggtcgtttc caagtatcgt ccgaaggctg ctatcgtagc ttacacgccg   1320
agcgaaaaag ttctgcgtca gctgaacctg cgttggggcg tatatccggt actcggcacc   1380
cagtggagcg atgtggatga aatgatcagc aatgcaacgg ctgctgctgt taaggaagac   1440
ctcgtacagc gcggcgacct caccatcatc acctccggtg tgaagatgga atcccgtacg   1500
cgtgctatcg ctcatgctac ggacatctaa ggctgctgcc ccggctgctg ctaatctaga   1560
taatagtgat cccggccgct actaaagcct gatttgtctt gatagctgct cctgcctttg   1620
ggcaggggct tttttctgtc tgccattctt gaggatggcg gactctttcc cttttgctct   1680
acgcccatga atgcgatcgc agtctcccct gtccagcacg ttggagtgat tggtggtggc   1740
cagttagctt ggatgctggc accagcagcg caacagttgg ggatgtcgct gcacgttcaa   1800
acacccaatg atcacgaccc agcagtagcg atcgcggatc aaaccgtatt agcagcagtt   1860
gctgacgcgg ttctctcttc tgccgtta                                      1888
```

<210> SEQ ID NO 52
<211> LENGTH: 2188
<212> TYPE: DNA
<213> ORGANISM: Artificial Sequence
<220> FEATURE:
<223> OTHER INFORMATION: Synthetic Construct- Sequence No. 52, Example 52: designer nirA-promoter-controlled Pyruvate-Decarboxylase DNA construct (2188 bp)

<400> SEQUENCE: 52

```
agaaaatctg gcaccacacc cttcttgcag aacatgcatg atttacaaaa agttgtagtt     60
tctgttacca attgcgaatc gagaactgcc taatctgccg agtatatgct cgagcatatg    120
gtatcaacct acccagaatc agaggttact ctaggaaggt acctctttga gcgactccac    180
caattgaaag tggacaccat tttcggcttg ccgggtgact tcaacctttc cttattggac    240
aaagtgtatg aagttccgga tatgaggtgg gctggaaatg ccaacgaatt gaatgctgcc    300
tatgctgccg atggttactc cagaataaag ggattgtctt gcttggtcac aacttttggt    360
gttggtgaat tgtctgcttt aaacggagtt ggtggtgcct atgctgaaca cgtaggactt    420
ctacatgtcg ttggagttcc atccatatcg tcacaggcta aacagttgtt gctccaccat    480
accttgggta atggtgactt cactgttttt cacagaatgt ccaatagcat ttctcaaact    540
acagcatttc tctcagatat ctctattgca ccaggtcaaa tagatagatg catcagagaa    600
gcatatgttc atcagagacc agtttatgtt ggtttaccgg caaatatggt tgatctcaag    660
gttccttcta gtctcttaga aactccaatt gatttgaaat tgaaacaaaa tgatcctgaa    720
gctcaggaag aagttgttga aacagtcctg aagttggtgt cccaagctac aaaccccatt    780
atcttggtag acgcttgtgc cctcagacac aattgcaaag aggaagtcaa acaattggtt    840
gatgccacta attttcaagt ctttacaact ccaatgggta aatctggtat ctccgaatct    900
catccaagat ttggcggtgt ctatgtcggg acaatgtcga gtcctcaagt caaaaaagcc    960
gttgaaaatg ccgatcttat actatctgtt ggttcgttgt tatcggactt caatacaggt   1020
tcattttcat actcctacaa gacgaagaat gttgttgaat tccactctga ctatatgaaa   1080
atcagacagg ccaccttccc aggagttcaa atgaaagaag ccttgcaaca gttgataaaa   1140
agggtctctt cttacatcaa tccaagctac attcctactc gagttcctaa aaggaaacag   1200
ccattgaaag ctccatcaga agctcctttg acccaagaat atttgtggtc taaagtatcc   1260
ggctggttta gagagggtga tattatcgta accgaaactg gtacatctgc tttcggaatt   1320
```

```
attcaatccc attttcccag caacactatc ggtatatccc aagtcttgtg gggctcaatt   1380

ggtttcacag taggtgcaac agttggtgct gccatggcag cccaggaaat cgaccctagc   1440

aggagagtaa ttttgttcgt cggtgatggt tcattgcagt tgacggttca ggaaatctct   1500

acgttgtgta aatgggattg taacaatact tatctttacg tgttgaacaa tgatggttac   1560

actatagaaa ggttgatcca cggcaaaagt gccagctaca acgatataca gccttggaac   1620

catttatcct tgcttcgctt attcaatgct aagaaatacc aaaatgtcag agtatcgact   1680

gctggagaat tggactcttt gttctctgat aagaaatttg cttctccaga taggataaga   1740

atgattgagg tgatgttatc gagattggat gcaccagcaa atcttgttgc tcaagcaaag   1800

ttgtctgaac gggtaaacct tgaaaattga ggctgctgcc ccggctgctg ctaatctaga   1860

taatagtgat cccggccgct actaaagcct gatttgtctt gatagctgct cctgcctttg   1920

ggcaggggct tttttctgtc tgccattctt gaggatggcg gactctttcc cttttgctct   1980

acgcccatga atgcgatcgc agtctcccct gtccagcacg ttggagtgat tggtggtggc   2040

cagttagctt ggatgctggc accagcagcg caacagttgg ggatgtcgct gcacgttcaa   2100

acacccaatg atcacgaccc agcagtagcg atcgcggatc aaaccgtatt agcagcagtt   2160

gctgacgcgg ttctctcttc tgccgtta                                      2188
```

```
<210> SEQ ID NO 53
<211> LENGTH: 1510
<212> TYPE: DNA
<213> ORGANISM: Artificial Sequence
<220> FEATURE:
<223> OTHER INFORMATION: Synthetic Construct- Sequence No. 53,
      Example 53: designer nirA-promoter-controlled NAD(P)H-dependent
      Alcohol-Dehydrogenase DNA construct (1510 bp)

<400> SEQUENCE: 53
```

```
agaaaatctg gcaccacacc cttcttgcag aacatgcatg atttacaaaa agttgtagtt     60

tctgttacca attgcgaatc gagaactgcc taatctgccg agtatatgtt agctacctct    120

gtgccagaaa cccaaaaggg tgttattttc tatgagaatg gtggtaaatt ggaatacaag    180

gacattccag ttccaaagcc aaagccaaat gaaatcttga tcaacgtcaa gtactccggt    240

gtgtgtcata ccgatttgca cgcatggaag ggtgactggc cattgccaac caagttgcca    300

ttggtcggtg gtcacgaagg tgctggtgtc gttgttgcta tgggtgaaaa cgtcaagggc    360

tggaacattg gtgactttgc gggtatcaaa tggttgaacg gttcttgtat gtcctgtgaa    420

tactgtgaat tgtccaatga atccaactgt ccagatgctg acttgtctgg ttacacccac    480

gatggttctt tccaacaata ccgtaccgca gatgctgttc aagctgccag aattccaaag    540

ggtaccgatt tggctgaagt tgctccaacc ctatgtgccg gtgttactgt ttacaaggct    600

ttgaaaagtg ctaacttgaa ggctggtgac tgggttgcca tctctggtgc tgctggtggt    660

ctaggttctc tagctgtcca atacgccaag gccatgggtt acagagtcgt tggtatcgac    720

ggtggtgaag aaaagggtaa gttggtcaag caattgggtg gtgaagcctt tgttgatttc    780

accaaaacca aggacatggt tgctgaaatc caagaaatca ccaacggtgg tccacacggt    840

gtcattaacg tctctgtttc tgaagctgcc atgaacgctt ccactcaatt cgtcagacca    900

actggtactg tcgtattggt cggtttgcca gctggtgccg tcatcaagtc cgaagtcttc    960

tcccacgtcg ttaagtctat taacatcaag ggttcttacg tcggtaacag agctgacacc   1020

agagaagcta tcaacttctt cgctaacggt cacgtccact ctccaatcaa ggttgttggt   1080
```

-continued

```
ttgtccgaac taccaaaggt ttacgaattg atggaacaag gtaagatttt gggtagatac   1140

gttgttgaca cctccaacta gggctgctgc cccggctgct gctaatagtg atcccggccg   1200

ctactaaagc ctgatttgtc ttgatagctg ctcctgcctt tgggcagggg ctttttctg    1260

tctgccattc ttgaggatgg cggactcttt cccttttgct ctacgcccat gaatgcgatc   1320

gcagtctccc ctgtccagca cgttggagtg attggtggtg gccagttagc ttggatgctg   1380

gcaccagcag cgcaacagtt ggggatgtcg ctgcacgttc aaacacccaa tgatcacgac   1440

ccagcagtag cgatcgcgga tcaaaccgta ttagcagcag ttgctgacgc ggttctctct   1500

tctgccgtta                                                          1510


<210> SEQ ID NO 54
<211> LENGTH: 56
<212> TYPE: PRT
<213> ORGANISM: Artificial Sequence
<220> FEATURE:
<223> OTHER INFORMATION: Synthetic Construct- Sequence No. 54,
      Example 54: designer selected Hyd1 transit peptide (amino acids
      sequence)

<400> SEQUENCE: 54

Met Ser Ala Leu Val Leu Lys Pro Cys Ala Ala Val Ser Ile Arg Gly
1               5                   10                  15

Ser Ser Cys Arg Ala Arg Gln Val Ala Pro Arg Ala Pro Leu Ala Ala
            20                  25                  30

Ser Thr Val Arg Val Ala Leu Ala Thr Leu Glu Ala Pro Ala Arg Arg
        35                  40                  45

Leu Gly Asn Val Ala Cys Ala Ala
    50                  55


<210> SEQ ID NO 55
<211> LENGTH: 45
<212> TYPE: PRT
<213> ORGANISM: Artificial Sequence
<220> FEATURE:
<223> OTHER INFORMATION: Synthetic Construct- Sequence No. 55,
      Example 55: designer selected RbcS2 transit peptides (amino
      acids sequence)

<400> SEQUENCE: 55

Met Ala Ala Val Ile Ala Lys Ser Ser Val Ser Ala Ala Val Ala Arg
1               5                   10                  15

Pro Ala Arg Ser Ser Val Arg Pro Met Ala Ala Leu Lys Pro Ala Val
            20                  25                  30

Lys Ala Ala Pro Val Ala Ala Pro Ala Gln Ala Asn Gln
        35                  40                  45


<210> SEQ ID NO 56
<211> LENGTH: 7
<212> TYPE: PRT
<213> ORGANISM: Artificial Sequence
<220> FEATURE:
<223> OTHER INFORMATION: Synthetic Construct- Sequence No. 56,
      Example 56: designer selected ferredoxin transit peptide
      (amino acids sequence)

<400> SEQUENCE: 56

Met Ala Met Ala Met Arg Ser
1               5


<210> SEQ ID NO 57
<211> LENGTH: 33
```

<212> TYPE: PRT
<213> ORGANISM: Artificial Sequence
<220> FEATURE:
<223> OTHER INFORMATION: Synthetic Construct- Sequence No. 57,
Example 57: designer selected CF0CF1 subunit-a transit peptide
(amino acids sequence)

<400> SEQUENCE: 57

Met Leu Ala Ala Lys Ser Ile Ala Gly Pro Arg Ala Phe Lys Ala Ser
1 5 10 15

Ala Val Arg Ala Ala Pro Lys Ala Gly Arg Arg Thr Val Val Val Met
20 25 30

Ala

<210> SEQ ID NO 58
<211> LENGTH: 1417
<212> TYPE: DNA
<213> ORGANISM: Artificial Sequence
<220> FEATURE:
<223> OTHER INFORMATION: Synthetic Construct- Sequence No. 58,
Exmaple 58: designer nirA-promoter-controlled NADPH-dependent
Glyceraldehyde-3-Phosphate Dehydrogenase DNA construct (1417 bp)

<400> SEQUENCE: 58
agaaaatctg gcaccacacc tgaccccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catgacttgc acttacagtt tcttttgatg tcaaaagtgc tccaatttgc 300
tcagcaacat ctacaactct atttgaataa ccccattcat tatcatacca agcaataact 360
tttactttat tccctgacat gaccattgtt gattttgcat caataatagc tgaatttgga 420
ttagtattaa aatcaacaga cactagtggt tgatgttcga cttctatgat accttctaaa 480
cctgcatttt caaaagcttg gtttacttct tctgcagtta cttctttttc taaatcaaca 540
actaaatcaa cgagcgatac attctttgtt ggtacacgta atgccatgcc gtgtaattta 600
ccttctaatt ctggtaatac ttcttttaaa gctttcgccg caccagtaga agtaggaata 660
atgctttcat tacatgaacg tgcacgtctt aaatctttat gtggattatc aatatttttt 720
tggtcatttg taatagcgtg aacagtagtc attaaaccat taactattcc aaactgatta 780
tttaaaactt ttgcaactgg accaatgcaa ttagtagtac atgaagcatt actaaaaatg 840
tcaaatgctt ctatatctaa ttggttatca tttacgcctt taactaacat ttgaacatgt 900 ccacctttttg aaggaccagt taacaatact tttttggcac ctgctttaat atgtgcgatg 960
gctttatcac catgattaaa tttaccagtt gcatctatag caatatcgat atctaattct 1020
ttccatggca agttttcagg attgcgatca gcaaccaatt taattttatg atcaccaact 1080
tgcaatccat tttcaatcgg ttcaactttt agattatatt ttccatgtgt tgtatcgtaa 1140
ttgattaaat gtgcaattgt ttcgggtgga taactagcat ttatcgctac tacatttaaa 1200
tttttatttt gtaatgcaat acgtaatacc attcttccaa ttctacccat accattaatt 1260
gcaatattcg ttgacattaa ggctgagatc ttcttcagtg cattgtagtt gaatgaaggg 1320 ttaggggggga aatgcccccc tattttttgt ctagccatcc tgccacgttt gacagggtag 1380
caatttcgac acgatagggt tctctcttct gccgtta 1417

<210> SEQ ID NO 59

<211> LENGTH: 1387
<212> TYPE: DNA
<213> ORGANISM: Artificial Sequence
<220> FEATURE:
<223> OTHER INFORMATION: Synthetic Construct- Sequence No. 59,
Exmaple 59: designer nirA-promoter-controlled NAD-dependent
Glyceraldehyde-3-Phosphate Dehydrogenase DNA construct (1387 bp)

<400> SEQUENCE: 59
agaaaatctg gcaccacacc tgacccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catgcttaga gatgtgtgcg atcagatcca gaactttgtt ggagtagcca 300
gtttcgttgt cataccaaga aaccagtttc acgaagttgt cgttcagaga gataccggcg 360
tcggcatcaa acacggaggt gcatacttcg ccgttgaagt cggtagaaac gacggcttcg 420
tcggtgtagc ccagaacgcc tttcatttcg ccttcagaag cggccttcat cacgtcacag 480
atctgctgat aggtcgccgg cttggccagg cgagcagtca ggtcaacaac ggagacgttc 540
ggggtcggaa cgcggaaagc cataccggtc agtttgccgt tcagctccgg gatgaccttg 600
ccaacggcct tggctgcacc ggtagaggac gggatgatgt tctggctagc gccgcggccg 660
ccgcgccaat ctttcatgga cggcgccgtcg acagtttttct gggtcgcggt ggtagcgtga 720
acggtggtca tcagcgcttc aacgatgccg aagttgtcgt tcaggacttt agccagcgga 780
gccaggcagt tggtggtgca ggatgcgttg gaaacgatct cctggccagc gtagttcttg 840
tggtttacgc ccataacgaa catcggggta gcatctttag acgggccagt catgacgact 900
ttcttggcac cggcggcgat gtgcttacgc gcggtttcgt cggtcaggaa cagaccggtc 960
gcttcggcaa caacgtcaac gccgatttcg ttccacttca ggttagccgg atctctttca 1020
gcggtaacac ggattttttt accgttaacg atcaggtggc catctttcac ttcaacagtg 1080
ccgttgaaac gaccgtgagt agagtcgtac ttcagcatgt atgccatgta gttggcatcc 1140
agcagatcgt tgatgccaac gatttcgatg tcagaacgtt cctgagcagc acggaaaaca 1200
atacggccga tacggccaaa accgttgata cctactttga tagtcattaa ggctgagatc 1260
ttcttcagtg cattgtagtt gaatgaaggg ttaggggggga aatgcccccc tattttttgt 1320
ctagccatcc tgccacgttt gacagggtag caatttcgac acgatagggt tctctcttct 1380
gccgtta 1387

<210> SEQ ID NO 60
<211> LENGTH: 1627
<212> TYPE: DNA
<213> ORGANISM: Artificial Sequence
<220> FEATURE:
<223> OTHER INFORMATION: Synthetic Construct- Sequence No. 60,
Exmaple 60: designer nirA-promoter-controlled phosphoglycerate
mutase DNA construct (1627 bp)

<400> SEQUENCE: 60
agaaaatctg gcaccacacc tgacccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catgggcccc gaacttttgc agcttgcccg cgtgcgccag caggagcggc 300
agcacgtggg tgccgtgcag gtcgccgagc gcgccccctg ccgcctcgtc ctcggtgaag 360
cggcgggccg cgtcggcgcg caggttgggg ccgtagagca ggaagggcac cgggtgccag 420
gagtgcgcct tcatcacgct gggcgtggag tggtcgccgg tgatggcgat cacctcgggc 480
tccagcgcca gcagctcggg cagcagggcg tcgaaggcct cgatcttgtg caccttcgcg 540
tcgaagtcgc cgtcctcgcc ggtggagtcg gtcttcttga agtgcaggta gaagtagtcg 600
aaggcttccc agtgggcctt cagggccgcg agcttgcctt cgggggcgtc ggggtcctcg 660
cccacctcga cctccagcgc ggtcatcccc accagcgagg ccaccccgcg gtacatcggg 720
tagctggcga ccgccgcggg ggtgagcccg gtgatctcgc ccagggtggg ccagaccggg 780
cgcttggaga cgccgcgaag cagcaccccg ttgatcctgg gctcgtccgc gagcgcctgc 840
cgcgccagcg cgctgaactt gttgagcacg tcggccgtct tggcgctggg ctcgtcgctt 900
tcgtcgtgcg gacgggccgc gagcggcggc accccggtct tctgggggtc ggtgtcgtgg 960
acccggtcgc ccagccccac gccccgcagc accagcacga agcggtgctc cgactcggtg 1020
tggagctcga tcctgacgcc gtcgatctcg cggatgcgct ccctcagctt ggcgagcacc 1080
cgccggtttt cctcggtggg ggggcggccg gcgcggcggt cggcgatggt gccgtcgggg 1140
ttcaaggtgg cgaagttgcc gcgcaccgcg acgtcgtcgg gccccagctc gatgcccagc 1200
cccagcgccg agaggacgcc gcgcccgacc tcgtagcgga aggggtcgta gccgaagagg 1260
ctcaggtggc cgggcccgga gccgggcgcg aagccggggg ccaccagggt gactcgcccc 1320
aggttggcct tttcggccag ggcgtcgagg ttgggggtgc gggccgcggc cagctccgtg 1380
ggcccgcccg gctcgcgggg cagcccgccc accccgtcga gcacgacgaa gaggatcttg 1440
ctgggcgtgg tgcggctcag ttccttgagg tgggggagga ggtccattaa ggctgagatc 1500
ttcttcagtg cattgtagtt gaatgaaggg ttagggggga aatgcccccc tatttttttgt 1560 ctagccatcc tgccacgttt gacagggtag caatttcgac acgatagggt tctctcttct 1620
gccgtta 1627

<210> SEQ ID NO 61
<211> LENGTH: 1678
<212> TYPE: DNA
<213> ORGANISM: Artificial Sequence
<220> FEATURE:
<223> OTHER INFORMATION: Synthetic Construct- Sequence No. 61, Exmaple 61: designer nirA-promoter-controlled Enolase DNA construct (1678 bp)

<400> SEQUENCE: 61
agaaaatctg gcaccacacc tgacccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catgtttttg taaattatag aaaacccccca acccacgata cagcccgata 300
tcgcttaatt cttcttctat ccgcaacagc tggttgtatt tcgctacccg gtcagtcctg 360
gccggagccc cggtctttat ctgccctacg ttggtcgcta ctaccaggtc agcgatgaag 420
gtgtcctccg tctccccgga acggtgggat actacacagg tgtaaccggc tcttttagcc 480
atttcaatcg tatccaaggt ctcagtgacc gtgcctatct gattcagttt gataagtatg 540
ctgttggcca caccctttttt tattcctgtg gtaaaacgct ggggattggt tacgaaaata 600

```
tcatctccga cgatctgaat cttcttgccc agcttacggg tgagcttttt ccacccttcc    660
cagtcttctt cctgcagccc gtcttccagg gatatgatag gatacttacg cacaaggcca    720
tcgtaaaact cgaccacctc atcggcggtc agctcttggc cggtgctggc aaaaacgtat    780
ttcccgtcct tgaaaatctc attggcagca acatccagtc ccaggtaaat atccttcccc    840
ggcttgtacc ccgccgtttt aatagcctcc aaaattactt caatcgcggc ttcattcgaa    900
ggcaagttgg gagcaaatcc tccttcatcc ccgatggaag tagaaaaccc tttttttactc   960
aataccttct tcagggtatg gtagacctcc acccccatgc gcagggcctc ggcaaaagaa   1020
gtagctccta ccggtaggat caagaattct tgaatgtcca cattattatc cgcgtgcttg   1080
ccgccgttca agatgttcat ttgcgggatc ggcagttctt tggcgtttac gccgcccagg   1140
tactggtaaa gcggcatgga taggtaggaa gcagcagccc gcgccacagc catcgacacg   1200
cctaagatag cgttagctcc cagcttgccc ttgttgtcag tcccatcgag gtcaatcatc   1260
aaccggtcaa tccccacctg gtcgagcgca tccatcccca caacctccgg ggcgatgacc   1320
gtgttgacgt tatccaccgc attcagcacg cctttgccgc cgaaacgctc tgcgtcccca   1380
tcccgcagtt ccaccgcctc aaaagcacca gtggacgcgc cggaaggaac cgcagcccgt   1440
cccatggtcc catcttctaa aaggacctcg acctccaccg tcgggtttcc ccgcgaatcc   1500
agtatttctc tggcgtaaac ctcggtgata atactcacta aggctgagat cttcttcagt   1560
gcattgtagt tgaatgaagg gttagggggg aaatgccccc ctattttttg tctagccatc   1620
ctgccacgtt tgacagggta gcaatttcga cacgataggg ttctctcttc tgccgtta     1678
```

<210> SEQ ID NO 62
<211> LENGTH: 2137
<212> TYPE: DNA
<213> ORGANISM: Artificial Sequence
<220> FEATURE:
<223> OTHER INFORMATION: Synthetic Construct- Sequence No. 62,
      Exmaple 62: designer nirA-promoter-controlled Pyruvate Kinase
      DNA construct (2137 bp)

<400> SEQUENCE: 62

```
agaaaatctg gcaccacacc tgacccccat cgagagactc cgaacgtggc aaatggaggg     60
accagagttg ttcagttcac aggtagataa tgtcgcgggt cttgatagtt agcaataaat    120
acagtttcag aatatctgta atacaaaaac tgtatcgaga caagaaaaaa gtagcaaaat    180
ttacaaatgt tcatgattca tctggctaaa ttggatgttc aactgaccca ttgaagacaa    240
gggcaacaac catgccgcac ttgggcttgg ccgcggtaga tttgtcccct agccgtatcc    300
atggttatgg tttctccgtc ttggatgaca cgggttgcct cggcggctcc aacgatgaca    360
ggaatatcca agttaatacc tactatggct gcatgagaag tcaggcctcc ctgttccgtg    420
ataatccccc cggccttttc caacaacggc atatagtcct tgtctgttcc gactgccacc    480
actatatctc ccggagcaaa cgagcccggt ttgcccggat ccagtatcac ccgcgcctta    540
ctggtaacgg cccggctacc tatacccgtt cccttaacca gcaccttgcc tactacttga    600
actctcagta gattggtagt cccagggatt ccaggagtac ctgcggttat gactaccagg    660
tcaccggggg agattagccc tcgcctgact gcggcatcca gggctgtttc tatcatctgg    720
tcagttccgt gggtttccgg gaccgtgagc gcgtataccc cccataccaa agttagcttg    780
cgtaccactt cgggtgaagg cgtagtagcc acgatcggag cccggggacg gtacttggcc    840
accattctcg ccgtatggcc cgattttgta gcagtaacaa tggccgaggc ccccaggtcg    900
gtagcggtag cacaggtggc ataactgatg gcatcggtca cggtacgcct gccttcgaat    960
```

```
cgtcttgccg ccagcatgtt ctcatagggc aaagccatct ccgtccgccg ggctattcgc   1020

gccatggttt ccaccgcaac taccggatat ttaccggctg cggtctctgc cgacagcata   1080

atggcgtctg ccccctcaaa tatggcatta gccacgtctg acgcttcggc ccgggtgggg   1140

cgcggcacgt ttaccatcga ttcgagcatc tgggtggcaa ttatcaccgg cttaccctga   1200

gcccggcatt tctcgattat aaccttttgc accagaggta cttcttcggt aggtatttca   1260

acccccaggt ctccccgggc gaccatgacg ccatcagcaa cctttattat gtcatccagg   1320

ttgtccagcc cctcctggct ctcaatctta gcgattatat cgatgtcggc tccctttttcc  1380

tctaatatgc gtctgatatc caaaacatca tcggccgtcc ttacgaacga ggcagcaatg   1440

aaatccatat tctgctggat gccgaagtta atgtcttcga tgtctttctg gctcaaaaaa   1500

ggcaggttgg ttctcacacc cggcaggttt atgcctttcc tttcaccgag tactcctccc   1560

gcaaccacct ggcagacgat gtcggtgtcg ttcgcctcta aaacagacag ctggatgacg   1620

ccgtcagcga tcaatatgca gtcacccgct tttacctgcg aaggtaactc atggtaactt   1680

atctggacct cgtcttcgtt accttcaacc ggacggttgg tgagaacgaa cttttgacca   1740

ggacgcagct ctatcttacc ttctttcaag ggcccggtcc tgatctccgg ccctttggta   1800

tcaagcatca accctacttc cgcattcagt tcccgcgcca cctcacgcac catgcggatg   1860

cggcgctcat gctcatcata agtgccgtgt gaaaaattca aacgggccac gttcatgccg   1920

ttggtgatca aagctcttag ccgctcataa tcatcggtgg aaggtcccag ggtacagatg   1980

attttggtct tccgcaataa ggctgagatc ttcttcagtg cattgtagtt gaatgaaggg   2040

ttagggggga aatgcccccc tattttttgt ctagccatcc tgccacgttt gacagggtag   2100

caatttcgac acgatagggt tctctcttct gccgtta                            2137
```

```
<210> SEQ ID NO 63
<211> LENGTH: 2163
<212> TYPE: DNA
<213> ORGANISM: Artificial Sequence
<220> FEATURE:
<223> OTHER INFORMATION: Synthetic Construct- Sequence No. 63,
      Example 63: designer nirA-promoter-controlled citramalate
      synthase DNA construct (2163 bp)

<400> SEQUENCE: 63

agaaaatctg gcaccacacc tgatctgcaa gagacgctca cgcgatacct ctgggcgtgc     60

aatcaccgca ttccccaacg cgctttgggc cacatgaccc ccatcgagag actccgaacg    120

tggcaaatgg agggaccaga gttgttcagt tcacaggtag ataatgtcgc gggtcttgat    180

agttagcaat aaatacagtt tcagaatatc tgtaatacaa aaactgtatc gagacaagaa    240

aaaagtagca aaatttacaa atgttcatga ttcatctggc taaattggat gttcaactga    300

cccattgaag acaagggcaa caaccatgga gcaggttttt atctacgaca ccaccttgag    360

ggatggctcg caggcagaag gtataaactt ttccgtagag gataagatgc gcatacttca    420

aaaactggac gaatttggag tgcattacat agagtgcgga tggcccggtg cgaacccaaa    480

agacactatt ctctttgaaa ggctgagaaa gataaaaact caaaatgcca aaatagtagc    540

ctttggtgca acaagaaaag ctggaaagaa ggcgcacgaa gataagcagg tggaaaacct    600

tttgaaatcg ggtgccaagg tgataaccgt atttggcaag agctgggact ttcatgtaac    660

gcatgccata gggaccacct tagaggaaaa cctggacatg gtttacgaga cggtaagcta    720

tcttaaaaag catgtggagg aggttatctt tgacgcagag cacttctttg acggatacag    780
```

gcacaacgaa agctatgctt ttaaggtatt ggaggcagct tttcaggcag gtgcggactg 840
gatagtcctc tgcgatacca acggtggcac ccttcccaat gaggtttatg agataaccaa 900
aaaggttgta caaaagtttc cacaggcacg cgtaggcata cacgctcaca acgattcaga 960
tactgctgtg gctaactctc ttatggcggt gcttgcaggt gcaaggcagg ttcacggcac 1020
tataaacggc ttgggggaaa gaacgggcaa tgctaatctg tgttccataa tacctaacct 1080
tcagctcaag ctgggcttta gtgtagtgcc ttcccaaaac ctcaaaaagc tcaccgagct 1140
tgctcacttt gtctccgaaa tctccaacac gccactgccc aaaaacatgc cttatgtagg 1200
ggagagtgct tttacccaca aagcaggcgt acacgcctct gcagttatga aaaggtcaga 1260
aacatacgaa cacatagacc cttctttggt aggaaacaga aggaaggtga cagtgtctga 1320
cctttctgga aggagtaata tactttacaa gctcagggaa atggggcttg aggtggatga 1380
taagtcccct gagcttatca aactccttga aaagataaag gaacttgaga aggaaggcta 1440
ccactttgaa gcagctgaag cttcttttga gcttctttgc aagaggcatt ttgggcttgt 1500
taaaaactat tttgaccttg atgcttacag ggtgctaata gccagaagga gtacagacct 1560
atctcctgtt tcggaagcca ccgtaagact ctatgtggaa gacataaagg agcatacagc 1620
agctcttggt aacggaccag tgagcgccct tgacagagcc ctcagaaaag ccttggaaga 1680
gttttatcca agccttaaag atgttcagct catagactac aaggtgagaa tagttaacga 1740
atcggagggt acatctgcca aagtgagggt gcttatagaa tctaccgatg gtagaagaaa 1800
gtggggaacg gtgggagttt cggaaaacat aatagaagcc tcttggatag ccttaactga 1860
tagcctcgta tataaactct taaaagacga agaagagggt ataatgtgat aaggctgaga 1920
tcttcttcag tgcattgtag ttgaatgaag ggttaggggg gaaatgcccc cctatttttt 1980
gtctagccat cctgccacgt ttgacagggt agcaatttcg acacgatagc gtgctgtact 2040 gtttttgct cgtcagggtt gggttttgtc atcgacaccc aaggattgga gtcggtgctc 2100
aataatcgcc agttgctgtt gggcagccgc caattgcgcc tgaggttctc tcttctgccg 2160
tta 2163

<210> SEQ ID NO 64
<211> LENGTH: 2878
<212> TYPE: DNA
<213> ORGANISM: Artificial Sequence
<220> FEATURE:
<223> OTHER INFORMATION: Synthetic Construct- Sequence No. 64,
Example 64: designer nirA-promoter-controlled 3-Isopropylmalate/
(R)-2-Methylmalate Dehydratase DNA construct (2878 bp)

<400> SEQUENCE: 64
agaaaatctg gcaccacacc tgacccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catgtaccat gtctgctgtt gctatctcgc ccttgattgc tgatgctgta 300
acagtagccg ctgaagcaag atatacaaaa gaatctttat gtcctgcacg tcccttgaag 360
tttcgtgtac ctgtactgat aagagtctca ccctcaccga taacaccctg acagcttccc 420
cagcatacag agcagttagg attcataaca attgcacctg cgtccatgaa tatatcaagg 480
agtccctctt tcatagcctg aagatatacc gaacggcttg caggaactac aaggaatctt 540
accttaggag caacctttt ccctttgatg atcgctgcgc caactcttaa atcctcgatt 600

```
cgtccattgt tacatgaacc aagaaatgct tcatcaatct ttacaccaag tgattcctta    660

gccggaacta cattgtcaac aaaatgtggc tttgcaacaa ttggctgtat tgttgaaagg    720

tcaatatcat aaacctgctc aaatactgca tcatcatctg atgtaaagca tgcctttggc    780

tctctgccat gctccttaag ataatccatt gcaacatcat caacttccat gagtgcagtc    840

ttagcacctg cctctacaca aaggttacag attgatattc tgtctgccat tgaaaggctg    900

tgtaagcctt ctcctgcaaa ttccattgct ttatagttag caccgttagc gccaatcttt    960

ccaataatag agagtattaa atctcttgca tatactccat cgttaagctt tcccttaagg   1020

ttgaatctta atgttcccgg aaccattacc catgatgttc ctgtaaccat tgcatacaaa   1080

taatctgtac aaccaacacc tgtaccaaat gcacctaacg caccatatgc acaagtatgg   1140

ctgtctgctc caaatataag ctcacccggc actacatgat tttccatcat aacctgatga   1200

cacacaccct cgccctcgta gaacttaata tcattagcct tagcaaagtc tctcatcttc   1260

ttctgtgagg ctgctgtctt aggactgtct gatggaatat tgtggtctac aatccataca   1320

agcttatcct tgtcagcaat atgaggattc tttaacttct catacatacc aatagtaaga   1380

tgtgttgttc catcattact cataagtctg tcaagagtaa cagttgcaat atcaccagcc   1440

ttaacctgtg aaagacctgc tgcccttgcg ataatcttct ctgcaatagt catgccatgc   1500

tttgcctcat ctgcaggtac ggctgtactc tcagactctt ctttctcacc atcaagtgat   1560

gcaataagac caccctgatt aagaatagcc tgcatcttgg ctggaagctt agtacatgta   1620

taagtctttc cattaacagt tataattcca tcttctaatg aaagctcaca ttcatccccc   1680

gcattaactt cgtcatggag ttctttacat acaataacag gaagtcctat attaatagca   1740

ttacgataga atattcttgc aaatgatttg gcaatcactg ccttgacacc taatgcctta   1800

agtacgcttg gtgcctgctc tcttgatgaa ccacatccaa agttgtcatc tgcaacaacg   1860

aaatctcccg gctttacggc agaagcaaaa tcagagtcta atgattcaaa tgtatgactc   1920

ttcatctcat caattgtcgg aaacaaaaga tactgcgatg caataatctg atctgtatca   1980

acatctttat caaacttaaa tatcctaccc attgaccccc atcgagagac tccgaacgtg   2040

gcaaatggag ggaccagagt tgttcagttc acaggtagat aatgtcgcgg gtcttgatag   2100

ttagcaataa atacagtttc agaatatctg taatacaaaa actgtatcga gacaagaaaa   2160

aagtagcaaa atttacaaat gttcatgatt catctggcta aattggatgt tcaactgacc   2220

cattgaagac aagggcaaca accatggtca agaccgttaa gctttctcat tgccttaaca   2280

agtccgcctg cattaagtat atccacaaga ttatcaggaa gtgaagcaat aggatatgct   2340

tttccattgt gtgtaatctt tgcatttact tcaacatcaa tagtatcgcc ttccgtaact   2400

tcgtcgtgaa ggtctgcatt ctctataagg agaagtccgt tattaataga atttctgaag   2460

aatattcttg catatgattt ggcaataaca catttaatac ctaatgcctt aataacctca   2520

ggtgcctgct ctcttgatga accacaacca aagttctttc ctgcaacaat gatgtcgcct   2580

ggcttaatct gacctgcaag ttctggtctt aatggcgaaa atgcatatgg tttcatatct   2640

tctactgtct ttaatgcaag gtactctgta gggataatga tatctgtatc aatgtcatca   2700

ccaagtaccc atactttacc gctaaatttc tcgttcatta aggctgagat cttcttcagt   2760

gcattgtagt tgaatgaagg gttagggggg aaatgccccc ctattttttg tctagccatc   2820

ctgccacgtt tgacagggta gcaatttcga cacgataggg ttctctcttc tgccgtta     2878
```

<210> SEQ ID NO 65

```
<211> LENGTH: 2380
<212> TYPE: DNA
<213> ORGANISM: Artificial Sequence
<220> FEATURE:
<223> OTHER INFORMATION: Synthetic Construct- Sequence No. 65,
      Example 65: designer nirA-promoter-controlled 3-isopropylmalate
      dehydratase DNA construct (2380 bp)

<400> SEQUENCE: 65

agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catgaatgaa tcttcttgga tctgtgatgt atccggttac cgcggtggct    300

gccgccgttg caggagaagc aaggtatatc tccgcattgg gattccccat ccttcccttg    360

aagtttctgt tctgcgtgga aagtaccctc tctccgtctc caagaacacc catgtggatt    420

ccaacacatg ggccgcaacc tggtggtata actgccgctc cgagttcaac aaatttcttg    480

attattccct tttcaagggc gtccatgtag accttccttg aagcggggcc gacgatcagc    540

ctcacatccg ggtgctttcc gtgtttctca agaattttca aagcgatctc aagatcctga    600

agtcttccgt tcgtacaggt tcctatgaac acttgatcta tctttatctt ttccttttca    660

acctcgctca cctttctcac gttgtccaca tagtgaggca aagagacgag tggttcgagt    720

gtgtcggcat ctatctctat ctctgtctcg taaaccgcgt ctggatctgc tttcaactct    780

ctgaagtcct cctctcttcc catctttttc aggaactctc tggtcttctc atcagaaggc    840

atgagacctg ctttcgctcc cacttccacc gccatgttgg aaatggtgag tctgtcctcc    900

acattcatat tttcgataca gcttccatgg aactccaacg ctttgtaagt tgcgccgtcg    960

cttcccagaa ttctcgcgat ctcgagaatg atgtctttcg cgtaaactcc atcctgtaac   1020

ttcccgttca ccacaacctt gatcgtctca ggtactttga accagttctg tccaagcccg   1080

aagatgatcg caacatctgt ggaccccatt cccgttccga aagcaccgag cccaccggca   1140

gtgcaggtgt gcgaatccgc acctgctacc agatcgccgg gtttcacgta tttttccgcg   1200

aggatctggt gggatatccc gtctcccgca tcgaaaacct tgactcccat ctcttttcca   1260

aattctctca tcatcttctg cgaattcgaa agctctttcc tcgggctcgg agaagcgtga   1320

tcgatgaaga ggaaggcctt cgggaccttc acttctttga agccgagttc tctgaattcg   1380

tttatcatca gggggcctgt tccatcctgg gccatggcta tatccactct cgcgagtacg   1440

atttctccgg ctttcacgtc tcttccagta tgttcagaaa agatcttttc tgcgagtgtc   1500

ttacccattg acccccatcg agagactccg aacgtggcaa atggagggac cagagttgtt   1560

cagttcacag gtagataatg tcgcgggtct tgatagttag caataaatac agtttcagaa   1620

tatctgtaat acaaaaactg tatcgagaca agaaaaaagt agcaaaattt acaaatgttc   1680

atgattcatc tggctaaatt ggatgttcaa ctgacccatt gaagacaagg gcaacaacca   1740

tgaactcttg ggaaggaacc gtgctttttc agatagttca ctataccgtc ttctttcagt   1800

atctcgagga gaaacttcgg aatcggagtg aatctgtatt cttttcctgt tgtgaggttc   1860

ttcaaaacac cgttttcgag atctatctca agttcgtctc cctggttgat ctcgtcgact   1920

tccttgagct ctatgactgg aagtcccaca ttgatggcgt ttcggtagaa gatccttgcg   1980

aaagacttcg ccacgataca ggaaacacca gcgatcttta tgatacgcgc agcgtgctct   2040

ctggaagaac caagtccgaa gttcttgcca gccacgatga tgtcaccttt ctgcaccttc   2100
```

ttcgcgaaat cctccatggc atcttccaag acgtgttttg cgagctcctc aagattgttc 2160
ctcagatgaa aataccttcc aggtgctata tggtcagtcg atatattgtc accgaatttc 2220
cagactcttc cccttatcat taaggctgag atcttcttca gtgcattgta gttgaatgaa 2280
gggttagggg ggaaatgccc ccctattttt tgtctagcca tcctgccacg tttgacaggg 2340
tagcaatttc gacacgatag ggttctctct tctgccgtta 2380

<210> SEQ ID NO 66
<211> LENGTH: 1456
<212> TYPE: DNA
<213> ORGANISM: Artificial Sequence
<220> FEATURE:
<223> OTHER INFORMATION: Synthetic Construct- Sequence No. 66,
Example 66: designer nirA-promoter-controlled 3-Isopropylmalate
Dehydrogenase DNA construct (1456 bp)

<400> SEQUENCE: 66
agaaaatctg gcaccacacc tgacccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catgccatat ttcttcgagt tttttacata tgagatctcc catctgagag 300
gtcgaaaccg ccttttctgg atcctctgcg atgtctctgg ttctgtatcc ctcttctatc 360
accagctcaa ccgctctttc tatctttctt gcctcttcca ccattccaaa ggaatgctcg 420
agcatcatgg cgagagagag gatctgtgcg atcgggttgg cgatgttctt tccggctata 480
tcaggagcgg aacctcctgc cggctcgtag aggttcttat caccgaaaga cgcggacggc 540
agaagaccaa gagaaccagg aagtgccgca ctctcatccg agagaatgtc tccaaacatg 600
ttcgttgtga ggatcacatc gaactgcgat ggtttcagga tgagctgcat ggcagcgttg 660
tccacataca tgtgcgtcag ctccacatca gggtattctc tcgctacttc gttcacaact 720
ttcctccaca gcatggaact gtagaggacg ttcgctttgt caacggaggt gaccttttt 780 cttctgtttt ttgcgatttc aaaggcagtt ctcgcgatcc gttccacggt ttttctgtcg 840
tagatcatgg tgtcgaatcc cttttcttca tccaatcccc tcggctggcc gtagtaaact 900
ccgtaggaaa gttccctgac ggtcacaaga tcgaccccgg atccaatcac cttttctttc 960
aaaggagaga catgcacaag cgatctgtag acctttatcg gtcttatgtt tgcgtaaagg 1020
ttgagcatct tccttagggc aagaagcccc cctatttccg gcctcttctc cggaggaaga 1080
tcgtcccatt taggtcctcc gacgcttcca aggaagatcg cgtcggcttc cagacatatc 1140
ttttttgtct cttcaggaag ggttcaccg aatttgtcta tggcatcccc tccgatgtgt 1200
ccaaagactt tctcaaaggt tttccccgtt ttcttttcca ccacctcgag cactttaaga 1260
gcttccctta caacctcggg acctatgccg tctccaggca aaaccgctat cttcattaag 1320
gctgagatct tcttcagtgc attgtagttg aatgaagggt taggggggaa atgcccccct 1380
attttttgtc tagccatcct gccacgtttg acagggtagc aatttcgaca cgatagggtt 1440
ctctcttctg ccgtta 1456

<210> SEQ ID NO 67
<211> LENGTH: 1933
<212> TYPE: DNA
<213> ORGANISM: Artificial Sequence
<220> FEATURE:

<223> OTHER INFORMATION: Synthetic Construct- Sequence No. 67,
Example 67: designer nirA-promoter-controlled 2-Isopropylmalate
Synthase DNA construct (1933 bp)

<400> SEQUENCE: 67

```
agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catgctcagc acccccgttt tttctgagaa ggcctttagc gatgaggtac    300

ttgtttattg cgtttatgta agctatcgca gaggcttcca ctatgtccgt ggagacaccc    360

cttccactgt agagttcacc gtttattctc aacgtgagtt tgacctctcc ctgtgcgttc    420

tttccagttc caaccgcctg aattatgtac tcctcgagct tcggttgaat accgagcgct    480

ttgtctatag ccttgaagat agcatccact ggaccgtttc ctgcctctgc tgcttctttc    540

ttttcatctc caacctgaag cacgaccgcc gcggttggaa gcagcgtgtt tccggtgtgt    600

acatggaagt gaacgagctt gtaaccgttg atgggctccc tcaaaacttc cgagacgatc    660

gagaaaagat catcgtcgta aacctctttc tttctgtcgg cgagttctgt gaacttctcg    720

aacactttct ggaaggtctc ttcgtcgagt ttgatgccgt agctctccag cttctttctg    780

agggcgtgct ttccggagtg tcttccaagc acgagcgtct cggaagacct gccgatatcg    840

gatggtttca tgatctcgta ggtctccctg tgtttcagca caccatcctg gtgtataccc    900

gactcgtgaa ggaacacgtt ctctcccact atgggtttgt ttctggacgg gatgagcccc    960

gttatatgtg tgaggagcct ggaagcgggg tatatgagct ctgtctttat acccgtctcg   1020

tagggaagtt tgtctttcct caccttgagg atcatcacga actcttccag ggcacagttt   1080

cctgccctct ctccgatacc gttcagagtc acttcgacct gggtggctcc gttctgaacg   1140

gcagcgaggg agttcgccac agcgagtcca agatcgttgt gacagtgcac agaaagatcg   1200

acattctcta taccgggcac accctctctc aaggtcttta tgagttctcc aaactcatcg   1260

ggaagggcgt accccaccgt gtccggaaca ttgatcgttg tggctccggc ttcgatcgcc   1320

gtcttgtagg cttctatcaa aaagggaacc tccgttctcg aagcgtcttc cgccgagaac   1380

tccacaaggt cgaaaaactg ttttgcgtag ccgacgtatc ttctgatcct ctcgaggatt   1440

tcctctttct ccattctcag tttgtatttt ctgtgaatcg gagaggtcgc tatgaaaacg   1500

tgtatcatac gtttgtcttt tggtcgatcc ttgagagcct cgtacaccgc gtctatgtcc   1560

ttttcaacac accttgcgag tcccaccact atgggtttct gaacggcgct cgcaactctt   1620

tttacagctt caaactgcac gggagatgaa acgggaaacc cagcctcgat gagatcgaca   1680

ccgagatcct ctaacatgag tgccatttct actttttcct caaccgacat cgaagcccct   1740

ggggattgct ctccatccct caacgttgta tcgaagatct taattctcct cattaaggct   1800

gagatcttct tcagtgcatt gtagttgaat gaagggttag gggggaaatg ccccccctatt   1860

ttttgtctag ccatcctgcc acgtttgaca gggtagcaat ttcgacacga tagggttctc   1920

tcttctgccg tta                                                      1933
```

<210> SEQ ID NO 68
<211> LENGTH: 2632
<212> TYPE: DNA
<213> ORGANISM: Artificial Sequence
<220> FEATURE:
<223> OTHER INFORMATION: Synthetic Construct- Sequence No. 68, -continued Example 68: designer nirA-promoter-controlled Isopropylmalate Isomerase DNA construct (2632 bp)

<400> SEQUENCE: 68

```
agaaaatctg gcaccacacc tgacccccat cgagagactc cgaacgtggc aaatggaggg     60
accagagttg ttcagttcac aggtagataa tgtcgcgggt cttgatagtt agcaataaat    120
acagtttcag aatatctgta atacaaaaac tgtatcgaga caagaaaaaa gtagcaaaat    180
ttacaaatgt tcatgattca tctggctaaa ttggatgttc aactgaccca ttgaagacaa    240
gggcaacaac catgacagac cggctcggct tcaagctggc gcacatcgac aaaatgtccg    300
taaatcgcag ccgccgcggc catcaccggg ctgacgagat gcgtgcgcgc ccctttccct    360
tgccgccctt caaagttgcg gttcgacgtt gacgcacagt gctcgccttc tgggatgatg    420
tccgggttca tgcccaaaca ggcgctgcag ccggagtcgc gccattcaaa accggcgtcg    480
atgaaaattt gtgccaaccc ttccgcttcg gcttgttttt tcacttgctg cgatccaggc    540
acgacgagcg cccgtacacc aggagccact tttttccctt tcacgatgct cgccgccgcg    600
cgcaaatcgc tgaggcgtga gttggtgcac gaaccgatga agacgtgctg caccggaata    660
tccgtaatcg gcgtgcccgg cttgagcccc atgtactcaa gcgcccggcg caccgcgttt    720
tgctctgttt tgctttcaaa ttgctcggga tgcggcacga cgccatcgac ggaagtgctc    780
atcgcggggt tcgtccccca cgtcaccatc ggagcgatcg tcgacgcatc gatttcaatc    840
gttttatcgt attttgcccc ctcatcgctg gctaacgccc gccaccgttc caccgccttg    900
tcaaactcct cgccttttgg tgcatatttg cggccgcgca aataggcgaa cgtcgtttca    960
tccggactga tgaggccggc tctcgcccca gcttcaatcg acatgttgca aatcgtcatt   1020
cgctcttcca tcgacatgcg tcggatcgct tcgcctgtaa attcgataat ataaccggtg   1080
ccgacgccaa cgccatagcg gccgataatg gccaagatga cgtctttggc ggtcactcct   1140
ttgccgaggc ggccgttgat gcagatttgc agcgttttcg gcttatgctg ccaaagcgtt   1200
tgtgtagcca atacatgctc gacttcgctc gtgccgatgc caaacgccaa ggcgccaaac   1260
gccccgtgcg tcgacgtatg gctgtcgccg caaacgatcg ttttccccgg ctgggtcaac   1320
ccgagctctg ggccgatgac gtgaacgatt ccttgctctt cgctgtgtag gtcggcgagc   1380
ggaatgccga actcgcggca gttgcgctca agcgcagcga tttggttgcg cgccacttcg   1440
tcggtaatca caaatcggtt aacggttggc acgttatggt ccatcgtcgc aaaggtcaaa   1500
tccggccgcc gcaccttccg tcctttttgc cgcaaccctt caaacgcttg cggcgaggtc   1560
acttcatgca ctaagtgcaa atcgatgtac aataaatccg gtttgccctc ctcacggtag   1620
acgacgtggt tttcccaaat tttatcgatg atcgttttcg gcttcattga cccccatcga   1680
gagactccga acgtggcaaa tggagggacc agagttgttc agttcacagg tagataatgt   1740
cgcgggtctt gatagttagc aataaataca gtttcagaat atctgtaata caaaaactgt   1800
atcgagacaa gaaaaaagta gcaaaattta caaatgttca tgattcatct ggctaaattg   1860
gatgttcaac tgacccattg aagacaaggg caacaaccat gcggccgtgg acaatgccgt   1920
cgttcgtagg cggcgatatg cgcttcgtac acaaacgtca aatcaatttc gtcccatcct   1980
tttagcaaca gctgttttcg atacgggtcg atgtcaaacg gacgcgaaaa tccttcatcg   2040
tcaaataccc gctgttcttc aagcgaaacc gtcagttcat agtctgcgcg ctcgctttgg   2100
cgcagcaagt agcggacatc ctctttatcc agccggatcg gcaacagtcc atttttaag    2160
cagttgttgt aaaaaatatc ggcaaacgat ggggcaatga ttacgcggaa tccgtaatct   2220
```

```
tgcagcgccc acggcgcatg ttcgcgcgat gagccgcaac cgaagttttc atcggcgact   2280
aaaatcgtcg ccccttcgtt ttccgggcgg ttgagctcaa actccggatt tggcgtgccg   2340
tcgctcaaat accgccaatc gtaaaagaga aactggccaa agccggtgcg ttcaatccgt   2400
ttcaaaaact gctttggaat gatttgatcg gtatcaatat tcgcccgatc gatgccggcg   2460
gtttttccgc gatggatcgt aaacggcttc attaaggctg agatcttctt cagtgcattg   2520
tagttgaatg aagggttagg ggggaaatgc ccccctattt tttgtctagc catcctgcca   2580
cgtttgacag ggtagcaatt tcgacacgat agggttctct cttctgccgt ta           2632
```

<210> SEQ ID NO 69
<211> LENGTH: 2035
<212> TYPE: DNA
<213> ORGANISM: Artificial Sequence
<220> FEATURE:
<223> OTHER INFORMATION: Synthetic Construct- Sequence No. 69, Example 69: designer nirA-promoter-controlled 2-Keto Acid Decarboxylase DNA construct (2035 bp)

<400> SEQUENCE: 69

```
agaaaatctg gcaccacacc tgacccccat cgagagactc cgaacgtggc aaatggaggg     60
accagagttg ttcagttcac aggtagataa tgtcgcgggt cttgatagtt agcaataaat    120
acagtttcag aatatctgta atacaaaaac tgtatcgaga caagaaaaaa gtagcaaaat    180
ttacaaatgt tcatgattca tctggctaaa ttggatgttc aactgaccca ttgaagacaa    240
gggcaacaac catgtataca gtaggagatt acctgttaga ccgattacac gagttgggaa    300
ttgaagaaat ttttggagtt cctggtgact ataacttaca atttttagat caaattattt    360
cacgcgaaga tatgaaatgg attggaaatg ctaatgaatt aaatgcttct tatatggctg    420
atggttatgc tcgtactaaa aaagctgccg catttctcac cacatttgga gtcggcgaat    480
tgagtgcgat caatggactg gcaggaagtt atgccgaaaa tttaccagta gtagaaattg    540
ttggttcacc aacttcaaaa gtacaaaatg acggaaaatt tgtccatcat acactagcag    600
atggtgattt taaacacttt atgaagatgc atgaacctgt tacagcagcg cggactttac    660
tgacagcaga aaatgccaca tatgaaattg accgagtact ttctcaatta ctaaaagaaa    720
gaaaaccagt ctatattaac ttaccagtcg atgttgctgc agcaaaagca gagaagcctg    780
cattatcttt agaaaaagaa agctctacaa caaatacaac tgaacaagtg attttgagta    840
agattgaaga aagtttgaaa aatgcccaaa aaccagtagt gattgcagga cacgaagtaa    900
ttagttttgg tttagaaaaa acggtaactc agtttgtttc agaaacaaaa ctaccgatta    960
cgacactaaa ttttggtaaa agtgctgttg atgaatcttt gccctcattt ttaggaatat   1020
ataacgggaa actttcagaa atcagtctta aaaattttgt ggagtccgca gactttatcc   1080
taatgcttgg agtgaagctt acggactcct caacaggtgc attcacacat catttagatg   1140
aaaataaaat gatttcacta aacatagatg aaggaataat tttcaataaa gtggtagaag   1200
attttgattt tagagcagtg gtttcttctt tatcagaatt aaaaggaata gaatatgaag   1260
gacaatatat tgataagcaa tatgaagaat ttattccatc aagtgctccc ttatcacaag   1320
accgtctatg gcaggcagtt gaaagtttga ctcaaagcaa tgaaacaatc gttgctgaac   1380
aaggaacctc atttttttgga gcttcaacaa ttttcttaaa atcaaatagt cgttttattg   1440
gacaaccttt atggggttct attggatata cttttccagc ggctttagga agccaaattg   1500
cggataaaga gagcagacac cttttattta ttggtgatgg ttcacttcaa cttaccgtac   1560
aagaattagg actatcaatc agagaaaaac tcaatccaat ttgttttatc ataaataatg   1620
```

```
atggttatac agttgaaaga gaaatccacg gacctactca aagttataac gacattccaa   1680

tgtggaatta ctcgaaatta ccagaaacat ttggagcaac agaagatcgt gtagtatcaa   1740

aaattgttag aacagagaat gaatttgtgt ctgtcatgaa agaagcccaa gcagatgtca   1800

atagaatgta ttggatagaa ctagttttgg aaaaagaaga tgcgccaaaa ttactgaaaa   1860

aaatgggtaa attatttgct gagcaaaata aatagtaagg ctgagatctt cttcagtgca   1920

ttgtagttga atgaagggtt aggggggaaa tgccccccta tttttgtct agccatcctg   1980

ccacgtttga cagggtagca atttcgacac gatagggttc tctcttctgc cgtta        2035
```

<210> SEQ ID NO 70
<211> LENGTH: 1426
<212> TYPE: DNA
<213> ORGANISM: Artificial Sequence
<220> FEATURE:
<223> OTHER INFORMATION: Synthetic Construct- Sequence No. 70, Example 70: designer nirA-promoter-controlled NAD-dependent Alcohol Dehydrogenase DNA construct (1426 bp)

<400> SEQUENCE: 70

```
agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catggggtat caggactgcc ctgcctagaa cttcaccttt ctctagcctc    300

tcaagcacat cgtttatttc atctagcttg tggatatcaa cctctaccct gaccttaccc    360

tgaagggcta acgtgactag ctcatggagc tctacatagt ttcctactag gcttccttca    420

aaggatacct cagaggatat caccctgatc gtggggaatc taagctcacc cccatagcct    480

acgatgataa gcctccccat cctccctagc aggtatggtg tataatcgac tgtagcctga    540

gagcctacga agtccattgc aacgttaact cctctccccc tggtaagctc catgacctgc    600

tttacagggt ctcgtctagc gtcaaccacg tgatccgctc caagcctctc ggccagcttt    660

agtttttctt ccttaacgtc cagtgctatc accgtcgcgg gtgtcataac tttaagtagc    720

tgaactgcaa tatgacctaa tcctcccacg cccactatag cgacgtatgc gccgggatag    780

agggttcggg cggccttctt aacagcccta taagccgtta tcccagcgtc cgctagaggg    840

gccatttcaa caagtttctc cctgctaata tccttaggca gctttatcac agacctgtgc    900

gaggtcctca tgaactctgc aaatccacca tcgatattaa gtcctgggaa ctctaggttc    960

tcgcagtgca tatcctcacc agctctacag gctagacagg ttccatctgt gaccgccggg   1020

tgaagaatta ccgggtcccc cttctctaag ccttccactc cttcggcaac ttcttcaata   1080

tacccgacgt tctcatggcc taaagtgtag ggtagcttag gctgcaatag ctcatgccac   1140

attccctgga caaggtggag gtccgtatgg catacgccag cgcctgcaat ccttacaata   1200

acgtcaaatc taccttctag cctcggatag tcgacatcct ctatcctcaa cggcttgtta   1260

tactcgtgga gcctggcagc tttcaataag gctgagatct tcttcagtgc attgtagttg   1320

aatgaagggt taggggggaa atgcccccct atttttgtc tagccatcct gccacgtttg    1380

acagggtagc aatttcgaca cgatagggtt ctctcttctg ccgtta                  1426
```

<210> SEQ ID NO 71
<211> LENGTH: 1468
<212> TYPE: DNA

<213> ORGANISM: Artificial Sequence
<220> FEATURE:
<223> OTHER INFORMATION: Synthetic Construct- Sequence No. 71,
Example 71: designer nirA-promoter-controlled NADPH-dependent
Alcohol Dehydrogenase DNA construct (1468 bp)

<400> SEQUENCE: 71
agaaaatctg gcaccacacc tgacccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catggcgtac ccagacacct ttgaaggatt tgccgtcact gacactgcaa 300
aatggtccac aaccaagaag atagaattca ccccaaaaag gttccaggaa catgatatcg 360
atgtcaagat ccatgcctgt ggtatctgcg ggagtgatgt tcacactgtt tgcgggggat 420
gggcaaaacc agaccttccc gtgatcccag gacatgagat cgttggtgag gttgttagag 480
tgggcccaaa agtgaaggga tttgaaattg ggcaaagagt tggtgttgga gctcaagttt 540
gggcctgtct agagtgcgac acatgcaagg ataacaacga aacgtactgt cctcaatggg 600
tggacactta caatgccact tatcctgatg gtgacaaggc atggggtggt tattcctctc 660
acatcagagt ccacgatcac tttgtattcc ctattcctga tgaacttcca actaatgctg 720
tggccccaat gttgtgcgct ggtatcacca cgtactctcc gttggtaaga aatggagctg 780
gtccaggaaa gaaggtgggt atcatcggaa ttggagggtt gggacatttt gccatcatgt 840
gggctagggc tcttggttgc gaagtgtaca cgtttttctag aacacatagc aaggaagctg 900
atgctaagaa attgggaact gaccatttta ttgcgacgtg ggaggacaaa gactgggcca 960
agaagattgg cagaaagctg gactttatca tttcgtgtgg aaattcggcc acgaactttg 1020
atatggatgg ttacctcagt gtgctgaagg ttcatggtaa actcatttcc gtcggccttc 1080
cagaggagcc attcacgctg tctgctggaa gctttatcaa gaacggttgc tacttgggat 1140
cgtcccactt ggggaacaga caggagatgc ttgatatgct gaaacttgct gctgataagg 1200
gcattggttc ttggtatgag gagctcccaa tctctgagga agggctgaag gaaggactgg 1260
agagatgcca caacaatgac gttaagtata ggttcaccct gaccggttac gataaggcat 1320
tcaaatagta aggctgagat cttcttcagt gcattgtagt tgaatgaagg gttagggggg 1380
aaatgccccc ctattttttg tctagccatc ctgccacgtt tgacagggta gcaatttcga 1440
cacgataggg ttctctcttc tgccgtta 1468

<210> SEQ ID NO 72
<211> LENGTH: 1555
<212> TYPE: DNA
<213> ORGANISM: Artificial Sequence
<220> FEATURE:
<223> OTHER INFORMATION: Synthetic Construct- Sequence No. 72,
Example 72: designer nirA-promoter-controlled NADH-dependent
Butanol Dehydrogenase DNA construct (1555 bp)

<400> SEQUENCE: 72
agaaaatctg gcaccacacc tgacccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catgcaggga agcgcgcaaa atggcgagca catcatcgcg gttcaatgtt 300

```
ttgaaacggc cgaactcgcc aaacgccatc gctttatcgg ccatcagctc caagttttcc    360

tcgccgatgc catagtccgc aagccgcgac ggcgccccga ggctcgacca gaactcgcgc    420

agccgctcga tgccttcaag cgccacatcc cgctccgatt tgcccgccgg atcgacatca    480

aagacgcgca ccgcgagctg ggcgaaacgg ctgacatttt catcgagcac atgcttcatc    540

cagttcggga acaaaatcgc caatccccg gcgtgcggga tgtcatacac ggcggaaacg    600

gcatgctcaa tattgtgcgt cgcccagtcg ccgcggacgc ccatttgcaa gaagccgttt    660

aaggcgatcg tgcccgagta catgatcgtc tcgcgcagct cgtagttttc caaatcgttg    720

atcagtttgg gcgccgtttc gatcacggtt ttcaacaccg cttcacacat ccggtcttgc    780

aatggcgtgt tcggcgtatg gtggaaatat tgctcaaaca catgcgacat catatcgaca    840

atgccgtaaa ccgtatggtc tttcggaacg gtcatcgtat acgtcggatc caaaatcgaa    900

aattgcggga acgtaaacgg gctgccccag ccgtattttt ctttcgtctc ccagtttgtg    960

atcaccgaac cagaattcat ctccgacccg gtcgccgcca gcgtcaagac gacgccaaac   1020

ggcagggcgc cggtgacggg cgctttttc gtgataaact cccacggatc gccatcgaat   1080

ttcgccccgg cggcgatcgc tttcgtgcag tcgatgacgc tgccgccgcc aaccgccagc   1140

aaaaattcga cgccttcccg cttgcaaatg tccacccctt ttcttacggt cgagacgcgc   1200

gggttcggtt cgacgcctgg cagttcgatg acctcggcgc caatattccc caatatcttc   1260

atgacttcct catacaatcc gtttcgtttg atgctgccgc cgccatacac gagcagcact   1320

ttcttgccgt agcgcggcac ttcttctttg agacgttcga gctgcccttt tccgaaaatc   1380

agtttcgtcg ggttgcggaa aataaactct tgcattaagg ctgagatctt cttcagtgca   1440

ttgtagttga atgaagggtt aggggggaaa tgccccccta tttttgtct agccatcctg   1500

ccacgtttga cagggtagca atttcgacac gatagggttc tctcttctgc cgtta         1555
```

<210> SEQ ID NO 73
<211> LENGTH: 1558
<212> TYPE: DNA
<213> ORGANISM: Artificial Sequence
<220> FEATURE:
<223> OTHER INFORMATION: Synthetic Construct- Sequence No. 73, Example 73: designer nirA-promoter-controlled NADPH-dependent butanol dehydrogenase DNA construct (1558 bp)

<400> SEQUENCE: 73

```
agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catgaaaatc cacatcactg ccgtaatatg cacaagtata taatttttcc    300

atagtttcat cattaatctc ccttggattt gatcctgtgc atggatctaa aacagcatta    360

tgagctataa atttaagatt agctttaaat tcattctcat ctattccata ctctttcatt    420

gatgaaggta tatttaattc cttattaaac ttatttatta aatctattag gtcatctgtt    480

aattctcttt cactttctcc ctttaatcca atatgtcttg caatgttagc atatctattt    540

tcacaagctt ttctattata tttaattaca tatggcaaga agatagcatt agcacatcca    600

tgtggtatat ggaatacagc ccctacctta tgagccatag aatgtactat tcctaaaagg    660

gcattagaga aggccattcc tgctaaacat tgagcctcat gcatttctcc cctagcttcc    720
```

```
atatctccct tatatgaatt tactaagtgc atattaacca tttcaattgc ctttaaagct    780

aaaggatctg taaagtttga tcttaaactt gcagtataag cctcaatagc atgagttaag    840

gcatccattc ctgtgtgagc tactaacttc tctggcatag tttctgctaa gctaggatca    900

acaatagcta tatctggagt tatttcaaaa tctgctaaag gatatttaat cttagcctta    960

taatcagtta ttactgagaa ggcagttacc tctgtagcag ttccagaagt tgatggaata   1020

gctacaaact ttgcttttct tctaagctta ggtaatccaa aggaacaat ggccttttca   1080

aaagtaaaat caggatactc gtagaaaatc cacatagcct ttgctgcatc aataggtgaa   1140

cctcctccta tggaaactat ccagtctgga ttaaattcct ccatttcctt tgcacccttc   1200

ataacagttt ctactgatgg atctggttct actccttcaa aaacctttgt ttccatatta   1260

gcttccttta aataacttaa aaccttatct aaaaagccaa atcttttcat tgatccgcca   1320

ccaataacta taaaggcctt tttaccttct aaactcttta atacttctaa ggaatctttt   1380

ccatgatata tgtcccttgg taaagtaaat cttgccatta aggctgagat cttcttcagt   1440

gcattgtagt tgaatgaagg gttagggggg aaatgccccc ctattttttg tctagccatc   1500

ctgccacgtt tgacagggta gcaatttcga cacgataggg ttctctcttc tgccgtta     1558
```

<210> SEQ ID NO 74
<211> LENGTH: 3646
<212> TYPE: DNA
<213> ORGANISM: Artificial Sequence
<220> FEATURE:
<223> OTHER INFORMATION: Synthetic Construct- Sequence No. 74,
Example 74: designer nirA-promoter-controlled Phosphoenolpyruvate
Carboxylase DNA construct (3646 bp)

<400> SEQUENCE: 74

```
agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catggccggc gttccgcaag cccgccgcga tgcccaggat ggagagcagc    300

agcgcccgct ccagggccgg gcgctcgggg tcgccttccg gcgaggcccg gtaccgggcc    360

agcagctcca cctgcaggta gctgatgggg tcgacgtacg ggttgcgcaa ggccgtctgc    420

cgcgccagca cggggtggtg ggccagaagc ggcccgccga aggtctcctc caagagcgcc    480

cgggtccgca ccatggcctc ctcgagccgg gggaagaacc ggttcgccag gggcccgggc    540

accagccgca ggtactccct ggccacggcc aggtcggcct tggccagggc cagggccgcg    600

ccgtccagca ccgagcggaa gaagggccag cgggcaaaca tcgcctggcg aaggtcccgc    660

ggcaccgccg caagaccttc ggccagcccg taccagccgg gcagcagaag acgcacctgg    720

gtccaggcca tcacccaggg gatggcccgc agatcctgga cgcgccgggc ccggcccgtg    780

cgggccaccg ggcgggaagc gatcttcagg gcggcgatct cccggatcgg ggtgaagtgc    840

tcgaagaact cgaagaaccc gggctccgcc agcagctggc ggtaggcctc cgccgaccgg    900

gcggcggccc ggtccatggc ctcccgccag gccgccggga cgggggaacc gcccggggcg    960

agcccctggc gcccgccgcc cggcctgctc ggcgcggtcc cggccccgcc gggcgggccg   1020

ggttcctccg gcgaaagcac cgcctcttgg gcctgggcca gcgtgtcccg ggccgccgcc   1080

agaaggaagt ggtagaggag ctgctccagg ttgcgcaggg ccagctcggg gtgagcgtag   1140

cggtccgcca gcgcctctcc ctgctcggtg agccgcaggc ggcggcccac ggtgcccggc   1200
```

```
ggcaggctgg cgatggcgcg gccggcggtc cccccgccgc cccgggctgt ggacgtgccg   1260
cgaccgtgga agaaggacac cggcacgccc gccgcccggg ccaccgccgc gatgccctcc   1320
tgggcccggt agagggccca gttggccgcc aggtagcccg cgtccttgct ggagtcggag   1380
tagccgatca tcacctcgca gccgccgcgg ccgcgggcgt ggacgccgaa gacggggttc   1440
tgcagcagct gctccatggc gcggggcgcc gcctccaggt cggccagggt ctcgaacagg   1500
gggaccacgt caaagggcaa ggggtggccg gggcggtaca gccccacctc ccgcgccagg   1560
acgaacacct ccagcacgtc ggcggggccg cggcagccgc tgatgatgta agccccccgg   1620
tcctgccagg cccgcagagc atccagggcc acggccagct cgcggctgcg gggccggtag   1680
cccaccggcg ccagcggccg gggcgaagcc agctcccggg tcagcaccgc ctcccgcccg   1740
gcggcatcca gggccaggta ctcccctgcc gccatgaccc caccggcttc cagcagctcc   1800
gccaccgccc gcccgtgggc ctcggcatgc tcccgcaggt cgaggggcgc catggcctcg   1860
ccaaagacct gggcccgcca gcgcagggga cgcaccaggg tggccgccgc ctcgcccagc   1920
ccggcatccc gcagcccctc ttccacctgg aagagcaggc gatccagggc ggtggaaccg   1980
gcggcctccg gcccctcgcc ggccggcggt tccccggcgg tcccctttgg tggcgcggcc   2040
gcggcgggcc gggaaggccg ttcgccggct gggtccgctg gaacggcggg ccctccaggg   2100
atgccctccg ctgaagcggg cggccgggga ggcattgccg ctccctccgg cggagccgcc   2160
ggccggggag gcggtgccgt tgcctcgact gcagcgtccg gccggtgggg tacagccggt   2220
gcctcggctg gagccgccgc ccgggcgggc gtctcgctcc acacctcttc cggcaccgcc   2280
cttgccgccc agtgccgctg cagccggtag gcgaaccgcc ggtagggctc gccggggaac   2340
cggccggcgg ccgccggcgg caggggcgcc acggcctctg cgggcaagga gggcagggga   2400
ggcagggaag cccgttcttc cgccacggac agatcccgcg tcagggcggc caggcctccg   2460
gcgtactttc gggcgatctc ggcccgcgcg taggcctggg cccaggcggt gacctccggg   2520
gtcacaaagg ggttgccgtc ccggtcacca ccgatccagc tccggaaggc caggcgcggg   2580
ggaagaaccg gccgccgccc gtagcgggcg gccaccgccc cctcgagggc ctccatgagc   2640
cggggcaccg cctcccacag ggtggtgggc aggtagtaga ggccgccgcg gacctcgtcc   2700
tccacccggg gcggggccgg gcgcagctcg cgggtggtcc agagcagggt gacccgggcc   2760
accacctcgt ccaggtcccc ctcgccccgc tccagccggt ccagggcctg gttgagctgc   2820
agcaggtggt ggcgcagggt gcgccgccgc gtctcggtcg gatgggccgt gaaggtcagc   2880
tccagccggg ccgaggcgag gaggcgcacc acgtcgtcga attccatccc ttgggcctga   2940
agctgggtga ccagggccag cagcgactcg ggccggggcc ggtcgggcgt gctggcctgc   3000
tcgcgccggc ggttcacccg cacccggtgc cgctcctccg ccaggttgac cagatggaaa   3060
taggtcgaaa aggcccggat cagcccttcg gccgcggcca ccgaaagccc gccgatctcg   3120
gcccgcagcg cctgccgggc ggcgtcgtcc cccgggtgct gccggaggtg cttggtgtgg   3180
gcgcggatgt cctcttccag ttcgaacagg cgatcccccg agaggcggcg gatggcctcc   3240
cccagggccc gtcccaggag gtcgacctcc cgcttgagaa gggggtacag ctcctcttcc   3300
ggccgcccat ccggcggggg aacggatccc gccggggcag gcaacgcctc gccggacgag   3360
ccggccgccg cagggcggct cccctgcccg ccgccccggt cctggcggtc ctgaccgtcc   3420
ttgcggtccc ggccgtcctt caggtcccgg ctccccttcc ccgccgccga gccggcccct   3480
gccggccggt caccctcgcc gctcactaag gctgagatct tcttcagtgc attgtagttg   3540
```

-continued aatgaagggt tagggggggaa atgcccccct attttttgtc tagccatcct gccacgtttg 3600
acagggtagc aatttcgaca cgatagggtt ctctcttctg ccgtta 3646

<210> SEQ ID NO 75
<211> LENGTH: 1591
<212> TYPE: DNA
<213> ORGANISM: Artificial Sequence
<220> FEATURE:
<223> OTHER INFORMATION: Synthetic Construct- Sequence No. 75,
Example 75: designer nirA-promoter-controlled Aspartate
Aminotransferase DNA construct (1591 bp)

<400> SEQUENCE: 75
agaaaatctg gcaccacacc tgacccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catgagaatt tcggaaagat caaaaaaggc gccggcgagt cccataagaa 300
aattagtgcc atttgccgag gaagctgtaa aaaaaggtaa aaaaatctat tatttaaaca 360
taggtcaacc tgatatacca acaccttcaa tttattttca gtatgaggaa aaacacagac 420
cccagattgt agcttataca cactcagcag gtcttctgcc actgagggag gcttttacaa 480
aatattacgc cagattcgat atagatgttt tcccggatga aatcatcgtt accaatggtg 540
gaagtgaagc tgtcctgttc gctatgacag tcgtggcgga tccgggagat gaaatacttg 600
ttctggagcc gttctatgcc aattacgctg gatttgctgc tcaacttggt atcaatcttg 660
ttccagttag aactcgcccg gaggatggat atcaaatacc aaagatgggt gatttttctgg 720 agaaaatcag tcacaggact aaagcaatca ttttttccaa tccctgcaat cctacggggg 780
ctgtttacga tgaaaaacaa cttgaagtta ttgctgaagt tgctttgaag agagatttgt 840
ttgtgatttc agacgaggtt tatagagaat tcacttttga tggttttagg gccatatcta 900
tgatgagttt ttctaatatt tctgacaaag tcatagttgt tgacagtatt tctaaaagat 960
atagtgcctg cggcgcgcgg attggtacat ttattaccaa gaataaagat atatatcaag 1020
cagctatgaa actggctcag gcgagactct gtcctgctat gacatctcaa tacggtacta 1080
ttggtcttct gacgcttgac gatttgtatt attcacaaat gagaaaagag tatgaaatga 1140
gaagagatgt tgtttacgaa gaacttcagc gcattgatgg agcagtcttc aagaaacctc 1200
acggggcttt ttatatttcg gtgaaacttc caatcgacaa ttctgaagat tttgtgaaat 1260
ttatgttgac ggagtatgag gttgaaggaa aaacgacaat ggtggcacct ctcagtggat 1320
tttatgtaac accatctacg gggatgagtg agatcagaat agcgtatgtt ctggaacgcg 1380
aacaactgag ggatgcagtt gcaattttga cttcaggttt gaaaacttac atagagagaa 1440
gaaataaata ataaggctga gatcttcttc agtgcattgt agttgaatga agggttaggg 1500
gggaaatgcc cccctatttt ttgtctagcc atcctgccac gtttgacagg gtagcaattt 1560
cgacacgata gggttctctc ttctgccgtt a 1591

<210> SEQ ID NO 76
<211> LENGTH: 1588
<212> TYPE: DNA
<213> ORGANISM: Artificial Sequence
<220> FEATURE:
<223> OTHER INFORMATION: Synthetic Construct- Sequence No. 76,
Example 76: designer nirA-promoter-controlled Aspartate Kinase
DNA construct (1588 bp)

<400> SEQUENCE: 76
agaaaatctg gcaccacacc tgacccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catgtagtcc gaaaacttga cagagttctt tcaacaaatc ttctgcttta 300
tcttcatgta caaggcatga tatctttatt tcagaagttg ttatcatttc tggctctatg 360
tttttctttc tcaaaacttc aaaaaatttt gctgcaacac ctcgttgata tttcattcct 420
aaacctatta ttgatacctt agaaaacccc cctgtgatct taatttcaca atcaagatct 480
ctcattgcct tctgtacgtc aaccgagtta ctttcaacaa ttgtgaaaga tagattaatg 540
tctcctgagt tactcaccaa cgatatcata tcaacgttaa agcctttttc agcgagttct 600
ctaaatacgt cggcggttgc tttagaattt ttcaagctat aaacgctgac ctttacctga 660
tttttctcta tcgtcgcgcc tgtaacaacg ggtcgctcaa gccattccgg aagttttccc 720
atcacccacg ttccctcctc atttgaaaac gaagaagcgc aataaattgg tacgctgtat 780
ttttttgcta tctcaacact tcgagaatgt agaaccctgg caccaagtgc ggagaattcc 840
aacatttcat cgtatgtaat ataagacagt ttttttgcct ggggaaagat cctgggatct 900
gttgtatata tgccagcgac gtcgctgtat atttcgcaga ttgttccaag ttttgcggca 960
atagcaacag cagaagtatc tgatcctcct cttccaagag ttgtcagttc atcgttttcg 1020
tttattccct gaaaccctgt aacaagtaaa acatcgttat gaaaagccag cgatcttaat 1080
tttcggtcat ctatatcttt tatccttgcc gaattaaaat cgctggttgt cagaatccga 1140
gcctgaaacg cattcaaaga tacagctttc atacctattc tgtcaaggta tatggatagc 1200
aaagcagcgg atatttgttc gccacaggat aacaacatat ccagttctct tggattgggt 1260
ttttcagaca gccttcttgc aagaaaaacc aatttgtctg ttgtttttcc cattgcagag 1320
acaacaacga ttaacttttt cccatttttt actgttttca ctattttctc ggtaattttt 1380
ttgattcttt ctatgctggc aagcgatgag ccaccatatt tttgtacaac aagtttcaga 1440
aaaatcacta aggctgagat cttcttcagt gcattgtagt tgaatgaagg gttagggggg 1500
aaatgccccc ctatttttttg tctagccatc ctgccacgtt tgacagggta gcaatttcga 1560
cacgataggg ttctctcttc tgccgtta 1588

<210> SEQ ID NO 77
<211> LENGTH: 1411
<212> TYPE: DNA
<213> ORGANISM: Artificial Sequence
<220> FEATURE:
<223> OTHER INFORMATION: Synthetic Construct- Sequence No. 77, Example 77: designer nirA-promoter-controlled Aspartate-Semialdehyde Dehydrogenase DNA construct (1411 bp)

<400> SEQUENCE: 77
agaaaatctg gcaccacacc tgacccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catgtcccct gaaaatatta taaatctctg cattgagaac tgcacacccg 300

```
gcagcccctc tgattgtatt atgaacaaga gcaacgaacc caaactgttt gttcgaatac    360
tgtttcaacc tgccaacact gacactcatt ccaccaccaa gatctctgtg aaacttcggc    420
tgcggagaat caactcctgt caaataaaaa acaggttttt caggtgcggt tggaagatac    480
attcctttaa gtggttgaaa atcttcaaaa gctctcacaa tttcacttaa agtggccttt    540
tcctgagttt tgatagttat agatagcata tgaccgtcaa caacggctac cctgttgcac    600
tgtgcgaaaa tatcgagatt cgccgggtat atttttccat ctttcaatct gccaagtatt    660
tttttgatt cggtcatgat tttttcttcc tcattttta tgaacggcac aacattgtca      720
attatatcca tagatggtac accgggatat cccgcgccag agatagcctg cattgtgaca    780
acatttgcct cttctatacc gaatctatcc attatgggtt taagaaccat tgtaaaacct    840
atcgttgagc aattagggtt ggtgattatt tttccttttc tcttttgagt ttcggttatt    900
ttcaaatgat ccagattaac ttcagggata attagaggta catcctcgtc cattctatgg    960
cttgcggcat ttgagaaaac aatgtatcct gcgtttgcaa attcctcctc aatttcgcct   1020
gcaacatctg aaggcaaagc agaaaacaca taatcacaat ctatatcagg tgtgcatttt   1080
tttaaaacca tatctcctgc tttttcggct acaggaacat tcaagcgcca ttgaactgct   1140
tctctgtact tttttcccgc agaattatca gaagctgcca gagctgttat ctcaaaaaat   1200
ggatgatttg aaagcaattg aacaaatctc tgtccaacaa gccctgttgc accaagaata   1260
gctaccttca ttaaggctga gatcttcttc agtgcattgt agttgaatga agggttaggg   1320
gggaaatgcc cccctatttt ttgtctagcc atcctgccac gtttgacagg gtagcaattt   1380
cgacacgata gggttctctc ttctgccgtt a                                  1411
```

<210> SEQ ID NO 78
<211> LENGTH: 1684
<212> TYPE: DNA
<213> ORGANISM: Artificial Sequence
<220> FEATURE:
<223> OTHER INFORMATION: Synthetic Construct- Sequence No. 78, Example 78: designer nirA-promoter-controlled Homoserine Dehydrogenase DNA construct (1684 bp)

<400> SEQUENCE: 78

```
agaaaatctg gcaccacacc tgacccccat cgagagactc cgaacgtggc aaatggaggg     60
accagagttg ttcagttcac aggtagataa tgtcgcgggt cttgatagtt agcaataaat    120
acagtttcag aatatctgta atacaaaaac tgtatcgaga caagaaaaaa gtagcaaaat    180
ttacaaatgt tcatgattca tctggctaaa ttggatgttc aactgaccca ttgaagacaa    240
gggcaacaac catgaacttt actatcttcg ccttccaccc ggatgacgtt gcaaatctct    300
gccactatac tcatttctcc caacaccatc agggcatctc gcaggtcaga ttcaggaact    360
ctatgggtca ctaagaccag ctgggcgaac tcctcgccgc ttgtcttctg cagcacggta    420
gctatgctca gctgatggct gccaaaaacc ccggcgatgg ccgccaatac cccagggcgg    480
tccttaacca gcatccgaat atagaacttg ctctccactt tgtcgatagg aataatctcc    540
ttggcttcaa aacaagtaca gcccagcatg ccggtggtac catgactgag gttatggcat    600
atctccatta tgtctcccac caccgcgcta gcagtgggca tctgccctgc ccctcttcca    660
aagaacatga cttctcccac cgcgtccccg ttcacgaata cggcgttgta aaccccccttt   720
accgcggcca gagggtggtg cataggtatg aaagccgggt ggacccgggc ttgcacccgg    780
ccgtcgattt cctgcgcgat agccaggagc ttcaccacat agcccaattc ataaccgtac    840
ttgatatcta aagggcttaa acgggtaatt ccttcaacgt aaacgttttc gaacgtaacc    900
```

```
cggctgttga aggcgatcga agccaggatg gcaattttac gagcagcatc atagccttct    960
acgtctgaag taggatcagc ttcagcatac cccagttcct gcgcctcttt caaagccctc   1020
gaaaactcta ggccttcctc gctcatctta gtaaggatgt agttggttgt cccgttaaca   1080
atccccatta cttctttgat tcgattggca cctagcgaat gcttcaaagg ataaattaag   1140
gggatgcccc caccaacact ggcttcaaaa aagaagtcca ccttgttctc ttcagctgcg   1200
gccagcagtt cctgcccgtg gaccgctatt aaatctttat tggcagtcac cacgttcttg   1260
cctttgcgta acgcctgcaa aataaaggtt cgagccggtt cgatgcctcc tatgagttct   1320
acaacaacac ttatatggtc atcatccagt atgtctttga tatcggcgca aaggacgtct   1380
tcgcttaaac ctagactcaa aaccttctcc gggtcttttt cgaggattcg cttgatcgcg   1440
actccttgtc cggtacggag cgaaataaca tcccggtttg aggctaaaag cttgaccaca   1500
ccggatccaa ccgttccaca acccaagagg ccaatattaa ccactaaggc tgagatcttc   1560
ttcagtgcat tgtagttgaa tgaagggtta ggggggaaat gccccccctat tttttgtcta   1620
gccatcctgc cacgtttgac agggtagcaa tttcgacacg atagggttct ctcttctgcc   1680
gtta                                                                1684
```

```
<210> SEQ ID NO 79
<211> LENGTH: 1237
<212> TYPE: DNA
<213> ORGANISM: Artificial Sequence
<220> FEATURE:
<223> OTHER INFORMATION: Synthetic Construct- Sequence No. 79,
      Example 79: designer nirA-promoter-controlled Homoserine Kinase
      DNA construct (1237 bp)

<400> SEQUENCE: 79

agaaaatctg gcaccacacc tgacccccat cgagagactc cgaacgtggc aaatggaggg     60
accagagttg ttcagttcac aggtagataa tgtcgcgggt cttgatagtt agcaataaat    120
acagtttcag aatatctgta atacaaaaac tgtatcgaga caagaaaaaa gtagcaaaat    180
ttacaaatgt tcatgattca tctggctaaa ttggatgttc aactgaccca ttgaagacaa    240
gggcaacaac catgaaggtc ctggtaccgg ccacaacgac caatctcgga gcgggattcg    300
acgtctttgg actcgcgctg gatcttttca acgaagtgga gttttctttc gatacaaaag    360
agacaaccat agaaagtact ggaaaatacg cttcggattt gaaggaccac aatctgtttt    420
tcgaagtctt caggttcttt gagagaaaaa ccgggtacag agttccgcca gtcaggatca    480
agcagacatg caacatccct gtatcgagcg gtcttggatc gagcgccgct gtgatcgtcg    540
cggcactcca cattgcgaac gaaggaacgg gcagaaatct ttcacgggaa gatcttatga    600
aactcgctgt ggagctggaa ggacaccctg acaacgttgt acccgctttc acagggggggc    660
ttgtggtctg ttatcaaaac ggaagtcatc ttgattttga aaagttcgag atcgatcttt    720
ctctcacatt tttcgttcca aacttttcga tgtgcacgaa cgagatgaga aagatccttc    780
cggagaaggt ccctttcgaa gatgcggtct tcaacataaa gaattcatgc cagttccttg    840
caaagatcgc agctggaaag atcaaagagg ctctgaaata cgtgggagat cgacttcacc    900
agaactacag gataaacggc aataagaaga tgaaagagtt tgtggaagcc atcttatcaa    960
aaaatcccga gtactggttt gtgagcggat ccggtccttc tgtttgttcc aatataaatg   1020
actttgaagg gattccctat ctcaaggacg ttctgaagct gagggtgaac aacaggggga   1080
tgatagtttc agaatagtaa ggctgagatc ttcttcagtg cattgtagtt gaatgaaggg   1140
```

ttagggggga aatgcccccc tattttttgt ctagccatcc tgccacgttt gacagggtag 1200
caatttcgac acgatagggt tctctcttct gccgtta 1237

<210> SEQ ID NO 80
<211> LENGTH: 1438
<212> TYPE: DNA
<213> ORGANISM: Artificial Sequence
<220> FEATURE:
<223> OTHER INFORMATION: Synthetic Construct- Sequence No. 80, Example 80: a designer nirA-promoter-controlled Threonine Synthase DNA construct (1438 bp)

<400> SEQUENCE: 80
agaaaatctg gcaccacacc tgacccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catgaaattg ggaatactcg aaaagtacag agaatttctt cccgtaacag 300
acaaaacccc catgctctct ttgaatgaag ggaacactcc tctcataccc ctcgtgaaca 360
tgagcaggga actcggaata aacatctacg taaaatacga aggggccaat ccgacggggt 420
ccttcaaaga cagaggaatg gtcgttgccg tcgcaaaggc actggaagaa ggctcgaaag 480
ccatcatgtg cgcttcaacg gggaacacct ccgcatccgc tgccgcgtac gccgcaaggg 540
caggaataaa ggcgatcgtt ctgataccag aagggaagat cgcactcgga aagctggctc 600
aggcgatgat atacggcgcc gtggtgcttc aggtgagagg gaatttcgac aagtgtctgg 660
aactggtcaa ggagatcaca tccaaatatc ccatcacact cgtgaacagt atcaatccct 720
acagactcga aggtcagaaa acggccgctt ttgagatagt cgacgagctc ggagatgcac 780
cggactacca cttcatcccc gtgggaaacg cgggcaacat ctccgcttac tggatgggat 840
acaaggagta ttatcagcat gggttctcca ccaaactgcc gaagatgatg ggattccagg 900
cggaaggggc cgcccccata gttcgcggtc atcccataga aaacccggag acggtcgcca 960
ctgcaataag gatcggtaac cccgcgaact gggaaaaagc ggtccgggca cgcgatgaat 1020
cgggtggaga catcgacatg gtgagcgacg aagaaatact gcgcgcacag agactcttgg 1080
ctcagaaaga agggatcttc tgtgagcccg catccgctgc atcgatagcg gggcttttga 1140
agaagcacag acagggaatc ttcaggggtg gagagatcgt tgtgtgtacc ctcacaggga 1200
acggtttgaa agatccgaac atcgtcatct cacagcttga acccccaagg atcatagaag 1260
gaagagtaga agagattctg gaggtactcg acatatgata aggctgagat cttcttcagt 1320
gcattgtagt tgaatgaagg gttagggggg aaatgccccc ctattttttg tctagccatc 1380
ctgccacgtt tgacagggta gcaatttcga cacgataggg ttctctcttc tgccgtta 1438

<210> SEQ ID NO 81
<211> LENGTH: 1600
<212> TYPE: DNA
<213> ORGANISM: Artificial Sequence
<220> FEATURE:
<223> OTHER INFORMATION: Synthetic Construct- Sequence No. 81, Example 81: designer nirA-promoter-controlled Threonine Ammonia-Lyase DNA construct (1600 bp)

<400> SEQUENCE: 81
agaaaatctg gcaccacacc tgacccccat cgagagactc cgaacgtggc aaatggaggg 60
accagagttg ttcagttcac aggtagataa tgtcgcgggt cttgatagtt agcaataaat 120

```
acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catgttgaca ttagcagaca ttgaacaagc gcgagcgaaa atgaaaggca    300

tcgtccatca aacgccgctt gagcattcgc aaacgttcag ccggctgtct ggcaatgatg    360

tatatatgaa actcgaaaat ttgcaaaaaa cgggctcgtt taaagtaaga ggttcattca    420

ataaaattat gtcgctcacg gaagaagaga gggcgcgcgg cgtcatcgcc gcttcggccg    480

gcaaccacgc ccaaggggtc gcctatgcga gcggcatgct tcatattccg tgcacgatcg    540

tcatgccaaa aggcgcgccg ctcagcaaaa ttgaagcgac gaaaagctac ggggcggaag    600

tcgtgctgta cggcgatgtg tttgacgagt ctttggaata tgcgttagag ttgcagcgtg    660

aacgggggat gacgtttgtt catccgtttg acgacttggc ggtgatggcc ggccaaggga    720

cgatcggctt agagctgatc gagcagcttc ccgacgtcga tgtcgttctt tgtccagtcg    780

gcggcggcgg gttgcttgcg ggggtggcgc ttacgttaaa acagctgaag ccgtcggttg    840

aagtgtacgg cgttgagtca tcggcttgcc ccggcatgac ggcggccata cgccataaac    900

agcccgtctc cattgccgca tcgaatacga tcgccgatgg gattgccgtg aaaaagccgg    960

gcaatattac gtaccaatac attgagcaat acgtcgatgg cgttgtatgc gtggaagagg   1020

cggaaatttc gcggacgatg ctgtatgtgc tcgagcggaa caagctgttg atcgaagggg   1080

cggcagcttg tccgctggcg gcattgttgt atcaaaagct gccgtttcgc ggcaaaaaag   1140

tcgccgccat tttaagcggc ggcaacgtcg atgtgacgct catttcccgc atcatcgagc   1200

gggggctcgt cgaagccggg cgattcgtta cgtttacaac ggtcatctcc gacaagccgg   1260

gccagttgaa caagctgctg cgcattattg cggagcttga ggcaaacgtg atgtcgattc   1320

atcatcagcg catcggcgcc aaagtgctgc caggtcaggc ggaaattcac ttttcgctcg   1380

agacaaaaaa cgaagaccac attcagcaaa tctaccaagt gttgttgaaa gaaggctacg   1440

atgtacagtt ttaccgatga taaggctgag atcttcttca gtgcattgta gttgaatgaa   1500

gggttagggg ggaaatgccc ccctattttt tgtctagcca tcctgccacg tttgacaggg   1560

tagcaatttc gacacgatag ggttctctct tctgccgtta                         1600
```

<210> SEQ ID NO 82
<211> LENGTH: 2107
<212> TYPE: DNA
<213> ORGANISM: Artificial Sequence
<220> FEATURE:
<223> OTHER INFORMATION: Synthetic Construct- Sequence No. 82, Example 82: designer nirA-promoter-controlled Acetolactate Synthase DNA construct (2107 bp)

<400> SEQUENCE: 82

```
agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catgttgaca aaagcaacaa aagaacaaaa atcccttgtg aaaaacagag    300

gggcggagct tgttgttgat tgcttagtgg agcaaggtgt cacacatgta tttggcattc    360

caggtgcaaa aattgatgcg gtatttgacg ctttacaaga taaaggacct gaaattatcg    420

ttgcccggca cgaacaaaac gcagcattca tggcccaagc agtcggccgt ttaactggaa    480
```

```
aaccgggagt cgtgttagtc acatcaggac cgggtgcctc taacttggca acaggcctgc    540

tgacagcgaa cactgaagga gaccctgtcg ttgcgcttgc tggaaacgtg atccgtgcag    600

atcgtttaaa acggacacat caatctttgg ataatgcggc gctattccag ccgattacaa    660

aatacagtgt agaagttcaa gatgtaaaaa atataccgga agctgttaca aatgcattta    720

ggatagcgtc agcagggcag gctggggccg cttttgtgag ctttccgcaa gatgttgtga    780

atgaagtcac aaatacgaaa aacgtgcgtg ctgttgcagc gccaaaactc ggtcctgcag    840

cagatgatgc aatcagtgcg gccatagcaa aaatccaaac agcaaaactt cctgtcgttt    900

tggtcggcat gaaaggcgga agaccggaag caattaaagc ggttcgcaag cttttgaaaa    960

aggttcagct tccatttgtt gaaacatatc aagctgccgg taccctttct agagatttag   1020

aggatcaata ttttggccgt atcggtttgt tccgcaacca gcctggcgat ttactgctag   1080

agcaggcaga tgttgttctg acgatcggct atgacccgat tgaatatgat ccgaaattct   1140

ggaatatcaa tggagaccgg acaattatcc atttagacga gattatcgct gacattgatc   1200

atgcttacca gcctgatctt gaattgatcg gtgacattcc gtccacgatc aatcatatcg   1260

aacacgatgc tgtgaaagtg gaatttgcag agcgtgagca gaaaatcctt tctgatttaa   1320

aacaatatat gcatgaaggt gagcaggtgc ctgcagattg gaaatcagac agagcgcacc   1380

ctcttgaaat cgttaaagag ttgcgtaatg cagtcgatga tcatgttaca gtaacttgcg   1440

atatcggttc gcacgccatt tggatgtcac gttatttccg cagctacgag ccgttaacat   1500

taatgatcag taacggtatg caaacactcg gcgttgcgct tccttgggca atcggcgctt   1560

cattggtgaa accgggagaa aaagtggttt ctgtctctgg tgacggcggt ttcttattct   1620

cagcaatgga attagagaca gcagttcgac taaaagcacc aattgtacac attgtatgga   1680

acgacagcac atatgacatg gttgcattcc agcaattgaa aaaatataac cgtacatctg   1740

cggtcgattt cggaaatatc gatatcgtga aatatgcgga aagcttcgga gcaactggct   1800

tgcgcgtaga atcaccagac cagctggcag atgttctgcg tcaaggcatg aacgctgaag   1860

gtcctgtcat catcgatgtc ccggttgact acagtgataa cattaattta gcaagtgaca   1920

agcttccgaa agaattcggg gaactcatga aaacgaaagc tctctagtaa ggctgagatc   1980

ttcttcagtg cattgtagtt gaatgaaggg ttagggggga aatgcccccc tatttttttgt   2040

ctagccatcc tgccacgttt gacagggtag caatttcgac acgatagggt tctctcttct   2100

gccgtta                                                             2107
```

<210> SEQ ID NO 83
<211> LENGTH: 1405
<212> TYPE: DNA
<213> ORGANISM: Artificial Sequence
<220> FEATURE:
<223> OTHER INFORMATION: Synthetic Construct- Sequence No. 83, Example 83: designer nirA-promoter-controlled Ketol-Acid Reductoisomerase DNA construct (1405 bp)

<400> SEQUENCE: 83

```
agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catgttttac ctctttaagc caaggcatca tcgccctaag ttccttacct    300

actttttcta tcaggtgctc ctgccctttc ctccgcaagg cactgaagac cggacggccc    360
```

```
acttggaatt cgagcaagag ctcccgggca aaagttccat cctggatggc agccaaaacc    420

tttttcatct cagccctggt gttttcgttt attatgcgcg gacctaccgt gaggtcgccg    480

tactcagcgg tatcactgac cgagtaccgc ataaggccga taccgccttc gtatataagg    540

tctactatga gcttaagctc gtgcaggcac tcgaaatagg ctatctccgg ctggtatcct    600

gcctctacca aggtatcaaa accggcttta ataagttcag tgaccccgcc acagagcaca    660

cattgttctc cgaataggtc ggtctcggtt tcttctttaa aagtagtagc gatgacacct    720

gcacgggtac agccgatacc tttagcatag gctaaccccg tttccaaggc tttccccgta    780

tggtcattat gtacggctat gagcccgggg actcccactc cttgcctgta catacgcctg    840

accagatgac caggactctt aggcgctacc atgaagacat cgacggaagg cggaggcaca    900

atttgcccga aatgtatgtt gaacccatga gaaaatccca acgcatcgcc ttcgttaagg    960

taaggttcga tcttttcccg gtaaaccttg gcctggatat catccggcac caaaatctgg   1020

attatctggg cagctcgggc cgcttcatct accggtaaag gcgtaagccc gtcggctaca   1080

acctgattcc actccgcagt ggtaaaatcg tcctccggct tacgcaaccc taccaccact   1140

tcgagaccac tgtcgtgaag gttctgggcc tgagcgtgtc cctggctgcc ataaccgatc   1200

acggcaatgg tcttgccttt aagcaggtca aggtttgcat cagcatcata atacatccta   1260

gccattaagg ctgagatctt cttcagtgca ttgtagttga atgaagggtt aggggggaaa   1320

tgcccccccta tttttgtct agccatcctg ccacgtttga cagggtagca atttcgacac   1380

gatagggttc tctcttctgc cgtta                                         1405
```

<210> SEQ ID NO 84
<211> LENGTH: 2056
<212> TYPE: DNA
<213> ORGANISM: Artificial Sequence
<220> FEATURE:
<223> OTHER INFORMATION: Synthetic Construct- Sequence No. 84, Example 84: designer nirA-promoter-controlled Dihydroxy-Acid Dehydratase DNA construct (2056 bp)

<400> SEQUENCE: 84

```
agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catggggctt cctgaagatt gccccccttgc tcgccgactg tacgaagaat    300

gcgtaccttc tcaggtaatc gctgtccact tctttcacca gaggcgtgaa ctctttcatt    360

cttctttcga actcttcgtc tgagatcaag agattcaggg ttctcttttc aaaatctatc    420

tcgatgaggt ccccgtcttt cacgatacct ataggaccgc cttctgccgc ttctggagaa    480

acgtgaccta tcacggcacc gtgcgatcca cccgagaacc taccgtctgt gatgagagcc    540

acgtcctccg caaggcccat ccccacgatg gcggaggtgg gtgagagcat ctctctcatc    600

ccgggaccgc ccttcggccc ttcgtagcgg atcacaacca catctccttt tttgatcttt    660

ccagatagaa tggcttttgt cgcctcttct ccgtcttcaa agacgacggc cgggccaacg    720

tggtgcatca tcttctcggg aacaccggag agtttggcaa ccgctccttc tggagcgagg    780

ttcccgaaga ggataccgag tccgccctct ttgtggtacg gattatcgaa gggcctgatc    840

acatcttcat tcaggatctt agcctctctg acgagatctc caatctttct caaatagatg    900
```

-continued

```
gtcatggcgt cttccttcaa aagaccattt tcctggagac gtttcatcac agcgtagata    960

ccaccagcat cgtcgagatc ctggatgtgg tacggaccaa cgggagagat gttgcagatg   1020

tgaggaatct tcctgctgag ttcgtcaaag agctttatat cgaaatctat tccaaaactc   1080

tcggctatcg ccttcaaatg cagaactgtg ttcgtggaac ctcccgttgc gaggtccacc   1140

atgacagcgt tcatgaaaga gtccagagtg acgatatccc ttggttttac atctcttttc   1200

acgagttcca caacgagcat ccccgcttct ttcgccattc tcaacctctt cgcgtggacg   1260

gccggtacag tcccattccc cctcggtgca attccgagag cttccgccag agagttcatc   1320

gtgttcgcgg tgaacaatcc agcacacgaa ccggcaccgg gacacgcgag gtcttctatc   1380

gctttgagcg tttcttcatc gacttttccc actttgtatc caccaaccgc ttcgaagacg   1440

gtgatgagat cgatgtctct gccgttgtag cgacctgcga gcatgggacc gccggatatc   1500

agaacggacg ggatgttcaa tcttcccatg gccatcatca tgccgggtgt gatcttgtcg   1560

cagttgggga cgaagaccaa accatcgaag gggaaaccgc ttgcaacgat ctctatggag   1620

tccgctatga gttccctcga gggcaaggaa aacttcatcc ccctgtgatc cattgctatt   1680

ccgtcacaga tcccgatcgt tggaaagacg aagggaactc cccggccat tctcacaccg    1740

gctttcaccg cttcaacgac cttgtcaagg tggacatggc cgggaatgat ctcgttccac   1800

gaggacacta tgccgatgaa aggccttcgc atttcgtcgt ccgttattcc gagcgctttc   1860

aaaagtgatc tatggggagc cctttcgaga cctttcttta tcacatcact cctcattaag   1920

gctgagatct tcttcagtgc attgtagttg aatgaagggt tagggggaa atgcccccct    1980

attttttgtc tagccatcct gccacgtttg acagggtagc aatttcgaca cgatagggtt   2040

ctctcttctg ccgtta                                                   2056
```

<210> SEQ ID NO 85
<211> LENGTH: 1360
<212> TYPE: DNA
<213> ORGANISM: Artificial Sequence
<220> FEATURE:
<223> OTHER INFORMATION: Synthetic Construct- Sequence No. 85,
Example 85: designer nirA-promoter-controlled 2-
Methylbutyraldehyde Reductase DNA construct (1360 bp)

<400> SEQUENCE: 85

```
agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catggcttct gtaaatgact actttgagaa cgccaagacg acgtacttta    300

ctttgagatc gggtgacaag atccccgctg ttggattggg tacttggcaa tcacccacca    360

acgagactaa agaggcagtc aagtacgctt tgcagcacgg ttaccgtcac atcgatgctg    420

ccgccattta tggtaacgaa gacgaggttg gtgacggtat caaggagagt ggaatccctc    480

gtgaccaaat ctgggtcaca tctaagctct ggtgcaatgc tcatgctccc gaggctgtcc    540

ccaaggcttt ggagaagacc ttgcgtgagc tgaaacttga ttaccttgac ctttacctca    600

tccactggcc tatttctttg aagaccggcg atgacttggt tcccaaggac aaggacggca    660

acaccatcac tgtcgaaatt cccctcgagg acacctggaa ggctatggag ggtcttgtga    720

agtccggcaa ggtgaagaac attggtattt ccaatttcaa caacgaagag ttggatcgta    780

ttttgaaggt tgccgagatt cctcctgccg tccaccaaat ggaaactcat ccttacttga    840
```

```
agcagacgga gttcattgag aagcacaaga agcttggcat tcacgtcacc gcttactcgc    900

ctttggccaa ccaaaatgct ctttacggca atgccgttcc caagttgatt gagcacaaga    960

ctcttgtcga cattgccaag accaagggtg agggcgtcac tggtgccaac attgctattt   1020

cttgggcagt caagcgcggt acttcggtta ttcctaagtc tgttcatgcc aacagaatta   1080

agagcaactt cctcgttgtt cccttgactg atgacgagat gaaggccatc gataacattg   1140

gtgtcagcaa gcgtttcaat tggagcaaag ttttctgcaa tgagaattgt ttctacggtc   1200

ttgaggatgg tcctcagtaa taaggctgag atcttcttca gtgcattgta gttgaatgaa   1260

gggttagggg ggaaatgccc ccctattttt tgtctagcca tcctgccacg tttgacaggg   1320

tagcaatttc gacacgatag ggttctctct tctgccgtta                         1360
```

<210> SEQ ID NO 86
<211> LENGTH: 1420
<212> TYPE: DNA
<213> ORGANISM: Artificial Sequence
<220> FEATURE:
<223> OTHER INFORMATION: Synthetic Construct- Sequence No. 86, Example 86: designer nirA-promoter-controlled 3-Methylbutanal Reductase DNA construct (1420 bp)

<400> SEQUENCE: 86

```
agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catgtcagtt ttcgtttcag gtgctaacgg gttcattgcc caacacattg    300

tcgatctcct gttgaaggaa gactataagg tcatcggttc tgccagaagt caagaaaagg    360

ccgagaattt aacggaggcc tttggtaaca acccaaaatt ctccatggaa gttgtcccag    420

acatatctaa gctggacgca tttgaccatg ttttccaaaa gcacggcaag gatatcaaga    480

tagttctaca tacggcctct ccattctgct ttgatatcac tgacagtgaa cgcgatttat    540

taattcctgc tgtgaacggt gttaagggaa ttctccactc aattaaaaaa tacgccgctg    600

attctgtaga acgtgtagtt ctcacctctt cttatgcagc tgtgttcgat atggcaaaag    660

aaaacgataa gtctttaaca tttaacgaag aatcctggaa cccagctacc tgggagagtt    720

gccaaagtga cccagttaac gcctactgtg gttctaagaa gtttgctgaa aaagcagctt    780

gggaatttct agaggagaat agagactctg taaaattcga attaactgcc gttaacccag    840

tttacgtttt tggtccgcaa atgtttgaca aagatgtgaa aaaacacttg aacacatctt    900

gcgaactcgt caacagcttg atgcatttat caccagagga caagataccg gaactatttg    960

gtggatacat tgatgttcgt gatgttgcaa aggctcattt agttgccttc caaaagaggg   1020

aaacaattgg tcaaagacta atcgtatcgg aggccagatt tactatgcag gatgttctcg   1080

atatccttaa cgaagacttc cctgttctaa aaggcaatat tccagtgggg aaaccaggtt   1140

ctggtgctac ccataacacc cttggtgcta ctcttgataa taaaaagagt aagaaattgt   1200

taggtttcaa gttcaggaac ttgaaagaga ccattgacga cactgcctcc caaattttaa   1260

aatttgaggg cagaatataa taaggctgag atcttcttca gtgcattgta gttgaatgaa   1320

gggttagggg ggaaatgccc ccctattttt tgtctagcca tcctgccacg tttgacaggg   1380

tagcaatttc gacacgatag ggttctctct tctgccgtta                         1420
```

<210> SEQ ID NO 87
<211> LENGTH: 1540
<212> TYPE: DNA
<213> ORGANISM: Artificial Sequence
<220> FEATURE:
<223> OTHER INFORMATION: Synthetic Construct- Sequence No. 87,
Example 87: designer nirA-promoter-controlled 3-Ketothiolase
DNA construct (1540 bp)

<400> SEQUENCE: 87

```
agaaaatctg gcaccacacc tgacccccat cgagagactc cgaacgtggc aaatggaggg     60
accagagttg ttcagttcac aggtagataa tgtcgcgggt cttgatagtt agcaataaat    120
acagtttcag aatatctgta atacaaaaac tgtatcgaga caagaaaaaa gtagcaaaat    180
ttacaaatgt tcatgattca tctggctaaa ttggatgttc aactgaccca ttgaagacaa    240
gggcaacaac catgcgtgaa gcggtcattg tcgaagcggt caggacgccg gtcggcaagc    300
ggaacggcgt cttccgggac gttcatccgg tccatttggc cgcggtggtg ctcgatgaag    360
tcgtgcgccg ggccggcatg gacaaagggg cggtggaaga catcgtcatg ggctgcgtga    420
cgccggtcgc cgaacaaggg tacaacatcg gccggctggc ggcgcttgag gccggattcc    480
cgatcgaagt gccggcagtg caaatcaacc gaatgtgcgg ctcggggcag caggcgattc    540
atttcgccgc ccaggaaatc cgctccggcg atatggatgt cacgatcgcc gccggggtcg    600
aaagcatgac gaaagtgccg attttaagcg atggcaacga gcggacgatt ccgccgtcgc    660
tgcatgaaaa atacgaattc atccaccaag gcgtctcggc tgagcggatc gccaaaaaat    720
acggcctaac gcgcgaggag cttgacgcct acgcgtacga aagccatcaa cgcgccttgg    780
cggccttgcg cgaagggaag tttcgcgcgg aaatcgtccc ggtgaaaggg cttgaccgcg    840
atggccgcga aatccttgtc accgatgatg aagggccgcg ggccgacaca tcgccggaag    900
cgctcgccgc gctcaagccg gtgtttcaag aagacggtct catcaccgct ggcaatgcga    960
gccaaatgag cgacggggcg gccgctgtgc ttttgatgga acgggaggcg gcgaggcggt   1020
tcggactgaa gccgaaagcg cgcattgtcg cgcaaacggt cgtcggctcc gacccgacgt   1080
atatgctcga tggcgtcatt ccggcgacga ggcaagtgct gaaaaaagcc ggcctctcga   1140
tcgatgacat cgacctcatt gaaatcaacg aagcgttcgc cccggtcgtg ctcgcctggc   1200
aaaaagaaat cggcgctccg cttgagaagg tgaatgtcaa cggcggcgcc attgcgcttg   1260
gccatccgct cggcgccacc ggtgcgaagc tcatgacgtc gcttgttcat gaacttgaac   1320
ggcgcggcgg ccgctatggg ctattgacga tttgcatcgg ccacgggatg gcgacggcca   1380
cgatcatcga gcgggagtaa taaggctgag atcttcttca gtgcattgta gttgaatgaa   1440
gggttagggg ggaaatgccc ccctattttt tgtctagcca tcctgccacg tttgacaggg   1500
tagcaatttc gacacgatag ggttctctct tctgccgtta                         1540
```

<210> SEQ ID NO 88
<211> LENGTH: 1231
<212> TYPE: DNA
<213> ORGANISM: Artificial Sequence
<220> FEATURE:
<223> OTHER INFORMATION: Synthetic Construct- Sequence No. 88,
Example 88: designer nirA-promoter-controlled 3-Hydroxyacyl-CoA
Dehydrogenase DNA construct (1231 bp)

<400> SEQUENCE: 88

```
agaaaatctg gcaccacacc tgacccccat cgagagactc cgaacgtggc aaatggaggg     60
accagagttg ttcagttcac aggtagataa tgtcgcgggt cttgatagtt agcaataaat    120
```

```
acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catgatactt aaagaaacct tctccggtct tacgccccag cttccctgca    300

cggaccatct taaccaagag cgggcaagga cgatacttgt catcgccaaa ctcgcgatgc    360

aaagtctgca tgatagccaa acatatatct agcccaatca tgtctgctaa agcgagggga    420

cccataggat gccctgctcc gagcttcatg gaggtatcca cgtcctcggg gcttgcaacc    480

ccctccatga cggcatacat accttcgttc agcattggaa taagcaggcg gttgacaaca    540

aagccaggag cttcgttgat ctcaaccggg gtcttgccca gcttaattga aagatccttg    600

atggtattaa aagtttcctg gctagtagaa gcccctttga taatctcgat aagcttcatt    660

gccggtaccg ggttgaagaa atgcatgcct attaccctgt ctgcccgctt ggttgctgct    720

cctatctcgg ttatgctcag agctgatgtg ttagaagcca ggatacattc aggcttgcag    780

atctcgtcca gttccttgaa aatcgctttt ttgatgtcca tattctcgat agcagcttca    840

attaccacat ccacatcttt ggccgcagcc atgtcgaccg taccgctaat cctggccatc    900

accgcgttct tgtcatctgc gctcatcttg cccttttcga ccattttgct gagacccttg    960

tcgatgcctt ttataccatt gtcaacaaac tcttgtttaa tatcacgtac gattacttcg   1020

aacccagctt gagcagcgac ttgaacaatc ccagctccca tagtacctgc gcctaaaacc   1080

attattttca ttaaggctga gatcttcttc agtgcattgt agttgaatga agggttaggg   1140

gggaaatgcc cccctatttt ttgtctagcc atcctgccac gtttgacagg gtagcaattt   1200

cgacacgata gggttctctc ttctgccgtt a                                  1231
```

```
<210> SEQ ID NO 89
<211> LENGTH: 1162
<212> TYPE: DNA
<213> ORGANISM: Artificial Sequence
<220> FEATURE:
<223> OTHER INFORMATION: Synthetic Construct- Sequence No. 89,
      Example 89: designer nirA-promoter-controlled Enoyl-CoA
      Dehydratase DNA construct (1162 bp)

<400> SEQUENCE: 89

agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catgacggtt cgactggaat acgatggcgg gttcgcgcac ctgacgctca    300

gccgcccgca ggtcctgaat gcgctcagtt tcgagctgct cgccgagttg agccgggcgc    360

ttgccggcgt cgccgaatcc gatgcgcgcg ccctgatcgt cacgggcgag ggcgacaagg    420

cgttctgcgc cggcgcggac attcccgagc tgatgaatcg gccgctcatg caagagctcg    480

aaggggccgc gaaaggccag gcggtgttca gccggatcgc cgagctgaag attccgtctg    540

tcgccgtcat ccagggttat gccttcggcg gcgggctgga gcttgccctg gcatgcacat    600

tccgcgttgc cactgatcgc gcccgcatgg ggctgcccga ggtcaagctc ggcctgatcc    660

cgggttatgg cggaacgcag cgtctgccga ggctgatcgg cgaggggcgc gcactcgacc    720

tgatcatgtc cggccgcacg atagacggcg gggaagccga gcgaatcggc ctggtcaatc    780

gcatagacaa cgaggggacg cccctggaga tcggcaagcg gtttctggag ccttatctca    840
```

```
agcacagtct ctgcgccttg tattttgccc gcgaggccgt gcagagggga ggcggtgtcg    900

ccattgcgga tggcctgcgc atcgagcggg atctttccac gctggcttac cggagccagg    960

atgcggccga ggggctgcgc gcttttgtgg aaaaacggcc cgcgtctttc aaggactgct   1020

gataaggctg agatcttctt cagtgcattg tagttgaatg aagggttagg ggggaaatgc   1080

ccccctattt tttgtctagc catcctgcca cgtttgacag ggtagcaatt tcgacacgat   1140

agggttctct cttctgccgt ta                                            1162


<210> SEQ ID NO 90
<211> LENGTH: 1561
<212> TYPE: DNA
<213> ORGANISM: Artificial Sequence
<220> FEATURE:
<223> OTHER INFORMATION: Synthetic Construct- Sequence No. 90,
      Example 90: designer nirA-promoter-controlled 2-Enoyl-CoA
      Reductase DNA construct (1561 bp)

<400> SEQUENCE: 90

agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catggccggc gcgcagcagg atcttgccgc tgcgtccggg cttgtcgctg    300

gccgcggcgg ccttggcggc atcgtgcagg tcgaacaccg cttccaccgg cagcgccagg    360

ctgccatcga gcgcggcggt gagcagttcg ccgatcatgc ggcgcttgtc ctcggccttg    420

gtggcctgca tcaccttgct gccccagaag ccacgcacgg tggcctgctt gaagatcaca    480

tcgccgctgg atatctgcag cggctcgccg gtcatcgagc caaaggaaat cagctcgccg    540

ccttcggcca gcaaggccat cagctcaccc gctgcattgc cggccaccga atcgatggcg    600

cgcacgatgg gcgcatcgcc ggccagcgcg cgcaccttgt cctgccagcc tgcttgcgca    660

gtggagattg cgttgccgat gcccagcgct ttcagctcgt ccacgccggc gtcgcggcgc    720

accaggttga tcacgttgat gccgcgtgcg gcggcgagca tcgccaccgt cttgccgacc    780

gcaccgttgg cggtgttctg cacgatccag tcgccctgtt tcacctgcag gaattcgatc    840

agcatcagcg cgctcagcgg catggcgatc aactggcaac cacgctcgtc gtccaggcca    900

tccggcaacg gcaccacgcc ggaggcgtcg gcaaggaagt actcggccca ggcctcatgc    960

acaccggcgg cgaccacgcg ctggccaacc tgcaagccct cgacaccctc acccagcgca   1020

tcgatgacac ccgccgcttc gctgccgccg atggctggca gttccggctt gtagccgtaa   1080

ttgccgcgca cggtccacag gtcatggtta tggatcggcg cgcgccgcat cgcaacgcgc   1140

acctggccct tgcctggctg cggcgtgggg cgctcgccca gttcgagcac cttggccgga   1200

tcgccgaatt gggtatggat ggctgcgcgc atggaggtct cctgccgggc acgctcttgc   1260

tgcgacgcgc ccgatcgttg tgaaaggtgg cgcgatgcta tcggcagggc tgcaaggaag   1320

ggatgaagcg aacggaactg ctgtgtgaag ttgttggcgt gcgcgcgtag tgacgatgct   1380

ctgctgcagc gccggaggac tgcgtgcagg ccgaccctca ttaaggctga gatcttcttc   1440

agtgcattgt agttgaatga agggttaggg gggaaatgcc cccctatttt ttgtctagcc   1500

atcctgccac gtttgacagg gtagcaattt cgacacgata gggttctctc ttctgccgtt   1560

a                                                                   1561
```

```
<210> SEQ ID NO 91
<211> LENGTH: 1747
<212> TYPE: DNA
<213> ORGANISM: Artificial Sequence
<220> FEATURE:
<223> OTHER INFORMATION: Synthetic Construct- Sequence No. 91,
      Example 91: designer nirA-promoter-controlled Acyl-CoA Reductase
      DNA construct (1747 bp)

<400> SEQUENCE: 91

agaaaatctg gcaccacacc tgacccccat cgagagactc cgaacgtggc aaatggaggg     60

accagagttg ttcagttcac aggtagataa tgtcgcgggt cttgatagtt agcaataaat    120

acagtttcag aatatctgta atacaaaaac tgtatcgaga caagaaaaaa gtagcaaaat    180

ttacaaatgt tcatgattca tctggctaaa ttggatgttc aactgaccca ttgaagacaa    240

gggcaacaac catgtagttg tctactaact acgtaagtca tttcctgcaa attgtgcatt    300

ccatcatgag aagttcctgg ataatgtgct ggcatttccc ctggcttagt gactatgctt    360

acaccaagta acgtcatttt ttcaataaat tcgtggtcgt caccactata ccccatagtt    420

tgaaggaatt gctttaaatt ttcttcaaca taatcatgta cttcatcttt attttcatat    480

gggcaaacaa atataagtct attaaagcat ctatcaatat cctttttttc aggcattctg    540

ttgcttaaaa tcacagtata gtcggcatta cacgatgcaa acacctttgc cggtttctcc    600

tcatcaacac tatattttaa taaacaatac tgtcggtctt gtattgattt catagaactc    660

caaggactca gatatgcctt tgggaaaacc tctgtaagct ctttcaagct ttctgctaca    720

gtttctgcaa gaatattaat gtctattttt ttattggcaa ataccatcct aggagacaaa    780

caggcttttt gctcccaaca tatcacatca ctagcaatac cttttgcaat agtcttaata    840

tcttctactt tatctataac ttcaaaacta attttagcac catgcattat taaatgagaa    900

ttatattttg cacataactc tgccattatc cttcctgaat attctccacc ccaatgtata    960

acacaatcca tttctctcac gacagtctca tatatatcag aacattcact actaaagtat   1020

aaaacagata gtctatcttt tatacttgga tcaagctgta ccaaactttc atagaaagca   1080

tacgcaaaat atggttcatc agcagaaacc tttactaaat tacagttctt tgataataac   1140

cccatacct a tacttgtcgg aacaactaca aatgcatttc cagaaatatt atgaaacatc   1200

acacctcttg gctgtctatg cacagctcca taacttgttg gaacccaatt atctagtata   1260

tcaatgttac caagttcttc tttaatgatt atctcaagat tttctcttaa aagcattctc   1320

atactatttt caagttcata tgttacaagt tcttcacttt gattcaatat gttagctaat   1380

ctttctatat gtactttgga gtatcctcta tcaagccaca atcttccaca cctatccaaa   1440

agatcaattg tatcctgcac tgatattgca tgactcttac ttttactttt tctaagtctt   1500

tttatttcct caattacctg atctctactt gagtaagtta attctaattc caggccattt   1560

atattcttta ttaaaacatt actttcacaa acagtttcgc tcttcattaa ggctgagatc   1620

ttcttcagtg cattgtagtt gaatgaaggg ttaggggggga aatgcccccc tattttttgt   1680

ctagccatcc tgccacgttt gacagggtag caatttcgac acgatagggt tctctcttct   1740

gccgtta                                                             1747


<210> SEQ ID NO 92
<211> LENGTH: 1450
<212> TYPE: DNA
<213> ORGANISM: Artificial Sequence
<220> FEATURE:
<223> OTHER INFORMATION: Synthetic Construct- Sequence No. 92,
      Example 92: designer nirA-promoter-controlled Hexanol dehydronase
```

DNA construct (1450 bp)

<400> SEQUENCE: 92

```
agaaaatctg gcaccacacc tgacccccat cgagagactc cgaacgtggc aaatggaggg      60
accagagttg ttcagttcac aggtagataa tgtcgcgggt cttgatagtt agcaataaat     120
acagtttcag aatatctgta atacaaaaac tgtatcgaga caagaaaaaa gtagcaaaat     180
ttacaaatgt tcatgattca tctggctaaa ttggatgttc aactgaccca ttgaagacaa     240
gggcaacaac catggaactc gacctcgacg gtcccggggt tggtgaagtg ctgatcaagt     300
acaccgccgc ggggttgtgc cattcggacc tgcacttgac cgacggggac ctaccgccgc     360
gctatccaat cgtcgggggg cacgaggggt caggcatcat cgaggacgtc ggacctgggg     420
tcaccaaggt caaaccaggc gatcacgttg tttgcagctt catcccgaac tgcggaacct     480
gtcggtactg cgccaccgga cgctccaacc tctgcgatat gggcgccacc atcctcgaag     540
ggtgcatgcc cgacggcagt taccggttcc acagtaacgg cctggatttc ggtgcgatgt     600
gcatgctcgg cacattctcc gaacgcgcaa ctatctccca gcattcggtg gtcaagatcg     660
acgactggct gccgctcgag accgcggtgg tcgtcggctg cggcgtgccg actggctggg     720
gcacctccgt ctatgccggc ggggttcgtt gcggtgacac caccgtcatc tatggcgtcg     780
gcggcctggg agtcaacgcc gtccaaggcg cggtgagtgc gggcgcgaag tacatcgtgg     840
tcgtcgatcc ggttgcgttc aaacgcgaca ccgcgctcaa gttcggcgcc acccacgcgt     900
tcgccgacgc cgccaccgcc gcggccaagg tcgacgaact gacctgggga cagggtgccg     960
atcaggcgct gatcctggtc ggcaccgtcg acgaggacgt ggtctcggcg gcgactgcgg    1020
tgatcggtaa gggaggcacc gtcgtgatca ccggactggc ggacccagca aagctcacgg    1080
tgcacgtttc gggaacggac ctgacgctta acgagaagac aatcaagggc acgttgttcg    1140
gctcgtccaa tccgcaatac gacatcgtac ggctgctccg tctctacgac gccggccagc    1200
taaaactcga cgatctgatc accacccgat acacgctcga ccaggtcaac cagggctacc    1260
aggatctgcg agacggcaag aacatccgcg gcgtgatcat ccacgcctga taaggctgag    1320
atcttcttca gtgcattgta gttgaatgaa gggttagggg ggaaatgccc ccctattttt    1380
tgtctagcca tcctgccacg tttgacaggg tagcaatttc gacacgatag ggttctctct    1440
tctgccgtta                                                           1450
```

<210> SEQ ID NO 93
<211> LENGTH: 1074
<212> TYPE: DNA
<213> ORGANISM: Artificial Sequence
<220> FEATURE:
<223> OTHER INFORMATION: Synthetic Construct- Sequence No. 93, Example 93: designer nirA-promoter-controlled Octanol Dehydrogenase DNA construct (1074 bp)

<400> SEQUENCE: 93

```
agaaaatctg gcaccacacc tgacccccat cgagagactc cgaacgtggc aaatggaggg      60
accagagttg ttcagttcac aggtagataa tgtcgcgggt cttgatagtt agcaataaat     120
acagtttcag aatatctgta atacaaaaac tgtatcgaga caagaaaaaa gtagcaaaat     180
ttacaaatgt tcatgattca tctggctaaa ttggatgttc aactgaccca ttgaagacaa     240
gggcaacaac catgttggga ggccaagaag ccgctggtga ttgaggacat tgaggtggcg     300
ccacctcagg cttggcaggt tcgcatcaag attacagcca ctggcgtttg ccacacggat     360
tctttttcgt tgagcggctc tgatcctgag ggtctctttc ccgtggtcct tggccatgag     420
```

ggcgccggca tcgtggagag cgttggcgag ggcgtaacca actttaaggc cggcgatcat 480
gtcattgccc tctacatacc ccagtgcaat gagtgcaaat tctgcaagag cggcaagaca 540
aatctctgcc agaagattcg cctcacccag ggcgctggtg tcatgcccaa tggatcctcc 600
cgcttgtcgt gcaagggtca gcagctgttc catttcatgg gcacctcaac tttcgccgag 660
tacgcggtgg tggccgacat atcggtgacc aaaatcaacg agtcggctcc attggagaag 720
gtgtgccttc tgggctgtgg catttccacg ggctatggtg ccgccttgaa cacctttagg 780
tggaacctgg cagcacttgc gccgtctggg gtctgggtgc tgttggactg gcagtgggtc 840
tgggctgcaa gaaggctggc gccgccaagg tctacggcat cgacatcaat ccctccaaat 900
tcgagctggc caggaagttc ggcttcaccg actttaaggc tgagatcttc ttcagtgcat 960
tgtagttgaa tgaagggtta ggggggaaat gccccccctat tttttgtcta gccatcctgc 1020
cacgtttgac agggtagcaa tttcgacacg atagggttct ctcttctgcc gtta 1074

<210> SEQ ID NO 94
<211> LENGTH: 1096
<212> TYPE: DNA
<213> ORGANISM: Artificial Sequence
<220> FEATURE:
<223> OTHER INFORMATION: Synthetic Construct- Sequence No. 94, Example 94: designer nirA-promoter-controlled Short Chain Alcohol Dehydrogenase DNA construct (1096 bp)

<400> SEQUENCE: 94
agaaaatctg gcaccacacc tgaccccccat cgagagactc cgaacgtggc aaatggaggg 60
accagagttg ttcagttcac aggtagataa tgtcgcgggt cttgatagtt agcaataaat 120
acagtttcag aatatctgta atacaaaaac tgtatcgaga caagaaaaaa gtagcaaaat 180
ttacaaatgt tcatgattca tctggctaaa ttggatgttc aactgaccca ttgaagacaa 240
gggcaacaac catgaaggtt gccgtaatta ctggggcatc ccgtggaatc ggggaagcta 300
tagcaaaggc ccttgctgaa gatggatatt cccttgcctt aggggctaga agtgttgata 360
ggttagagaa gattgccaag gaactcagcg aaaaacatgg ggtggaggta ttttacgact 420
acctcgatgt atcaaaacca gaaagcgttg aagagtttgc aaggaaaacg ctagctcact 480
ttggagatgt ggacgttgtt gtggccaatg cggggcttgg ttactttggt aggcttgaag 540
agcttacaga agagcagttc cacgaaatga ttgaagtaaa ccttttggga gtttggagaa 600
caataaaagc tttcttaaac tccttaaagc ggactggagg agtggctatt gttgttactt 660
cagatgtttc tgcaaggcta cttccatacg gtggaggtta tgtggcaact aaatgggctg 720
caagagcatt ggtaaggacc ttccagattg agaatccaga tgtgaggttc ttcgagctaa 780
gacctggagc agtagataca tattttggag ggagcaaagc tgggaagcca aaggagcaag 840
ggtatttaaa acctgaggaa gttgctgagg cagtaaaata cctcctaaga cttccaaagg 900
atgttagggt tgaggaatta atgttgcgct caatttatca aaaacctgag tattgataag 960
gctgagatct tcttcagtgc attgtagttg aatgaagggt taggggggaa atgcccccct 1020
attttttgtc tagccatcct gccacgtttg acagggtagc aatttcgaca cgatagggtt 1080
ctctcttctg ccgtta 1096

<210> SEQ ID NO 95
<211> LENGTH: 1438
<212> TYPE: DNA
<213> ORGANISM: Artificial Sequence
<220> FEATURE:

<223> OTHER INFORMATION: Synthetic Construct- Sequence No. 95,
Example 95: designer Synechococcus sp. strain PCC 7942 nirA-
promoter-controlled NADPH-dependent Glyceraldehyde-3-Phosphate-
Dehydrogenase DNA construct (1438 bp)

<400> SEQUENCE: 95
agaaaatctg gcaccacacc cttcttgcag aacatgcatg atttacaaaa agttgtagtt 60
tctgttacca attgcgaatc gagaactgcc taatctgccg agtatatgat gtcaacgaat 120
attgcaatta atggaatggg tagaattgga agaatggtgc taagaatagc actaaagaat 180
gaagcattga atgtagttgc catcaatgct agctatcctc ctgaaacaat tgcacattta 240
attaattatg acacaacaca tgggagatac gataaaagag tagaacctat tgaaagtgga 300
attcgagtgg aaggccatga tattaaatta gtgtctgata gaaacccaga aaatttaccc 360
tggaaagatt tagaaataga tatcgtcatt gaagcgaccg gtaaatttaa ccatggtgat 420
aaagctaagg cacatattca agcaggagct aaaaaagtgt tattgacagg accatcaaaa 480
ggcggaaaag tacagatggt ggttaaaggt gttaacgatc aagacttaga tacagataca 540
tatgacatat ttagtaatgc gtcgtgtact acgaattgta tcggaccagt tgcaaaagtt 600
ttaaatgata gttttggcat tgaaaatggc ttaatgacaa cggtacatgc aattacaaat 660
gatcaaaata atatagataa tccgcataaa gatttgagaa gagcgcgttc ttgtggggaa 720
agtattatac caacatcaac aggtgctgct aaagcattaa aagaagttat gccagaattg 780
aatggcaaac tacatggcat agcacttcgt gtgccaactc aaaatgtatc attagttgat 840
ttagtcattg atttaaaaca aaaagtgaca gtagatgaag ttaatcatgc atttagagat 900
gcaaacttac aaggaattat tgatgttgaa gaggcccctc tagtttctaa ggactataat 960
acaaatcctc attcagcagt tatagatgct aaaaatacaa tggtcatggg agataataag 1020
gttaaagtta tagcctggta tgataacgaa tggggatatt ctaatagagt agttgaggta 1080
gcaaatcaac ttggagaact aattaaataa taatagtgat cccggccgct actaaagcct 1140
gatttgtctt gatagctgct cctgcctttg ggcaggggct tttttctgtc tgccattctt 1200
gaggatggcg gactctttcc cttttgctct acgcccatga atgcgatcgc agtctcccct 1260
gtccagcacg ttggagtgat tggtggtggc cagttagctt ggatgctggc accagcagcg 1320
caacagttgg ggatgtcgct gcacgttcaa acacccaatg atcacgaccc agcagtagcg 1380
atcgcggatc aaaccgtatt agcagcagtt gctgacgcgg ttctctcttc tgccgtta 1438

<210> SEQ ID NO 96
<211> LENGTH: 1447
<212> TYPE: DNA
<213> ORGANISM: Artificial Sequence
<220> FEATURE:
<223> OTHER INFORMATION: Synthetic Construct- Sequence No. 96,
Example 96: designer Synechococcus sp. strain PCC 7942 nirA-
promoter-controlled NAD-dependent Glyceraldehyde-3-Phosphate-
Dehydrogenase DNA construct (1447 bp)

<400> SEQUENCE: 96
agaaaatctg gcaccacacc cttcttgcag aacatgcatg atttacaaaa agttgtagtt 60
tctgttacca attgcgaatc gagaactgcc taatctgccg agtatatgat ggcagtaaaa 120
gtagcaatta atggttttgg tagaattggt cgtttagcat tcagaagaat tcaagaagta 180
gaaggtcttg aagttgtagc agtaaacgac ttaacagatg acgacatgtt agcgcattta 240
ttaaaatatg acactatgca aggtcgtttc acaggtgaag tagaggtagt tgatggtggt 300
ttccgcgtaa atggtaaaga agttaaatca ttcagtgaac cagatgcaag caaattacct 360

```
tggaaagact taaatatcga tgtagtgtta gaatgtactg gtttctacac tgataaagat    420

aaagcacaag ctcatattga agcaggcgct aaaaaagtat taatctcagc accagctact    480

ggtgacttaa aaacaatcgt attcaacact aaccaccaag agttagacgg ttctgaaaca    540

gttgtttcag gtgcttcatg tactacaaac tcattagcac cagttgctaa agttttaaac    600

gatgactttg gtttagttga aggtttaatg actacaattc acgcttacac aggtgatcaa    660

aatacacaag acgcacctca cagaaaaggt gacaaacgtc gtgctcgtgc agcggcagaa    720

aacatcatcc ctaactcaac aggtgctgct aaagctatcg gtaaagttat tcctgaaatc    780

gatggtaaat tagatggtgg tgcacaacgt gttcctgtag ctacaggttc attaactgaa    840

ttaacagtag tattagaaaa acaagacgta acagttgaac aagttaacga agctatgaaa    900

aatgcttcaa acgaatcatt cggttacact gaagacgaaa tcgtttcttc agacgttgta    960

ggtatgactt acggttcatt attcgacgct acacaaactc gtgtaatgtc agttggcgac   1020

cgtcaattag ttaaagttgc agcttggtat gataacgaaa tgtcatatac tgcacaatta   1080

gttcgtacat tagcatactt agctgaactt tctaaataat aatagtgatc ccggccgcta   1140

ctaaagcctg atttgtcttg atagctgctc ctgcctttgg gcaggggctt ttttctgtct   1200

gccattcttg aggatggcgg actctttccc ttttgctcta cgcccatgaa tgcgatcgca   1260

gtctcccctg tccagcacgt tggagtgatt ggtggtggcc agttagcttg gatgctggca   1320

ccagcagcgc aacagttggg gatgtcgctg cacgttcaaa cacccaatga tcacgaccca   1380

gcagtagcga tcgcggatca aaccgtatta gcagcagttg ctgacgcggt tctctcttct   1440

gccgtta                                                             1447
```

<210> SEQ ID NO 97
<211> LENGTH: 2080
<212> TYPE: DNA
<213> ORGANISM: Artificial Sequence
<220> FEATURE:
<223> OTHER INFORMATION: Synthetic Construct- Sequence No. 97, Example 97: designer Synechococcus sp. strain PCC 7942 nirA-promoter-controlled 2-Keto Acid Decarboxylase DNA construct (2080 bp)

<400> SEQUENCE: 97

```
agaaaatctg gcaccacacc cttcttgcag aacatgcatg atttacaaaa agttgtagtt     60

tctgttacca attgcgaatc gagaactgcc taatctgccg agtatatgat gtatacagta    120

ggagattacc tgttagaccg attacacgag ttgggaattg aagaaatttt tggagttcct    180

ggtgactata acttacaatt tttagatcaa attatttcac gcgaagatat gaaatggatt    240

ggaaatgcta atgaattaaa tgcttcttat atggctgatg gttatgctcg tactaaaaaa    300

gctgccgcat ttctcaccac atttggagtc ggcgaattga gtgcgatcaa tggactggca    360

ggaagttatg ccgaaaattt accagtagta gaaattgttg gttcaccaac ttcaaaagta    420

caaaatgacg gaaaatttgt ccatcataca ctagcagatg gtgattttaa acactttatg    480

aagatgcatg aacctgttac agcagcgcgg actttactga cagcagaaaa tgccacatat    540

gaaattgacc gagtactttc tcaattacta aaagaaagaa aaccagtcta tattaactta    600

ccagtcgatg ttgctgcagc aaaagcagag aagcctgcat tatctttaga aaaagaaagc    660

tctacaacaa atacaactga acaagtgatt ttgagtaaga ttgaagaaag tttgaaaaat    720

gcccaaaaac cagtagtgat tgcaggacac gaagtaatta gttttggttt agaaaaaacg    780

gtaactcagt ttgtttcaga aacaaaacta ccgattacga cactaaattt tggtaaaagt    840
```

```
gctgttgatg aatctttgcc ctcattttta ggaatatata acgggaaact ttcagaaatc    900

agtcttaaaa attttgtgga gtccgcagac tttatcctaa tgcttggagt gaagcttacg    960

gactcctcaa caggtgcatt cacacatcat ttagatgaaa ataaaatgat ttcactaaac   1020

atagatgaag gaataatttt caataaagtg gtagaagatt ttgattttag agcagtggtt   1080

tcttctttat cagaattaaa aggaatagaa tatgaaggac aatatattga taagcaatat   1140

gaagaattta ttccatcaag tgctccctta tcacaagacc gtctatggca ggcagttgaa   1200

agtttgactc aaagcaatga aacaatcgtt gctgaacaag gaacctcatt ttttggagct   1260

tcaacaattt tcttaaaatc aaatagtcgt tttattggac aacctttatg ggttctatt    1320

ggatatactt ttccagcggc tttaggaagc caaattgcgg ataaagagag cagacacctt   1380

ttatttattg gtgatggttc acttcaactt accgtacaag aattaggact atcaatcaga   1440

gaaaaactca atccaatttg ttttatcata aataatgatg gttatacagt tgaaagagaa   1500

atccacggac ctactcaaag ttataacgac attccaatgt ggaattactc gaaattacca   1560

gaaacatttg gagcaacaga agatcgtgta gtatcaaaaa ttgttagaac agagaatgaa   1620

tttgtgtctg tcatgaaaga agcccaagca gatgtcaata gaatgtattg gatagaacta   1680

gttttggaaa aagaagatgc gccaaaatta ctgaaaaaaa tgggtaaatt atttgctgag   1740

caaaataaat agtaatagtg atcccggccg ctactaaagc ctgatttgtc ttgatagctg   1800

ctcctgcctt tgggcagggg ctttttttctg tctgccattc ttgaggatgg cggactcttt   1860

ccccttttgct ctacgcccat gaatgcgatc gcagtctccc ctgtccagca cgttggagtg   1920

attggtggtg gccagttagc ttggatgctg gcaccagcag cgcaacagtt ggggatgtcg   1980

ctgcacgttc aaacacccaa tgatcacgac ccagcagtag cgatcgcgga tcaaaccgta   2040

ttagcagcag ttgctgacgc ggttctctct tctgccgtta                          2080
```

<210> SEQ ID NO 98
<211> LENGTH: 1603
<212> TYPE: DNA
<213> ORGANISM: Artificial Sequence
<220> FEATURE:
<223> OTHER INFORMATION: Synthetic Construct- Sequence No. 98, Example 98: designer Synechococcus sp. strain PCC 7942 nirA-promoter-controlled NADH-dependent Butanol Dehydrogenase DNA construct (1603 bp)

<400> SEQUENCE: 98

```
agaaaatctg gcaccacacc cttcttgcag aacatgcatg atttacaaaa agttgtagtt     60

tctgttacca attgcgaatc gagaactgcc taatctgccg agtatatgat gtcaagattt    120

acactaccaa gagatattta tttcggagaa aacactttag aaactttaaa aactttaaaa    180

ggtaagaaag ctataattgt tgttggagga ggatcaatga aaaaatttgg tttccttcaa    240

aaagttgaag aatatctaaa agaagcagga atggaaataa aattaataga aggtgttgaa    300

ccagatccat cagttgaaac cgttatgaaa ggtgcagaaa tcatgagaga ttttgagcct    360

gattggatag tatccatagg tggaggatca ccaatagatg ctgctaaagc tatgtggata    420

ttctatgaat acccagaatt tacttttgag caagctgttg ttcctttttgg aataccagat   480

ttaagacaaa aagctaaatt tgttgctata ccatctacaa gtggaacagc tacagaagtt    540

actgcttttt cagttataac tgattacaaa gctaagataa aatatccttt agctgatttt    600

aatttaacac cagatgtagc tattatagat ccagctcttg ctcaaacaat gcctgcaaaa    660

ttaacagctc atacaggtat ggatgcttta actcatgcaa tagaagctta tgtagcagga    720
```

```
ttaagatcat atttctcaga tcctcttgca atgcaagcta tagttatgac aaaagataat    780

ttaataaaat cctatgaagg agataaagaa gcaagagatg aaatgcatat agctcaatgt    840

ttagcaggaa tggcattctc aaatgcgcta cttggaatta ctcatagtat ggcacataag    900

acaggagcag tattccacat tcctcatggt tgtgcaaatg ctatattcct tccttatgta    960

atagatttta ataagaaaac atgtaaagat agatatgcaa ctatagctaa aactttaggt   1020

ttagcaggaa atactgatga tgaattagta gatgcattaa cttctatgat acaagaaatg   1080

aataagaaaa tggatatacc actaaactta aaagaatatg gagtaacaga agaagatttt   1140

aatgaaaact tagatttcat agcacataat gcagtgttag atgcatgtac tggatcaaat   1200

ccaagaccta taactgaaga agaaatgaaa aaagtattca aatgcacatt tactggagag   1260

aaagttaatt tttaataata gtgatcccgg ccgctactaa agcctgattt gtcttgatag   1320

ctgctcctgc ctttgggcag ggcttttttt ctgtctgcca ttcttgagga tggcggactc   1380

tttccctttt gctctacgcc catgaatgcg atcgcagtct cccctgtcca gcacgttgga   1440

gtgattggtg gtggccagtt agcttggatg ctggcaccag cagcgcaaca gttggggatg   1500

tcgctgcacg ttcaaacacc caatgatcac gacccagcag tagcgatcgc ggatcaaacc   1560

gtattagcag cagttgctga cgcggttctc tcttctgccg tta                     1603
```

```
<210> SEQ ID NO 99
<211> LENGTH: 1654
<212> TYPE: DNA
<213> ORGANISM: Artificial Sequence
<220> FEATURE:
<223> OTHER INFORMATION: Synthetic Construct- Sequence No. 99,
      Example 99: designer Synechococcus sp. strain PCC 7942 nirA-
      promoter-controlled NADPH-dependent Butanol Dehydrogenase DNA
      construct (1654 bp)

<400> SEQUENCE: 99
```

```
agaaaatctg gcaccacacc cttcttgcag aacatgcatg atttacaaaa agttgtagtt     60

tctgttacca attgcgaatc gagaactgcc taatctgccg agtatatgct agaaatcaac    120

ttctgtatcg taataacagc acttaagcag tttttccatt tcttctacgc ttggctgtct    180

tgggttagaa cctgtgcagg catcgcctat ggcattaact gcaatgtcat gtaacctctc    240

caggaataca ttttcaggca caaatccctg tgcaaccgga tagctgtctg caccgtaatt    300

tttaatgcag tgcggtatat taagttcatc attcatctta cggagataac cgattaatga    360

agctaccttt tcatcaaggt ctgctccgcc aagtcccatg aaatcagcaa tttcaccata    420

acgcttctta gcctgttcat cctttgcgtt aaatgcaatt accttaggga gatacattgc    480

attcgcagca ccgtgaatga tgtgtgcgcc gtaatcggca aatgccgcac ctgttttatg    540

cgccattgaa tgtacaatac caagaagtgc attagaaaat gccattcctg cgagacattg    600

tgcattatgc attgaatctc ttttttccat atcaccgtta tatgaaccga caaggtctct    660

ttgaatcatt ttaattgcat ggagtgccaa tgggtctgta aaatcacaat ttgcggtgga    720

tacatatgcc tcgatagcat gtgtcattgc atccatacct gtatgtgcca ccaatttttg    780

tggcatggtc tctgccagtt cagggtctac tattgcaaca tcaggtgtta tttcaaaatc    840

ggctattgga tattttattc ctttttcata atctgtaata attgaaaaag cagttacctc    900

ggtagcggtt cctgaagtag aagatattgc acaaaaatgt gctttttttac gaagtgaagg    960

tatgccaaat actttacaca tatcctcaaa ggtaatatca ggatattcat atttaatcca   1020

cattgcttta gccgcatcaa tcggagaacc tccgcctatt gcaacaatcc agtcaggttc   1080
```

aaactctgac atcgctttgg cacctttcat aacggtttcc accgaagggt caggttcaat 1140
tccttcaaaa agtctgactt ccataccggc ttccttaaga tactgttctg ccctgtcaag 1200
gaaaccaaaa cgtttcattg aacctccgcc aacacaaatc atggcttttt tgccttgaaa 1260
tgtcttaagt gcctctaatg caccctttcc atgatacaaa tctcttggta acgtaaatct 1320
tgccattaat agtgatcccg gccgctacta aagcctgatt tgtcttgata gctgctcctg 1380
cctttgggca ggggcttttt tctgtctgcc attcttgagg atggcggact ctttcccttt 1440
tgctctacgc ccatgaatgc gatcgcagtc tcccctgtcc agcacgttgg agtgattggt 1500
ggtggccagt tagcttggat gctggcacca gcagcgcaac agttggggat gtcgctgcac 1560
gttcaaacac ccaatgatca cgacccagca gtagcgatcg cggatcaaac cgtattagca 1620
gcagttgctg acgcggttct ctcttctgcc gtta 1654

<210> SEQ ID NO 100
<211> LENGTH: 1440
<212> TYPE: DNA
<213> ORGANISM: Artificial Sequence
<220> FEATURE:
<223> OTHER INFORMATION: Synthetic Construct- Sequence No. 100, Example 100: designer Synechocystis sp. PCC 6803 nirA-promoter-controlled NAD-dependent Glyceraldehyde-3-Phosphate Dehydrogenase DNA construct (1440 bp)

<400> SEQUENCE: 100
atggtagtta aagttggtat taacggtttc ggtcgtatcg gacgtcttgc attccgccgt 60
attcaaaata tcgaaggtgt tgaagtaact cgtatcaacg accttacaga tccaaatatg 120
cttgcacact tgttgaaata cgatacaact caaggtcgtt ttgatggaac agttgaagtt 180
aaagaaggtg gatttgaagt aaacggaaac ttcattaaag tttctgctga acgtgatcca 240
gaaaacatcg actgggcaac tgatggggtt gaaatcgttc ttgaagcaac tggtttcttt 300
gctaaaaaag aagcagctga aaaacactta catgctaacg gtgctaaaaa agttgttatc 360
acagctcctg gtggaaacga tgttaaaaca gttgttttca acactaacca cgacattctt 420
gacggtactg aaacagttat ctcaggtgct tcatgtacta caaactgttt agctcctatg 480
gctaaagctc ttcacgatgc attcggtatt caaaaaggtc ttatgactac aatccacgct 540
tacactggtg accaaatgat ccttgacgga ccacaccgtg gtggtgacct tcgtcgtgca 600
cgcgctggtg ctgcaaatat cgttcctaac tcaactggtg ctgctaaagc tatcggtctt 660
gttatcccag aacttaacgg taaacttgac ggtgctgcac aacgtgttcc tgttccaact 720
ggatcagtaa ctgagttggt tgtaactctt gacaaaaacg tttctgttga cgaaatcaac 780
gctgctatga aagctgcttc aaacgatagc ttcggttaca ctgaagatcc aatcgtttct 840
tcagatatcg taggcgtatc atacggttca ttgtttgacg caactcaaac taaagtaatg 900
gaagttgacg gatcccaatt ggttaaagtt gtatcatggt atgacaacga aatgtcttac 960
actgctcaac ttgtacgtac tcttgagtac ttcgcaaaaa ttgctaaata atagtaatga 1020
gttacagttt tggcaattac taaaaaactg acttcaattc aatgttagcc cgctcccgcg 1080 ggtttttgt tgctttttca cagtgactat aggtaatcag caacacaata cggccctgtt 1140
ctttggacag tttttgtata atgttgaccg catcctgacc ggattttta tctaagtggg 1200 gaattgtcaa ttgtcaatta aagctaagtt ctactaatgt tttagaaggc attgtcgatt 1260
gaaaataagg gttgaatgga gaaaattttg agcctttgtc aaagataaaa atttatttca 1320
acagtttttt aactagccga accagagaat gacccagtgg cgctgacttt gctcccgagt 1380

```
ttttgttaga aattaccctc aagaagtaat ctaataataa ggttctctct tctgccgtta   1440


<210> SEQ ID NO 101
<211> LENGTH: 2182
<212> TYPE: DNA
<213> ORGANISM: Artificial Sequence
<220> FEATURE:
<223> OTHER INFORMATION: Synthetic Construct- Sequence No. 101,
      Example 101: designer Synechocystis sp. PCC 6803 nirA-promoter-
      controlled 2-Keto Acid Decarboxylase dehydrogenase DNA construct
      (2182 bp)

<400> SEQUENCE: 101

agaaaatctg gcaccacacc ctaaatgcgt aaactgcata tgccttggct gagtgtaatt     60

tacgttacaa attttaacga aacgggaacc ctatattgat ctctacatga tgtatacagt    120

aggagattac ctgttagacc gattacacga gttgggaatt gaagaaattt ttggagttcc    180

tggtgactat aacttacaat ttttagatca aattatttca cgcgaagata tgaaatggat    240

tggaaatgct aatgaattaa atgcttctta tatggctgat ggttatgctc gtactaaaaa    300

agctgccgca tttctcacca catttggagt cggcgaattg agtgcgatca atggactggc    360

aggaagttat gccgaaaatt taccagtagt agaaattgtt ggttcaccaa cttcaaaagt    420

acaaaatgac ggaaaatttg tccatcatac actagcagat ggtgatttta aacactttat    480

gaagatgcat gaacctgtta cagcagcgcg gactttactg acagcagaaa atgccacata    540

tgaaattgac cgagtacttt ctcaattact aaaagaaaga aaaccagtct atattaactt    600

accagtcgat gttgctgcag caaaagcaga gaagcctgca ttatctttag aaaaagaaag    660

ctctacaaca aatacaactg aacaagtgat tttgagtaag attgaagaaa gtttgaaaaa    720

tgcccaaaaa ccagtagtga ttgcaggaca cgaagtaatt agttttggtt tagaaaaaac    780

ggtaactcag tttgtttcag aaacaaaact accgattacg acactaaatt ttggtaaaag    840

tgctgttgat gaatctttgc cctcattttt aggaatatat aacgggaaac tttcagaaat    900

cagtcttaaa aattttgtgg agtccgcaga ctttatccta atgcttggag tgaagcttac    960

ggactcctca acaggtgcat tcacacatca tttagatgaa aataaaatga tttcactaaa   1020

catagatgaa ggaataattt tcaataaagt ggtagaagat tttgatttta gagcagtggt   1080

ttcttcttta tcagaattaa aaggaataga atatgaagga caatatattg ataagcaata   1140

tgaagaattt attccatcaa gtgctccctt atcacaagac cgtctatggc aggcagttga   1200

aagtttgact caaagcaatg aaacaatcgt tgctgaacaa ggaacctcat tttttggagc   1260

ttcaacaatt ttcttaaaat caaatagtcg ttttattgga caacctttat ggggttctat   1320

tggatatact tttccagcgg ctttaggaag ccaaattgcg gataaagaga gcagacacct   1380

tttatttatt ggtgatggtt cacttcaact taccgtacaa gaattaggac tatcaatcag   1440

agaaaaactc aatccaattt gttttatcat aaataatgat ggttatacag ttgaaagaga   1500

aatccacgga cctactcaaa gttataacga cattccaatg tggaattact cgaaattacc   1560

agaaacattt ggagcaacag aagatcgtgt agtatcaaaa attgttagaa cagagaatga   1620

atttgtgtct gtcatgaaag aagcccaagc agatgtcaat agaatgtatt ggatagaact   1680

agttttggaa aaagaagatg cgccaaaatt actgaaaaaa atgggtaaat tatttgctga   1740

gcaaaataaa tagtagtaat gagttacagt tttggcaatt actaaaaaac tgacttcaat   1800

tcaatgttag cccgctcccg cgggtttttt gttgcttttt cacagtgact ataggtaatc   1860

agcaacacaa tacggccctg ttctttggac agtttttgta taatgttgac cgcatcctga   1920
```

```
ccggattttt tatctaagtg gggaattgtc aattgtcaat taaagctaag ttctactaat   1980

gttttagaag gcattgtcga ttgaaaataa gggttgaatg gagaaaattt tgagcctttg   2040

tcaaagataa aaatttattt caacagtttt ttaactagcc gaaccagaga atgacccagt   2100

ggcgctgact ttgctcccga gtttttgtta gaaattaccc tcaagaagta atctaataat   2160

aaggttctct cttctgccgt ta                                            2182
```

<210> SEQ ID NO 102
<211> LENGTH: 1705
<212> TYPE: DNA
<213> ORGANISM: Artificial Sequence
<220> FEATURE:
<223> OTHER INFORMATION: Synthetic Construct- Sequence No. 102, Example 102: designer Synechocystis sp. PCC 6803 nirA-promoter-controlled NADH-dependent Butanol Dehydrogenase DNA construct (1705 bp)

<400> SEQUENCE: 102

```
agaaaatctg gcaccacacc ctaaatgcgt aaactgcata tgccttggct gagtgtaatt     60

tacgttacaa attttaacga aacgggaacc ctatattgat ctctacatga tgtcaagatt    120

tacactacca agagatattt atttcggaga aaacacttta gaaactttaa aaactttaaa    180

aggtaagaaa gctataattg ttgttggagg aggatcaatg aaaaaatttg gtttccttca    240

aaaagttgaa gaatatctaa aagaagcagg aatggaaata aaattaatag aaggtgttga    300

accagatcca tcagttgaaa ccgttatgaa aggtgcagaa atcatgagag attttgagcc    360

tgattggata gtatccatag gtggaggatc accaatagat gctgctaaag ctatgtggat    420

attctatgaa tacccagaat ttacttttga gcaagctgtt gttccttttg gaataccaga    480

tttaagacaa aaagctaaat ttgttgctat accatctaca agtggaacag ctacagaagt    540

tactgctttt tcagttataa ctgattacaa agctaagata aaatatcctt tagctgattt    600

taatttaaca ccagatgtag ctattataga tccagctctt gctcaaacaa tgcctgcaaa    660

attaacagct catacaggta tggatgcttt aactcatgca atagaagctt atgtagcagg    720

attaagatca tatttctcag atcctcttgc aatgcaagct atagttatga caaaagataa    780

tttaataaaa tcctatgaag gagataaaga agcaagagat gaaatgcata tagctcaatg    840

tttagcagga atggcattct caaatgcgct acttggaatt actcatagta tggcacataa    900

gacaggagca gtattccaca ttcctcatgg ttgtgcaaat gctatattcc ttccttatgt    960

aatagatttt aataagaaaa catgtaaaga tagatatgca actatagcta aaactttagg   1020

tttagcagga aatactgatg atgaattagt agatgcatta acttctatga tacaagaaat   1080

gaataagaaa atggatatac cactaaactt aaaagaatat ggagtaacag aagaagattt   1140

taatgaaaac ttagatttca tagcacataa tgcagtgtta gatgcatgta ctggatcaaa   1200

tccaagacct ataactgaag aagaaatgaa aaaagtattc aaatgcacat ttactggaga   1260

gaaagttaat ttttaatagt aatgagttac agttttggca attactaaaa aactgacttc   1320

aattcaatgt tagcccgctc ccgcgggttt tttgttgctt tttcacagtg actataggta   1380

atcagcaaca caatacggcc ctgttctttg gacagttttt gtataatgtt gaccgcatcc   1440

tgaccggatt ttttatctaa gtggggaatt gtcaattgtc aattaaagct aagttctact   1500

aatgttttag aaggcattgt cgattgaaaa taagggttga atggagaaaa ttttgagcct   1560

ttgtcaaaga taaaaattta tttcaacagt tttttaacta gccgaaccag agaatgaccc   1620

agtggcgctg actttgctcc cgagtttttg ttagaaatta ccctcaagaa gtaatctaat   1680
```

```
aataaggttc tctcttctgc cgtta                                         1705


<210> SEQ ID NO 103
<211> LENGTH: 1756
<212> TYPE: DNA
<213> ORGANISM: Artificial Sequence
<220> FEATURE:
<223> OTHER INFORMATION: Synthetic Construct- Sequence No. 103,
      Example 103: designer Synechocystis sp. PCC 6803 nirA-promoter-
      controlled NADPH-dependent Butanol Dehydrogenase DNA construct
      (1756 bp)

<400> SEQUENCE: 103

agaaaatctg gcaccacacc ctaaatgcgt aaactgcata tgccttggct gagtgtaatt     60

tacgttacaa attttaacga aacgggaacc ctatattgat ctctacatgc tagaaatcaa    120

cttctgtatc gtaataacag cacttaagca gtttttccat ttcttctacg cttggctgtc    180

ttgggttaga acctgtgcag gcatcgccta tggcattaac tgcaatgtca tgtaacctct    240

ccaggaatac attttcaggc acaaatccct gtgcaaccgg atagctgtct gcaccgtaat    300

ttttaatgca gtgcggtata ttaagttcat cattcatctt acggagataa ccgattaatg    360

aagctacctt ttcatcaagg tctgctccgc caagtcccat gaaatcagca atttcaccat    420

aacgcttctt agcctgttca tcctttgcgt taaatgcaat taccttaggg agatacattg    480

cattcgcagc accgtgaatg atgtgtgcgc cgtaatcggc aaatgccgca cctgttttat    540

gcgccattga atgtacaata ccaagaagtg cattagaaaa tgccattcct gcgagacatt    600

gtgcattatg cattgaatct ctttttttcca tatcaccgtt atatgaaccg acaaggtctc    660

tttgaatcat tttaattgca tggagtgcca atgggtctgt aaaatcacaa tttgcggtgg    720

atacatatgc ctcgatagca tgtgtcattg catccatacc tgtatgtgcc accaattttt    780

gtggcatggt ctctgccagt tcagggtcta ctattgcaac atcaggtgtt atttcaaaat    840

cggctattgg atattttatt cctttttcat aatctgtaat aattgaaaaa gcagttacct    900

cggtagcggt tcctgaagta gaagatattg cacaaaaatg tgcttttttta cgaagtgaag    960

gtatgccaaa tactttacac atatcctcaa aggtaatatc aggatattca tatttaatcc   1020

acattgcttt agccgcatca atcggagaac ctccgcctat tgcaacaatc cagtcaggtt   1080

caaactctga catcgctttg gcacctttca taacggtttc caccgaaggg tcaggttcaa   1140

ttccttcaaa aagtctgact tccataccgg cttccttaag atactgttct gccctgtcaa   1200

ggaaaccaaa acgtttcatt gaacctccgc caacacaaat catggctttt ttgccttgaa   1260

atgtcttaag tgcctctaat gcaccctttc catgatacaa atctcttggt aacgtaaatc   1320

ttgccattag taatgagtta cagttttggc aattactaaa aaactgactt caattcaatg   1380

ttagcccgct cccgcgggtt ttttgttgct ttttcacagt gactataggt aatcagcaac   1440

acaatacggc cctgttcttt ggacagtttt tgtataatgt tgaccgcatc ctgaccggat   1500

tttttatcta agtggggaat tgtcaattgt caattaaagc taagttctac taatgtttta   1560

gaaggcattg tcgattgaaa ataagggttg aatggagaaa attttgagcc tttgtcaaag   1620

ataaaaattt atttcaacag ttttttaact agccgaacca gagaatgacc cagtggcgct   1680

gactttgctc ccgagttttt gttagaaatt accctcaaga agtaatctaa taataaggtt   1740

ctctcttctg ccgtta                                                   1756


<210> SEQ ID NO 104
<211> LENGTH: 1655
```

<212> TYPE: DNA
<213> ORGANISM: Artificial Sequence
<220> FEATURE:
<223> OTHER INFORMATION: Synthetic Construct- Sequence No. 104, Example 104: designer Anabaena PCC 7120 hox-promoter-controlled NAD-dependent Glyceraldehyde-3-Phosphate Dehydrogenase DNA construct (1655 bp)

<400> SEQUENCE: 104
agaaaatctg gcaccacacc gcagaaatat aggggctagg agttgagggt actctggttc 60
gtcaagcatt tgggatgatt tcccctcaca agttcctcaa attattctcc tataaacaat 120
agatataagg tcaaaacttg agttatgagt gctgagtaaa aaattactct ccacgcctca 180
gaggtagata tgatggtagt taaagttggt attaacggtt tcggtcgtat cggacgtctt 240
gcattccgcc gtattcaaaa tatcgaaggt gttgaagtaa ctcgtatcaa cgaccttaca 300
gatccaaata tgcttgcaca cttgttgaaa tacgatacaa ctcaaggtcg ttttgatgga 360
acagttgaag ttaaagaagg tggatttgaa gtaaacggaa acttcattaa agtttctgct 420
gaacgtgatc cagaaaacat cgactgggca actgatgggg ttgaaatcgt tcttgaagca 480
actggtttct ttgctaaaaa agaagcagct gaaaaacact tacatgctaa cggtgctaaa 540
aaagttgtta tcacagctcc tggtggaaac gatgttaaaa cagttgtttt caacactaac 600
cacgacattc ttgacggtac tgaaacagtt atctcaggtg cttcatgtac tacaaactgt 660
ttagctccta tggctaaagc tcttcacgat gcattcggta ttcaaaaagg tcttatgact 720
acaatccacg cttacactgg tgaccaaatg atccttgacg gaccacaccg tggtggtgac 780
cttcgtcgtg cacgcgctgg tgctgcaaat atcgttccta actcaactgg tgctgctaaa 840
gctatcggtc ttgttatccc agaacttaac ggtaaacttg acggtgctgc acaacgtgtt 900
cctgttccaa ctggatcagt aactgagttg gttgtaactc ttgacaaaaa cgtttctgtt 960
gacgaaatca acgctgctat gaaagctgct tcaaacgata gcttcggtta cactgaagat 1020
ccaatcgttt cttcagatat cgtaggcgta tcatacggtt cattgtttga cgcaactcaa 1080
actaaagtaa tggaagttga cggatcccaa ttggttaaag ttgtatcatg gtatgacaac 1140
gaaatgtctt acactgctca acttgtacgt actcttgagt acttcgcaaa aattgctaaa 1200
taatgaagta agtaggaagc agggagcagg ggaaagaaaa ttgacaactg tacaagatta 1260
atcgcgtctc tgagcaatga ccaaatacat ctacctccac ggttttcttc cagcccccta 1320
tctgcgaaag cacaagatat tagcaagcgt ttcgcccaaa ttcacataca gctaacaatc 1380
cctgatctca atgctggtga attttctcag ttaacaatca cgcgccaaat tcaacaagtt 1440
gccgcaattt tccctgataa ttctgaacca ataacgctga taggttctag tttaggcggt 1500
ttaactgctg cttatctagg acagcgatat ttacaagtac aacgcttagt tttattagcg 1560
ccagtttggt tttttatccc attggttgcc caaaatgggt gaagaagctg tcacaagttg 1620
gcaacaaacg atataggttc tctcttctgc cgtta 1655

<210> SEQ ID NO 105
<211> LENGTH: 2303
<212> TYPE: DNA
<213> ORGANISM: Artificial Sequence
<220> FEATURE:
<223> OTHER INFORMATION: Synthetic Construct- Sequence No. 105, Example 105: designer Anabaena PCC 7120 hox-promoter-controlled Acetolactate Synthase DNA construct (2303 bp)

<400> SEQUENCE: 105
agaaaatctg gcaccacacc gcagaaatat aggggctagg agttgagggt actctggttc 60

-continued

```
gtcaagcatt tgggatgatt tcccctcaca agttcctcaa attattctcc tataaacaat    120
agatataagg tcaaaacttg agttatgagt gctgagtaaa aaattactct ccacgcctca    180
gaggtagata tgctaagggg tgcagctgag ctccccaaga cgttggttaa agcgcagatt    240
ttcactatag tccacaggga catcaatgag agtgggaaca ttctgtgcca aggcggtttt    300
gagggttggg ataaagtcag tggtctcctc aatgcgatag cctttgagtc ccatgctttc    360
ggctaacttg acaaaatcgg gattactaaa gtggacatag gcagattcac caaagtagcg    420
ctgctgcttc cactcaatga gaccatagcc gccgtcatta aagatgatgg tggtaaagtt    480
tgtccccata cgcagggcag tttccagttc ttggaaattc atcatgaagc caccatcccc    540
cgtgactgcc accacatgcc gctgcggata gactaatttg gcggccattg cccccggtac    600
cgcaatcccc attgccgcaa agccattgga aatcaagcag gtgttggggc gatcgcagtg    660
gtagtgacga gcaatccaca ttttatgggc acccacatca gaaataacaa tgtcctcggg    720
ccccatgact tggcgcaggt catagattag cttttggggc ttaaccggaa aactctcatc    780
ctgggcatat tggtaatagt ccgccacaat ctcctgacgc agttgcacgg catagggggt    840
gggcttatct tggcgatcgg cccgcttaag aatttcatag agggagtcag aaatatcgcc    900
gacaacctca acgacaggga tatagctgct gtcaatttcc gcaggagtgg ccgcaatatg    960
gataatcggc aagcggccct cggggttcca gctttttggg gaatactcaa ttaagtcata   1020
gccaacggca atcactaagt cagcatgatc aaagccgcag ctaatgtaat cccgctgttg   1080
gagccccacg gtccacagag caaggggggtg ttgataggga atgacccctt tgcccatgaa   1140
ggtattggcc acggggatat tcagcttttc ggcaaaatgg gtgagggcag cggcagcatg   1200
ggcgcgaatg gcgccattcc ccactaggat caggggggttc tcggcagcat tgatgagttc   1260
agcggcctta agaatactct ggaaagaggc ataggttttt tcgggggagc tgggcttaag   1320
gggagcgccc tcggcttcca tggcggcaat gttttcaggc acatcaatgt gaacggcgcc   1380
cggcttctca ttctgggcaa ttttaaaggc cttgcggaca atttctgggg taatactagg   1440
gcggacaatc tgggcattcc atttggttac ggggctaaac atggccacca agtccaaata   1500
ttggtgggac tcgatgtgca tgcgatccgt ccccacttgc cctgtaatcg ccaccagggg   1560
agcgccgtcg aggttggcat cggcaacacc ggtcattaaa ttcgtggccc cggggccgag   1620
ggtagaaaga cagacccctg ctttgccggt gaggcgacca tagacatcgg ccataaaggc   1680
cgcccccctgt tcgtggcggg tggttataaa ttgaatccga gagcgatgga gggcatggag   1740
gacatctaga ttctcttccc ccggcaaacc aaaaatatat tcaacgcctt cattttcaag   1800
gcattttacg agtaattcgg cggtattcat aggatgggcg atcgcaggca ctgaagtaag   1860
taggaagcag ggagcagggg aaagaaaatt gacaactgta caagattaat cgcgtctctg   1920
agcaatgacc aaatacatct acctccacgg ttttcttcca gccccctatc tgcgaaagca   1980
caagatatta gcaagcgttt cgcccaaatt cacatacagc taacaatccc tgatctcaat   2040
gctggtgaat tttctcagtt aacaatcacg cgccaaattc aacaagttgc cgcaattttc   2100
cctgataatt ctgaaccaat aacgctgata ggttctagtt taggcggttt aactgctgct   2160
tatctaggac agcgatattt acaagtacaa cgcttagttt tattagcgcc agtttggttt   2220
tttatcccat tggttgccca aaatgggtga agaagctgtc acaagttggc aacaaacgat   2280
ataggttctc tcttctgccg tta                                           2303
```

<210> SEQ ID NO 106

<211> LENGTH: 1661
<212> TYPE: DNA
<213> ORGANISM: Artificial Sequence
<220> FEATURE:
<223> OTHER INFORMATION: Synthetic Construct- Sequence No. 106, Example 106: designer Anabaena PCC 7120 hox-promoter-controlled Ketol-Acid Reductoisomerase DNA construct (1661 bp)

<400> SEQUENCE: 106

```
agaaaatctg gcaccacacc gcagaaatat aggggctagg agttgagggt actctggttc     60

gtcaagcatt tgggatgatt tcccctcaca agttcctcaa attattctcc tataaacaat    120

agatataagg tcaaaacttg agttatgagt gctgagtaaa aaattactct ccacgcctca    180

gaggtagata tgttaatttt tatccttatc cactatcttt ccttttccaa gccagctcat    240

catacttcta agtttagatc ccacctgctc gatgggatgg ttttcatcag ccctggtgag    300

ggcattaaat actggtctgc cagctttatt ttccagcatc cattcttttg caaattctcc    360

tgattgtatc tgtcttaaaa cttccctcat gttgtcttta acctggggat ctattaccac    420

aggccccctt gtgaggtcac catattgggc tgtgttgctt atggaatatc tcatgttgga    480

gataccacct tcatagagaa gatccactat cagttttacc tcatgcatac attcaaaata    540

agccatttct ggagcgtagc cagcctccac caatgtttca aaaccatatt taataagctg    600

tgtcaaacca ccacataaaa ccgcctgctc accgaaaaga tctgtttctg tttcctcttt    660

gaagtttgtt tcaagcacac ctgctctggc tccaccaatg gcagctgcgt atgacaaagc    720

cacctctctt gaatcaccgg aatagtcttg atgcacagcg atgaggcatg gtactccgcc    780

accctttgta tattctgctc ttacaagatg ccctggccct ttaggtgcaa tcattataac    840

gtttacgttt ttaggaggca ctatctgtcc aaaatggatg ttgaaaccgt gggcaaatgc    900

aagatatgtc ccctctttta tataaggggc aatctgctct ctgtaaagat ccccctgtat    960

ctcatcagga acgagtatca tgatgaggtc tgcccatttt gtggcctctg atatctccat   1020

aactttaagc ccggagcttt ccgctttttt ccaggaatca ccaccctttc ttagggcaac   1080

ggcaacgtca acaccactat ctttgaggtt attagaatgt ccataaccct gacttccgta   1140

accaactatg gccacctttt tctttttaat caattctaaa tttgcatcct tttcgtagta   1200

tactttcatt gaagtaagta ggaagcaggg agcaggggaa agaaaattga caactgtaca   1260

agattaatcg cgtctctgag caatgaccaa atacatctac ctccacggtt ttcttccagc   1320

cccctatctg cgaaagcaca agatattagc aagcgtttcg cccaaattca catacagcta   1380

acaatccctg atctcaatgc tggtgaattt tctcagttaa caatcacgcg ccaaattcaa   1440

caagttgccg caattttccc tgataattct gaaccaataa cgctgatagg ttctagttta   1500

ggcggtttaa ctgctgctta tctaggacag cgatatttac aagtacaacg cttagtttta   1560

ttagcgccag tttggttttt tatcccattg gttgcccaaa atgggtgaag aagctgtcac   1620

aagttggcaa caaacgatat aggttctctc ttctgccgtt a                        1661
```

<210> SEQ ID NO 107
<211> LENGTH: 2324
<212> TYPE: DNA
<213> ORGANISM: Artificial Sequence
<220> FEATURE:
<223> OTHER INFORMATION: Synthetic Construct- Sequence No. 107, Example 107: designer Anabaena PCC 7120 hox-promoter-controlled Dihydroxy-Acid Dehydratase DNA construct (2324 bp)

<400> SEQUENCE: 107

```
agaaaatctg gcaccacacc gcagaaatat aggggctagg agttgagggt actctggttc     60
```

```
gtcaagcatt tgggatgatt tcccctcaca agttcctcaa attattctcc tataaacaat    120
agatataagg tcaaaacttg agttatgagt gctgagtaaa aaattactct ccacgcctca    180
gaggtagata tgttataaat ccgttataca tccaaaagat gctgatgata ccagcttgct    240
atacttcctt aagcttccac tcacatttcg ctcgggcttt ataggagttt gctcctttcg    300
tttttcccat tcctcttcct ccatcaatac actaattgaa ttttccactg catctattct    360
gatgcggtcg ccattttcta cataagctaa tgcgccatta tcaaaagctt cgggtgaaat    420
gtgtcccact acaaaaccgt gagttcctcc tgagaacctt ccatctgtaa tgagggctac    480
tttctttccc aaacctgctc ccattatagc agcagttggc tttaacattt cgggcattcc    540
aggacctcct tttggccctt catatcgaat caccactaca tcaccttctt ttatctcgcc    600
tctggcaata ccatcattgg ccagaaattc accatcataa actctagcag ttccttcgaa    660
tatctctcct tcctttccgg tgattttagc aacagctcct ccaggtgcta aattgccttt    720
caatattcgc aaatgacctg agcttttgat tggatttttc acagagtgaa tgatgtcttg    780
cttttcgcct aaaccctgaa catctttata attttcagct aaagttttac ctgttatggt    840
catgcaatcg ccatgaagaa gtccttcccc caacatcatt ttcatcactg caggaatccc    900
gccattttga tgaagatctt ccatcaagta tttaccagaa ggctttaagt cggctagata    960
aggagtttcg gcactgattc gagcgaaatc ttccaatgtt aaatcgattt caaaagcatt   1020
ggcaacagct aataaatgta aaactgcatt ggtcgatcct cccaaaactg taatcaaccg   1080
tatggcgttt tcaaatgatt ttttagtgac gatatcccgt ggcttcaaat cattttcaat   1140
caatttttta atggctaaac cagcctctgc acattctttc cttttctcag cactttgagc   1200
gggattggaa gcaccataag gcaagcataa tcctaaggct tcaatagcgg atgccatcgt   1260
attggcagtg tacattcctc cacaggctcc aggacctggg catgcatttg ccactactcc   1320
cttaaaatct tcttcagaaa tagtgttggc ttgcttctta cctaaagctt caaaagcaga   1380
aaccacatct aatttttctc cattatggca acctggagca atggttcctc cataaattat   1440
gagtgaaggt cgattcaatc tgcccatagc cagtaaggcg cctggcatat ttttatcgca   1500
tcccgtaata gcaatcatgg catcgtaagc ttgcgcattc actaccgttt ccatggaatc   1560
ggctatgata tcgcgggaag gcaatgaata gcgcattccg ttggtaccca tagaaatacc   1620
atcgcttact ccaatagtat tgaaaatcaa ccctacccac tcataagatt tgatgctttt   1680
cttgacctct acagccaaat cattcaaatg catattacat ggattgccct caaaaccagt   1740
gcttgcaata cctatttgtg gtttttccaa atcttcatca gacaaaccaa tggcatgcaa   1800
catggcttga gcggcaggtt gtgtaggatc ttgtgtaact gctttactat atggatttaa   1860
ttccttcgcc attgaagtaa gtaggaagca gggagcaggg gaaagaaaat tgacaactgt   1920
acaagattaa tcgcgtctct gagcaatgac caaatacatc tacctccacg gttttcttcc   1980
agccccctat ctgcgaaagc acaagatatt agcaagcgtt tcgcccaaat tcacatacag   2040
ctaacaatcc ctgatctcaa tgctggtgaa ttttctcagt taacaatcac gcgccaaatt   2100
caacaagttg ccgcaatttt ccctgataat tctgaaccaa taacgctgat aggttctagt   2160
ttaggcggtt taactgctgc ttatctagga cagcgatatt tacaagtaca acgcttagtt   2220
ttattagcgc cagtttggtt ttttatccca ttggttgccc aaaatgggtg aagaagctgt   2280
cacaagttgg caacaaacga tataggttct ctcttctgcc gtta                    2324
```

<210> SEQ ID NO 108

<211> LENGTH: 2288
<212> TYPE: DNA
<213> ORGANISM: Artificial Sequence
<220> FEATURE:
<223> OTHER INFORMATION: Synthetic Construct- Sequence No. 108, Example 108: designer Anabaena PCC 7120 hox-promoter-controlled branched-chain alpha-Ketoacid Decarboxylase DNA construct (2288 bp)

<400> SEQUENCE: 108

```
agaaaatctg gcaccacacc gcagaaatat aggggctagg agttgagggt actctggttc     60

gtcaagcatt tgggatgatt tcccctcaca agttcctcaa attattctcc tataaacaat    120

agatataagg tcaaaacttg agttatgagt gctgagtaaa aaattactct ccacgcctca    180

gaggtagata tgatgtatac agtaggagat tacctgttag accgattaca cgagttggga    240

attgaagaaa tttttggagt tcctggtgac tataacttac aatttttaga tcaaattatt    300

tcacgcgaag atatgaaatg gattggaaat gctaatgaat taaatgcttc ttatatggct    360

gatggttatg ctcgtactaa aaaagctgcc gcatttctca ccacatttgg agtcggcgaa    420

ttgagtgcga tcaatggact ggcaggaagt tatgccgaaa atttaccagt agtagaaatt    480

gttggttcac caacttcaaa agtacaaaat gacggaaaat ttgtccatca tacactagca    540

gatggtgatt ttaaacactt tatgaagatg catgaacctg ttacagcagc gcggacttta    600

ctgacagcag aaaatgccac atatgaaatt gaccgagtac tttctcaatt actaaaagaa    660

agaaaaccag tctatattaa cttaccagtc gatgttgctg cagcaaaagc agagaagcct    720

gcattatctt tagaaaaaga aagctctaca acaaatacaa ctgaacaagt gattttgagt    780

aagattgaag aaagtttgaa aaatgcccaa aaaccagtag tgattgcagg acacgaagta    840

attagttttg gtttagaaaa aacggtaact cagtttgttt cagaaacaaa actaccgatt    900

acgacactaa attttggtaa aagtgctgtt gatgaatctt tgccctcatt tttaggaata    960

tataacggga aactttcaga aatcagtctt aaaaatttg tggagtccgc agactttatc    1020

ctaatgcttg gagtgaagct tacggactcc tcaacaggtg cattcacaca tcatttagat   1080

gaaaataaaa tgatttcact aaacatagat gaaggaataa ttttcaataa agtggtagaa   1140

gattttgatt ttagagcagt ggtttcttct ttatcagaat taaaaggaat agaatatgaa   1200

ggacaatata ttgataagca atatgaagaa tttattccat caagtgctcc cttatcacaa   1260

gaccgtctat ggcaggcagt tgaaagtttg actcaaagca atgaaacaat cgttgctgaa   1320

caaggaacct catttttttgg agcttcaaca attttcttaa aatcaaatag tcgttttatt   1380

ggacaacctt tatggggttc tattggatat actttttccag cggctttagg aagccaaatt   1440

gcggataaag agagcagaca ccttttattt attggtgatg gttcacttca acttaccgta   1500

caagaattag gactatcaat cagagaaaaa ctcaatccaa tttgttttat cataaataat   1560

gatggttata cagttgaaag agaaatccac ggacctactc aaagttataa cgacattcca   1620

atgtggaatt actcgaaatt accagaaaca tttggagcaa cagaagatcg tgtagtatca   1680

aaaattgtta gaacagagaa tgaatttgtg tctgtcatga aagaagccca agcagatgtc   1740

aatagaatgt attggataga actagttttg gaaaaagaag atgcgccaaa attactgaaa   1800

aaaatgggta aattatttgc tgagcaaaat aaatagtgaa gtaagtagga agcagggagc   1860

aggggaaaga aaattgacaa ctgtacaaga ttaatcgcgt ctctgagcaa tgaccaaata   1920

catctacctc cacggttttc ttccagcccc ctatctgcga aagcacaaga tattagcaag   1980

cgtttcgccc aaattcacat acagctaaca atccctgatc tcaatgctgg tgaattttct   2040
```

```
cagttaacaa tcacgcgcca aattcaacaa gttgccgcaa ttttccctga taattctgaa   2100

ccaataacgc tgataggttc tagtttaggc ggtttaactg ctgcttatct aggacagcga   2160

tatttacaag tacaacgctt agttttatta gcgccagttt ggtttttat cccattggtt    2220

gcccaaaatg ggtgaagaag ctgtcacaag ttggcaacaa acgatatagg ttctctcttc   2280

tgccgtta                                                              2288


<210> SEQ ID NO 109
<211> LENGTH: 1613
<212> TYPE: DNA
<213> ORGANISM: Artificial Sequence
<220> FEATURE:
<223> OTHER INFORMATION: Synthetic Construct- Sequence No. 109,
      Example 109:  designer Anabaena PCC 7120 hox-promoter-controlled
      2-Methylbutyraldehyde Reductase DNA construct (1613 bp)

<400> SEQUENCE: 109

agaaaatctg gcaccacacc gcagaaatat aggggctagg agttgagggt actctggttc     60

gtcaagcatt tgggatgatt tcccctcaca agttcctcaa attattctcc tataaacaat    120

agatataagg tcaaaacttg agttatgagt gctgagtaaa aaattactct ccacgcctca    180

gaggtagata tgatggcttc tgtaaatgac tactttgaga acgccaagac gacgtacttt    240

actttgagat cgggtgacaa gatccccgct gttggattgg gtacttggca atcacccacc    300

aacgagacta aagaggcagt caagtacgct ttgcagcacg gttaccgtca catcgatgct    360

gccgccattt atggtaacga agacgaggtt ggtgacggta tcaaggagag tggaatccct    420

cgtgaccaaa tctgggtcac atctaagctc tggtgcaatg ctcatgctcc cgaggctgtc    480

cccaaggctt tggagaagac cttgcgtgag ctgaaacttg attaccttga cctttacctc    540

atccactggc ctatttcttt gaagaccggc gatgacttgg ttcccaagga caaggacggc    600

aacaccatca ctgtcgaaat tcccctcgag gacacctgga aggctatgga gggtcttgtg    660

aagtccggca aggtgaagaa cattggtatt tccaatttca acaacgaaga gttggatcgt    720

attttgaagg ttgccgagat tcctcctgcc gtccaccaaa tggaaactca tccttacttg    780

aagcagacgg agttcattga gaagcacaag aagcttggca ttcacgtcac cgcttactcg    840

cctttggcca accaaaatgc tctttacggc aatgccgttc ccaagttgat tgagcacaag    900

actcttgtcg acattgccaa gaccaagggt gagggcgtca ctggtgccaa cattgctatt    960

tcttgggcag tcaagcgcgg tacttcggtt attcctaagt ctgttcatgc caacagaatt   1020

aagagcaact tcctcgttgt tcccttgact gatgacgaga tgaaggccat cgataacatt   1080

ggtgtcagca agcgtttcaa ttggagcaaa gttttctgca atgagaattg tttctacggt   1140

cttgaggatg gtcctcagta atgaagtaag taggaagcag ggagcagggg aaagaaaatt   1200

gacaactgta caagattaat cgcgtctctg agcaatgacc aaatacatct acctccacgg   1260

ttttcttcca gcccccctatc tgcgaaagca caagatatta gcaagcgttt cgcccaaatt  1320

cacatacagc taacaatccc tgatctcaat gctggtgaat ttctcagtt aacaatcacg    1380

cgccaaattc aacaagttgc cgcaattttc cctgataatt ctgaaccaat aacgctgata   1440

ggttctagtt taggcggttt aactgctgct tatctaggac agcgatattt acaagtacaa   1500

cgcttagttt tattagcgcc agtttggttt tttatcccat tggttgccca aaatgggtga   1560

agaagctgtc acaagttggc aacaaacgat ataggttctc tcttctgccg tta           1613


<210> SEQ ID NO 110
<211> LENGTH: 1300
```

<212> TYPE: DNA
<213> ORGANISM: Artificial Sequence
<220> FEATURE:
<223> OTHER INFORMATION: Synthetic Construct- Sequence No. 110,
      Example 110: designer Prochlorococcus marinus MIT9313 groE-
      promoter-controlled NAD-dependent Glyceraldehyde-3-Phosphate
      Dehydrogenase DNA construct (1300 bp)

<400> SEQUENCE: 110
agaaaatctg gcaccacacc ccctttcaga gcggcgcaac attaccactg catggcgaga 60
tcttctcagg gttcggtgac ccgcacaggt atccactagt cggcacagca tcaacacaca 120
tagggttggc actcaatggc cacgagtgct actcatgtta tgccaagccg actttacgaa 180
ccaattccgc ggtgcgcgtg gcgtaaccca tttcgttgtc ataccaagtg tagattttca 240
ccattcgctt accaaccacc atggtggaga gcgcatccac aattgttgaa cgttgatcgc 300
cttggtaatc aatcgacacc agtggacgct cttcaaaacc cagaatgcct ttaagctcgt 360
tttctgaggc ttgttttaac agctgattga tctcttccac cgtcgtatca cgctgcacat 420
caaaaatgat gtcggttaac gaggcattcg ccaacggtac acgtacggcg tgtccatcaa 480
tcttgccttt cagatccggg aaaatttcga taatcgcttt agcagagccg gtggttgtgg 540
ggatgaggct cataccgcaa gcacgtgcac ggcgtaaatc tttatgcggt gcatccaaaa 600
tggtttgcgt attggttagg ttatggatgg tagtaaaaga ggcttgtgcg atacccagtt 660
tttcatggat tactttcacc actggagcaa tacagttagt ggtacaagaa gcggcagtga 720
caatgcgatg ttgctccgga ttgaagatgt gatcgttcac cccgaccacg atattggcga 780
tcccctcttc tttgacaggc gctgaaacga cgacgcgttt tactccttgt gccaaatact 840
ggttcaagaa ttcgccttta cggtgcttac ccgtagcctc aatcaccaca tcacagcccg 900
accaatccac tgcatcaatc gatttttctt gtgttgtgcg aatgcgtttg ccgttgatca 960
ggatagcatc cgcttcactg cccacagcat gatgccaacg accttgtacc gaatcgaact 1020
ccaaaaggtg cgctaatgtt gcagcatcac ccgccacatc gttgatctgt acaaactcaa 1080
tctcaggcca atcaaacgaa gctcttaaag ccaaacgccc aatacgacca aatccattaa 1140
ttccgacttt aattgccatt gatttagttt cggtgtctat ctcttaatag cctcgattta 1200
ttttcggggc tattaatcaa ctctcagagg cgacaagctt cttcttccct tacgacgttt 1260
ttattggttg gacatggcaa ggttctctct tctgccgtta 1300

<210> SEQ ID NO 111
<211> LENGTH: 1498
<212> TYPE: DNA
<213> ORGANISM: Artificial Sequence
<220> FEATURE:
<223> OTHER INFORMATION: Synthetic Construct- Sequence No. 111,
      Example 111: designer Prochlorococcus marinus MIT9313 groE-
      promoter-controlled Phosphoglycerate Mutase DNA construct
      (1498 bp)

<400> SEQUENCE: 111
agaaaatctg gcaccacacc ccctttcaga gcggcgcaac attaccactg catggcgaga 60
tcttctcagg gttcggtgac ccgcacaggt atccactagt cggcacagca tcaacacaca 120
tagggttggc actcaatggc cacgagtgct actcatgaaa tatgtaatct tacttggcga 180
cggcatggcc gacgaaaaaa ttgccgaact ggacggcaaa acgcctcttc aatacgccag 240
cacacccaat atggacaggc tggcggcagg cggggaaacc ggcatggtac ataccgtccc 300
ggatggattt ccgcctggca gcgatgtagc caacctctcg gtaatggggt acaatccgcg 360

```
ggaatattat accgggcgtt ctccgctgga agcggtaagc atgggggttg aactttcaga    420

tgacgatgta gccttccgct gcaacctggt taccctgtca gaagaagagg tatatgaaaa    480

caagattatg gtggattaca gctcggacga aattaccacc tctgaatcgc atgaactgat    540

cagggaagtc gccaaccgcc tgggcagtaa agagttgcgc ttttacccgg gtttcggatt    600

tagacacctt cttgtatgga aaacagggcc tgttggcggg aagctaacac caccccacga    660

tatctcgggg cgtaccattg ccccatacct ccccaaaggc gagggtagcg acactttaaa    720

gcggttaatg aaagaaagca acaggttcct gccagagcac ccggttaacc aaaaaagggt    780

aagggccggt cttaggcctg ccacttccat ctggttctgg ggacagggaa agaaaccctc    840

gataccgaag ttctacgaca aatacggggt aaccggctct gttatctctg ccgtggacct    900

gattaagggg attggcatct gtgccggctt cgatatagtt aaggtggagg gtgtaacggg    960

caccatccat accaacttcc gggggaaagt gcaggccgcc ctggaagaac tgaaaaaggg   1020

aaaggacctg gtctacattc acgttgaggc tccggacgca gcaagccaca ggggtgaaac   1080

tgttaccaaa gttaaagcta ttgaaatggt ggacaacatg ctgggccagc ttttaaacaa   1140

actggacgaa ttcggcatgt acaaaataat gctcttgccc gatcatccaa ccccgctcag   1200

cactaaaacc cactctaaca gccctgtccc ctttgttatc tatgccaagg ggcggaaaaa   1260

taaaagcgcc gcttcttttg acgaagaaac ggcggcaaaa agcggacttg ttttccgggc   1320

gggccatgag ttaatggatt actttatccg cagctaatga tttagtttcg gtgtctatct   1380

cttaatagcc tcgatttatt ttcggggcta ttaatcaact ctcagaggcg acaagcttct   1440

tcttccctta cgacgttttt attggttgga catggcaagg ttctctcttc tgccgtta     1498
```

<210> SEQ ID NO 112
<211> LENGTH: 1588
<212> TYPE: DNA
<213> ORGANISM: Artificial Sequence
<220> FEATURE:
<223> OTHER INFORMATION: Synthetic Construct- Sequence No. 112, Example 112: designer Prochlorococcus marinus MIT9313 groE-promoter-controlled Enolase DNA construct (1588 bp)

<400> SEQUENCE: 112

```
agaaaatctg gcaccacacc ccctttcaga gcggcgcaac attaccactg catggcgaga     60

tcttctcagg gttcggtgac ccgcacaggt atccactagt cggcacagca tcaacacaca    120

tagggttggc actcaatggc cacgagtgct actcatggtg tacgtggaaa tcgtggatgt    180

aagagcaaga gaggtcctgg attcgagagg aaatcccacc gttgaagcgg aagtcgtgct    240

tgaagacgga acaatgggaa gagccatcgt gccctctggt gcctccactg gaaaattcga    300

agccctggaa atcagagaca aagacaagaa gagatacctc gggaagggtg ttctgaaggc    360

cgtagagaac gtgaacgaaa ccatagctcc cgcgctgatt ggaatgaacg cattcgacca    420

gccactcgtt gacaagacac tgatagaact ggatggcaca gagaacaaat ctaaactggg    480

tgccaacgct atactcgccg tttctatggc agttgccaga gcggcggcga attacctcgg    540

attgcccctc tacaaatacc ttggaggagt caacgcaaag gttctgccag tacctttgat    600

gaacgtgatc aacggtggac agcacgcaga caacaatctt gaccttcagg aattcatgat    660

cgttcccgcc ggatttgaca gcttcagaga agctttgagg gcaggagcgg aaatattcca    720

cacgttgaaa aagatactcc acgaagccgg tcacgtgaca gcagtaggag acgagggtgg    780

attcgcaccc aatctgtctt ccaacgaaga agccataaag gttctgattg aagccataga    840

gaaagctggc tacaagcccg gagaagaagt cttcatagct cttgattgcg cagcatcttc    900
```

```
cttctacgat gaggaaaagg gagtttacta cgtcgatggt gaagaaaaat ccagcgaagt     960
tctcatggga tactacgaag aactggtggc gaagtacccc atcatatcca tcgaagatcc    1020
gttcgcggag gaagactggg atgcatttgt ggaattcaca aagagagtag gaaacaaggt    1080
tcagatcgtt ggagatgacc tttacgtgac caacgtgaaa agactttcca aaggaataga    1140
actcaaagcg accaactcca tactcatcaa actcaatcag ataggcaccg tcacggaaac    1200
tctcgacgcg gtggagatgg cacagaagaa caacatgaca gccatcattt cccacagatc    1260
tggagagagt gaagacacgt tcattgcgga tctcgctgtg gcaacgaacg ctggtttcat    1320
caagacaggt tccctctcca gaagcgaaag gatagccaag tacaaccagc ttttgagaat    1380
cgaggaagaa ctcggaaaag tggcagaatt cagaggtttg aaatctttct actctataaa    1440
gagataatga tttagtttcg gtgtctatct cttaatagcc tcgatttatt ttcggggcta    1500
ttaatcaact ctcagaggcg acaagcttct tcttccctta cgacgttttt attggttgga    1560
catggcaagg ttctctcttc tgccgtta                                       1588
```

<210> SEQ ID NO 113
<211> LENGTH: 1717
<212> TYPE: DNA
<213> ORGANISM: Artificial Sequence
<220> FEATURE:
<223> OTHER INFORMATION: Synthetic Construct- Sequence No. 113, Example 113: designer Prochlorococcus marinus MIT9313 groE-promoter-controlled Pyruvate Kinase DNA construct (1717 bp)

<400> SEQUENCE: 113

```
agaaaatctg gcaccacacc ccctttcaga gcggcgcaac attaccactg catggcgaga      60
tcttctcagg gttcggtgac ccgcacaggt atccactagt cggcacagca tcaacacaca     120
tagggttggc actcaatggc cacgagtgct actcatgatg agaaaaacca agcttatatg     180
ttcgatagga cctaaaaccg agaaaccaga gaaaataaag gaattgctaa aaagaggggt     240
aaatgctttt aggataagcg cagttcatta cacgatggaa aaaatcacag agctggtaga     300
gctaatcaaa gatattagat atgaactcaa aatgcctgtt tccatcattc ttgatttacc     360
aggttgcaaa ctccggacgg gagatcagaa agaagaaatc atcgaactta gacaaggtga     420
aaaagtgact gtaacaagcg aaaaaacttt ttcttctcgg gatactataa gcataaattt     480
ttccggacca tttcagggtg taaaaaccgg cgatttaatc ctcgtagatg atggaaaaat     540
acaactcaga gtggaaagaa tttctccaaa aaaagtagaa tgcgtcgtgg agataggagg     600
aattttgaag aaaaacagtg gcgtcaattt tcccaattct gatctacctg tcgaagtacc     660
aacagaagaa gatattaaga tcatagctga aactgtcaat atgggactgg actattactg     720
tgtatcattt gcaagaaacg caaaagatgt tcaaaaaatc aaaaaacatc ttgaatcttt     780
cgattcaagt gcgaaaattc ttacgaaaat agaaacaaaa aaatccatag aaacgctgga     840
agatatatgt cgcgtgagcg atggaataat cgtagcaaga ggagatttag cggtggagac     900
atctctgata gatttgccga tattgcaaaa aaagataata aataccgcat caaattataa     960
aatacctgtg atcgtcgcaa ccgaaatact caattctatg atcaacagtt catcaccaac    1020
aagggttgaa ataatggatg ttgcaaacat agttttagat ggagcagatg ctatactgct    1080
aacctctgaa acagctgtgg ggaactttcc gatcgaaaca gttgaaaaaa ttaatgagat    1140
tgttgaaaat gttgagaact acctacccga aatcaatgct cattttaaag aacgcaggtt    1200
tgaaaaaatc gaagatccat ctgaagctat tgcaaggagt agttactaca tttctgaaga    1260
```

aataaatgcc aaagctataa taatatcaac agcttctgga agcactgcaa gaagggtggc 1320
ctatttcaag ccacttcgtc ctatcatagc tacgacccca gatgaaaaca cctttcatca 1380
gttgtctatt gtttggggga tagttccgat gctaattcca gaagtccatt ccacagatat 1440
aatgatccac gtggccgtcg agaaggttaa agctgtcgga tatgttcaaa attccgacat 1500
tgtggttgtt acttctggtg ctccgtgtgg tattgttgga acaactaaca tgctcaaagt 1560
tcacatagtt gagtagtgat ttagtttcgg tgtctatctc ttaatagcct cgatttattt 1620
tcggggctat taatcaactc tcagaggcga caagcttctt cttcccttac gacgttttta 1680
ttggttggac atggcaaggt tctctcttct gccgtta 1717

<210> SEQ ID NO 114
<211> LENGTH: 2017
<212> TYPE: DNA
<213> ORGANISM: Artificial Sequence
<220> FEATURE:
<223> OTHER INFORMATION: Synthetic Construct- Sequence No. 114, Example 114: designer Prochlorococcus marinus MIT9313 groE-promoter-controlled Acetolactate Synthase DNA construct (2017 bp)

<400> SEQUENCE: 114
agaaaatctg gcaccacacc ccctttcaga gcggcgcaac attaccactg catggcgaga 60
tcttctcagg gttcggtgac ccgcacaggt atccactagt cggcacagca tcaacacaca 120
tagggttggc actcaatggc cacgagtgct actcatgtca agattgctta gaggcttctt 180
tattaaaatg ttcctcaaat ttttttggaa aacgctgatc ggccaaatga atgttgtcgc 240
tgtaatcgac cggaatatca atgacaacag gcccctctgc atcaagacca gctttaagca 300
cctctgccaa ttcgtcaggt gaattgaccc ttaaaccttt tgcaccaaag ctttcagcat 360
attttacaat atcgattccg ccgaagtcga ctccggacgt ccgcttgtat ttcatctcct 420
gctggaacgc aaccatatcg tatgtgctgt cattccagac aatgtgaacg atcggcgctt 480
ttaatctgac cgctgtctca agctccatcg cggagaacag gaagccccccg tccccggaaa 540 cagacacgac tttctgtccc ggattgacca gcgttgctgc aatcgcccac ggcaaagcca 600
ccccaagcgt ctgcatgccg ttggaaatca gcagtccatg cggacggtag gtgcggaaat 660
atctagacat ccaaatcgca tgggagccga tgtcgcaagt caccgttatg tcatcgctca 720
gcagttcacg caaatcgcga acgatttgca gcggatgaac aagatcagtt tttgtttctt 780
taggaggttc gctttgctcc tccagtgctt tcttcaagta atcaaggaca ggtgcaaagg 840
actcgtcgat ggaaaccggc agagaatcat gttcaatatg gtttaacgtc tctgcgatat 900
cgccgatcaa ctcgatttcg ggctgatagt catgatcgat atcggcttgt atttcgtcaa 960
gatgaatcac gcttcgttcg ccttttccat tccaaaagac cggatcgtat tcaatcggat 1020
catagccgac cgtcaaaacg acatccgctt tttccaatag catgtctccg ggctgattgc 1080
ggaatagtcc gatccggccg aagtactggt cttccaaatc gtgagacagc gtacccgctg 1140
cttggtatgt ttcaacaaac ggcagtttca ctttccttag cagacgccga accgcttcaa 1200
tcgcttcagg tcttccgcct ttcatcccga caagcacgac aggaaggttc gcattgtgaa 1260
ttttggcgat ggccgcgctg atttgttcgt ccgaagccgc gcccagcttc ggcgccggca 1320
tggttttcac cggcttggca gttgccggac cggccgtaac gtcctgcgga aagctgagaa 1380
acgctgcgcc agcctgtcca gaagccgccg ctctgaatgc attggttaca gcctcaggta 1440
tgttgttcgc atcttccact tctgcgctat atttcgtaat cggctgaaac aacgccgcat 1500

-continued

```
tatccatcga ttgatgagtt tttttgagac gatccgctct ttttacagca cccgccaggg   1560

caacaaccgg atctccttct gtattggctg ttacaagacc ggtcgctaaa ttagacgctc   1620

ccggacctga agtcaccagg caaacaccgg gctttccagt caatcgtccg actgccgccg   1680

ccataaatgc tgcattctgc tcgtgacggc aaacgatcaa ttcaggcccc ttgtctttca   1740

atacgtcaaa caccgcatcg attttcgctc ccggaatacc gaaaacatga gtgacacctt   1800

gctgaatgag actatccacc acaagctctg ctcctcttac agtaagagtt tcatttttag   1860

cggctacatt attcaatgat ttagtttcgg tgtctatctc ttaatagcct cgatttattt   1920

tcggggctat taatcaactc tcagaggcga caagcttctt cttcccttac gacgttttta   1980

ttggttggac atggcaaggt tctctcttct gccgtta                             2017
```

<210> SEQ ID NO 115
<211> LENGTH: 1588
<212> TYPE: DNA
<213> ORGANISM: Artificial Sequence
<220> FEATURE:
<223> OTHER INFORMATION: Synthetic Construct- Sequence No. 115, Example 115: designer Prochlorococcus marinus MIT9313 groE-promoter-controlled Ketol-Acid Reductoisomerase DNA construct (1588 bp)

<400> SEQUENCE: 115

```
agaaaatctg gcaccacacc ccctttcaga gcggcgcaac attaccactg catggcgaga     60

tcttctcagg gttcggtgac ccgcacaggt atccactagt cggcacagca tcaacacaca    120

tagggttggc actcaatggc cacgagtgct actcatgtca ctcctcatcc acgttcctct    180

ccttgagcca aggcatcatt tttctgagtt cttttcctac tttttctatg agatgctctg    240

attctttctt tctcatggtg tagaagtagg gtcttcccgc ctgattttcg agtatccagt    300

ccttggcgaa ctttcccgtc tgaatgtcct tgagcatctg cttcatgttc tccctcactt    360

cttttgtaac gatcttttcc tgactgatgt agtcaccgta ctccgcggtg ttgctgacgg    420

agtatctcat gaaagagaga ccaccctcgt agatgaggtc aacgatgagc ttgagctcat    480

tgagacactc aaagtaagct atttccggtt gataacccgc ctccacaaga gtttcgaaac    540

cagcttttat gagagccgtt actccaccac agaggaccgc ctgctctcca aacaaatccg    600

tttccgtctc ttccttgaag gtcgtctcta tcacacccgc ccttgtcaca ccgatacctt    660

tggcataagc gagcgctata tctttggctt taccggtgta gtcctgatag accgctacga    720

gagccggcac acccccttcct tcgacgtatt ctcttctcac gatgtgacca gggctcttcg    780

gagcgatcat cgtcacatcc acgttcttcg gaggtatgat ctggtgatag tggatgttga    840

acccgtgggc gaacatcagc atcttaccct cggtgaggtg tttttctatg tatttttttgt    900

agatctccgg ctggttctca tctgggatga gcatcatgat gatgtcggcc tcttttgccg    960

cttcttctat tgctttcacg gtgagaccct gttcctccgc cttcttccag ctcttgcttc   1020

cctctctcaa tccgaccaca acgttgagac cgctgtcttt cagattcaac gcgtgcgcat   1080

gcccctgact tccgtaccct atgatcgcga tctttttgtc cctgatcagt tcgagatccg   1140

cgtctttgtc ataataaatc actgccattg atttagtttc ggtgtctatc tcttaatagc   1200

ctcgatttat tttcggggct attaatcaac tctcagaggc gacaagcttc ttcttccctt   1260

acgacgtttt tattggttgg acatggcaaa acaatccagt cgagagctag cgcttgaacg   1320

ccgtaaggcc ctgagtaatt caggtaagaa atcaaccaca ttaaatggat caagtcctaa   1380

tcgcatccgt actgcctctg atgcacgtct aaccaggact gatcaatctt tcgttaaggc   1440
```

```
tgggaaagaa tctgtgcagc taaccgctcc taagagagag caactagata cgtcttttgt   1500

tgcttctaga gaatcatccg gagcttcgcg ccgtcaagtg aaaacgatcc gaaattcaag   1560

cagagaatgg ttctctcttc tgccgtta                                       1588


<210> SEQ ID NO 116
<211> LENGTH: 1960
<212> TYPE: DNA
<213> ORGANISM: Artificial Sequence
<220> FEATURE:
<223> OTHER INFORMATION: Synthetic Construct- Sequence No. 116,
      Example 116: designer Prochlorococcus marinus MIT9313 groE-
      promoter-controlled Dihydroxy-Acid Dehydratase DNA construct
      (1960 bp)

<400> SEQUENCE: 116

agaaaatctg gcaccacacc ccctttcaga gcggcgcaac attaccactg catggcgaga     60

tcttctcagg gttcggtgac ccgcacaggt atccactagt cggcacagca tcaacacaca    120

tagggttggc actcaatggc cacgagtgct actcatgcta atctttcaag atagcgcctg    180

tactggcgga ttgcaccatt tttgaatatc ttttcatata gcctgagttt atcttgggtt    240

ccggaactcg ccactgcgtt ctcctggcag caagttcctc gtcgctaagt cgtacactaa    300

ggctgtggtt cggtatatca atgacgatta tgtctccgtc ctgaataaga gcaatattgc    360

ccccttgtgc cgcctcggga gatacgtgcc ctatagaagc tccccgggta gcaccagaaa    420

aacggccatc ggttataagg gctacgtcct tgtctagccc catccccgct atagcagaag    480

taggcgtgag catttccctc atccctggcc ctccgcgcgg cccttcatac cggattacga    540

cgacttctcc tttttcaatc ttgcctccta gaatggctgc aacagcttct tcttccgagt    600

cgaaaacccg tgctttaccc tcgtgataga gcatgtccgg gtcaactgcc cccttcttca    660

ccaccgcgcc ctcctcggcc aggttaccga acagtatagc caaccccccg gtagtactgt    720

gcggattctc tatactacgg atgacctcgt ggtccttcac agggtagtca ttgataacct    780

ccccaaccgt cttaccagta accgtcaggc actggcggtt taccagccct gccttgtcta    840

actcgttgaa aatggcctga actccacccg cagcgtacaa gtcttctata aaatggttgc    900

cggcaggttc gattttacat aggtgaggag tggtatcgct gatatggttt atcaggttca    960

agtccagctt aacgccggct tcgtgagcga tagccataag atgcaaaacc gtattggtag   1020

aacaacctat tgccatgtcc aggcgtaagg cattgatgaa agcctcttgg gtcatgatat   1080

cccggggctt tatgtccctt tcccatagct ccatcacttt catgcccgcc tgtttggcta   1140

gacggattcg ttcagagtgt accgccggta tagttccgtt cccgggtaag cccattccta   1200

ccgcttccgt caggcagttc atggaattag cggtaaacat accggcacag ctgccacaac   1260

ccgggcaagc tacatcttca agctccgcta agtccgaaag cgacatctta cctgcgctga   1320

ccgcgcctac cccttcaaag accgtgttga ggctgacctt gcgcccccgg aaattgccag   1380

ccaacatcgg ccctccgctg acaaacatac aaggaagatt gaggcgagcg gccgccatca   1440

gcatcccagg gatgattttg tcgcagttag gtataaaaac cagggcatcg aaaggatgag   1500

ccatagccat tatctcaata gaatcggcaa tcagttcccg gctggccaga gagtatttca   1560

taccgatatg gttcatggca ataccatcgc ataccoctat agtagaaaac tctataggag   1620

tgccccottt catcctcacc ccggctttga ccgcctcggc tatacggtct agatgaatat   1680

gccctggaat aatctcgttg gccgagttga ctataccgac taagggtctc tccaactcct   1740

catcggtcaa tcctaaagct ttaaacagtg aacggtgagg tgctttttct agacccttt    1800
```

```
tcgccaggtc acttctcatt gatttagttt cggtgtctat ctcttaatag cctcgattta   1860

ttttcggggc tattaatcaa ctctcagagg cgacaagctt cttcttccct tacgacgttt   1920

ttattggttg gacatggcaa ggttctctct tctgccgtta                         1960
```

<210> SEQ ID NO 117
<211> LENGTH: 1945
<212> TYPE: DNA
<213> ORGANISM: Artificial Sequence
<220> FEATURE:
<223> OTHER INFORMATION: Synthetic Construct- Sequence No. 117, Example 117: designer Prochlorococcus marinus MIT9313 groE-promoter-controlled 2-Keto Acid Decarboxylase DNA construct (1945 bp)

<400> SEQUENCE: 117

```
agaaaatctg gcaccacacc ccctttcaga gcggcgcaac attaccactg catggcgaga     60

tcttctcagg gttcggtgac ccgcacaggt atccactagt cggcacagca tcaacacaca    120

tagggttggc actcaatggc cacgagtgct actcatgtta tgatttattt tgttcagcaa    180

atagtttacc catttttttc agtacttttg gtgcatcttc ttttgccaaa actaactcaa    240

tccagtacat tctatttgga tctgcttgag cttctttcat gacagacaca aattcatttt    300

cagttctaac gattttcgag actactcgtt cttctgttgc tccaaatgat tctggtaatt    360

ttgagtaatt ccacattgga atatcattgt agctttgatt tggtccatga atttctcttt    420

cgactgtata accatcatta ttgataataa agcaaattgg attaattttt tctctgattg    480

ctaatcctaa ttcttgcact gtaagttgaa gtgaaccatc accaataaat aaaaggtgtc    540

tgctttcttt atctgcaatt tggcttccta atgctgctgg gaatgtatat ccaattgatc    600

cccataaggg ttgaccaata aaatgactct ttggttttaa gaaaattgat gaagcgccaa    660

agaatgatgt cccttgttca gcaacgattg tttcattgct ttgagttagg ttttcaactg    720

cttgccatag gcggtcttgt gataaaagcg catttgatgg aacaaagtct tcttgctttt    780

tatcgatata ttttcctttg tattctattc cgcttaggtc taagagagag gagatgaggg    840

attcaaaatc aaaatttgg atgctttcgt taaatatttt tccttcgtct atgttcagtg    900

aaatcatttt attttcattt aaatgatggg taaatgctcc tgttgaagag tctgtgagtt    960

taactccaag catcaggatg aagtcggctg attccacgaa ttctttaaga ttaggctctg   1020

agagtttacc attatagatt cctaaaaatg aagggagagt ttcatcaact gaactttttc   1080

caaagtttaa tgtcgtaata gggagttttg tctttgaaat aaattgagtg actgtatttt   1140

ctaagccaaa gctaattatt tcatgtcctg taatcacgat tggtttttttg gcatttttca   1200

agctttcttg aattttattc aaaatctctt ggtcacttgt atttgaagtt ggattttctt   1260

ttttcaaagg gagtgagggt ttctctgctt ttgcagcagc aacatcaact ggtaagttga   1320

tatagacagg ttttctttct tttagtagtg cagaaagtac tcggtcaatt tcaacggttg   1380

cattttctgc tgtcagtaaa gttcgagctg ctgtaacagg ttcgtgcatt ttcataaagt   1440

gtttaaaatc accgtcagcc agcgtatgat gaacaaattt tccttcattt tggacttttg   1500

atgtaggtga tcccactatt tctactactg gtaaattttc ggcgtaactt cctgctaatc   1560

cattaactgc actcaattca cctactccaa aggttgtaag aaatgcggca gcttttttag   1620

tacgagcata gccatcagcc atataagaag catttaattc attagcattt ccgacccatt   1680

tcatatcctt gcgggaaata atttgatcta aaaattgtaa gttatagtct ccagggactc   1740

caaaaatttc ttcaattcct aactcgtgta atcggtctaa taggtaatct cctactgtat   1800
```

```
acattgattt agtttcggtg tctatctctt aatagcctcg atttattttc ggggctatta   1860

atcaactctc agaggcgaca agcttcttct tcccttacga cgtttttatt ggttggacat   1920

ggcaaggttc tctcttctgc cgtta                                         1945
```

<210> SEQ ID NO 118
<211> LENGTH: 1138
<212> TYPE: DNA
<213> ORGANISM: Artificial Sequence
<220> FEATURE:
<223> OTHER INFORMATION: Synthetic Construct- Sequence No. 118, Example 118: designer Prochlorococcus marinus MIT9313 nirA-promoter-controlled Alcohol Dehydrogenase DNA construct (1138 bp)

<400> SEQUENCE: 118

```
agaaaatctg gcaccacacc cctctagttg ccaacatcag ccgggttcag aatgtacaca     60

aagacaccaa ttcttgaatt tcacacaaat gctcagtttt gttcaatctg ataccgccaa    120

taccctcttc catcaggctt aatgactcca ttcgcaactt acccttgctt caataatggc    180

agggcctaaa aaccatggct atcgaatgcg cgaataaaat ttaaacaaca tgatcacttc    240

ttttcaagtt taatttcaac aaaatttcat gttgtcaccg gtggagcgaa tgggatcggc    300

aaggcgatcg ctagagcaat tcgcaaaaca gggagcgaac gtcgtgatca tcgaccgcga    360

tattcaaaac ggtgaagcgt tcgccgcgca attgcaatcg gacgggttcg aggcgatctt    420

tgtggcggcg gatgtgcgga aggtggacga tattgaacgg tttgtacaag aagctgccgg    480

ccgcttcggc cgcattgact atttgatcaa caatgctggc gtctcacgct ggaagtcgcc    540

gtatgagctg acggttgagg agtgggatga cgtgctgtca acgaatttgc gcagcgcttt    600

ttttgcttct cgagaagcag ctaaatatat gcgccgcaat gcaaaaggcg gagcaatcgt    660

caacattgcc tcgacaaggg cgctcatgtc cgagccgaat tccgaggcgt acgctgcatc    720

gaaaggcggc cttgtcgctt tgacccatgc gctggcggtg tcgtttgcgg atgatcgcat    780

tcgcgtcaat tgcatcagcc ccggttggat tgaaacgggc gattatgggc aactgcgaga    840

cattgaccac cggcagcacc cggccggccg cgtcggcaaa ccggatgata tcgcccgcgc    900

ttgtctgtat ttatgcgatg aggaaaacga ttttatcacc ggggtaaatt tggtcatcga    960

cgggggaatg accaggaaaa tgatttatat tgagtagtga tttagtttcg gtgtctatct   1020

cttaatagcc tcgatttatt ttcggggcta ttaatcaact ctcagaggcg acaagcttct   1080

tcttccctta cgacgttttt attggttgga catggcaagg ttctctcttc tgccgtta     1138
```

<210> SEQ ID NO 119
<211> LENGTH: 1816
<212> TYPE: DNA
<213> ORGANISM: Artificial Sequence
<220> FEATURE:
<223> OTHER INFORMATION: Synthetic Construct- Sequence No. 119, Example 119: designer Prochlorococcus marinus MIT9313 groE-promoter-controlled 2-Isopropylmalate Synthase DNA construct (1816 bp)

<400> SEQUENCE: 119

```
agaaaatctg gcaccacacc ccctttcaga gcggcgcaac attaccactg catggcgaga     60

tcttctcagg gttcggtgac ccgcacaggt atccactagt cggcacagca tcaacacaca    120

tagggttggc actcaatggc cacgagtgct actcatggtg agccagcgcg tttatatttt    180

tgacaccact ttgagggacg gcgagcagtc gcccggcgta agcctgaacg taggcgagaa    240

ggtgcaaatt gccaggcagt tagccaagct cggggtggac ataattgagg ccggctttcc    300
```

gattacctcg ccgggggact ttaaagccgt aagcgaaatt gcccggcagg tgaagggcgt 360
tacggtggcc gccctggcca gggccaactt ccaggatatc gaccgggcct gggaggccgt 420
gcgccacgcc gagcagccgc ggattcatac ctttattgcc acttccgaca ttcatttaaa 480
atacaagctg cgcatgagcc gggaggaagt cctggatgcg gcggtggcgg cggtaaagcg 540
cgccagggcc tacaccggcg atgtggagtt ttcggcggag gacgcctccc gctccgacct 600
ggacttcctc tgccgggtgc tggccgcggc cattgaggcg ggggctaccg taataaatat 660
accggatacg gtcggttatg ccgttcctga ggaatggggg aaatttatca atactattta 720
tcataaagtt cccggaattg aaaaggtcat tgtcagcgtg cactgccaca acgacctggg 780
catggccgtg gccaactccc ttgctgccgt aatgaacggc gccaggcagg tggaaggggc 840
catcaacggc attggcgagc gggcgggaaa cgctgccatc gaagagatgg taatggccct 900
ttatacccgt aaagatcagt acaaccttta caccaacatc aaaaccgagg aaatttacag 960
gaccagcaag ctggtgagcg ccctgacggg catgaaggtg cagccgaaca aggccgtggt 1020
gggcaaaaac gcctttgccc acgaggccgg cattcaccag gacggggtgc tgaaggagcg 1080
caccacctac gagataatga acccggccat ggtagggatc agcaagagca acctggtgct 1140
gggcaagcat tccgggcggc atgcattccg ccaccggctg gaggaaatgg gctacaatct 1200
ttcggacgaa gagctgaaca gcgcctttga gcgcttcaaa aagctggccg acaagaagat 1260
ggagattacc gacgaagacc tggaagccat tatagaagaa gaaatgcgcc ttgtgccgca 1320
cacctacacc cttgagtacc tgcatatttc cagcggcacc acggtggtgc ctaccgccac 1380
ggtgggctta aagcgggacg ggcagcttat ggaagaggcg gcctgcggca acggcccggt 1440
ggacgccatc tgcaaggcaa ttgataaaat aacggggctt aactgcacca tgacgagctg 1500
gggaatcaac gccgtcactg cgggcaagga cgcccttggc gacgtcagcc tgaaggtgac 1560
cgccgacggc gagaaggttt acgttgggcg cggaatcagc accgatgtgc tggaggccag 1620
cgccaaagct tacgtcaacg cggtcaacaa actcatctgg gattcgcaga aataatgatt 1680
tagtttcggt gtctatctct taatagcctc gatttatttt cggggctatt aatcaactct 1740
cagaggcgac aagcttcttc ttcccttacg acgtttttat tggttggaca tggcaaggtt 1800
ctctcttctg ccgtta 1816

<210> SEQ ID NO 120
<211> LENGTH: 2199
<212> TYPE: DNA
<213> ORGANISM: Artificial Sequence
<220> FEATURE:
<223> OTHER INFORMATION: Synthetic Construct- Sequence No. 120, Example 120: designer Prochlorococcus marinus MIT9313 groE-promoter-controlled 3-Isopropylmalate Dehydratase DNA construct (2199 bp)

<400> SEQUENCE: 120
agaaaatctg gcaccacacc ccctttcaga gcggcgcaac attaccactg catggcgaga 60
tcttctcagg gttcggtgac ccgcacaggt atccactagt cggcacagca tcaacacaca 120
tagggttggc actcaatggc cacgagtgct actcatgatg gccatgacca taaccgaaaa 180
aattctggcc gatcacgccg gcaaaaagca ggttgagccc ggcgaactga tcagcgtaaa 240
ggttgatctg gtgctgggca acgacataac ggcgccggtg gcgattaaag agtttgagaa 300
aataggggtg gcggaagtct ttgaccggga gcgggtggcc ctggtcccgg atcactttac 360
ccctaacaag gacattaagt cggcggaaca gtctaaaatt ctaagggagt tttccaaaaa 420
gcacaacctt gccaactatt tcgaggtggg ccgggccggc attgagcact gccttctgcc 480
cgaggaaggg ctggtaggcc ccggcgacct ggttatcggc gccgactcgc acacctgcac 540
ctacggcgcc ctgggggcct tctccacggg cgtgggcagc accgacctgg cggctgccat 600
ggcgctgggg gaaacctggc tgaaagtgcc ggagtcaatc aaattcgaat atgacgggga 660
aatgcagccc tgggtaggcg gcaaggacat gatcctgcac acaatcgggg atatcggggt 720
ggacggggcc ctttacaagg ctatggagtt taccggcccg gccgttgaaa aactttccat 780
ggacgggcgc tttaccatgt gcaacatggc cgtagaggcc gggggtaaga acggcattat 840
tgctccggac gaaacaaccc gggtctatgt cgagggccgc tgcaagcgac cctatcgttt 900
ttatcggagc gacccggacg ccaaatacga aaagatctac cgctacgacg cggcgcagat 960
cgaaccgcag gtggcctttc cccacctgcc cgaaaactcc cggccggtca gcgaggcagg 1020
caacattgaa atcgatcagg ttgttatcgg ctcctgcacc aacggccgga tggaggacct 1080
gcgggaggcc gccagggtgc tgaagggcag aaaagtgcat aaaaacgtcc gccttattat 1140
ttttccggga acgccgaaaa tttacctgca ggccttgcgg gaggggctga tcgaaacttt 1200
tgtcgaagct ggcggagtcg tgagcacgcc cacctgcggg ccctgcctgg gcggccactc 1260
gggcattctg gccaggggag agcgctgcgt tgccaccacc aaccgcaact ttgtaggcag 1320
gatggggcat cctgaaagcg aagtgtacct gtccaacccg gcagttgccg cggcttcggc 1380
cgtgctgggc cggataggcg gtccatggga ggtggattga ccctttcaga gcggcgcaac 1440
attaccactg catggcgaga tcttctcagg gttcggtgac ccgcacaggt atccactagt 1500
cggcacagca tcaacacaca tagggttggc actcaatggc cacgagtgct actcatgatg 1560
gaaattaaag ggaaagtgtg gaagttcggc ccggatatcg atacagacgc cattataccg 1620
gcaaggtacc tcaacacctc cgacccggaa gaactggcca ggcactgcat ggaggatgcc 1680
gacccgtcct ttcccgcccg ggtcaggccc ggcgacgtga ttgtggccgg caagaatttc 1740
gggtgcggca gttcccggga gcacgccccc atagcaatca aggccgccgg ggtgtcgtgc 1800
gtgattgccg cgtcgtttgc gcggatcttc taccgcaacg ccttcaacat agggctgccc 1860
attttcgagt ctcccgaagc cgccgggggc attggccagg gcgacgaggt ggcggtggac 1920
gcggctgccg gcattataac cgacctgacc accggcaaga cctaccgggc ggcgccggtt 1980
ccgcctttca tgcggcagat cattgccgcc ggagggctga tcaattacgt ggccgggaag 2040
gtgagaggca atgcataatg atttagtttc ggtgtctatc tcttaatagc ctcgatttat 2100
tttcggggct attaatcaac tctcagaggc gacaagcttc ttcttccctt acgacgtttt 2160
tattggttgg acatggcaag gttctctctt ctgccgtta 2199

<210> SEQ ID NO 121
<211> LENGTH: 1378
<212> TYPE: DNA
<213> ORGANISM: Artificial Sequence
<220> FEATURE:
<223> OTHER INFORMATION: Synthetic Construct- Sequence No. 121, Example 121: designer Prochlorococcus marinus MIT9313 groE-promoter-controlled 3-Isopropylmalate Dehydrogenase DNA construct (1378 bp)

<400> SEQUENCE: 121
agaaaatctg gcaccacacc ccctttcaga gcggcgcaac attaccactg catggcgaga 60
tcttctcagg gttcggtgac ccgcacaggt atccactagt cggcacagca tcaacacaca 120
tagggttggc actcaatggc cacgagtgct actcatgcta cacctcgacc tcctcaactt 180

```
ttctcgctac taaatcaccc atttccctgg tgttaaccag cttctgatcc ggctccgtaa    240

tgtccggcgt ccggtagcct tcggccagaa cttcgcggac cgcctgctca accgccaaag    300

cctcttgttc caaatcgaac gaatacctca gcatcatggc agccgacagt atcgtagcca    360

acgggtttgc tttcccctgc ccggcgatat cgggagctga cccgtgagaa ggctcataca    420

ttcctacttt cccgccaata gaggcagaag gtagcattcc caaagatccg gtcagcatag    480

aggcttcgtc ggtcaatata tctccaaaca tgttttcagt tacgatcaca tcgaattgac    540

gcggattgcg tatgagctgc atggcacagt tgtcgacgta catgtggctg aattcgacgt    600

caggatactc cagagctact cgattggcca cctcgcgcca taacctagag ctttctagaa    660

cattggcctt gtccaccgat gtcactttct ttctccgttt cctcgccgcc tcgcaggcca    720

aacgaactat gcgttcgatc tcatacgtcg agtactccag aacatcgata gccctttctc    780

cgcccagaag cttctcccgc cgcttctccc cgaagtacaa cccgccggtc agttccctca    840

ctaccaagag atctactccc tcgataatat cgggtttcag ggaggaagca tgaaccagtt    900

ccgggaacag gtaagcgggc cgcaggttag cgtaaagccc aagttcctta cgcagagcca    960

acagcgctgc cgcctcgggc ctgagcgcag ccggcaggtt atcccatttg ggaccaccta   1020

tggctcctag aagaacagcg tcgctatctt tgcacagggc cagggtttct tcaggcaaag   1080

gaacccccac ctcgtcgata gccgctcccc cgaccagggc ttcggtaaaa gcgaattcgt   1140

gtttgaacct cttagcaact gctttcaata ctttttgcgc ttcaggtacg atctcggtcc   1200

cgataccatc cccgggtaac acggctatct taaacactga tttagtttcg gtgtctatct   1260

cttaatagcc tcgatttatt ttcggggcta ttaatcaact ctcagaggcg acaagcttct   1320

tcttccctta cgacgttttt attggttgga catggcaagg ttctctcttc tgccgtta     1378
```

```
<210> SEQ ID NO 122
<211> LENGTH: 1327
<212> TYPE: DNA
<213> ORGANISM: Artificial Sequence
<220> FEATURE:
<223> OTHER INFORMATION: Synthetic Construct- Sequence No. 122,
      Example 122: designer Prochlorococcus marinus MIT9313 groE-
      promoter-controlled 3-Methylbutanal Reductase DNA construct
      (1327 bp)

<400> SEQUENCE: 122

agaaaatctg gcaccacacc ccctttcaga gcggcgcaac attaccactg catggcgaga     60

tcttctcagg gttcggtgac ccgcacaggt atccactagt cggcacagca tcaacacaca    120

tagggttggc actcaatggc cacgagtgct actcatgatg tcagttttcg tttcaggtgc    180

taacgggttc attgcccaac acattgtcga tctcctgttg aaggaagact ataaggtcat    240

cggttctgcc agaagtcaag aaaaggccga gaatttaacg gaggcctttg gtaacaaccc    300

aaaattctcc atggaagttg tcccagacat atctaagctg gacgcatttg accatgtttt    360

ccaaaagcac ggcaaggata tcaagatagt tctacatacg gcctctccat tctgctttga    420

tatcactgac agtgaacgcg atttattaat tcctgctgtg aacggtgtta agggaattct    480

ccactcaatt aaaaaatacg ccgctgattc tgtagaacgt gtagttctca cctcttctta    540

tgcagctgtg ttcgatatgg caaaagaaaa cgataagtct ttaacattta acgaagaatc    600

ctggaaccca gctacctggg agagttgcca aagtgaccca gttaacgcct actgtggttc    660

taagaagttt gctgaaaaag cagcttggga atttctagag gagaatagag actctgtaaa    720

attcgaatta actgccgtta acccagttta cgtttttggt ccgcaaatgt ttgacaaaga    780
```

tgtgaaaaaa cacttgaaca catcttgcga actcgtcaac agcttgatgc atttatcacc 840
agaggacaag ataccggaac tatttggtgg atacattgat gttcgtgatg ttgcaaaggc 900
tcatttagtt gccttccaaa agagggaaac aattggtcaa agactaatcg tatcggaggc 960
cagatttact atgcaggatg ttctcgatat ccttaacgaa gacttccctg ttctaaaagg 1020
caatattcca gtggggaaac caggttctgg tgctacccat aacacccttg gtgctactct 1080
tgataataaa aagagtaaga aattgttagg tttcaagttc aggaacttga aagagaccat 1140
tgacgacact gcctcccaaa ttttaaaatt tgagggcaga atataatgat ttagtttcgg 1200
tgtctatctc ttaatagcct cgatttattt tcggggctat taatcaactc tcagaggcga 1260
caagcttctt cttcccttac gacgttttta ttggttggac atggcaaggt tctctcttct 1320
gccgtta 1327

<210> SEQ ID NO 123
<211> LENGTH: 2004
<212> TYPE: DNA
<213> ORGANISM: Artificial Sequence
<220> FEATURE:
<223> OTHER INFORMATION: Synthetic Construct- Sequence No. 123, Example 123: designer Cyanothece sp. ATCC 51142 nirA-promoter-controlled 2-Isopropylmalate Synthase DNA construct (2004 bp)

<400> SEQUENCE: 123
agaaaatctg gcaccacacc tattaaatct aaaatagctg ttttagctaa aatagtcaat 60
agcaagtctt ataggtaatc aaacgcaact aaaatgcaaa aaatccataa ttaaaatgca 120
aaaaacggat ttttaataca attttgttac attagctaca aaatatctca aatggtagag 180
gttaaatagg tacaactcga ccagatggag ggttttccct gtgatgaact gttccttctt 240
cccttatact ctccttggat agaatgtagt tccttctcat gatggctctg tttaaggcat 300
ctacaaaacc gcttacgctg gcttttatta tgtccgtatc cacgcctcta cctgaggctt 360
ttacattatc cagctctatc acaaggcgcg cctctgcctg cgcatccgtg ttgggggtga 420
gagcttttat agaaaagtca atgagtctgg gctccacctt aagagctttc tgtatggctt 480
ttatcacagc atccacagga ccgtttcccg tagatgtggc agtcctttct tcacctctaa 540
agctcagcac tactgtagcg gtaggaagca ggttgtcccc tgtctgaacc tgatagtgtt 600
ttacctttat aggctcttcc tcctccacct tcataaactc ttcgtatatg agggcttcca 660
aatcctcatc atatacctcc tttttcttat ccgcaagagc cttgaacttt tcaaagatcc 720
tctccaggtc ttcatcgctt agcttaaagc caagttcatt cagtctcctc tttagagcgt 780
gcctccctga gtgtttacca agtattattc tggtggaggg aaaacctaca tcctcggggt 840
tcattatctc gtaggtgaga gggtgagcca gcacaccgtg ctggtgtatg cccgattcat 900
gagcaaaggc attatccccc actatagcct tgttgggttg aacaaaagag ccggttatcc 960
tgcaaaggag cctgctggtt ttgtatatct ctctggtgtt tatgtccgtg tagagccctc 1020
caaagaagtc tttgcgcact ttgagagcca tcactatctc ctcaagggct gcgtttcctg 1080
ctctttcacc tatgccgttg atggtgcact ctacctgtct tgcaccgtgc tttaccgcca 1140
taagggagtt ggcaacagcc atcccaaggt catcatgaca gtgcacgctt ataatggctc 1200
tgtctatgtt gggcacgttg ttccttatgt cctctatgag ccttgcaaac tcttctggca 1260
ccgcatagcc aacggtgtcg ggaatgttta taacggtagc acctgccttt atggctgttt 1320
ctatcaccct gtagaggaac tctctctggc ttctggtggc atcctcgcag gaaaactcca 1380
catcgtcagt aaaccttctg gcaaactcca cagctttttt agccctttcc agaacctcct 1440
ctggggacat cctaagcttg tacttcatgt gtatctcgga agtagctatg aaggtgtgta 1500
tcctctttct tctggctggc tttagagcct cccctgctag ctctatgtcc ttttccaatg 1560
ctctggcaag ggagcatatt atcggacctt ctacctgctg tgctatcaga tggacgctct 1620
caaagtctcc cttagatgct gctgcaaagc ctgcctctat aacatccacc cccagcttgg 1680
caagttggtg agccatctga agtttttcat cagcagtcat agaaaaaccc ggcgcttgct 1740
ctccgtctct cagcgtggtg tcaaatatgt aaaccttctc cattaagctg ttttagagaa 1800
atttgttcgg taaatattag cctacctaca gttgttgtgg gtaggctaat attatgaatt 1860
gagtcctact gaaccaatga ttatcgttac gactaaaagt aataaatgtc atcagcagga 1920
taggggttga taggaaaagt tttttaatcg gatggttttc gagttagagg ttagggtttc 1980
tttaggttct ctcttctgcc gtta 2004

<210> SEQ ID NO 124
<211> LENGTH: 2648
<212> TYPE: DNA
<213> ORGANISM: Artificial Sequence
<220> FEATURE:
<223> OTHER INFORMATION: Synthetic Construct- Sequence No. 124, Example 124: designer Cyanothece sp. ATCC 51142 nirA-promoter-controlled Isopropylmalate Isomerase large/small subunits DNA construct (2648 bp)

<400> SEQUENCE: 124
agaaaatctg gcaccacacc tattaaatct aaaatagctg ttttagctaa aatagtcaat 60
agcaagtctt ataggtaatc aaacgcaact aaaatgcaaa aaatccataa ttaaaatgca 120
aaaaacggat ttttaataca attttgttac attagctaca aaatatctca aatggtagag 180
gttaaatagg tacaactcga ccagatggag ggttttccct gtgatggtgc caaagacgat 240
tattgaaaaa atttgggatg aacacgtggt ttaccgtgaa gatgggaaac ccgatttatt 300
atatattgat ttacatctcg ttcatgaagt gacatcgccg caagcttttg aaggattgcg 360
acaaaaagga agaaaagtgc gtcgcccaga tttaacattt gcgacgatgg accataacgt 420
tccaacgatt aatcggtccg ttgttgaaga tgaagtggcg aaaaatcaaa tgacagcatt 480
ggagcggaac tgtcgtgagt tcggtgttcc gcttgccgat ttaaacagtc cagaacaagg 540
gattgttcat gtcatcggtc cagaactcgg gttgacacag cctgggaaaa ccattgtgtg 600
tggagatagc catacgtcta cacatggcgc ttttggggca ttagcgttcg ggatcggaac 660
gagtgaagtc gaacacgtat tagcgacgca aacgttatgg caacatcgtc caaagacgat 720
gcaagtgaac gttacgggat cgttagcacc gggcgtatca gcaaaagacg ttattttagc 780
gatcattggc aagtttggag ttgattttgg cacaggctac gtgcttgagt ttacaggcga 840
tgttattcgt cgtatgtcaa tggaagagcg gatgacaatt tgcaatatgt cgattgaagc 900
aggggcacga gctgggttaa ttgccccaga tgatgtgacg tttgcatatt taaaagagag 960
aaaatatgca ccgaaaggag aagcgtttga gcaggcagtt gaaaagtgga agcagttatg 1020
cacagatgaa ggagcggtat acgatcgtgt cgttcatatt gatggaagtg aaattgctcc 1080
aacagtgaca tggggcacaa cgccagcaat gagctctccg atcgatggaa ctgttccaga 1140
tccgaacgag tttgcgacag aaacagagag aaaagctgta cagttagcgt tgcaatatat 1200
gggattaaag ccaggaacga aaatgacgga tattgcggtg caacatgtgt ttatcggatc 1260
atgcacaaac tcgcgcataa gcgatttacg ggaagcggcg caaattgtaa aaggaaaaaa 1320
agtcgcaccg ggcgtcagag cgctcgtcgt tccgggctca caacaagtaa aaaagcaggc 1380

```
agaagaagaa ggaattgctc aaacgtttat tgacgcaggc tttgaatggc gcgattccgg   1440

ctgtagcatg tgtcttggaa tgaatccaga tactgttcca gcaggggaac attgcgcctc   1500

aacgtcaaac cgcaatttcg aagggagaca aggaaaaggg gcgcgcacgc atctcgtgag   1560

tccagcaatg gcagccgcgg ctgcgattta cgggcatttt gtcgatgtgc gtacattgta   1620

taaagaagtg gtaagatagt attaaatcta aaatagctgt tttagctaaa atagtcaata   1680

gcaagtctta taggtaatca aacgcaacta aaatgcaaaa aatccataat taaaatgcaa   1740

aaaacggatt tttaatacaa ttttgttaca ttagctacaa aatatctcaa atggtagagg   1800

ttaaataggt acaactcgac cagatggagg gttttccctg tgatggaacc attcgtcgtt   1860

cataaaggaa aagtggctgg cttagatcga gcaaatatag atacggatca aattattccg   1920

aaacaatttt taaaacgaat tgaacgcacc ggatttggtc aatttctttt ttacgattgg   1980

cgttatttat cggacggaac accaaaccca cattttgagt taaaccgtcc tgaaaacgag   2040

ggcgcgacca ttttagtcgc aaatgaaaat ttcggatgtg gttcatcgcg cgaacacgct   2100

ccttgggcgc ttgcggatta cggatttcgt gccattattg ctccttcatt tgctgatatt   2160

ttttacaaca actgtttgaa aaatagttta cttcctatta aacttccaaa agaagacgtc   2220

gcttatttgt taaaacaagc ggaacgggca gattacgaac taacgatttc gcttgaacaa   2280

caagtcgttt ttgatgatga agggtttaca agctcgttcg acatcgatcc gtatcgaaaa   2340

cagctccttt taaaaggttg ggacgaaatt gatttaacgt tcgtgtatga accatatatt   2400

atcgcctacg aaaaaaaacg ctcttgataa gctgttttag agaaatttgt tcggtaaata   2460

ttagcctacc tacagttgtt gtgggtaggc taatattatg aattgagtcc tactgaacca   2520

atgattatcg ttacgactaa aagtaataaa tgtcatcagc aggatagggg ttgataggaa   2580

aagtttttta atcggatggt tttcgagtta gaggttaggg tttctttagg ttctctcttc   2640

tgccgtta                                                            2648
```

<210> SEQ ID NO 125
<211> LENGTH: 1530
<212> TYPE: DNA
<213> ORGANISM: Artificial Sequence
<220> FEATURE:
<223> OTHER INFORMATION: Synthetic Construct- Sequence No. 125, Example 125: designer Cyanothece sp. ATCC 51142 nirA-promoter-controlled 3-Isopropylmalate Dehydrogenase DNA construct (1530 bp)

<400> SEQUENCE: 125

```
agaaaatctg gcaccacacc tattaaatct aaaatagctg ttttagctaa aatagtcaat     60

agcaagtctt ataggtaatc aaacgcaact aaaatgcaaa aaatccataa ttaaaatgca    120

aaaaacggat ttttaataca attttgttac attagctaca aaatatctca aatggtagag    180

gttaaatagg tacaactcga ccagatggag ggttttccct gtgatggcaa ccacgtatcg    240

cattgctgtt ttggcggggg atggtattgg cccagaaatt acggccgttg cccttgatgt    300

attgcgggcg atcgcccctc gctttgggtt ggactttgac tttgttcccg cccttgtggg    360

gggctgcgcc attgatgctg tgggggaacc cttgccagca gcaacgctag ccacctgtcg    420

tcagagtgat gccgtgctcc tagctgccat tggcggaacg cagtgggata gcctaccccg    480

tcatctgcgc ccggaaaccg gattacttgc cctgcggtct ggtctaggtt tatttgccaa    540

cctacgcccc gccaaaatct ttccccagct tctccatgcc tcctccctca agccggaagt    600

gattgccggt gtggatctca tggtggtgcg cgaactgacg ggtggcattt actttggtca    660
```

accgcgcggt attttcacca ctgaaacggg tgagcagcgg ggggtgaata cgatggccta 720
taccgccacg gaaattgatc gcattggccg tgttgccttt gaaaccgctc gcaaacggca 780
gggcaaactc tgctccgtgg ataaggccaa tgtccttgaa gtctcccaac tgtggcgcga 840
tcgcctgacc gccctcagtg ctgagtaccc ggatgtggaa ctgacgcacc tttatgtgga 900
caatgcagca atgcaactgg tgcgcgcccc gaaacagttt gacacgattg tgaccagtaa 960
cctctttggt gatatcctct ccgatattgc cgccatgctc accggtagta ttggcatgct 1020
tccctccgcc agcctagggg aatcggggcc agctctgttt gaaccggttc atggctctgc 1080 cccgacatt gccggccaag acaaggccaa ccccctcgcc atggtgctca gtgcggcaat 1140
gatgctgcgt tatggtctga accaaccagc ggcagcgcaa gcgatcgaag aggccattac 1200
tgccgtttta gatcagggct accgcaccgg cgatttaatg tctgagggct gcacgcttgt 1260
gggctgtcgc gaaatgggca acctcctaat caaggaattg tcccgataat aagctgtttt 1320
agagaaattt gttcggtaaa tattagccta cctacagttg ttgtgggtag gctaatatta 1380
tgaattgagt cctactgaac caatgattat cgttacgact aaaagtaata aatgtcatca 1440
gcaggatagg ggttgatagg aaaagttttt taatcggatg gttttcgagt tagaggttag 1500
ggtttcttta ggttctctct tctgccgtta 1530

<210> SEQ ID NO 126
<211> LENGTH: 2088
<212> TYPE: DNA
<213> ORGANISM: Artificial Sequence
<220> FEATURE:
<223> OTHER INFORMATION: Synthetic Construct- Sequence No. 126, Example 126: designer Cyanothece sp. ATCC 51142 nirA-promoter-controlled 2-Keto Acid Decarboxylase DNA construct (2088 bp)

<400> SEQUENCE: 126
agaaaatctg gcaccacacc tattaaatct aaaatagctg ttttagctaa aatagtcaat 60
agcaagtctt ataggtaatc aaacgcaact aaaatgcaaa aaatccataa ttaaaatgca 120
aaaaacggat ttttaataca attttgttac attagctaca aaatatctca aatggtagag 180
gttaaatagg tacaactcga ccagatggag ggttttccct gtgatgtata cagtaggaga 240
ttacctgtta gaccgattac acgagttggg aattgaagaa atttttggag ttcctggtga 300
ctataactta caatttttag atcaaattat ttcacgcgaa gatatgaaat ggattggaaa 360
tgctaatgaa ttaaatgctt cttatatggc tgatggttat gctcgtacta aaaaagctgc 420
cgcatttctc accacatttg gagtcggcga attgagtgcg atcaatggac tggcaggaag 480
ttatgccgaa aatttaccag tagtagaaat tgttggttca ccaacttcaa aagtacaaaa 540
tgacggaaaa tttgtccatc atacactagc agatggtgat tttaaacact ttatgaagat 600
gcatgaacct gttacagcag cgcggacttt actgacagca gaaaatgcca catatgaaat 660
tgaccgagta ctttctcaat tactaaaaga aagaaaacca gtctatatta acttaccagt 720
cgatgttgct gcagcaaaag cagagaagcc tgcattatct ttagaaaaag aaagctctac 780
aacaaataca actgaacaag tgattttgag taagattgaa gaaagtttga aaaatgccca 840
aaaaccagta gtgattgcag gacacgaagt aattagtttt ggtttagaaa aaacggtaac 900
tcagtttgtt tcagaaacaa aactaccgat tacgacacta aattttggta aaagtgctgt 960
tgatgaatct ttgccctcat ttttaggaat atataacggg aaactttcag aaatcagtct 1020
taaaaatttt gtggagtccg cagactttat cctaatgctt ggagtgaagc ttacggactc 1080
ctcaacaggt gcattcacac atcatttaga tgaaaataaa atgatttcac taaacataga 1140
tgaaggaata attttcaata aagtggtaga agattttgat tttagagcag tggtttcttc 1200
tttatcagaa ttaaaaggaa tagaatatga aggacaatat attgataagc aatatgaaga 1260
atttattcca tcaagtgctc ccttatcaca agaccgtcta tggcaggcag ttgaaagttt 1320
gactcaaagc aatgaaacaa tcgttgctga acaaggaacc tcattttttg gagcttcaac 1380
aattttctta aaatcaaata gtcgttttat tggacaacct ttatggggtt ctattggata 1440
tacttttcca gcggctttag gaagccaaat tgcggataaa gagagcagac acctttttatt 1500 tattggtgat ggttcacttc aacttaccgt acaagaatta ggactatcaa tcagagaaaa 1560
actcaatcca atttgtttta tcataaataa tgatggttat acagttgaaa gagaaatcca 1620
cggacctact caaagttata acgacattcc aatgtggaat tactcgaaat taccagaaac 1680
atttggagca acagaagatc gtgtagtatc aaaaattgtt agaacagaga atgaatttgt 1740
gtctgtcatg aaagaagccc aagcagatgt caatagaatg tattggatag aactagtttt 1800
ggaaaaagaa gatgcgccaa aattactgaa aaaaatgggt aaattatttg ctgagcaaaa 1860
taaatagtaa gctgttttag agaaatttgt tcggtaaata ttagcctacc tacagttgtt 1920
gtgggtaggc taatattatg aattgagtcc tactgaacca atgattatcg ttacgactaa 1980
aagtaataaa tgtcatcagc aggatagggg ttgataggaa aagtttttta atcggatggt 2040
tttcgagtta gaggttaggg tttctttagg ttctctcttc tgccgtta 2088

<210> SEQ ID NO 127
<211> LENGTH: 1503
<212> TYPE: DNA
<213> ORGANISM: Artificial Sequence
<220> FEATURE:
<223> OTHER INFORMATION: Synthetic Construct- Sequence No. 127, Example 127: designer Cyanothece sp. ATCC 51142 nirA-promoter-controlled Hexanol Dehydronase DNA construct (1503 bp)

<400> SEQUENCE: 127
agaaaatctg gcaccacacc tattaaatct aaaatagctg ttttagctaa aatagtcaat 60
agcaagtctt ataggtaatc aaacgcaact aaaatgcaaa aaatccataa ttaaaatgca 120
aaaaacggat ttttaataca attttgttac attagctaca aaatatctca aatggtagag 180
gttaaatagg tacaactcga ccagatggag ggttttccct gtgatggaac tcgacctcga 240
cggtcccggg gttggtgaag tgctgatcaa gtacaccgcc gcggggttgt gccattcgga 300
cctgcacttg accgacgggg acctaccgcc gcgctatcca atcgtcgggg ggcacgaggg 360
gtcaggcatc atcgaggacg tcggacctgg ggtcaccaag gtcaaaccag gcgatcacgt 420
tgtttgcagc ttcatcccga actgcggaac ctgtcggtac tgcgccaccg gacgctccaa 480
cctctgcgat atgggcgcca ccatcctcga agggtgcatg cccgacggca gttaccggtt 540
ccacagtaac ggcctggatt tcggtgcgat gtgcatgctc ggcacattct ccgaacgcgc 600
aactatctcc cagcattcgg tggtcaagat cgacgactgg ctgccgctcg agaccgcggt 660
ggtcgtcggc tgcggcgtgc cgactggctg ggcacctcc gtctatgccg gcggggttcg 720
ttgcggtgac accaccgtca tctatggcgt cggcggcctg ggagtcaacg ccgtccaagg 780
cgcggtgagt gcgggcgcga agtacatcgt ggtcgtcgat ccggttgcgt tcaaacgcga 840
caccgcgctc aagttcggcg ccacccacgc gttcgccgac gccgccaccg ccgcggccaa 900
ggtcgacgaa ctgacctggg gacagggtgc cgatcaggcg ctgatcctgg tcggcaccgt 960
cgacgaggac gtggtctcgg cggcgactgc ggtgatcggt aagggaggca ccgtcgtgat 1020

```
caccggactg gcggacccag caaagctcac ggtgcacgtt tcgggaacgg acctgacgct   1080

taacgagaag acaatcaagg gcacgttgtt cggctcgtcc aatccgcaat acgacatcgt   1140

acggctgctc cgtctctacg acgccggcca gctaaaactc gacgatctga tcaccacccg   1200

atacacgctc gaccaggtca accagggcta ccaggatctg cgagacggca agaacatccg   1260

cggcgtgatc atccacgcct gataagctgt tttagagaaa tttgttcggt aaatattagc   1320

ctacctacag ttgttgtggg taggctaata ttatgaattg agtcctactg aaccaatgat   1380

tatcgttacg actaaaagta ataaatgtca tcagcaggat aggggttgat aggaaaagtt   1440

ttttaatcgg atggttttcg agttagaggt tagggtttct ttaggttctc tcttctgccg   1500

tta                                                                 1503
```

<210> SEQ ID NO 128
<211> LENGTH: 1149
<212> TYPE: DNA
<213> ORGANISM: Artificial Sequence
<220> FEATURE:
<223> OTHER INFORMATION: Synthetic Construct- Sequence No. 128, Example 128: designer Cyanothece sp. ATCC 51142 nirA-promoter-controlled short-chain Alcohol Dehydrogenase DNA construct (1149 bp)

<400> SEQUENCE: 128

```
agaaaatctg gcaccacacc tattaaatct aaaatagctg ttttagctaa aatagtcaat     60

agcaagtctt ataggtaatc aaacgcaact aaaatgcaaa aaatccataa ttaaaatgca    120

aaaaacggat ttttaataca attttgttac attagctaca aaatatctca aatggtagag    180

gttaaatagg tacaactcga ccagatggag ggttttccct gtgatgaagg ttgccgtaat    240

tactggggca tcccgtggaa tcggggaagc tatagcaaag gcccttgctg aagatggata    300

ttcccttgcc ttaggggcta gaagtgttga taggttagag aagattgcca aggaactcag    360

cgaaaaacat ggggtggagg tattttacga ctacctcgat gtatcaaaac cagaaagcgt    420

tgaagagttt gcaaggaaaa cgctagctca ctttggagat gtggacgttg ttgtggccaa    480

tgcggggctt ggttactttg gtaggcttga agagcttaca gaagagcagt tccacgaaat    540

gattgaagta aaccttttgg gagtttggag aacaataaaa gctttcttaa actccttaaa    600

gcggactgga ggagtggcta ttgttgttac ttcagatgtt tctgcaaggc tacttccata    660

cggtggaggt tatgtggcaa ctaaatgggc tgcaagagca ttggtaagga ccttccagat    720

tgagaatcca gatgtgaggt tcttcgagct aagacctgga gcagtagata catattttgg    780

agggagcaaa gctgggaagc caaaggagca agggtattta aaacctgagg aagttgctga    840

ggcagtaaaa tacctcctaa gacttccaaa ggatgttagg gttgaggaat taatgttgcg    900

ctcaatttat caaaaacctg agtattgata agctgtttta gagaaatttg ttcggtaaat    960

attagcctac ctacagttgt tgtgggtagg ctaatattat gaattgagtc ctactgaacc   1020

aatgattatc gttacgacta aaagtaataa atgtcatcag caggataggg gttgatagga   1080

aaagtttttt aatcggatgg ttttcgagtt agaggttagg gtttctttag gttctctctt   1140

ctgccgtta                                                           1149
```

<210> SEQ ID NO 129
<211> LENGTH: 1910
<212> TYPE: DNA
<213> ORGANISM: Artificial Sequence
<220> FEATURE:
<223> OTHER INFORMATION: Synthetic Construct- Sequence No. 129, Example 129: a designer Nial-promoter-controlled chloroplast-targeted Phosphoglycerate Mutase DNA construct (1910 bp)

<400> SEQUENCE: 129

```
agaaaatctg gcaccacacc atggtagggt gcgagtgacc ccgcgcgact tggaagggtt     60
caaacgaccc cgccgtacga acttttgtcg gggggcgctc ccggatggta gggtgcgagt    120
gaccccgcgc gacttggaag ggttcaaacg accccgccgt acgaactttt gtcggggggc    180
gctcccggat ggccgccgtc attgccaagt cctccgtctc cgcggccgtg gctcgcccgg    240
cccgctccag cgtgcgcccc atggccgcgc tgaagcccgc cgtcaaggct gcccccgtgg    300
ctgccccggc tcaggccaac cagatgactc gtgtcatcat tgtgcgtcat ggtcaaagta    360
catataatgt tgaacgacgt atccaaggac gtactgatgc gtcaacttta acggataaag    420
gtcggagcga tgctggtaaa gtgggtaaag ccctgagtaa tatagcattt acagcaatat    480
atagcagtcc tctcaaccga gcgaagacga cagcggaaat tattcgcagt gagttggttg    540
aacattcgtc cgtgattcag gtttctgaac atctggttga agtagattta cctttgtggg    600
caggaatgtt atctcttgat gtgaaagaga agtttcctga tgactatagt atttggaaaa    660
aacgtcccca cgaattgcat atgattgtca gtgacgcaca cgggacacga gaacttttcc    720
cagttctggc tttatatgaa caagccaagc agttttggca agaaatgtta tctcgtcatc    780
aaggggaaac tattctcatt gttggacata atggtattaa ccgcgctctg attagtacgg    840
ctttgggtat tcctcccagt gtttatcacg gactacaaca gtctaattgc gcgattagcg    900
ttttaaattt tgcgggtggt ttgggtgata cggttcagct agattcaatg aatcagacgc    960
aacatttgga agatacttta cccactttgc gaccaaatca tcaaggattt agattattat   1020
tagtacgtca tggggaaaca gaatggaatc gtcaaggtaa gtttcaaggc caaattgacg   1080
ttcctctgaa tgataatggc agagcgcaag caggaaaaac tggggagttt ctccaagagg   1140
tggcgcttga ttttgctttt agtagcacta tggcgcgtcc aaaagaaaca gcggaaatta   1200
ttcttcagaa gcatgctgat ataaagttgg aattactaga tggtttacgg gaaatcagtc   1260
acggcagttg ggaaggcaag tttgagtcag aaatagaaca agagtttccc ggagtgttgg   1320
aacgctggcg tactgtacct gctgaagtac aaatgccgca aggggaaaat ttacaacagc   1380
tatgggaacg tagtgtggct gcttggcagt caatattaca atcggctgag gtaaatcaat   1440
ggcaaattgg gttggtagtg gctcacgatg ctactaataa aactttactc tgcaatatct   1500
tgggtttatc tccagaaaat ttctggaatt tccgtcaagg taatggggca gttagtgtta   1560
ttgactaccc tttaggcgct agtggtttac cagtactgca agcgatgaac attactagtc   1620
atttgagtgg tggtgtatta gataaaacgg cagcaggagc attgtagtaa atggaggcgc   1680
tcgttgatct gagccttgcc ccctgacgaa cggcggtgga tggaagatac tgctctcaag   1740
tgctgaagcg gtagcttagc tccccgtttc gtgctgatca gtctttttca acacgtaaaa   1800
agcggaggag ttttgcaatt ttgttggttg taacgatcct ccgttgattt tggcctcttt   1860
ctccatgggc gggctgggcg tatttgaagc ggttctctct tctgccgtta               1910
```

<210> SEQ ID NO 130
<211> LENGTH: 1856
<212> TYPE: DNA
<213> ORGANISM: Artificial Sequence
<220> FEATURE:
<223> OTHER INFORMATION: Synthetic Construct- Sequence No. 130,
Example 130: designer Nial-promoter-controlled chloroplast-
targeted Enolase DNA construct (1856 bp)

<400> SEQUENCE: 130
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatgctta ggtcctaaac caacagtacc agcataaaca 360
gcgcgatcgc ctaattcatc ttcaattctg agtaaacgat tgtattttgc tacccgttca 420
ctacgacaaa gagaaccagt tttaatttga cctgcacgag tggctacagc caaatcagca 480
atagttgtat cctcagtttc accagaacga tggctaatga ctgagcggaa accgttgcga 540
gtagctaaat caatagtttc caaagtttca gtcagtgaac caatttgatt caacttaatc 600
aaaatcgagt tacctgcttt ttgctcaatc cctttttgta accgagtagc gttagtaaca 660
aataaatcat cacccaccaa ctgtactcgt gaacccaact tctgagtcag taattgccaa 720
ctttcccaat cttcctcatg taaaccatct tcaatggaaa caatcggata ttggtcaacc 780
aactggccta aataatcaat aaactcaact gggctatggg gtttaccatc ataaacatac 840
tgcccatttt tgtaaaactc actcgctgcc acatccaagg ctaaagcaac ttcttcccca 900
ggcttgtaac cagcttgttt aatagcagct agcaataatt ctaaagctac ttggttagag 960
tccaggttag gtgcaaaacc accttcatca ccaacaccag tcagcaaacc cttatcatcc 1020
aaaaccttgc tgagagttgc aaaaacttcc gcaccccaac gcaaagcttc ctggaaggaa 1080
ggcgcactga cgggtacaat cataaactcc tgaaaatcga cattattggc tgcgtgcgct 1140
ccaccattga tcacattcat caaaggtaca ggtagcaaat ttgctaaagg cccacccaca 1200
tagcgataca aaggaattcc caaagactca gcagcagctt tagcagctgc tagtgaaacc 1260
gacaaaattg catttgcgcc caaattagct ttattgggtg aaccatccaa agagatcatg 1320
attttatcta atgattcttg gtctagggca tccaagccta acaattgggg tgctaatacc 1380
tctttcacat tctgcactgc cttgagtact cctttgccac cataacggct tttatcacca 1440
tctcgcagtt catgagcctc aaaagtacct gtggaagcac cgctaggaac ttgcgctagt 1500
cctactgtac cattagccaa atgtactgca gcctcaacag tcggtcttcc ccgtgaatca 1560
agaatttcgc gggcgataat agcttcaata gcggtatcca gaaattttgt cattaaatgg 1620
aggcgctcgt tgatctgagc cttgccccct gacgaacggc ggtggatgga agatactgct 1680
ctcaagtgct gaagcggtag cttagctccc cgtttcgtgc tgatcagtct ttttcaacac 1740
gtaaaaagcg gaggagtttt gcaattttgt tggttgtaac gatcctccgt tgattttggc 1800
ctctttctcc atgggcgggc tgggcgtatt tgaagcggtt ctctcttctg ccgtta 1856

<210> SEQ ID NO 131
<211> LENGTH: 1985
<212> TYPE: DNA
<213> ORGANISM: Artificial Sequence
<220> FEATURE:
<223> OTHER INFORMATION: Synthetic Construct- Sequence No. 131, Example 131: designer Nial-promoter-controlled chloroplast-targeted Pyruvate-Kinase DNA construct (1985 bp)

<400> SEQUENCE: 131
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180

```
gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatgaaac ccttaaattt tcggactaaa attgttgcta    360

ctatcggtcc tgcgagtaat actcccgaag tattacgtca aatgctctta gccggagtca    420

atgttgcgcg gttgaatttt tcccacggta gctacgaaga tcacgctcag atggttaaac    480

tcttacgttc tttgtccgaa gaattagact taccccctgac cattttacaa gaccttcaag    540

gtccaaaaat tcgggtaggc aaattacccc cagacggact taacctcatc gaaggacaat    600

ctctaacctt ggttcccctt gctgcttgga aaaatcaagc caataccgtt ggcattgatt    660

atccctacgt cgctgaagaa gcgcaacccg gtactcaagt gctgcttgat gacggtttat    720

tggagttaac cgttgaacaa gtcaagggaa atgaggtcat ctgtcaagtg gttgaaggag    780

gcattctcaa aagcaataag gggggttaatt tgccaaccct caatctacgc ttgccttcca    840

tgaccgaaaa agataagaaa gatctcgaat ttggactatc ccaaggcgtt gacatcattt    900

ccctaagctt tgtccgcaaa cccgaagata ttcaagaact caaggaattt attgcccaaa    960

gatcggcaaa agttcccgtt ttagcgaaaa ttgaaaagcc ccaagccgtt gacaatattg   1020

aagccattat cgatgaatgc gatgctatta tggttgcgcg gggagactta ggggtagaaa   1080

tgcgccccga aaaggttcca ggtatccaaa aacgcatcat taagctgtgt aaccaaaaag   1140

gcatccccgt tattaccgcc acccagatgc tcgatagcat gattcgtaac ccccgtccca   1200

cccgtgctga agccagtgac gtagccaatg ctatcattga tggaaccgat gcggttatgt   1260

tatcaggaga atcagcgatc ggagattatc ccgtgcaagc ggtgcaaatg ctggctaata   1320

ttgccaaaga tattgaacca ggactgaatt ttgccaatta tcctcctcga cggcagaata   1380

aagcccacgc catagccgaa gctctcaata ccatcgacaa gattcttgat ttacaatgta   1440

ttgtcacctt tacggaaacc gggtattctg ctaaattagc tgctgctgaa cggccacggg   1500

ttcccatagt ggctttaaca cctgatcacc aagtttatca tcgccttaat ttagtttggg   1560

gagtccgacc cattttattt gactacgatg agtcttccct agacgacttg atggttaaag   1620

tagaagatat gttaaaaacc cgaaactacg cgacatcagg ggataaagtg ttgattatgg   1680

gtggtttacc cctcagaaaa gccagtacca cgagttttct cgatattcat acgattactt   1740

aataaatgga ggcgctcgtt gatctgagcc ttgccccctg acgaacggcg gtggatggaa   1800

gatactgctc tcaagtgctg aagcggtagc ttagctcccc gtttcgtgct gatcagtctt   1860

tttcaacacg taaaaagcgg aggagttttg caattttgtt ggttgtaacg atcctccgtt   1920

gattttggcc tctttctcca tgggcgggct gggcgtattt gaagcggttc tctcttctgc   1980

cgtta                                                                1985
```

```
<210> SEQ ID NO 132
<211> LENGTH: 1568
<212> TYPE: DNA
<213> ORGANISM: Artificial Sequence
<220> FEATURE:
<223> OTHER INFORMATION: Synthetic Construct- Sequence No. 132,
      Example 132: designer Nial-promoter-controlled NADPH-dependent
      chloroplast-targeted NADPH-dependent Glyceraldehyde-3-phosphate
      dehydrogenase DNA construct (1568 bp)

<400> SEQUENCE: 132
```

```
agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120
```

```
gaccccgcgc gacttggaag ggttcaaacg accccgccgt acgaactttt gtcggggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatgtcaa cgaatattgc aattaatgga atgggtagaa    360

ttggaagaat ggtgctaaga atagcactaa agaatgaagc attgaatgta gttgccatca    420

atgctagcta tcctcctgaa acaattgcac atttaattaa ttatgacaca acacatggga    480

gatacgataa aagagtagaa cctattgaaa gtggaattcg agtggaaggc catgatatta    540

aattagtgtc tgatagaaac ccagaaaatt taccctggaa agatttagaa atagatatcg    600

tcattgaagc gaccggtaaa tttaaccatg gtgataaagc taaggcacat attcaagcag    660

gagctaaaaa agtgttattg acaggaccat caaaaggcgg aaaagtacag atggtggtta    720

aaggtgttaa cgatcaagac ttagatacag atacatatga catatttagt aatgcgtcgt    780

gtactacgaa ttgtatcgga ccagttgcaa aagttttaaa tgatagtttt ggcattgaaa    840

atggcttaat gacaacggta catgcaatta caaatgatca aaataatata gataatccgc    900

ataaagattt gagaagagcg cgttcttgtg ggaaagtat tataccaaca tcaacaggtg     960

ctgctaaagc attaaaagaa gttatgccag aattgaatgg caaactacat ggcatagcac   1020

ttcgtgtgcc aactcaaaat gtatcattag ttgatttagt cattgattta aaacaaaaag   1080

tgacagtaga tgaagttaat catgcattta gagatgcaaa cttacaagga attattgatg   1140

ttgaagaggc ccctctagtt tctaaggact ataatacaaa tcctcattca gcagttatag   1200

atgctaaaaa tacaatggtc atgggagata ataaggttaa agttatagcc tggtatgata   1260

acgaatgggg atattctaat agagtagttg aggtagcaaa tcaacttgga gaactaatta   1320

aataataaat ggaggcgctc gttgatctga gccttgcccc ctgacgaacg gcggtggatg   1380

gaagatactg ctctcaagtg ctgaagcggt agcttagctc cccgtttcgt gctgatcagt   1440

ctttttcaac acgtaaaaag cggaggagtt ttgcaatttt gttggttgta acgatcctcc   1500

gttgattttg gcctctttct ccatgggcgg gctgggcgta tttgaagcgg ttctctcttc   1560

tgccgtta                                                            1568
```

<210> SEQ ID NO 133
<211> LENGTH: 1571
<212> TYPE: DNA
<213> ORGANISM: Artificial Sequence
<220> FEATURE:
<223> OTHER INFORMATION: Synthetic Construct- Sequence No. 133, Example 133: designer Nial-promoter-controlled chloroplast-targeted NAD-dependent Glyceraldehyde-3-Phosphate Dehydrogenase DNA construct (1571 bp)

<400> SEQUENCE: 133

```
agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcggggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatgtaaa ctggctgaat gtacaagcat atccgcaagt    360

ttgttggagt aacccatttc gttatcgtac catgaaacta ctttcacgaa atttggagat    420

aacataattc ccgcatcctt gtcgaatacc gaagttctct tctcgcccac gaaatcctga    480
```

```
gaaaccacag cgtcttcagt ataccctaaa attcctttaa gttcaccttc cgatgccgct    540

ttcattgctg cacagatttc ttcgtatgaa gtagatttct ctaatctgac cgttaaatcc    600

actacagaaa catctgcagt tgggactctg aatgacatac cggttaattt accgttaagg    660

gcaggaatta cttttcctac tgcttttgca gctccggtag aagatgggat gatgttgttc    720

aatgcagaac gcccgcctct ccagtctttc atagaaggcc cgtcaacagt tttctgggtt    780

gcagtagttg cgtgcacggt cgtcattaaa ccttcgatga ttccgaaatt atcgtgaagt    840

acttttgcta atggagcaag acagttagtc gtacagctcg cgttagaaaa aatagtaacg    900

tcatctgtaa gatccttgtg gttaacaccc attacgaaca tcggcgtatc gtcttttgaa    960

ggagcagaaa ggattgcttt ttttgcaccc gcgttgatat gtgcctgtgc cgcctccttg   1020

gtaaggaata aaccggttga ttccacgatg tattctgcgc ctacttcgtt ccatttcagg   1080

ttgttaggat ctttttcggc ggttacacga atctttttgc cattcacgat aaggtcgttt   1140

ccttctacag aaacttcgcc cgcaaatgtg ccgtgtaccg agtcatactt aagcatgtac   1200

gccatatatt tggcatcgat aagatcgtta attcccacca cttcgatgtt ttctctctcg   1260

gccatcgctc tgaaaaccaa gcgtccaatc ctaccgaatc cgttgattcc tactttaatt   1320

gttgacatta aatggaggcg ctcgttgatc tgagccttgc cccctgacga acggcggtgg   1380

atggaagata ctgctctcaa gtgctgaagc ggtagcttag ctccccgttt cgtgctgatc   1440

agtctttttc aacacgtaaa aagcggagga gttttgcaat tttgttggtt gtaacgatcc   1500

tccgttgatt ttggcctctt tctccatggg cgggctgggc gtatttgaag cggttctctc   1560

ttctgccgtt a                                                         1571
```

```
<210> SEQ ID NO 134
<211> LENGTH: 2150
<212> TYPE: DNA
<213> ORGANISM: Artificial Sequence
<220> FEATURE:
<223> OTHER INFORMATION: Synthetic Construct- Sequence No. 134,
      Example 134: designer Nial-promoter-controlled chloroplast-
      targeted Citramalate Synthase DNA construct (2150 bp)

<400> SEQUENCE: 134

agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcgggggc     180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatggagc aggtttttat ctacgacacc accttgaggg    360

atggctcgca ggcagaaggt ataaactttt ccgtagagga taagatgcgc atacttcaaa    420

aactggacga atttggagtg cattacatag agtgcggatg gcccggtgcg aacccaaaag    480

acactattct ctttgaaagg ctgagaaaga taaaaactca aaatgccaaa atagtagcct    540

ttggtgcaac aagaaaagct ggaaagaagg cgcacgaaga taagcaggtg gaaaaccttt    600

tgaaatcggg tgccaaggtg ataaccgtat ttggcaagag ctgggacttt catgtaacgc    660

atgccatagg gaccacctta gaggaaaacc tggacatggt ttacgagacg gtaagctatc    720

ttaaaaagca tgtggaggag gttatctttg acgcagagca cttctttgac ggatacaggc    780

acaacgaaag ctatgctttt aaggtattgg aggcagcttt tcaggcaggt gcggactgga    840
```

-continued

```
tagtcctctg cgataccaac ggtggcaccc ttcccaatga ggtttatgag ataaccaaaa    900

aggttgtaca aaagtttcca caggcacgcg taggcataca cgctcacaac gattcagata    960

ctgctgtggc taactctctt atggcggtgc ttgcaggtgc aaggcaggtt cacggcacta   1020

taaacggctt gggggaaaga acgggcaatg ctaatctgtg ttccataata cctaaccttc   1080

agctcaagct gggctttagt gtagtgcctt cccaaaacct caaaaagctc accgagcttg   1140

ctcactttgt ctccgaaatc tccaacacgc cactgcccaa aaacatgcct tatgtagggg   1200

agagtgcttt tacccacaaa gcaggcgtac acgcctctgc agttatgaaa aggtcagaaa   1260

catacgaaca catagaccct tctttggtag gaaacagaag gaaggtgaca gtgtctgacc   1320

tttctggaag gagtaatata ctttacaagc tcagggaaat ggggcttgag gtggatgata   1380

agtcccctga gcttatcaaa ctccttgaaa agataaagga acttgagaag gaaggctacc   1440

actttgaagc agctgaagct tcttttgagc ttctttgcaa gaggcatttt gggcttgtta   1500

aaaactattt tgaccttgat gcttacaggg tgctaatagc cagaaggagt acagacctat   1560

ctcctgtttc ggaagccacc gtaagactct atgtggaaga cataaaggag catacagcag   1620

ctcttggtaa cggaccagtg agcgcccttg acagagccct cagaaaagcc ttggaagagt   1680

tttatccaag ccttaaagat gttcagctca tagactacaa ggtgagaata gttaacgaat   1740

cggagggtac atctgccaaa gtgagggtgc ttatagaatc taccgatggt agaagaaagt   1800

ggggaacggt gggagtttcg gaaaacataa tagaagcctc ttggatagcc ttaactgata   1860

gcctcgtata taaactctta aaagacgaag aagagggtat aatgtgataa atggaggcgc   1920

tcgttgatct gagccttgcc ccctgacgaa cggcggtgga tggaagatac tgctctcaag   1980

tgctgaagcg gtagcttagc tccccgtttc gtgctgatca gtctttttca acacgtaaaa   2040

agcggaggag ttttgcaatt ttgttggttg taacgatcct ccgttgattt tggcctcttt   2100

ctccatgggc gggctgggcg tatttgaagc ggttctctct tctgccgtta              2150
```

<210> SEQ ID NO 135
<211> LENGTH: 3125
<212> TYPE: DNA
<213> ORGANISM: Artificial Sequence
<220> FEATURE:
<223> OTHER INFORMATION: Synthetic Construct- Sequence No. 135, Example 135: designer Nial-promoter-controlled chloroplast-targeted 3-Isopropylmalate/(R)-2-Methylmalate Dehydratase large/small subunits DNA construct (3125 bp)

<400> SEQUENCE: 135

```
agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcggggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatgtacc atgtctgctg ttgctatctc gcccttgatt    360

gctgatgctg taacagtagc cgctgaagca agatatacaa aagaatcttt atgtcctgca    420

cgtcccttga agtttcgtgt acctgtactg ataagagtct caccctcacc gataacaccc    480

tgacagcttc cccagcatac agagcagtta ggattcataa caattgcacc tgcgtccatg    540

aatatatcaa ggagtccctc tttcatagcc tgaagatata ccgaacggct tgcaggaact    600

acaaggaatc ttaccttagg agcaaccttt ttccctttga tgatcgctgc gccaactctt    660
```

-continued

```
aaatcctcga ttcgtccatt gttacatgaa ccaagaaatg cttcatcaat ctttacacca    720
agtgattcct tagccggaac tacattgtca acaaaatgtg gctttgcaac aattggctgt    780
attgttgaaa ggtcaatatc ataaacctgc tcaaatactg catcatcatc tgatgtaaag    840
catgcctttg gctctctgcc atgctcctta agataatcca ttgcaacatc atcaacttcc    900
atgagtgcag tcttagcacc tgcctctaca caaaggttac agattgatat tctgtctgcc    960
attgaaaggc tgtgtaagcc ttctcctgca aattccattg ctttatagtt agcaccgtta   1020
gcgccaatct ttccaataat agagagtatt aaatctcttg catatactcc atcgttaagc   1080
tttcccttaa ggttgaatct taatgttccc ggaaccatta cccatgatgt tcctgtaacc   1140
attgcataca aataatctgt acaaccaaca cctgtaccaa atgcacctaa cgcaccatat   1200
gcacaagtat ggctgtctgc tccaaatata agctcacccg gcactacatg attttccatc   1260
ataacctgat gacacacacc ctcgccctcg tagaacttaa tatcattagc cttagcaaag   1320
tctctcatct tcttctgtga ggctgctgtc ttaggactgt ctgatggaat attgtggtct   1380
acaatccata caagcttatc cttgtcagca atatgaggat tctttaactt ctcatacata   1440
ccaatagtaa gatgtgttgt tccatcatta ctcataagtc tgtcaagagt aacagttgca   1500
atatcaccag ccttaacctg tgaaagacct gctgcccttg cgataatctt ctctgcaata   1560
gtcatgccat gctttgcctc atctgcaggt acggctgtac tctcagactc ttctttctca   1620
ccatcaagtg atgcaataag accaccctga ttaagaatag cctgcatctt ggctggaagc   1680
ttagtacatg tataagtctt tccattaaca gttataattc catcttctaa tgaaagctca   1740
cattcatccc ccgcattaac ttcgtcatgg agttctttac atacaataac aggaagtcct   1800
atattaatag cattacgata gaatattctt gcaaatgatt tggcaatcac tgccttgaca   1860
cctaatgcct taagtacgct tggtgcctgc tctcttgatg aaccacatcc aaagttgtca   1920
tctgcaacaa cgaaatctcc cggctttacg gcagaagcaa aatcagagtc taatgattca   1980
aatgtatgac tcttcatctc atcaattgtc ggaaacaaaa gatactgcga tgcaataatc   2040
tgatctgtat caacatcttt atcaaactta aatatcctac ccatatggta gggtgcgagt   2100
gaccccgcgc gacttggaag ggttcaaacg accccgccgt acgaactttt gtcgggggc    2160
gctcccggat ggtagggtgc gagtgacccc gcgcgacttg gaagggttca aacgaccccg   2220
ccgtacgaac ttttgtcggg gggcgctccc ggatggccgc cgtcattgcc aagtcctccg   2280
tctccgcggc cgtggctcgc ccggcccgct ccagcgtgcg ccccatggcc gcgctgaagc   2340
ccgccgtcaa ggctgccccc gtggctgccc cggctcaggc caaccagatg gtcaagaccg   2400
ttaagctttc tcattgcctt aacaagtccg cctgcattaa gtatatccac aagattatca   2460
ggaagtgaag caataggata tgcttttcca ttgtgtgtaa tctttgcatt tacttcaaca   2520
tcaatagtat cgccttccgt aacttcgtcg tgaaggtctg cattctctat aaggagaagt   2580
ccgttattaa tagaatttct gaagaatatt cttgcatatg atttggcaat aacacattta   2640
atacctaatg ccttaataac ctcaggtgcc tgctctcttg atgaaccaca accaaagttc   2700
tttcctgcaa caatgatgtc gcctggctta atctgacctg caagttctgg tcttaatggc   2760
gaaaatgcat atggtttcat atcttctact gtctttaatg caaggtactc tgtagggata   2820
atgatatctg tatcaatgtc atcaccaagt acccatactt taccgctaaa tttctcgttc   2880
attaaatgga ggcgctcgtt gatctgagcc ttgccccctg acgaacggcg gtggatggaa   2940
gatactgctc tcaagtgctg aagcggtagc ttagctcccc gtttcgtgct gatcagtctt   3000
tttcaacacg taaaaagcgg aggagttttg caattttgtt ggttgtaacg atcctccgtt   3060
```

gattttggcc tctttctcca tgggcgggct gggcgtattt gaagcggttc tctcttctgc 3120
cgtta 3125

<210> SEQ ID NO 136
<211> LENGTH: 2879
<212> TYPE: DNA
<213> ORGANISM: Artificial Sequence
<220> FEATURE:
<223> OTHER INFORMATION: Synthetic Construct- Sequence No. 136, Example 136: designer Nial-promoter-controlled chloroplast-targeted 3-Isopropylmalate Dehydratase large/small subunits DNA construct (2879 bp)

<400> SEQUENCE: 136
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatgaatg aactgcctta catcagaaac ttttccatta 360
accgccgccg ccactaccat cgctggactc atcaataaag tgcgaccggt tgatgacccc 420
tgacggcctt taaaattacg gttagaagaa gaagcactaa tttgatcgcc aactaactta 480
tcagggttca tggctaaaca catggaacag ccggcttctc gccattcaaa cccggcttgg 540
gtaaaaattt tatcgagtcc ttcggcttct gcttgttgtt taaccctttc cgatccggga 600
acgacaaatg ctttaacccc tgatgctacc tgtcttcctt gggcaaattt agccgcttct 660
cgtagatcgc tgatgcgtcc attggtacaa ctaccaataa aacagacatc gacaggagtc 720
cccataatag gcgatccggg tttgagttgc atatattcat aagcttcttg agcaataaag 780
cgatcgcctt ctggtaaact ttcaggagta ggaaccactt cagtcacgcc tattccttga 840
ccgggggtaa taccccaagt aacagtcggt tcgatctcac cggcatcaaa caccacgaca 900
tcatcatatt gggcattcgc atcactgcgg atactcttcc accattcgac ggccttatcc 960
cagtcttggc ctttgggaga aaagtctctg cctttgaggt attcaaaagt cacctcatca 1020
gggttaatat agccgcatct agcgccgcct tcgatggcca tattacaaac ggtcattcgt 1080
tcttccatcg acatggcctc aaaggtagtg ccggcatatt cataagcgta acctacgccg 1140
ccttttaccc ctaatttgcg gatgatgtgc aggacgacat ctttggcata gactccgggg 1200
ggtaaggttc cgttaacttc aattttacgg actttgagtt tagagagggc tagggtttgg 1260
gtagcgagga catctcgcac ttgggaggtt cctatgccaa aagcgatggc cccaaaagcg 1320
ccatgagtgg aggtatgaga gtcaccgcaa gcaatggtca ttccgggttg agttagtcct 1380
tgttcggggg cgatcacatg aacaataccc tgatttcctg agccgatatt ataaaaaggg 1440
atattattat ctttagcatt agtttcaata gcccgcatca tttcttcagc gaggtcgtct 1500
acaaagggac ggtgttggtt ctcggtgggt acaatatgat ccactgtggc gacggtgcga 1560
tcggggaata ataccttcag ttttctgtcc cgtagcatag caaaagcttg tggactggta 1620
acttcatgaa tgaggtgaag tcctataaat agttgggttt gtcccgatgg taagatgcgg 1680
acggtatgta agtcccaaac tttgtcaaac agtgttcctg tactcatatg gtagggtgcg 1740
agtgaccccg cgcgacttgg aagggttcaa acgaccccgc cgtacgaact tttgtcgggg 1800
ggcgctcccg gatggtaggg tgcgagtgac cccgcgcgac ttggaagggt tcaaacgacc 1860
ccgccgtacg aacttttgtc ggggggcgct cccggatggc cgccgtcatt gccaagtcct 1920
ccgtctccgc ggccgtggct cgcccggccc gctccagcgt gcgccccatg gccgcgctga 1980
agcccgccgt caaggctgcc cccgtggctg ccccggctca ggccaaccag ttatacctct 2040
acggcatttt tccaatttaa ataaggtaat tttttagcag tttcttgaat ttcagaaagg 2100
ttttgaatga gttgtccgca gctatcccaa gagccttcaa ttaacatttg tctagaccct 2160
tctcccatgc taacatcagc aacaaattcg ccacattgca ctttcatagc ggctaaatct 2220
aaactgaggg acaaggcagg attttcttgc aggagagatt gtatttttc tacggtttca 2280 ggagaagctg tcacacaggg aaccccgtta gcaatacaat tgccaaagaa aatttcagca 2340
aaactttcac cgataattgc tttaattccc caacgaataa tggcttgtgg ggcgtgttct 2400
cttgaagatc cacagccaaa attagcgtta actaccaaga gattagctcc ctgatattgc 2460
ggcagatcaa agggatgttt tccttgcatc tgttggcgat catcaataaa aacttgttct 2520
cctaagcctt caaaggtgac gcaacgtaga aaccgcgcag gaataatacg atcagtatcg 2580
atatcatcgc ccactaaagg gatacctcgt cctgaaattt gggtgacttg actcattaaa 2640
tggaggcgct cgttgatctg agccttgccc cctgacgaac ggcggtggat ggaagatact 2700
gctctcaagt gctgaagcgg tagcttagct ccccgtttcg tgctgatcag tctttttcaa 2760
cacgtaaaaa gcggaggagt tttgcaattt tgttggttgt aacgatcctc cgttgatttt 2820
ggcctctttc tccatgggcg ggctgggcgt atttgaagcg gttctctctt ctgccgtta 2879

<210> SEQ ID NO 137
<211> LENGTH: 1661
<212> TYPE: DNA
<213> ORGANISM: Artificial Sequence
<220> FEATURE:
<223> OTHER INFORMATION: Synthetic Construct- Sequence No. 137, Example 137: designer Nial-promoter-controlled chloroplast-targeted 3-Isopropylmalate Dehydrogenase DNA construct (1661 bp)

<400> SEQUENCE: 137
agaaaatctg gcaccacacc atggtagggt gcgagtgacc ccgcgcgact tggaagggtt 60
caaacgaccc cgccgtacga acttttgtcg ggggcgctc ccggatggta gggtgcgagt 120
gaccccgcgc gacttggaag ggttcaaacg accccgccgt acgaactttt gtcgggggc 180 gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatgactc ggcaacaccg cataacccta cttcctggcg 360
atggtatcgg acctgaaatt ttagccgtaa ccgtagatgt cctaaaggtg ataggcaaac 420
aattcgacct aaattttgag tttacagaag ccctcatcgg cggtgctgcc attgatgcaa 480
ccggaaaccc cttacccgaa gaaaccttaa agatttgtcg caacagtgat gcagtgcttt 540
tagccgccat cgggggttat aagtgggata atttgccccg tcatcaacgc ccagaaacgg 600
gattattagg catcagagcc ggcttaggat tatttgctaa cttacgtccg gccaccattt 660
taccgcagtt aatcgacgct tccaccctca aacgagaagt cgtcgaaggc gtggacatta 720
tggtggtgcg agaactcacc ggcggcattt attttggtca accgaaggga atttttgaga 780
cagaaagcgg cgaaaaacgg ggcgtgaata ccatggccta tacagaatca gaaatagacc 840
gcattgctca aatcggcttt gaaacagccc aaaaacgtcg aggaaagctc tgttctgtgg 900
ataaagccaa tgtcttagat gtctcccaat tatggcgcga tcgcgtaact ttaatggccg 960

```
aaaaataccc agatgtagaa ctgtctcatc tctatgttga caatgcggct atgcagctag   1020

tgcgtaaccc aaaacaattt gataccatcg tcaccggcaa tttatttggc gatatcctct   1080

cggatgcagc cgctatgtta accggtagta ttgggatgtt accctctgct agtttaggtt   1140

cagatggacc cggactattt gaaccggtac atggttcagc cccgatatt gcaggacttg   1200

ataaagctaa cccgcttgct caggtactca gtgccgccat gatgttgaaa tatggcttaa   1260

atgagccaga agccgccgat caaatcgaac aagcggtttt agccgtatta gaaaaaggct   1320

atcgtacagg agacatcatg tcagaaggaa tgacgttagt gggatgtaag ggcatgggag   1380

aagttttgat taatgtctta gaatctttac aagggtgata aatggaggcg ctcgttgatc   1440

tgagccttgc cccctgacga acggcggtgg atggaagata ctgctctcaa gtgctgaagc   1500

ggtagcttag ctccccgttt cgtgctgatc agtctttttc aacacgtaaa aagcggagga   1560

gttttgcaat tttgttggtt gtaacgatcc tccgttgatt ttggcctctt tctccatggg   1620

cgggctgggc gtatttgaag cggttctctc ttctgccgtt a                       1661
```

```
<210> SEQ ID NO 138
<211> LENGTH: 2174
<212> TYPE: DNA
<213> ORGANISM: Artificial Sequence
<220> FEATURE:
<223> OTHER INFORMATION: Synthetic Construct- Sequence No. 138,
      Example 138: designer Nial-promoter-controlled chloroplast-
      targeted 2-Isopropylmalate Synthase DNA construct (2174 bp)

<400> SEQUENCE: 138

agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcggggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatgtgat gctgtaacag ccgcttgttc tttttgggtt    360

ttttcttgtt ctagggcaac ataaagacgg ttaagagcgc taatataagc ccgtgccgaa    420

gcaacgataa tatcagtatt agcggcatga cccgagaaag ttcggttttc gtatttcaga    480

cgaatggtga cttctcccat tgcatcaatg ccttctgtga ctgacttaac cgaaaattca    540

atcaactggt taggaacatt aaccactcgg ttaatcgctt tataaaccgc atctacgggt    600

ccggttccaa tagccgcatc cattaattct tcgccgttgg gaccttttaa gatcacggtt    660

gctgttggac gggcctgatc gccacatgac acttgtacta attcgagacg gaagatttct    720

ggggcaacat gaatttcatc attgacgatg gcttctaagt cccagtcagt aatttctttg    780

cgcttgtctg ccacttcttt aaagcgtaca aaggctttat ttagctcagt ttccgtcaat    840

tcaaagccta attcttttag acgagtgccg aaagcattac gccctgagag tttcccgagg    900

acaatttgat tattggttaa cccgatagac tcagcgtcca taatttcgta ggttaattta    960

ttttttagca cgccatcctg atgaataccg gattcatgag cgaaagcatt agcgccgaca   1020

attgccttat tcggttgtac cgccatcccg gtgagactgg aaactaaacg ggatgttttg   1080

tagatttctt tggtattgat attggttagg ggttcagtgg agtctgctgg tcgtcctaag   1140

aaaggattgt aataggagcg gcgtacatga agcgccatca ctaattcttc taaggcggcg   1200

ttgccggctc gttctcctat gccgttaata gtacattcta actgtctggc tccattttta   1260

acggcttcaa ggaagttagc caccgctaac cctaaatcat tatgtccatg aaccgagata   1320
```

atagcattgt ctatgttagg aacattttct ttgatgccgc gaatcaattg accaaattca 1380
gagggagtta aatagcctac ggtatcggga atattaacgg tagttgctcc ggctgctatg 1440
gctctttcta atacttgata caaaaattct gggtcactac ggcctgcatc ttctggggaa 1500
aattctacat catctacaaa agacttcgca taagccacca tttctgggac gatttctagg 1560
acttcttgac gagtcttttt gagtttatag gccaagtgaa tatcggaggt agccaaaaag 1620
gtatgaatgc ggggtttagc ggcgggtttg agggcttctg cggctttagt gatatcttgt 1680
cgagtggctc ttgccaagcc gcaaattgtg gggcctcctt ggactcctac tactttagcg 1740 atttttgta cagcttcaaa atctccggga cttgcgtaag gaaaacccgc ttctatgaca 1800
tctactccca gtcgtgccag tgcgcgagca acggttagct tctcatcaac attcagggtt 1860
gctcccgggg actgttcccc atctcggaga gtggtatcga agatgataac gcgatcgggt 1920
tgtttactca ttaaatggag gcgctcgttg atctgagcct tgccccctga cgaacggcgg 1980
tggatggaag atactgctct caagtgctga agcggtagct tagctccccg tttcgtgctg 2040
atcagtcttt ttcaacacgt aaaaagcgga ggagttttgc aattttgttg gttgtaacga 2100
tcctccgttg attttggcct ctttctccat gggcgggctg ggcgtatttg aagcggttct 2160
ctcttctgcc gtta 2174

<210> SEQ ID NO 139
<211> LENGTH: 2882
<212> TYPE: DNA
<213> ORGANISM: Artificial Sequence
<220> FEATURE:
<223> OTHER INFORMATION: Synthetic Construct- Sequence No. 139, Example 139: designer Nial-promoter-controlled chloroplast-targeted Isopropylmalate Isomerase large/small subunits DNA construct (2882 bp)

<400> SEQUENCE: 139
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gccccccgtgg 300 ctgccccggc tcaggccaac cagatgcaac aactcccgca catccgcaac ttcaccctga 360
atcgccgcag tagcgaccat cgccggactc attaacaaag tgcgaccgga agctgatcct 420
tgtcgtcctt taaagttgcg gttggaggag gaagcactaa tttgtctacc ttccagcttg 480
tcggggttca tggctagaca catagaacat ccaggttcgc gccattcaaa gcctgctgct 540
tcaaagattt tatctaaacc ttcagcttcg gcagcttttt tcactcgttc ggaaccggga 600
accacaaaag ccttgactcc ttccgctacg tggcgacctt tggcaatttt cgcggcttct 660
tgcaggtcac taagtctacc gttagtgcag ctaccgataa agcaaacgtc aattttcgtt 720
cccttaatcg gttgaccagg atataaatcc atgtaacggt aagcttcttc agctacaaag 780
cggtcttctt ctaggagttc ttctggctgg ggaatcaact gattcacacc aataccttga 840
ccgggggtaa ttccccaggt aacagtgggg ggaatatccg cagcgttgaa tactattaca 900
tcatcgtatt cagcatcagc atcactcttg attgattccc accaagccac ggctttttcc 960
caatcagcgc cttgggggc aaagtctcta ccttggagat aatcataggt aacttgatca 1020
ggattgacat aaccgcatct agcgccaccc tcaatggcca tgttgcagac agtcatccgt 1080
tcttccatat tcatttgctc aaaagtcgta cccgcgtatt cgtaggcgta acctacacca 1140
cctttcactc ccagggtacg gatgatatgc aggatgacat ctttggcata aaccccaggg 1200
ttgagtgtgc cgttaacttc aattttacgg actttgagtt tggataggga taaggtttgg 1260
gaggcgagaa cgtcccgcac ttggctagta ccaataccaa aagcgatcgc cccaaacgcc 1320
ccatgacttg aagtgtggct atcaccacag gcgatcgtca ttcccggctg tgtcagtccc 1380
agttctggcg caatcacatg aactatacct tgattgccgg aaccaatgtt ataaaaagta 1440
atgttatttt cttgacaatt ctgctctagg gcttggatca tttcctcagc caagcgatcg 1500
acaaaaggac gcgcctgatt ctctgtaggc acgatgtgat ccacagtagc cacagtccgc 1560
tcaggaaata gtacctttaa acctcgttcc cgtaacatag caaaggcttg tggactagta 1620
acttcatgga ctaggtgcag gccaataaat agctgtgtta gccctgaagg aagtgtacca 1680
acagtgtgta agtcccaaac tttatcaaac agggtgcctt tgctcatatg gtagggtgcg 1740
agtgaccccg cgcgacttgg aagggttcaa acgaccccgc cgtacgaact tttgtcgggg 1800
ggcgctcccg gatggtaggg tgcgagtgac cccgcgcgac ttggaagggt tcaaacgacc 1860
ccgccgtacg aacttttgtc ggggggcgct cccggatggc cgccgtcatt gccaagtcct 1920
ccgtctccgc ggccgtggct cgcccggccc gctccagcgt gcgcccccatg gccgcgctga 1980 agcccgccgt caaggctgcc cccgtggctg ccccggctca ggccaaccag atgaccagca 2040
gccagtttac cccaactcac ataaggtaac ttagcagatg ttacccgcac ttgctcggtg 2100
ttcgctacca actgaccgca agcatcccaa gccccagtaa taaaggtgct tctggttcct 2160
tcaccaatgg agattggcgc ggtgaaatca ccaacttgta cttgcagagt ttctaagttg 2220
atgctgacat tagcttgagg attagcggct actaactctt gcaattgttt aacgatcgcc 2280
tcatcagcag tgacacaagg tacaccgatg gctacgcaat taccgaagaa aatttctgca 2340
aaactttcac caatcacgga ttgaatcccc catttagaaa gggcttgggg tgcgtgttcc 2400
cgtgaagaac cacagccaaa gttgcggtta actatgagga tatttgcgcc ttgatactgc 2460
ggttggtcaa aaggatgctc cccttttagg gctgtgcggt catcaataaa cgcgccttca 2520
cgtaacccat caaaggtaat ggctttgaga taacgagcag gaataatgcg atcggtatca 2580
atatcattac ccactaaggg tatgccacgc cctgtaactt ctttaacttc actgaccatt 2640
aaatggaggc gctcgttgat ctgagccttg ccccctgacg aacggcggtg gatggaagat 2700
actgctctca agtgctgaag cggtagctta gctccccgtt tcgtgctgat cagtcttttt 2760
caacacgtaa aaagcggagg agttttgcaa ttttgttggt tgtaacgatc ctccgttgat 2820
tttggcctct ttctccatgg gcgggctggg cgtatttgaa gcggttctct cttctgccgt 2880
ta 2882

<210> SEQ ID NO 140
<211> LENGTH: 2210
<212> TYPE: DNA
<213> ORGANISM: Artificial Sequence
<220> FEATURE:
<223> OTHER INFORMATION: Synthetic Construct- Sequence No. 140, Example 140: designer Nial-promoter-controlled chloroplast-targeted 2-Keto Acid Decarboxylase DNA construct (2210 bp)

<400> SEQUENCE: 140
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120

-continued

```
gaccccgcgc gacttggaag ggttcaaacg accccgccgt acgaactttt gtcggggggc    180
gctcccggat ggccgccgtc attgccaagt cctccgtctc cgcggccgtg gctcgcccgg    240
cccgctccag cgtgcgcccc atggccgcgc tgaagcccgc cgtcaaggct gcccccgtgg    300
ctgccccggc tcaggccaac cagatgtata cagtaggaga ttacctgtta gaccgattac    360
acgagttggg aattgaagaa atttttggag ttcctggtga ctataactta caatttttag    420
atcaaattat ttcacgcgaa gatatgaaat ggattggaaa tgctaatgaa ttaaatgctt    480
cttatatggc tgatggttat gctcgtacta aaaaagctgc cgcatttctc accacatttg    540
gagtcggcga attgagtgcg atcaatggac tggcaggaag ttatgccgaa aatttaccag    600
tagtagaaat tgttggttca ccaacttcaa aagtacaaaa tgacggaaaa tttgtccatc    660
atacactagc agatggtgat tttaaacact ttatgaagat gcatgaacct gttacagcag    720
cgcggacttt actgacagca gaaaatgcca catatgaaat tgaccgagta ctttctcaat    780
tactaaaaga aagaaaacca gtctatatta acttaccagt cgatgttgct gcagcaaaag    840
cagagaagcc tgcattatct ttagaaaaag aaagctctac aacaaataca actgaacaag    900
tgattttgag taagattgaa gaaagtttga aaaatgccca aaaaccagta gtgattgcag    960
gacacgaagt aattagtttt ggtttagaaa aaacggtaac tcagtttgtt tcagaaacaa   1020
aactaccgat tacgacacta aattttggta aaagtgctgt tgatgaatct ttgccctcat   1080
ttttaggaat atataacggg aaactttcag aaatcagtct taaaaatttt gtggagtccg   1140
cagactttat cctaatgctt ggagtgaagc ttacggactc ctcaacaggt gcattcacac   1200
atcatttaga tgaaaataaa atgatttcac taaacataga tgaaggaata attttcaata   1260
aagtggtaga agattttgat tttagagcag tggtttcttc tttatcagaa ttaaaaggaa   1320
tagaatatga aggacaatat attgataagc aatatgaaga atttattcca tcaagtgctc   1380
ccttatcaca agaccgtcta tggcaggcag ttgaaagttt gactcaaagc aatgaaacaa   1440
tcgttgctga acaaggaacc tcattttttg gagcttcaac aattttctta aaatcaaata   1500
gtcgttttat tggacaacct ttatggggtt ctattggata tacttttcca gcggctttag   1560
gaagccaaat tgcggataaa gagagcagac accttttatt tattggtgat ggttcacttc   1620
aacttaccgt acaagaatta ggactatcaa tcagagaaaa actcaatcca atttgtttta   1680
tcataaataa tgatggttat acagttgaaa gagaaatcca cggacctact caaagttata   1740
acgacattcc aatgtggaat tactcgaaat taccagaaac atttggagca acagaagatc   1800
gtgtagtatc aaaaattgtt agaacagaga atgaatttgt gtctgtcatg aaagaagccc   1860
aagcagatgt caatagaatg tattggatag aactagtttt ggaaaaagaa gatgcgccaa   1920
aattactgaa aaaaatgggt aaattatttg ctgagcaaaa taaatagtaa atggaggcgc   1980
tcgttgatct gagccttgcc ccctgacgaa cggcggtgga tggaagatac tgctctcaag   2040
tgctgaagcg gtagcttagc tccccgtttc gtgctgatca gtctttttca acacgtaaaa   2100
agcggaggag ttttgcaatt ttgttggttg taacgatcct ccgttgattt tggcctcttt   2160
ctccatgggc gggctgggcg tatttgaagc ggttctctct tctgccgtta               2210
```

<210> SEQ ID NO 141
<211> LENGTH: 1724
<212> TYPE: DNA
<213> ORGANISM: Artificial Sequence
<220> FEATURE:
<223> OTHER INFORMATION: Synthetic Construct- Sequence No. 141,
Example 141: designer Nial-promoter-controlled chloroplast-
targeted NADH-dependent Alcohol Dehydrogenase DNA construct (1724 bp)

<400> SEQUENCE: 141
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatgggcg gcggcttcga gtatctgacg gctgacgtca 360
agggtaatat cgccgttttc acccagatgg gtcatgccgt ggtcctccaa ctgctgcacc 420
aggtcggtaa tgccttgcgc accgatgtca taggcggaca ggcgggtcgg cacaccaagg 480
ttttcaaaga attcctccgt cttgcggata accgcattga tccgctcatc ttccgttcca 540
tcggtcaggt tccatacccg tactgcatac tgaagcagtt tggcacgctt ttcctcgcga 600
cgcaccttca gcagggcagg aaataccatg gccagcgtcc gggcgtggtc aatgtggtat 660
tttgccgtga tttcgtggcc gatcatatgc gtgctccagt catgtggcac ccctgcgccg 720
atcaggccat taagcgccaa tgtcgccacc cacatgaggt tggagcgcag gtcataatca 780
tcgggtgccg ccatgatacg tggcccgatt tccacaaggc tggagagcag cccttcggaa 840
aagcgatcct gcgccattcc gtccacagga taggtcatgt actgttccat cacatggacg 900
aaggagtcca caacaccgtt gataacctgc ttcatcggca ggctcatggt gcgtgtcggg 960
tcaagcacgg aaaagcgtgg atagaccagg ggattggaaa acaggagctt atccccagtg 1020
gactgccgtg aaatcacgct catgcagttc atttcagacc ccgtggcagg cagggtgacc 1080
accgtgccca gtggcagggc cttggtcgcg gctgtgcctt tgctggtcag gatgtcccat 1140
gcctcacctt catatgggac agcggcagcg acgaacttgg tcccatccat gacagagccc 1200
ccacccacgg caagcaggaa gtcgagccct tcttcacgca ccatggttac ggccttcatc 1260
agggtttcat aggtgggatt ggcctcgatg ccaccgaatt cccgaaaggt ccggctaccg 1320
agggcggcgc gtacctcggc aagcgtcccg ctgcgctcgg cgcttgaacc gccatacagg 1380
acgaggacac gggcctgggg tgacaactga tcatctagac ggccaatcat gcctttgccg 1440
aacaggacac gtgttgggtt atagaattcg aaattctgca ttaaatggag gcgctcgttg 1500
atctgagcct tgccccctga cgaacggcgg tggatggaag atactgctct caagtgctga 1560
agcggtagct tagctccccg tttcgtgctg atcagtcttt ttcaacacgt aaaaagcgga 1620
ggagttttgc aattttgttg gttgtaacga tcctccgttg attttggcct ctttctccat 1680
gggcgggctg ggcgtatttg aagcggttct ctcttctgcc gtta 1724

<210> SEQ ID NO 142
<211> LENGTH: 1676
<212> TYPE: DNA
<213> ORGANISM: Artificial Sequence
<220> FEATURE:
<223> OTHER INFORMATION: Synthetic Construct- Sequence No. 142, Example 142: designer Nial-promoter-controlled chloroplast-targeted NADPH-dependent Alcohol Dehydrogenase DNA construct (1676 bp)

<400> SEQUENCE: 142
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120

```
gaccccgcgc gacttggaag ggttcaaacg accccgccgt acgaactttt gtcgggggc     180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatgccta tatacttttt caaataattt ctttaaatct    360

tttaaattta cttctctgac atttccacta gtacaaatat cttcaagagc agatttagac    420

ataatattta tttcattaaa atatttttct tcatctattg ctaaatcttt tacacaacta    480

ggaagtccta agtttttatt taaaacttcc actgccacag ctaaactttc tgctccttct    540

tctgtattat ttgcaggaaa acctaaatct tttgaaattt cataatatct ttgagcagta    600

gttttatttt ctgaattgaa tctaattatg tagggtaata tagttccatt tatttttcca    660

tgagctatat gaaactttcc accaatagcg tgggctatac tatgatttat tcctaaacca    720

gatttttcaa aagcaaaacc tgctatacaa gatgcctttg ccatttcaat cctagcttcc    780

tcatctttta tatctctata cattctcaaa agatttttaa aaataagtct tatagctgaa    840

agagcatata tttgagtata aaaatttgct tctttgcaag tgtatgactc aatagcatga    900

gttagagcat ctatacctga atcagctaca actgattttg gtagtgtttt tgtaagttca    960

ggatctagta ttgcatattc aggtatcatc tcattatctt ttaatggaat ttttacatta   1020

ttctttttat ctgtaagaac tgcataggaa cttacttctg aacctgttcc acttgtagtt   1080

ggtaaggcta ttaaagggat agataatcca gatttttta caaaatattt aattgactta    1140

gcagtatcaa gagaagaacc tcctcctatt gctaccatca catctggaag aaaatcaata   1200

accttatcta aggctttact aactatttca aatgctggat caacttcaac ttcattaaaa   1260

atcctataat ctatattttt ttgcttaaat atattttcaa attttttagt cattcctatt   1320

tttgacataa ctgaatcagt tactataaag gctttttag ctttaatttt attaataact    1380

tcatcaaatt tgtctcctac ataaacattt gtatttactt caaaaatttt cattaaatgg   1440

aggcgctcgt tgatctgagc cttgcccct gacgaacggc ggtggatgga agatactgct    1500

ctcaagtgct gaagcggtag cttagctccc cgtttcgtgc tgatcagtct tttcaacac    1560

gtaaaaagcg gaggagtttt gcaattttgt tggttgtaac gatcctccgt tgattttggc   1620

ctctttctcc atgggcgggc tgggcgtatt tgaagcggtt ctctcttctg ccgtta       1676
```

<210> SEQ ID NO 143
<211> LENGTH: 3629
<212> TYPE: DNA
<213> ORGANISM: Artificial Sequence
<220> FEATURE:
<223> OTHER INFORMATION: Synthetic Coonstruct- Sequence No. 143,
      Example 143: designer Nial-promoter-controlled chloroplast-
      targeted Phosphoenolpyruvate Carboxylase DNA construct (3629 bp)

<400> SEQUENCE: 143

```
agaaaatctg gcaccacacc atggtagggt gcgagtgacc ccgcgcgact tggaagggtt     60

caaacgaccc cgccgtacga acttttgtcg ggggcgctc ccggatggta gggtgcgagt     120

gaccccgcgc gacttggaag ggttcaaacg accccgccgt acgaactttt gtcgggggc     180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatgaccg gtatttctca ttcctgccgc aattccatta    360

atggttaata gcgctcctct gagcaactct tccttagaat aacggaaatt aatgactcca    420

gactcagctt gtgcgttgta ctgacgtagg cgtttgatga gagatacttg caaaaatcct    480
```

agaggaacaa ttgttccatt gcgtaactga acagaacgct gtaaggtggg atcgccatct 540
aggagccgtt tattctcggt aatttctaag actaagcggc aagtgcgatg atattcttgg 600
gctatttgct caaacagccg ctcaaagcgt tctctatctt ccggttgaga caattccttt 660
acataatgat aggcaatttg caaatctacc ttagataagg tcatttccac ttttgagatg 720
accattttaa agaagggcca tttgagataa aaatagcgca acagtttcaa atgttcttca 780
ggttcggtgc taataaactg ttctaaagcg gttcctaccc cataccaagc gggtaacaga 840
aaacgggttt gagtccaact aaagacccaa ggaattgcgc gtagggtact gaggtctttt 900
ttcccacttt tacgtctagc cgggcgagaa ctaatttgga gttgactaat ttcttgaatg 960
ggggtgacag acatgaagaa atccacaaaa tccggttctt cataaatcaa ggcacgatag 1020
gctttacgag aacaactggc gagttcttcc atgatctcat tccaaacctg aatatcatca 1080
aagccgcagc ctaacaaact cgattgaata acggcagtaa caatggtttc taggttataa 1140
agggctaatt cagggagaga atatttagaa gcgaggactt ctccctgttc agtaatttta 1200
attctgccat taaccgtcgc tgtcggttga gcgagaatag cggcataagc gggtccaccg 1260
cctcgtccta ctgaaccccc gcgtccgtga aacaggcgta aatctaagcc atatctttta 1320
gcgacttttt gtaaagcttt ttgggcttta tgaatctccc aattactgct taaaaaccca 1380
gaatctttgt tactgtcgga ataaccgacc ataatttctt gtaggttagt gggttctaag 1440
agggggggtt taagttcgcc cacattttcc ccctgtaaag aggctaaatg atcatatcct 1500
cctgccaaag tggcgcggta aagagtcaat tcaaatagcg cccgcatgat ttcgggtgcc 1560
cgtttaaggt cttctacggt ttcaaatagg ggtacaatgc ggatcgtgct ggaacaagtg 1620
gccgggtcat agagtccggc ttcttgtgcc aagagaagaa cctctaagac atcgctgacc 1680
tcattagtca tactgataat gtaggtatga cagatctcta aaccaaattc ttgttgtagc 1740
tgccgcaaca tcctcaaggt ttctatcact tcgcaggttt tctcagaaaa cggcatttcc 1800
tggggaatga gaggacgacg agtttttaat tcttcgatta accaggcggt tctttcggct 1860
tcagtcagtt ggttgtaggg tttaggcaga atttgtaaat attctgctat ttcgttgatc 1920
gcatctgagt ggttactcga ctcttggcgg aaatctagtt gcgtgaggtt aaacccataa 1980
acttctacct gacaaattaa gctatctaat tcttgacaac ttaagccagt gctttctagg 2040
ttacgccgca ttaatttgag ttcttctata aactcttctt tattttggta attgttggcg 2100
ttggttgtct tgaacactaa aaggcgttct tctgggttag ctaggcggct attgcggtcg 2160
cgggtatttt ccaggcgttt tttaatataa gctaacttaa gacgataggg ttcttgacgg 2220
taacgaatgg ctaactgatt ataaacttgt gggatttgta cgcggtcttt ttctagggag 2280
tctaacaaat ccggcaggac gttacaccaa tggagggaag gactaaggat attcgataac 2340
tcatctaccc tttcgatata tttttcgata acgacattgc gttgataaca ggccgtggcc 2400
caagtcactt ctggtgtaac aaaggggttc ccatctcgat cgcctcccac ccaagagcca 2460
aaataacaga aattattctt cggtgggcgt agtctgggga aggcactttt tagagttcgt 2520
ttgagacgaa gggctaattg aggaattgcc tcaaagagga cttcattaaa atagtgtagg 2580
gagtagtcca cttcatctaa cacggtgggt ttaaactggt gtaactcatc ggtacgccac 2640
cagaggcgaa tttcttcttt aagctgttct ttagcttctt ctgcttccca ggagttggtt 2700
agccccattc ctctaaaggt ttcttctgcc tggtctaact tttgtaaaat atgagcgata 2760
cgccgttgtt tgcgtcgaat ggtgtggcga acaatttcgg tgggatgggc tgtaaaaacc 2820
aggcgcacat ctagttgttc gagtaggcgt tgaatttgtt gaggtggaac atttaattgt 2880
tttaaatagg gaaatagcca gtgaaaagtt cctatttttt gatcattttg tttttcatcg 2940
ttcaaacttc tttctaacca atttgctcca aatgccgagg agaatatact ggtttgctcg 3000
ccgttaatgc catttttggc actggactct ccttcattgt aggtggcccg tcgtgagagt 3060
tgttggtctc gttgttcgta gtgttgttca acaatattaa tgagttggaa atagagagca 3120
aaagcgcgag acgttcttac tgcttcattg aggtcgagtt tttcaatcaa ttgggtaatg 3180
gagtcttcta acgctttttg ggcttgtcct tgttcagaac aaattgcacg cagttttatg 3240
agcagatcca ccaaatcttg cccgcattct gcctttagca cggcttccca taaatcttcg 3300
actaatttta gtctagcttg taaaaataag tctgatgtgg agaagaattg taatggggtt 3360
gtggggactt gaactagcga actcattaaa tggaggcgct cgttgatctg agccttgccc 3420
cctgacgaac ggcggtggat ggaagatact gctctcaagt gctgaagcgg tagcttagct 3480
ccccgtttcg tgctgatcag tctttttcaa cacgtaaaaa gcggaggagt tttgcaattt 3540
tgttggttgt aacgatcctc cgttgatttt ggcctctttc tccatgggcg ggctgggcgt 3600
atttgaagcg gttctctctt ctgccgtta 3629

<210> SEQ ID NO 144
<211> LENGTH: 1745
<212> TYPE: DNA
<213> ORGANISM: Artificial Sequence
<220> FEATURE:
<223> OTHER INFORMATION: Synthetic Construct- Sequence No. 144, Example 144: designer Nial-promoter-controlled chloroplast-targeted Aspartate Aminotransferase DNA construct (1745 bp)

<400> SEQUENCE: 144
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gccccccgtgg 300 ctgccccggc tcaggccaac cagatgaacc gagacaccaa gcaggctgtt ttggaagagc 360
tgtaaccgtt ccagaccctt ttcaatcgtt tggcagtcag tggcgtagga gagccggatg 420
ctgcgatcgt cgccaaaggc aatgccggga atggctgcaa cttgatgttg atccaacagt 480
tgacggcaat aggtcatcga gtcgagacct gttttgctga tgtccacgaa gacgtagaac 540
gccccttccg gtattggaca ggagagcccc gcgatttgat tcagtccgtt caagatcaac 600
tgacgccgct ccgtaaaggc agccagcatt tctgccacac aatcctgtgg accttgcaga 660
gctgcgatcg cgccgtactg ggcaaaggtg cagacgtttg aggtgctgtg gctttgcagc 720
gatgcagcag cagcaattag ctcgctcgga cccgcgaggt agccaacccg ccatcctgtc 780
atcgagtagg ctttggcgaa gccgttgctg atcagcgttc gttcaaaaca ggcggggctc 840
aagctgccaa tgctgtggtg atcggctccg tcgtaaagga tcttttcgta aatttcatca 900
gaaacgaccc aaaagtcatg ggcttcaatg atcggcgcga tcgcttccag ttcttgccgg 960
ctatagacca tccccgtggg attggagggg gaattcagca ctagcagccg tgtccgaggc 1020
gtaatcgccc ctgccaattg ctgcggctgg agtttaaagc cgtcgctggc gaaagtttca 1080
acgatgacgg gcacaccgcc cgccaacttg accatttcgg gatagctcaa ccagtaaggt 1140
gcggggataa tcacctcatc gcccggatcg agcagcacct gcatcaggtt gtagagtgac 1200

```
tgcttaccgc cattggtgac gagaatgttg gcggcttggt aatcgagtcc gttgtcggcg   1260

cgcaattttt gggcgatcgc ttcgcgcaga tcaggttcac cggctgcagg accgtagcga   1320

gttttgccct ctgctagcgc ttgagctgct gcattgcgaa tgtgcaaagg tgtttcaaag   1380

tcgggctccc cggcgctgaa gctgcagaca tccaagccct cagctttcat cgctttggct   1440

tgggcagcga tcgcgagagt caacgatggt gacactcgcc ccacacgctc ggatagtttc   1500

attaaatgga ggcgctcgtt gatctgagcc ttgccccctg acgaacggcg gtggatggaa   1560

gatactgctc tcaagtgctg aagcggtagc ttagctcccc gtttcgtgct gatcagtctt   1620

tttcaacacg taaaaagcgg aggagttttg caattttgtt ggttgtaacg atcctccgtt   1680

gattttggcc tctttctcca tgggcgggct gggcgtattt gaagcggttc tctcttctgc   1740

cgtta                                                               1745
```

<210> SEQ ID NO 145
<211> LENGTH: 2366
<212> TYPE: DNA
<213> ORGANISM: Artificial Sequence
<220> FEATURE:
<223> OTHER INFORMATION: Synthetic Construct- Sequence No. 145, Example 145: designer Nial-promoter-controlled chloroplast-targeted Aspartokinase DNA construct (2366 bp)

<400> SEQUENCE: 145

```
agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcggggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gccccccgtgg   300

ctgccccggc tcaggccaac cagatggcgt taattgtcca aaaatacggt ggaacctctg    360

tcggttcagt agaacgcatt caaacagttg cccaacggat tcaaaaaaca gcccaaaatg    420

gcaatcaagt cgtggttgtt gtttcggcca tgggaaaaac caccgatact ttagtcaatt    480

tagccaaaga gattacccca aatccctgtc gtcgggaaat ggatatgtta ttgtccacgg    540

gagaacaagt atcgatcgcc ttgatgagta tggccttaca gaaattagga caagcggcca    600

tctccttaac tggggcacaa gtggggatcg tcaccgaagc agaacacagt cgagcccgca    660

tcctttccat taaaccccat cgcattcaac gccatctcga tcgcggtgaa gttgtcgtgg    720

tcgccgggtt tcaaggcatt actaacgcag atgacttaga aattaccacc ctagggcgag    780

gggggctcaga tacctccgcc gtcgccattg cggcagcctt aaaagccagt tgctgcgaaa   840

tctatacaga tgtccccggc attctcacca ccgatccccg catcgtcccc gatgcccaat    900

taatgggggga aattacctgc gatgagatgc tagagttggc cagtttaggg gctaaggttc   960

ttcatccgag ggcggtggaa attgcgcgta attatggcat tcctttagtg gtgcgatcga   1020

gttggagtga tgcccccgga acccgcgtga cttctcccat tcctaaaccg cgatcgctag   1080

aaggcttaga actgacaaaa gccgttgatg gggtgcaatt tgaccccgat caagccaaaa   1140

tcgccttgtt acgagtcccc gatcgccccg gagtcgctgc ccgcctattt ggggaaattg   1200

cccaccagca ggtggatgta gacttaatta ttcaatcgat ccacgaaggg aatagtaacg   1260

atatcgcctt tacggtggtt aaaaatgtac tcactaaggc cgaagccgtc gctgaagcga   1320

tcgccccggc tttacggagt cattcagcga atagcgatga agcagaggta ttagtcgaga   1380
```

cgggagtggc gaaaattgcc atttcagggg caggaatgat cggacggcca ggtattgccg 1440
cgaaaatgtt caaaattctc gcccaagagg ggattaatat cgaaatgatc tccacctcgg 1500
aagtgaaggt cagttgtgtg attcgtcaag aagagggcga tcgcgccatt aaagccctat 1560
gccaagggtt tgaggtggaa ttgtccccga cggggattcc tgagtcagta gtagcggtgt 1620
tacctccagt tcgaggagtc gctttagatg aaaaacaagc acaaatcgcc ctaattcatg 1680
ttcaagatcg gccggggatg gctgctagta tctttggagt cttagcggat cataacatca 1740
gtattgatac gattattcaa tcccaacgct gtcgaattgt tgagggaata cccacccgtg 1800
atatcgcctt taccgttgcc caaattgatg tagaagctgc tcaaaatgcg ttaaaaaccc 1860
tagccagtgc gtttagtgaa atgatcgtcg atagcgatgt tgctaaagtc agtattgtag 1920
gggcgggaat ggcgggacaa cccggggtag cggccaagtt ttttgatgct ttagctagac 1980
atcaaattaa tattaaaatg attgcaactt cagaaataaa aattagttgt gttgttagca 2040
aagatcaagg aattaaagct ttaaaagcag ttcatgaagc ctttcaatta gccggagaag 2100
aacgggtaga agttccagct taataaatgg aggcgctcgt tgatctgagc cttgcccccct 2160 gacgaacggc ggtggatgga agatactgct ctcaagtgct gaagcggtag cttagctccc 2220
cgtttcgtgc tgatcagtct ttttcaacac gtaaaaagcg gaggagtttt gcaattttgt 2280
tggttgtaac gatcctccgt tgattttggc ctctttctcc atgggcgggc tgggcgtatt 2340
tgaagcggtt ctctcttctg ccgtta 2366

<210> SEQ ID NO 146
<211> LENGTH: 1604
<212> TYPE: DNA
<213> ORGANISM: Artificial Sequence
<220> FEATURE:
<223> OTHER INFORMATION: Synthetic Construct- Sequence No. 146, Example 146: designer Nial-promoter-controlled chloroplast-targeted Aspartate-Semialdehyde Dehydrogenase DNA construct (1604 bp)

<400> SEQUENCE: 146
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatgtcag attcatacag agtagcaata ttaggagcaa 360
ctggtgcagt aggtacggaa ttactagaat tactggaaac tcggaacttt ccagtaggag 420
aattaaaact cttagcttca gaattttcag cgggtaagac cttaaaattt aaggaacaaa 480
gtttacaagt agaagctgta acaaatgatt catttaataa agtagattta gtgctagcat 540
cagcaggtgc atctgtatca aaagtatggg caaagaaagc agtagaggct ggagctgtag 600
ttattgacaa ttctagtgct tttcgtatgg actcccaagt acctcttgta gtcccagaag 660
ttaacccaga agcagcggct ttacataaag gtatagttgc taaccctaac tgcacaacaa 720
tattaatgag tgtagcagtg tggccattgc acaaaatcca gccagtccaa aggttagtag 780
tggccactta tcaatcagca agtggggccg ggtcaagggc tatggcagaa atgaaaattc 840
aggcccaaga aatcttagat ggaaaaactc caacaacaga tatttttccc tacccattag 900
catttaattt gttccctcat aattctcaac tcaatgagca gggatattgt caagaagaaa 960

```
tgaaaatgct tgatgaaacc agaaaaatat ttggctctaa ggaactgaga attacagcaa   1020

cttgtattcg agtaccagta ttaagagctc attcagaagc aattaatttg gaatttgctg   1080

aaccatttag tgtagttaaa gcacgggaag tattaagtca agcaccagga gtgacactgg   1140

tagaaaattg gcaagaaaat tattttccta tgcctatggt tgcaagtggt aaagatgatg   1200

tattggtggg gagaattcgt caggatattt ctcaagctga ggggttagaa ttatggttaa   1260

gtggagacca ggtaagaaaa ggagctgcct tgaatgcagt acaaatagct gaattattgg   1320

tggcaaaaaa ttggctgaga ataccagtag gaacatttta ataaatggag gcgctcgttg   1380

atctgagcct tgcccccctga cgaacggcgg tggatggaag atactgctct caagtgctga   1440

agcggtagct tagctccccg tttcgtgctg atcagtcttt ttcaacacgt aaaaagcgga   1500

ggagttttgc aattttgttg gttgtaacga tcctccgttg attttggcct ctttctccat   1560

gggcgggctg ggcgtatttg aagcggttct ctcttctgcc gtta                    1604
```

<210> SEQ ID NO 147
<211> LENGTH: 1868
<212> TYPE: DNA
<213> ORGANISM: Artificial Sequence
<220> FEATURE:
<223> OTHER INFORMATION: Synthetic Construct- Sequence No. 147, Example 147: designer Nial-promoter-controlled chloroplast-targeted Homoserine Dehydrogenase DNA construct (1868 bp)

<400> SEQUENCE: 147

```
agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcggggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gccccccgtgg   300

ctgccccggc tcaggccaac cagatgaagc actcgcagga cgctaggaat gctattaatc    360

gcttgagatt gctcaatttc agctaaggct tgccgaaaat tgccttctcg tacatcatga    420

gtgaccacga cgatttctgc taactgtccc tgaaatccaa tttgaacgac ggattctaga    480

ctaacatggt gctgaccaaa acaagttcct aaatgcccaa tcaccccagg gacatcttca    540

cagagaaagc gggcataaaa gcgagttttt aaatcttcaa ttggggtcag actacaataa    600

tgttgatggg tgacgttcaa taaaggatct aaagattgtg cttgtcctcc actgctttgc    660

agaatgccga cgatattcat aatatctgaa acgactgcac tggcggttgg acctgccccc    720

gcaccgggtc caaaaaacat cacttgtcct aacggttctc ccttgaccaa aatggcgtta    780

taaaccccat taatactggc tagtggatga tctttggcta ttaaagtggg atgtactcgc    840

acttgtaagg tttctgaatc atctccttta gaaccttggg caatggctaa taatttaatc    900

acaaatccga gtttatcagc ataagtaata tcggcggcac tgacttgacg aatgccctca    960

caataaatct cttcgcgttt tacccgtccg gcaaaaccga tggaggccaa aatagcaatt   1020

ttatcggctg catctaatcc gtctacatct gccgtcggat cggcttcagc atagcctaat   1080

ttttgggctt ctgctaatac ctcgccaaaa tcggctccct cagaggtcat ttggctgagg   1140

atataattgg tcgttccgtt aataatgcca ataatattac taatccgatt ggcccctaat   1200

gattgtttga ggggtttaat cactggaatt cccccccca cagccgcttc taataacaca    1260

taaacgccgg ctgcattggc cgcttcataa atttcatccc cataacgagc gatcactgcc   1320

ttattggccg tgacaatgtg ctttttatgg gcaatggcct tcatgatgag tgacttggct   1380
```

ggttctagtc ctccgagcag ttctacgaca atatcaatct ctggatcaat gacaatactt 1440
tctagatctg ttgtaatcac ggcgggaggg agttgaactt gacggggttt gtcaagagag 1500
cgcactcctg cccgtttaat ctcgatatct tttaagatag gattacgtcc ccagggatcg 1560
agtagaattt gtgctgtccc cgttcccaca gttcccaagc ctaataaacc tattttaaat 1620
gccactaaat ggaggcgctc gttgatctga gccttgcccc ctgacgaacg gcggtggatg 1680
gaagatactg ctctcaagtg ctgaagcggt agcttagctc cccgtttcgt gctgatcagt 1740
ctttttcaac acgtaaaaag cggaggagtt ttgcaatttt gttggttgta acgatcctcc 1800
gttgattttg gcctctttct ccatgggcgg gctgggcgta tttgaagcgg ttctctcttc 1860
tgccgtta 1868

<210> SEQ ID NO 148
<211> LENGTH: 1472
<212> TYPE: DNA
<213> ORGANISM: Artificial Sequence
<220> FEATURE:
<223> OTHER INFORMATION: Synthetic Construct- Sequence No. 148,
Example 148: designer Nial-promoter-controlled chloroplast-
targeted Homoserine Kinase DNA construct (1472 bp)

<400> SEQUENCE: 148
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatgatta acaattttgg ccccttccat atctaaagag 360
agtgcttgca cttgcgccgc taccccttca ttttcccacg ccaccctcat cgcttcagtc 420
accctatccg cttcaccctg agaacttaaa gcgagtaaag tgggacctgc cccactgatt 480
accataccat aagccccggc tgcgatagcc gctcgtttca ccgcttcgta acctttaatt 540
aaaccttgac gatagggttg atgcagctta tcctccatcg ccatagctaa ccagtctcct 600
cgcccctgtt cgagtccttg taacaataac cctaaacgtg caatattaaa aatagcatca 660
gcgcggctat actgagtggg taaaacgcct ctcgcttctt gagtagataa ttcaaaatcc 720
ggaatagcca caatgggaat cagtttgtca taccagggaa tctcgcaaat ttgccaattc 780
cccatttccc ccacacataa gcgactgctt cccaataaag cgggaaccac attatcggga 840
tgtccttcta aagatatggc taattccatc acttcagatt gagttaaagg gttaccggct 900
agataatttg cccccactaa accccctaca atggctgtgg ctgaacttcc taaccctctg 960
gctaaaggaa cccctaattt gatctcaatt tctacagcag gaaccggttg attgagatgt 1020
tgatagaaaa gcgcaaaaga ttgataaagt aaattagttt tatctcgact aacccgttct 1080
gcttctgcgc cgcttacgag aattttctct tcggtttctg aagtgagagt aaacttaaat 1140
tgattataaa gggttaaagc ggctcctaga caatcaaagc ctggaccaag attagcggta 1200
gtagcaggaa cggttagggt aacggtcatt aaatggaggc gctcgttgat ctgagccttg 1260
ccccctgacg aacggcggtg gatggaagat actgctctca agtgctgaag cggtagctta 1320
gctccccgtt tcgtgctgat cagtcttttt caacacgtaa aaagcggagg agttttgcaa 1380
ttttgttggt tgtaacgatc ctccgttgat tttggcctct ttctccatgg gcgggctggg 1440
cgtatttgaa gcggttctct cttctgccgt ta 1472

<210> SEQ ID NO 149
<211> LENGTH: 1655
<212> TYPE: DNA
<213> ORGANISM: Artificial Sequence
<220> FEATURE:
<223> OTHER INFORMATION: Synthetic Construct- Sequence No. 149, Example 149: designer Nial-promoter-controlled chloroplast-targeted Threonine Synthase DNA construct (1655 bp)

<400> SEQUENCE: 149
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac caggtgaccc taacttggcc tatttctaaa tctgcgtcct 360
ggtcaggtct gatcaacgcc taccgttcct atttacctgt cacggaagcc actccgattg 420
tcaccctgca tgaagggaac acgcccctga ttccggtgcc cagcattgcc gctgaaattg 480
gccggcaagt tcaggtctat gtcaagtacg acggtttgaa ccccacgggc agctttaaag 540
atcggggtat gaccatggcg atctccaagg ctaaggaagc cggagccaag gcggtgatct 600
gtgccagtac cggcaatacc tctgcggcgg cagcggccta tggacggcgg ggcggcatgc 660
gggtctttgt cctcatcccc gatggttatg tcgctctggg aaaattagcc caagccctgg 720
tctatggcgc agaggtgctg gccattcagg gcaactttga tcaggcattg accctggtgc 780
agcaattagc cgaaacccag cccgtcaccc tggtgaattc cgtcaacccc taccggctgg 840
aaggtcagaa aactgctgcc tttgaagtgg tggatgccct gggtaatgcc cccgactggc 900
tctgtattcc cgtgggcaat ggcggcaata tcaccgctta ctggatggga ttctgtcagt 960
atcgggaaca ggatcgttgc gatcgtctac cccggatgat gggttttcaa gcagccggct 1020
ctgctcccct tgtccatggc caggtggtga cccatcctga aactgtagcg accgccattc 1080
ggattggtaa cccggccaac tggcagcggg cgatggccgt gcgggatgcc agccagggag 1140
aattcaatgc tgtcagcgat gccgaaattc tcgctgccta ccgtctgctg gccagtcagg 1200
aagggatctt ttgtgaaccc gccagtgccg cgtccgtcgc cggtctatta aaggtgaaag 1260
atcaggttcc gacgggggca acggtggtct gtgtcctgac ggggaatgga ttgaaagatc 1320
ctgatagcgc aattaagcag caaagtaacc agttccatca gggcatccca gctcagctcg 1380
aagccgtggc agccgtgatg ggcttccgtt agtaaatgga ggcgctcgtt gatctgagcc 1440
ttgcccccctg acgaacggcg gtggatggaa gatactgctc tcaagtgctg aagcggtagc 1500
ttagctcccc gtttcgtgct gatcagtctt tttcaacacg taaaaagcgg aggagttttg 1560
caattttgtt ggttgtaacg atcctccgtt gattttggcc tctttctcca tgggcgggct 1620
gggcgtattt gaagcggttc tctcttctgc cgtta 1655

<210> SEQ ID NO 150
<211> LENGTH: 2078
<212> TYPE: DNA
<213> ORGANISM: Artificial Sequence
<220> FEATURE:
<223> OTHER INFORMATION: Synthetic Construct- Sequence No. 150, Example 150: designer Nial-promoter-controlled chloroplast-targeted Threonine Ammonia-Lyase DNA construct (2078 bp)

<400> SEQUENCE: 150
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatgtaag aagagtcgat aggctggatt gtcactttcg 360
ttccagtacc gatagcccag ggttttgaga aatgattccc actgagccat ctcttgtgga 420
gggacttgca tcccgacgac gattctgccg tagtctgcgc cgtgattgcg gtagtggaat 480
aggctgatgt tccaatctgg gctcattttc gtgacaaagt tagctaatgc gcccggtcgc 540
tcaggaaatt caaaccgata gagcagttcg ttttgagcta gcggtgactt gccgcctacc 600
atgtgccgca aatgcatctt ggctagctca tcatcagtta gatctagcgt cttaaatcca 660
ttgtctctaa acttgtgggc gatcgcctgc gcatcggctc tattttctat ctgaatgccc 720
acaaaaatat gagcttgatc ggcatctgca atccgatagt tgaattcgct aaggctgtgg 780
ctaccgagga tatcgcaaaa tttgctgaga ctgcctgccc gctctggaat cgtaacggca 840
aagacggctt ctcttccttc tcctagctcg gctcgctcgg ctacaaagcg cagacgatca 900
aagttcatat tggccccaca agcgatcgcc accaacgttt ctccctgaat ttcttctcgc 960
tctacatagg ctttgatacc tgcgatcgcg agcgccccag cgggttccaa aattgagcga 1020
gtatcttcaa atacgtcctt gatcgcggcg caggtatcat ctgtagttac cagcaacaca 1080
tcatcgacat actgttggca cagacgaaac gtttcctccc cgacctggcg caccgctacg 1140
ccatctgcaa acaggcctac ttgatccaac ttgacacgat tccctttttgc taatgattga 1200 cgcatggcat cagcatccac cggctccaca ccaatgatct taacttcagg acgtaagcgt 1260
ttgatataag cggcaatgcc cgaaattaaa ccaccccccc caatcgcaac aaaaatggca 1320
tgaatcggct tctgatgctg tcgcaagatc tccatgccga tcgttccctg cccggcaatg 1380
acgtctggat cgtcaaacgg atgcacaaag gtaagtcctt tttccacttc tagctggcgt 1440
gcgtgtgcat aggcatcgtc gtaggtgtca ccgtgtaaga caacgagtcc gcctctggcc 1500
ttcaccgcat caatcttgac ttgcggcgtc gtgatcggca taacaattac cgctgacgta 1560
cccaattctc tagcgcctag cgccaccccc tgtgcgtggt tgcccgcaga agctgcaatc 1620
accccacgct gcaacagttc tgaaggtagc tgcgccattt tgttataggc accgcgtagt 1680
ttgaaggaga aaacagactg tacatcttcc cgttttagca gcacctgatt acctagccgc 1740
tccgatagcc tcggcgcgat atctaaaggc gtttcttgcg ccacgtcata aacgcgggcc 1800
ttcaaaatgc gttctaaata gtcagaataa accactaaat ggaggcgctc gttgatctga 1860
gccttgcccc ctgacgaacg gcggtggatg gaagatactg ctctcaagtg ctgaagcggt 1920
agcttagctc cccgtttcgt gctgatcagt ctttttcaac acgtaaaaag cggaggagtt 1980
ttgcaatttt gttggttgta acgatcctcc gttgattttg gcctctttct ccatgggcgg 2040
gctgggcgta tttgaagcgg ttctctcttc tgccgtta 2078

<210> SEQ ID NO 151
<211> LENGTH: 2282
<212> TYPE: DNA
<213> ORGANISM: Artificial Sequence
<220> FEATURE:

<223> OTHER INFORMATION: Synthetic Construct- Sequence No. 151, Example 151: designer Nial-promoter-controlled chloroplast-targeted Acetolactate Synthase DNA construct (2282 bp)

<400> SEQUENCE: 151

```
agaaaatctg gcaccacacc atggtagggt gcgagtgacc ccgcgcgact tggaagggtt     60
caaacgaccc cgccgtacga acttttgtcg gggggcgctc ccggatggta gggtgcgagt    120
gaccccgcgc gacttggaag ggttcaaacg accccgccgt acgaactttt gtcggggggc    180
gctcccggat ggccgccgtc attgccaagt cctccgtctc cgcggccgtg gctcgcccgg    240
cccgctccag cgtgcgcccc atggccgcgc tgaagcccgc cgtcaaggct gcccccgtgg    300
ctgccccggc tcaggccaac cagatgttga caaaagcaac aaaagaacaa aaatcccttg    360
tgaaaaacag aggggcggag cttgttgttg attgcttagt ggagcaaggt gtcacacatg    420
tatttggcat tccaggtgca aaaattgatg cggtatttga cgctttacaa gataaaggac    480
ctgaaattat cgttgcccgg cacgaacaaa acgcagcatt catggcccaa gcagtcggcc    540
gtttaactgg aaaaccggga gtcgtgttag tcacatcagg accgggtgcc tctaacttgg    600
caacaggcct gctgacagcg aacactgaag gagaccctgt cgttgcgctt gctggaaacg    660
tgatccgtgc agatcgttta aaacggacac atcaatcttt ggataatgcg gcgctattcc    720
agccgattac aaaatacagt gtagaagttc aagatgtaaa aaatataccg gaagctgtta    780
caaatgcatt taggatagcg tcagcagggc aggctggggc cgcttttgtg agctttccgc    840
aagatgttgt gaatgaagtc acaaatacga aaaacgtgcg tgctgttgca gcgccaaaac    900
tcggtcctgc agcagatgat gcaatcagtg cggccatagc aaaaatccaa acagcaaaac    960
ttcctgtcgt tttggtcggc atgaaaggcg gaagaccgga agcaattaaa gcggttcgca   1020
agcttttgaa aaaggttcag cttccatttg ttgaaacata tcaagctgcc ggtacccttt   1080
ctagagattt agaggatcaa tattttggcc gtatcggttt gttccgcaac cagcctggcg   1140
atttactgct agagcaggca gatgttgttc tgacgatcgg ctatgacccg attgaatatg   1200
atccgaaatt ctggaatatc aatggagacc ggacaattat ccatttagac gagattatcg   1260
ctgacattga tcatgcttac cagcctgatc ttgaattgat cggtgacatt ccgtccacga   1320
tcaatcatat cgaacacgat gctgtgaaag tggaatttgc agagcgtgag cagaaaatcc   1380
tttctgattt aaaacaatat atgcatgaag gtgagcaggt gcctgcagat tggaaatcag   1440
acagagcgca ccctcttgaa atcgttaaag agttgcgtaa tgcagtcgat gatcatgtta   1500
cagtaacttg cgatatcggt tcgcacgcca tttggatgtc acgttatttc cgcagctacg   1560
agccgttaac attaatgatc agtaacggta tgcaaacact cggcgttgcg cttccttggg   1620
caatcggcgc ttcattggtg aaaccgggag aaaaagtggt ttctgtctct ggtgacggcg   1680
gtttcttatt ctcagcaatg gaattagaga cagcagttcg actaaaagca ccaattgtac   1740
acattgtatg gaacgacagc acatatgaca tggttgcatt ccagcaattg aaaaaatata   1800
accgtacatc tgcggtcgat ttcggaaata tcgatatcgt gaaatatgcg gaaagcttcg   1860
gagcaactgg cttgcgcgta gaatcaccag accagctggc agatgttctg cgtcaaggca   1920
tgaacgctga aggtcctgtc atcatcgatg tcccggttga ctacagtgat aacattaatt   1980
tagcaagtga caagcttccg aaagaattcg gggaactcat gaaaacgaaa gctctctagt   2040
aaatggaggc gctcgttgat ctgagccttg ccccctgacg aacggcggtg gatggaagat   2100
actgctctca agtgctgaag cggtagctta gctccccgtt tcgtgctgat cagtcttttt   2160
caacacgtaa aaagcggagg agttttgcaa ttttgttggt tgtaacgatc ctccgttgat   2220
```

tttggcctct ttctccatgg gcgggctggg cgtatttgaa gcggttctct cttctgccgt 2280
ta 2282

<210> SEQ ID NO 152
<211> LENGTH: 1562
<212> TYPE: DNA
<213> ORGANISM: Artificial Sequence
<220> FEATURE:
<223> OTHER INFORMATION: Synthetic Construct- Sequence No. 152, Example 152: designer Nial-promoter-controlled chloroplast-targeted Ketol-Acid Reductoisomerase DNA construct (1562 bp)

<400> SEQUENCE: 152
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatgagcc ttttttagcc aactaaacat agctcgtaaa 360
tctttaccga cttcttcaat aggatgttca gcttcttgac gacgcatggc gataaatccg 420
ggttttcctg actggttttc taagacaaat tcccgagcaa attgaccgga ttgaatttct 480
ttaaggattt tccgcatttc ttgccgggtt tgatccgtaa caatacgagg acctctagta 540
tagtctccat attctgccgt attggaaatg ctatcgcgca tcttagctaa tccgccttct 600
accaccagat caacgattag tttaacttcg tggagacatt caaaataagc caattcaggc 660
tgatatccgg cttcgactaa ggtttcaaat ccggctttaa ttaaagcact tagaccgcca 720
cagaggacta cttgttcacc aaataaatca gtttctgttt cttctcggaa agtcgtttct 780
aaaacaccgg cacgagttcc tccaatccct ttagcataag ccatagcgcg atcgcgggct 840
tgtcctgaag catcttgaaa gactgcaaat aaacagggga ctccttcgcc ttgggtgtag 900
gtacgtctga cgagatgtcc tggacctttt ggtgccacca taaccacatc taccgtagaa 960
ggaggaatta cttgtccaaa atgaatatta aatccatgag caaacaaaag aactttgcct 1020
tcttttaaat ggggttcaat ttcattttta tagacgcttt tttgtacctc atctggcagc 1080
aaaatcataa tccagtcggc ggcggcggcg gcatcggcta cacttttaac cgttaagccg 1140
gcttcagtgg ctttttgggc tgacttactc ccaggataca gccccacaat aacattaact 1200
ccgctatctt taagattaag ggcatgggca tggccttgag aaccatagcc gataatggca 1260
accgttttat tagcaagtaa gtctaaattg gcatcttcat cgtaatacat tcgagccatt 1320
aaatggaggc gctcgttgat ctgagccttg ccccctgacg aacggcggtg gatggaagat 1380
actgctctca agtgctgaag cggtagctta gctccccgtt tcgtgctgat cagtcttttt 1440
caacacgtaa aaagcggagg agttttgcaa ttttgttggt tgtaacgatc ctccgttgat 1500
tttggcctct ttctccatgg gcgggctggg cgtatttgaa gcggttctct cttctgccgt 1560
ta 1562

<210> SEQ ID NO 153
<211> LENGTH: 2252
<212> TYPE: DNA
<213> ORGANISM: Artificial Sequence
<220> FEATURE:
<223> OTHER INFORMATION: Synthetic Construct- Sequence No. 153, Example 153: designer Nial-promoter-controlled chloroplast-targeted -continued Dihydroxy-Acid Dehydratase DNA construct (2252 bp)

<400> SEQUENCE: 153

```
agaaaatctg gcaccacacc atggtagggt gcgagtgacc ccgcgcgact tggaagggtt     60
caaacgaccc cgccgtacga acttttgtcg gggggcgctc ccggatggta gggtgcgagt    120
gaccccgcgc gacttggaag ggttcaaacg accccgccgt acgaactttt gtcggggggc    180
gctcccggat ggccgccgtc attgccaagt cctccgtctc cgcggccgtg gctcgcccgg    240
cccgctccag cgtgcgcccc atggccgcgc tgaagcccgc cgtcaaggct gcccccgtgg    300
ctgccccggc tcaggccaac cagatgtcag ataattacag aagtcgcatc attacacaag    360
gcagtcaacg tacaccaaac cgggccatgc ttcgggcggt aggttttgga gataatgact    420
ttactaagcc cattgtggga gtggctaacg gatacagcac cattacccct tgtaatatgg    480
gcatcaatga tctcgcgctg cgggccgaag ccggactcaa gcaagcggga gccatgccgc    540
aaattttcgg caccattacc gtgagtgacg gaatttctat gggaacagaa ggaatgaaat    600
actccctcgt ctcgcgcgat gtgatcgctg actctatcga aaccgcttgt aacggtcaaa    660
gtatggatgg tgtgcttgcc attggcggct gtgataaaaa tatgcccggg gccatgatcg    720
ccatcgctcg tatgaatatc cctgctatct tcgtctatgg cggtaccatt aaacccggaa    780
aatacaacgg acaagattta accgttgtca gtgcctttga agccgtagga caacatagtg    840
ccggtaaaat agatgatgct caattattag gaatagaacg gaatgcttgc cccggggcgg    900
gttcctgtgg gggaatgttt accgctaaca ccatgtcctc cgcttttgaa gtaatgggga    960
tgagcttacc ttattcttcc actatggcag cagaagatgc agaaaaagcc gacagtaccg   1020
aaaaatccgc ttttgtgctg gtagatgcca tcagaaagca aattttgccc agtcagattt   1080
taacccgtaa agcctttgag aatgcgattt ccgtgattat ggccgttggg ggatcgacca   1140
acgcggtttt acatttatta gcgatcgctc ataccatagg ggtagaactg agcatcgatg   1200
actttgaagc cattagagct agagttcccg tactttgtga cctcaaaccg agtggacgct   1260
atgtcatcgt tgatttacat caggcggggg gcattcccca agtgatgaaa atgcttctcg   1320
tccatgactt attacacggg gatgctttaa ccatcaccgg tcaaacggtt gcagaagttt   1380
taaaagacgt acccgatgaa ccccctcaag gacaagatgt cattcgtcct tggaataacc   1440
cagtgtataa agaaggacac ctagcgatct taaaaggaaa tttagccacc gagggagcag   1500
tcgctaaaat tagcggggtc aaaaatccta aaattaccgg tccggcgcga gtatttgaat   1560
ccgaggaaag ctgtctagag gcgattcttg caggtaaaat tcaagctggc gatgtgatta   1620
ttgttcgtta tgaagggccc aaaggtggcc ccggtatgag agaaatgtta gccccgactt   1680
cagccattat tggggcagga ttgggagatt ccgtaggatt aattactgat gggcgttttt   1740
ctgggggaac ttacgggcta gtcgtcggtc atgttgcccc agaagcagca gtaggcggaa   1800
atattgccct cgtacaagag ggagatagca ttaccattga tgcgaaagag cgattattac   1860
agcttaatgt agctgaagat gaattaatcc gtcgtcgcgc taactggcaa ccgcccatcc   1920
ctcgttatac caaaggtgta ttagcgaaat atgccaaatt agtctcttct agtagtatag   1980
gagcggttac cgacaaagat ttattctaat aaatggaggc gctcgttgat ctgagccttg   2040
ccccctgacg aacggcggtg gatggaagat actgctctca agtgctgaag cggtagctta   2100
gctccccgtt tcgtgctgat cagtcttttt caacacgtaa aaagcggagg agttttgcaa   2160
ttttgttggt tgtaacgatc ctccgttgat tttggcctct ttctccatgg gcgggctggg   2220
cgtatttgaa gcggttctct cttctgccgt ta                                 2252
```

<210> SEQ ID NO 154
<211> LENGTH: 1496
<212> TYPE: DNA
<213> ORGANISM: Artificial Sequence
<220> FEATURE:
<223> OTHER INFORMATION: Synthetic Construct- Sequence No. 154,
Example 154: designer Nial-promoter-controlled chloroplast-
targeted 2-Methylbutyraldehyde Reductase DNA construct (1496 bp)

<400> SEQUENCE: 154
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatggcag ttccatccaa ttctactaaa actttcaagc 360
tgaacaacgg cctgtccatt ccagcagtcg gtctcggaac atggcaatcc accgatgaag 420
aggcttacaa tgccgttatt gctgcattga aagctggata cagacacatc gacacagctt 480
actgttacgg aaatgaagag ccaattggca aagctattaa ggactctgga gttgcaagaa 540
aggacatttt tattactacc aaactttggg gaactgacca caccagaact gaggaaggtt 600
tggataggtc tctgaaattg ttgggtttgg actatgttga tctgttcttg atgcattggc 660
cagttccaat gaaccctaat ggaaaccacg acaaatttcc tacattacca gacggtaaac 720
gtgacattct gtttgactgg aacttcgttg atacatacag agagatgcaa aaattagttg 780
cctctggaaa gaccaaggca atcggtgtgt ccaatttttc tatcactaac ttgaagaaat 840
tgcttgcaga cccagaaatc accatcaagc cagttgtcaa ccaagttgaa attcacgggt 900
atctgccgca gcagagactt ttggagtatg cgaaggaaaa tgatattgtt ttggaggcat 960
attcaccgtt gggatccact ggtgccccat tgctgaaaga tgagctggtg caggacctag 1020
ccaagaagaa tggtatttct gaatctactc tcttaatttc ctgggcagtg tggagaggta 1080
tcgtcgtttt accaaaatct gtaacgcctt ccagaattgc tgataatctt aagatcattg 1140
agttgtgtga ggaggatgga aaaaaactta atgaattggc ctcgattaga ggagaaaaac 1200
gattagttag ccctccttgg gatcctattg tcgtcttcaa cgatgaagac taataaatgg 1260
aggcgctcgt tgatctgagc cttgccccct gacgaacggc ggtggatgga agatactgct 1320
ctcaagtgct gaagcggtag cttagctccc cgtttcgtgc tgatcagtct ttttcaacac 1380
gtaaaaagcg gaggagtttt gcaattttgt tggttgtaac gatcctccgt tgattttggc 1440
ctctttctcc atgggcgggc tgggcgtatt tgaagcggtt ctctcttctg ccgtta 1496

<210> SEQ ID NO 155
<211> LENGTH: 1595
<212> TYPE: DNA
<213> ORGANISM: Artificial Sequence
<220> FEATURE:
<223> OTHER INFORMATION: Synthetic Construct- Sequence No. 155,
Example 155: designer Nial-promoter-controlled chloroplast-
targeted 3-Methylbutanal Reductase DNA construct (1595 bp)

<400> SEQUENCE: 155
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120

-continued

```
gaccccgcgc gacttggaag ggttcaaacg accccgccgt acgaactttt gtcgggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatgtcag ttttcgtttc aggtgctaac gggttcattg    360

cccaacacat tgtcgatctc ctgttgaagg aagactataa ggtcatcggt tctgccagaa    420

gtcaagaaaa ggccgagaat ttaacggagg cctttggtaa caacccaaaa ttctccatgg    480

aagttgtccc agacatatct aagctggacg catttgacca tgttttccaa aagcacggca    540

aggatatcaa gatagttcta catacggcct ctccattctg ctttgatatc actgacagtg    600

aacgcgattt attaattcct gctgtgaacg gtgttaaggg aattctccac tcaattaaaa    660

aatacgccgc tgattctgta gaacgtgtag ttctcacctc ttcttatgca gctgtgttcg    720

atatggcaaa agaaaacgat aagtctttaa catttaacga agaatcctgg aacccagcta    780

cctgggagag ttgccaaagt gacccagtta acgcctactg tggttctaag aagtttgctg    840

aaaaagcagc ttgggaattt ctagaggaga atagagactc tgtaaaattc gaattaactg    900

ccgttaaccc agtttacgtt tttggtccgc aaatgtttga caaagatgtg aaaaaacact    960

tgaacacatc ttgcgaactc gtcaacagct tgatgcattt atcaccagag gacaagatac   1020

cggaactatt tggtggatac attgatgttc gtgatgttgc aaaggctcat ttagttgcct   1080

tccaaaagag ggaaacaatt ggtcaaagac taatcgtatc ggaggccaga tttactatgc   1140

aggatgttct cgatatcctt aacgaagact tccctgttct aaaaggcaat attccagtgg   1200

ggaaaccagg ttctggtgct acccataaca cccttggtgc tactcttgat aataaaaaga   1260

gtaagaaatt gttaggtttc aagttcagga acttgaaaga gaccattgac gacactgcct   1320

cccaaatttt aaaatttgag ggcagaatat aataaatgga ggcgctcgtt gatctgagcc   1380

ttgccccctg acgaacggcg gtggatggaa gatactgctc tcaagtgctg aagcggtagc   1440

ttagctcccc gtttcgtgct gatcagtctt tttcaacacg taaaaagcgg aggagttttg   1500

caattttgtt ggttgtaacg atcctccgtt gattttggcc tctttctcca tgggcgggct   1560

gggcgtattt gaagcggttc tctcttctgc cgtta                              1595
```

```
<210> SEQ ID NO 156
<211> LENGTH: 1739
<212> TYPE: DNA
<213> ORGANISM: Artificial Sequence
<220> FEATURE:
<223> OTHER INFORMATION: Synthetic Construct- Sequence No. 156,
      Example 156: designer Nial-promoter-controlled chloroplast-
      targeted NADH-dependent Butanol Dehydrogenase DNA construct
      (1739 bp)

<400> SEQUENCE: 156

agaaaatctg gcaccacacc atggtagggt gcgagtgacc ccgcgcgact tggaagggtt     60

caaacgaccc cgccgtacga acttttgtcg ggggcgctc ccggatggta gggtgcgagt    120

gaccccgcgc gacttggaag ggttcaaacg accccgccgt acgaactttt gtcgggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatgaata attttacttt ttataatcct actaaaatta    360

actttggtag aggagttgaa tcctctgttg gagaagagat taaaagctta ggagctagta    420

aagtgctttt tcattatggt ggaggaagta ttagaaaaaa tgggttatat gatagaattt    480
```

tagattcttt aaataaagca ggattacatg taatagaact tggaggagtt aagcctaatc 540
ctagattaag cttagttaaa aagggaatag aactttgtaa aaatagtaaa gttgatttta 600
tacttgcagt tggaggagga agtgttattg actcagctaa agccatagct cttggtgttc 660
cttatgatgg agatgtatgg gatttcttta ctaaaaatat taaaatagaa aaagctttac 720
cattaggtac agtattaaca ataccagcgg caggaagtga atcaagctca ggaactgtta 780
taactaatga agatggatgg tataagagat caacaggatc accacttcta tatcctaaat 840
tttcaatgtt aaatccagaa ctatgcttta ctttaccaga atatcaaata gcatcaggaa 900
gtgcagatat tttagcacat ttaatggaaa gatatttcac aaacacaaag aatgttgaac 960
ttatagatag attaattgag ggaacaatga aaacagtaat aaataatgtt cctaaggtat 1020
taaaaaataa ggaagactat gatagctttg cagaggttat gtgggctgga acaatagcac 1080
ataataatct tttaagcaca ggaagagaaa cagattgggc atcacataat atagaacatg 1140
aattaagtgg aatatatgat gttactcatg gtgcaggatt agctgttata ttcccagctt 1200
ggatgaagtt tgtttataag catgatttag atagattcaa ccaatttgct actagagtat 1260
ttgatgttca agttgaagat aaaactaagg aagaggttgc cttagaagga attaagaaac 1320
ttgaagaatt cttcaaatca ataaatcttc cagtaacttt aaaagagtta gaaataggtg 1380
aagatagatt agaagaaatg gctaaaaaat gcacagataa tgatgagcat acagtaggtc 1440
attttgtaga attaaacaca gaggacatcc ttgaaatata caaattagct ttatagtaaa 1500
tggaggcgct cgttgatctg agccttgccc cctgacgaac ggcggtggat ggaagatact 1560
gctctcaagt gctgaagcgg tagcttagct ccccgtttcg tgctgatcag tctttttcaa 1620
cacgtaaaaa gcggaggagt tttgcaattt tgttggttgt aacgatcctc cgttgatttt 1680
ggcctctttc tccatgggcg ggctgggcgt atttgaagcg gttctctctt ctgccgtta 1739

<210> SEQ ID NO 157
<211> LENGTH: 1733
<212> TYPE: DNA
<213> ORGANISM: Artificial Sequence
<220> FEATURE:
<223> OTHER INFORMATION: Synthetic Construct- Sequence No. 157, Example 157: designer Nial-promoter-controlled NADPH-dependent chloroplast-targeted NADPH-dependent Butanol Dehydrogenase DNA construct (1733 bp)

<400> SEQUENCE: 157
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatgatga gatttacatt accaagagat atttattatg 360
gaaaaggatc actagaacaa ctaaaaaatc ttaaaggtaa aaaggcaatg ctagtacttg 420
gtggcggttc gatgaaaaga tttggatttg tcgataaggt gttaggatac ttaaaggaag 480
ctggaataga agtaaaatta atagaaggag ttgaaccaga cccatcagtt gaaacagtgt 540
tcaagggcgc tgagttaatg agacaatttg aaccagattg gattatagct atgggtggtg 600
gatcaccaat tgatgctgca aaagcaatgt ggatttttta tgaacaccca gaaaaaactt 660
ttgatgacat taaagatccg tttacagtac cagaattaag aaataaggct aagttcctag 720
cgattccatc aacaagtggt acagcaacag aagtaacagc attttctgta attacagatt 780
ataagactga aataaaatat cctttagctg attttaatat aactccagat gtagctgtag 840
tagattcaga attagctgaa acaatgccac ctaagttaac tgcccataca ggaatggatg 900
cattaactca tgcaattgaa gcttatgtag caacattaca ttcaccattt actgatccac 960
tagctatgca agcgattgaa atgattaatg aacatttatt taaatcatat gaaggcgata 1020
aagaagctag agaacaaatg cattatgctc aatgtttagc tggaatggct ttctctaatg 1080
cactattagg aatatgtcat agtatggcgc ataaaacagg ggctgtattc catatccctc 1140
atggatgtgc gaatgcaatc tatttaccat atgtaattaa gtttaattca aaaacttcat 1200
tagaaagata tgctaaaata gcaaaacaaa tttcattagc aggaaataca aatgaggaat 1260
tagttgattc attaataaac ttagttaaag aattaaataa gaagatgcaa ataccaacaa 1320
cattaaaaga atatggtatt catgaacaag aatttaagaa taaggttgat ttgatttcag 1380
aaagagctat tggagatgct tgtactggat caaatccaag acaattaaat aaagatgaaa 1440
tgaaaaagat ttttgaatgc gtatattatg gtacagaagt tgatttttaa taaatggagg 1500
cgctcgttga tctgagcctt gccccctgac gaacggcggt ggatggaaga tactgctctc 1560
aagtgctgaa gcggtagctt agctccccgt ttcgtgctga tcagtctttt tcaacacgta 1620
aaaagcggag gagttttgca attttgttgg ttgtaacgat cctccgttga ttttggcctc 1680
tttctccatg ggcgggctgg gcgtatttga agcggttctc tcttctgccg tta 1733

<210> SEQ ID NO 158
<211> LENGTH: 1745
<212> TYPE: DNA
<213> ORGANISM: Artificial Sequence
<220> FEATURE:
<223> OTHER INFORMATION: Synthetic Construct- Sequence No. 158, Example 158: designer Nial-promoter-controlled chloroplast-targeted 3-Ketothiolase DNA construct (1745 bp)

<400> SEQUENCE: 158
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcgggggc 180 gctcccggat ggccgccgtc attgccaagt cctccgtctc cgcggccgtg gctcgcccgg 240
cccgctccag cgtgcgcccc atggccgcgc tgaagcccgc cgtcaaggct gcccccgtgg 300
ctgccccggc tcaggccaac cagatgaccg acatcgtcat cgtcgccgca gcccgcaccg 360
ccgtgggcaa gttcggcggc tcgctggcca agatcccggc gcctgagctg ggcgctgccg 420
tgatcaaggc cctgctggaa aaaaccggcg tgggcgccga ccagatcggt gaagtcatca 480
tgggccaggt gctggccgcc ggcgcgggcc agaacccggc tcgccaggcc atgatgaagg 540
cgggcatcgc caaggaaacg ccggcgctga ccatcaacgc cgtgtgcggc tccggcctga 600
aggccgtgat gctggcggcc caagccatcg cctggggcga cagcgagatc gtcatcgccg 660
gcggccagga aaacatgtcc gccagcccgc acgtgctgca aggcagccgc gacggccagc 720
gcatgggcga ctggaagatg gtcgacacca tgatcaacga cggcctgtgg gacgtgtaca 780
acaagtacca catgggcatc acggccgaga acgtcgccaa ggcgcacgac atcacccgtg 840
agcagcagga cgccctggcc ctggccagcc agcaaaaggc caccgccgcc caggaagccg 900
gcaagttcaa ggacgagatc gttcccgtcg ccattccgca gcgcaagggc gatccggtga 960
tgttcgacac cgacgagttc atcaacaaga agaccaacgc cgaagcgctg gccggcctgc 1020

```
gtccggcctt cgacaaggcc ggctcggtga ccgcgggcaa cgcctccggc atcaacgacg   1080

gcgccgccgc cgtgatggtc atgtcggccg ccaaggccga gcaactgggc ctgaagccgc   1140

tggcgcgcat cgccagcttc ggcaccagcg gcctggaccc cgccaccatg ggcatgggcc   1200

cggtgccggc cacgcgcaag gcgctggagc gcgccggctg gcaagtcggc gacgtggacc   1260

tgttcgagct gaacgaagcc ttcgccgccc aagcctgcgc ggtgaacaag gagctgggcg   1320

tggacccggc caaggtcaac gtcaacggtg gcgccatcgc catcggccac cccatcggcg   1380

cctccggctg ccgcgtgctg gtgacgctgc tgcacgaaat gcagcgccgc gacgccaaga   1440

agggcgtggc cgcgctgtgc atcggtggcg gcatgggcgt gtcgctggcc gtcgagcgct   1500

gataaatgga ggcgctcgtt gatctgagcc ttgccccctg acgaacggcg gtggatggaa   1560

gatactgctc tcaagtgctg aagcggtagc ttagctcccc gtttcgtgct gatcagtctt   1620

tttcaacacg taaaaagcgg aggagttttg caattttgtt ggttgtaacg atcctccgtt   1680

gattttggcc tctttctcca tgggcgggct gggcgtattt gaagcggttc tctcttctgc   1740

cgtta                                                               1745
```

<210> SEQ ID NO 159
<211> LENGTH: 1439
<212> TYPE: DNA
<213> ORGANISM: Artificial Sequence
<220> FEATURE:
<223> OTHER INFORMATION: Synthetic Construct- Sequence No. 159, Example 159: designer Nial-promoter-controlled chloroplast-targeted 3-Hydroxyacyl-CoA dehydrogenase DNA construct (1439 bp)

<400> SEQUENCE: 159

```
agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcggggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatggaga ttcggaagat cggcgtgatc ggcgcagggc    360

agatggggtc gggcatcgcc caggtggcgg cccagtcggg ttacgaggtc gtgctaatgg    420

acgtcgagga gctgagcctc aagaaggggc tcgaggccat ccgaaggtcg ctcgaccgct    480

tcctgcgcaa ggagaagatc acccaggagg aggccgaaaa ggccctggcc cgcatcaaga    540

cgacgctcaa ccccgccgac ttcgcggact gcgacctggt cgtcgaggcc atcgtggaga    600

acgagtcggt caagggtaag ctcttccaga cgctcgacaa ggtggtgaag cctgaggccg    660

tcttcgcttc caacacctcc tcgattccca tcaccaagct ggccagctac acctcccgcc    720

ccgagcgttt catcggcatg cacttcatga acccggtgcc gctgatgaag ctcgtcgagg    780

tcatccgcgg ctacaagacc tcggacgagg tcacccgggt ggtcatggcg acggccgaga    840

agatgggcaa ggtgccggtc gaggtcaacg actaccccgg cttcgtctcc aaccgcgtgc    900

tcatccccat gctcaacgag gccatccaag cggtcatgga gggcgtggcc acccccgagg    960

ccatcgacac cgtgatgaag ctgggcatga accaccccat gggcccgctg acgctcgccg   1020

acttcatcgg cctcgacacc gtgctggcca tcatggaggt gctgcacgag ggctttggcg   1080

acagcaagta ccgcccctcg ccgctgctca agaagatggt ccaggcgggt ctgctgggcc   1140

gcaagagcgg gcaggggttc tacaagtacg acgagaaggg gaacaagatc ggctagtaaa   1200
```

```
tggaggcgct cgttgatctg agccttgccc cctgacgaac ggcggtggat ggaagatact   1260

gctctcaagt gctgaagcgg tagcttagct ccccgtttcg tgctgatcag tctttttcaa   1320

cacgtaaaaa gcggaggagt tttgcaattt tgttggttgt aacgatcctc cgttgatttt   1380

ggcctctttc tccatgggcg ggctgggcgt atttgaagcg gttctctctt ctgccgtta    1439
```

<210> SEQ ID NO 160
<211> LENGTH: 1337
<212> TYPE: DNA
<213> ORGANISM: Artificial Sequence
<220> FEATURE:
<223> OTHER INFORMATION: Synthetic Construct- Sequence No. 160, Example 160: designer Nial-promoter-controlled chloroplast-targeted Enoyl-CoA Dehydratase DNA construct (1337 bp)

<400> SEQUENCE: 160

```
agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcggggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatgacgg ttcgactgga atacgatggc gggttcgcgc    360

acctgacgct cagccgcccg caggtcctga atgcgctcag tttcgagctg ctcgccgagt    420

tgagccgggc gcttgccggc gtcgccgaat ccgatgcgcg cgccctgatc gtcacgggcg    480

agggcgacaa ggcgttctgc gccggcgcgg acattcccga gctgatgaat cggccgctca    540

tgcaagagct cgaaggggcc gcgaaaggcc aggcggtgtt cagccggatc gccgagctga    600

agattccgtc tgtcgccgtc atccagggtt atgccttcgg cggcgggctg gagcttgccc    660

tggcatgcac attccgcgtt gccactgatc gcgcccgcat ggggctgccc gaggtcaagc    720

tcggcctgat cccgggttat ggcggaacgc agcgtctgcc gaggctgatc ggcgaggggc    780

gcgcactcga cctgatcatg tccggccgca cgatagacgg cggggaagcc gagcgaatcg    840

gcctggtcaa tcgcatagac aacgagggga cgcccctgga gatcggcaag cggtttctgg    900

agccttatct caagcacagt ctctgcgcct tgtattttgc ccgcgaggcc gtgcagaggg    960

gaggcggtgt cgccattgcg gatggcctgc gcatcgagcg ggatctttcc acgctggctt   1020

accggagcca ggatgcggcc gaggggctgc gcgcttttgt ggaaaaacgg cccgcgtctt   1080

tcaaggactg ctgataaatg gaggcgctcg ttgatctgag ccttgccccc tgacgaacgg   1140

cggtggatgg aagatactgc tctcaagtgc tgaagcggta gcttagctcc ccgtttcgtg   1200

ctgatcagtc tttttcaaca cgtaaaaagc ggaggagttt tgcaattttg ttggttgtaa   1260

cgatcctccg ttgattttgg cctctttctc catgggcggg ctgggcgtat ttgaagcggt   1320

tctctcttct gccgtta                                                  1337
```

<210> SEQ ID NO 161
<211> LENGTH: 1736
<212> TYPE: DNA
<213> ORGANISM: Artificial Sequence
<220> FEATURE:
<223> OTHER INFORMATION: Synthetic Construct- Sequence No. 161, Example 161: designer Nial-promoter-controlled chloroplast-targeted 2-Enoyl-CoA Reductase DNA construct (1736 bp)

<400> SEQUENCE: 161
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240
cccgctccag cgtgcgcccc atggccgcgc tgaagcccgc cgtcaaggct gccccccgtgg 300 ctgccccggc tcaggccaac cagatggccg gcgcgcagca ggatcttgcc gctgcgtccg 360
ggcttgtcgc tggccgcggc ggccttggcg gcatcgtgca ggtcgaacac cgcttccacc 420
ggcagcgcca ggctgccatc gagcgcggcg gtgagcagtt cgccgatcat gcggcgcttg 480
tcctcggcct tggtggcctg catcaccttg ctgccccaga agccacgcac ggtggcctgc 540
ttgaagatca catcgccgct ggatatctgc agcggctcgc cggtcatcga gccaaaggaa 600
atcagctcgc cgccttcggc cagcaaggcc atcagctcac ccgctgcatt gccggccacc 660
gaatcgatgg cgcgcacgat gggcgcatcg ccggccagcg cgcgcacctt gtcctgccag 720
cctgcttgcg cagtggagat tgcgttgccg atgcccagcg ctttcagctc gtccacgccg 780
gcgtcgcggc gcaccaggtt gatcacgttg atgccgcgtg cggcggcgag catcgccacc 840
gtcttgccga ccgcaccgtt ggcggtgttc tgcacgatcc agtcgccctg tttcacctgc 900
aggaattcga tcagcatcag cgcgctcagc ggcatggcga tcaactggca accacgctcg 960
tcgtccaggc catccggcaa cggcaccacg ccggaggcgt cggcaaggaa gtactcggcc 1020
caggcctcat gcacaccggc ggcgaccacg cgctggccaa cctgcaagcc ctcgacaccc 1080
tcacccagcg catcgatgac acccgccgct tcgctgccgc cgatggctgg cagttccggc 1140
ttgtagccgt aattgccgcg cacggtccac aggtcatggt tatggatcgg cgcgcgccgc 1200
atcgcaacgc gcacctggcc cttgcctggc tgcggcgtgg ggcgctcgcc cagttcgagc 1260
accttggccg gatcgccgaa ttgggtatgg atggctgcgc gcatggaggt ctcctgccgg 1320
gcacgctctt gctgcgacgc gcccgatcgt tgtgaaaggt ggcgcgatgc tatcggcagg 1380
gctgcaagga agggatgaag cgaacggaac tgctgtgtga agttgttggc gtgcgcgcgt 1440
agtgacgatg ctctgctgca gcgccggagg actgcgtgca ggccgaccct cattaaatgg 1500
aggcgctcgt tgatctgagc cttgccccct gacgaacggc ggtggatgga agatactgct 1560
ctcaagtgct gaagcggtag cttagctccc cgtttcgtgc tgatcagtct ttttcaacac 1620
gtaaaaagcg gaggagtttt gcaattttgt tggttgtaac gatcctccgt tgattttggc 1680
ctctttctcc atgggcgggc tgggcgtatt tgaagcggtt ctctcttctg ccgtta 1736

<210> SEQ ID NO 162
<211> LENGTH: 2036
<212> TYPE: DNA
<213> ORGANISM: Artificial Sequence
<220> FEATURE:
<223> OTHER INFORMATION: Synthetic Construct- Sequence No. 162, Example 162: designer Nial-promoter-controlled chloroplast-targeted Acyl-CoA Reductase DNA construct (2036 bp)

<400> SEQUENCE: 162
agaaaatctg gcaccacacc atggtagggt gcgagtgacc ccgcgcgact tggaagggtt 60
caaacgaccc cgccgtacga acttttgtcg gggggcgctc ccggatggta gggtgcgagt 120
gaccccgcgc gacttggaag ggttcaaacg accccgccgt acgaactttt gtcggggggc 180
gctcccggat ggccgccgtc attgccaagt cctccgtctc cgcggccgtg gctcgcccgg 240

```
cccgctccag cgtgcgcccc atggccgcgc tgaagcccgc cgtcaaggct gcccccgtgg    300
ctgccccggc tcaggccaac cagatggatg acgataatgt tgtaaaaccc atttactatg    360
gtaaaataga ggttcaaaat aatggcacgg gagtatggga gcctaccgtt gagtggttga    420
atgagttttt aaaccggagt atggaactat cacagagtct tttacaacta ggctttagta    480
gaagggttag agtgttgagc gagatgggga agatttggag ggagaagctt tcgttagtcg    540
aggagaaact agctcctaat atttctaaga atacaggcta cagcgtggag aatgtgaaaa    600
tggacttaag actggttgaa gaagtgttta atgagaccaa tattgttgag ctcttcgata    660
aaggcttaat cgggggatgg cgtagtcttg acaagcccgt tgaaatcatt gatggggagt    720
tcgtgtggaa tagaccgcta ggcgtatccc ttataatatc ctccggaaac accgtcatac    780
cagctattct cccagcagtg gtttctttag catcggggaa cgtaactata ctaaggccgt    840
ctttcagcaa ctaccaagca gtagtcgaaa tttttaaaac acttttcgat ctagcagaca    900
gctccgtaga aggtgctaga gaaatggctt cggctcttct ggtcgcatac tttaaacatg    960
agagcaaggt atttgaacac ctattagcat cagcacctct cggcatcgtc aattactggg   1020
gcggggagcc aggtagaagc gtgatcgcta gtagggtttt gaagaatccg tttcatccta   1080
agttaatcgt caatggacct ctaacggggt tagcgataat agatgaagag tcagcgtcgg   1140
aaaaagtagc ctacggatta gcgagggatg tggtactgta tgatcaacag ttatgtagct   1200
ctcccactta cgccatattc ataggttcga aagatagcgc gttgaagttt gcacagagac   1260
taggggaagc cctgaataat gtggggagaa ggttcccccg tgatttgaag gaaggagaac   1320
tgtacaattt aatactgctt aggaaaaacc ttgagatcca aggtgtgaga gttttctact   1380
cggaaaaccc cggaaatgct tggacgattg cggtgaaaac actagagtca gtcactaatt   1440
ttgcatatag tttaaaatat ccacatacaa tccctaggag acggttcatt gaaataatag   1500
tgttgaaaga cgccaaagaa ctcaaggaga cgatcttaca cctaattgaa gacttgagga   1560
gaaacggggt tgataagttc cagacagcat cgataaaggt ttctgaaaga aaccttaacc   1620
acttattgaa ggttctctat attcttggga tttacagggt tgtcccaata ggggaatcct   1680
tttttagaac gccgttagaa ccgtacgatg gtgaattctt acctaaatac ttcacttaca   1740
cgatgtatct tagatttatc gagaagtcgg atgcgctaaa acaccctgaa tgataaatgg   1800
aggcgctcgt tgatctgagc cttgccccct gacgaacggc ggtggatgga agatactgct   1860
ctcaagtgct gaagcggtag cttagctccc cgtttcgtgc tgatcagtct ttttcaacac   1920
gtaaaaagcg gaggagtttt gcaattttgt tggttgtaac gatcctccgt tgattttggc   1980
ctctttctcc atgggcgggc tgggcgtatt tgaagcggtt ctctcttctg ccgtta       2036
```

<210> SEQ ID NO 163
<211> LENGTH: 1625
<212> TYPE: DNA
<213> ORGANISM: Artificial Sequence
<220> FEATURE:
<223> OTHER INFORMATION: Synthetic Construct- Sequence No. 163, Example 163: designer Nial-promoter-controlled chloroplast-targeted Hexanol Dehydronase DNA construct (1625 bp)

<400> SEQUENCE: 163

```
agaaaatctg gcaccacacc atggtagggt gcgagtgacc ccgcgcgact tggaagggtt     60
caaacgaccc cgccgtacga acttttgtcg gggggcgctc ccggatggta gggtgcgagt    120
gaccccgcgc gacttggaag ggttcaaacg accccgccgt acgaactttt gtcgggggc     180
gctcccggat ggccgccgtc attgccaagt cctccgtctc cgcggccgtg gctcgcccgg    240
```

-continued

```
cccgctccag cgtgcgcccc atggccgcgc tgaagcccgc cgtcaaggct gcccccgtgg    300

ctgccccggc tcaggccaac cagatggaac tcgacctcga cggtcccggg gttggtgaag    360

tgctgatcaa gtacaccgcc gcggggttgt gccattcgga cctgcacttg accgacgggg    420

acctaccgcc gcgctatcca atcgtcgggg ggcacgaggg gtcaggcatc atcgaggacg    480

tcggacctgg ggtcaccaag gtcaaaccag gcgatcacgt tgtttgcagc ttcatcccga    540

actgcggaac ctgtcggtac tgcgccaccg gacgctccaa cctctgcgat atgggcgcca    600

ccatcctcga agggtgcatg cccgacggca gttaccggtt ccacagtaac ggcctggatt    660

tcggtgcgat gtgcatgctc ggcacattct ccgaacgcgc aactatctcc cagcattcgg    720

tggtcaagat cgacgactgg ctgccgctcg agaccgcggt ggtcgtcggc tgcggcgtgc    780

cgactggctg ggcacctcc gtctatgccg gcggggttcg ttgcggtgac accaccgtca    840

tctatggcgt cggcggcctg ggagtcaacg ccgtccaagg cgcggtgagt gcgggcgcga    900

agtacatcgt ggtcgtcgat ccggttgcgt tcaaacgcga caccgcgctc aagttcggcg    960

ccacccacgc gttcgccgac gccgccaccg ccgcggccaa ggtcgacgaa ctgacctggg   1020

gacagggtgc cgatcaggcg ctgatcctgg tcggcaccgt cgacgaggac gtggtctcgg   1080

cggcgactgc ggtgatcggt aagggaggca ccgtcgtgat caccggactg gcggacccag   1140

caaagctcac ggtgcacgtt tcgggaacgg acctgacgct taacgagaag acaatcaagg   1200

gcacgttgtt cggctcgtcc aatccgcaat acgacatcgt acggctgctc cgtctctacg   1260

acgccggcca gctaaaactc gacgatctga tcaccacccg atacacgctc gaccaggtca   1320

accagggcta ccaggatctg cgagacggca agaacatccg cggcgtgatc atccacgcct   1380

gataaatgga ggcgctcgtt gatctgagcc ttgccccctg acgaacggcg gtggatggaa   1440

gatactgctc tcaagtgctg aagcggtagc ttagctcccc gtttcgtgct gatcagtctt   1500

tttcaacacg taaaaagcgg aggagttttg caattttgtt ggttgtaacg atcctccgtt   1560

gattttggcc tctttctcca tgggcgggct gggcgtattt gaagcggttc tctcttctgc   1620

cgtta                                                               1625
```

<210> SEQ ID NO 164
<211> LENGTH: 1249
<212> TYPE: DNA
<213> ORGANISM: Artificial Sequence
<220> FEATURE:
<223> OTHER INFORMATION: Synthetic Construct- Sequence No. 164, Example 164: designer Nial-promoter-controlled chloroplast-targeted Octanol Dehydrogenase DNA construct (1249 bp)

<400> SEQUENCE: 164

```
agaaaatctg gcaccacacc atggtagggt gcgagtgacc ccgcgcgact tggaagggtt     60

caaacgaccc cgccgtacga acttttgtcg gggggcgctc ccggatggta gggtgcgagt    120

gaccccgcgc gacttggaag ggttcaaacg accccgccgt acgaactttt gtcgggggc    180

gctcccggat ggccgccgtc attgccaagt cctccgtctc cgcggccgtg gctcgcccgg    240

cccgctccag cgtgcgcccc atggccgcgc tgaagcccgc cgtcaaggct gcccccgtgg    300

ctgccccggc tcaggccaac cagatgttgg gaggccaaga agccgctggt gattgaggac    360

attgaggtgg cgccacctca ggcttggcag gttcgcatca agattacagc cactggcgtt    420

tgccacacgg attctttttc gttgagcggc tctgatcctg agggtctctt tcccgtggtc    480

cttggccatg agggcgccgg catcgtggag agcgttggcg agggcgtaac caactttaag    540

gccggcgatc atgtcattgc cctctacata ccccagtgca atgagtgcaa attctgcaag    600
```

```
agcggcaaga caaatctctg ccagaagatt cgcctcaccc agggcgctgg tgtcatgccc    660
aatggatcct cccgcttgtc gtgcaagggt cagcagctgt tccatttcat gggcacctca    720
actttcgccg agtacgcggt ggtggccgac atatcggtga ccaaaatcaa cgagtcggct    780
ccattggaga aggtgtgcct tctgggctgt ggcatttcca cgggctatgg tgccgccttg    840
aacaccttta ggtggaacct ggcagcactt gcgccgtctg gggtctgggt gctgttggac    900
tggcagtggg tctgggctgc aagaaggctg gcgccgccaa ggtctacggc atcgacatca    960
atccctccaa attcgagctg gccaggaagt tcggcttcac cgactttaaa tggaggcgct   1020
cgttgatctg agccttgccc cctgacgaac ggcggtggat ggaagatact gctctcaagt   1080
gctgaagcgg tagcttagct ccccgtttcg tgctgatcag tctttttcaa cacgtaaaaa   1140
gcggaggagt tttgcaattt tgttggttgt aacgatcctc cgttgatttt ggcctctttc   1200
tccatgggcg ggctgggcgt atttgaagcg gttctctctt ctgccgtta               1249
```

<210> SEQ ID NO 165
<211> LENGTH: 1769
<212> TYPE: DNA
<213> ORGANISM: Artificial Sequence
<220> FEATURE:
<223> OTHER INFORMATION: Synthetic Construct- Sequence No. 165, Example 165: designer Nial-promoter-controlled chloroplast-targeted Short Chain Alcohol Dehydrogenase DNA construct (1769 bp)

<400> SEQUENCE: 165

```
agaaaatctg gcaccacacc atggtagggt gcgagtgacc ccgcgcgact tggaagggtt     60
caaacgaccc cgccgtacga acttttgtcg gggggcgctc ccggatggta gggtgcgagt    120
gaccccgcgc gacttggaag ggttcaaacg accccgccgt acgaactttt gtcggggggc    180
gctcccggat ggccgccgtc attgccaagt cctccgtctc cgcggccgtg gctcgcccgg    240
cccgctccag cgtgcgcccc atggccgcgc tgaagcccgc cgtcaaggct gcccccgtgg    300
ctgccccggc tcaggccaac cagatgatca tcaaaccgcg cgtgcgtggc ttcatctgcg    360
tgaccactca tccggtcggc tgcgaggcca acgtcaagga acagatcgac tacgtgactt    420
cgcacggccc gatcgccaac ggcccgaaga aggtgctcgt gatcggcgcg tcgaccggct    480
acggcctcgc ggcccggatc tcggccgcct tcggctcggg cgcggacacg cttggcgtgt    540
tcttcgagcg cgccggcagc gacaccaagc cgggcaccgc cggctggtac aacagcgccg    600
cgttcgagaa attcgccgcc gaaaaggggc tctatgcgcg cagcatcaac ggcgacgcgt    660
tctccgacaa ggtcaagcag atcacgatcg acacgatcaa gcaggacctc ggcaaggtcg    720
atctggtcgt ctacagcctg gccgcgccgc gccgcacgca tccgaagacg ggcgagacga    780
tcagctcgac gctgaagccg gtcggcaagt cggtgacgtt ccgcggcctc gacaccgaca    840
aggaaacgat ccgcgaggtg acgctcgagc cggcgacgca ggaagagatc gacggcaccg    900
tcgccgtgat gggcggcgag gactggcaga tgtggatcga cgcgctcgcc gacgccggcg    960
tgctggccga cggcgcgaag accaccgcgt tcacgtatct cggcgagcag atcacgcacg   1020
acatctactg gaacggctcg atcggtgagg cgaagaagga tctcgacaag aaggtcgtgt   1080
cgatccgcga gaagctcgcc gtgcatggcg gcgacgcgcg cgtgtcggtg ctgaaggccg   1140
tcgtcacgca ggcgagctcg gcgatcccga tgatgccgct gtacctgtcg ctgctgttca   1200
aggtgatgaa ggaaaagggc acgcacgaag gctgcatcga gcaggtgtac gggctgctga   1260
aggacagcat gtacggcgcg acgccgcaca tcgacgaaga aggccggctg cgcgcggact   1320
acaaggaact cgatccgcag gtgcaggcgc aggtcgtcgc gatgtgggac aaggtcacga   1380
```

-continued

```
acgacaacct gtacgagatg accgacttcg ccggttacaa gaccgagttc ctgcgtctgt   1440

tcggcttcga gatcgccggc gtcgactacg acgcggacgt gaacccggac gtgaagatcc   1500

ccggcatcat cgacacgacg gcctgataaa tggaggcgct cgttgatctg agccttgccc   1560

cctgacgaac ggcggtggat ggaagatact gctctcaagt gctgaagcgg tagcttagct   1620

ccccgtttcg tgctgatcag tctttttcaa cacgtaaaaa gcggaggagt tttgcaattt   1680

tgttggttgt aacgatcctc cgttgatttt ggcctctttc tccatgggcg ggctgggcgt   1740

atttgaagcg gttctctctt ctgccgtta                                     1769
```